United States Patent
Alcacio et al.

(10) Patent No.: US 10,570,115 B2
(45) Date of Patent: Feb. 25, 2020

(54) MODULATOR OF CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATOR

(71) Applicant: Vertex Pharmaceuticals Incorporated, Boston, MA (US)

(72) Inventors: Timothy Alcacio, San Diego, CA (US); Minson Baek, San Diego, CA (US); Peter Grootenhuis, Del Mar, CA (US); Sara Sabina Hadida Ruah, La Jolla, CA (US); Robert M. Hughes, San Diego, CA (US); Ali Keshavarz-Shokri, San Diego, CA (US); Rachel McAuley-Aoki, San Diego, CA (US); Jason McCartney, Cardiff by the Sea, CA (US); Mark Thomas Miller, San Diego, CA (US); Fredrick Van Goor, San Diego, CA (US); Beili Zhang, San Diego, CA (US); Corey Anderson, San Diego, CA (US); Thomas Cleveland, San Marcos, CA (US); Bryan A. Frieman, La Jolla, CA (US); Haripada Khatuya, San Diego, CA (US); Pramod Virupax Joshi, San Diego, CA (US); Paul John Krenitsky, San Diego, CA (US); Vito Melillo, Escondido, CA (US); Fabrice Jean Denis Pierre, La Jolla, CA (US); Andreas P. Termin, Encinitas, CA (US); Johnny Uy, San Diego, CA (US); Jinglan Zhou, San Diego, CA (US); Alexander Russell Abela, San Diego, CA (US); Brett Bradley Busch, San Diego, CA (US); Prasuna Paraselli, San Diego, CA (US); David Andrew Siesel, San Diego, CA (US)

(73) Assignee: Vertex Pharmaceuticals Incorporated, Boston, MA (US)

(*) Notice: Subject to any disclaimer, the term of this patent is extended or adjusted under 35 U.S.C. 154(b) by 0 days.

(21) Appl. No.: 15/721,390

(22) Filed: Sep. 29, 2017

(65) Prior Publication Data
US 2018/0093969 A1 Apr. 5, 2018

Related U.S. Application Data

(60) Provisional application No. 62/402,838, filed on Sep. 30, 2016, provisional application No. 62/410,353, (Continued)

(51) Int. Cl.
*C07D 401/14* (2006.01)
*A61K 31/465* (2006.01)
*A61K 31/455* (2006.01)
*A61K 31/4155* (2006.01)
*A61K 31/4025* (2006.01)
(Continued)

(52) U.S. Cl.
CPC .......... *C07D 401/14* (2013.01); *C07B 59/002* (2013.01); *C07D 471/14* (2013.01); *C07D 498/14* (2013.01); *C07B 2200/05* (2013.01)

(58) Field of Classification Search
CPC .. C07D 401/14; A61K 31/465; A61K 31/455; A61K 31/4155; A61K 31/4025
USPC .............. 514/341, 343, 407, 422; 546/275.4, 546/279.4; 548/364.1, 518
See application file for complete search history.

(56) References Cited

U.S. PATENT DOCUMENTS

| 5,410,061 A | 4/1995 | Gilmore et al. |
| 6,441,004 B1 | 8/2002 | Faull et al. |

(Continued)

FOREIGN PATENT DOCUMENTS

| CA | 2145473 A1 | 9/1995 |
| EP | 0 194 599 A2 | 9/1986 |

(Continued)

OTHER PUBLICATIONS

Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.

(Continued)

*Primary Examiner* — Matthew P Coughlin
*Assistant Examiner* — Sagar Patel
(74) *Attorney, Agent, or Firm* — Finnegan, Henderson, Farabow, Garrett & Dunner, LLP

(57) ABSTRACT

Compounds of Formula I:

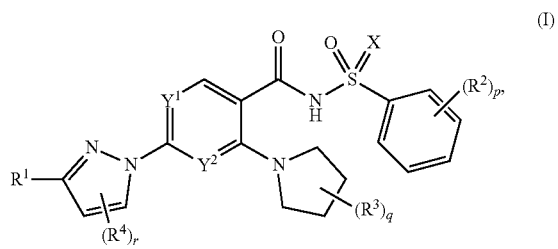

pharmaceutically acceptable salts thereof, deuterated derivatives of any of the foregoing, and metabolites of any of the foregoing are disclosed. Pharmaceutical compositions comprising the same, methods of treating cystic fibrosis using the same, and methods for making the same are also disclosed.

18 Claims, 19 Drawing Sheets

Related U.S. Application Data filed on Oct. 19, 2016, provisional application No. 62/415,409, filed on Oct. 31, 2016, provisional application No. 62/419,935, filed on Nov. 9, 2016.

(51) Int. Cl.
*C07D 471/14* (2006.01)
*C07D 498/14* (2006.01)
*C07B 59/00* (2006.01)

(56) References Cited

U.S. PATENT DOCUMENTS

| | | |
|---|---|---|
| 6,787,651 B2 | 9/2004 | Stolle et al. |
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 2002/0055631 A1 | 5/2002 | Augeri et al. |
| 2002/0086887 A1 | 7/2002 | Augeri et al. |
| 2005/0171185 A1 | 8/2005 | Yamasaki et al. |
| 2005/0197376 A1 | 9/2005 | Kayakiri et al. |
| 2011/0165118 A1 | 7/2011 | Chan et al. |
| 2013/0267493 A1 | 10/2013 | Bhattacharya et al. |
| 2013/0317000 A1 | 11/2013 | Chowdhury et al. |
| 2013/0317001 A1 | 11/2013 | Andrez et al. |
| 2015/0322002 A1 | 11/2015 | Dehnhardt et al. |
| 2016/0095858 A1* | 4/2016 | Miller .......... A61K 31/506 514/253.09 |
| 2018/0099932 A1 | 4/2018 | Altenbach et al. |
| 2018/0141954 A1 | 5/2018 | Strohbach et al. |
| 2018/0162839 A1 | 6/2018 | Abela et al. |
| 2018/0170938 A1 | 6/2018 | Strohbach et al. |
| 2018/0185364 A1 | 7/2018 | Miller et al. |
| 2018/0244611 A1 | 8/2018 | Altenbach et al. |
| 2018/0244640 A1 | 8/2018 | Altenbach et al. |
| 2019/0077784 A1 | 3/2019 | Altenbach et al. |
| 2019/0153000 A1 | 5/2019 | Munoz et al. |

FOREIGN PATENT DOCUMENTS

| | | |
|---|---|---|
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2005/054191 A1 | 6/2005 |
| WO | WO 2005/070006 A2 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/113327 A2 | 10/2007 |
| WO | WO 2008/005457 A1 | 1/2008 |
| WO | WO 2008/100867 A2 | 8/2008 |
| WO | WO 2008/141385 A1 | 11/2008 |
| WO | WO 2009/027730 A1 | 3/2009 |
| WO | WO 2009/032116 A1 | 3/2009 |
| WO | WO 2009/064848 A1 | 5/2009 |
| WO | WO 2009/071947 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/022307 A2 | 2/2010 |
| WO | WO 2010/025295 A2 | 3/2010 |
| WO | WO 2010/065824 A1 | 6/2010 |
| WO | WO 2010/083441 A2 | 7/2010 |
| WO | WO 2010/102758 A2 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/068560 A1 | 6/2011 |
| WO | WO 2011/102514 A1 | 8/2011 |
| WO | WO 2011/128251 A1 | 10/2011 |
| WO | WO 2011/150016 A1 | 12/2011 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/082102 A1 | 6/2013 |
| WO | WO 2013/118805 A1 | 8/2013 |
| WO | WO 2013/177224 A1 | 11/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |

(56) References Cited

FOREIGN PATENT DOCUMENTS

| | | |
|---|---|---|
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/160787 A1 | 10/2015 |
| WO | WO 2016/057572 A1 | 4/2016 |
| WO | WO 2016/105484 A1 | 6/2016 |
| WO | WO 2016/105485 A2 | 6/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/201126 A1 | 11/2018 |
| WO | WO 2019/071078 A1 | 4/2019 |

OTHER PUBLICATIONS

Chen, Y. (Jan. 26, 2016) "*N*-Monoacylation of Sulfonimidamides" *Synthesis*, 48(7):1019-1028.
Database Caplus, Accession No. 1965:51408. Abstract of French Patent No. FR M2868, filed Nov. 23, 1964, by Roussel-Uclaf [online]. Retrieved Jan. 6, 2017 (1 page).
Database Caplus, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database Pubchem, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).
Database Pubchem, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, SCHEMBL13395127. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).
Database Pubchem, CID: 58132855. Compound Summary, SCHEMBL831192. Nih, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
International Patent Application No. PCT/US2015/54316: International Search Report and Written Opinion, dated Feb. 5, 2016 (11 pages).
International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).

International Patent Application No. PCT/US2017/065425: International Search Report and Written Opinion, dated Feb. 27, 2018 (10 pages).
U.S. Appl. No. 15/836,627, filed Dec. 8, 2017, by Abela et al.
Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2018/036610: International Search Report and Written Opinion, dated Sep. 19, 2018 (9 pages).
International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/044963: International Search Report and Written Opinion, dated Sep. 25, 2018 (15 pages).
International Patent Application No. PCT/US2018/056772: International Search Report and Written Opinion, dated Jan. 29, 2019 (13 pages).
Jain, B.C. et al. (1947) "Studies in Sulphanilamides. Part XIII. Reaction With Dicarboxylic Acids. Some NEWN1- and N4-Acyl and Heterocycic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Lai, J.T. et al. (1980) "Rearrangement of 2,2,6,6-tetramethyl-4-piperidone in phase-transfer catalyzed reactions," *Journal of Organic Chemistry*, 45(8):1513-1514.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Passarella, D. et al. (2001) "Cyclodimerization of indol-2-ylacetylenes. An example of intermolecular enyne-alkyne cycloaddition" *Journal of the Chemical Society, Perkin Transactions* 1, 127-129.
Rosebraugh, C.J. (2015) "Highlights of Presescribing Information for Orkambi," [online] Retrieved from the Internet: https://www.accessdata.fda.gov/drugsatfda_docs/label/2015/206038Orig1s000lbl.pdf, on Aug. 24, 2017.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal far Pracktische Chemie*, 331(3):503-506.
Tullis, E. et al. (2018) "Preliminary safety and efficacy of triple-combination CFTR modulator regimens," *Respirology*, 23(51):33.
U.S. Appl. No. 16/258,024, filed Jan. 25, 2019, by Miller et al.
U.S. Appl. No. 16/165,849, filed Oct. 19, 2018, by Dhamankar et al.
U.S. Appl. No. 16/267,222, filed Feb. 4, 2019, by Chu et al.
U.S. Appl. No. 16/267,350, filed Feb. 14, 2019, by Clemens et al.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.
Wainwright, C.E. et al. (2015) "Lumacaftor-Ivacaftor in Patients with Cystic Fibrosis Homozygous for Phe508del CFTR," *The New England Journal of Medicine*, 373(3):220-231.

(56) References Cited

OTHER PUBLICATIONS

Winn, M. et al. (1993) "2-(Alkylamino)nicotinic Acid and Analogs. Potent Angiotensin II Antagonists" *Journal of Medicinal Chemistry*, 36(18):2676-2688.
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.
Verardo, G. et al. (1999) "Reductive One Batch Synthesis of N-Substituted Pyrrolidines from Primary Amines and 2,5-Dimethoxytetrahydrofuran" Synthesis, (1):74-79.

\* cited by examiner

FIG. 4

| Mutation cDNA Name | Mutation Protein Name | Mutation Legacy Name |
|---|---|---|
| c.1A>G | p.? (unknown) | M1V |
| c.54-5940_273+10250del21kb | pSer18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |

FIG. 4 (continued)

| Mutation cDNA Name | Mutation Protein Name | Mutation Legacy Name |
|---|---|---|
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| c.595OT | p.His199Tyr | H199Y |
| c.613CM | p.Pro205Ser | P205S |
| c.617T>G | p.Leu206Trp | L206W |
| c.658OT | p.Gln220X | Q220X |
| c.580T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 1079C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |

FIG. 4 (continued)

| Mutation cDNA Name | Mutation Protein Name | Mutation Legacy Name |
|---|---|---|
| c.1202G>A or c.1203G>A | p.Trp401X | W401X |
| c.1209+1G>A | No protein name | 1341+1G->A |
| c.1210-12[5] | No protein name | 5T |
| c.1210-12(7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1G47T>G | p.Ser549Arg | S549R |
|  |  |  |
| c.1646G>A | p.Ser549Asn | S549N |
| c.1650delA | p.Gly551ValfsX8 | 1782delA |
| c.1651G>A | p.Gly551Ser | G551S |

FIG. 4 (continued)

| Mutation cDNA Name | Mutation Protein Name | Mutation Legacy Name |
|---|---|---|
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.205 1_2052delAAinsG | p.Lys684SerfsX38 | 2183delAA->G# |

FIG. 4 (continued)

| Mutation cDNA Name | Mutation Protein Name | Mutation Legacy Name |
|---|---|---|
| c.2052_2053insA | p.Gln685ThrfsX4 | 2184insA |
| c.2052delA | p.Lys684AsnfsX38 | 2184delA |
| c.2125C>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547C>A | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG |  | 2869insG |
| c.2739T>A | p.Tyr913X | Y913X |
| c.2764_2765insAG | p.Val922GlufsX2 | 2896insAG |
| c.2780T>C | p.Leu927Pro | L927P |

FIG. 4 (continued)

| Mutation cDNA Name | Mutation Protein Name | Mutation Legacy Name |
|---|---|---|
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |

FIG. 4 (continued)

| Mutation cDNA Name | Mutation Protein Name | Mutation Legacy Name |
|---|---|---|
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3718-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764delA | p.Ser1255X | S1255X |
| c.3773_3774insT | p.Leu1258PhefsX7 | 3905insT |
| c.3808G>A | p.Asp1270Asn | D1270N |
| c.3846G>A | p.Trp1282X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |

FIG. 4 (continued)

| Mutation cDNA Name | Mutation Protein Name | Mutation Legacy Name |
|---|---|---|
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

MODULATOR OF CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATOR

Disclosed herein is a modulator of Cystic Fibrosis Transmembrane Conductance Regulator (CFTR), pharmaceutical compositions containing the modulator, methods of treatment of cystic fibrosis, and a process for making the modulator.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respirator epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451) To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

Disclosed herein are novel compounds, including compounds of Formulae I-IV and pharmaceutically acceptable salts thereof. For example, compounds of Formula I can be depicted as:

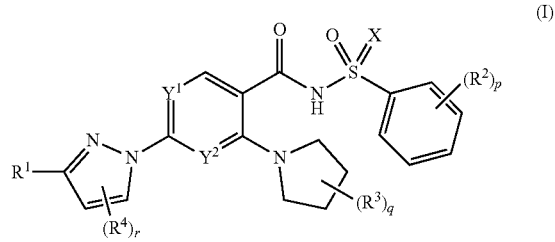

or a pharmaceutically acceptable salt thereof,
wherein:
one of $Y^1$ and $Y^2$ is N and the other is CH;
X is chosen from O, NH, and N($C_1$-$C_4$ alkyl) groups;
$R^1$ is chosen from —$(CR_2)_k$—O—$(CR_2)_m(CR)_n$(Ring A)$_{n+1}$ groups,
  wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
  wherein each R is independently chosen from H, OH, and $C_1$-$C_2$ alkyl groups optionally substituted with one or more halogens;
each $R^2$ is independently chosen from $C_1$-$C_2$ alkyl groups, OH, $C_1$-$C_2$ alkoxy groups, halogens, and cyano;
each $R^3$ is independently chosen from $C_1$-$C_2$ alkyl groups optionally substituted with one or more OH groups;
each $R^4$ is independently a halogen;
k is 0 or 1;
r is 0 or 1;
m is 0, 1, 2, or 3;
n is 0 or 1;

p is 0, 1, 2, 3, 4, or 5; and q is 0, 1, 2, 3, 4, 5, 6, 7, or 8.

Also disclosed herein are pharmaceutical compositions comprising at least one of the novel compounds disclosed herein and/or at least one pharmaceutically acceptable salt thereof, which compositions may further include at least one additional active pharmaceutical ingredient and/or at least one carrier. Also disclosed are methods of treating the CFTR-mediated disease cystic fibrosis comprising administering at least one of the novel compounds disclosed herein and/or at least one pharmaceutically acceptable salt thereof, optionally as part of a pharmaceutical composition comprising at least one additional component, to a subject in need thereof.

Also disclosed are methods of treating the CFTR-mediated disease cystic fibrosis comprising administering at least one of the novel compounds disclosed herein and/or at least one pharmaceutically acceptable salt thereof, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), and N-[2,4-bis(1,1-dimethylethyl)-5-hydroxyphenyl]-1,4-dihydro-4-oxoquinoline-3-carboxamide (Compound III), optionally as part of at least one pharmaceutical composition comprising at least one additional component, to a patient in need thereof.

BRIEF DESCRIPTION OF THE DRAWINGS

FIG. 4 is a representative list of CFTR genetic mutations.

DEFINITIONS

Figure 1:
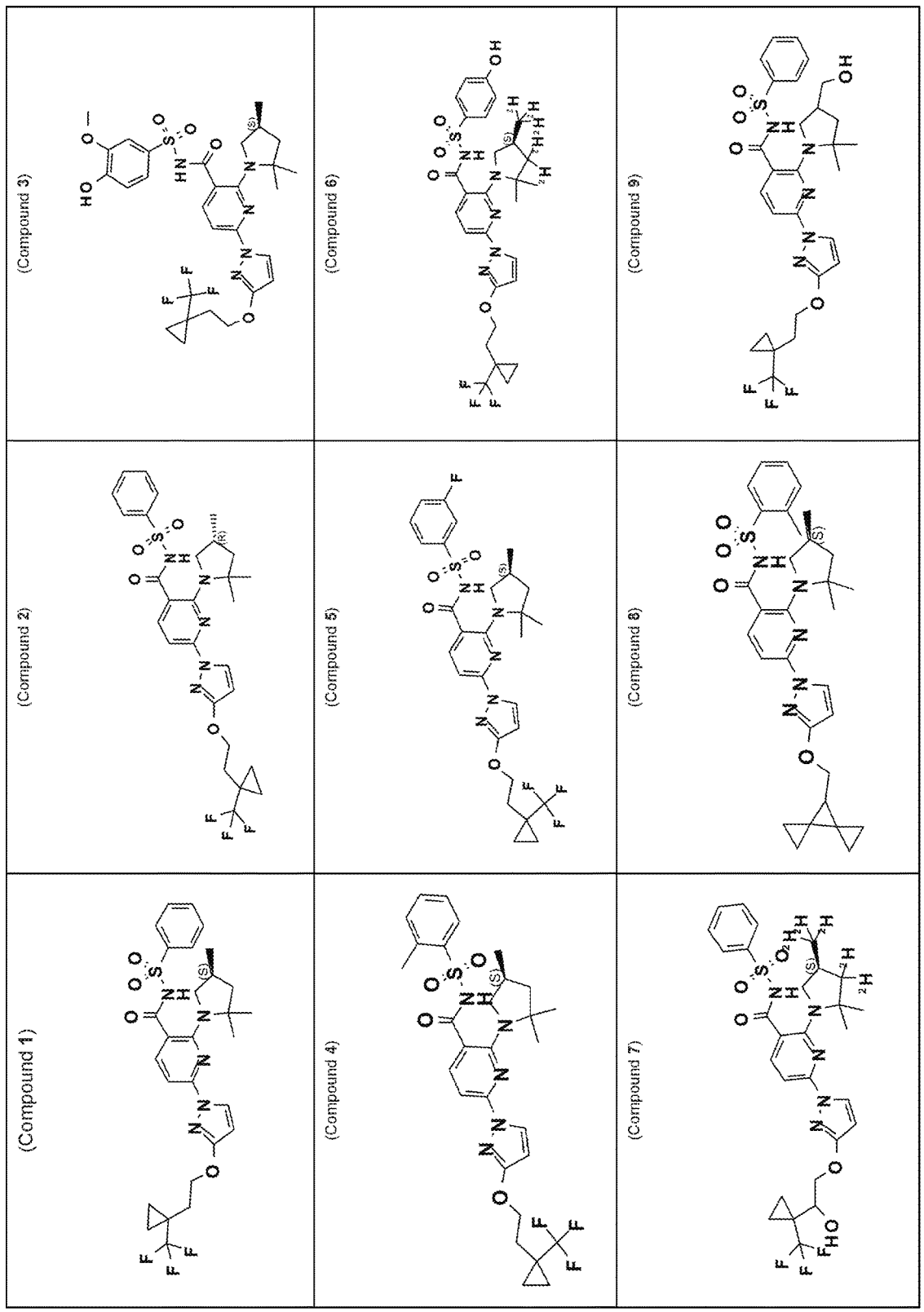
FIG. 1 shows the structures of non-limiting examples of novel compounds disclosed herein.
Figure 1:
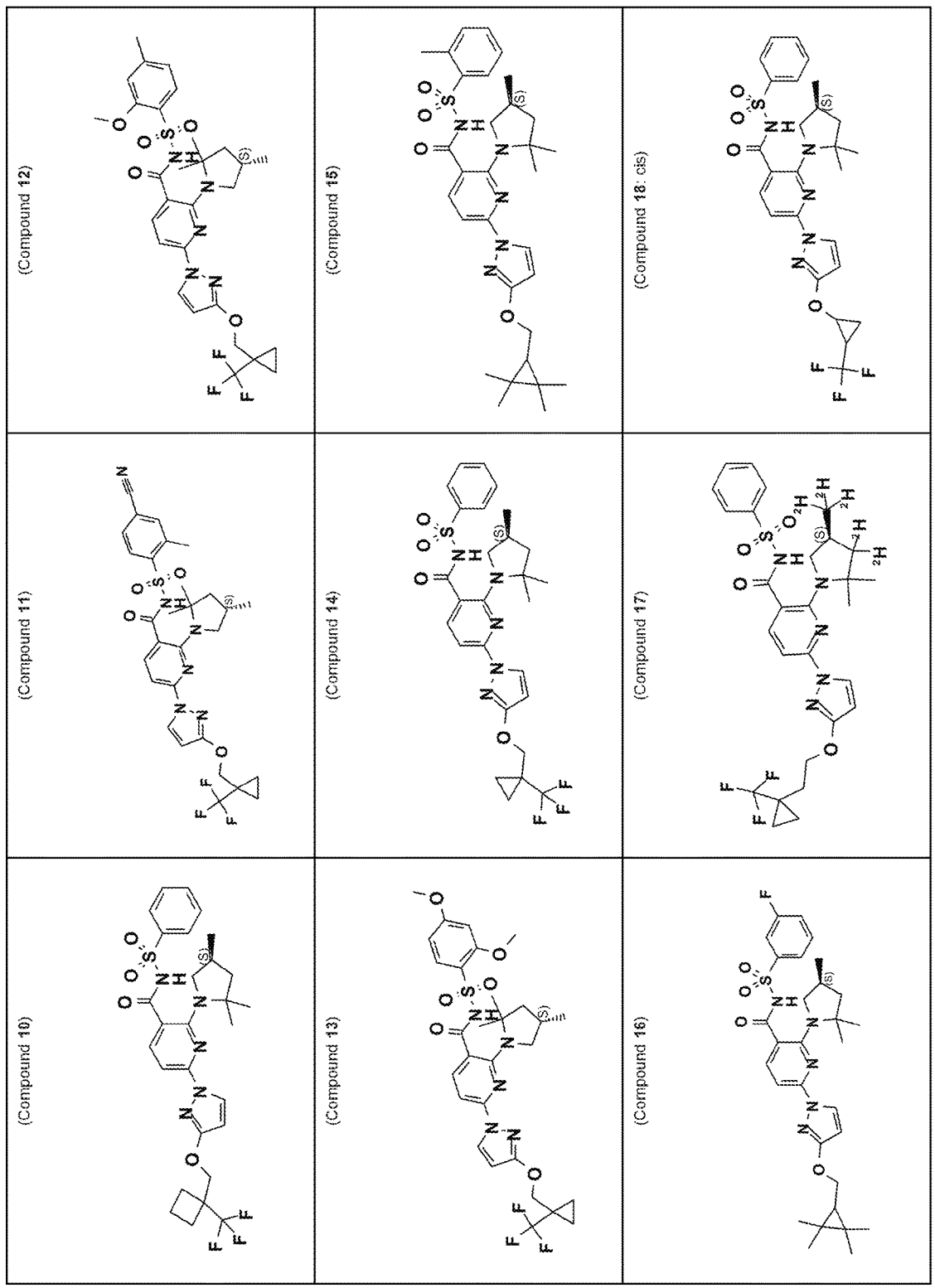
Figure 1:
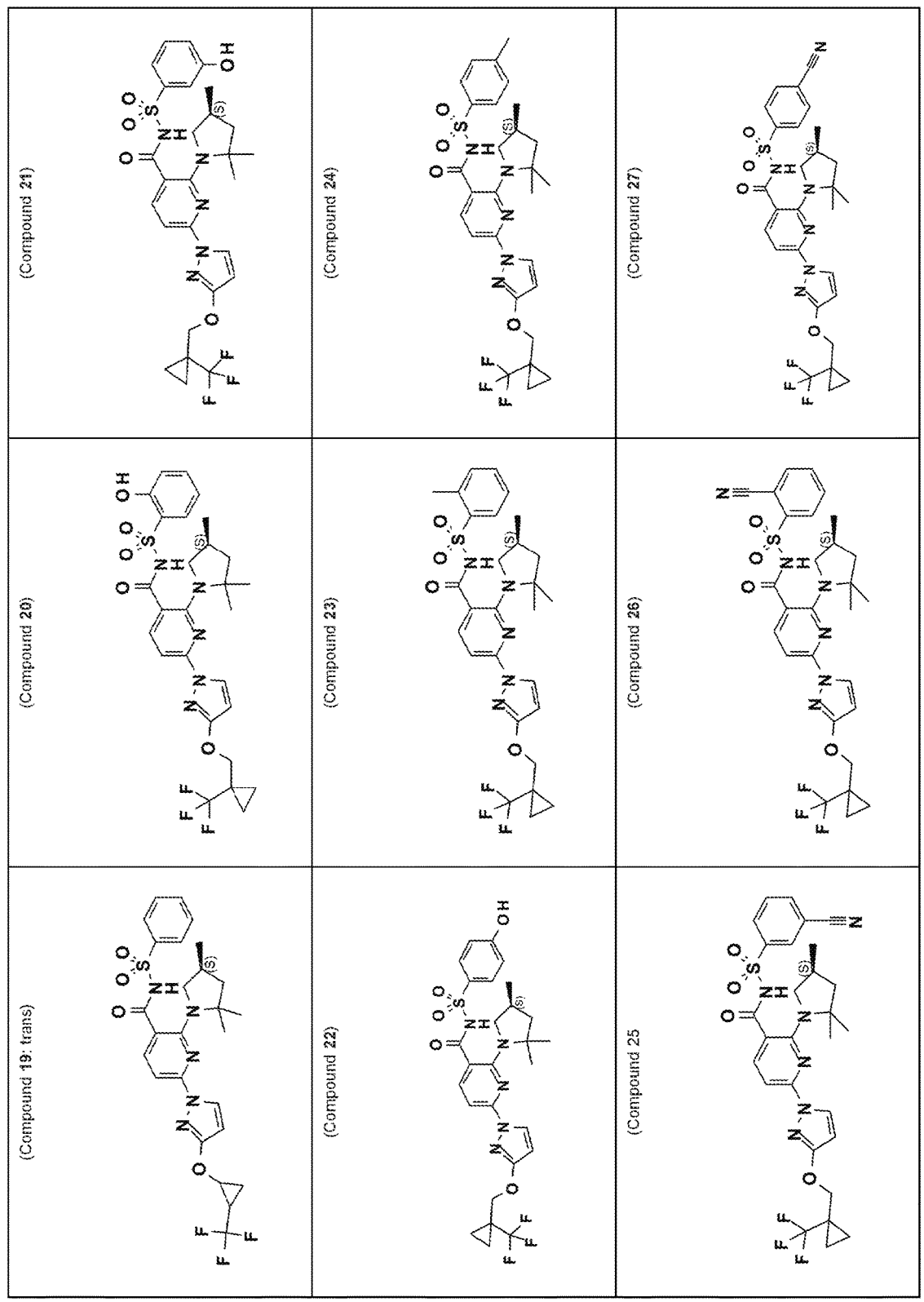
Figure 1:
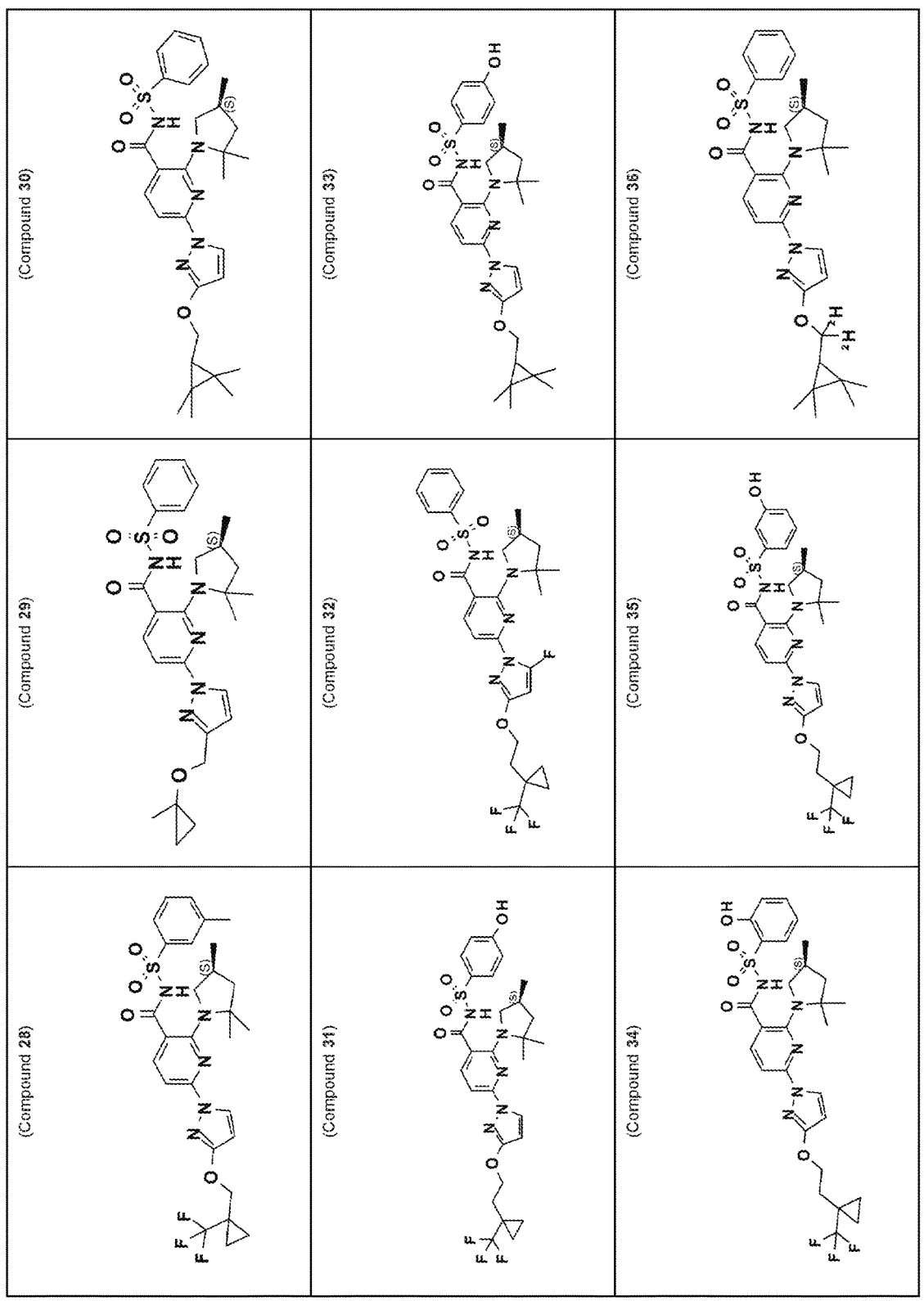
Figure 1:
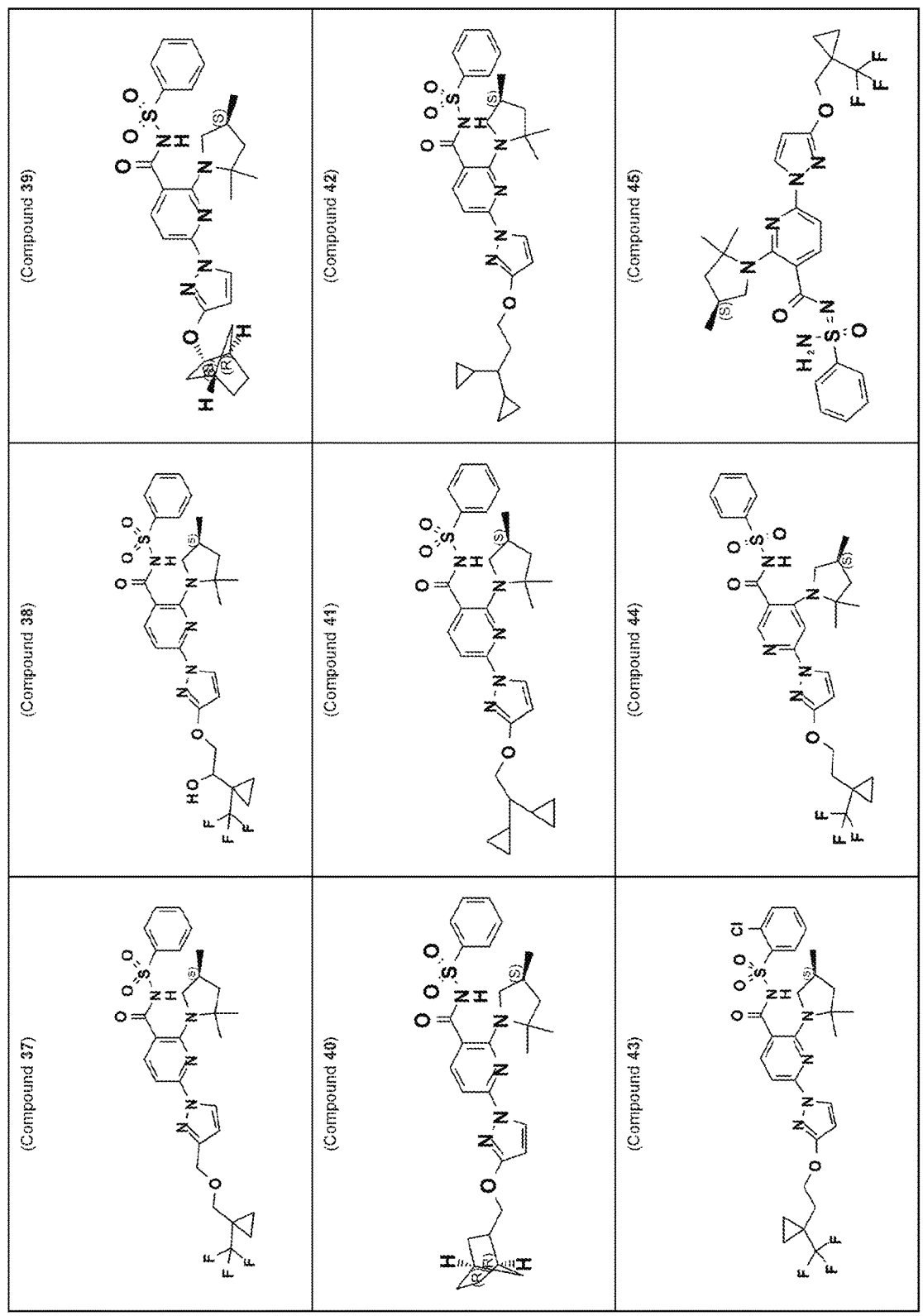
Figure 1:
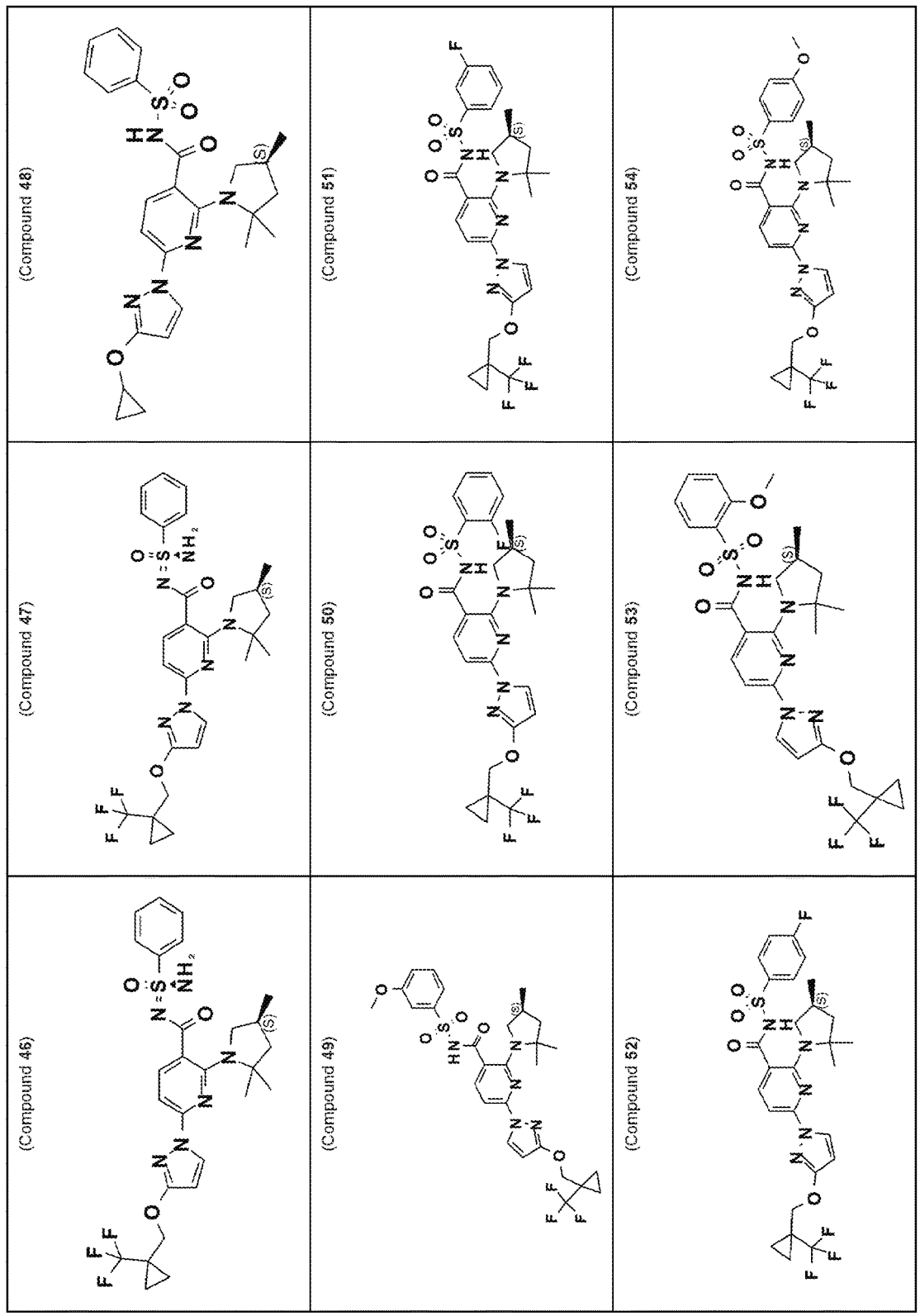
Figure 1:
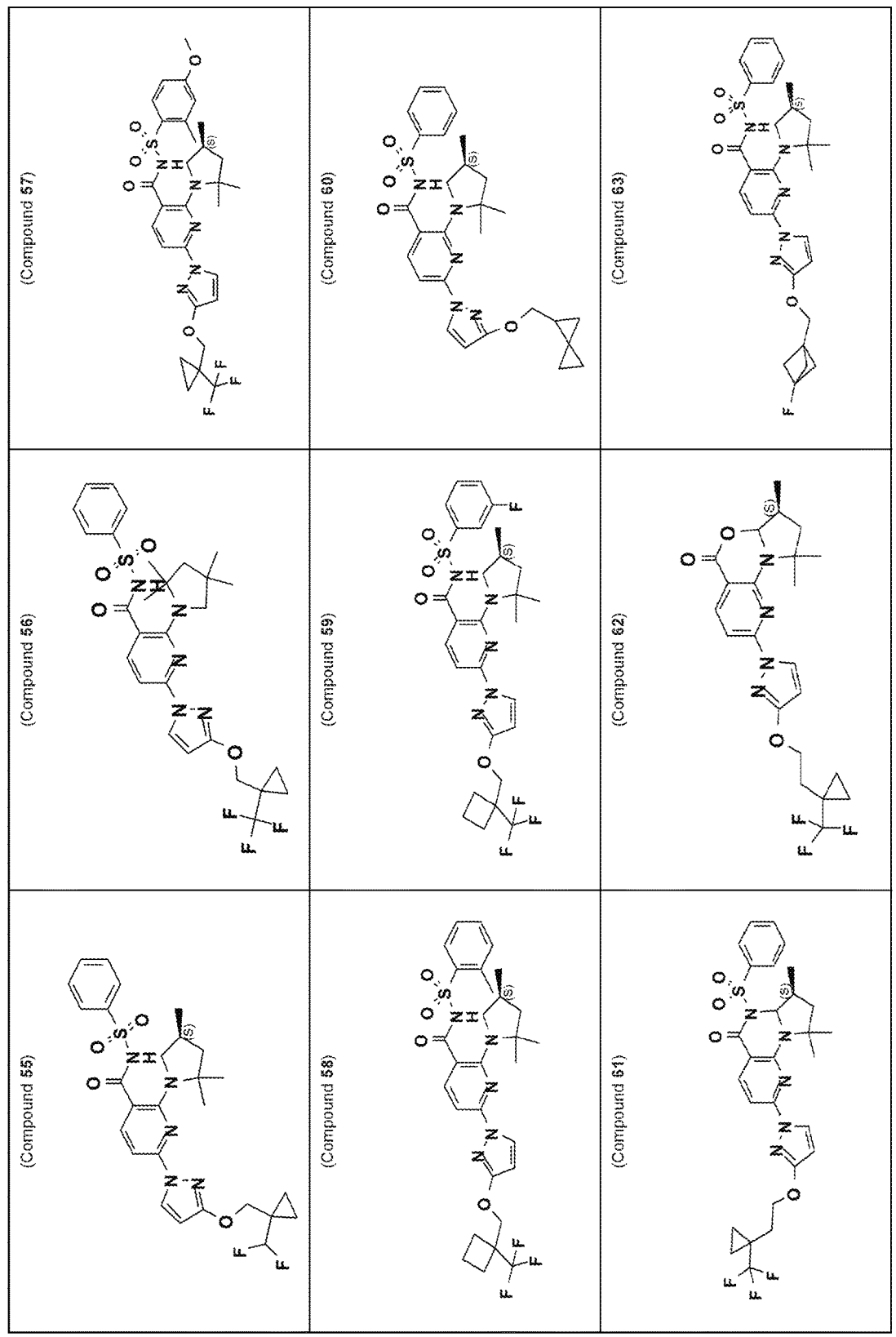
Figure 1:
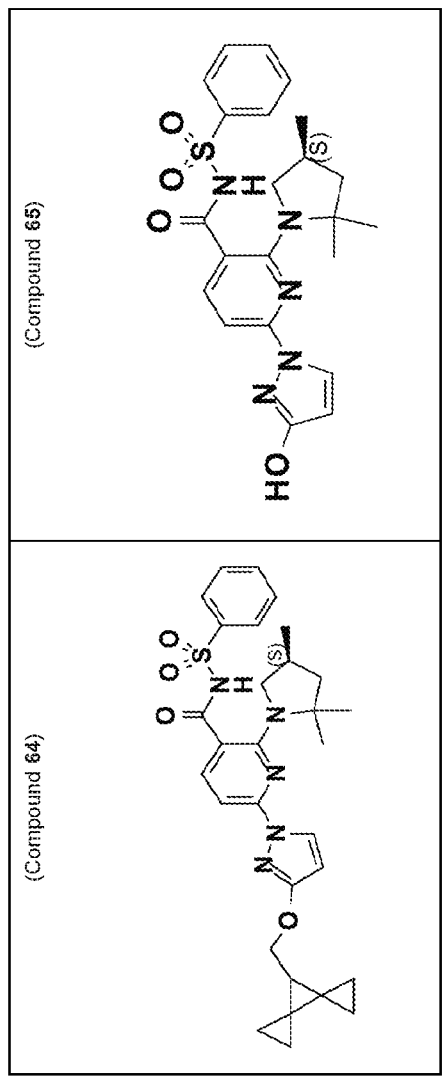

As used herein, the term "alkyl" refers to a saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

The term "alkoxy" as used herein refers to an alkyl or cycloalkyl covalently bonded to an oxygen atom. Alkoxy groups may be substituted or unsubstituted.

As used herein, "cycloalkyl" refers to a cyclic, bicyclic, tricyclic, or polycyclic non-aromatic hydrocarbon groups having 3 to 12 carbons (such as, for example 3-10 carbons). "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, and dispiro[2.0.2.1]heptane. Cycloalkyl groups may be substituted or unsubstituted.

"Substituted," whether preceded by the term "optionally" or not, indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

As used herein, "deuterated derivative(s)" means the same chemical structure, but with one or more hydrogen atoms replaced by a deuterium atom.

As used herein, "CFTR" means cystic fibrosis transmembrane conductance regulator.

As used herein, "mutations" can refer to mutations in the CFTR gene or the CFTR protein. A "CF, R gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds of Formulae (I), (II), (III), (IV), and (V), and Compound II, and their pharmaceutically acceptable salts thereof disclosed herein are CFTR correctors.

As used herein, the term "CFTR potentiator" refers to a compound that increases the channel activity of CFTR protein located at the cell surface, resulting in enhanced ion transport. Compound III disclosed herein is a CFTR potentiator.

As used herein, the term "active pharmaceutical ingredient" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describe pharmaceutically acceptable salts in detail in *J. Pharmaceutical Sciences,* 1977, 66, 1-19.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD) pattern. Broad peaks are characteristic of an amorphous solid. See, US 2004/0006237 for a comparison of XRPDs of an amorphous material and crystalline material.

As used herein, the term "substantially amorphous" refers to a solid material having little or no long range order in the position of its molecules. For example, substantially amorphous materials have less than 15% crystallinity (e.g., less than 10% crystallinity or less than 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

Each of Compounds of Formulae (I), (II), (III), (IV), and (V), and Compounds II, III, IV, and pharmaceutically acceptable salts thereof described, and their deuterated derivatives herein independently can be administered once daily, twice daily, or three times daily. In some embodiments, at least one compound chosen from Compounds of Formulae (I), (II), (III), (IV), and (V), and pharmaceutically acceptable salts thereof, and their deuterated derivatives is administered once daily. In some embodiments, at least one compound chosen from Compounds of Formulae (I), (II), (III), (IV), and (V), and pharmaceutically acceptable salts thereof, and their deuterated derivatives are administered twice daily. In some embodiments, at least one compound chosen from Compound II and pharmaceutically acceptable salts thereof is administered once daily. In some embodiments, at least one compound chosen from Compound II and pharmaceutically acceptable salts thereof is administered twice daily. In some embodiments, at least one compound chosen from Compound III and pharmaceutically acceptable salts thereof is administered once daily. In some embodiments, at least one compound chosen from Compound III and pharmaceutically acceptable salts thereof is administered twice daily. In some embodiments, at least one compound chosen from Compound IV and pharmaceutically acceptable salts thereof is administered once daily. In some embodiments, at least one compound chosen from Compound IV and pharmaceutically acceptable salts thereof is administered twice daily. In some embodiments, a deuterated derivative of Compound ii, III, and/or IV or a pharmaceutically acceptable salt thereof is employed in any one of these embodiments.

In some embodiments, 10 mg to 1,500 mg of a compound disclosed herein, a pharmaceutically acceptable salt thereof, or a deuterated derivative of such compound or salt are administered daily.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "10 mg of at least one compound chosen from compounds of Formula (I) and pharmaceutically acceptable salts thereof" includes 10 mg of a compound of Formula (I) and a concentration of a pharmaceutically acceptable salt of compounds of Formula (I) equivalent to 10 mg of compounds of Formula (I).

As stated above, disclosed herein are compounds of Formula (I):

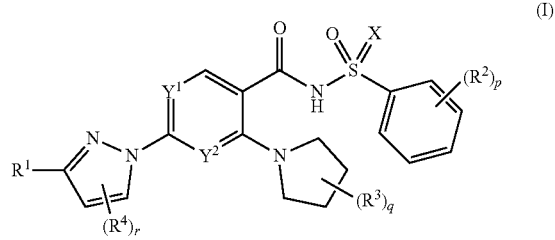

(I)

and pharmaceutically acceptable salts thereof,
wherein:
one of $Y^1$ and $Y^2$ is N and the other is CH;
X is chosen from O, NH, and N($C_1$-$C_4$ alkyl) groups;

$R^1$ is chosen from —$(CR_2)$—O—$(CR_2)_m(CR)_n$(Ring A)$_{n+1}$ groups, wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and wherein each R is independently chosen from H, OH, and $C_1$-$C_2$ alkyl groups optionally substituted with one or more halogens;

each $R^2$ is independently chosen from $C_1$-$C_2$ alkyl groups, OH, $C_1$-$C_2$ alkoxy groups, halogens, and cyano;

each $R^3$ is independently chosen from $C_1$-$C_2$ alkyl groups optionally substituted with one or more OH groups;

each $R^4$ is independently chosen from halogens;

k is 0 or 1;

r is 0 or 1;

m is 0, 1, 2, or 3;

n is 0 or 1;

p is 0, 1, 2, 3, 4, or 5; and q is 0, 1, 2, 3, 4, 5, 6, 7 or 8.

Also disclosed herein are compounds of Formula (II):

(II)

and pharmaceutically acceptable salts thereof,
wherein:

X is chosen from O, NH, and N($C_1$-$C_4$ alkyl) groups;

$R^1$ is chosen from —$(CR_2)_k$—O—$(CR_2)_m(CR)_n$(Ring A)$_{n+1}$ groups, wherein each Ring A is independently chosen from $C_3$-$C_1$ cycloalkyl groups optionally substituted with one or more substituents each independently chosen from $C_1$-$C_2$ alkyl groups, halogenated $C_1$-$C_2$ alkyl groups, and halogens, and wherein each R is independently chosen from H, OH, and $C_1$-$C_2$ alkyl groups optionally substituted with one or more halogens;

each $R^2$ is independently chosen from $C_1$-$C_2$ alkyl groups, OH, $C_1$-$C_2$ alkoxy groups, halogens, and cyano;

each $R^3$ is independently chosen from $C_1$-$C_2$ alkyl groups optionally substituted with one or more OH groups;

each $R^4$ is independently chosen from halogens;

k is 0 or 1;

r is 0 or 1;

m is 0, 1, 2, or 3;

n is 0 or 1;

p is 0, 1, 2, 3, 4, or 5; and q is 0, 1, 2, 3, 4, 5, 6, 7, or 8.

Encompassed within the scope of Formulae (I) and (II) are compounds comprising an group (where R' is H or $C_1$-$C_4$ alkyl), i.e., wherein X is chosen from NH and N($C_1$-$C_4$ alkyl) groups. Non-limiting examples of such compounds include compounds having the following structure:

and pharmaceutically acceptable salts thereof, either as a isomeric mixture or enantioenriched (e.g., >90% ee, >959/0 ee, or >9890 ee) isomers.

Also disclosed herein are compounds of Formula (III):

(III)

and pharmaceutically acceptable salts thereof,
wherein:

$R^1$ is chosen from —$(CR_2)_k$—O—$(CR_2)_m(CR)_n$(Ring A)$_{n+1}$ groups, wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and wherein each R is independently chosen from H, OH, and $C_1$-$C_2$ alkyl groups optionally substituted with one or more halogens;

each $R^2$ is independently chosen from $C_1$-$C_2$ alkyl groups, OH—, $C_1$-$C_2$ alkoxy groups, halogens, and cyano;

each $R^3$ is independently chosen from $C_1$-$C_2$ alkyl groups optionally substituted with one or more OH groups;

each $R^4$ is independently chosen from halogens;

k is 0 or 1;

r is 0 or 1;

m is 0, 1, 2, or 3;

n is 0 or 1;

p is 0, 1, 2, 3, 4, or 5; and q is 0, 1, 2, 3, 4, 5, 6, 7, or 8.

In some embodiments, in compounds of Formula (I), (II), (III), and pharmaceutically acceptable salts thereof, if $R^2$ is cyano, then $R^2$ is meta or para relative to the sulfur atom.

In some embodiments, in compounds of Formula (I), (II), (III), and pharmaceutically acceptable salts thereof:
- each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
- each R is independently chosen from H and OH;
- each $R^2$ is independently chosen from $C_1$-$C_2$ alkyl groups, OH, $C_1$-$C_2$ alkoxy groups, and halogens;
- $R^4$ is F;
- k is 0;
- p is 0, 1, or 2;
- q is 0, 1, 2, 3, or 4;
- r is 0; and
- m and n are not 0 at the same time.

In some embodiments, in compounds of Formula (I), (II), (III), and pharmaceutically acceptable salts thereof:
- $R^1$ is chosen from —O—$(CR_2)_m$-Ring A groups, wherein Ring A is chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
- m is 1 or 2.

In some embodiments, in compounds of Formula (I), (II), (III), and pharmaceutically acceptable salts thereof, each $R^3$ is a methyl group and q is 3 or 4.

Also disclosed herein are compounds of Formula (IV):

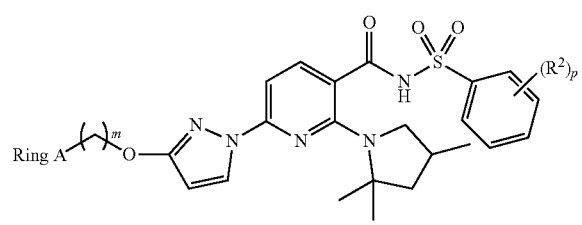

(IV)

and pharmaceutically acceptable salts thereof, wherein:
- Ring A is chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens; and
- each $R^2$ is independently chosen from $C_1$-$C_2$ alkyl groups, OH, F, Cl, and $C_1$-$C_2$ alkoxy groups;
- m is 1 or 2; and
- p is 0, 1, or 2. In some embodiments, p is 0 or 1. In some embodiments, p is 0.

Also disclosed herein are compounds of Formula V:

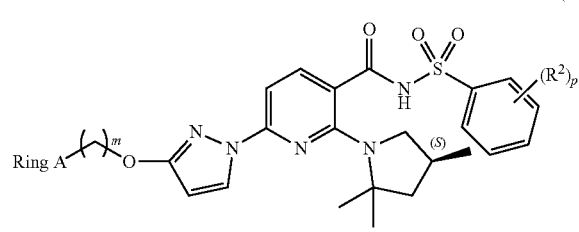

(V)

and pharmaceutically acceptable salts thereof, wherein:
- Ring A is chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens; and
- each $R^2$ is independently chosen from $C_1$-$C_2$ alkyl groups, OH, F, Cl, and $C_1$-$C_2$ alkoxy groups;
- m is 1 or 2; and
- p is 0, 1, or 2.

In some embodiments, in compounds of Formula (I), (II), (III), (IV), (V), and pharmaceutically acceptable salts thereof, each $R^2$ is independently chosen from $CH_3$, OH, F, and $OCH_3$. In some embodiments, p is 0 or 1. In some embodiments, p is 0.

In some embodiments, in compounds of Formula (I), (II), (III), (IV), (V), and pharmaceutically acceptable salts thereof, Ring A is a cyclopropyl group substituted with a halogenated $C_1$ alkyl group or a halogenated $C_2$ alkyl group. In some embodiments, Ring A is a cyclopropyl group substituted with a $CF_3$ group.

In some embodiments, in compounds of Formula (I), (II), (III), (IV), (V), and pharmaceutically acceptable salts thereof, m is 1, Ring A is a cyclopropyl group substituted with a $CF_3$ group, p is 0 or 1, and $R^2$, if present, is a methyl group, a hydroxy group, or a methoxy group. In some embodiments, m is 2, Ring A is a cyclopropyl group substituted with a $CF_3$ group, and p is 0.

In some embodiments, in compounds of Formula (I), (II), (III), (IV), (V), and pharmaceutically acceptable salts thereof, m is 2, Ring A is a $C_3$ cycloalkyl group substituted with a $CF_3$ group, p is 0 or 1, and $R^2$, if present, is a methyl group, a hydroxy group, or a methoxy group. In some embodiments, m is 2, Ring A is a cyclopropyl group substituted with a $CF_3$ group, and p is 0.

In some embodiments, m is 2, Ring A is a cyclopropyl group substituted with a $CF_3$ group, and p is 0.

In some embodiments, in compounds of Formula (I), (II), (III), (IV), (V), and pharmaceutically acceptable salts thereof, Ring A is chosen from $C_5$ bicycloalkyl groups optionally substituted with one or more substituents each independently chosen from $C_1$-$C_2$ alkyl groups, halogenated $C_1$-$C_2$ alkyl groups, and halogens. In some embodiments, Ring A is a $C_5$ bicycloalkyl group optionally substituted with a halogen.

In some embodiments, in compounds of Formula (I), (II), (III), (IV), (V), and pharmaceutically acceptable salts thereof, Ring A is chosen from $C_7$ bicycloalkyl groups and $C_7$ tricycloalkyl groups optionally substituted with one or more substituents each independently chosen from $C_1$-$C_2$ alkyl groups, halogenated $C_1$-$C_2$ alkyl groups, and halogens. In some embodiments, Ring A is an unsubstituted $C_7$ tricycloalkyl group.

Also disclosed herein are compounds having a formula chosen from any one of the formulae depicted in FIG. 1 and pharmaceutically acceptable salts thereof.

Also disclosed herein are Compounds 1-5, 8, 10-16, 18-30, 32, 33, 35-37, 39-60, 63, and 64, and pharmaceutically acceptable salts thereof.

Also disclosed herein are Compounds 9, 31, 34, 38, 61, 62, and 65, and pharmaceutically acceptable salts thereof.

Also disclosed herein are Compounds 6, 7, and 17, and pharmaceutically acceptable salts thereof.

Also disclosed herein are deuterated derivatives of any one of Compounds 1-5, 8, 10-16, 18-65, and pharmaceutically acceptable salts thereof.

Also disclosed herein are a compound having the following formula:

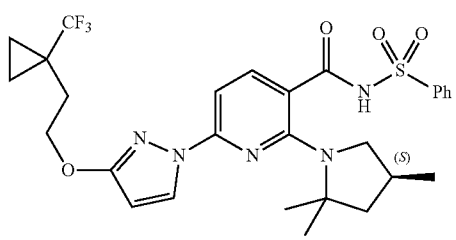

and pharmaceutically acceptable salts thereof.

Also disclosed herein are a compound having the following formula:

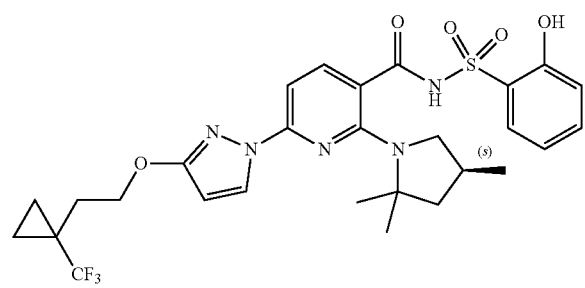

and pharmaceutically acceptable salts thereof.

Also disclosed herein are a compound having the following formula:

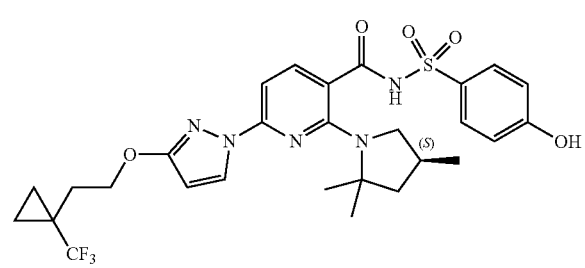

and pharmaceutically acceptable salts thereof.

Also disclosed herein are a compound having the following formula:

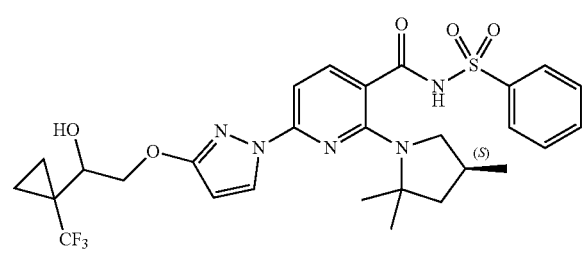

and pharmaceutically acceptable salts thereof.

Also disclosed herein are a compound having the following formula:

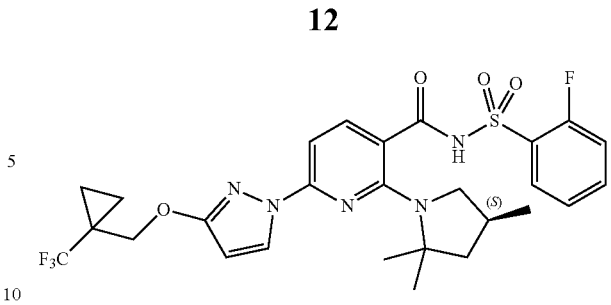

and pharmaceutically acceptable salts thereof.

Also disclosed herein are a compound having the following formula:

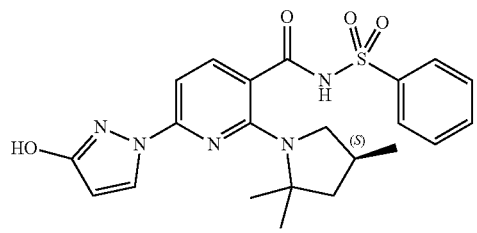

and pharmaceutically acceptable salts thereof.

Also disclosed herein are a compound having the following formula:

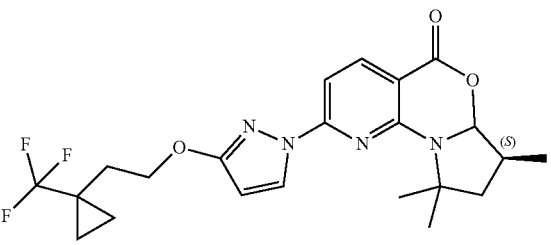

and pharmaceutically acceptable salts thereof.

In some embodiments, at least one novel compound (and/or at least one pharmaceutically acceptable salt thereof and/or at least one deuterated derivative of such compound or salt) can be administered in combination with at least one additional active pharmaceutical ingredient. In some embodiments, at least one additional active pharmaceutical ingredient is chosen from:

(a) Compound II

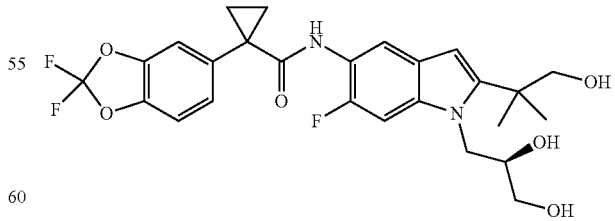

and pharmaceutically acceptable salts thereof.

A chemical name for Compound II is (R)-1-(2,2-difluorobenzo[d][1,3]dioxol-5-yl)-N-(1-(2,3-dihydroxypropyl)-6-fluoro-2-(1-hydroxy-2-m ethylpropan-2-yl)-1H-indol-5-yl)cyclopropanecarboxamide;

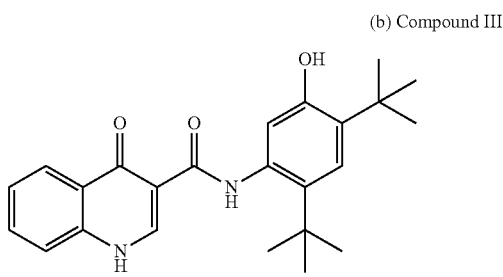 [SMILES: CC(C)(C)c1cc(C(C)(C)C)c(NC(=O)c2c[nH]c3ccccc3c2=O)cc1O]
(b) Compound III and pharmaceutically acceptable salts thereof
A chemical name for Compound III is N-(5-hydroxy-2,4-di-tert-butyl-phenyl-4-oxo-1H-quinoline-3-carboxamide; and

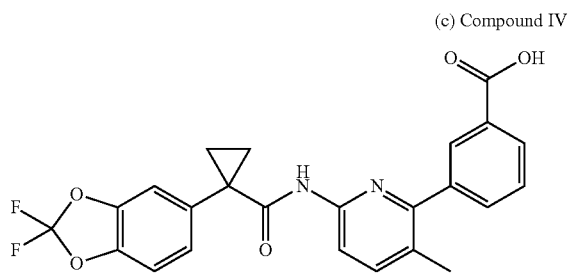 [SMILES: Cc1ccc(NC(=O)C2(c3ccc4c(c3)OC(F)(F)O4)CC2)nc1-c1cccc(C(=O)O)c1]
(c) Compound IV and pharmaceutically acceptable salts thereof.
A chemical name for Compound IV is 3-(6-(1-(2,2-difluorobenzo[d][1,3]dioxol-5-yl)cyclopropanecarboxamido)-3-methyl pyridin-2-yl)benzoic acid.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

In some embodiments, at least one compound chosen from the novel compounds disclosed herein, pharmaceutically acceptable salts thereof, and deuterated derivatives of the foregoing is administered in combination with at least one compound chosen from Compound II, pharmaceutically acceptable salts thereof, and deuterated derivatives of the foregoing. In some embodiments, at least one compound chosen from the novel compounds disclosed herein, pharmaceutically acceptable salts thereof, and deuterated derivatives of the foregoing is administered in combination with at least one compound chosen from Compound III and pharmaceutically acceptable salts thereof. In some embodiments, at least one compound chosen from the novel compounds disclosed herein, pharmaceutically acceptable salts thereof, and deuterated derivatives of the foregoing is administered in combination with at least one compound chosen from Compound IV and pharmaceutically acceptable salts thereof. In some embodiments, at least one compound chosen from the novel compounds disclosed herein, pharmaceutically acceptable salts, and deuterated derivatives of the foregoing thereof is administered in combination with Compounds II or a pharmaceutically acceptable salt or deuterated derivative thereof and at least one compound chosen from Compound III, pharmaceutically acceptable salts thereof, and deuterated derivatives of any of the foregoing. In some embodiments, at least one compound chosen from the novel compounds disclosed herein, pharmaceutically acceptable salts, and deuterated derivatives of any of the foregoing thereof is administered in combination with at least one compound chosen from Compound III, pharmaceutically acceptable salts thereof, and deuterated derivatives of any of the foregoing and at least one compound chosen from Compound IV, pharmaceutically acceptable salts thereof, and deuterated derivatives of any of the foregoing.

Any of the novel compounds disclosed herein, such as for example, compounds of Formula (I), (II), (III), (IV), (V) and their pharmaceutically acceptable salts thereof, and deuterated derivatives of such compounds and salts can be comprised in a single pharmaceutical composition or separate pharmaceutical compositions in combination with other additional active pharmaceutical ingredient(s) (e.g., Compound II, III, or IV, or its pharmaceutically acceptable salt thereof, or a deuterated derivative of such Compound or salt). Such pharmaceutical compositions can be administered once daily or multiple times daily, such as twice daily. In some embodiments, the disclosure features a pharmaceutical composition comprising at least one compound chosen from any of the compounds disclosed herein and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound II and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound II and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound III and pharmaceutically acceptable salts thereof, at least one compound chosen from Compound IV and pharmaceutically acceptable salts thereof, and at least one pharmaceutically acceptable carrier.

In some embodiments, pharmaceutical compositions disclosed herein comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises (i) a compound of Formulae (I), (II), (III), (IV), or (V), or a pharmaceutically acceptable salt thereof or a deuterated derivative of such compound or salt; and (ii) at least two additional active pharmaceutical ingredients, one of which is a CFTR corrector and one of which is a CFTR potentiator.

In some embodiments, at least one additional active pharmaceutical ingredient is selected from mucolytic agents, bronchodialators, antibiotics, anti-infective agents, and anti-inflammatory agents.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure, including a pharmaceutical composition comprising combinations described previously, can be employed in combination therapies; that is, the compositions can be administered concurrently with, prior to, or subsequent to, at least one additional active pharmaceutical ingredient or medical procedures.

Pharmaceutical compositions comprising these combinations are useful for treating cystic fibrosis.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

It will also be appreciated that a pharmaceutical composition of this disclosure, including a pharmaceutical composition comprising any of the combinations described previously, can be employed in combination therapies; that is, the compositions can be administered concurrently with, prior to, or subsequent to, at least one active pharmaceutical ingredients or medical procedures.

In some embodiments, the methods of the disclosure employ administering to a patient in need thereof at least one compound chosen from any of the compounds disclosed herein and pharmaceutically acceptable salts thereof, and at least one compound chosen from Compound II, Compound III, Compound IV, and pharmaceutically acceptable salts of any of the foregoing.

Any suitable pharmaceutical compositions known in the art can be used for the novel compounds disclosed herein, Compound II, Compound III, Compound IV, and pharmaceutically acceptable salts thereof. Some exemplary pharmaceutical compositions for Compound I and its pharmaceutically acceptable salts are described in the Examples. Some exemplary pharmaceutical compositions for Compound II and its pharmaceutically acceptable salts can be found in WO 2011/119984 and WO 2014/015841, all of which are incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, all of which are incorporated herein by reference. Some exemplary pharmaceutical compositions for Compound IV and its pharmaceutically acceptable salts can be found in WO 2010/037066, WO 2011/127241, WO 2013/112804, and WO 2014/071122, all of which are incorporated herein by reference.

In some embodiments, a pharmaceutical composition comprising at least one compound chosen from the novel compounds disclosed herein and pharmaceutically acceptable salts thereof is administered with a pharmaceutical composition comprising Compound II and Compound III. Pharmaceutical compositions comprising Compound II and Compound III are disclosed in PCT Publication No. WO 2015/160787, incorporated herein by reference. An exemplary embodiment is shown in the following Table:

TABLE 2

Exemplary Tablet Comprising 100 mg of Compound II and 150 mg of Compound III.

| | Ingredient | Amount per tablet (mg) |
|---|---|---|
| Intra-granular | Compound II SDD (spray dried dispersion) (80 wt % Compound II, 20 wt % HPMC) | 125 |
| | Compound III SDD (80 wt % Compound III, 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

In some embodiments, a pharmaceutical composition comprising at least one compound chosen from the novel compounds disclosed herein and pharmaceutical salts thereof is administered with a pharmaceutical composition comprising Compound III Pharmaceutical compositions comprising Compound III are disclosed in PCT Publication No. WO 2010/019239, incorporated herein by reference. An exemplary embodiment is shown in the following Table:

TABLE 3

Ingredients for Exemplary Tablet of Compound III.

| Tablet Formulation | Percent Dose % Wt./Wt. | Dose (mg) | Batch (g) |
|---|---|---|---|
| Compound III SDD (80 wt % Compound III, 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing about 6.9 mg) was formulated to have approximately 50 mg of Compound III per 26 mini-tablets and approximately 75 mg of Compound III per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III, 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

In some embodiments, the pharmaceutical compositions are a tablet. In some embodiments, the tablets are suitable for oral administration.

These combinations are useful for treating cystic fibrosis.

In some embodiments, disclosed herein is a method of treating, lessening the severity of, or symptomatically treating cystic fibrosis in a patient comprising administering an effective amount of at least one pharmaceutical composition of this disclosure to the patient, such as a human, wherein said patient has cystic fibrosis and is chosen from patients with F508del/minimal function (MF) genotypes, patients with F508del/F508del genotypes, patients with F508del/gating genotypes, and patients with F508del/residual function (RF) genotypes.

In some embodiments, the patient is heterozygous for F508del, and the other CFTR genetic mutation is any CF-causing mutation, and is expected to be and/or is responsive to any combinations of (i) the novel compounds disclosed herein, such as Compound I, and (ii) Compound II, and/or Compound III and/or Compound IV genotypes based on in vitro and/or clinical data.

Patients with an F508del/minimal function genotype are defined as patients that are heterozygous F058delG-CTFR with a second CFTR allele containing a mutation that is predicted to result in a CFTR protein with minimal function and that is not expected to respond to Compound II, Compound III, or the combination of Compound II and Compound III. These CFTR mutations were defined using 3 major sources:

biological plausibility for the mutation to respond (i.e., mutation class)
evidence of clinical severity on a population basis (per CFTR2 patient registry; accessed on 15 Feb. 2016)
average sweat chloride >86 mmol/L, and
prevalence of pancreatic insufficiency (PI)>50%
in vitro testing
mutations resulting in baseline chloride transport <10% of wild-type CFTR were considered minimal function
mutations resulting in chloride transport <10% of wild-type CFTR following the addition of Compound II and/or Compound III were considered nonresponsive.

In some embodiments, disclosed herein is a method of treating, lessening the severity of, or symptomatically treating cystic fibrosis in a patient comprising administering an effective amount of a pharmaceutical composition of this disclosure to the patient, such as a human, wherein the patient possesses a CFTR genetic mutation G551D. In some embodiments, the patient is homozygous for the G551D genetic mutation. In some embodiments, the patient is heterozygous for the G551D genetic mutation. In some embodiments, the patient is heterozygous for the G551D genetic mutation, having the G551D mutation on one allele and any other CF-causing mutation on the other allele. In some embodiments, the patient is heterozygous for the G551D genetic mutation on one allele and the other CF-causing genetic mutation on the other allele is any one of F508del, G542X, N1303K, W1282X, R117H, R553X, 1717-1G->A, 621+1G->T, 2789+5G->A, 3849+10kbC->T, R1162X, G85E, 3120+1G->A, ΔI507, 1898+1G->A, 3659delC, R347P, R560T, R334W, A455E, 2184delA, or 711+1G->T. In some embodiments, the patient is heterozygous for the G551D genetic mutation, and the other CFTR genetic mutation is F508del. In some embodiments, the patient is heterozygous for the G551D genetic mutation, and the other CFTR genetic mutation is R117H.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation F508del. In some embodiments, the patient is homozygous for the F508del genetic mutation. In some embodiments, the patient is heterozygous for the F508del genetic mutation wherein the patient has the F508del genetic mutation on one allele and any CF-causing genetic mutation on the other allele. In some embodiments, the patient is heterozygous for F508del, and the other CFTR genetic mutation is any CF-causing mutation, including, but not limited to G551D, G542X, N1303K, W1282X, R1117H, R553X, 1717-1G->A, 621+1G->T, 2789+5G->A, 3849+10kbC->T, R1162X, G85E, 3120+1G->A, ΔI507, 1898+1G->A, 3659delC, R347P, R560T, R334W, A455E, 2184delA, or 711+1G->T. In some embodiments, the patient is heterozygous for F508del, and the other CFTR genetic mutation is G551D. In some embodiments, the patient is heterozygous for F508del, and the other CFTR genetic mutation is R117H.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, (G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, 621+3A->G, 1949del84, 3141del9, 3195del6, 3199del6, 3905InsT, 4209TGTT->A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G->A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L15P, L165S, L320V, L346P, L453S, L571S, L967S, M101R, M152V, MIT. M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S118F, S1159F, S1159P, S13F, S549R(A->C), S549R(T->G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C. In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, and 621+3A->G.

In some embodiments, the patient has at least one combination mutation chosen from: 1949del84, 3141del9, 3195del6, 3199del6, 3905InsT, 4209TGTT->A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F31 del, F311L, F508C, F575Y, G1061R, G1249R, G126D, G149R, G194R, G194V, G27R, G314E, G458V, G463V, G480C, G622D, G628R, G628R(G->A), G91R, G970D, H1054D, H1085P, H1085R, H1375P, H139R, H199R, H609R, H939R, I1005R, I11234V, I11269N, I11366N, I175V, I502T, I506S, I506T, I601F, 1618F, 1807M, I980K, L02R, L1324P, L1335P, L138ins, L1480P, L15P, L165S, L320V, L346P, L453S, L571S, L967S, M101R, M152V, MIT, M1V, M265R, M952I, M952T, P574H, P5L, P750L, P99L, Q100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S11118F, S1159F, S1159P, S13F, S549R(A->C), S549R(T->G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from:
D443Y;G576A;R668C,
F508C;S1251N,
G576A; R668C,
G970R M470V,
R74W;D I270N,
R74W;V201M, and
R74W;V201M;D1270N.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V and G1069R. In some embodiments, this disclosure provides a method of treating CFTR comprising administering a compound of Formula (I), (II), (III), (IV), (V), or a pharmaceutically acceptable salt thereof to a patient possessing a human CFTR mutation selected from G178R, G551S, G970R, G1244E, S1255P, G1349D, S549N, S549R and S1251N. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R. In some embodiments, the method produces an increase in chloride transport relative to baseline chloride transport of the patient of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H. In some embodiments, the method produces an increase in chloride transport above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V and G1069R, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R and S1251N, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R, and a human CFTR mutation selected from F508del, R117H, and G551D. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D. In some embodiments, the method produces an increase in chloride transport which is above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G, and a human CFTR mutation selected from F508del, R117H.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V, G1069R, R117C, D110H, R347H, R352Q, E56K. P67L, L206W, A455E, D579G, S1235R, S945L, R1070W. F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G55 ID.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V and G1069R. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R and S1251N. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H. In some embodiments, the method produces an increase in chloride transport which is above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 71+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D, and one or more human CFTR mutations selected from F508del, R117H, and G551D.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R, S1251N, E193K, F1052V and G1069R, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551 S, G970R, G1244E, S1255P, G1349D, S549N, S549R and S1251N, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R, and one or more human CFTR mutations selected from F508del, R117H, and G551D. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, R117C, D110H, R347H, R352Q, E56K, P67L, L206W, A455E, D579G, S1235R, S945L, R1070W, F1074L, D110E, D1270N and D1152H, and one or more human CFTR mutations selected from F508del, R117H, and G551D. In some embodiments, the method produces an increase in chloride transport which is above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 71 l+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and one or more human CFTR mutations selected from F508del, R117H, and G55 ID. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G, and one or more human CFTR mutations selected from F508del, R117H, and G551D.

In some embodiments, the patient is heterozygous having one CF-causing mutation on one allele and another CF-causing mutation on the other allele. In some embodiments, the patient is heterozygous for F508del, and the other CFTR genetic mutation is any CF-causing mutation, including, but not limited to F508del on one CFTR allele and a CFTR mutation on the second CFTR allele that is associated with minimal CFTR function, residual CFTR function, or a defect in CFTR channel gating activity.

In some embodiments, the CF-causing mutation is selected from Table 5A. In some embodiments, the patient is heterozygous having one CF-causing mutation on one CFTR allele selected from the mutations listed in the table from FIG. 4 and another CF-causing mutation on the other CFTR allele is selected from the CFTR mutations listed in Table 5A.

TABLE 5A

CFTR Mutations

Q39X
W57X
E60X
R75X
E92X
Q98X
Y122X
L218X
Q220X
C276X
Q290X
G330X
W401X
Q414X
S434X
S466X
S489X
Q493X
W496X
Q525X
G542X
Q552X
R553X
E585X
G673X
R709X
K710X
L732X
R764X
R785X
R792X
E822X
W846X
R851X
Q890X
S912X
W1089X
Y1092X
E1104X
R1158X
R1162X
S1196X
W1204X
S1255X
W1282X
Q1313X
621 + 1G→T
711 + 1G→T
711 + 5G→A
712 − 1G→T
405 + 1G→A
405 + 3A→C
406 − 1G→A
621 + 1G→T
1248 + 1G→A
1341 + 1G→A
1717 − 1G→A
1811 + 1.6 kbA→G
1811 + 1G→C
1812 − 1G→A
1898 + 1G→A
2622 + 1G→A
3120 + 1G→A
3120G→A
3850 − 1G→A
4005 + 1G→A
4374 + 1G→T
663delT
2183AA→G
CFTRdel2, 3
3659delC
394delTT
2184insA
3905insT
2184delA
1078delT
1154insTC
2183delAA→G

TABLE 5A-continued

CFTR Mutations

2143delT
1677delTA
3876delA
2307insA
4382delA
4016insT
2347delG
3007delG
574delA
2711delT
3791delC
CFTRdele22-23
457TAT→G
2043delG
2869insG
3600 + 2insT
3737delA
4040delA
541delC
A46D
T338I
R347P
L927P
G85E
S341P
L467P
I507del
V520F
A559T
R560T
R560S
A561E
Y569D
L1065P
R1066C
R1066M
L1077P
H1085R
M1101K
N1303K
2789 + 5G→A
3849 + 10 kbC→T
3272 − 26A→G
711 + 3A→G
E56K
P67L
R74W
D110E
D110H
R117C
L206W
R347H
R352Q
A455E
D579G
E831X
S945L
S977F
F1052V
R1070W
F1074L
D1152H
D1270N
R117H
G178R
S549N
S549R
G551D
G551S
G1244E
S1251N
S1255P
G1349D

TABLE 5B

CFTR Mutations

| Criteria | Mutation | | | | |
|---|---|---|---|---|---|
| Truncation mutations | S4X | C276X | G542X | R792X | E1104X |
| % PI > 50% and/or | G27X | Q290X | G550X | E822X | R1158X |
| SwCl⁻ > 86 mmol/L | Q39X | G330X | Q552X | W846X | R1162X |
| no full-length protein | W57X | W401X | R553X | Y849X | S1196X |
| | E60X | Q414X | E585X | R851X | W1204X |
| | R75X | S434X | G673X | Q890X | L1254X |
| | E92X | S466X | Q685X | S912X | S1255X |
| | Q98X | S489X | R709X | Y913X | W1282X |
| | Y122X | Q493X | K710X | W1089X | Q1313X |
| | E193X | W496X | L732X | Y1092X | E1371X |
| | L218X | C524X | R764X | W1098X | Q1382X |
| | Q220X | Q525X | R785X | R1102X | Q1411X |
| Splice mutations | 185 + 1G→T | 711 + 5G→A | 1717 − 8G→A | 2622 + 1G→A | 3121 − 1G→A |
| % PI > 50% and/or | 296 + 1G→A | 712 − 1G→T | 1717 − 1G→A | 2790 − 1G→C | 3500 − 2A→G |
| SwCl⁻ > 86 mmol/L | 405 + 1G→A | 1248 + 1G→A | 1811 + 1G→C | 3040G→C | 3600 + 2insT |
| no or little mature | 405 + 3A→C | 1249 − 1G→A | 1811 + 1.6 kbA→G | (G970R) | 3850 − 1G→A |
| mRNA | 406 − 1G→A | 1341 + 1G→A | 1812 − 1G→A | 3120G→A | 4005 + 1G→A |
| | 621 + 1G→T | 1525 − 2A→G | 1898 + 1G→A | 3120 + 1G→A | 4374 + 1G→T |
| | 711 + 1G→T | 1525 − 1G→A | 1898 + 1G→C | 3121 − 2A→G | |
| Small (≤3 nucleotide) | 182delT | 1119delA | 1782delA | 2732insA | 3876delA |
| insertion/deletion (ins/del) | 306insA | 1138insG | 1824delA | 2869insG | 3878delG |
| frameshift mutations | 365-366insT | 1154insTC | 2043delG | 2896insAG | 3905insT |
| % PI > 50% and/or | 394delTT | 1161delC | 2143delT | 2942insT | 4016insT |
| SwCl⁻ > 86 mmol/L | 442delA | 1213delT | 2183AA→G [a] | 2957delT | 4021dupT |
| garbled and/or | 444delA | 1259insA | 2184delA | 3007delG | 4040delA |
| truncated protein | 457TAT→G | 1288insTA | 2184insA | 3028delA | 4279insA |
| | 541delC | 1471delA | 2307insA | 3171delC | 4326delTC |
| | 574delA | 1497delGG | 2347delG | 3659delC | |
| | 663delT | 1548delG | 2585delT | 3737delA | |
| | 935delA | 1609delCA | 2594delGT | 3791delC | |
| | 1078delT | 1677delTA | 2711delT | 3821delT | |
| Non-small (>3 nucleotide) | CFTRdele2, 3 | | 1461ins4 | | 2991del32 |
| insertion/deletion (ins/del) | CFTRdele22, 23 | | 1924del7 | | 3667ins4 |
| frameshift mutations | 124del23bp | | 2055del9→A | | 4010del4 |
| % PI > 50% and/or | 852del22 | | 2105-2117del13insAGAAA | | 4209TGTT→AA |
| SwCl⁻ > 86 mmol/L | | | | | |
| garbled and/or | 991del5 | | 2721del11 | | |
| truncated protein | | | | | |
| Class II, III, IV mutations | A46D[b] | V520F | Y569D[b] | N1303K | |
| not responsive to | G85E | A559T[b] | L1065P | | |
| Compound III alone or in | R347P | R560T | R1066C | | |
| combination with | L467P[b] | R560S | L1077P[b] | | |
| Compound II or Compound IV | I507del | A561E | M1101K | | |
| % PI > 50% and/or | | | | | |
| SwCl⁻ > 86 mmol/L | | | | | |
| AND | | | | | |
| Not responsive in vitro | | | | | |
| to Compound III alone | | | | | |
| or in combination with | | | | | |
| Compound II or Compound IV | | | | | |

Note:
% PI: percentage of F508del-CFTR heterozygous patients in the CFTR2 patient registry who are pancreatic insufficient;
SwCl⁻: mean sweat chloride of F508del-CFTR heterozygous patients in the CFTR2 patient registry
[a] Also known as 2183delAA→G.
[b] Unpublished data.

Table 5B above includes certain exemplary CFTR minimal function mutations, which are detectable by an FDA-cleared genotyping assay, but does not include an exhaustive list.

In some embodiments, disclosed herein is a method of treating, lessening the severity of, or symptomatically treating cystic fibrosis in a patient with F508del/MF (F/MF) genotypes (heterozygous for F508del and an MF mutation not expected to respond to CFTR modulators, such as Compound III); with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, a patient with F508del/MF (F/MF) genotypes has a MF mutation that is not expected to respond to Compound II, Compound III, and both of Compound II and Compound III. In some embodiments, a patient with F508del/MF (F/MF) genotypes has any one of the MF mutations in Table 5B.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table 5B.

In some embodiments, the patient is heterozygous for F508del, and the other CFTR genetic mutation is a splice mutation. In some specific embodiments, the splice mutation is a splice mutation listed in Table 5B.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤3 nucleotide) insertion or deletion (ins/del) frameshift mutation listed in Table 5B.

In some embodiments, the patient is heterozygous for F508del, and the other CFTR genetic mutation is any CF-causing mutation expected to be and/or is responsive to, based on in vitro and/or clinical data, any combination of (i) a novel compound chosen from those disclosed herein (e.g., compounds of Formula (I), (II), (III), (IV), or (V), and pharmaceutically acceptable salts thereof, and their deuterated derivatives), and (ii) Compound II, and/or Compound III, and/or Compound IV.

In some embodiments, the patient is heterozygous for F508del, and the other CFTR genetic mutation is any CF-causing mutation expected to be and/or is responsive, based on in vitro and/or clinical data, to the triple combination of a novel compound chosen from those disclosed herein (e.g., compounds of Formula (I), (II), (III), (IV), or (V), and pharmaceutically acceptable salts thereof, and their deuterated derivatives), and Compound II, and Compound III.

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table 5B.

In some embodiments, the patient is heterozygous for F508del, and the other CFTR genetic mutation is a Class II, III, IV mutations not responsive to Compound III alone or in combination with Compound II or Compound IV. In some specific embodiments, the Class II, III, IV mutations not responsive to Compound III alone or in combination with Compound II or Compound IV is a Class II, III, IV mutations not responsive to Compound III alone or in combination with Compound II or Compound IV listed in Table 5B.

In some embodiments, the patient is heterozygous for F508del, and the other CFTR genetic mutation is any mutation listed in Table 5B.

In some embodiments, the patient is heterozygous for F508del, and the other CFTR genetic mutation is any mutation listed in Table 5A, 5B, and FIG. 4.

In some embodiments, the patient is heterozygous for F508del, and the other CFTR genetic mutation is any mutation listed in Table 5A. In some embodiments, the patient is heterozygous for F508del, and the other CFTR genetic mutation is any mutation listed in Table 5B. In some embodiments, the patient is heterozygous for F508del, and the other CFTR genetic mutation is any mutation listed in FIG. 4.

In some embodiments, the patient is homozygous for F508del.

In some embodiments, the patient is heterozygous having one CF-causing mutation on one CFTR allele selected from the mutations listed in the table from FIG. 4 and another CF-causing mutation on the other CFTR allele is selected from the CFTR mutations listed in Table 5B.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

Patients with an F508del/residual function genotype are defined as patients that are heterozygous F508del-CFTR with a second CFTR allele that contains a mutation that results in reduced protein quantity or function at the cell surface which can produce partial CFTR activity. CFTR gene mutations known to result in a residual function phenotype include in some embodiments, a CFTR residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, and K1060T. In some embodiments, the CFTR residual function mutation is selected from R117H, S1235R, 11027T, R668C, G576A, M470V, L997F, R75Q, R1070Q, R31C, D614G, G1069R, R1162L, E56K, A1067T, E193K, or K1060T. In some embodiments, the CFTR residual function mutation is selected from R117H, S1235R, 11027T, R668C, G576A, M470V, L997F, R75Q, R1070Q. R3 IC, D614G, G1069R, R1162L, E56K, or A1067T.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from the mutations listed in FIG. 4.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively.

The isotope-labelled compounds and salts can be used in a number of beneficial ways. They can be suitable for medicaments and/or various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "$^2$H" or "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. For a further discussion, see S. L. Harbeson and R. D. Tung, *Deuterium In Drug Discovery and Development*, Ann. Rep. Med. Chem. 2011, 46, 403-417; and T. G. Gant "Using deuterium in drug discovery: leaving the label in the drug" J. Med. Chem. 2014, 57, 3595-3611, relevant portions of which are independently incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity as compared to the corresponding hydrogen analogs. The superior DMPK property or properties may have an impact on the exposure, half-life, clearance, metabolism, and/or even food requirements for optimal absorption of the drug product. Deuteration may also change the metabolism at other non-deuterated positions of the deuterated compound.

In some embodiments, the disclosure includes deuterated derivatives of the novel compounds disclosed herein and of their pharmaceutically acceptable salts. Non-limiting examples of deuterated compounds are disclosed in FIG. 1.

In some embodiments, Compound III' as used herein includes the deuterated compound disclosed in U.S. Pat. No. 8,865,902 (which is incorporated herein by reference), and CTP-656.

In some embodiments, Compound III' is:

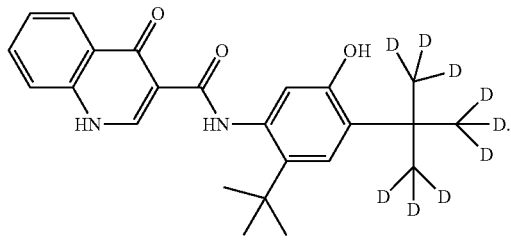

Exemplary embodiments of the disclosure include: The novel compounds disclosed herein (e.g., compounds of Formulae (I)-(V), pharmaceutically acceptable salts thereof, and deuterated derivatives of any of the foregoing, including the compounds in FIG. 1 and those specifically depicted herein) can be prepared by suitable methods known in the art. For example, they can be prepared in accordance with procedures described in WO2016/057572 and by the exemplary syntheses described below in the Examples. For example, deuterated derivatives of the novel compounds of Formulae (I)-(V) and pharmaceutically acceptable salts thereof can be prepared in a similar manner as those for compounds of Formulae (I)-(V) and pharmaceutically acceptable salts thereof by employing intermediates and/or reagents where one or more hydrogen atoms are replaced with deuterium. For example, see T. G. Gant "Using deuterium in drug discovery: leaving the label in the drug" J. Med. Chem. 2014, 57, 3595-3611, the relevant portions of which are incorporated herein by reference.

In some embodiments, compounds of Formulae (III), (IV) and (V) and pharmaceutically acceptable salts thereof, and deuterated derivatives of any of the foregoing are prepared as depicted in Schemes 1-2, wherein the variables therein are each and independently are as those for Formula (I), (II), (III), (IV), or (V) above, and wherein each $R^a$ is independently chosen from $C_1$-$C_4$ alkyl groups; and each $X^a$ is independently chosen from F or Cl. Suitable condition(s) known in the art can be employed for each step depicted in the schemes. In some embodiments, each $X^a$ for Formulae B, C, D, F, B-1, C-1, D-1, and F-1 in Schemes 2-4 is independently Cl. In some embodiments, each $X^a$ for Formulae D, L, O, and P in Scheme 6 is independently F.

In some embodiments, as shown in Scheme 1, the methods comprise reacting a compound of Formula (F) or a salt thereof with a compound of Formula (G) or a salt thereof to generate a compound of Formula (IIIa), a pharmaceutically acceptable salt thereof, or a deuterated derivative of any of the foregoing.

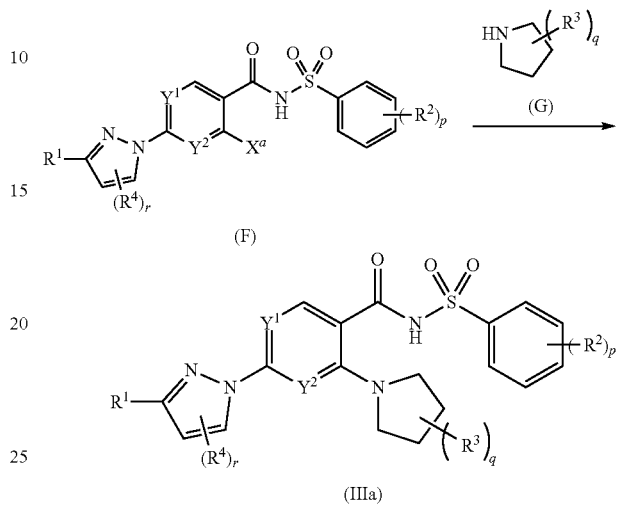

Any suitable conditions, such as those for a nucleophilic reaction of amine, known in the art can be used. In some embodiments, the reaction depicted in Scheme 1 is performed in the presence of a base, such as a metal carbonate (e.g., $Na_2CO_3$ or $K_2CO_3$).

In some embodiments, compounds of Formula (IIIa), pharmaceutically acceptable salts thereof, or deuterated derivatives of any of the foregoing, wherein $Y^2$ is N and $Y^1$ is CH in each of Formulae (F), (G) and (IIIa), are prepared by the methods in Scheme 1.

In some embodiments, a salt of a compound of Formula (G) is employed. In some embodiments, an HCl salt of a compound of Formula (G) is employed.

A compound of Formula (F) or a salt thereof and a compound of Formula (G) or a salt thereof can be prepared by any suitable method known in the art, for example, those in WO2016/57572 and those in the exemplary syntheses described below in the Examples.

In some embodiments, as shown in Scheme 2, a compound of Formula (F), a pharmaceutically acceptable salt thereof, or a deuterated derivative of any of the foregoing is prepared by a method that comprises reacting a compound of Formula (D) or a salt thereof with a compound of Formula (E) or a salt thereof. In some embodiments, compounds of Formula (D), salts thereof, or deuterated derivatives of any of the foregoing are prepared by a method that comprises reacting a compound of Formula (A) or a salt thereof with a compound of Formula (B) or a salt thereof to generate a compound of Formula (C) or a salt thereof; and hydrolyzing the —C(O)O$R^a$ of compound of Formula (C) to generate a compound of Formula (D) or a salt thereof. Any suitable conditions known in the art can be used for steps (a), (b), and (c) of Scheme 2 below, such as those for a coupling reaction between carboxylic acid and sulfonamide or those for an acylation of sulfonamide for step (a), those for hydrolysis of ester for step (b), and those for a nucleophilic reaction of amine for step (c).

In some embodiments, step (a) of Scheme 2 below is performed in the presence of a base. In some specific embodiments, step (a) is performed in the presence of a non-nucleophilic base. In some embodiments, in step (a), the reaction of a compound of Formula (D) or a salt thereof with a compound of Formula (E) or a salt thereof comprises reacting a compound of Formula (D) or a salt thereof with a coupling reagent, such as carbonyl diimidazole (CDI), and subsequently with a compound of Formula (E) or a salt thereof in the presence of a base, such as a non-nucleophilic base. In some embodiments, a compound of Formula (D) or a salt thereof is reacted with CDI prior to the reaction with a compound of Formula (E) or a salt thereof, and then subsequently with a compound of Formula (E) or a salt thereof in the presence of a base, such as DBU (1,8-Diazabicyclo(5.4.0)undec-7-ene).

In some embodiments, step (b) of Scheme 2 below is performed in the presence of a base. In some embodiments, step (b) is performed in the presence of an aqueous base, such as aqueous hydroxide. In some embodiments, step (b) is performed in the presence of an aqueous metal hydroxide, such as aqueous NaOH.

In some embodiments, step (c) of Scheme 2 below is performed in the presence of a base. In some embodiments, step (c) is performed in the presence of a metal carbonate (e.g., $Na_2CO_3$ or $K_2CO_3$).

In some embodiments, disclosed herein is a method of preparing a compound of the following formula:

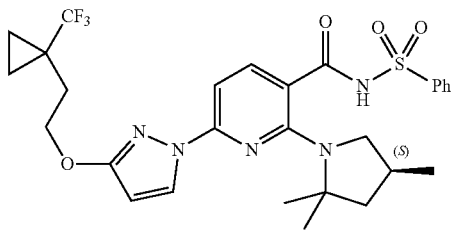

or a pharmaceutically acceptable salt thereof, or a deuterated derivative of any of the foregoing. The method comprises reacting a compound of Formula (F-1) or a salt thereof with a compound of Formula (G-1) or a salt thereof, wherein $X^a$ is F or Cl, as shown in Scheme 3:

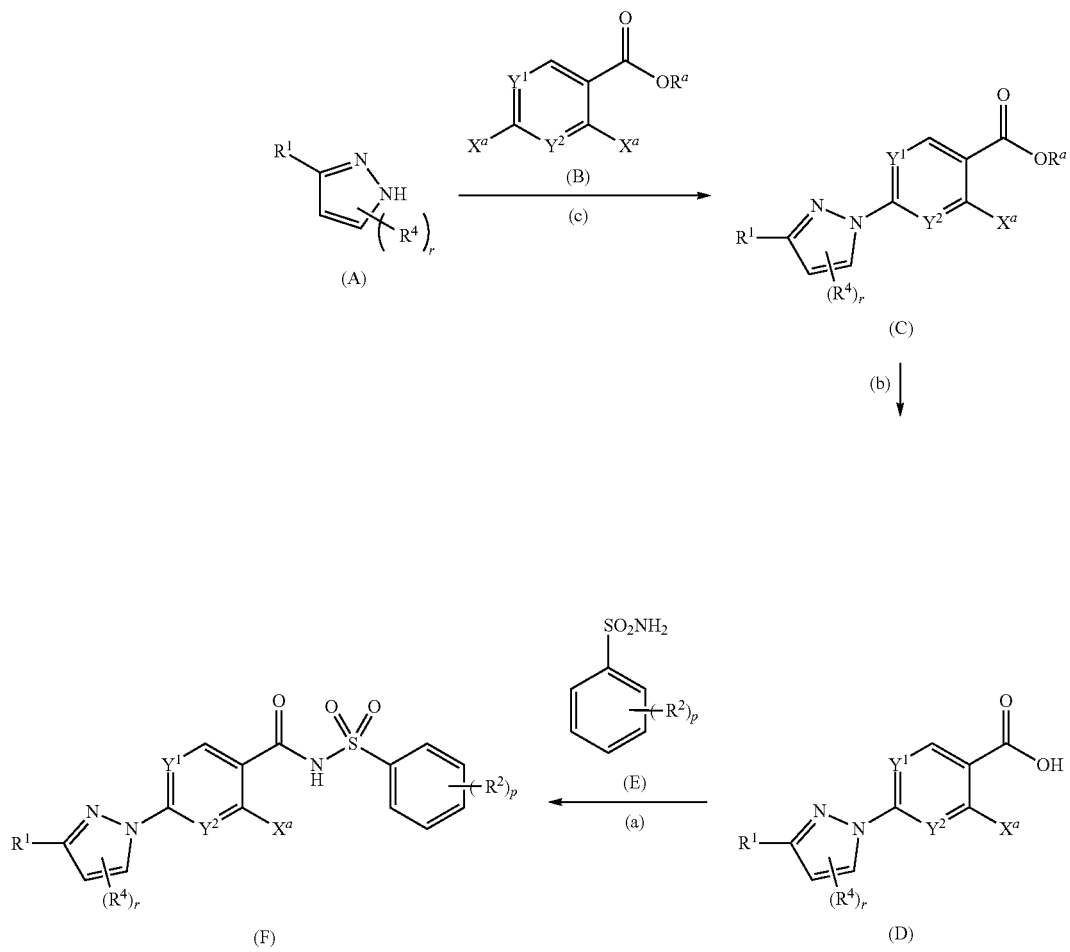

Scheme 3

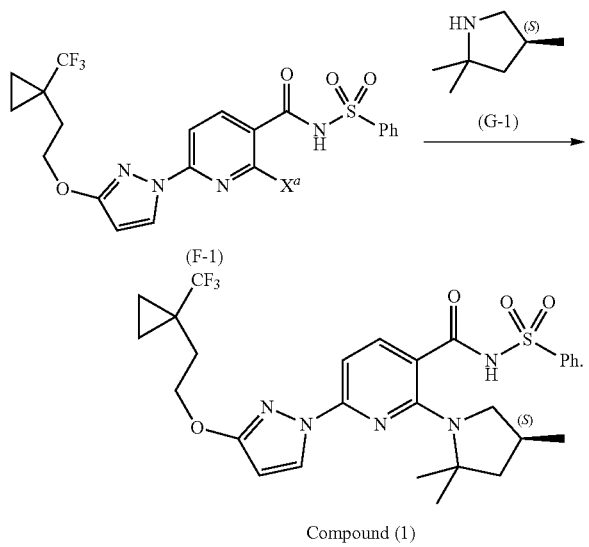

Any suitable conditions, such as those for a nucleophilic reaction of amine, known in the art can be used. In some embodiments, the reaction depicted in Scheme 3 is performed in the presence of a base, such as a metal carbonate (e.g., $Na_2CO_3$ or $K_2CO_3$).

In some embodiments, a salt of compound of Formula (G-1) is employed. In some embodiments, a HCl salt of a compound of Formula (G-1) is employed.

A compound of Formula (F-1) or a salt thereof and a compound of Formula (G-1) or a salt thereof can be prepared by any suitable method known in the art, for example, those in WO2016/57572 and those in the exemplary syntheses described below in the Examples.

In some embodiments, as shown in Scheme 4, a compound of Formula (F-1) or a salt thereof, or a deuterated derivative of any of the foregoing is prepared by a method that comprises reacting a compound of Formula (D-1) or a salt thereof with a compound of Formula (E-1) or a salt thereof. In some embodiments, compounds of Formula (D-1) or salts thereof, or their deuterated derivatives are prepared by a method that comprises reacting a compound of Formula (A-1) or a salt thereof with a compound of Formula (B-1) or a salt thereof to generate a compound of formula (C-1) or a salt thereof, and hydrolyzing the —C(O)OR$^a$ of compound of Formula (C-1) or salt thereof to generate a compound of formula (D-1) or a salt thereof. Any suitable conditions known in the art can be used for steps (a-1), (b-1), and (c-1) of Scheme 4 below, such as those for a coupling reaction between carboxylic acid and sulfonamide or those for an acylation of sulfonamide for step (a-1), those for hydrolysis of ester for step (b-1), and those for a nucleophilic reaction of amine for step (c-1).

In some embodiments, step (a-1) of Scheme 4 below is performed in the presence of a base. In some embodiments, step (a-1) of Scheme 4 below is performed in the presence of a non-nucleophilic base. In some embodiments, in step (a-1), the reaction of a compound of Formula (D-1) or a salt thereof with a compound of Formula (E-1) or a salt thereof comprises reacting a compound of Formula (D-1) or a salt thereof with a coupling reagent, such as carbonyl diimidazole (CDI), and subsequently with a compound of Formula (E-1) or a salt thereof in the presence of a base, such as a non-nucleophilic base. In some embodiments, (i) a compound of Formula (D-1) or a salt thereof is reacted with CDI prior to the reaction with a compound of Formula (E-1) or a salt thereof, and then subsequently (ii) the reaction product of step (i) is reacted with a compound of Formula (E-1) or a salt thereof in the presence of a base, such as DBU (1,8-Diazabicyclo(5.4.0)undec-7-ene).

In some embodiments, step (b-1) of Scheme 4 below is performed in the presence of a base. In some embodiments, step (b-1) is performed in the presence of an aqueous base, such as aqueous hydroxide. In some embodiments, step (b-1) is performed in the presence of an aqueous metal hydroxide, such as aqueous NaOH.

In some embodiments, step (c-1) of Scheme 4 below is performed in the presence of a base. In some embodiments, step (c-1) is performed in the presence of a metal carbonate (e.g., $Na_2CO_3$ or $K_2CO_3$).

Scheme 4

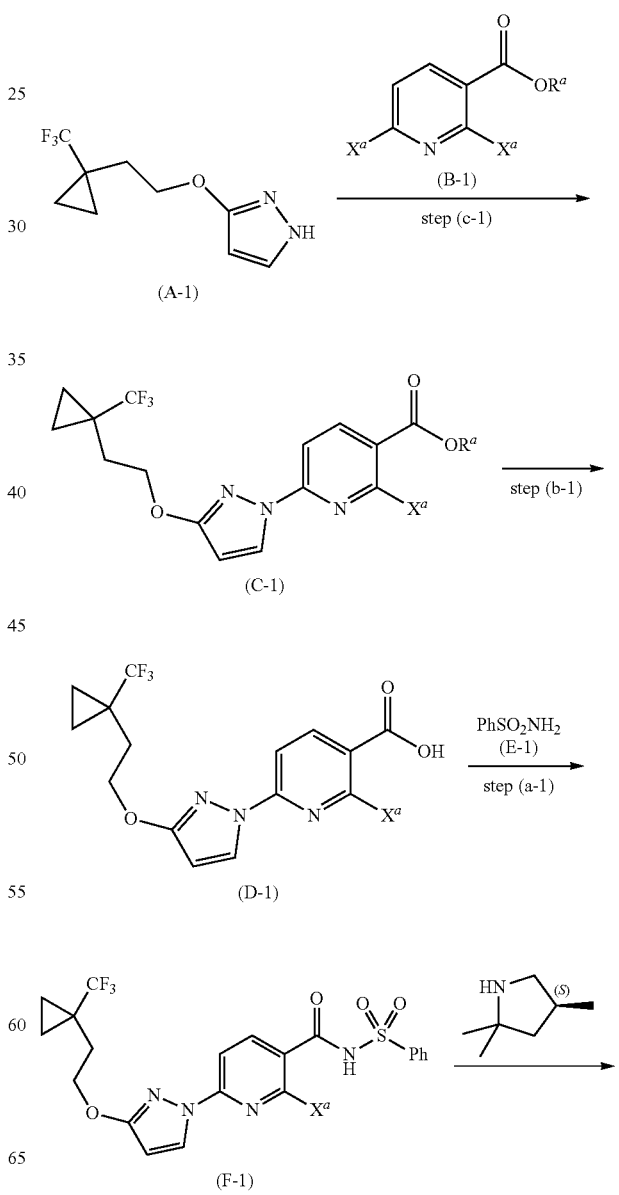

-continued

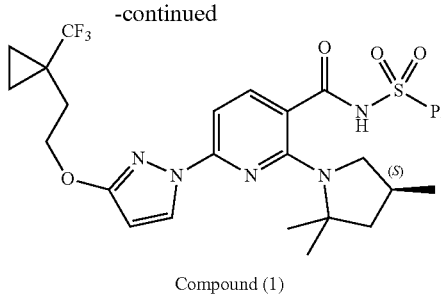

Compound (1)

Scheme 6

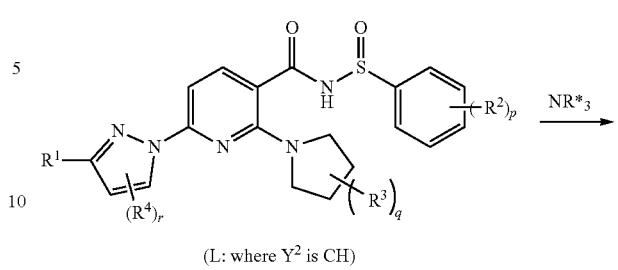

(L: where Y² is CH)

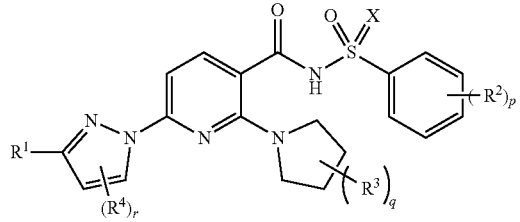

(II: where X is NR*)

In Scheme 4, R$^a$ is chosen from $C_1$-$C_4$ alkyl groups; and each X$^a$ is independently chosen from F or Cl.

In some embodiments, methods of preparing a compound of Formulae (I) and (II), wherein X is NH or N($C_1$-$C_4$ alkyl) or a pharmaceutically acceptable salt thereof, or a deuterated derivative of any of the foregoing, comprise reacting a compound of Formula (L) or a salt thereof with NR*$_3$ where R* is H or $C_1$-$C_4$ alkyl, as depicted in Schemes 5 and 6:

Scheme 5

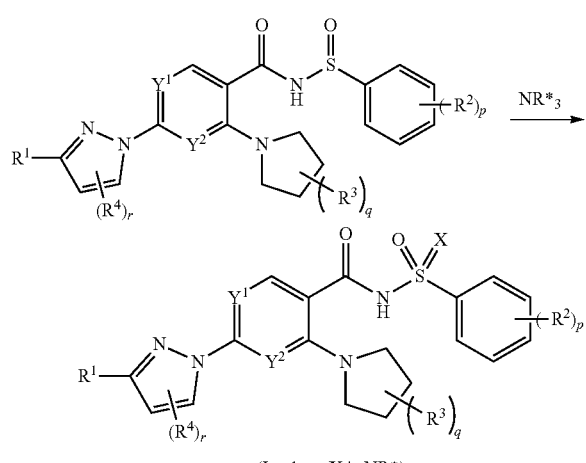

(I: where X is NR*)

Any suitable conditions known in the art can be used for the sulfoxamination reaction, for example, for those for electrophilic additions by amines. In some embodiments, the sulfoxamination reaction is performed in the presence of a chlorinating or oxidizing agent, such as N-chlorosuccinimide (NCS).

In some embodiments, a compound of Formula (L) or a salt thereof is prepared by a method comprising oxidizing the sulfur unit of the

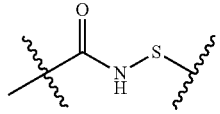 [SMILES: *SNC(*)=O]

group of a compound of Formula (M) or salt thereof as shown in Scheme 7 below:

Scheme 7

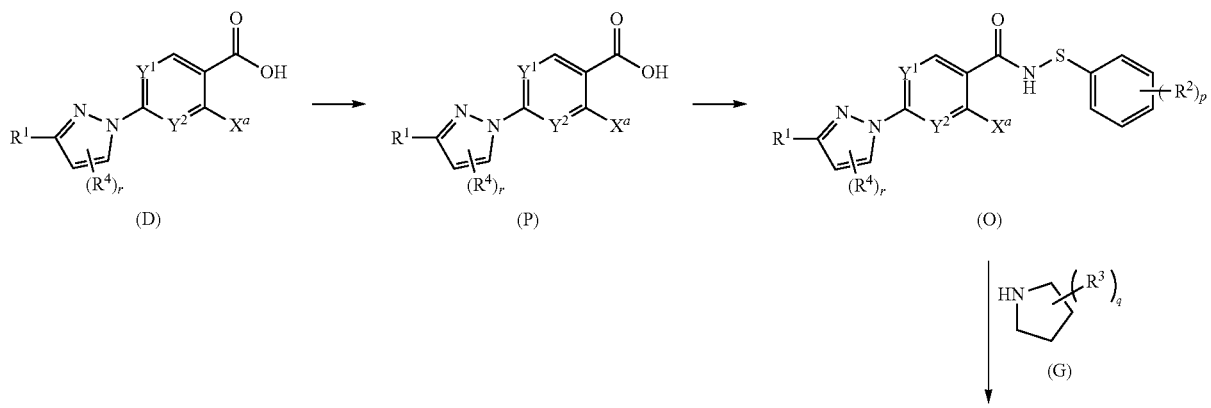

-continued

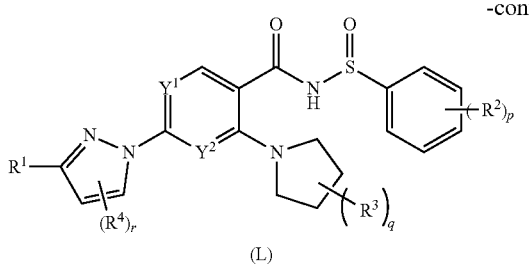

(L)

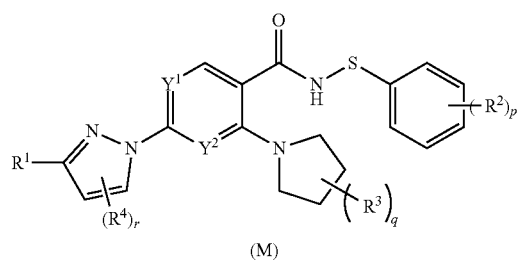

(M)

Any suitable conditions known in the art can be used for the oxidation reaction. In some embodiments, the oxidation is performed in the presence of a peroxycarboxylic acid, such as meta-Chloroperoxybenzoic acid (m-CPBA).

In some embodiments, a compound of Formula (M) or a salt thereof is prepared by a method comprising reacting a compound of Formula (O) with a compound of Formula (G) or a salt thereof. Any suitable conditions known in the art can be used.

In some embodiments, a compound of Formula (O) or a salt thereof is prepared by a method comprising reacting a compound of Formula (P) or salt thereof with a phenyl disulfide of Formula (Q):

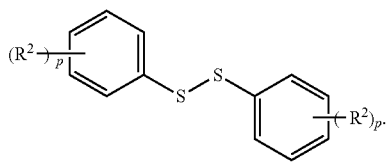

In some embodiments, a compound of Formula (P) or a salt thereof is prepared by amidating the —C(O)OH group of a compound of Formula (D) or salt thereof. Any suitable conditions known in the art can be used.

Additional embodiments include:
1. A compound of Formula I:

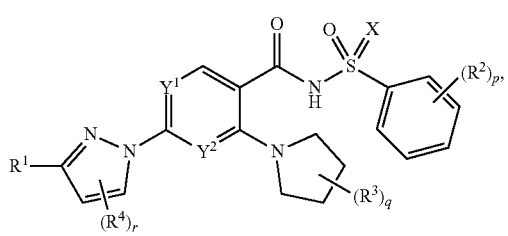

(I)

a pharmaceutically acceptable salt thereof, or a deuterated derivative of any of the foregoing, wherein:
one of $Y^1$ and $Y^2$ is N and the other is CH;
X is chosen from O, NH, and N($C_1$-$C_4$ alkyl) groups;
$R^1$ is chosen from —$(CR_2)_k$—O—$(CR_2)_m(CR)_n$(Ring A)$_{n+1}$ groups,
wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
wherein each R is independently chosen from H, OH, and $C_1$-$C_2$ alkyl groups optionally substituted with one or more halogens;
each $R^2$ is independently chosen from $C_1$-$C_2$ alkyl groups, OH, $C_1$-$C_2$ alkoxy groups, halogens, and cyano;
each $R^3$ is independently chosen from $C_1$-$C_2$ alkyl groups optionally substituted with one or more OH groups;
each $R^4$ is independently chosen from halogens;
k is 0 or 1;
r is 0 or 1;
m is 0, 1, 2, or 3;
n is 0 or 1,
p is 0, 1, 2, 3, 4, or 5; and
q is 0, 1, 2, 3, 4, 5, 6, 7, or 8.

2. A compound of Formula II:

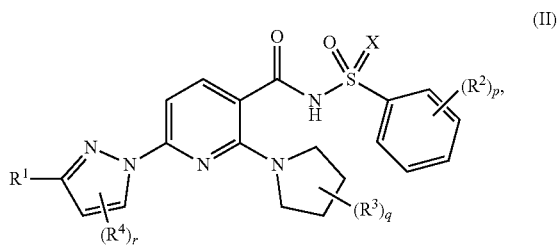

(II)

a pharmaceutically acceptable salt thereof, or a deuterated derivative of any of the foregoing,
wherein:
X is chosen from O, NH, and N($C_1$-$C_4$ alkyl) groups;
$R^1$ is chosen from —$(CR_2)_k$—O—$(CR_2)_m(CR)_n$(Ring A)$_{n+1}$ groups,
wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
wherein each R is independently chosen from H, OH, and $C_1$-$C_2$ alkyl groups optionally substituted with one or more halogens;
each $R^2$ is independently chosen from $C_1$-$C_2$ alkyl groups, OH, $C_1$-$C_2$ alkoxy groups, halogens, and cyano;
each $R^3$ is independently chosen from $C_1$-$C_2$ alkyl groups optionally substituted with one or more OH groups;
each $R^4$ is independently chosen from halogens;
k is 0 or 1;
r is 0 or 1;
m is 0, 1, 2, or 3;
n is 0 or 1;
p is 0, 1, 2, 3, 4, or 5; and
q is 0, 1, 2, 3, 4, 5, 6, 7, or 8.

3. A compound of Formula III:

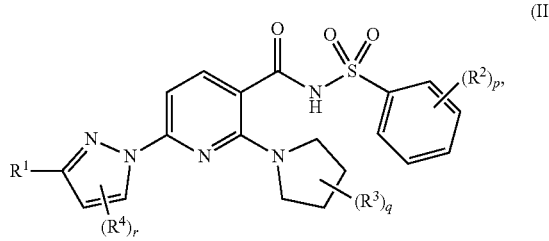

a pharmaceutically acceptable salt thereof, or a deuterated derivative of any of the foregoing, wherein:

$R^1$ is chosen from —$(CR_2)_k$—O—$(CR_2)_m(CR)_n$(Ring A)$_{n+1}$ groups,
wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
wherein each R is independently chosen from H, OH, and $C_1$-$C_2$ alkyl groups optionally substituted with one or more halogens;
each $R^2$ is independently chosen from $C_1$-$C_2$ alkyl groups, OH, $C_1$-$C_2$ alkoxy groups, halogens, and cyano;
each $R^3$ is independently chosen from $C_1$-$C_2$ alkyl groups optionally substituted with one or more OH groups;
each $R^4$ is independently chosen from halogens;
k is 0 or 1,
r is 0 or 1;
m is 0, 1, 2, or 3;
n is 0 or 1;
p is 0, 1, 2, 3, 4, or 5; and
q is 0, 1, 2, 3, 4, 5, 6, 7, or 8.

4. A compound according to any of embodiments 1-3, a pharmaceutically acceptable salt thereof, or a deuterated derivative of any of the foregoing, wherein if $R^2$ is cyano, then said $R^2$ is meta or para relative to the sulfur atom.

5. A compound according to any of embodiments 1-3, a pharmaceutically acceptable salt thereof, or a deuterated derivative of any of the foregoing, wherein:
each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
each R is independently chosen from H and OH;
each $R^2$ is independently chosen from $C_1$-$C_2$ alkyl groups, OH, $C_1$-$C_2$ alkoxy groups, and halogens;
$R^4$ is F;
k is 0;
p is 0, 1, or 2;
q is 0, 1, 2, 3, or 4;
r is 0; and
wherein m and n are not 0 at the same time.

6. A compound according to embodiment 5, a pharmaceutically acceptable salt thereof, or a deuterated derivative of any of the foregoing, wherein:
$R^1$ is chosen from —O—$(CR_2)_m$-Ring A groups,
wherein Ring A is chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
m is 1 or 2.

7. A compound according to embodiment 6, a pharmaceutically acceptable salt thereof, or a deuterated derivative of any of the foregoing, wherein each $R^3$ is a methyl group and q is 3 or 4.

8. A compound according to embodiment 7 having Formula IV:

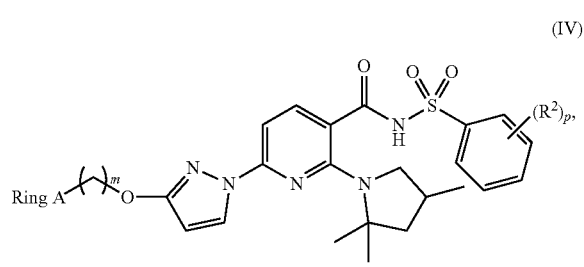

a pharmaceutically acceptable salt thereof, or a deuterated derivative of any of the foregoing, wherein:
Ring A is chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens; and
each $R^2$ is independently chosen from $C_1$-$C_2$ alkyl groups, OH, F, Cl, and $C_1$-$C_2$ alkoxy groups;
m is 1 or 2; and
p is 0, 1, or 2.

9. A compound according to embodiment 8, wherein p is 0 or 1.

10. A compound according to embodiment 8, wherein p is 0.

11. A compound according to embodiment 8 having Formula V:

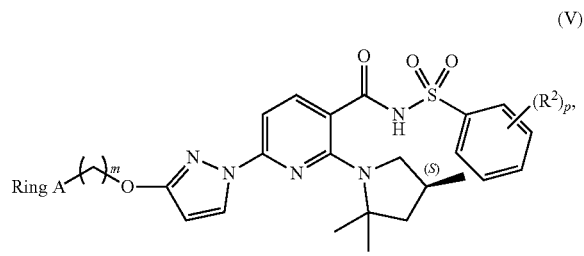

a pharmaceutically acceptable salt thereof, or a deuterated derivative of any of the foregoing, wherein:
Ring A is chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens; and
each $R^2$ is independently chosen from $C_1$-$C_2$ alkyl groups, OH, F, Cl, and $C_1$-$C_2$ alkoxy groups;
m is 1 or 2; and
p is 0, 1, or 2.

12. A compound according to any one of embodiments 1-11, a pharmaceutically acceptable salt thereof, or a deuterated derivative of any of the foregoing, wherein each $R^2$ is independently chosen from $CH_3$, OH, F, and $OCH_3$.

13. A compound according to embodiment 12, a pharmaceutically acceptable salt thereof, or a deuterated derivative of any of the foregoing, wherein p is 0 or 1.

14. A compound according to embodiment 13, a pharmaceutically acceptable salt thereof, or a deuterated derivative of any of the foregoing, wherein p is 0.

15. A compound according to embodiment 11, a pharmaceutically acceptable salt thereof, or a deuterated derivative of any of the foregoing, wherein Ring A is a cyclopropyl group substituted with a halogenated $C_1$ alkyl group or a halogenated $C_2$ alkyl group.

16. A compound according to embodiment 15, a pharmaceutically acceptable salt thereof, or a deuterated derivative of any of the foregoing, wherein Ring A is a cyclopropyl group substituted with a $CF_3$ group.

17. A compound according to embodiment 11, a pharmaceutically acceptable salt thereof, or a deuterated derivative of any of the foregoing, wherein m is 1, Ring A is a cyclopropyl group substituted with a $CF_3$ group, p is 0 or 1, and $R^2$, if present, is a methyl group, a hydroxy group, or a methoxy group.

18. A compound according to embodiment 11, a pharmaceutically acceptable salt thereof, or a deuterated derivative of any of the foregoing, wherein m is 2, Ring A is a $C_3$ cycloalkyl group substituted with a $CF_3$ group, p is 0 or 1, and $R^2$, if present, is a methyl group, a hydroxy group, or a methoxy group.

19. A compound according to embodiment 17 or 18, a pharmaceutically acceptable salt thereof, or a deuterated derivative of any of the foregoing, wherein m is 2, Ring A is a cyclopropyl group substituted with a $CF_3$ group, and p is 0.

20. A compound according to embodiment 11, a pharmaceutically acceptable salt thereof, or a deuterated derivative of any of the foregoing, wherein Ring A is chosen from $C_5$ bicycloalkyl groups optionally substituted with one or more substituents each independently chosen from $C_1$-$C_2$ alkyl groups, halogenated $C_1$-$C_2$ alkyl groups, and halogens.

21. A compound according to embodiment 20, a pharmaceutically acceptable salt thereof, or a deuterated derivative of any of the foregoing, wherein Ring A is a $C_5$ bicycloalkyl group optionally substituted with a halogen.

22. A compound according to embodiment 11, a pharmaceutically acceptable salt thereof, or a deuterated derivative of any of the foregoing, wherein Ring A is chosen from $C_7$ bicycloalkyl groups and $C_7$ tricycloalkyl groups optionally substituted with one or more substituents each independently chosen from $C_1$-$C_2$ alkyl groups, halogenated $C_1$-$C_2$ alkyl groups, and halogens.

23. A compound according to embodiment 22, a pharmaceutically acceptable salt thereof, or a deuterated derivative of any of the foregoing, wherein Ring A is an unsubstituted $C_7$ tricycloalkyl group.

24. A compound having a formula chosen from any one of the formulae depicted in FIG. 1, a pharmaceutically acceptable salt thereof, or a deuterated derivative of any of the foregoing.

25. A compound according to embodiment 1 having the following formula:

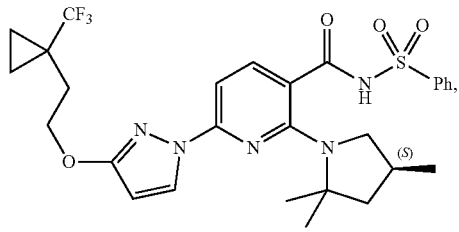

a pharmaceutically acceptable salt thereof, or a deuterated derivative of any of the foregoing.

26. A compound according to embodiment 1 having the following formula:

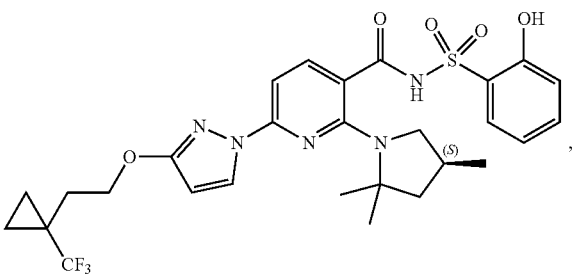

a pharmaceutically acceptable salt thereof, or a deuterated derivative of any of the foregoing.

27. A compound according to embodiment 1 having the following formula:

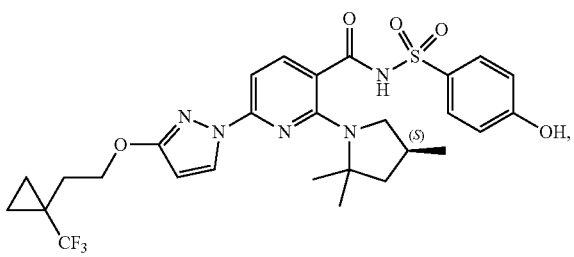

a pharmaceutically acceptable salt thereof, or a deuterated derivative of any of the foregoing.

28. A compound according to embodiment 1 having the following formula:

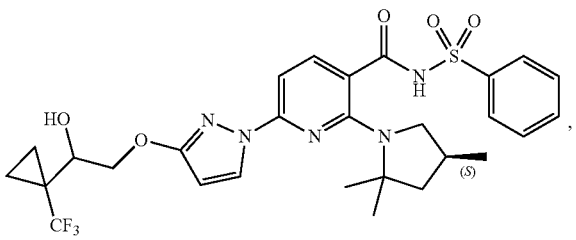

a pharmaceutically acceptable salt thereof, or a deuterated derivative of any of the foregoing.

29. A compound according to embodiment 1 having the following formula:

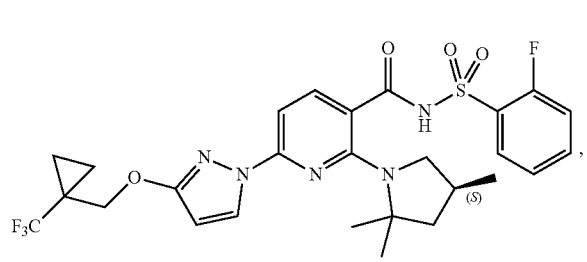

a pharmaceutically acceptable salt thereof, or a deuterated derivative of any of the foregoing.

30. A compound having the following formula:

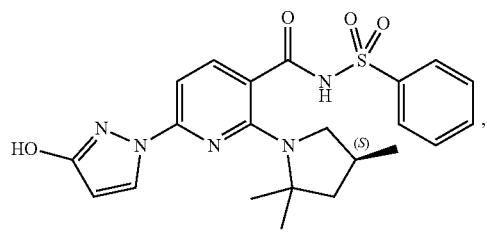

a pharmaceutically acceptable salt thereof, or a deuterated derivative of any of the foregoing.

31. A compound having any one of the following formulae:

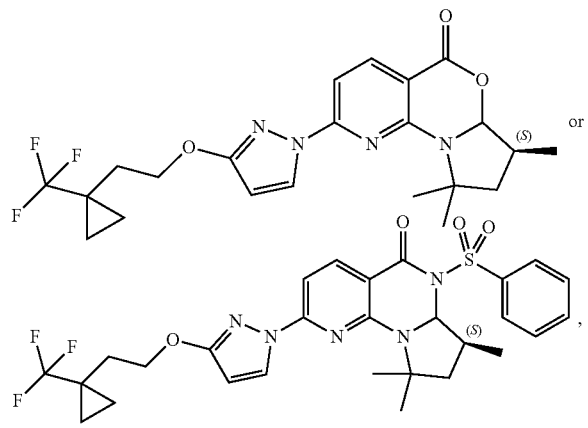

a pharmaceutically acceptable salt thereof, or a deuterated derivative of any of the foregoing.

32. A compound according to embodiment 1 having the following formula:

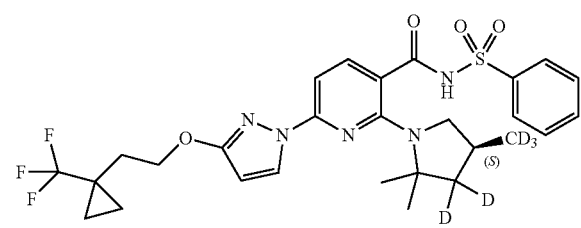

or a pharmaceutically acceptable salt thereof.

33. A compound having the following formula:

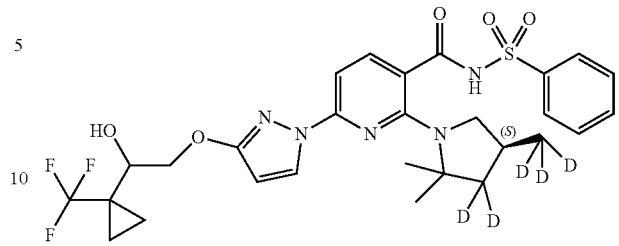

or a pharmaceutically acceptable salt thereof.

34. A compound according to embodiment 1 having the following formula:

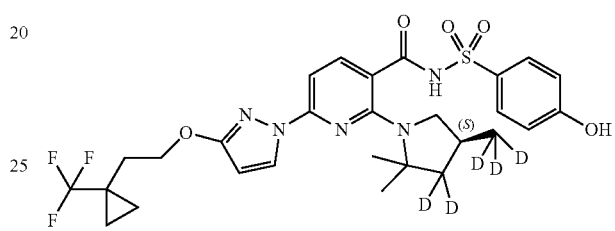

or a pharmaceutically acceptable salt thereof.

35. A pharmaceutical composition comprising at least one compound chosen from compounds of any one of embodiments 1-34, a pharmaceutically acceptable salt thereof, or a deuterated derivative of any of the foregoing, and optionally one or more of:

(a) Compound II

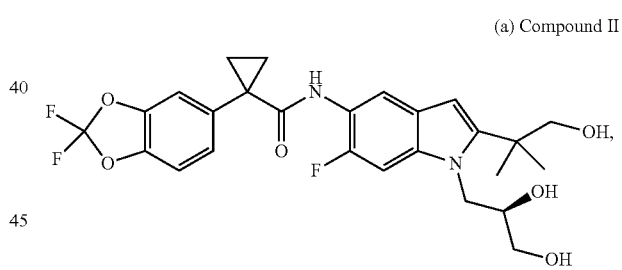

a pharmaceutically acceptable salt thereof, or a deuterated derivative of any of the foregoing;

(b) Compound III

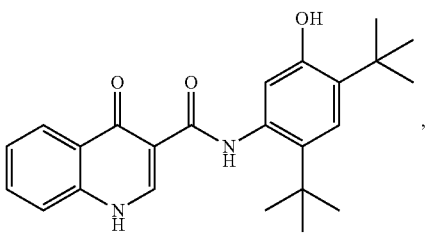

a pharmaceutically acceptable salt thereof, or a deuterated derivative of any of the foregoing; and (c) a pharmaceutically acceptable carrier.

36. A method of treating cystic fibrosis comprising administering to a patient in need thereof a pharmaceutical composition according to embodiment 35.

37. A method of preparing a compound of Formula (IIIa):

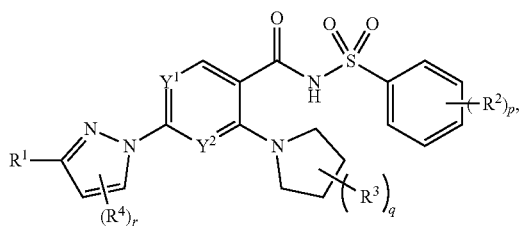

(III)

a pharmaceutically acceptable salt thereof, or a deuterated derivative of any of the foregoing, comprising reacting a compound of Formula (F) or a salt thereof with a compound of Formula (G) or a salt thereof to generate said compound of Formula (IIIa) or a pharmaceutically acceptable salt thereof, or a deuterated derivative of any of the foregoing:

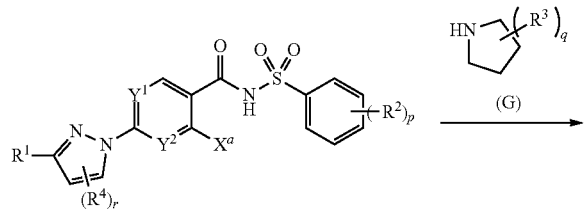

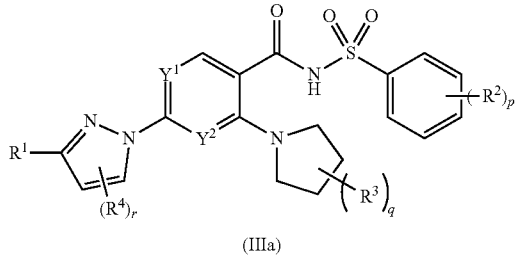

(IIIa)

wherein in each of said formulae:
one of $Y^1$ and $Y^2$ is N and the other is CH;
each $R^1$ is independently chosen from —$(CR_2)_k$—O—$(CR_2)_m(CR)_n$(Ring A)$_{n+1}$ groups,
wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and
wherein each R is independently chosen from H, OH, and $C_1$-$C_2$ alkyl groups optionally substituted with one or more halogens;
each $R^2$ is independently chosen from $C_1$-$C_2$ alkyl groups, OH, $C_1$-$C_2$ alkoxy groups, halogens, and cyano;
each $R^3$ is independently chosen from $C_1$-$C_2$ alkyl groups optionally substituted with one or more OH groups;
each $R^4$ is independently chosen from halogens;
$X^a$ is chosen from F or Cl;
each k is independently 0 or 1;
each r is independently 0 or 1;
each m is independently 0, 1, 2, or 3;

each n is independently 0 or 1;
each p is independently 0, 1, 2, 3, 4, or 5; and
each q is independently 0, 1, 2, 3, 4, 5, 6, 7, or 8.

38. The method of embodiment 37, wherein each $Y^2$ is independently N; and each $Y^1$ is independently CH.

39. The method of embodiment 37 or 38, wherein said reacting a compound of Formula (F) or a salt thereof with a compound of Formula (G) or a salt thereof is performed in the presence of a base.

40. The method of any one of embodiments 37-39, wherein a salt of compound of Formula (G) is employed.

41. The method of embodiment 40, wherein said salt of compound of Formula (G) is a HCl salt of a compound of Formula (G).

42. A method of preparing a compound of Formula (F) or a salt thereof:

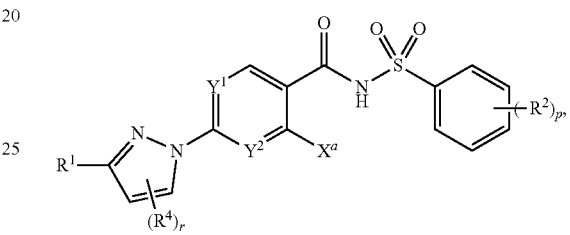

(F)

or a deuterated derivative of any of the foregoing, comprising reacting a compound of Formula (D) or salt thereof with a compound of Formula (E) or a salt thereof to generate a compound of Formula (F) or a salt thereof:

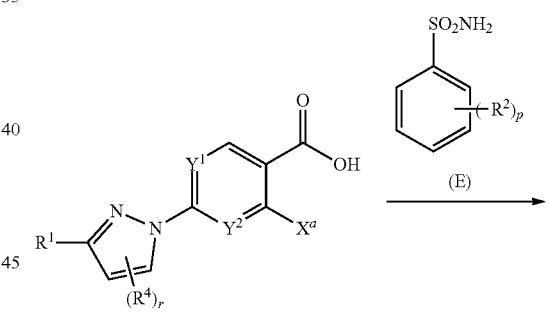

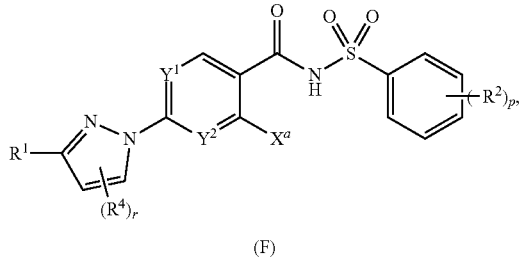

(F)

wherein in each of said formulae:
one of $Y^1$ and $Y^2$ is independently N and the other is independently CH;
each $R^1$ is independently chosen from —$(CR_2)_k$—O—$(CR_2)_m(CR)_n$(Ring A)$_{n+1}$ groups,
wherein each Ring A is independently chosen from $C_3$-$C_{10}$ cycloalkyl groups optionally substituted with one or more substituents each independently chosen from $C_1$-$C_2$ alkyl groups, halogenated $C_1$-$C_2$ alkyl groups, and halogens, and wherein each R is independently chosen from H, OH, and $C_1$-$C_2$ alkyl groups optionally substituted with one or more halogens, each $R^2$ is independently chosen from $C_1$-$C_2$ alkyl groups, OH, $C_1$-$C_2$ alkoxy groups, halogens, and cyano;

each $R^3$ is independently chosen from $C_1$-$C_2$ alkyl groups optionally substituted with one or more OH groups;

each $R^4$ is independently chosen from halogens;

$X^a$ is chosen from F or Cl;

each k is independently 0 or 1;

each r is independently 0 or 1;

each m is independently 0, 1, 2, or 3;

each n is independently 0 or 1;

each p is independently 0, 1, 2, 3, 4, or 5; and each q is independently 0, 1, 2, 3, 4, 5, 6, 7, or 8.

43. The method of embodiment 42, wherein each $Y^2$ is independently N; and each $Y^1$ is independently CH.

44. The method of embodiment 42 or 43, wherein said reacting a compound of Formula (D) or a salt thereof with a compound of Formula (E) or salt thereof is performed in the presence of a base.

45. The method of embodiment 42 or 43, wherein said reacting a compound of Formula (D) or salt thereof with a compound of Formula (E) or salt thereof comprises reacting a compound of Formula (D-1) with a coupling reagent and subsequently with a compound of Formula (E-1) in the presence of a base.

46. A method of preparing a compound of the following formula:

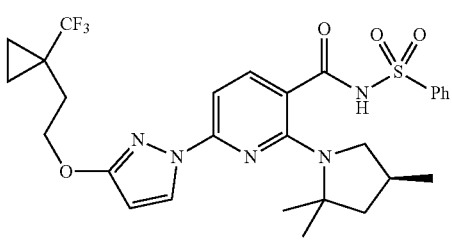 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

or a pharmaceutically acceptable salt thereof, or a deuterated derivative of any of the foregoing, comprising reacting a compound of Formula (F-1) or a salt thereof, wherein $X^a$ is chosen from F or Cl, with a compound of Formula (G-1) or a salt thereof to generate said compound or a pharmaceutically acceptable salt thereof, or a deuterated derivative of any of the foregoing:

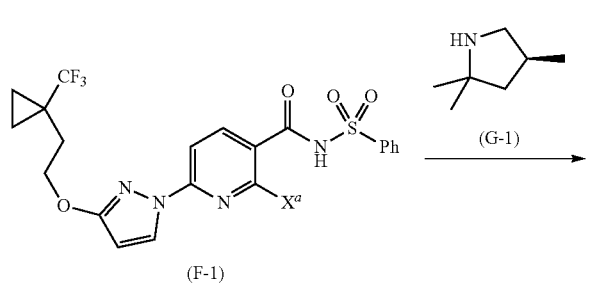

(F-1)   (G-1)

-continued

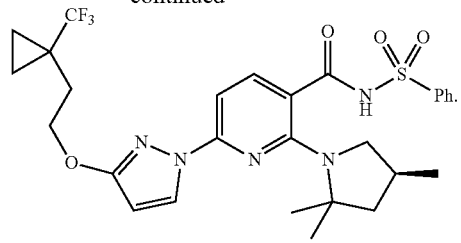

Compound (1)

47. The method of embodiment 46, wherein said reacting a compound of Formula (F-1) or a salt thereof with a compound of Formula (G-1) or a salt thereof is performed in the presence of a base.

48. The method of embodiment 46 or 47, wherein a salt of compound of Formula (G-1) is employed.

49. The method of embodiment 48, wherein said salt of compound of Formula (G-1) is a HCl salt of a compound of Formula (G-1).

50. A method of preparing a compound of Formula (F-1) or a salt thereof:

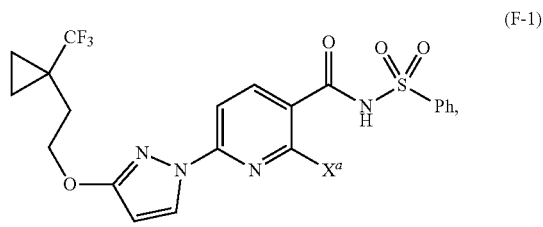

(F-1)

or a deuterated derivative of any of the foregoing, comprising reacting a compound of Formula (D-1) and a compound of Formula (E-1) to generate a compound of Formula (F-1) or a salt thereof:

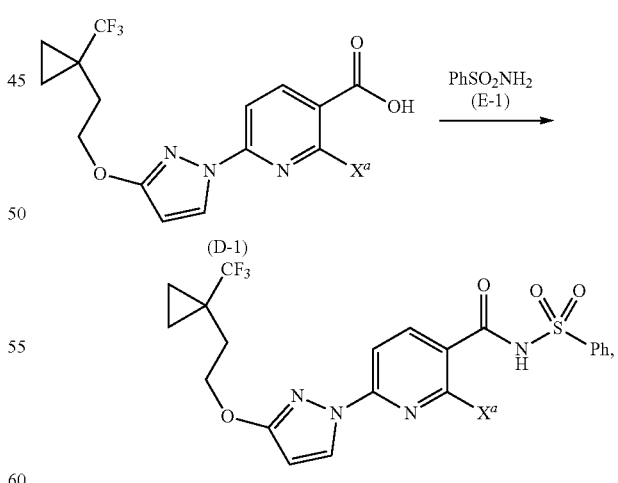

(D-1)

(F-1)

wherein each $X^a$ is independently chosen from F or Cl.

51. The method of embodiment 50, wherein said reacting a compound of Formula (D-1) or a salt thereof with a compound of Formula (E-1) or a salt thereof is performed in the presence of a base.

52. The method of embodiment 50, wherein said reacting a compound of Formula (D-1) or a salt thereof with a compound of Formula (E-1) or a salt thereof comprises reacting a compound of Formula (D-1) with a coupling reagent and subsequently with a compound of Formula (E-1) in the presence of a base.

53. A method of preparing a compound of Formula (D) or a salt thereof:

(D)

or a deuterated derivative of any of the foregoing, comprising:
(i) reacting a compound of Formula (A) or a salt thereof with a compound of Formula (B) or a salt thereof to generate a compound of Formula (C) or a salt thereof:

(A) (B)

(C)

and
(ii) hydrolyzing the —C(O)OR$^a$ group of a compound of Formula (C) to generate a compound of Formula (D) or a salt thereof, wherein in each said formulae:
one of Y$^1$ and Y$^2$ is independently N and the other is independently CH;
each R$^1$ is independently chosen from —(CR$_2$)$_k$—O—(CR$_2$)$_m$(CR)$_n$(Ring A)$_{n+1}$ groups,
wherein each Ring A is independently chosen from C$_3$-C$_{10}$ cycloalkyl groups optionally substituted with one or more substituents each independently chosen from C$_1$-C$_2$ alkyl groups, halogenated C$_1$-C$_2$ alkyl groups, and halogens, and
wherein each R is independently chosen from H, OH, and C$_1$-C$_2$ alkyl groups optionally substituted with one or more halogens;
each R$^2$ is independently chosen from C$_1$-C$_2$ alkyl groups, OH, C$_1$-C$_2$ alkoxy groups, halogens, and cyano;

each R$^3$ is independently chosen from C$_1$-C$_2$ alkyl groups optionally substituted with one or more OH groups;
each R$^4$ is independently chosen from halogens;
each R$^a$ is independently chosen from C$_1$-C$_4$ alkyl;
each X$^a$ is independently chosen from F or Cl;
each k is independently 0 or 1,
each r is independently 0 or 1;
each m is independently 0, 1, 2, or 3;
each n is independently 0 or 1;
each p is independently 0, 1, 2, 3, 4, or 5; and
each q is independently 0, 1, 2, 3, 4, 5, 6, 7, or 8.

54. The method of embodiment 53, wherein each Y$^2$ is independently N; and each Y$^1$ is independently CH.

55. The method of embodiment 53 or 54, wherein the hydrolysis of the —C(O)OR$^a$ group is performed in the presence of a base.

56. The method of any one of embodiments 53-55, wherein said reacting a compound of Formula (A) or a salt thereof with a compound of Formula (B) or salt thereof is performed in the presence of a base.

57. The method of any one of embodiments 53-56, wherein R$^a$ is ethyl or t-butyl.

58. A method of preparing a compound of Formula (D-1) or a salt thereof:

(D-1)

or a deuterated derivative of any of the foregoing, comprising:
(i) reacting a compound of Formula (A-1) or a salt thereof and a compound of Formula (B-1) or a salt thereof to generate a compound of Formula (C-1) or a salt thereof:

(A-1) (B-1)

(C-1)

and (ii) hydrolyzing the —C(O)OR$^a$ group of a compound of Formula (C-1) or a salt thereof to generate a compound of Formula (D-1) or a salt thereof, wherein each R$^a$ is independently chosen from C$_1$-C$_4$ alkyl; and each —X$^a$ is independently chosen from F or Cl.

59. The method of embodiment 58, wherein the hydrolysis of the —C(O)OR$^a$ group is performed in the presence of a base.

60. The method of 58 or 59, wherein said reacting a compound of Formula (A-1) or a salt thereof and a compound of Formula (B-1) or a salt thereof is performed in the presence of a base.

61. The method of any one of embodiments 58-60, wherein R$^a$ is ethyl or i-butyl.

62. A method of preparing a compound of Formula (I) or a pharmaceutically acceptable salt thereof, or a deuterated derivative of any of the foregoing, comprising reacting a compound of Formula (L) or a salt thereof with NR*$_3$:

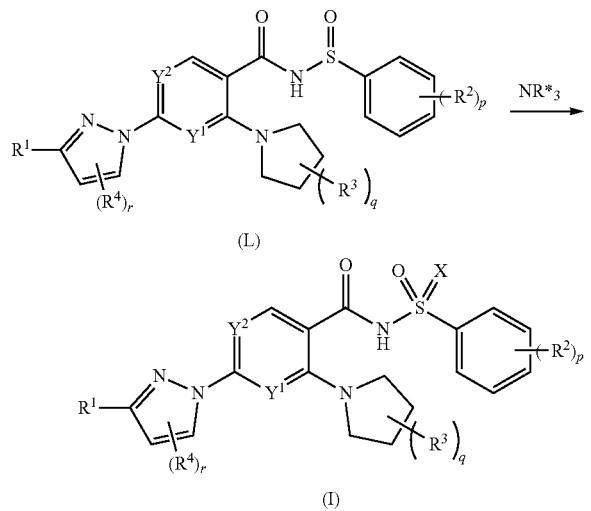

wherein in each of said formulae:
X is NH or N(C$_1$-C$_4$ alkyl);
one of Y$^1$ and Y$^2$ is independently N and the other is independently CH;
each R$^1$ is independently chosen from —(CR$_{2k}$—O—(CR$_2$)$_m$(CR)$_n$(Ring A)$_{n+1}$ groups,
wherein each Ring A is independently chosen from C$_3$-C$_{10}$ cycloalkyl groups optionally substituted with one or more substituents each independently chosen from C$_1$-C$_2$ alkyl groups, halogenated C$_1$-C$_2$ alkyl groups, and halogens, and
wherein each R is independently chosen from H, OH, and C$_1$-C$_2$ alkyl groups optionally substituted with one or more halogens;
each R$^2$ is independently chosen from C$_1$-C$_2$ alkyl groups, OH, C$_1$-C$_2$ alkoxy groups, halogens, and cyano;
each R$^3$ is independently chosen from C$_1$-C$_2$ alkyl groups optionally substituted with one or more OH groups;
each R$^1$ is independently chosen from halogens;
R* is H or C$_1$-C$_4$ alkyl.
X$^a$ is chosen from F or Cl;
each k is independently 0 or 1;
each r is independently 0 or 1;
each m is independently 0, 1, 2, or 3;

each n is independently 0 or 1;
each p is independently 0, 1, 2, 3, 4, or 5; and
each q is independently 0, 1, 2, 3, 4, 5, 6, 7, or 8.

63. Use of at least one compound chosen from compounds of any one of embodiments 1-34, a pharmaceutically acceptable salt thereof, or a deuterated derivative of any of the foregoing, and optionally one or more of:

(a) Compound II

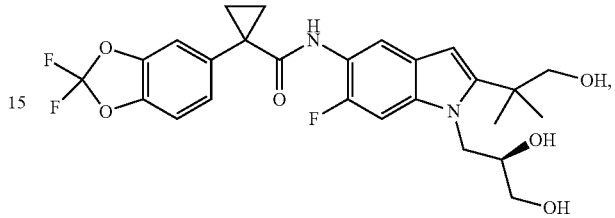

a pharmaceutically acceptable salt thereof, or a deuterated derivative of any of the foregoing; and (b) Compound III

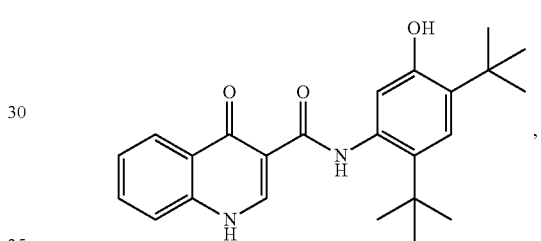

a pharmaceutically acceptable salt thereof, or a deuterated derivative of any of the foregoing; for treating cystic fibrosis.

Methods of Preparing Compounds

General Experimental Procedures

Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters. Final purity of compounds was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD5975C instrument, using a Restek Rt-βDEXcst (30 m×0.25 mm×0.25 um_df) column, with a 2.0 mL/min flow rate (H$_2$ carrier gas), at an injection temperature of 220° C. and an oven temperature of 120° C., 15 minutes.

EXAMPLE 1

Preparation of a Spray Dried Dispersion (SDD) of Compound 1

A spray dried dispersion of Compound 1 was prepared using Buchi Mini Spray Dryer B290. HPMCAS-HG (6.0 grams) was dissolved in 200 mL of MeOH (methanol)/DCM (dichloromethane) (1/1), and Compound 1 (6.0 grams) was added and stirred for 30 minutes forming a clear solution. The resulting solution was spray dried under the following conditions resulting in a 50% Compound 1/50% HPMCAS-HG spray dried dispersion (Yield: 80%, Solid load: 6%).

|  | Conditions |
| --- | --- |
| Inlet Temperature (° C.) | 77 |
| Outlet Temperature (° C.) | 39 |
| Nitrogen Pressure (PSI) | 95 |
| Aspirator (%) | 100 |
| Pump (%) | 30 |
| Rotameter (mm) | 60 |
| Filter Pressure (mBar) | −50 |
| Condenser Temperature (° C.) | −10 |

Powder X-Ray Diffraction

The powder x-ray diffraction measurements were performed using PANalytical's X-pert Pro diffractometer at room temperature with copper radiation (1.54060 Å). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s.

Figure 2:
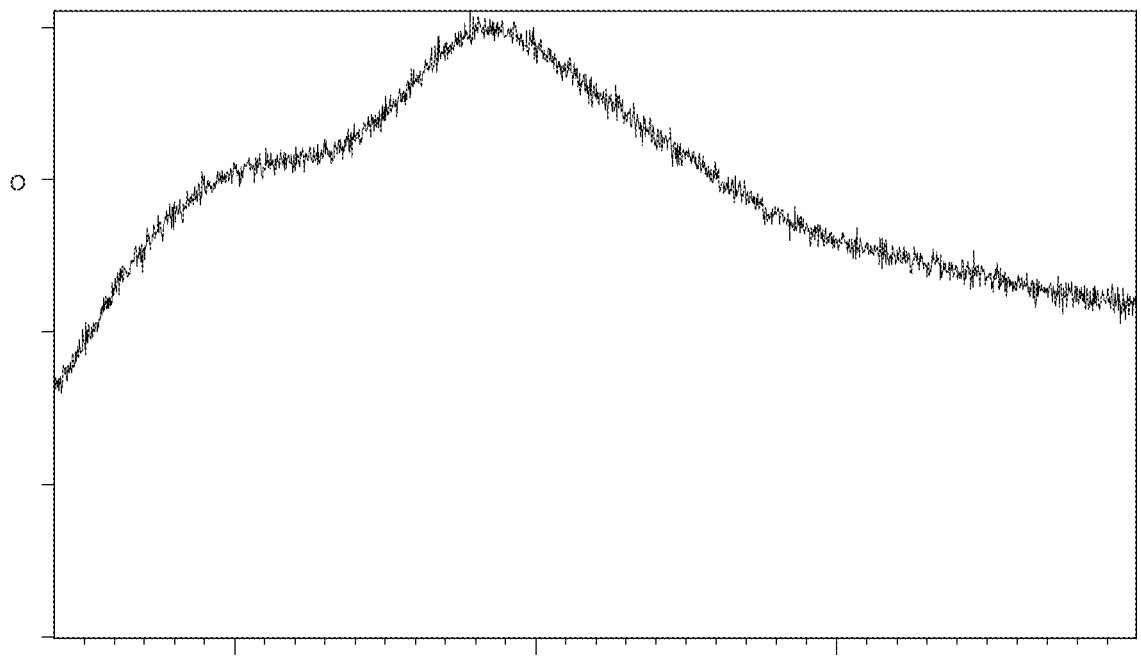
FIG. 2 is a X-ray Powder Diffractogram ("XRPD") of a spray dried dispersion (SDD) of 50% Compound 1 in HPMCAS-HG.

FIG. 2 shows the XRPD spectrum of a SDD of 50% Compound I in HPMCAS-HG, and shows that Compound I is amorphous in the SDD.

Modulated Differential Scanning Calorimetry (MDSC)

MDSC was used to determine the glass transition temperature of the amorphous material. MDSC was performed using TA Discovery DSC differential scanning calorimeter (TA Instruments, New Castle, Del.). The instrument was calibrated with indium. Samples of approximately 1-3 mg were weighed into hermetic pans that were crimped using lids with one hole. The MDSC sample was scanned from −20° C. to 210° C. at a heating rate of 2° C./min with +/−1° C. of modulation within 1 minute. Data was collected and analyzed by TA Instruments Trios Software (TA Instruments, New Castle, Del.).

Figure 3:
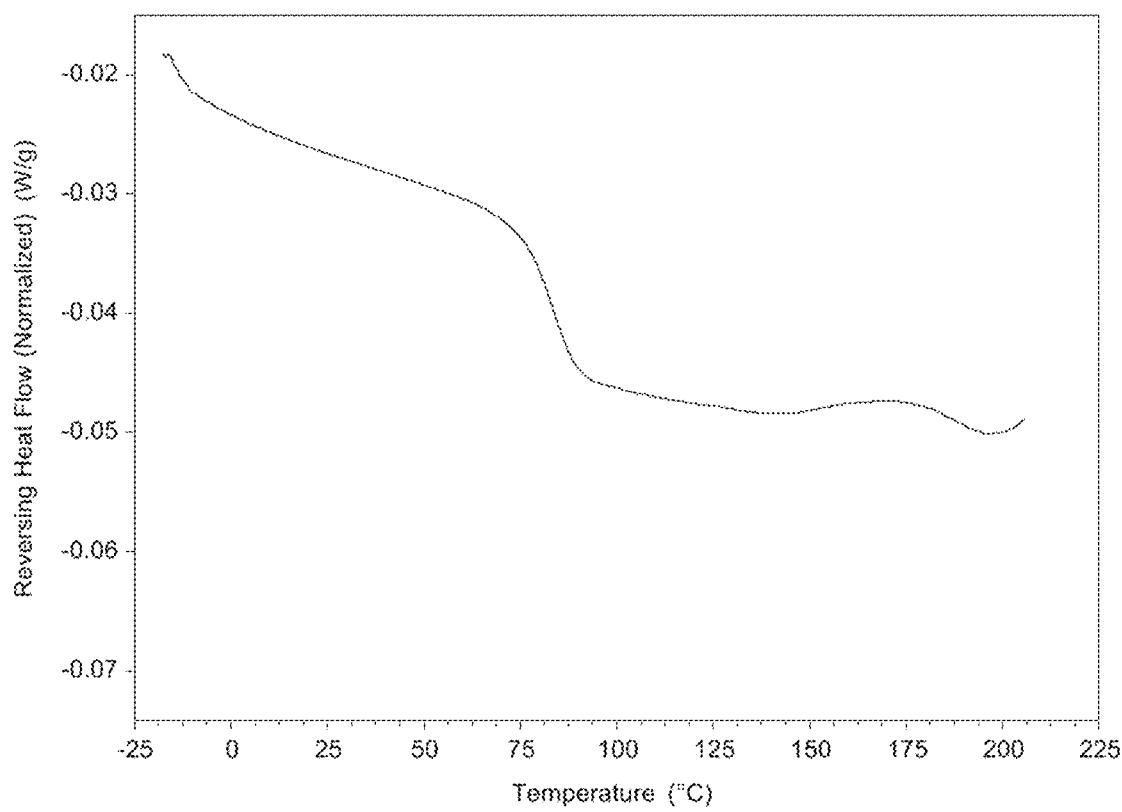
FIG. 3 is a spectrum showing a modulated differential scanning calorimetry (MDSC) spectrum of a spray dried dispersion (SDD) of 50% Compound 1 in HPMCAS-HG.

FIG. 3 shows a MDSC spectrum of a SDD of 50% Compound 1 in HPMCAS-HG, and shows that the SDD has an onset temperature of about 75.6° C., a midpoint temperature of about 82.7° C., and an offset temperature of about 89.7° C.

EXAMPLE 2

Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

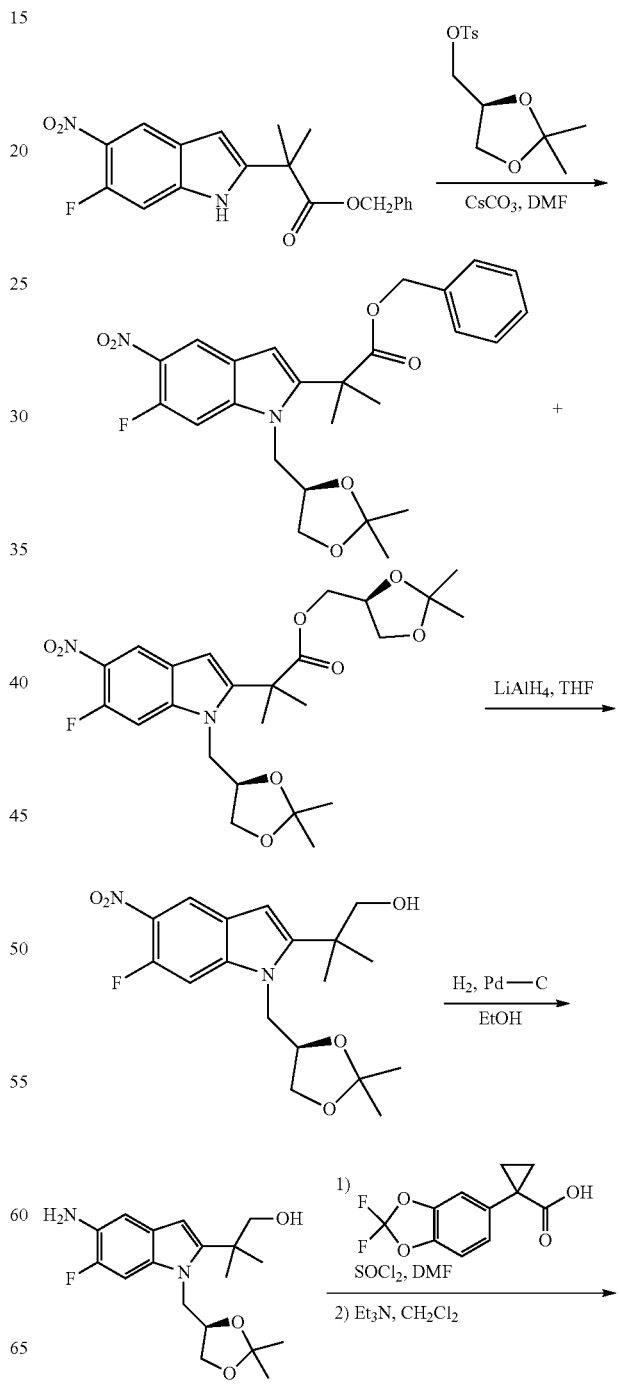

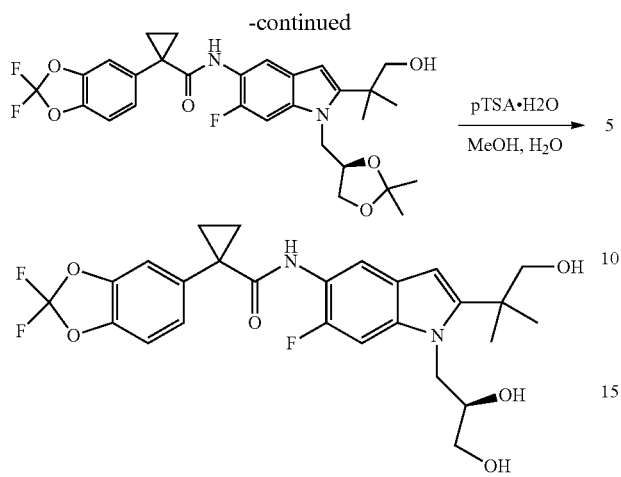

Step 1: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (N,N-dimethylformamide) (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO$_4$, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2, found 471.5 (M+1)$^+$. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5, found 495.7 (M+1)$^+$. Retention time 2.01 minutes.

Step 2: (R)-2-(1-((2,2-dimethyl-1,3-dioxolan-4-yl)methyl)-6-fluoro-5-nitro-1H-indol-2-yl)-2-methylpropan-1-ol The crude reaction mixture obtained in step (A) was dissolved in THF (tetrahydrofuran) (42 mL) and cooled in an ice-water bath. LiAlH$_4$ (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m/z calc. 366.4, found 367.3 (M+1)$^+$. Retention time 1.68 minutes. $^1$H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm. (DMSO is dimethylsulfoxide).

Step 3: (R)-2-(5-amino-1-((2,2-dimethyl-1,3-dioxolan-4-yl)methyl)-6-fluoro-1H-indol-2-yl)-2-methylpropan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N$_2$. Then Pd—C (250 mg, 5% wt) was added. The reaction was flushed with nitrogen again and then stirred under H$_2$ (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product (1.82 g, 79%). ESI-MS m/z calc. 336.2, found 337.5 (M+1)$^+$. Retention time 0.86 minutes. $^1$H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step 4: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO$_3$ solution and brine, dried over MgSO$_4$ and concentrated to yield the product (3 g, 100%). ESI-MS m/z calc. 560.6, found 561.7 (M+1). Retention time 2.05 minutes. $^1$H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm

Step 5: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH.H₂O (p-toluenesulfonic acid hydrate) (204 mg, 1.1 mmol). The reaction was heated at 80° C. for 45 minutes. The solution was concentrated and then partitioned between ethyl acetate and saturated NaHCO₃ solution. The ethyl acetate layer was dried over MgSO₄ and concentrated. The residue was purified by column chromatography (50-100% ethyl acetate-hexanes) to yield the product. (1.3 g, 47%, ee>98% by SFC). ESI-MS m.z calc. 520.5, found 521.7 (M+1)⁺. Retention time 1.69 minutes. ¹H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

EXAMPLE 3

Synthesis of Compound III: N-(2,4-di-tert-butyl-5-hydroxyphenyl)-4-oxo-1,4-dihydroquinoline-3-carboxamide Part A: Synthesis of 4-oxo-1,4-dihydroquinoline-3-carboxylic acid

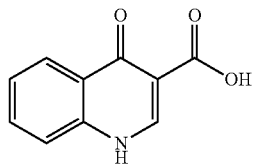 [SMILES: O=C(O)c1c[nH]c2ccccc2c1=O]

Step 1: 2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. ¹H NMR (DMSO-d₆) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step 2: 4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na₂CO₃ solution, filtered, washed with water and dried. 4-Hydroxyquinoline-3-carboxylic acid ethyl ester was obtained as a pale brown solid (15.2 g, 70%). The crude product was used in next step without further purification.

Step 3: 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). ¹H NMR (DMSO-d₆) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: Synthesis of N-(2,4-di-tert-butyl-5-hydroxyphenyl)-4-oxo-1,4-dihydroquinoline-3-carboxamide

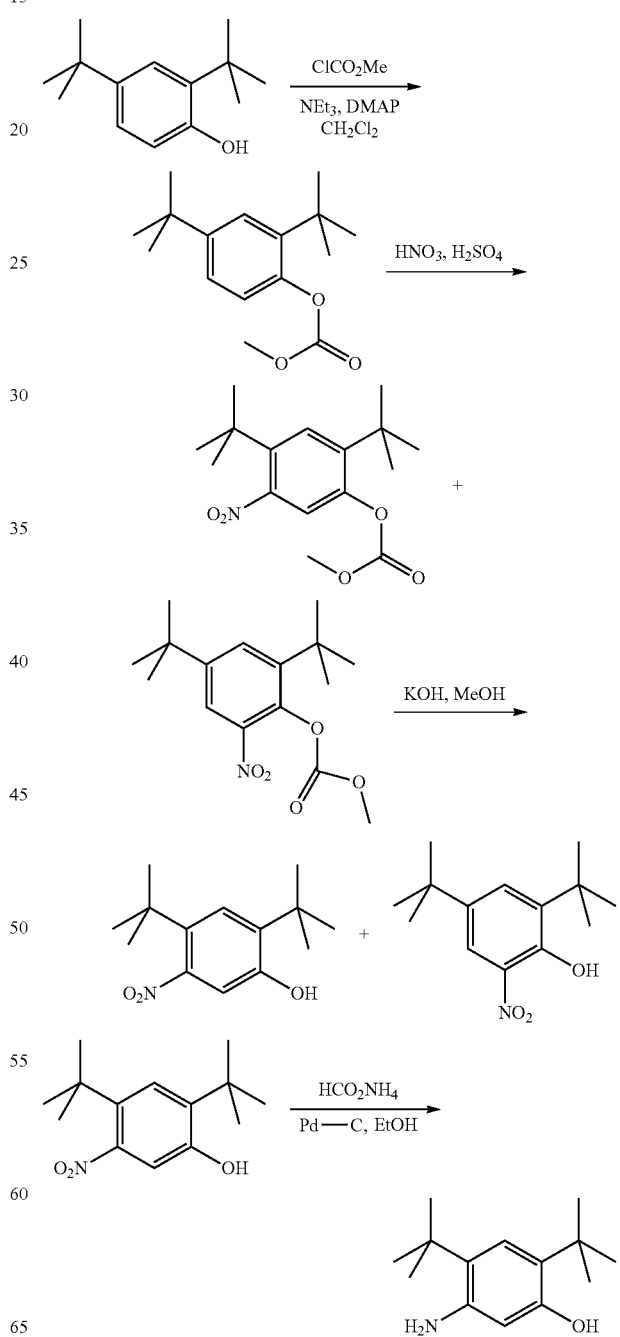

Step 1: Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et$_3$N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d$_6$) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step 2: Carbonic acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO$_4$), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step 3: 2,4-Di-tert-butyl-5-nitro-phenol and 2,4-Di-tert-butyl-6-nitro-phenol The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO$_4$), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d$_6$) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl$_3$) δ 11.48 (s, 1H), 7.98 (d, J=2.5 Hz, 1H), 7.66 (d, J=2.4 Hz, 1H), 1.47 (s, 9H), 1.34 (s, 9H).

Step 4: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d$_6$) δ 8.64 (s, 1H, OH), 6.84 (s, 1H), 6.08 (s, 1H), 4.39 (s, 2H, NH$_2$), 1.27 (m, 18H); HPLC ret. time 2.72 min, 10-99% CH$_3$CN, 5 min run; ESI-MS 222.4 m/z [M+H]$^+$.

Step 5: N-(5-hydroxy-2,4-di-tert-butyl-phenyl)-4-oxo-1H-quinoline-3-carboxamide

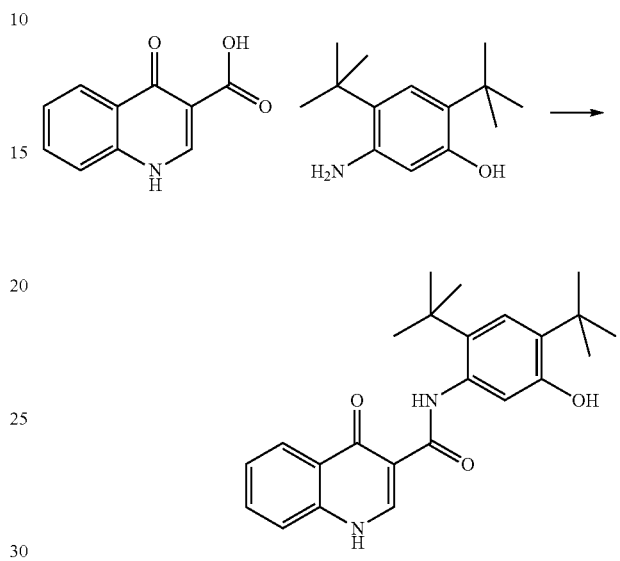

To a suspension of 4-oxo-1,4-dihydroquinolin-3-carboxylic acid (35.5 g, 188 mmol) and HBTU (85.7 g, 226 mmol) in DMF (280 mL) was added Et$_3$N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo. EtOH (ethyl alcohol) was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystallite. Et$_2$O (diethyl ether) was added to the solid obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide (38 g, 52%). HPLC ret. time 3.45 min, 10-99% CH$_3$CN, 5 min run; 1H NMR (400 MHz, DMSO-d$_6$) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]$^+$.

EXAMPLE 4

Synthesis of Compounds 1-65

SYNTHETIC EXAMPLE 1

Synthesis of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound 1)

Part A: Synthesis of (4S)-2,2,4-trimethylpyrrolidine hydrochloride

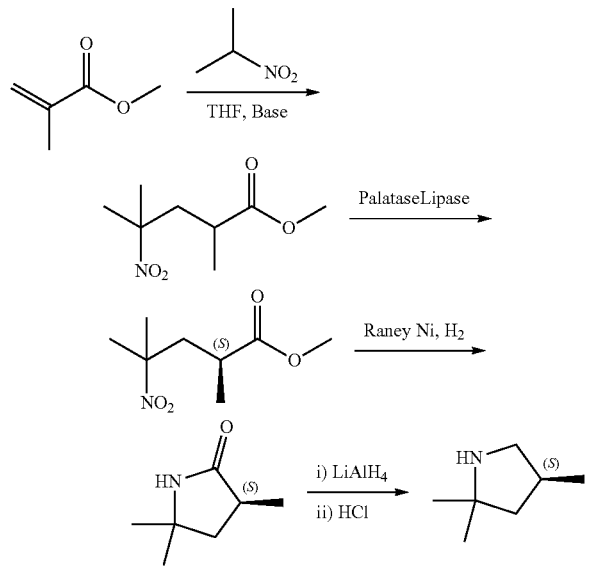

Step 1: Synthesis of methyl-2,4-dimethyl-4-nitro-pentanoate

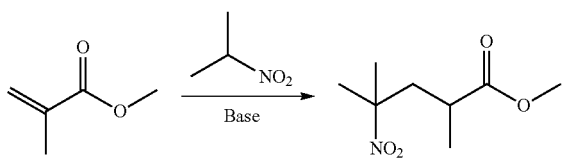

Tetrahydrofuran (THF, 4.5 L) was added to a 20 L glass reactor and stirred under $N_2$ at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. This was dried with $MgSO_4$ and filtered to afford methyl-2,4-dimethyl-4-nitro-pentanoate as a clear green oil (3.16 kg, 99% yield). $^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl (2S)-2,4-dimethyl-4-nitro-pentanoate

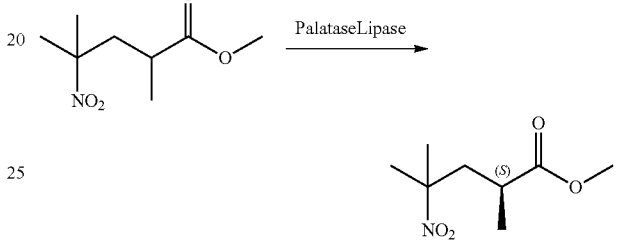

A reactor was charged with purified water (2090 L; 10 vol) and then potassium phosphate monobasic (27 kg, 198.4 moles: 13 g/L for water charge). The pH of the reactor contents was adjusted to pH 6.5 (±0.2) with 20% (w/v) potassium carbonate solution. The reactor was charged with racemic methyl-2,4-dimethyl-4-nitro-pentanoate (209 kg; 1104.6 moles), and Palatase 20000L lipase (13 L, 15.8 kg; 0.06 vol).

The reaction mixture was adjusted to 32±2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous $Na_2CO_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

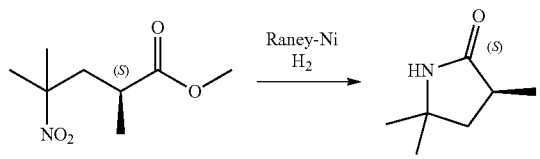

A 20 L reactor was purged with $N_2$. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H$_2$ and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine hydrochloride

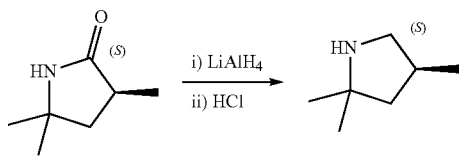

A glass lined 120 L reactor was charged with lithium aluminium hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/N$_2$ bleed) to afford (4S)-2,2,4-trimethylpyrrolidine*HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Synthesis of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

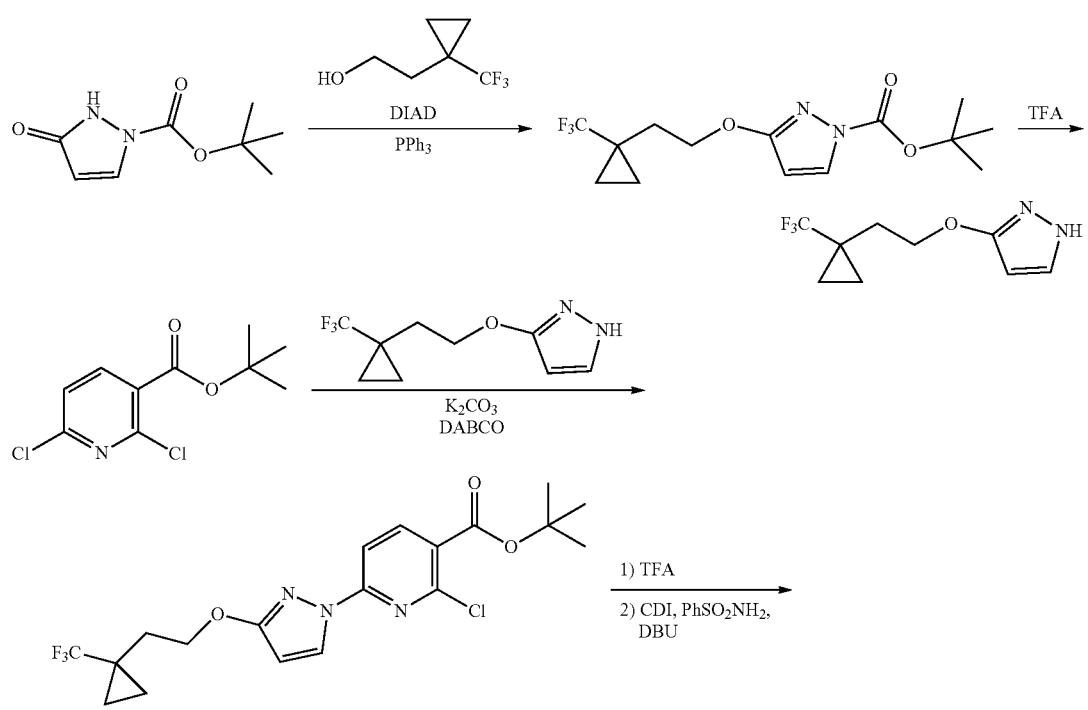

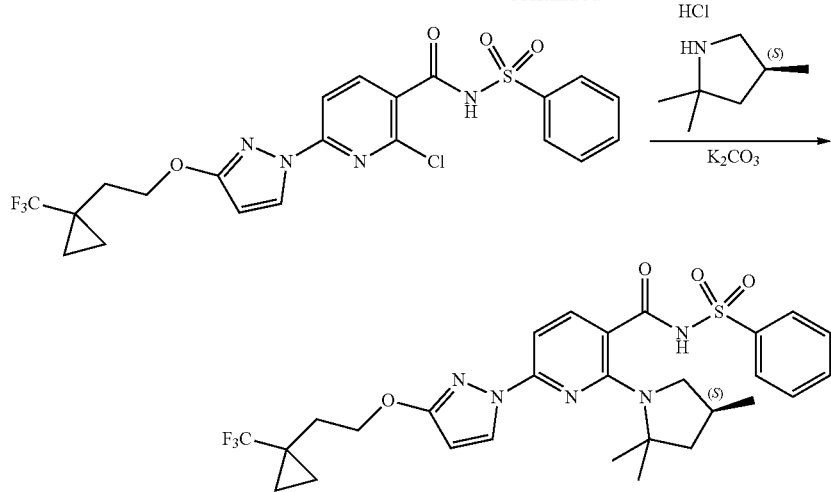

Synthesis of Starting Materials

Synthesis of tert-Butyl 2,6-dichloropyridine-3-carboxylate

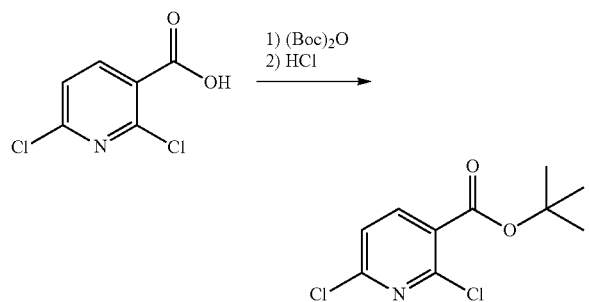

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and stirred overnight at room temperature. At this point, HCl 1N (400 mL) was added, and the mixture was stirred vigorously for about 10 minutes. The product was extracted with ethyl acetate (2×300 mL), and the combined organic layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.02, found 248.1 (M+1)$^+$; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Synthesis of tert-Butyl 3-oxo-2,3-dihydro-1H-pyrazole-1-carboxylate

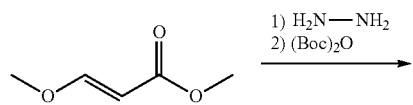

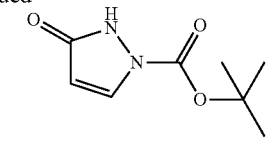

A 50 L reactor was started, and the jacket was set to 20° C., with stirring at 150 rpm, reflux condenser (10° C.) and nitrogen purge. MeOH (2.860 L) and methyl (E)-3-methoxyprop-2-enoate (2.643 kg, 22.76 mol) were added, and the reactor was capped. The reaction was heated to an internal temperature of 40° C., and the system was set to hold jacket temperature at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion-wise, maintaining reaction temperature <30° C. A solution of Boc anhydride (di-tert-butyl dicarbonate) (4.967 kg, 5.228 L, 22.76 mol) in MeOH (2.860 L) was added portion-wise maintaining temperature <45° C. The reaction mixture was stirred at 20° C. for 16 h. The reaction solution was partially concentrated to remove MeOH, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container, and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) and added dropwise. The jacket was set to 0° C. to absorb the quench exotherm. After the addition was complete (pH=5), the reaction mixture was stirred for 1 h. The solid was collected by filtration and washed with water (7.150 L), and washed a second time with water (3.575 L). The crystalline solid was transferred into a 20 L rotovap bulb, and heptane (7.150 L) was added. The mixture was slurried at 45° C. for 30 mins, and 1-2 volumes of solvent were distilled off. The slurry in the rotovap flask was filtered, and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. ¹H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Synthesis of 2-[1-(trifluoromethyl)cyclopropyl]ethanol

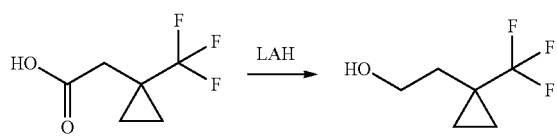 [SMILES: O=C(O)CC1(C(F)(F)F)CC1 ; OCCC1(C(F)(F)F)CC1]

To a solution of lithium aluminum hydride (293 mg, 7.732 mmol) in THF (10.00 mL) in an ice-bath, 2-[1-(trifluoromethyl)cyclopropyl]acetic acid (1.002 g, 5.948 mmol) in THF (3.0 mL) was added dropwise over a period of 30 minutes keeping the reaction temperature below 20° C. The mixture was allowed to gradually warm to ambient temperature and was stirred for 18 h. The mixture was cooled with an ice-bath and sequentially quenched with water (294 mg, 295 µL, 16.36 mmol), NaOH (297 µL of 6 M, 1.784 mmol), and then water (884.0 µL, 49.07 mmol) to afford a granular solid in the mixture. The solid was filtered off using celite, and the precipitate was washed with ether. The filtrate was further dried with MgSO₄ and filtered and concentrated in vacuo to afford the product with residual THF and ether. The mixture was taken directly into the next step without further purification.

Step 1: tert-Butyl 3-[2-[1-(trifluoromethyl)cyclopropyl]ethoxy]pyrazole-1-carboxylate

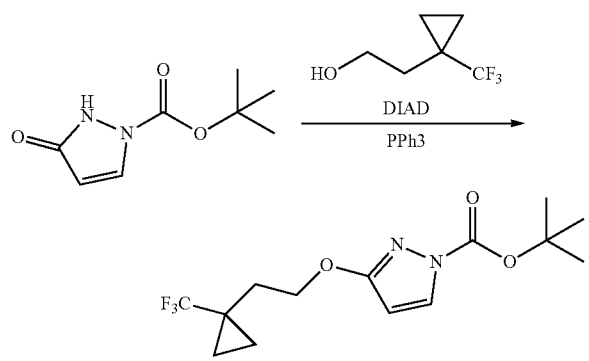

tert-Butyl 5-oxo-1H-pyrazole-2-carboxylate (1.043 g, 5.660 mmol), 2-[1-(trifluoromethyl)cyclopropyl]ethanol (916 mg, 5.943 mmol), and triphenyl phosphine (1.637 g, 6.243 mmol) were combined in THF (10.48 mL) and the reaction was cooled in an ice-bath. Diisopropyl azodicarboxylate (1.288 g, 1.254 mL, 6.368 mmol) was added dropwise to the reaction mixture, and the reaction was allowed to warm to room temperature for 16 hours. The mixture was evaporated, and the resulting material was partitioned between ethyl acetate (30 mL) and 1N sodium hydroxide (30 mL). The organic layer was separated, washed with brine (30 mL), dried over sodium sulfate, and concentrated. The crude material was purified by silica gel chromatography eluting with a gradient of ethyl acetate in hexanes (0-30%) to give tert-butyl 3-[2-[1-(trifluoromethyl)cyclopropyl]ethoxy]pyrazole-1-carboxylate (1.03 g, 57%). ESI-MS m/z calc. 320.13, found 321.1 (M+1)⁺; Retention time: 0.72 minutes.

Step 2: 3-[2-[1-(Trifluoromethyl)cyclopropyl]ethoxy]-1H-pyrazole

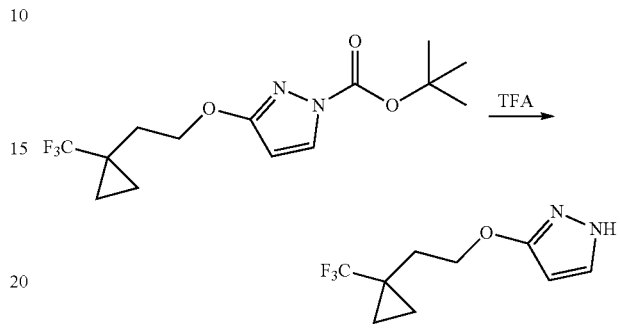

tert-Butyl-3-[2-[1-(trifluoromethyl)cyclopropyl]ethoxy]pyrazole-1-carboxylate (1.03 g, 3.216 mmol) was dissolved in dichloromethane (10.30 mL) with trifluoroacetic acid (2.478 mL, 32.16 mmol), and the reaction was stirred at room temperature for 2 hours. The reaction was evaporated, and the resulting oil was partitioned between ethyl acetate (10 mL) and a saturated sodium bicarbonate solution. The organic layer was separated, washed with brine, dried over sodium sulfate, and evaporated to give 3-[2-[1-(trifluoromethyl)cyclopropyl]ethoxy]-1H-pyrazole (612 mg, 86%). ESI-MS m/z calc. 220.08, found 221.0 (M+1)⁺; Retention time: 0.5 minutes. ¹H NMR (400 MHz, DMSO-d6) δ 11.86 (s, 1H), 7.50 (t, =2.1 Hz, 1H), 5.63 (t, J=2.3 Hz, 1H), 4.14 (t, J=7.1 Hz, 2H), 2.01 (t, J=7.1 Hz, 2H), 0.96-0.88 (m, 2H), 0.88-0.81 (m, 2H).

Step 3: tert-Butyl 2-chloro-6-[3-[2-[1-(trifluoromethyl)cyclopropyl]ethoxy]pyrazol-1-yl]pyridine-3-carboxylate

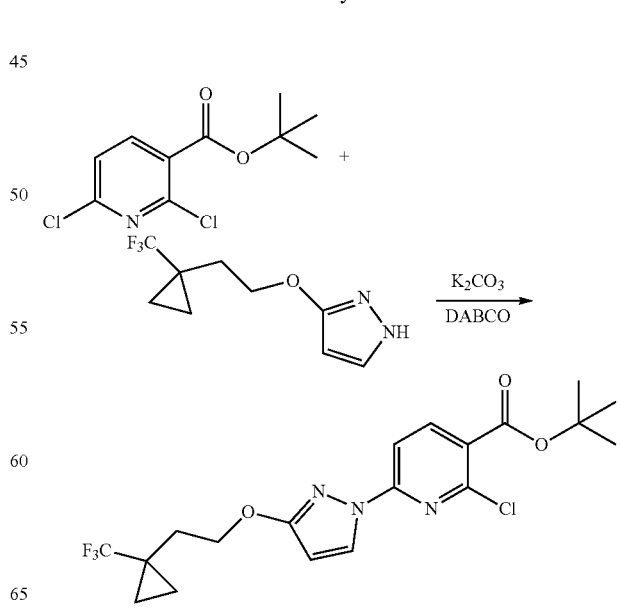

tert-Butyl 2,6-dichloropyridine-3-carboxylate (687 mg, 2.770 mmol), 3-[2-[1-(trifluoromethyl)cyclopropyl]ethoxy]-1H-pyrazole (610 mg, 2.770 mmol), and freshly ground potassium carbonate (459 mg, 3.324 mmol) were combined in anhydrous DMSO (13.75 mL). 1,4-diazabicyclo[2.2.2] octane (DABCO (1,4-diazabicyclo[2.2.2]octane), 62 mg, 0.5540 mmol) was added, and the mixture was stirred at room temperature under nitrogen for 16 hours. The reaction mixture was diluted with water (20 mL) and stirred for 15 minutes. The resulting solid was collected and washed with water. The solid was dissolved in dichloromethane and dried over magnesium sulfate. The mixture was filtered and concentrated to give tert-butyl 2-chloro-6-[3-[2-[1-(trifluoromethyl)cyclopropyl]ethoxy]pyrazol-1-yl]pyridine-3-carboxylate (1.01 g, 84%). ESI-MS m/z calc. 431.12, found 432.1 (M+1)$^+$; Retention time: 0.88 minutes.

Step 4: 2-Chloro-6-[3-[2-[1-(trifluoromethyl)cyclopropyl]ethoxy]pyrazol-1-yl]pyridine-3-carboxylic acid

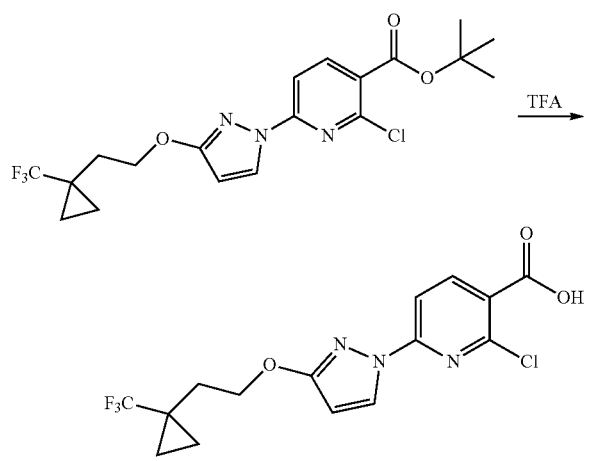

tert-Butyl 2-chloro-6-[3-[2-[1-(trifluoromethyl)cyclopropyl]ethoxy]pyrazol-1-yl]pyridine-3-carboxylate (1.01 g, 2.339 mmol) and trifluoroacetic acid (1.8 mL, 23.39 mmol) were combined in dichloromethane (10 mL) and heated at 40° C. for 3 h. The reaction was concentrated. Hexanes were added, and the mixture was concentrated again to give 2-chloro-6-[3-[2-[1-(trifluoromethyl)cyclopropyl]ethoxy]pyrazol-1-yl]pyridine-3-carboxylic acid (873 mg, 99%) ESI-MS m/z calc. 375.06, found 376.1 (M+1)$^+$; Retention time: 0.69 minutes.

Step 5: N-(Benzenesulfonyl)-2-chloro-6-[3-[2-[1-(trifluoromethyl)cyclopropyl]ethoxy]pyrazol-1-yl]pyridine-3-carboxamide

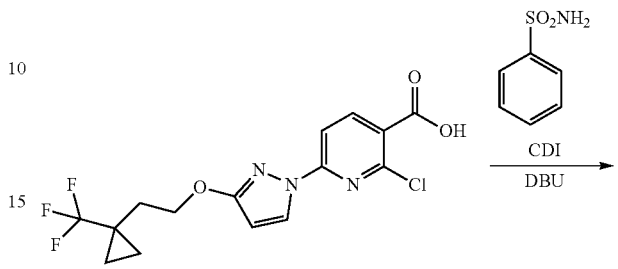

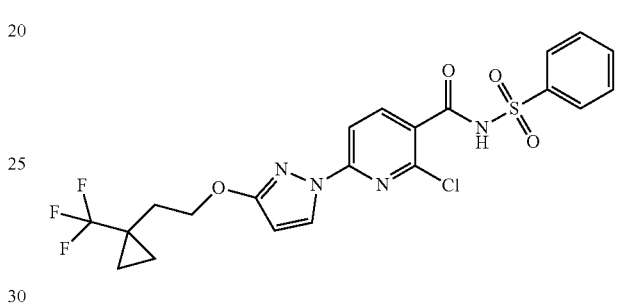

A solution of 2-chloro-6-[3-[2-[1-(trifluoromethyl)cyclopropyl]ethoxy]pyrazol-1-yl]pyridine-3-carboxylic acid (0.15 g, 0.3992 mmol) and carbonyl diimidazole (77 mg, 0.4790 mmol) in THF (2.0 mL) was stirred for one hour, and benzenesulfonamide (81 mg, 0.5190 mmol) and DBU (72 μL, 0.4790 mmol) were added. The reaction was stirred for 16 hours, acidified with 1 M aqueous citric acid, and extracted with ethyl acetate. The combined extracts were dried over sodium sulfate and evaporated. The residue was purified by silica gel chromatography eluting with a gradient of methanol in dichloromethane (0-5%) to give N-(benzenesulfonyl)-2-chloro-6-[3-[2-[1-(trifluoromethyl)cyclopropyl]ethoxy]pyrazol-1-yl]pyridine-3-carboxamide (160 mg, 78%). ESI-MS m/z calc. 514.07, found 515.1 (M+1)$^+$; Retention time: 0.74 minutes.

Step 6: N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

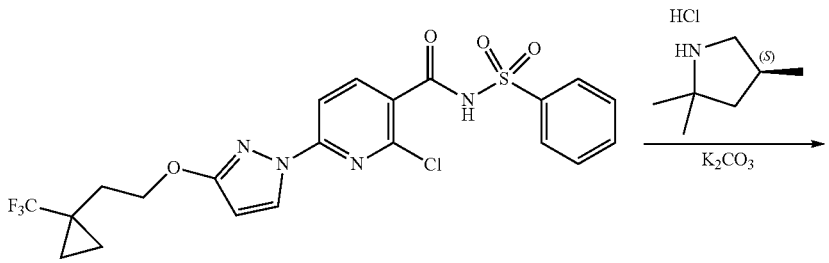

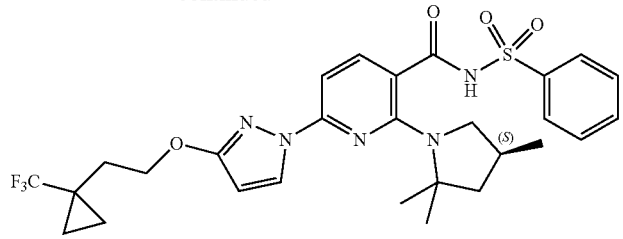

A mixture of N-(benzenesulfonyl)-2-chloro-6-[3-[2-[1-(trifluoromethyl)cyclopropyl]ethoxy]pyrazol-1-yl]pyridine-3-carboxamide (160 mg, 0.3107 mmol), (4S)-2,2,4-trimethylpyrrolidine hydrochloride salt (139 mg, 0.9321 mmol), and potassium carbonate (258 mg, 1.864 mmol) in DMSO (1.5 mL) was stirred at 130° C. for 17 hours. The reaction mixture was acidified with 1 M aqueous citric acid and extracted with ethyl acetate. The combined extracts were dried over sodium sulfate and evaporated to yield a crude product that was purified by reverse-phase HPLC utilizing a gradient of 10-99% acetonitrile in 5 mM aqueous HCl to yield N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (87 mg, 47%). ESI-MS m/z calc. 591.21, found 592.3 (M+1)$^+$; Retention time: 2.21 minutes. 1H NMR (400 MHz, DMSO-d6) δ 12.48 (s, 1H), 8.19 (d, J=2.8 Hz, 1H), 8.04-7.96 (m, 2H), 7.81 (d, J=8.2 Hz, 1H), 7.77-7.70 (m, 1H), 7.70-7.62 (m, 2H), 6.92 (d, J=8.2 Hz, 1H), 6.10 (d, J=2.8 Hz, 1H), 4.31 (t, J=7.0 Hz, 2H), 2.42 (t, J=10.5 Hz, 1H), 2.28 (dd, J=10.2, 7.0 Hz, 1H), 2.17-2.01 (m, 3H), 1.82 (dd, J=11.9, 5.5 Hz, 1H), 1.52 (d, J=9.4 Hz, 6H), 1.36 (t, J=12.1 Hz, 1H), 1.01-0.92 (m, 2H), 0.92-0.85 (m, 2H), 0.65 (d, J=6.3 Hz, 3H). pKa: 4.95+0.06.

Synthesis of sodium salt of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (sodium salt of Compound 1)

Figure 5:
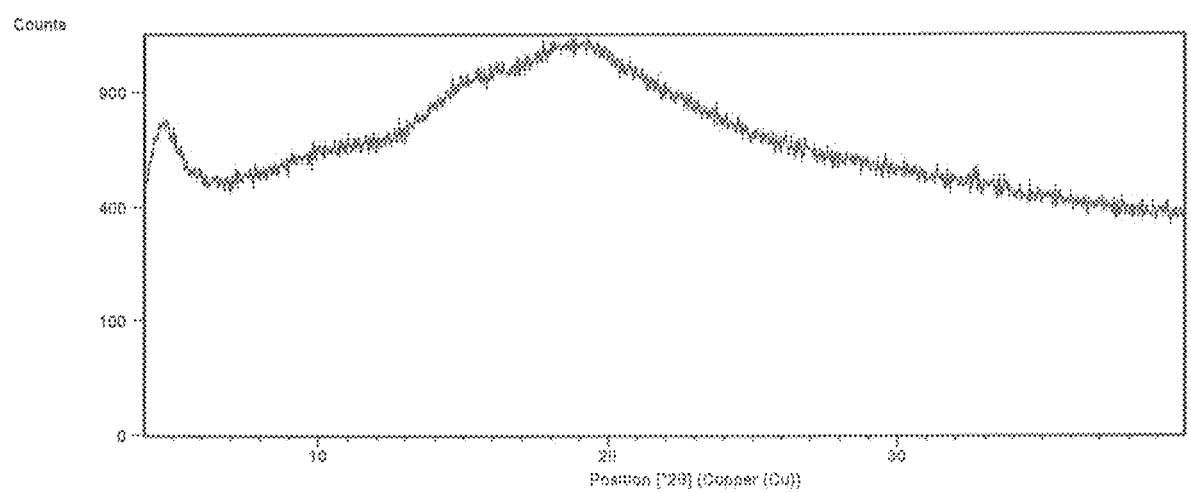
FIG. 5 is an XRPD) of a sample of the sodium salt of Compound 1 prepared as reported in the Example of the sodium salt of Compound 1.

N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (1000 mg, 1.679 mmol) was dissolved in ethanol (19.87 ml) under warming, filtered clear through a syringe filter (0.2 μm), washed with warm ethanol (10 ml) and the warm solution was treated with 1M NaOH (1.679 ml, 1.679 mmol). The solution was evaporated at 30-35° C., co-evaporated 3 times with ethanol (~20 ml), to give a solid, which was dried overnight under vacuum in a drying cabinet at 45° C. with a nitrogen bleed to give 951 mg of a cream colored solid. The solid was further dried under vacuum in a drying cabinet at 45° C. with a nitrogen bleed over the weekend. 930 mg (890) of the sodium salt of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide was obtained as an off-white amorphous solid. $^1$H NMR (400 MHz, DMSO-d$_6$) δ 8.15 (d, J=2.7 Hz, 1H), 7.81 (dd, J=6.7, 3.1 Hz, 2H), 7.61 (d, J=7.9 Hz, 1H), 7.39 (dd, J=4.9, 2.0 Hz, 3H), 6.74 (d, J=7.9 Hz, 1H), 6.01 (d, J=2.6 Hz, 1H), 4.29 (t, J=7.0 Hz, 2H), 2.93-2.78 (m, 2H), 2.07 (t, J=7.1 Hz, 3H), 1.78 (dd, J=11.8, 5.6 Hz, 1H), 1.52 (d, J=13.6 Hz, 6H), 1.33 (t, J=12.0 Hz, 1H), 1.00-0.92 (m, 2H), 0.89 (q, J=5.3, 4.6 Hz, 2H), 0.71 (d, J=6.3 Hz, 3H). ESI-MS m/z calc. 591.2127, found 592.0 (M+1)$^+$; Retention time: 3.28 minutes. XRPD (see FIG. 5).

Alternate Synthesis of 2-Chloro-6-[3-[2-[1-(trifluoromethyl)cyclopropyl]ethoxy]pyrazol-1-yl]pyridine-3-carboxylic acid Step 1: ethyl 3-hydroxy-1H-pyrazole-4-carboxylate

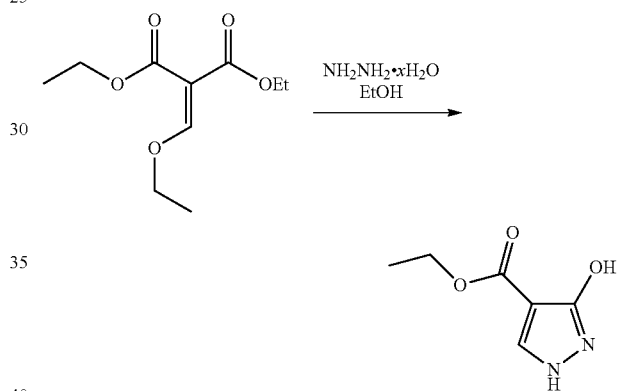

A mixture of EtOH (20.00 L, 10 vol) and diethyl 2-(ethoxymethylene)propanedioate (2000 g, 9.249 mol, 1.0 equiv) was added under nitrogen purge a to a 50 L reactor equipped with a reflux condenser (10° C.) and the jacket set to 40° C. The mixture was stirred, and then hydrazine hydrate (538.9 g of 55% w/w, 523.7 mL of 55% w/w, 9.249 mol, 1.00 equiv) was added in portions via an addition funnel. Once the addition was complete, the reaction was heated to 75° C. for 22 h to afford a solution of ethyl 3-hydroxy-1H-pyrazole-4-carboxylate that was used directly in the next step.

Step 2: 1-(tert-butyl) 4-ethyl 3-hydroxy-1H-pyrazole-1,4-dicarboxylate

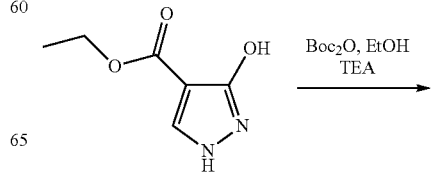

-continued

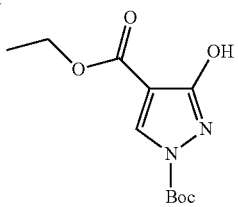

The solution of ethyl 3-hydroxy-1H-pyrazole-4-carboxylate was cooled from 75° C. to 40° C., then triethylamine (TEA) (46.80 g. 64.46 mL, 462.5 mmol, 0.05 eq.) was added. A solution of Boc anhydride (2.119 kg, 9.711 mol 1.05 equiv) in EtOH (2.000 L, 1 equiv) was added to the reactor over 35 min. The mixture was stirred for 4 hours to complete the reaction; then water (10.00 L, 5.0 vol) was added over 15 mins. The resulting mixture was cooled to 20° C. to complete crystallization of the product. The crystals were allowed to age for 1 hour, then the mixture was filtered. The solid was washed with a mixture of EtOH (4.000 L, 2.0 vol) and water (2.000 L, 1.0 vol). The solid was then dried in vacuo to afford 1-(tert-butyl)-4-ethyl-3-hydroxy-1H-pyrazole-1,4-dicarboxylate (1530 g, 65%) as colorless, fine needle, crystalline solid. $^1$H NMR (400 MHz, DMSO-$d_6$) δ 11.61 (s, 1H), 8.40 (s, 1H), 4.20 (q, J=7.1 Hz, 2H), 1.56 (s, 9H), 1.25 (t, J=7.1 Hz, 3H).

Step 3: 1-(tert-butyl) 4-ethyl 3-(2-(1-(trifluoromethyl)cyclopropyl)ethoxy)-1H-pyrazole-1,4-dicarboxylate

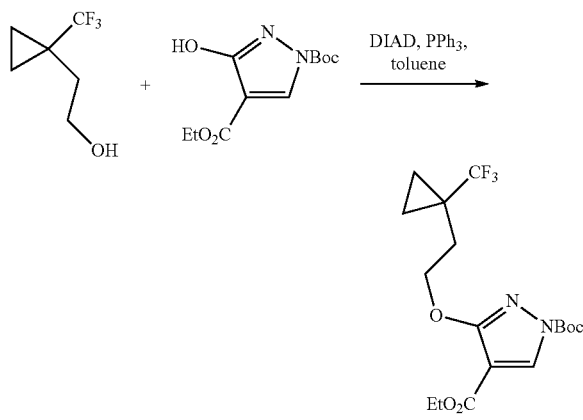

A 5 L reactor was started with the jacket set to 40° C., stirring at 450 rpm, reflux condenser at room temperature and nitrogen purge. The vessel was charged with toluene (1.0 L, 10.0 vol), 2-[1-(trifluoromethyl)cyclopropyl]ethanol (100.0 g, 648.8 mmol, 1.0 equiv), and 1-(tert-butyl) 4-ethyl 3-hydroxy-1H-pyrazole-1,4-dicarboxylate (166.3 g, 648.8 mmol), and the mixture was stirred. The reaction mixture was charged with triphenyl phosphine (195.7 g, 746.1 mmol, 1.15 equiv), then the reactor was set to maintain an internal temperature of 40° C. Diisopropyl azoldicarboxylate (150.9 g, 746.1 mmol, 1.15 equiv) was added into an addition funnel and was added to the reaction while maintaining the reaction temperature between 40 and 50° C. (addition was exothermic, exotherm addition controlled), and stirred for a total of 2.5 hours. Once the reaction was deemed complete by HPLC, heptane was added (400 mL, 4 vol), the solution was cooled to 20° C. over 60 minutes, and the bulk of triphenylphosphine oxide-DIAD complex (TPPO-DIAD) crystallized out. Once at room temp, the mixture was filtered, and the solid was washed with heptane (400 mL, 4.0 vol) and pulled dry. The filtrate was used in the next step as a solution in toluene-heptane without further purification.

Step 4: ethyl 3-(2-(1-(trifluoromethyl)cyclopropyl)ethoxy)-1H-pyrazole-4-carboxylate

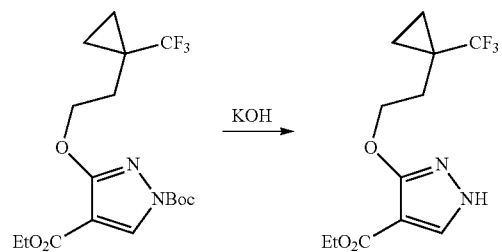 [SMILES: CCOC(=O)c1cn(C(=O)OC(C)(C)C)nc1OCCC1(C(F)(F)F)CC1 ; "KOH" ; CCOC(=O)c1c[nH]nc1OCCC1(C(F)(F)F)CC1]

A 500 mL reactor was started with the jacket set to 40° C., stirring at 450 rpm, reflux condenser at room temp, and nitrogen purge. The vessel was charged with a toluene solution consisting of approximately 160 mmol, 65.0 g of 1-(tert-butyl) 4-ethyl 3-(2-(1-(trifluoromethyl)cyclopropyl)ethoxy)-1H-pyrazole-1,4-dicarboxylate in 3 vol of toluene (prepared by concentrating a 25% portion of filtrate from previous reaction down to 4 volumes in a rotovap). The reaction was set to maintain an internal temperature at 40° C. and KOH (33.1 g, 1.5 eq. of aqueous 45% KOH solution) was added in one portion, resulting in a mild exothermic addition, while $CO_2$ was generated upon removal of the protecting group. The reaction proceeded for 1.5 hr, monitored by HPLC, with the product partially crystallizing during the reaction. Heptane (160 mL, 2.5 vol) was added to the reaction mixture and the reaction was cooled to room temperature over 30 minutes. The resulting mixture was filtered, and the solid was washed with heptane (80.00 mL, 1.25 vol), pulled dry, then dried in vacuo (55° C., vacuum). 52.3 g of ethyl 3-(2-(1-(trifluoromethyl)cyclopropyl)ethoxy)-1H-pyrazole-4-carboxylate was obtained as a crude, colorless solid that was used without further purification.

Step 5: 3-(2-(1-(trifluoromethyl)cyclopropyl)ethoxy)-1H-pyrazole-4-carboxylic acid

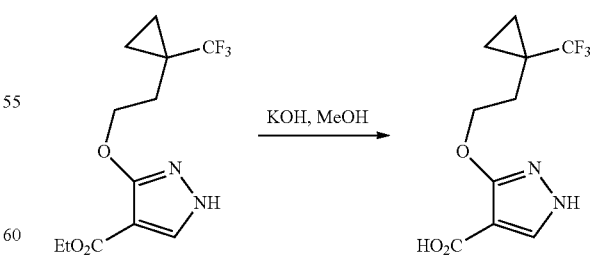

A 500 mL reactor was started with the jacket set to 40° C., stirring at 450 rpm, reflux condenser at room temp, and nitrogen purge. The vessel was charged with methanol (150.0 mL, 3.0 vol), a solution of ethyl 3-(2-(1-(trifluoromethyl)cyclopropyl)ethoxy)-1H-pyrazole-4-carboxylate (50.0 g, 171.1 mmol, 1.0 equiv), and the reaction was stirred to suspend the solids. The reactor was set to maintain internal temperature at 40° C. To the mixture was added KOH (96 g of aqueous 45% KOH, 1.71 mol, 10.0 equiv) in portions maintaining the internal temperature <50° C. Once addition was complete, the reaction was set to maintain temperature at 50° C., and the reaction proceeded for 23 hours, monitored by HPLC. Once complete the reaction was cooled to 10° C. then partially concentrated on a rotary evaporator to remove most of the MeOH. The resulting solution was diluted with water (250 mL, 5.0 vol) and 2-Me-THF (150 mL, 3.0 vol), and transferred to the reactor, stirred at room temp, then stopped, and layers were allowed to separate. The layers were tested, with remaining TPPO-DIAD complex in the organic layer and product in the aqueous layer. The aqueous layer was washed again with 2-Me-THF (100 mL, 2.0 vol), the layers separated, and the aqueous layer returned to the reactor vessel. The stirrer was started and set to 450 rpm, and the reactor jacket was set to 0° C. The pH was adjusted to pH acidic by addition of 6M aqueous HCl (427 mL, 15 equiv) portion wise, maintaining the internal temperature between 10 and 30° C. The product began to crystallize close to pH neutral and was accompanied with strong off-gassing, and so the acid was added slowly, and then further added to reach pH 1 once the off-gassing had ended. To the resulting suspension was added 2-Me-THF (400 mL, 8.0 vol), and the product was allowed to dissolve into the organic layer. Stirring was stopped, the layers were separated, and the aqueous layer was returned to the reactor, stirred and re-extracted with 2-Me-THF (100 mL, 2.0 vol). The organic layers were combined in the reactor and stirred at room temperature, washed with brine (100 mL, 2 vols), dried over Na$_2$SO$_4$, filtered through celite, and the solid was washed with 2-Me-THF (50 mL, 1.0 vol). The filtrate was transferred to a clean rotovap flask, stirred, warmed to 50° C. and heptane (200 mL, 4.0 vol) added, and then partially concentrated with the addition of heptane (300 mL, 6.0 vol) and then seeded with 50 mg of 3-(2-(1-(trifluoromethyl)cyclopropyl)ethoxy)-1H-pyrazole-4-carboxylic acid), and the product crystallized during solvent removal. The distillation was stopped when the bulk of the 2-Me-THF had distilled off. The bath heater was turned off, the vacuum removed, and the mixture was allowed to stir and cool to room temperature. The mixture was filtered (slow speed) and the solid was washed with heptane (100 mL, 2.0 vol), and the solid was collected and dried in vacuo (50° C., rotovap). 22.47 g of 3-(2-(1-(trifluoromethyl)cyclopropyl)ethoxy)-1H-pyrazole-4-carboxylic acid was obtained as an off-white solid. $^1$H NMR (400 MHz, DMSO-d$_6$) δ 12.45 (s, 2H), 8.01 (s, 1H), 4.26 (t, J=7.0 Hz, 2H), 2.05 (t, J=7.0 Hz, 2H), 0.92 (m, 4H).

Step 6: 3-(2-(1-(trifluoromethyl)cyclopropyl)ethoxy)-1H-pyrazole

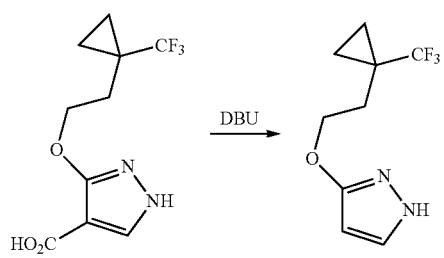 [SMILES: O=C(O)c1c[nH]nc1OCCC1(C(F)(F)F)CC1 ; "DBU" ; FC(F)(F)C1(CCOc2cc[nH]n2)CC1]

A mixture of toluene (490.0 mL), 3-(2-(1-(trifluoromethyl)cyclopropyl)ethoxy)-1H-pyrazole-4-carboxylic acid (70.0 g, 264.9 mmol), and DMSO (70.00 mL) was placed in a reactor and heated to 100° C. with stirring. DBU (approximately 20.16 g, 19.80 mL, 132.4 mmol) was added to the reactor over 15 min. The mixture was stirred for 20 h to complete the reaction and then cooled to 20° C. The mixture was washed with water (350.0 mL), then 0.5N aq HCl (280.0 mL), then water (2×140.0 mL), and lastly with brine (210.0 mL). The organic layer was dried with Na$_2$SO$_4$, and then activated charcoal (5 g, Darco 100 mesh) was added to the stirred slurry. The dried mixture was filtered through celite, and the solid was washed with toluene (140.0 mL) and then pulled dry. The filtrate was concentrated in a rotovap (50° C., vac) to afford 3-[2-[1-(trifluoromethyl)cyclopropyl]ethoxy]-1H-pyrazole (30.89 g, 53%) as an amber oil. $^1$H NMR (400 MHz, DMSO-d$_6$) δ 11.87 (s, 1H), 7.50 (d, J=2.4 Hz, 1H), 5.63 (d, J=2.4 Hz, 1H), 4.23-4.06 (m, 2H), 2.01 (t, J=7.1 Hz, 2H), 1.00-0.77 (m, 4H).

Step 7: ethyl 2-chloro-6-[3-[2-[1-(trifluoromethyl)cyclopropyl]ethoxy]pyrazol-1-yl]pyridine-3-carboxylate

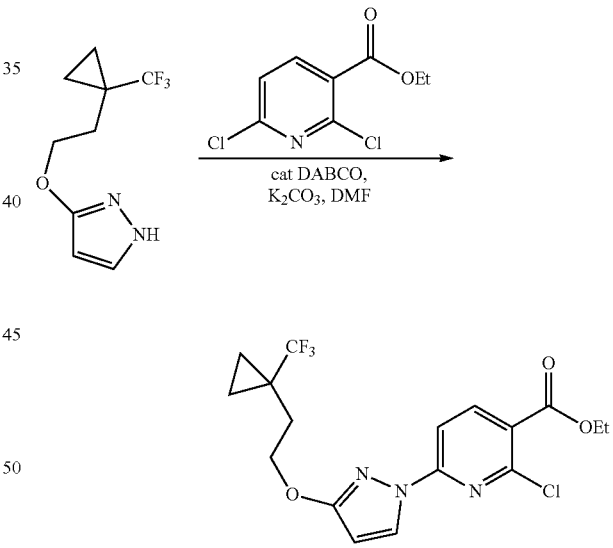

A mixture of DMF (180.0 mL), ethyl 2,6-dichloropyridine-3-carboxylate (approximately 29.97 g, 136.2 mmol), 3-[2-[1-(trifluoromethyl)cyclopropyl]ethoxy]-1H-pyrazole (30.0 g, 136.2 mmol), and K$_2$CO$_3$, (325 mesh, approximately 24.48 g, 177.1 mmol) was added to a stirred reactor at 20° C. DABCO (approximately 2.292 g, 20.43 mmol) was then added to the reactor, and the mixture was stirred at 20° C. for 1 hour, and then the temperature was increased to 30° C., and the mixture stirred for 24 hours to complete the reaction. The mixture was cooled to 20° C. then water (360 mL) was added slowly. The mixture was then drained from the reactor and the solid was isolated by filtration. The solid was then washed with water (2×150 mL), and then the solid was dried under vacuum at 55° C. to afford ethyl 2-chloro-6-[3-[2-[1-(trifluoromethyl)cyclopropyl]ethoxy]pyrazol-1-yl]pyridine-3-carboxylate (51.37 g, 93%) as a fine, beige colored solid. $^1$H NMR (400 MHz, DMSO-d$_6$) δ 8.44 (d, J=2.9 Hz, 1H), 8.41 (d, J 8.5 Hz, 1H), 7.75 (d, J=8.5 Hz, 1H), 6.21 (d, J=2.9 Hz, 1H), 4.34 (m, 4H), 2.09 (t, J=7.1 Hz, 2H), 1.34 (t, J=7.1 Hz, 3H), 1.00-0.84 (m, 4H).

Step 8: 2-Chloro-6-[3-[2-[1-(trifluoromethyl)cyclopropyl]ethoxy]pyrazol-1-yl]pyridin

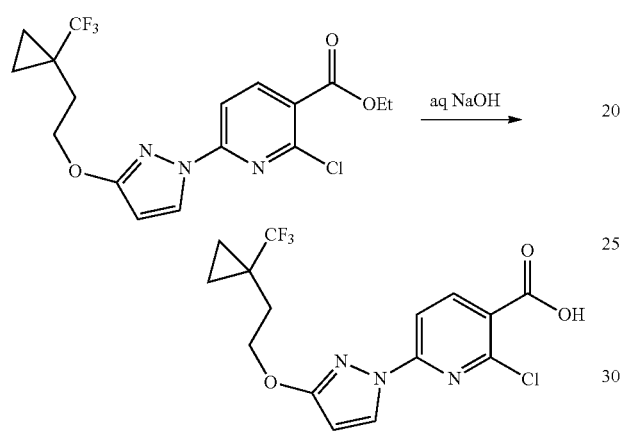

A solution of ethyl 2-chloro-6-[3-[2-[1-(trifluoromethyl)cyclopropyl]ethoxy]pyrazol-1-yl]pyridine-3-carboxylate (50.0 g, 123.8 mmol) in THF (300.0 mL) was prepared in a reactor at 20° C. EtOH (150.0 mL) was added, followed by aqueous NaOH (approximately 59.44 g of 10% w/w, 148.6 mmol). The mixture was stirred for 1 hour to complete the reaction; then aq 1N HCl (750.0 mL) was slowly added. The resulting suspension was stirred for 30 min at 10° C., and then the solid was isolated by filtration. The solid was washed with water (150 mL then 2×100 mL) and then pulled dry by vacuum. The solid was then further dried under vacuum with heating to afford 2-chloro-6-[3-[2-[1-(trifluoromethyl)cyclopropyl]ethoxy]pyrazol-1-yl]pyridine-3-carboxylic acid (42.29 g, 91%). $^1$H NMR (400 MHz, DMSO-d$_6$) δ 13.63 (s, 1H), 8.48-8.35 (m, 2H), 7.73 (d, J=8.4 Hz, 1H), 6.20 (d, J=2.9 Hz, 1H), 4.35 (t, J=7.1 Hz, 2H), 2.09 (t, J=7.1 Hz, 2H), 1.01-0.82 (m, 4H).

SYNTHETIC EXAMPLE 2

Synthesis of Compound 2, (R)—N-(Phenylsulfonyl)-6-(3-(2-(1-(trifluoromethyl)cyclopropyl)ethoxy)-1H-pyrazol-1-yl)-2-(2,2,4-trimethylpyrrolidin-1-yl)nicotinamide

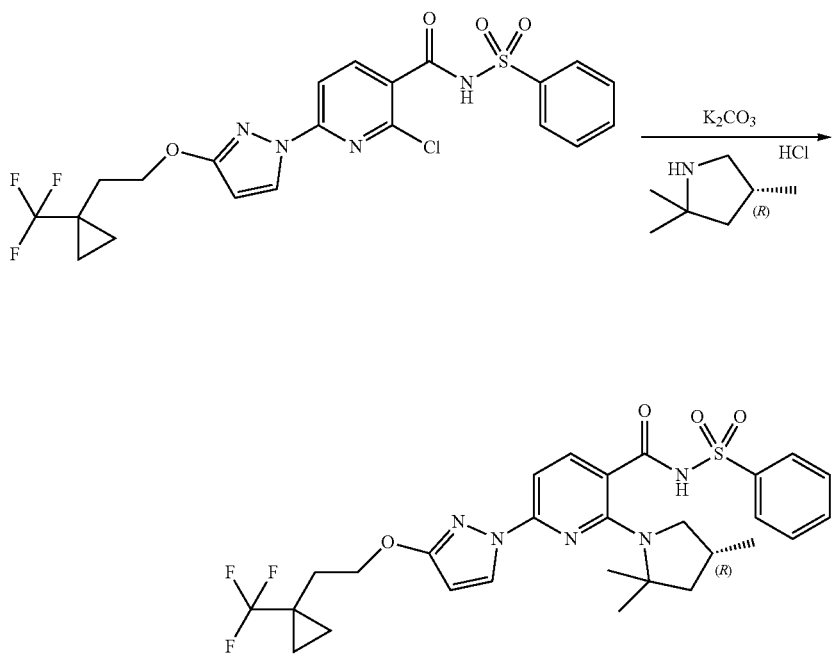

(R)—N-(Phenylsulfonyl)-6-(3-(2-(1-(trifluoromethyl)cyclopropyl)ethoxy)-1H-pyrazol-1-yl)-2-(2,2,4-trimethylpyrrolidin-1-yl)nicotinamide was synthesized in a manner analogous to Compound 1 using N-(benzenesulfonyl)-2-chloro-6-[3-[2-[1-(trifluoromethyl)cyclopropyl]ethoxy]pyrazol-1-yl]pyridine-3-carboxamide (1.5 g, 2.91 mmol), potassium carbonate (2.0 g, 14.56 mmol), (4R)-2,2,4-trimethylpyrrolidine (hydrochloride salt) (1.0 g, 6.7 mmol) in NMP (N-Methyl-2-pyrrolidone) (7.5 mL) and 1,2-diethoxyethane (1.5 mL) affording N-(benzenesulfonyl)-6-[3-[2-[1-(trifluoromethyl)cyclopropyl]ethoxy]pyrazol-1-yl]-2-[(4R)-2,2,4-trimethylpyrrolidin-1-yl]pyridine-3-carboxamide (1.38 g, 79%). ESI-MS m/z calc. 591.2127, found 592.0 (M+1)$^+$; Retention time: 2.3 minutes. $^1$H NMR (400 MHz, DMSO-d6) δ 12.51 (s, 1H), 8.19 (d, J=2.8 Hz, 1H), 8.03-7.96 (m, 2H), 7.81 (d, J=8.2 Hz, 1H), 7.76-7.69 (m, 1H), 7.66 (dd, J=8.3, 6.7 Hz, 2H), 6.91 (d, J=8.2 Hz, 1H), 6.11 (d, J=2.8 Hz, 1H), 4.31 (t, J=7.0 Hz, 2H), 2.41 (t, J=10.5 Hz, 1H), 2.27 (t, J=8.7 Hz, 1H), 2.07 (t, J=7.1 Hz, 3H), 1.82 (dd, J=11.9, 5.5 Hz, 1H), 1.52 (d, J=9.4 Hz, 6H), 1.36 (t, J=12.1 Hz, 1H), 0.99-0.92 (m, 2H), 0.88 (tt, J=3.9, 1.6 Hz, 2H), 0.64 (d, J=6.3 Hz, 3H).

SYNTHETIC EXAMPLE 3

Synthesis of Compound 3, (S)—N-((4-Hydroxy-3-methoxyphenyl)sulfonyl)-6-(3-(2-(1-(trifluoromethyl)cyclopropyl)ethoxy)-1H-pyrazol-1-yl)-2-(2,2,4-trimethylpyrrolidin-1-yl)nicotinamide Step A: 2-Chloro-N-((4-hydroxy-3-methoxyphenyl)sulfonyl)-6-(3-(2-(1-(trifluoromethyl)cyclopropyl)ethoxy)-1H-pyrazol-1-yl)nicotinamide

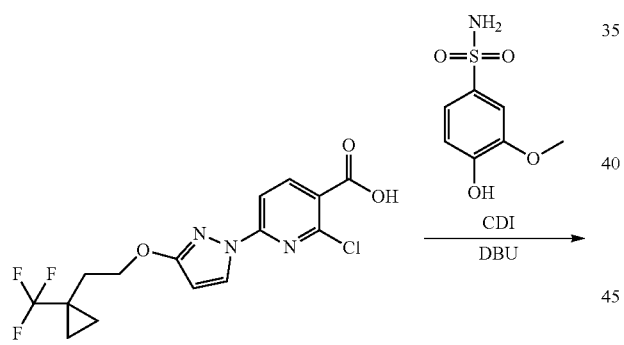

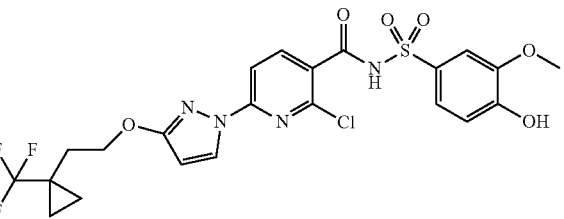

A solution of 2-chloro-6-[3-[2-[1-(trifluoromethyl)cyclopropyl]ethoxy]pyrazol-1-yl]pyridine-3-carboxylic acid (0.843 g, 2.24 mmol) and carbonyl diimidazole (434 mg, 2.68 mmol) in THF (2.5 mL) was stirred for 2.5 hours, and 4-hydroxy-3-methoxybenzenesulfonamide (0.500 g, 2.46 mmol) and DBU (0.5 mL, 3.35 mmol) were added. The reaction was stirred for 21 hours, diluted with ethyl acetate (5 mL) acidified with 1 N aqueous hydrochloric acid (10 mL), and extracted with ethyl acetate. The combined extracts were washed with brine, dried over sodium sulfate and evaporated. The residue was purified by silica gel chromatography eluting with a gradient of ethyl acetate in hexanes (50-100%) to give 2-chloro-N-((4-hydroxy-3-methoxyphenyl)sulfonyl)-6-(3-(2-(1-(trifluoromethyl)cyclopropyl)ethoxy)-1H-pyrazol-1-yl)nicotinamide (906 mg, 72%). ESI-MS m/z calc. 560.07, found 515.1 (M+1)$^+$; Retention time: 0.74 minutes.

Step B: (S)—N-((4-Hydroxy-3-methoxyphenyl)sulfonyl)-6-(3-(2-(1-(trifluoromethyl)cyclopropyl)ethoxy)-1H-pyrazol-1-yl)-2-(2,2,4-trimethylpyrrolidin-1-yl)nicotinamide

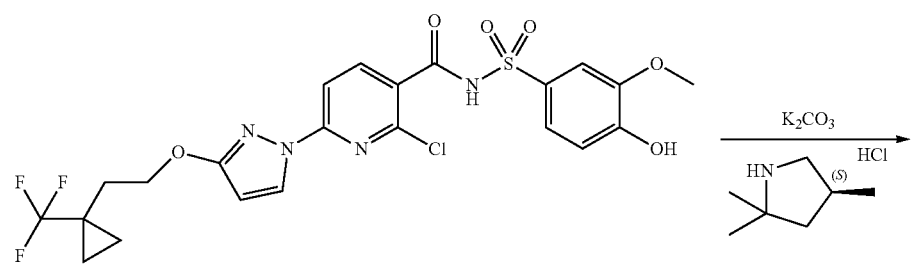

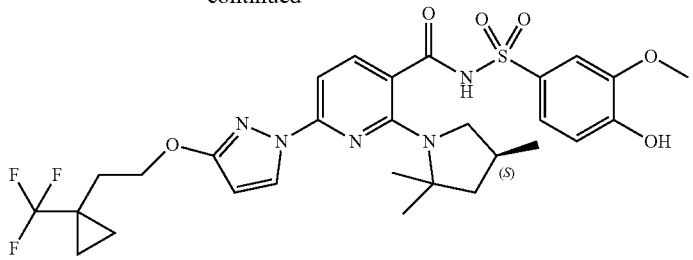

A mixture of 2-chloro-N-((4-hydroxy-3-methoxyphenyl)sulfonyl)-6-(3-(2-(1-(trifluoromethyl)cyclopropyl)ethoxy)-1H-pyrazol-1-yl)nicotinamide (906 mg, 1.62 mmol), (4S)-2,2,4-trimethylpyrrolidine hydrochloride salt (545 mg, 3.64 mmol), and potassium carbonate (1.29 g, 9.33 mmol) in DMSO (5.5 mL) was stirred at 120° C. for 24 hours. The reaction mixture was diluted with 15 mL of water and 5 mL of ethyl acetate. The reaction mixture was then acidified with 6 N aqueous hydrochloric acid the layers were separated. The aqueous layer was extracted with 10 mL of ethyl acetate. The combined extracts were washed with brine, dried over sodium sulfate and evaporated to yield a crude product that was purified by silica gel chromatography utilizing a gradient of ethyl acetate in hexanes to yield (S)—N-((4-hydroxy-3-methoxyphenyl)sulfonyl)-6-(3-(2-(1-(trifluoromethyl)cyclopropyl)ethoxy)-1H-pyrazol-1-yl)-2-(2,2,4-trimethylpyrrolidin-1-yl)nicotinamide (470 mg, 45%). ESI-MS m/z calc. 637.2, found 638.2 (M+1)$^+$; Retention time: 10.07 minutes.

SYNTHETIC EXAMPLE 4

Synthesis of Compound 4, N-(o-Tolylsulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide Step A: 2-Chloro-N-(o-tolylsulfonyl)-6-[3-[2-[1-(trifluoromethyl)cyclopropyl]ethoxy]pyrazol-1-yl]pyridine-3-carboxamide

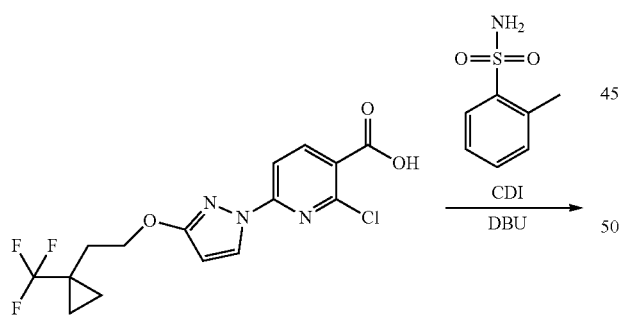

To 2-chloro-6-[3-[2-[1-(trifluoromethyl)cyclopropyl]ethoxy]pyrazol-1-yl]pyridine-3-carboxylic acid (196 mg, 0.5217 mmol) in THF (1.739 mL) was added 1,1'-carbonyldiimidazole (approximately 106.6 mg, 0.6573 mmol) and reaction was stirred for one hour. 2-Methylbenzenesulfonamide (approximately 89.32 mg, 0.5217 mmol) was added, followed by 1,8-diazabicyclo[5.4.0]undec-7-ene (DBU) (approximately 262.2 mg, 257.6 L, 1.722 mmol) and reaction was stirred for 3 hours. The reaction was diluted with ethyl acetate and 1 M aqueous citric acid and the layers were separated. The organic layers were dried and concentrated and resulting solid 2-chloro-N-(o-tolylsulfonyl)-6-[3-[2-[1-(trifluoromethyl)cyclopropyl]ethoxy]pyrazol-1-yl]pyridine-3-carboxamide (approximately 252 mg) was used for next step without characterization.

Step B: N-(o-Tolylsulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

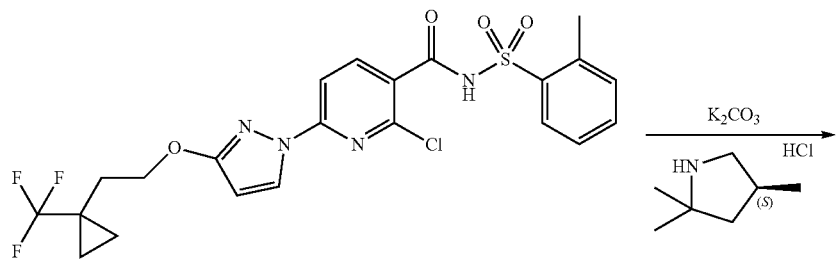

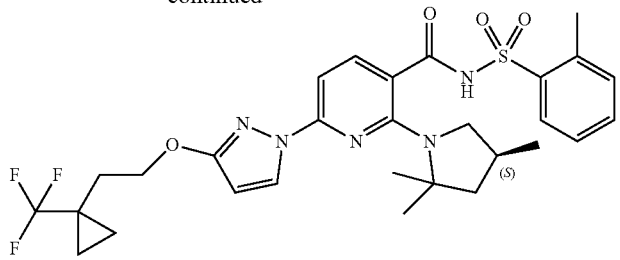

To 2-chloro-N-(o-tolylsulfonyl)-6-[3-[2-[1-(trifluoromethyl)cyclopropyl]ethoxy]pyrazol-1-yl]pyridine-3-carboxamide (approximately 252 mg) and potassium carbonate (392 mg, 2.84 mmol) in 0.4 mL of DMSO was added (4S)-2,2,4-trimethylpyrrolidine (hydrochloride salt) (212 mg, 1.42 mmol) and reaction was stirred at 130° C. for 16 hours. The reaction was cooled, diluted with ethyl acetate and 1 M aqueous citric acid and the layers were separated. The organics were dried, concentrated and the resulting residue was purified with silica gel (24 g) eluting with 0-14% methanol in dichloromethane to give N-(o-tolylsulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (60.6 mg, 19%) $^1$H NMR (400 MHz, DMSO-d6) δ 12.63 (s, 1H), 8.19 (d, J=2.8 Hz, 1H), 8.04 (dd, J=7.9, 1.4 Hz, 1H), 7.81 (d, J=8.2 Hz, 1H), 7.58 (td, J=7.5, 1.5 Hz, 1H), 7.50-7.40 (m, 2H), 6.93 (d, J=8.3 Hz, 1H), 6.10 (d, J=2.7 Hz, 1H), 4.31 (t, J=7.1 Hz, 2H), 2.64 (s, 3H), 2.39 (d, J=8.8 Hz, 2H), 2.16 (ddt, J=11.8, 9.0, 4.5 Hz, 1H), 2.08 (t, J=7.0 Hz, 2H), 1.82 (dd, J=11.9, 5.6 Hz, 1H), 1.52 (s, 6H), 1.35 (t, J=12.1 Hz, 1H), 1.00-0.93 (m, 2H), 0.92-0.84 (m, 2H), 0.69 (d, J=6.2 Hz, 3H). ESI-MS m/z calc. 605.23, found 606.4 (M+1)$^+$; Retention time: 1.92 minutes

SYNTHETIC EXAMPLE 5

Synthesis of Compound 5, N-(3-Fluorophenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide Step A: 2-Chloro-N-(3-fluorophenyl)sulfonyl-6-[3-[2-[1-(trifluoromethyl)cyclopropyl]ethoxy]pyrazol-1-yl]pyridine-3-carboxamide

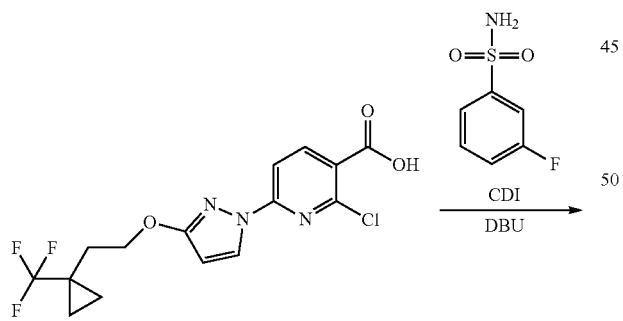

To 2-chloro-6-[3-[2-[1-(trifluoromethyl)cyclopropyl]ethoxy]pyrazol-1-yl]pyridine-3-carboxylic acid (0.200 g, 0.532 mmol) in THF (1.7 mL) was added 1,1'-carbonyldiimidazole (108.8 mg, 0.6707 mmol) and reaction was stirred for 1 hour. 3-Fluorobenzenesulfonamide (93.25 mg, 0.5323 mmol) was added, followed by 1,8-diazabicyclo(5.4.0)undec-7-ene (DBU) (267.5 mg, 262.8 µL, 1.757 mmol) and reaction was stirred for 2 hours. The reaction was diluted with ethyl acetate and 1 M aqueous citric acid and layers were separated. The organics were dried and concentrated and resulting solid 2-chloro-N-(3-fluorophenyl)sulfonyl-6-[3-[2-[1-(trifluoromethyl)cyclopropyl]ethoxy]pyrazol-1-yl]pyridine-3-carboxamide (approximately 259 mg) was used in the next step without characterization.

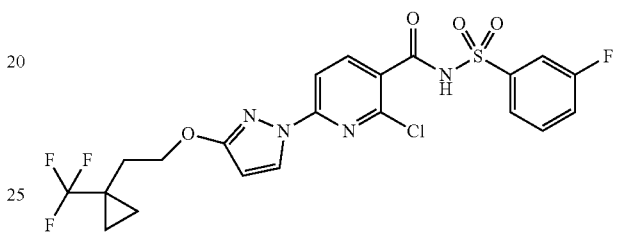

Step B: N-(3-Fluorophenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

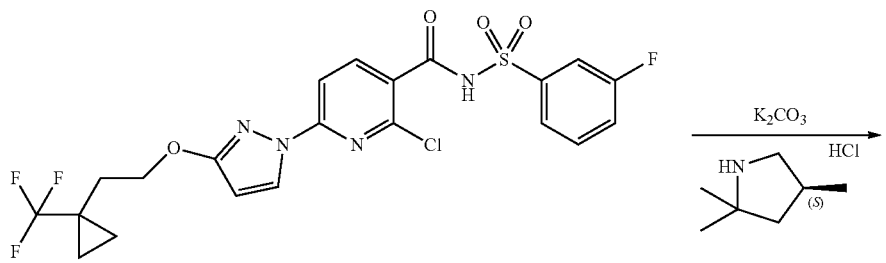

-continued

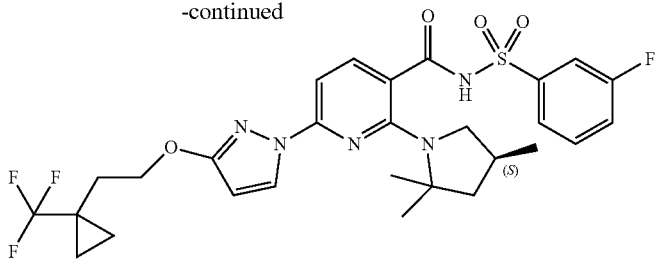

To 2-chloro-N-(3-fluorophenyl)sulfonyl-6-[3-[2-[1-(trifluoromethyl)cyclopropyl]ethoxy]pyrazol-1-yl]pyridine-3-carboxamide (approximately 259 mg, 0.486 mmol) and potassium carbonate (389.6 mg, 2.819 mmol) in 0.4 mL of DMSO was added (4S)-2,2,4-trimethylpyrrolidine (hydrochloride salt) (211.0 mg, 1.41 mmol) and the reaction was stirred at 130° C. for 16 hours. The reaction was cooled, diluted with ethyl acetate and 1 M aqueous citric acid and the layers were separated. The organics were dried, concentrated and resulting the residue was purified on silica gel (24 g) eluting with 0-14% methanol in dichloromethane to give N-(3-fluorophenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (50.0 mg, 15%) $^1$H NMR (400 MHz, Methanol-d4) δ 8.23 (d, J=2.7 Hz, 1H), 7.96-7.89 (m, 1H), 7.87-7.77 (m, 2H), 7.65 (td, J=8.1, 5.3 Hz, 1H), 7.46 (tdd, J=8.5, 2.5, 1.0 Hz, 1H), 7.02 (d, J=8.3 Hz, 1H), 5.95 (d, J=2.8 Hz, 1H), 4.37 (t, J=7.0 Hz, 2H), 3.34 (s, 1H), 2.68 (t, J=10.3 Hz, 1H), 2.56-2.48 (m, 1H), 2.28-2.16 (m, 1H), 2.10 (t, J=7.0 Hz, 2H), 1.89 (dd, J=11.9, 5.7 Hz, 1H), 1.59 (d, J=9.7 Hz, 6H), 1.48 (t, J=12.1 Hz, 1H), 1.02-0.96 (m, 2H), 0.86-0.77 (m, 5H). ESI-MS m/z calc. 609.2, found 610.3 (M+1)$^+$; Retention time: 0.81 minutes

SYNTHETIC EXAMPLE 6

Synthesis of Compound 6, 2-[(4S)-3,3-Dideuterio-2,2-dimethyl-4-(trideuteriomethyl)pyrrolidin-1-yl]-N-(4-hydroxyphenyl)sulfonyl-6-[3-[2-[1-(trifluoromethyl)cyclopropyl]ethoxy]pyrazol-1-yl]pyridine-3-carboxamide Step A: 2-Chloro-N-(4-hydroxyphenyl)sulfonyl-6-[3-[2-[1-(trifluoromethyl)cyclopropyl]ethoxy]pyrazol-1-yl]pyridine-3-carboxamide

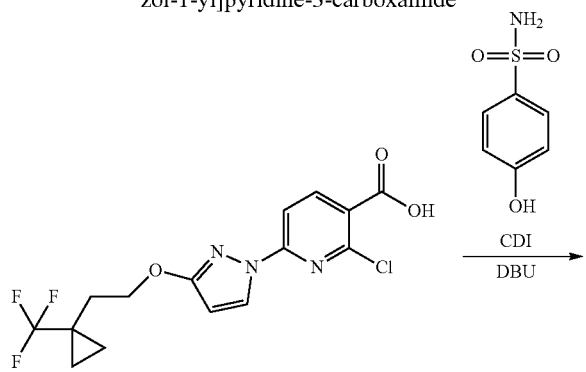

-continued

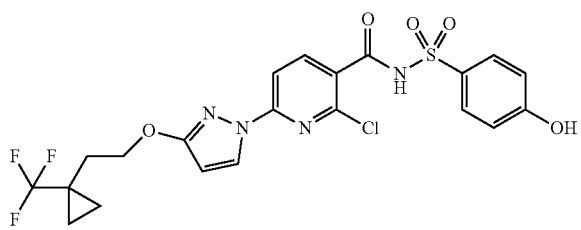

2-Chloro-6-[3-[2-[1-(trifluoromethyl)cyclopropyl]ethoxy]pyrazol-1-yl]pyridine-3-carboxylic acid (0.100 g, 0.266 mmol) and CDI (approximately 51.38 mg, 0.3169 mmol) were combined in THF (600.0 µL) and stirred at room temperature for 2 hours. 4-Hydroxybenzenesulfonamide (approximately 50.69 mg, 0.2927 mmol) was added followed by DBU (approximately 54.41 mg, 53.45 µL, 0.3574 mmol) and the reaction was stirred for an additional 16 hours at room temperature. The reaction mixture was diluted with 10 mL of 1 M aqueous citric acid, and extracted with three 10 mL portions of ethyl acetate. The combined organics were washed with brine, dried over sodium sulfate, and concentrated to give a white solid 2-chloro-N-(4-hydroxyphenyl)sulfonyl-6-[3-[2-[1-(trifluoromethyl)cyclopropyl]ethoxy]pyrazol-1-yl]pyridine-3-carboxamide (128 mg, 91%) which was used in the next step without further purification. ESI-MS m/z calc. 530.1, found 531.0 (M+1)$^+$; Retention time: 0.69 minutes.

Step B: 2-[(4S)-3,3-Dideuterio-2,2-dimethyl-4-(trideuteriomethyl)pyrrolidin-1-yl]-N-(4-hydroxyphenyl)sulfonyl-6-[3-[2-[1-(trifluoromethyl)cyclopropyl]ethoxy]pyrazol-1-yl]pyridine-3-carboxamide

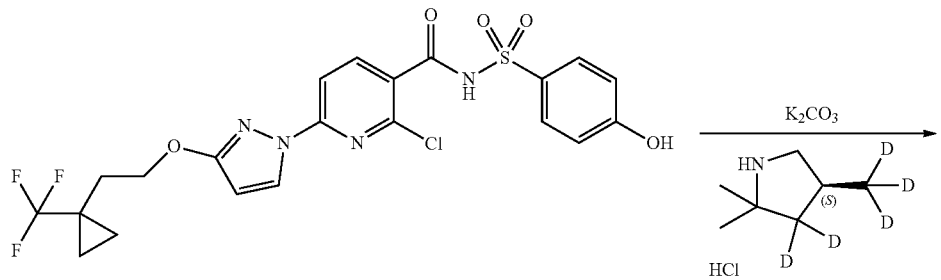

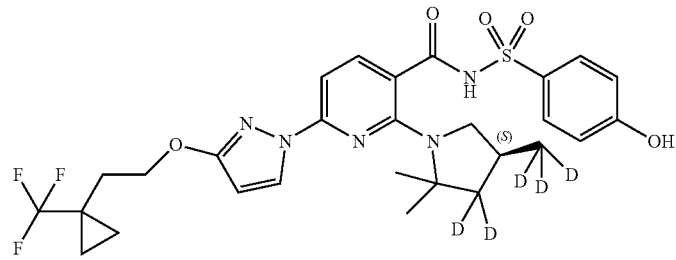

2-Chloro-N-(4-hydroxyphenyl)sulfonyl-6-[3-[2-[1-(trifluoromethyl)cyclopropyl]ethoxy]pyrazol-1-yl]pyridine-3-carboxamide (1.0 g, 1.9 mmol), (S)-2,2-dimethyl-4-(methyl-d)pyrrolidine-3,3-d$_2$ hydrochloride salt (0.892 g, 5.66 mmol) and potassium carbonate (1.55 g. 11.2 mmol) were combined in DMSO (6 mL) and heated to 130° C. for and 16 hours. The reaction was cooled to room temperature, and diluted with water (10 mL). After stirring for 15 minutes ethyl acetate (50 mL) was added to the mixture. The mixture was acidified with 1M aqueous citric acid (pH-3-4) (30 mL) and the layers were separated. The organics were combined, washed with brine, dried over sodium sulfate and concentrated. The crude material obtained was purified by column chromatography (24 g of silica gel) utilizing a gradient of 0-30% ethyl acetate in heptane. Individual fractions were analyzed by HPLC and the fractions that met the required purity specifications were combined, evaporated and triturated in a mixture of 9:1 ethyl acetate/MTBE. The organics were evaporated down to 10% and the solid obtained was filtered and dried overnight under high vacuum to afford 2-[(4S)-3,3-dideuterio-2,2-dimethyl-4-(trideuteriomethyl)pyrrolidin 1-yl]-N-(4-hydroxyphenyl)sulfonyl-6-[3-[2-[1-(trifluoromethyl)cyclopropyl]ethoxy]pyrazol-1-yl]pyridine-3-carboxamide (0.38 g, 32%) ESI-MS m/z calc. 612.2, found 613.7 (M+1)$^+$; Retention time: 1.40 minutes.

SYNTHETIC EXAMPLE 7

Synthesis of Compound 7, N-(Benzenesulfonyl)-2-[(4S)-3,3-dideuterio-2,2-dimethyl-4-(trideuteriomethyl)pyrrolidin-1-yl]-6-[3-[2-hydroxy-2-[1-(trifluoromethyl)cyclopropyl]ethoxy]pyrazol-1-yl]pyridine-3-carboxamide

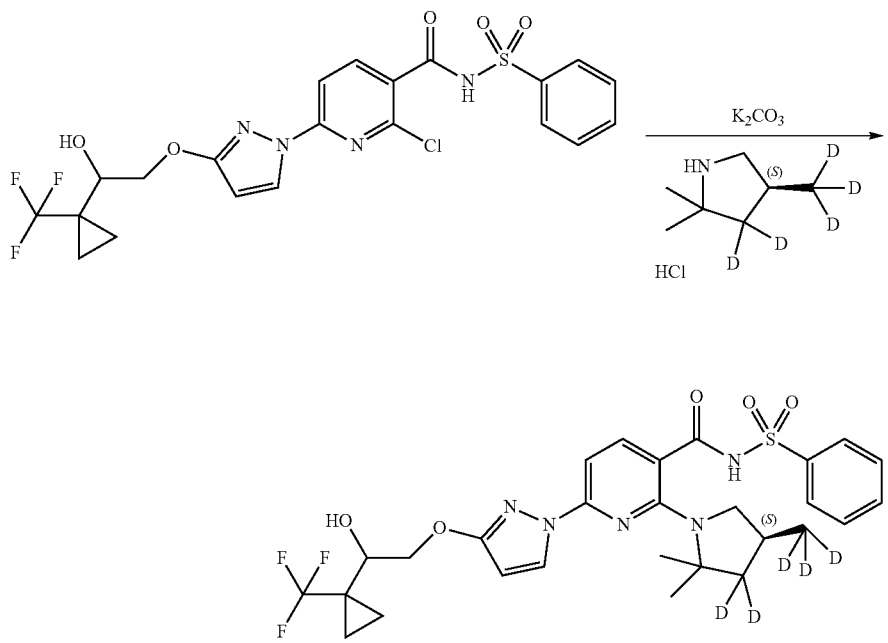

A reaction vessel was charged with N-(benzenesulfonyl)-2-chloro-6-[3-[2-hydroxy-2-[1-(trifluoromethyl)cyclopropyl]ethoxy]pyrazol-1-yl]pyridine-3-carboxamide (0.500 g, 0.942 mmol), (4S)-3,3-dideuterio-2,2-dimethyl-4-(trideuteriomethyl)pyrrolidine (Hydrochloride salt) (320 mg, 2.07 mmol), NMP (3.000 mL) and 1,2-diethoxyethane (500.0 µL) under an atmosphere of nitrogen. Potassium carbonate (650.8 mg, 4.709 mmol) was added and the reaction mixture was heated to 130° C. The reaction mixture was stirred overnight. The reaction mixture was cooled and diluted with water (2.000 mL) and adjusted pH to <3 with aqueous HCl (1.3 mL of 6 M, 7.800 mmol), which was added dropwise. The pH was adjusted further with hydrogen chloride (146.0 µL of 6 M, 0.8760 mmol). The aqueous layer was extracted with ethyl acetate (4 mL) twice and the combined organic layers were washed with water twice, brine, and dried over sodium sulfate. The organic layer was then concentrated to a residue which was purified on silica gel utilizing a gradient of 0-60% ethyl acetate in hexanes. This material was then triturated in a mixture of heptanes and MTBE to yield N-(benzenesulfonyl)-2-[(4S)-3,3-dideuterio-2,2-dimethyl-4-(trideuteriomethyl)pyrrolidin-1-yl]-6-[3-[2-hydroxy-2-[1-(trifluoromethyl)cyclopropyl]ethoxy]pyrazol-1-yl]pyridine-3-carboxamide (266 mg, 46%) ESI-MS m/z calc. 612.2, found 613.1 (M+1)$^+$, Retention time: 1.67 minutes. $^1$H NMR (400 MHz, DMSO-d6) δ 12.51 (s, 1H), 8.20 (d, J=2.8 Hz, 1H), 8.05-7.94 (m, 2H), 7.81 (d, J=8.3 Hz, 1H), 7.72 (d, J=7.3 Hz, 1H), 7.65 (t, J=7.6 Hz, 2H), 6.90 (d, J=8.2 Hz, 1H), 6.12 (d, J=2.8 Hz, 1H), 5.57 (dd, J=5.5, 2.7 Hz, 1H), 4.42-4.28 (m, 1H), 4.23-4.09 (m, 1H), 3.89 (d, J=4.9 Hz, 1H), 2.39 (d, J=10.5 Hz, 1H), 2.37-2.22 (m, 1H), 2.06 (dd, J=10.6, 7.0 Hz, 1H), 1.52 (d, J=9.7 Hz, 6H), 1.04-0.83 (m, 4H).

Synthesis of (4S)-3,3-Dideuterio-2,2-dimethyl-4-(trideuteriomethyl)pyrrolidine Hydrochloride

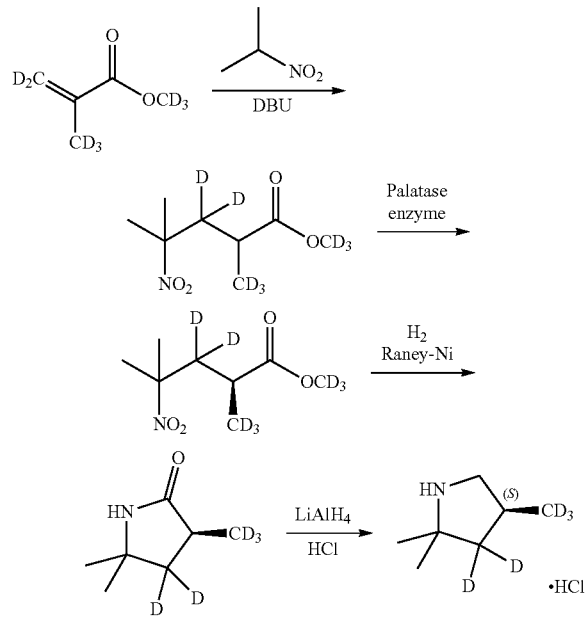

Step A: Methyl-d$_3$ 4-methyl-2-(methyl-d$_3$)-4-nitropentanoate-3,3-d$_2$

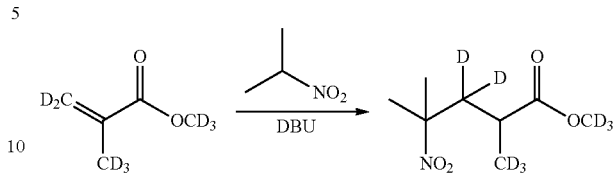

A 500-mL, three-neck round bottom flask equipped with a magnetic stir bar, a nitrogen line and a J-Kem thermocouple with heating mantle was charged with 2-nitropropane (34.3 g, 385 mmol), d$_8$-methyl methacrylate (50.0 g, 460 mmol), and was stirred at ambient temperature when 1,8-diazabicyclo[5.4.0]undec-7-ene (DBU, 1.47 g, 9.62 mmol) was added in one portion. The reaction solution exothermed from 20 to –40° C. and was allowed to stir without heating or cooling for 16 h. The reaction was only partially completed (HPLC) so the solution was warmed at 80° C. for 4 h. The reaction mixture is diluted with MTBE (170 mL), washed with 1 M HCl (15 mL), dried over magnesium sulfate, filtered and concentrated (29" Hg at 60° C.) to remove solvent and any residual starting materials to afford product as light yellow oil (75 g, 99%). It was used to the next step without further purification by distillation.

Step B: Methyl-d$_3$ (S)-4-methyl-2-(methyl-d$_3$)-4-nitropentanoate-3,3-d$_2$

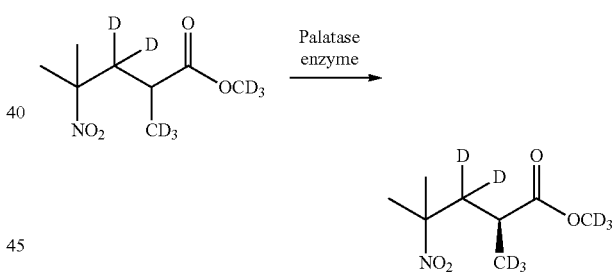

A 5-L, three-neck round bottom flask equipped an overhead mechanical stirrer, a nitrogen line and a J-Kem thermocouple with heating mantle was charged with methyl-d$_3$ 4-methyl-2-(methyl-d$_3$)-4-nitropentanoate-3,3-d$_2$ (75 g, 380 mmol) and 2000 mL of pH 7.5 Na-phosphate buffer @ 0.8 M. To this was added lipase from Rhizomucor miehei (sigma L4277, palatase from Novozymes) (0.5 vol) and stirred at 30° C. for 25 h. Chiral HPLC (ADH 4.6×250 mm, 5 µm, 1.0 mL/min, 98% Heptane/2% IPA) shows 99.8/0.2 ratio of enantiomers. The reaction mixture was extracted twice with MTBE (I L each time). The organic included any emulsion formed during the extractions. The combined organics were washed two times with an aqueous solution of sodium bicarbonate (5 vol), brine (5 vol), dried over sodium sulfate and concentrated under vacuum to afford the desired product methyl-d$_3$ (S)-4-methyl-2-(methyl-d$_3$)-4-nitropentanoate-3,3-d$_2$ as pale yellow oil (32.5 g, 43% yield).

Step C: (S)-5,5-Dimethyl-3-(methyl-d₃)pyrrolidin-2-one-4,4-d₂

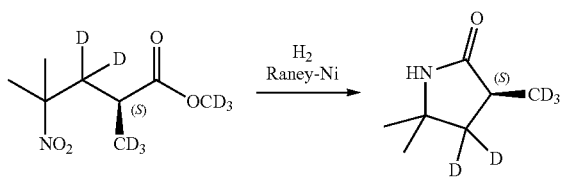

A high-pressure vessel (Parr shaker bottle, 500 mL) was purged with and maintained under N₂. The vessel was charged sequentially with deionized water rinsed (3 times) damp Raney®2800 Ni (6.1 g), methyl-d₃ (S)-4-methyl-2-(methyl-d₃)-4-nitropentanoate-3,3-d₂ (32.5 g, 165 mmol), and ethanol (290 mL). The vessel was sealed and evacuated/backfilled with N₂ (3 times). With no stirring, the vessel was then evacuated and backfilled with H₂ (30 psi). The Parr bottle was shaken while heating the contents to 60° C., and the H₂ pressure was maintained at 30 psi for 8 hours. The vessel was evacuated/backfilled with N₂ (3 times) and the contents were removed by vacuum filtration (Celite pad; N₂ blanket). The flask/filter-pad was washed with ethanol (3×50 mL). After the final wash, the solvent-wet filter-cake was transferred to another receiver and covered with water for disposal. Note: At no time should the catalyst be fully dried (keep damp throughout the filtration process). The filtrate and washes were combined and concentrated (40° C./40 torr) to afford (S)-5,5-dimethyl-3-(methyl-d₃)pyrrolidin-2-one-4,4-d₂ as white solid (20 g, 92%).

Step D: (4S)-3,3-Dideuterio-2,2-dimethyl-4-(trideuteriomethyl)pyrrolidine Hydrochloride

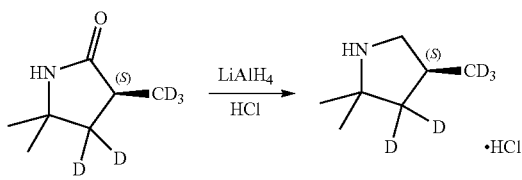

A 1-L, three-neck round bottom flask equipped an overhead mechanical stirrer, a nitrogen line and a J-Kem thermocouple was charged with lithium aluminum hydride pellets (7.6 g, 202 mmol) in THF (80 mL, 4 vol) warmed from 20-36° C. (heat of mixing). A solution of (S)-5,5-dimethyl-3-(methyl-d₃)pyrrolidin-2-one-4,4-d₂ (20 g, 150 mmol) in THF (120 mL, 6 vol) was added to the suspension over 30 minutes while allowing the reaction temperature to rise to ~60° C. The reaction temperature was increased to near reflux (~68° C.) and maintained there for 16 h. The reaction mixture was cooled to below 40° C. and diluted with 200 mL (10 vol) of MTBE. The mixture was quenched slowly with drop-wise addition of a saturated aqueous solution of sodium sulfate (1 vol) over 2 h. Note: Vigorous degassing (H₂) was observed, the mixture becomes thick then thins, and the dark gray mixture turns white. After the addition was completed, the reaction mixture was cooled to room temperature. The solid was removed by filtration (Celite pad) and washed with ethyl acetate (4 vol). With external cooling and a N₂ blanket, the filtrate and washings were combined and treated with drop-wise addition of anhydrous 4 M HCl in dioxane (38 mL, 152 mmol) while maintaining the temperature below 20° C. After the addition was completed (20 minutes), the resultant suspension was concentrated under vacuum at 45° C. The suspension was backfilled with heptanes (4 vol) twice during concentration. The suspension was cooled to below 30° C. when the solid was collected by filtration under a N₂ blanket. The solid was dried under N₂ suction and further dried under high vacuum at 45° C. to afford (4S)-3,3-dideuterio-2,2-dimethyl-4-(trideuteriomethyl)pyrrolidine hydrochloride (17.5 g, 75%). The product is quite hygroscopic so it was manipulated under nitrogen.

SYNTHETIC EXAMPLE 8

Synthesis of Compound 8, 6-[3-(Dispiro[2.0.2⁴.1³]heptan-7-ylmethoxy)pyrazol-1-yl]-N-(o-tolylsulfonyl)-2-[(4S)-2,2,4-trimethylpyrrolidin-1-yl]pyridine-3-carboxamide

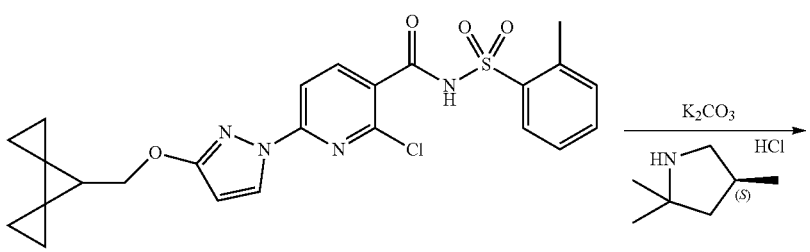

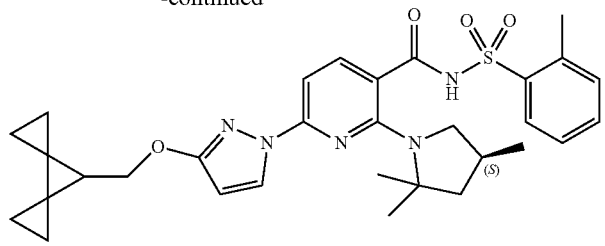

2-Chloro-6-[3-(dispiro[2.0.2⁴.1³]heptan-7-ylmethoxy)pyrazol-1-yl]-N-(o-tolylsulfonyl)pyridine-3-carboxamide (0.170 g, 0.341 mmol) and (4S)-2,2,4-trimethylpyrrolidine (Hydrochloride salt) (0.116 g, 1.02 mmol) were combined and dissolved in DMSO (2 mL). Finely ground potassium carbonate (95 mg, 0.68 mmol) was added. The reaction mixture was sealed and heated overnight to 130° C. After cooling to room temperature, the reaction mixture was diluted with ethyl acetate (50 mL) and washed with aqueous citric acid (1 M, 2×50 mL) and brine (1×50 mL). The organic layer was dried over sodium sulfate, filtered and concentrated under reduced pressure. The product was isolated by silica gel column chromatography eluting with a 0-20% gradient of methanol in dichloromethane on a 12 gram silica gel column to afford 6-[3-(dispiro[2.0.2⁴.1³]heptan-7-ylmethoxy)pyrazol-1-yl]-N-(o-tolylsulfonyl)-2-[(4S)-2,2,4-trimethylpyrrolidin-1-yl]pyridine-3-carboxamide (0.030 g, 15%). ESI-MS m/z calc. 575.26, found 576.36 (M+1)⁺; Retention time: 2.46 minutes.

SYNTHETIC EXAMPLE 9

Synthesis of Compound 9, N-(Benzenesulfonyl)-2-[4-(hydroxymethyl)-2,2-dimethyl-pyrrolidin-1-yl]-6-[3-[2-[1-(trifluoromethyl)cyclopropyl]ethoxy]pyrazol-1-yl]pyridine-3-carboxamide

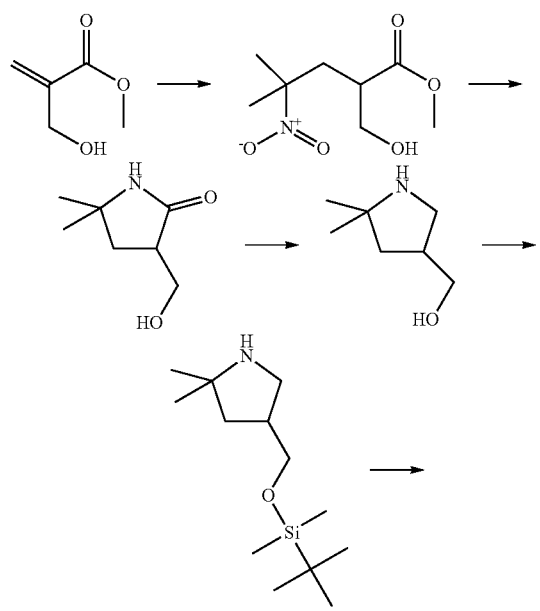

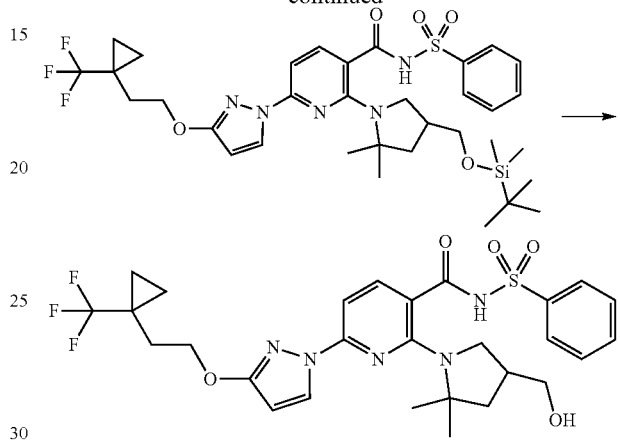

Step A:
2-Hydroxymethyl-4-methyl-4-nitro-pentanoic acid methyl ester

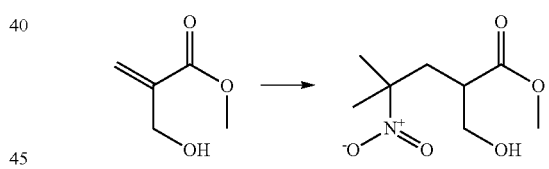

1,8-Diazabicyclo[5.4.0]undec-7-ene (3.6 mL, 24 mmol) was added to 2-nitropropane (26.5 mL, 292 mmol). This mixture was heated to 65° C. and the heat was turned off and methyl 2-(hydroxymethyl)acrylate (25 mL, 243 mmol) was added dropwise. The heat was then turned back on at 80° C. After heating for 1 h the heat was turned off and the reaction was stirred at room temperature overnight before heating at 80° C. for another 2 h. The reaction was diluted with ethyl acetate (250 mL) and washed with 1M hydrogen chloride (2×125 mL), aqueous bicarbonate (125 mL) and brine (125 mL). The reaction product mixture was chromatographed on a 330 g column of silica gel in 0-60% hexanes:ether eluting at 55-60% to give 2-hydroxymethyl-4-methyl-4-nitro-pentanoic acid methyl ester (29.68 g, 60%) as a light green oil. ESI-MS m/z calc. 205.21, found 206.1 (M+1)⁺. Retention time: 1.67 minutes. ¹H NMR (250 MHz, CDCl₃) ppm 1.50-1.59 (m, 6H) 1.85-1.98 (m, 1H) 2.10-2.23 (m, 1H) 2.36-2.50 (m, 1H) 2.60 (d, J=5.71 Hz, 1H) 3.66-3.77 (s, 3H)

Step B: 3-Hydroxymethyl-5,5-dimethyl-pyrrolidin-2-one

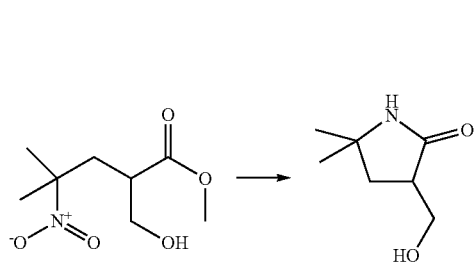

Hydroxymethyl-4-methyl-4-nitro-pentanoic acid methyl ester (4.45 g, 21.7 mmol) was added to absolute ethanol (60 mL) followed by Raney Nickel (1.7 g, ~15% wt). The reaction was heated at 60° C. under 2 bar of H₂ overnight. More Raney Nickel (1.0 g, ~50% wt) was added and the reaction heated at 60° C. under 5 bar H₂ for 3.5 h. At this point, more 2-hydroxymethyl-4-methyl-4-nitro-pentanoic acid methyl ester (3.95 g, 19.3 mmol) was added and the reaction heated for 72 h refilling H₂ to maintain 5 bar. The reaction was filtered through celite and washed with methanol. The crude reaction was chromatographed on silica gel and eluted with 0-10% dichloromethane:methanol at 10%, resulting 3-hydroxymethyl-5,5-dimethyl-pyrrolidin-2-one (3.69 g, 63%) as a white solid. ¹H NMR (250 MHz, CDCl₃) δ ppm 1.31 (d, J=9.01 Hz, 6H) 1.72 (dd, J=12.52, 10.33 Hz, 1H) 2.04 (dd, J=12.58, 8.84 Hz, 1H) 2.73-2.91 (m, 1H) 3.31 (d, J=4.72 Hz, 1H) 3.64-3.95 (m, 2H) 5.93 (br. s., 1H)

Step C: (5,5-Dimethyl-pyrrolidin-3-yl)-methanol

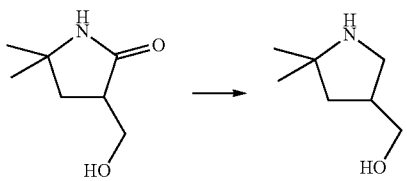

Lithium aluminum hydride (3.90 g, 103.00 mmol) was suspended in tetrahydrofuran (60 mL). Hydroxymethyl-5,5-dimethyl-pyrrolidin-2-one (3.69 g, 25.77 mmol) in tetrahydrofuran (30 mL) was then added dropwise and the reaction was heated at 65° C. for 40 h. The reaction was diluted with 2-methyl-tetrahydrofuran (125 mL) and then cooled in an ice bath before saturated aqueous Rochelle Salt (200 mL) was added dropwise. The organic layer was extracted with 2-methyl-tetrahydrofuran (2×200 mL) and dried over sodium sulfate to give crude (5,5-dimethyl-pyrrolidin-3-yl)-methanol (3.47 g, 104%). ¹H NMR (250 MHz, CDCl₃ δ ppm 1.06-1.24 (m, 6H) 1.29 (dd, J=12.58, 7.20 Hz, 2H) 1.43 (s, 1H) 1.68-1.89 (bs, 1H) 2.31-2.52 (m, 1H) 2.83 (dd, J=11.10, 5.49 Hz, 1H) 3.05-3.26 (m, 1H) 3.48-3.71 (m, 1H)

Step D: 4-(tert-Butyl-dimethyl-silanyloxymethyl)-2,2-dimethyl-pyrrolidine

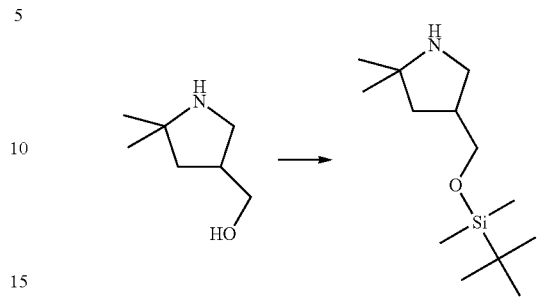

To (5,5-dimethyl-pyrrolidin-3-yl)-methanol (3.08 g, 23.8 mmol), tert-butyldimethylsilyl chloride (4.31 g, 28.6 mmol) in acetonitrile (24 mL) was added 1,8-Diazabicyclo[5.4.0]undec-7-ene (5.3 mL, 35.7 mmol). The reaction was stirred for 3.5 h. The reaction was diluted with chloroform (250 mL) and washed with water (125 mL) and brine (125 mL) then dried over sodium sulfate. The crude was chromatographed on silica gel and eluted with dichloromethane/methanol, eluting at 15-35% methanol to give 4-(tert-butyl-dimethyl-silanyloxymethyl)-2,2-dimethyl-pyrrolidine (3.88 g, 67%) as a yellow oil after two columns. ESI-MS m/z calc. 243.47, found 244.2 (M+1)⁺ Retention time: 2.52 minutes. ¹H NMR (250 MHz, CDCl₃) δ ppm −0.05-0.11 (m, 6H) 0.89 (s, 9H) 1.19 (d, J=18.02 Hz, 6H) 1.25-1.32 (m, 1H) 1.74 (dd, J=12.63, 8.79 Hz, 1H) 1.92 (br. s., 1H) 2.32-2.50 (m, 1H) 2.81 (dd, J=11.54, 6.37 Hz, 1H) 3.11 (dd, J=11.48, 7.97 Hz, 1H) 3.45-3.61 (m, 2H)

Step E: N-(Benzenesulfonyl)-2-[4-(hydroxymethyl)-2,2-dimethyl-pyrrolidin-1-yl]-6-[3-[2-[1-(trifluoromethyl)cyclopropyl]ethoxy]pyrazol-1-yl]pyridine-3-carboxamide

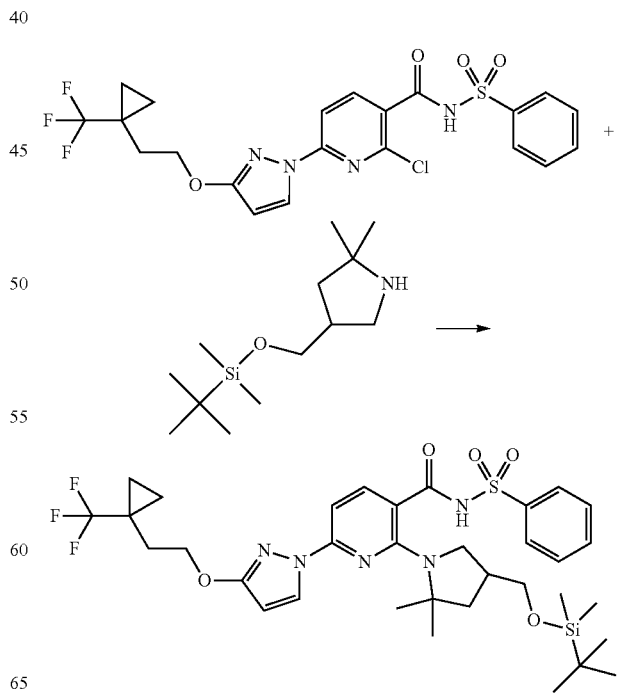

N-(benzenesulfonyl)-2-chloro-6-[3-[2-[1-(trifluoromethyl)cyclopropyl]ethoxy]pyrazol-1-yl]pyridine-3-carboxamide (25 mg, 0.04855 mmol), tert-butyl-[(5,5-dimethylpyrrolidin-3-yl)methoxy]-dimethyl-silane (approximately 35.45 mg, 0.1456 mmol), and K$_2$CO$_3$ (approximately 33.56 mg, 0.2428 mmol) were combined in DMSO (0.5 mL) and heated at 130° C. for 16 h. The reaction was partitioned between a 1M citric acid solution and ethyl acetate and the organics were separated. The organics were washed with brine, dried over sodium sulfate and evaporated. The crude material was purified by silica gel chromatography eluting with 0-10% methanol in dichloromethane to give N-(benzenesulfonyl)-2-[4-[[tert-butyl(dimethyl)silyl]oxymethyl]-2,2-dimethyl-pyrrolidin-1-yl]-6-[3-[2-[1-(trifluoromethyl)cyclopropyl]ethoxy]pyrazol-1-yl]pyridine-3-carboxamide (15 mg, 43%) ESI-MS m/z calc. 721.2941, found 722.4 (M+1)$^+$; Retention time: 0.97 minutes.

Step F: N-(Benzenesulfonyl)-2-[4-(hydroxymethyl)-2,2-dimethyl-pyrrolidin-1-yl]-6-[3-[2-[1-(trifluoromethyl)cyclopropyl]ethoxy]pyrazol-1-yl]pyridine-3-carboxamide

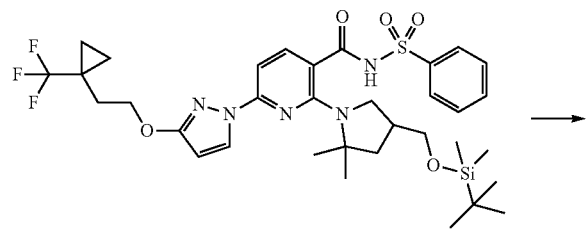

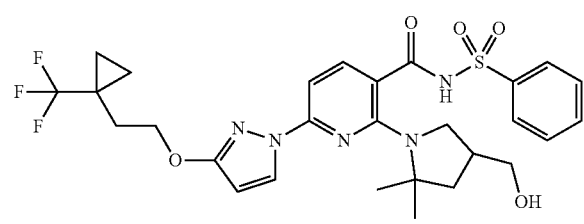

N-(Benzenesulfonyl)-2-[4-[[tert-butyl(dimethyl)silyl]oxymethyl]-2,2-dimethyl-pyrrolidin-1-yl]-6-[3-[2-[1-(trifluoromethyl)cyclopropyl]ethoxy]pyrazol-1-yl]pyridine-3-carboxamide (15 mg, 43%) was dissolved in THF (1 mL) and cooled in an ice bath. Tetra-n-butylammonium fluoride in THF (300 μL of 1 M, 0.3000 mmol) was added and the reaction was allowed to warm to room temperature. The reaction mixture was stirred for 1 h and then partitioned between ethyl acetate and 1M citric acid solution. The organics were washed with brine, dried over sodium sulfate and evaporated. The crude material was purified by silica gel chromatography eluting with 0-10% methanol in dichloromethane to give N-(benzenesulfonyl)-2-[4-(hydroxymethyl)-2,2-dimethyl-pyrrolidin-1-yl]-6-[3-[2-[1-(trifluoromethyl)cyclopropyl]ethoxy]pyrazol-1-yl]pyridine-3-carboxamide (8.5 mg, 290%) ESI-MS m/z calc. 607.20764, found 608.4 (M+1)$^+$; Retention time: 1.9 minutes.

SYNTHETIC EXAMPLE 10

Synthesis of Compound 10, N-(Benzenesulfonyl)-6-[3-[[1-(trifluoromethyl)cyclobutyl]methoxy]pyrazol-1-yl]-2-[(4S)-2,2,4-trimethylpyrrolidin-1-yl]pyridine-3-carboxamide (1-Trifluoromethyl-cyclobutyl)-methanol

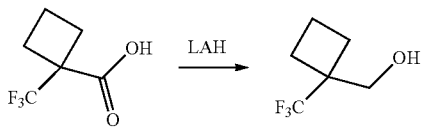 [SMILES: O=C(O)C1(C(F)(F)F)CCC1 ; OCC1(C(F)(F)F)CCC1]

1-Trifluoromethyl-cyclobutanecarboxylic acid (5.0 g, 30 mmol) was dissolved in diethyl ether (60 mL) and cooled to 0° C. Lithium aluminum hydride (38.66 mL, 1M in diethyl ether) was added dropwise and the solution was allowed to warm to room temperature overnight. The reaction solution was cooled to 0° C. with stirring, and sodium sulfate decahydrate was added, which resulted in gradual evolution of gas. Portionwise addition was continued until no more bubbling was observed at room temperature. The reaction solution was then filtered over a bed of Celite, washing with diethyl ether. The filtrate was concentrated under reduced pressure to give 5.44 g of a mixture containing the desired product and some diethyl ether residue (36% by NMR integration). This afforded 1-trifluoromethyl-cyclobutyl-methanol (3.46 g, 78%) as a colorless oil. $^1$H NMR (250 MHz, CDCl3) δ (ppm): 3.82 (s, 2H), 2.39-2.14 (m, 2H), 2.10-1.85 (m, 4H).

3-(1-Trifluoromethyl-cyclobutylmethoxy)-pyrazole-1-carboxylic acid tert-butyl ester

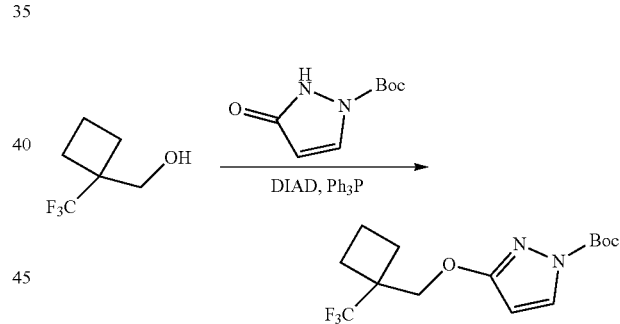

1-Trifluoromethyl-cyclobutyl-methanol (1.50 g, 9.73 mmol) and 3-oxo-2,3-dihydro-pyrazole-1-carboxylic acid tert-butyl ester (1.63 g, 8.85 mmol) were dissolved in anhydrous tetrahydrofuran (32 mL). The solution was degassed by sonication and flushed with nitrogen gas. Triphenylphosphine (2.55 g, 9.73 mmol) was added, and diisopropyl azodicarboxylate (1.92 mL, 9.73 mmol) was then added dropwise. Upon completion of addition, the reaction was heated to 50° C. for 16 hours. After cooling to room temperature, the reaction was diluted with ethyl acetate (100 mL) and washed with 1M sodium hydroxide solution (2×100 mL), then brine (125 mL). The organics were dried over sodium sulfate, filtered, and concentrated under reduced pressure. The crude yellow oil was purified by flash chromatography using a 0-10° % ethyl acetate in hexanes gradient method to afford 3-(1-trifluoromethyl-cyclobutylmethoxy)-pyrazole-1-carboxylic acid tert-butyl ester (2.48 g, 87%) as an off-white solid. ESI-MS m/z calc. 320.31, found 321.1 (M+1)$^+$. Retention time: 3.74 minutes.

3-(1-Trifluoromethyl-cyclobutylmethoxy)-1H-pyrazole hydrochloride salt

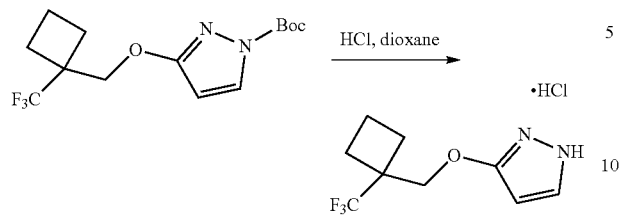

3-(1-Trifluoromethyl-cyclobutylmethoxy)-pyrazole-1-carboxylic acid tert-butyl ester (2.48 g, 7.74 mmol) was dissolved in 4M hydrogen chloride in dioxane (77 mL). The solution was stirred overnight at room temperature, followed by removal of the volatiles under reduced pressure to afford the hydrochloride salt of 3-(1-trifluoromethyl-cyclobutylmethoxy)-1H-pyrazole (1.95 g, 98%) as a white powder. ESI-MS m/z calc. 220.20, found 221.2 (M+1)$^+$. Retention time: 2.67 minutes.

tert-Butyl 2-chloro-6-(3-((1-(trifluoromethyl)cyclobutyl)methoxy)-1H-pyrazol-1-yl)nicotinate

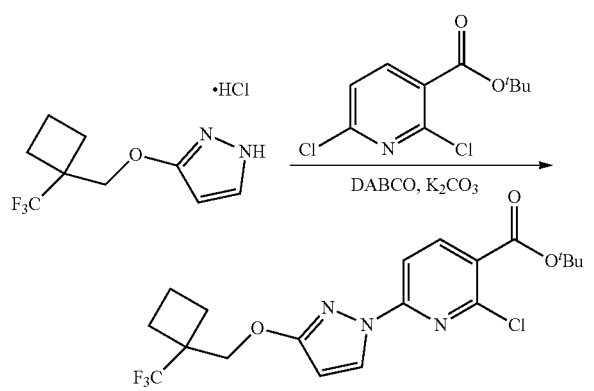

3-(1-Trifluoromethyl-cyclobutylmethoxy)-1H-pyrazole hydrochloride salt (1.95 g, 7.61 mmol) and 2,6-dichloronicotinic acid tert-butyl ester (1.89 g, 7.62 mmol) were dissolved in dimethylformamide (15 mL), and potassium carbonate (4.21 g, 30.5 mmol) was added followed by 1,4-diazabicyclo[2.2.2]octane (0.43 g, 3.8 mmol). The reaction was stirred at room temperature overnight, then water (150 mL) was added and the aqueous layer was extracted with 4:1 ethyl acetate:hexanes (100 mL). The organic phase was washed with brine (70 mL), dried over sodium sulfate, and concentrated under reduced pressure. The crude oil was purified by silica gel chromatography using a 0-10% ethyl acetate in hexanes gradient method to afford 2-chloro-6-[3-(1-trifluoromethyl-cyclobutylmethoxy)-pyrazole-1-yl]-nicotinic acid tert-butyl ester (1.94 g, 66%) as a white solid. ESI-MS m/z calc. 431.85, found 432.2 (M+1)$^+$. Retention time: 4.61 minutes.

2-Chloro-6-[3-(1-trifluoromethyl-cyclobutyl-methoxy)-pyrazole-1-yl]-nicotinic acid

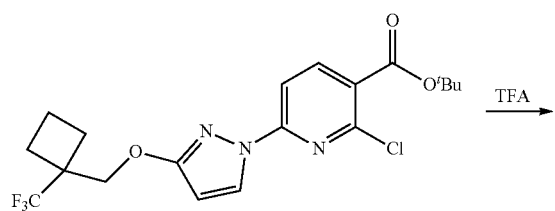

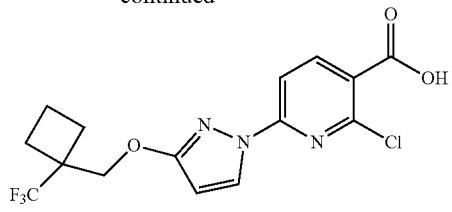

2-Chloro-6-[3-(-trifluoromethyl-cyclobutylmethoxy)-pyrazole-1-yl]-nicotinic acid tert-butyl ester (1.9 g, 4.40 mmol) was dissolved in dichloromethane (20 mL) and trifluoroacetic acid (5.0 mL) was added. The reaction solution was stirred at room temperature overnight, after which the volatiles were removed under reduced pressure to afford 2-chloro-6-[3-(1-trifluoromethyl-cyclobutylmethoxy)-pyrazole-1-yl]-nicotinic acid (1.61 g, 97%) as a white solid. ESI-MS m/z calc. 375.74, found 376.2 (M+1)$^+$. Retention time: 3.57 minutes.

Synthesis of N-(Benzenesulfonyl)-2-chloro-6-[3-[[1-(trifluoromethyl)cyclobutyl]methoxy]pyrazol-1-yl]pyridine-3-carboxamide

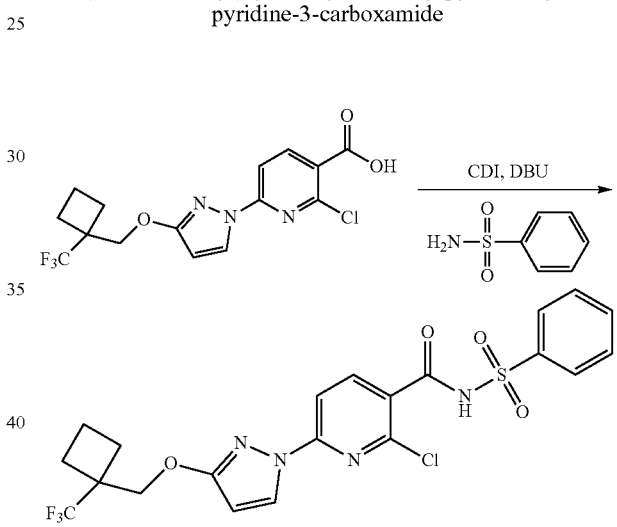

To a stirred solution of 2-chloro-6-[3-[[1-(trifluoromethyl)cyclobutyl]methoxy]pyrazol-1-yl]pyridine-3-carboxylic acid (0.150 g, 0.399 mmol) in anhydrous tetrahydrofuran (3.0 mL) was added CDI (78 mg, 0.4810 mmol) in one portion. The solution was stirred at ambient temperature for 2 h. Then solid benzenesulfonamide (76 mg, 0.48 mmol) was added in one portion, followed by DBU (183 mg, 1.20 mmol) and the tea-colored solution was stirred at ambient temperature for an additional 2 h. To the reaction mixture was slowly added citric acid (2.5 mL of 1.0 M, 2.500 mmol), followed by brine (5 mL). After stirring for 10 min, the homogeneous material was extracted with ethyl acetate (3×25 mL). The combined organic extracts were washed with brine (10 mL), dried over anhydrous sodium sulfate, filtered and concentrated under reduced pressure. After drying under vacuum for 1 h, N-(benzenesulfonyl)-2-chloro-6-[3-[[1-(trifluoromethyl)cyclobutyl]methoxy]pyrazol-1-yl]pyridine-3-carboxamide (181 mg, 88%) was obtained as white solid. It contained some starting acid impurity, and used in the subsequent step without further purification. ESI-MS m/z calc. 514.0689, found 515.1 (M+1)$^+$; Retention time: 1.98 minutes Synthesis of N-(Benzenesulfonyl)-6-[3-[[1-(trifluoromethyl)cyclobutyl]methoxy]pyrazol-1-yl]-2-[(4S)-2,2,4-trimethylpyrrolidin-1-yl]pyridine-3-carboxamide

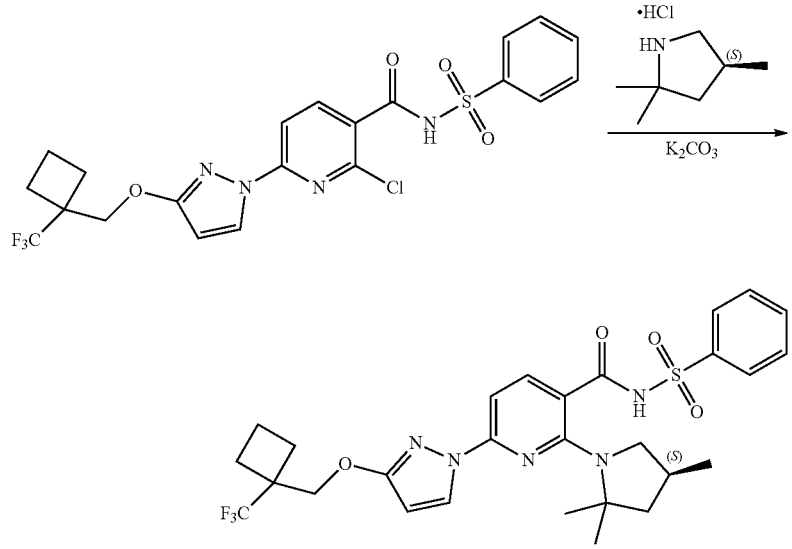

A mixture of N-(benzenesulfonyl)-2-chloro-6-[3-[[1-(trifluoromethyl)cyclobutyl]-methoxy]pyrazol-1-yl]pyridine-3-carboxamide (0.160 g, 0.311 mmol), (4S)-2,2,4-trimethylpyrrolidine (Hydrochloride salt) (139 mg, 0.932 mmol) and potassium carbonate (215 mg, 1.554 mmol) was stirred in in anhydrous dimethyl sulfoxide (2.7 mL) under an atmosphere of nitrogen at 130° C. for 18 h. The reaction was allowed to cool to ambient temperature and diluted with water (15 mL) and extracted with ethyl acetate (3×25 mL). The combined organics successively were washed with aqueous 1 M citric acid (310 µL of 1.0 M, 0.3107 mmol), and brine, dried over anhydrous sodium sulfate, filtered and evaporated to give yellow crude material. It was purified from CombiFlashRf system using 40 g gold silica gel column and eluting with 0-5% methanol in methylene chloride (over 45 min). The product came out at 25 min (2.6% methanol). The desired fractions were combined and concentrated under reduced pressure. Upon further drying overnight under high vacuum, N-(benzenesulfonyl)-6-[3-[[1-(trifluoromethyl)cyclobutyl]methoxy]pyrazol-1-yl]-2-[(4S)-2,2,4-trimethylpyrrolidin-1-yl]pyridine-3-carboxamide (HCl salt, 40 mg, 20%) was obtained. ESI-MS m/z calc. 591.2127, found 592.3 (M+1)$^+$; Retention time: 2.25 minutes. $^1$H NMR (400 MHz, DMSO-d6) δ 12.49 (s, 1H), 8.22 (d, J=2.8 Hz, 1H), 8.00 (dd, J=8.2, 2.1 Hz, 2H), 7.82 (d, J=8.2 Hz, 1H), 7.72 (tt, J=8.2, 2.0 Hz, 1H), 7.65 (dt, J=8.2, 2.0 Hz, 2H), 6.95 (d, J=8.2 Hz, 1H), 6.18 (d, J=2.8 Hz, 1H), 4.48 (s, 2H), 2.42 (t, J=10.5 Hz, 1H), 2.36-2.22 (m, 3H), 2.11 (td, J=12.1, 5.7 Hz, 4H), 1.95 (qd, J=9.7, 4.3 Hz, 1H), 1.83 (dd, J=12.0, 5.6 Hz, 1H), 1.54 (s, 3H), 1.51 (s, 3H), 1.37 (t, J=12.2 Hz, 1H), 0.65 (d, J=6.3 Hz, 3H).

SYNTHETIC EXAMPLE 11

Synthesis of Compound II, N-(4-Cyano-2-methyl-phenyl)sulfonyl-6-[3-[[1-(trifluoromethyl)cyclopropyl]methoxy]pyrazol-1-yl]-2-[(4S)-2,2,4-trimethyl-pyrrolidin-1-yl]pyridine-3-carboxamide Step A: 2-Chloro-N-(4-cyano-2-methyl-phenyl)sulfonyl-6-[3-[[1-(trifluoromethyl)cyclopropyl]methoxy]pyrazol-1-yl]pyridine-3-carboxamide

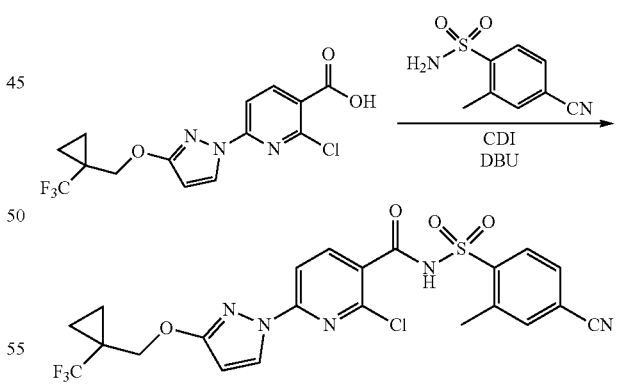

A solution of 2-chloro-6-[3-[[1-(trifluoromethyl)cyclopropyl]methoxy]pyrazol-1-yl]pyridine-3-carboxylic acid (186.4 mg, 0.5 mmol) and 1,1'-carbonyldiimidazole (97.29 mg, 0.60 mmol) in THF (2.5 mL) was stirred for 30 minutes, and 4-cyano-2-methyl-benzenesulfonamide (127.5 mg, 0.65 mmol) and 1,8-diazabicyclo(5.4.0)undec-7-ene (DBU) (89.7 µL, 0.60 mmol) were added. After 16 hours the reaction was diluted with 1 M aqueous citric acid and extracted with ethyl acetate. The combined extracts were dried over sodium sulfate and evaporated. The residue was purified by silica gel chromatography with 0-5% methanol in dichloromethane to give 2-chloro-N-(4-cyano-2-methyl-phenyl)sulfonyl-6-[3-[[1-(trifluoromethyl)cyclopropyl]methoxy]pyrazol-1-yl]pyridine-3-carboxamide (270 mg, 100%) ESI-MS m/z calc. 539.06, found 540.1 (M+1)+; Retention time: 0.73 minutes.

Step B: N-(4-Cyano-2-methyl-phenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

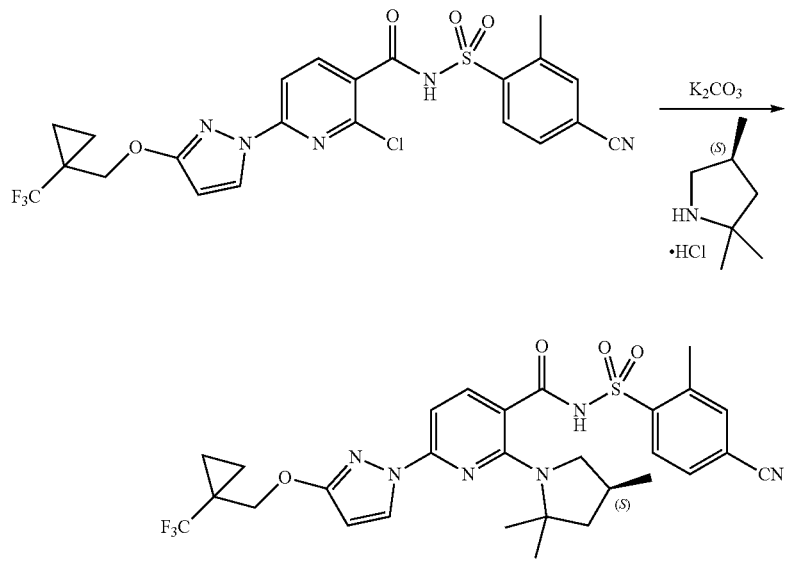

A mixture of 2-chloro-N-(4-cyano-2-methyl-phenyl)sulfonyl-6-[3-[[1-(trifluoromethyl)cyclopropyl]methoxy]pyrazol-1-yl]pyridine-3-carboxamide (270 mg, 0.50 mmol), (4S)-2,2,4-trimethylpyrrolidine (Hydrochloride salt) (168.1 mg, 1.123 mmol), and potassium carbonate (310.4 mg, 2.246 mmol) in DMSO (1.87 mL) was stirred at 130° C. for 15 hours. The reactions were acidified with 1 M aqueous citric acid and extracted with ethyl acetate. The combined extracts were washed with brine, dried over sodium sulfate, and evaporated. The residue was purified by silica gel chromatography with 0-5% methanol in dichloromethane to give impure product. The impure product was re-purified using a reverse phase HPLC-MS method using a Luna C18 (2) column (75×30 mm, 5 m particle size) sold by Phenomenex (pn: 00C-4252-U0-AX), and a dual gradient run from 1-99% mobile phase B over 15.0 minutes. Mobile phase A=H$_2$O (5 mM HCl). Mobile phase B=CH$_3$CN. Flow rate=50 mL/min, and column temperature=25° C. to provide N-(4-cyano-2-methyl-phenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (150 mg, 48%) ESI-MS m/z calc. 616.21, found 617.3 (M+1)+; Retention time: 2.06 minutes. $^1$H NMR (400 MHz, DMSO-d$_6$) δ 12.96 (s, 1H), 8.23-8.18 (m, 2H), 8.03 (d, J=1.6 Hz, 1H), 7.97 (dd, J=8.0, 1.8 Hz, 1H), 7.88 (d, J=8.3 Hz, 1H), 6.95 (d, J=8.3 Hz, 1H), 6.16 (d, H=2.7 Hz, 1H), 4.43-4.32 (m, 2H), 2.67 (s, 3H), 2.27 (d, J=3.5 Hz, 1H), 2.25 (s, 1H), 2.17 (dd, J=11.3, 5.7 Hz, 1H), 1.83 (dd, J=11.9, 5.3 Hz, 1H), 1.52 (d, J=4.4 Hz, 6H), 1.36 (s, 1H), 1.09 (dt, J=5.5, 1.6 Hz, 4H), 0.70 (d, 1=6.0 Hz, 3H).

SYNTHETIC EXAMPLE 12

Synthesis of Compound 12, N-(2-Methoxy-4-methyl-phenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(2-methoxy-4-methyl-phenyl)sulfonyl-6-[3-[[1-(trifluoromethyl)cyclopropyl]methoxy]pyrazol-1-yl]pyridine-3-carboxamide

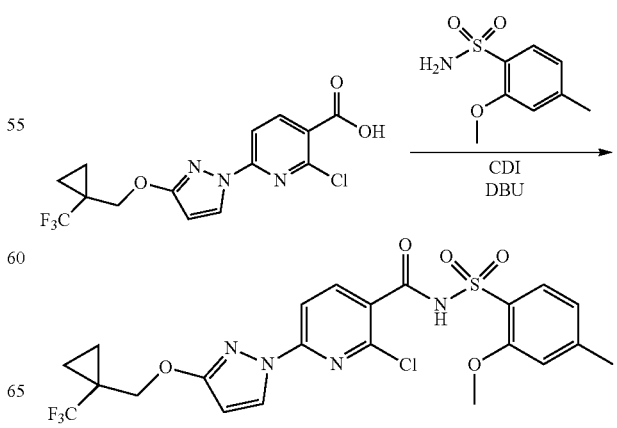

A solution of 2-chloro-6-[3-[[1-(trifluoromethyl)cyclopropyl]methoxy]pyrazol-1-yl]pyridine-3-carboxylic acid (186.4 mg, 0.5 mmol) and 1,1'-carbonyldiimidazole (97.29 mg, 0.60 mmol) in THF (2.5 mL) was stirred for 30 minutes, and 2-methoxy-4-methyl-benzenesulfonamide (130.8 mg, 0.65 mmol) and 1,8-diazabicyclo(5.4.0)undec-7-ene (DBU) (89.7 μL, 0.60 mmol) were added. After 16 hours the reaction was diluted with 1 M aqueous citric acid and extracted with ethyl acetate. The combined extracts were dried over sodium sulfate and evaporated. The residue was purified by silica gel chromatography with 0-5% methanol in dichloromethane to give 2-chloro-N-(2-methoxy-4-methyl-phenyl)sulfonyl-6-[3-[[1-(trifluoromethyl)cyclopropyl]methoxy]pyrazol-1-yl]pyridine-3-carboxamide (210 mg, 77%) ESI-MS m/z calc. 544.1, found 545.1 (M+1)$^+$; Retention time: 0.73 minutes as a colorless solid.

Step B: N-(2-Methoxy-4-methyl-phenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

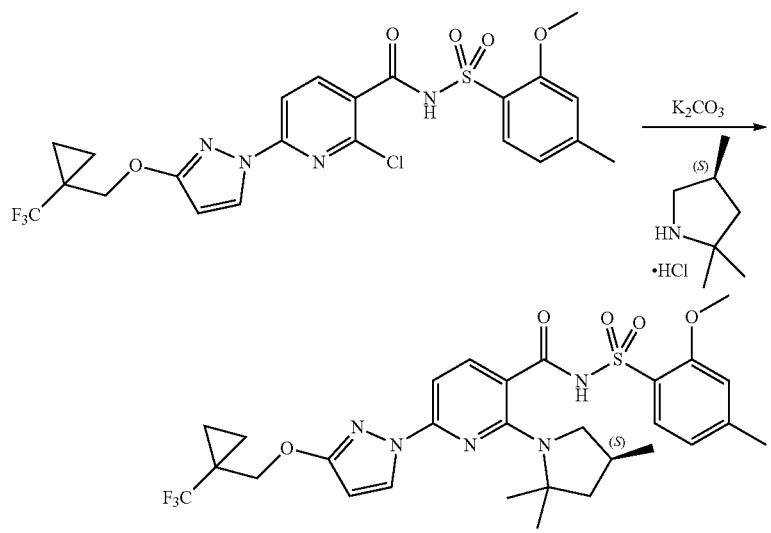

A mixture of 2-chloro-N-(2-methoxy-4-methyl-phenyl)sulfonyl-6-[3-[[1-(trifluoromethyl)cyclopropyl]methoxy]pyrazol-1-yl]pyridine-3-carboxamide (210 mg, 0.3854 mmol), (4S)-2,2,4-trimethylpyrrolidine (Hydrochloride salt) (168.1 mg, 1.123 mmol), and potassium carbonate (310.4 mg, 2.246 mmol) in DMSO (1.87 mL) was stirred at 130° C. for 15 hours. The reaction was acidified with 1 M aqueous citric acid and extracted with ethyl acetate. The combined extracts were washed with brine, dried over sodium sulfate, and evaporated. The residue was purified by silica gel chromatography with 0-5% methanol in dichloromethane to give impure product. The impure product was re-purified using a reverse phase HPLC-MS method using a Luna C18 (2) column (75×30 mm, 5 μm particle size) sold by Phenomenex (pn: 00C-4252-U0-AX), and a dual gradient run from 1-99% mobile phase B over 15.0 minutes. Mobile phase A=H$_2$O (5 mM HCl). Mobile phase B=CH$_3$CN. Flow rate=50 mL/min, and column temperature=25° C. to provide N-(2-methoxy-4-methyl-phenyl)sulfonyl-6-[3-[[1-(trifluoromethyl)cyclopropyl]methoxy]pyrazol-1-yl]-2-[(4 S)-2,2,4-trimethylpyrrolidin-1-yl]pyridine-3-carboxamide (95 mg, 39.25%) ESI-MS m/z calc. 621.2, found 622.3 (M+1)$^+$; Retention time: 2.19 minutes. $^1$H NMR (400 MHz, DMSO-d$_6$) δ 12.39 (s, 1H), 8.20 (d, J=2.8 Hz, 1H), 7.78 (t, J=8.5 Hz, 2H), 7.10 (d, J=1.4 Hz, 1H), 6.94 (dd, J=10.1, 8.1 Hz, 2H), 6.15 (d, J=2.7 Hz, 1H), 4.43-4.30 (m, 2H), 3.89 (s, 3H), 2.49-2.38 (m, 2H), 2.37 (s, 3H), 2.21 (dd, J=11.2, 6.1 Hz, 1H), 1.85 (dd, J=11.9, 5.5 Hz, 1H), 1.53 (d, J=11.0 Hz, 6H), 1.37 (s, 1H), 1.12-1.04 (m, 4H), 0.78 (d, J=6.2 Hz, 3H).

SYNTHETIC EXAMPLE 13

Synthesis of Compound 13: N-(2,4-Dimethoxyphenyl)sulfonyl-6-[3-[[1-(trifluoromethyl)cyclopropyl methoxy]pyrazol-1-yl]-2-[(4S)-2,2,4-trimethylpyrrolidin-1-yl]pyridine-3-carboxamide Step A: 2-Chloro-N-(2,4-dimethoxyphenyl)sulfonyl-6-[3-[[1-(trifluoromethyl)cyclopropyl]methoxy]pyrazol-1-yl]pyridine-3-carboxamide

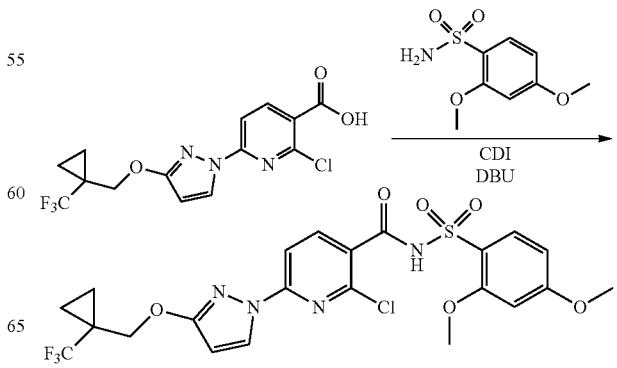

A solution of 2-chloro-6-[3-[[1-(trifluoromethyl)cyclopropyl]methoxy]pyrazol-1-yl]pyridine-3-carboxylic acid (186.4 mg, 0.5 mmol) and 1,1'-carbonyldiimidazole (97.29 mg, 0.60 mmol) in THF (2.5 mL) was stirred for 30 minutes, and 2,4-dimethoxybenzenesulfonamide (141.2 mg, 0.65 mmol) and 1,8-diazabicyclo(5.4.0)undec-7-ene (DBU) (89.7 µL, 0.60 mmol) were added. After 16 hours the reaction was diluted with 1 M aqueous citric acid and extracted with ethyl acetate. The combined extracts were dried over sodium sulfate and evaporated. The residue was purified by silica gel chromatography with 0-5% methanol in dichloromethane to give 2-chloro-N-(2,4-dimethoxyphenyl)sulfonyl-6-[3-[[1-(trifluoromethyl)cyclopropyl]methoxy]pyrazol-1-yl]pyridine-3-carboxamide (210 mg, 75%) ESI-MS m/z calc. 560.1, found 561.1 (M+1)$^+$; Retention time: 0.71 minutes as a colorless solid.

Step B: N-(2,4-Dimethoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide reverse phase HPLC-MS method using a Luna C18 (2) column (75×30 mm, 5 µm particle size) sold by Phenomenex (pn: 00C-4252-U0-AX), and a dual gradient run from 1-99% mobile phase B over 15.0 minutes. Mobile phase A=H$_2$O (5 mM HCl). Mobile phase B=CH$_3$CN. Flow rate=50 mL/min, and column temperature=25° C. to provide N-(2,4-dimethoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (110 mg, 46%) ESI-MS m/z calc. 637.2, found 638.3 (M+1)$^+$; Retention time: 2.14 minutes. $^1$H NMR (400 MHz, DMSO-d$_6$) δ 12.34 (s, 1H), 8.20 (d, J=2.8 Hz, 1H), 7.82 (d, J=8.8 Hz, 1H), 7.77 (d, J=8.3 Hz, 1H), 6.92 (d, J=8.2 Hz, 1H), 6.74 (d, J=2.3 Hz, 1H), 6.70 (dd, J=8.8, 2.3 Hz, 1H), 6.15 (d, J=2.7 Hz, 1H), 4.43-4.31 (m, 2H), 3.90 (s, 3H), 3.85 (s, 3H), 2.54 (s, 1H), 2.42 (dd, J=10.5, 7.0 Hz, 1H), 2.21 (dd, J=11.6, 5.9 Hz, 1H), 1.85 (dd, J=11.9, 5.5 Hz, 1H), 1.55 (s, 3H), 1.52 (s, 3H), 1.38 (s, 1H), 1.09 (dt, J=5.9, 1.6 Hz, 4H), 0.80 (d, J=6.3 Hz, 3H).

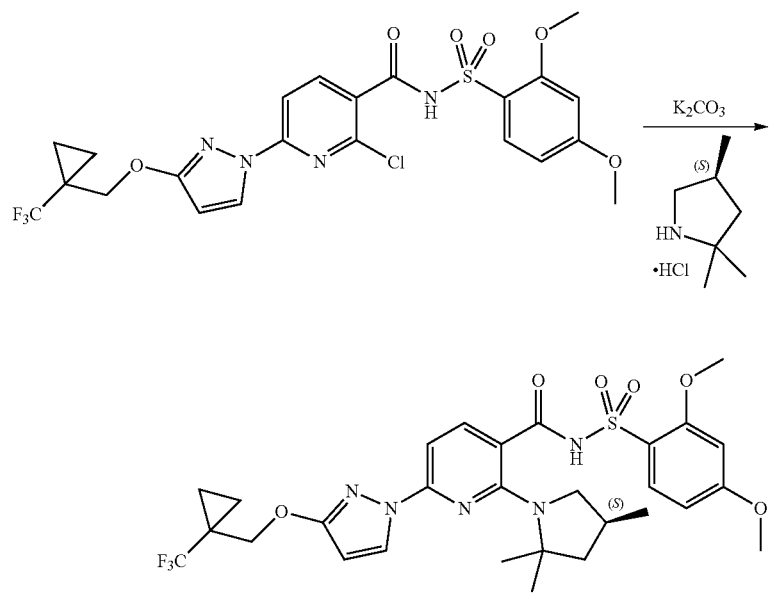

A mixture of 2-chloro-N-(2,4-dimethoxyphenyl)sulfonyl-6-[3-[[1-(trifluoromethyl)cyclo-propyl]methoxy]pyrazol-1-yl]pyridine-3-carboxamide (210 mg, 0.3744 mmol), (4S)-2,2,4-trimethylpyrrolidine (Hydrochloride salt) (168.1 mg, 1.123 mmol), and potassium carbonate (310.4 mg, 2.246 mmol) in DMSO (1.87 mL) was stirred at 130° C. for 15 hours. The reactions were acidified with 1 M aqueous citric acid and extracted with ethyl acetate. The combined extracts were washed with brine, dried over sodium sulfate, and evaporated. The residue was purified by silica gel chromatography with 0-5% methanol in dichloromethane to give impure product. The impure product was re-purified using a

SYNTHETIC EXAMPLE 14

Synthesis of Compound 14: N-(Benzenesulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

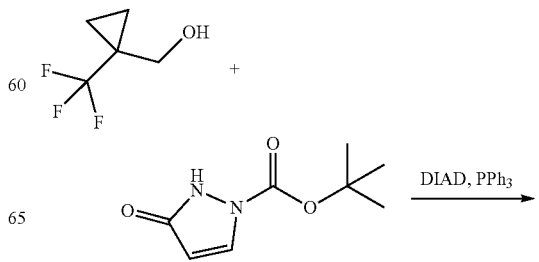

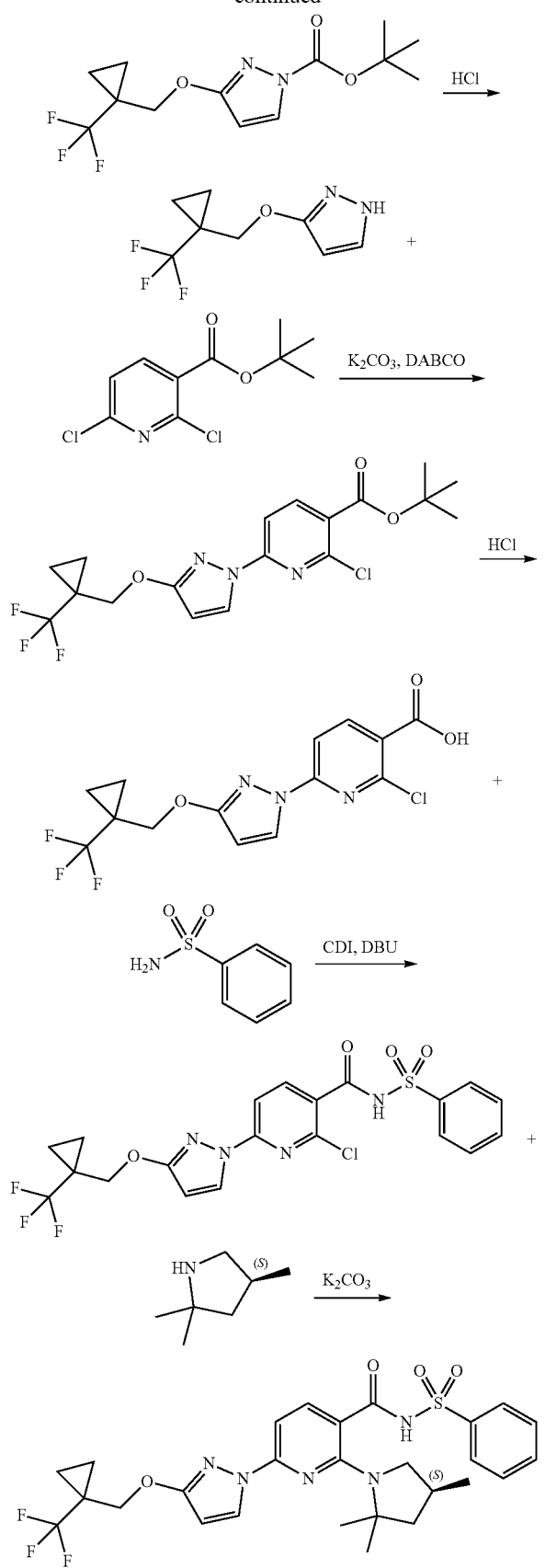

Step A: tert-Butyl 3-[[1-(trifluoromethyl)cyclopropyl]methoxy]pyrazole-1-carboxylate

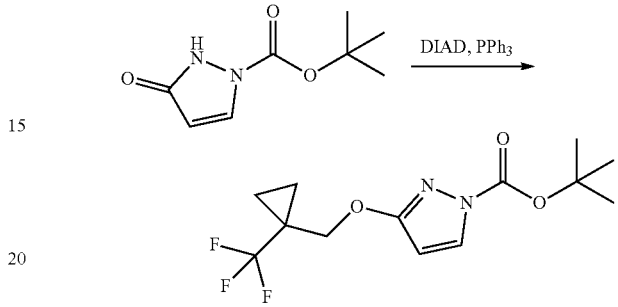

A 5000 mL 3 neck round bottom flask as fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 5-oxo-1H-pyrazole-2-carboxylate (70 g, 0.3800 mol) and tetrahydrofuran (840 mL, 12 mL/g) which provided a clear pale yellow solution. Stirring was commenced and the pot temperature was recorded at 19° C. The vessel was then charged with [1-(trifluoromethyl)cyclopropyl]methanol (58.56 g, 0.4180 mol) added neat in one portion followed by triphenylphosphine (109.6 g, 0.4180 mol) added as a solid in one portion. The resulting clear pale yellow solution was then treated with diisopropyl azodicarboxylate (clear reddish-orange liquid) (82.3 mL, 0.4180 mol) added neat dropwise over 1 hour which resulted in a gradual exotherm to 40° C. and a clear light amber solution. The reaction mixture was then heated to a pot temperature of 50° C. and the condition was maintained for 2 hours when analysis by LC/MS indicated complete consumption of the starting material. The clear amber reaction mixture was concentrated under reduced pressure and the resulting clear dark amber oil was suspended in toluene (560 mL) and stirred at room temperature for 1 hour during which time a solid (triphenylphosphine oxide MW=278.28) precipitated. The thick slurry was filtered through a glass frit Buchner funnel and the filter cake was displacement washed with toluene (150 mL) and then pulled for 30 minutes. The clear amber filtrate was concentrated under reduced pressure to provide a clear amber oil. The material was purified by silica gel column flash chromatography (solid load on Celite 1.5 kg RediSep column) eluting with a gradient of 100% hexane to 20% EtOAc in hexane collecting 450 mL fractions. The product elutes around 5% EtOAc in hexane. The desired fractions were combined and concentrated under reduced pressure to provide a clear pale yellow oil as the desired product tert-butyl 3-[[1-(trifluoromethyl)cyclopropyl]methoxy]pyrazole-1-carboxylate (81 g, 0.264 mol, 70%). $^1$H NMR (400 MHz, DMSO-d6) 8.10 (d, J=2.9 Hz, 1H), 6.14 (d, J=3.0 Hz, 1H), 4.31 (s, 2H), 1.55 (s, 9H), 1.07 (dp, J=4.9, 1.3 Hz, 4H). ESI-MS m/z calc. 306.11914, found 259.0 (M−48)$^+$; Retention time: 1.76 minutes

Step B: 3-[[1-(Trifluoromethyl)cyclopropyl]methoxy]-1H-pyrazole

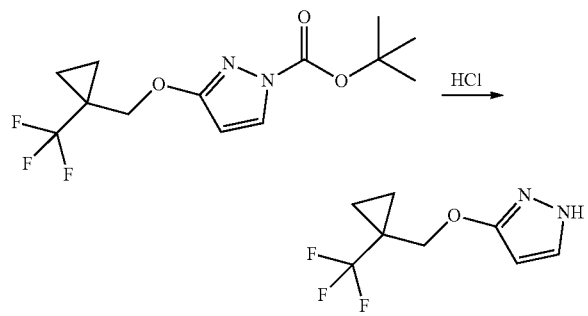

A 5000 mL 3 neck round bottom flask was fitted with a mechanical stirrer, a heating mantle, a J-Kem temperature probe, a water cooled reflux condenser, an addition funnel and a nitrogen inlet/outlet. The vessel was charged under a nitrogen atmosphere with tert-butyl 3-[[1-(trifluoromethyl)cyclopropyl]methoxy]pyrazole-1-carboxylate (80 g, 0.2612 mol), dichloromethane (320 mL, 4 mL/g) and methyl alcohol (320 mL, 4 mL/g) which provided a clear pale yellow solution. Stirring was commenced and the pot temperature was recorded at 19° C. The addition funnel was charged with 4 M HCl in 1,4-dioxane (195.9 mL, 0.7836 mol) which was subsequently added dropwise over 1 hour which resulted in a gradual exotherm to 30° C. The resulting clear pale yellow solution was heated to a pot temperature of 45° C. and the condition was maintained for 1 hour when analysis by LC/MS indicated reaction completion. The reaction mixture was allowed to cool to room temperature and then concentrated under reduced pressure. The remaining residue was dissolved in tert-butyl methyl ether (640 mL) and then transferred to a separatory funnel and partitioned with 2 M sodium hydroxide solution (391.8 mL, 0.7836 mol). The organic layer was removed and the residual aqueous was extracted with tert-butyl methyl ether (2×200 mL). The combined organic was washed with saturated sodium chloride solution (500 mL), dried over sodium sulfate (300 g) and then filtered through a glass flit Buchner funnel. The clear pale yellow filtrate was concentrated under reduced pressure to provide a clear light yellow oil which solidified upon standing to provide a white solid (49.5 g, 0.240 mol, 92%) as the desired product 3-[[1-(trifluoromethyl)cyclopropyl]methoxy]-1H-pyrazole. $^1$H NMR (400 MHz, DMSO-d6) δ 11.90 (s, 1H), 7.51 (d, J=2.4 Hz, 1H), 5.67 (d, J=2.4 Hz, 1H), 4.19 (s, 2H), 1.09-0.97 (m, 4H). ESI-MS m/z calc. 206.0667, found 207.0 (M+1)⁺; Retention time: 1.07 minutes.

Step C: tert-Butyl 2-chloro-6-[3-[[1-(trifluoromethyl)cyclopropyl]methoxy]pyrazol-1-yl]pyridine-3-carboxylate

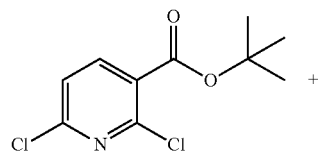

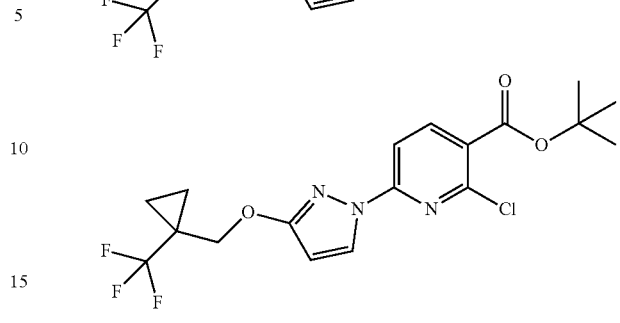

A 5000 mL 3 neck round bottom flask was fitted with a mechanical stirrer, a cooling bath used as secondary containment, a J-Kem temperature probe, a water cooled reflux condenser, an addition funnel and a nitrogen inlet/outlet. The vessel was charged under a nitrogen atmosphere with 3-[[1-(trifluoromethyl)cyclopropyl]methoxy]-1H-pyrazole (45 g, 0.2183 mol) and N,N-dimethylformamide (540 ml, 12 mL/g) which provided a clear pale yellow solution. Stirring was commenced and the pot temperature was recorded at 17° C. The vessel was then charged with tert-butyl 2,6-dichloropyridine-3-carboxylate (54.16 g, 0.2183 mol) added as a solid in one portion. The resulting clear pale yellow solution was then treated with potassium carbonate (39.22 g, 0.2838 mol) added as a solid in one portion followed by 1,4-diazabicyclo[2.2.2]octane (3.67 g, 0.03274 mol) added as a solid in one portion. The resulting pale yellow suspension was allowed to stir at room temperature for 24 hours. The reaction mixture was cooled to 10° C. with a crushed ice/water cooling bath. The addition funnel was charged with water (540 mL) added dropwise over 45 minutes which resulted in a thick suspension and an exotherm to 15° C. The resulting suspension was continued to stir at 15° C. for 30 minutes and then filtered through a glass frit Buchner funnel. The filter cake was displacement washed with water (2×500 ml) and then pulled in the Buchner for 2 hours. The material was then allowed to air dry overnight to provide (73 g, 0.175 mol, 80%) of a white granular solid as tert-butyl 2-chloro-6-[3-[[1-(trifluoromethyl)cyclopropyl]methoxy]pyrazol-1-yl]pyridine-3-carboxylate. ESI-MS m/z calc. 361.0441, found 361.9 (M+1)⁺; Retention time: 2.27 minutes.

Step D: 2-Chloro-6-[3-[[1-(trifluoromethyl)cyclopropyl]methoxy]pyrazol-1-yl]pyridine-3-carboxylic acid

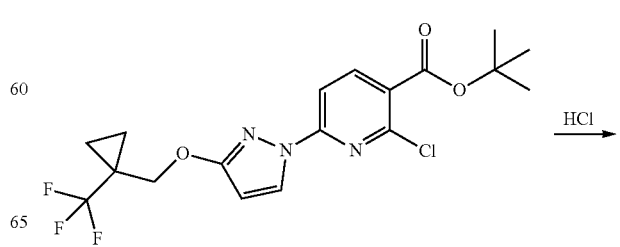

-continued

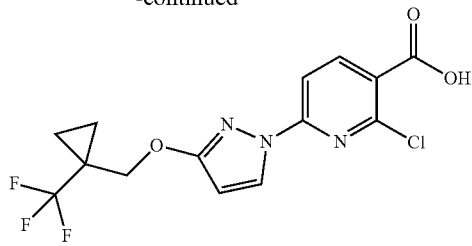

A 1000 mL 3 neck round bottom flask as fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 2-chloro-6-[3-[[1-(trifluoromethyl)cyclopropyl]methoxy]pyrazol-1-yl]pyridine-3-carboxylate (70 g, 0.1675 mol) and 2-propanol (350 mL) which provided an off-white suspension. Stirring was commenced and the pot temperature was recorded at 19° C. The addition funnel was charged with aqueous 6 M HCl (139.6 mL, 0.8375 mol) which was added dropwise over 10 minutes which resulted in an exotherm to 30° C. The resulting suspension was then heated to reflux (pot temperature ~82° C.) Upon heating the suspension turns to a clear pale yellow solution (pot temperature ~75° C. at this point). After stirring at reflux for ~30 minutes a solid began to precipitate. The suspension was continued to stir at reflux for an additional 30 minutes at which point water (210 mL) was added dropwise over 15 minutes. The heat was then removed and the suspension was continued to stir and allowed to slowly cool to room temperature. The material was collected by vacuum filtration in a glass frit Buchner funnel and the filter cake was displacement washed with 1:1 water/2-propanol (100 mL) followed by water (2×100 mL) and then pulled in the Buchner for 30 minutes. The material was further dried in a vacuum oven at 45° C. for 24 hours to provide 2-chloro-6-[3-[[1-(trifluoromethyl)cyclopropyl]methoxy]pyrazol-1-yl]pyridine-3-carboxylic acid (56 g, 0.155 mol, 92%) as a white solid. $^1$H NMR (400 MHz, DMSO-d$_6$) δ 13.64 (s, 1H), 8.44 (d, J=2.9 Hz, 1H), 8.41 (d, J=8.4 Hz, 1H), 7.74 (d, J=8.4 Hz, 1H), 6.24 (d, J=2.9 Hz, 1H), 4.41 (s, 2H), 1.16-1.07 (m, 4H). ESI-MS m/z calc. 361.0441, found 361.9 (M+1)$^+$; Retention time: 3.23 minutes Step E: N-(Benzenesulfonyl)-2-chloro-6-[3-[[1-(trifluoromethyl)cyclopropyl]methoxy]pyrazol-1-yl]pyridine-3-carboxamide

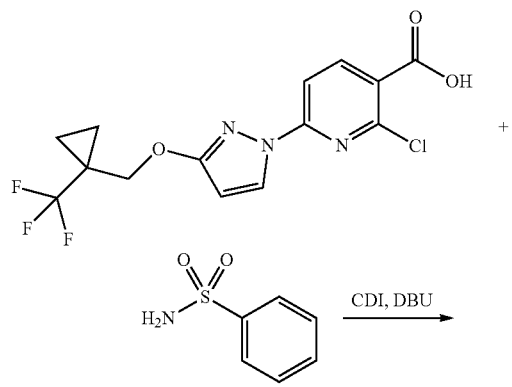

-continued

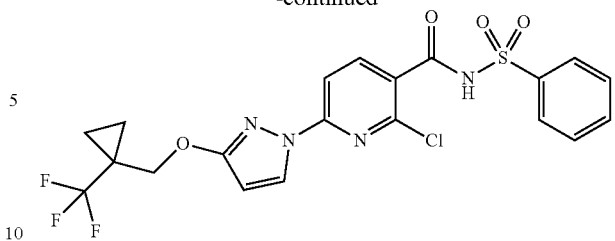

2-Chloro-6-[3-[[1-(trifluoromethyl)cyclopropyl]methoxy]pyrazol-1-yl]pyridine-3-carboxylic acid (150 mg, 0.4144 mmol) was dissolved in THF (2.000 mL). CDI (approximately 80.64 mg, 0.4973 mmol) was added. The reaction mixture was stirred at room temperature for 1.5 hours. Benzenesulfonamide (approximately 84.68 mg, 0.5387 mmol) was added followed by DBU (approximately 126.2 mg, 124.0 µL, 0.8288 mmol). The reaction mixture was allowed to stir at room temperature for another 1.5 hours. The reaction mixture was concentrated to half volume, diluted with dichloromethane and directly injected onto a 12 gram silica gel column and subjected to a 0-10% methanol in dichloromethane gradient; product eluted at 10%. Fractions containing the desired product were combined and concentrated. N-(benzenesulfonyl)-2-chloro-6-[3-[[1-(trifluoromethyl)cyclopropyl]methoxy]pyrazol-1-yl]pyridine-3-carboxamide (168 mg, 81%) was obtained as a clear colorless oil. ESI-MS m/z calc. 500.05328, found 501.0 (M+1)$^+$; Retention time: 1.92 minutes (3 minute run).

Step F: N-(Benzenesulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

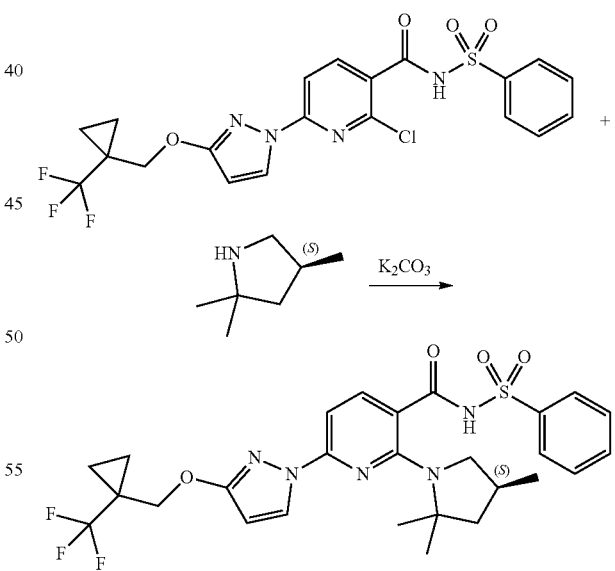

N-(Benzenesulfonyl)-2-chloro-6-[3-[[1-(trifluoromethyl)cyclopropyl]methoxy]pyrazol-1-yl]pyridine-3-carboxamide (168 mg, 0.3354 mmol) and (4S)-2,2,4-trimethylpyrrolidine (Hydrochloride salt) (approximately 150.6 mg, 1.006 mmol) were combined and dissolved in DMSO (0.5 mL). Finely ground potassium carbonate (approximately 278.1 mg, 2.012 mmol) was added, and the reaction mixture was allowed to stir at 130° C. overnight. The reaction mixture was diluted with EtOAc (50 mL) and washed with aqueous 1 M citric acid (2×50 mL) and brine (1×50 mL). The organic layer was dried over sodium sulfate, filtered and concentrated under reduced pressure. The crude product was purified by silica gel column chromatography: 24 gram silica gel column, 0-5% MeOH/DCM gradient; product eluted at 2.5%. Pure fractions were combined and concentrated under reduced pressure, and azeotroped with MeOH, to provide N-(benzenesulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (74.9 mg, 39%). $^1$H NMR (400 MHz, DMSO-d6) δ 12.51 (s, 1H), 8.20 (d, J=2.8 Hz, 1H), 8.05-7.95 (m, 2H), 7.82 (d, J=8.2 Hz, 1H), 7.78-7.70 (m, 1H), 7.66 (dd, J=8.3, 6.7 Hz, 2H), 6.92 (d, J=8.3 Hz, 1H), 6.15 (d, J=2.7 Hz, 1H), 4.43-4.30 (m, 2H), 2.40 (t, J=10.5 Hz, 1H), 2.26 (t, J=8.6 Hz, 1H), 2.09 (dt, J=12.3, 6.4 Hz, 1H), 1.82 (dd, J=12.0, 5.6 Hz, 1H), 1.53 (s, 3H), 1.51 (s, 3H), 1.36 (t, J=12.1 Hz, 1H), 1.15-1.04 (m, 4H), 0.64 (d, J=6.2 Hz, 3H). ESI-MS m/z calc. 577.1971, found 578.3 (M+1)$^+$; Retention time: 2.16 minutes (3 minute run).

SYNTHETIC EXAMPLE 15

Synthesis of Compound 15: N-(o-Tolylsulfonyl)-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

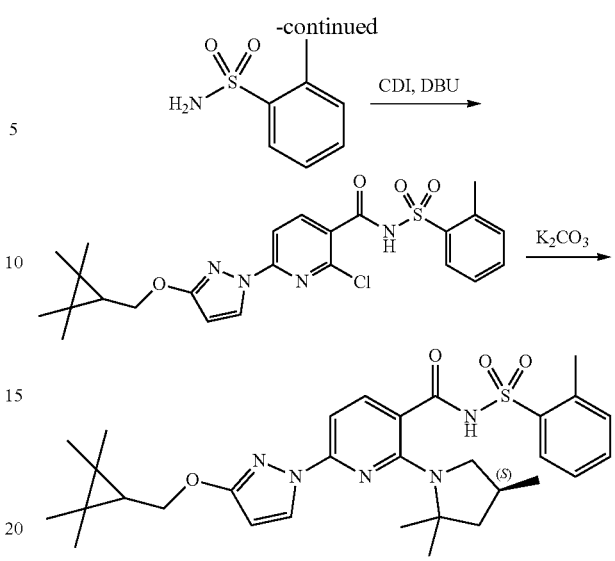

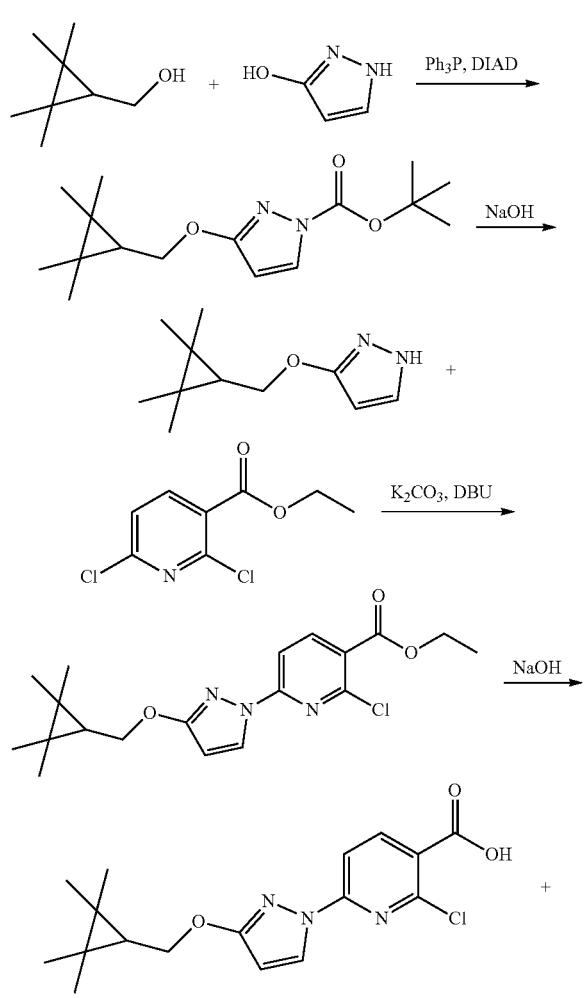

Step A: tert-Butyl 3-[(2,2,3,3-tetramethylcyclopropyl)methoxy]pyrazole-1-carboxylate

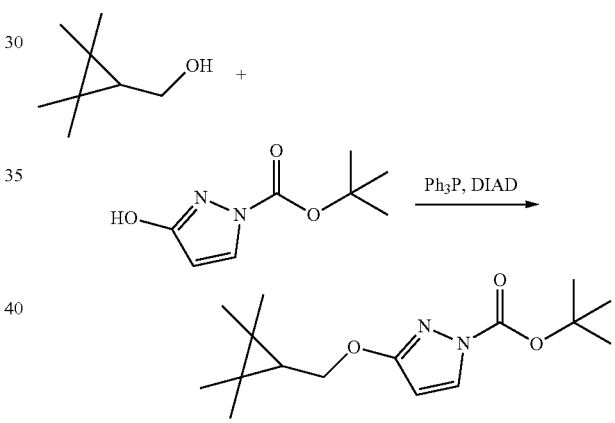

To a degassed solution of Ph$_3$P (approximately 51.28 g, 195.5 mmol) in toluene (360.0 mL) under nitrogen gas at 0° C. was added DIAD (diisopropylazodicarboxylate) (approximately 39.53 g, 37.86 mL, 195.5 mmol) dropwise. The mixture was stirred at 0° C. for 30 min affording a white slurry. To the mixture was added a solution of (2,2,3,3-tetramethylcyclopropyl)methanol (approximately 29.84 g of 70% w/w, 162.9 mmol) and tert-butyl 3-hydroxypyrazole-1-carboxylate (30 g, 162.9 mmol) in toluene (600.0 mL) dropwise at −5° C. over 2 hours. The mixture was allowed to warm to ambient temperature and stirred for 18 hours. The mixture was heated to 75° C. for a total of 6 hours and then allowed to cool to ambient temperature. The slurry was diluted with heptane (900.0 mL) and stirred at ambient temperature for 3 hours. The slurry was filtered over celite and the precipitate washed 3× with 100 mL of heptane. The filtrate was concentrated in vacuo affording a thick yellow oil. The crude product chromatographed on a 750 gram silica gel column loading with dichloromethane and eluting with a 0-20% EtOAc/hexanes gradient. Collected fractions containing product were concentrated in vacuo affording an off-white solid. tert-butyl 3-[(2,2,3,3-tetramethylcyclopropyl)methoxy]pyrazole-1-carboxylate (30.1 g, 63%) was obtained. $^1$H NMR (400 MHz, Chloroform-d) δ 7.82 (d, J=3.0 Hz, 1H), 5.88 (d, J=2.9 Hz, 1H), 4.30 (d, J=7.7 Hz, 2H), 1.61 (s, 9H), 1.12 (s, 6H), 1.04 (s, 6H), 0.70 (t, J=7.8 Hz, 1H). ESI-MS m/z calc. 294.19434, found 295.0 (M+1)$^+$; Retention time: 2.19 minutes Step B: 3-[(2,2,3,3-Tetramethylcyclopropyl)methoxy]-1H-pyrazole

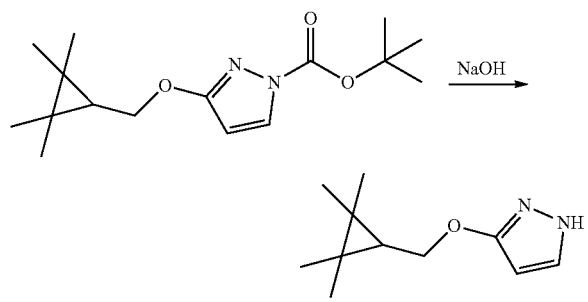

To a solution of tert-butyl 3-[(2,2,3,3-tetramethylcyclopropyl)methoxy]pyrazole-1-carboxylate (127 g, 431.4 mmol) in THF (317.5 mL) and ethyl alcohol (635.0 mL) was slowly added sodium hydroxide (approximately 431.4 mL of 2 M, 862.8 mmol) and stirred at room temperature overnight. Most of the solvent was removed under reduced pressure. The aqueous residue was diluted with water (400 mL) and extracted with methyl t-butyl ether (762.0 mL). The organic phase was washed twice with brine (2×300 mL) and the aqueous phases were back extracted once with methyl t-butyl ether (250 mL). The combined organic phases were dried, filtered and evaporated to give 3-[(2,2,3,3-tetramethylcyclopropyl)methoxy]-1H-pyrazole (75 g, 89%) as a viscous oil. $^1$H NMR (400 MHz, DMSO-d6) δ 11.78 (s, 1H), 7.48 (t, J=2.1 Hz, 1H), 5.65 (s, 1H), 4.05 (d, J=7.7 Hz, 2H), 1.08 (s, 6H), 1.00 (s, 6H), 0.67 (t, J=7.7 Hz, 1H). ESI-MS m/z calc. 194.1419, found 195.0 (M+1)$^+$; Retention time: 1.43 minutes.

Step C: Ethyl 2-chloro-6-[3-[(2,2,3,3-tetramethylcyclopropyl)methoxy]pyrazol-1-yl]pyridine-3-carboxylate

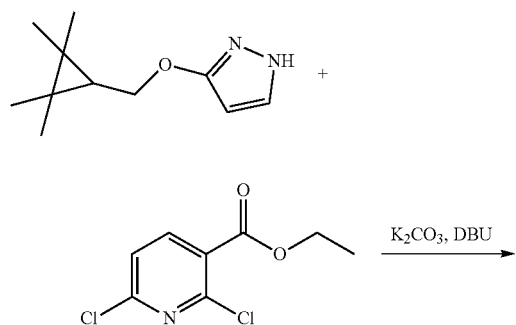

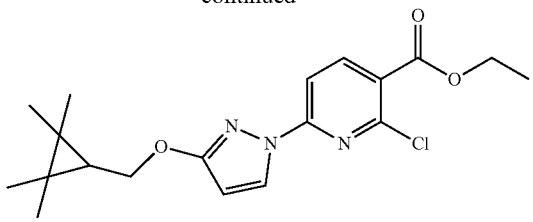

To the ethyl 2,6-dichloropyridine-3-carboxylate (16.8 g, 76.35 mmol) and 3-[(2,2,3,3-tetramethylcyclopropyl)methoxy]-1H-pyrazole (approximately 14.83 g, 76.35 mmol) in DMF (201.6 mL) was added potassium carbonate (approximately 13.72 g, 99.26 mmol) followed by DABCO (approximately 1.284 g, 11.45 mmol). The slurry was stirred at ambient temperature for 16 hours. The cream fine suspension was slowly diluted with water (201.6 mL), and the resulting thick slurry was stirred at ambient temperature for 30 minutes with an overhead stirrer. The precipitate was collected using an medium frit and washed 3 times with 25 mL of water. The solid was air dried for 30 minutes, and then dried in vacuo using an EtOAc azeotrope. Ethyl 2-chloro-6-[3-[(2,2,3,3-tetramethylcyclopropyl)methoxy]pyrazol-1-yl]pyridine-3-carboxylate (28.8 g, 100%) was obtained as an off-white solid. ESI-MS m/z calc. 377.1506, found 378.37 (M+1)$^+$; Retention time: 2.47 minutes. $^1$H NMR (400 MHz, DMSO-d6) δ 8.43 (dd, J=2.9, 0.9 Hz, 1H), 8.39 (dd, J=8.5, 0.9 Hz, 1H), 7.76 (dd, J=8.5, 0.9 Hz, 1H), 6.24 (dd, J=2.9, 0.9 Hz, 1H), 4.34 (td, J=7.5, 6.6 Hz, 2H), 4.28 (d, J=7.8 Hz, 2H), 1.34 (td, J=7.1, 0.9 Hz, 3H), 1.11 (s, 6H), 1.05 (s, 6H), 0.75 (t, J=7.8 Hz, 1H).

Step D: 2-Chloro-6-[3-[(2,2,3,3-tetramethylcyclopropyl)methoxy]pyrazol-1-yl]pyridine-3-carboxylic acid

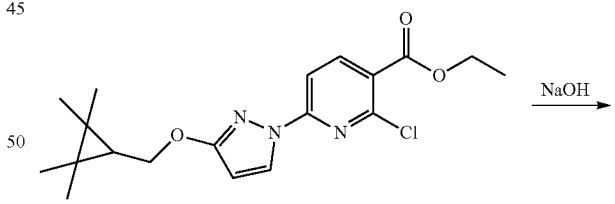

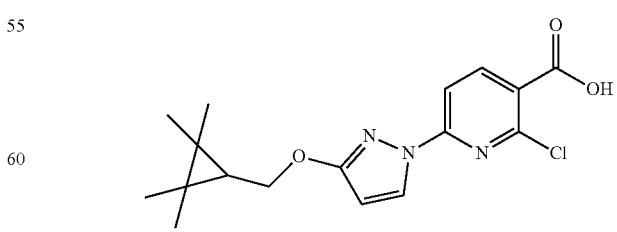

Ethyl 2-chloro-6-[3-[(2,2,3,3-tetramethylcyclopropyl)methoxy]pyrazol-1-yl]pyridine-3-carboxylate (146 g, 386.4 mmol) in THF (730.0 mL) and EtOH (292.0 mL) was treated with NaOH (approximately 772.8 mL of 1 M, 772.8 mmol) and the solution was stirred at room temperature for 5 hours. Most of the solvent was removed under reduced pressure, and the solution was acidified by addition of citric acid (approximately 148.5 g, 89.19 mL, 772.8 mmol) under ice cooling. The formed thick suspension (pH 2-3) was stirred in the ice bath for 1 hour, filtered, washed with plenty of water and dried in a drying cabinet under vacuum at 45° C. with a nitrogen bleed for two days to give 2-chloro-6-[3-[(2,2,3,3-tetramethylcyclopropyl)methoxy]pyrazol-1-yl]pyridine-3-carboxylic acid (128.2 g, 90%) as an off white solid. ESI-MS m/z calc. 349.11932, found 350.0 (M+1)+; Retention time: 2.11 minutes. $^1$H NMR (400 MHz, DMSO-d6) δ 13.64 (s, 1H), 8.69-8.22 (m, 2H), 7.73 (d, J=8.4 Hz, 1H), 6.22 (d, J=2.9 Hz, 1H), 4.28 (d, J=7.8 Hz, 2H), 1.08 (d, J=24.9 Hz, 12H), 0.75 (t, J=7.8 Hz, 1H).

Step E: 2-Chloro-N-(o-tolylsulfonyl)-6-[3-[(2,2,3,3-tetramethylcyclopropyl)methoxy]pyrazol-1-yl]pyridine-3-carboxamide

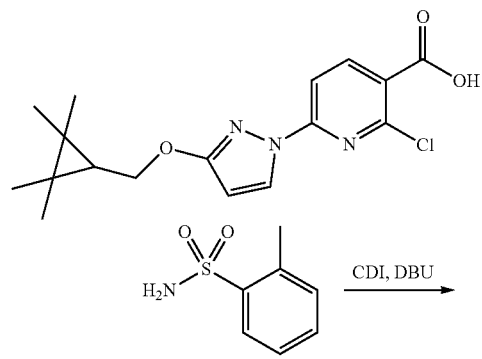

2-Chloro-6-[3-[(2,2,3,3-tetramethylcyclopropyl)methoxy]pyrazol-1-yl]pyridine-3-carboxylic acid (150 mg 0.429 mmol) and was dissolved/suspended in THF (2 mL), and carbonyl diimidazole (64.2 mg, 0.396 mmol) was added. The suspension was allowed to stir at room temperature for 1.5 hours. 2-Methylbenzenesulfonamide (73.4 mg, 0.429 mmol) was then added followed by DBU (59.2 μL, 0.396 mmol). The resulting solution was then stirred for another 1.5 hours. Volatiles were evaporated. The remaining residue was taken up in dichloromethane (2 mL) and washed with aqueous 1 M citric acid (1×2 mL). The organic layer was injected onto a silica gel column for chromatography: 12 gram silica gel column, 0-10% MeOH/DCM gradient. 2-chloro-N-(o-tolylsulfonyl)-6-[3-[(2,2,3,3-tetramethylcyclopropyl)methoxy]pyrazol-1-yl]pyridine-3-carboxamide (115 mg, 53%) was obtained. ESI-MS m/z calc. 502.14417, found 503.0 (M+1)+; Retention time: 2.25 minutes.

Step F: N-(o-Tolylsulfonyl)-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

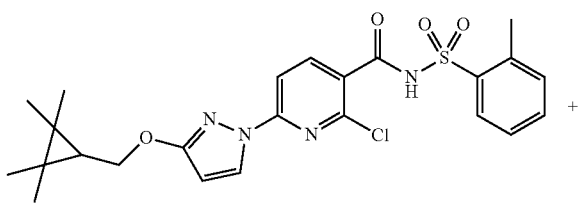

2-Chloro-N-methylsulfonyl-6-[3-[(2,2,3,3-tetramethylcyclopropyl)methoxy]pyrazol-1-yl]pyridine-3-carboxamide (115 mg, 0.229 mmol) and (4S)-2,2,4-trimethylpyrrolidine (Hydrochloride salt) (106 mg, 0.935 mmol) were combined and dissolved in DMSO (1 mL). Finely ground potassium carbonate (258 mg, 1.87 mmol) was added. The reaction mixture was sealed and heated overnight at 130° C. After cooling to room temperature, the reaction mixture was diluted with EtOAc (50 mL) and washed with aqueous citric acid (1 M, 2×50 mL) and brine (1×50 mL). The organic layer was dried over sodium sulfate, filtered and concentrated under reduced pressure. The product was isolated by silica gel column chromatography eluting with a 0-5% MeOH/DCM gradient on a 12 gram silica gel column. N-(o-Tolylsulfonyl)-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (57.2 mg, 42%) was obtained. ESI-MS m/z calc. 579.2879, found 580.3 (M+1)+; Retention time: 2.52 minutes. $^1$H NMR (400 MHz, DMSO-d6) δ 12.62 (s, 1H), 8.18 (d, J=2.8 Hz, 1H), 8.04 (dd, J=8.0, 1.4 Hz, 1H), 7.79 (d, J=8.2 Hz, 1H), 7.59 (td, J=7.5, 1.5 Hz, 1H), 7.50-7.40 (m, 2H), 6.93 (d, J=8.2 Hz, 1H), 6.13 (d, J=2.7 Hz, 1H), 4.24 (d, J=7.8 Hz, 2H), 2.63 (s, 3H), 2.38 (d, J=8.8 Hz, 2H), 2.16 (d, J=10.3 Hz, 1H), 1.82 (dd, J=11.9, 5.5 Hz, 1H), 1.52 (d, J=1.6 Hz, 6H), 1.35 (t, J=12.1 Hz, 1H), 1.10 (s, 6H), 1.04 (d, J=1.1 Hz, 6H), 0.77-0.67 (m, 4H).

SYNTHETIC EXAMPLE 16

Synthesis of Compound 16: N-(3-Fluorophenyl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

Step A: 2-Chloro-N-(3-fluorophenyl)sulfonyl-6-[3-[(2,2,3,3-tetramethylcyclopropyl)methoxy]pyrazol-1-yl]pyridine-3-carboxamide

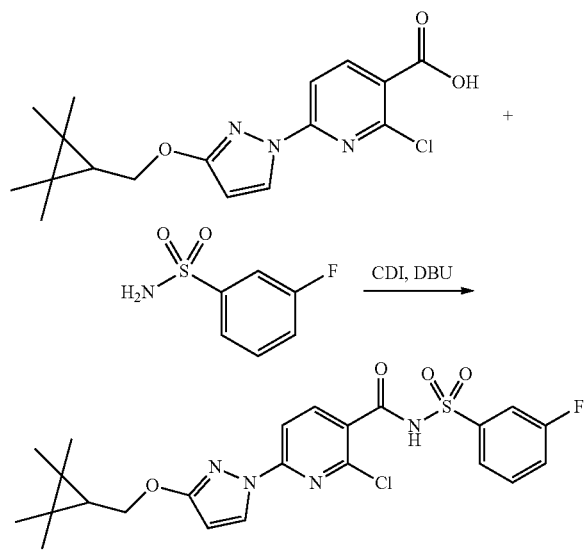

2-Chloro-6-[3-[(2,2,3,3-tetramethylcyclopropyl)methoxy]pyrazol-1-yl]pyridine-3-carboxylic acid (150 mg, 0.429 mmol) was dissolved/suspended in THF (2 mL), and carbonyl diimidazole (64.2 mg, 0.396 mmol) was added. The suspension was allowed to stir at room temperature for 1.5 hours. 3-fluorobenzenesulfonamide (75.1 mg, 0.429 mmol) was then added followed by DBU (59.2 μL, 0.396 mmol). The resulting solution was then stirred for another 1.5 hours. Volatiles were evaporated. The remaining residue was taken up in dichloromethane (2 mL) and washed with aqueous 1 M citric acid (1×2 mL). The organic layer was injected onto a silica gel column to be purified by chromatography: 12 gram silica gel column, 0-10% MeOH/DCM gradient. 2-chloro-N-(3-fluorophenyl)sulfonyl-6-[3-[(2,2,3,3-tetramethylcyclopropyl)methoxy]pyrazol-1-yl]pyridine-3-carboxamide (150 mg, 70%) was obtained. ESI-MS m/z calc. 506.11908, found 507.0 (M+1)⁺; Retention time: 2.24 minutes

Step B: N-(3-fluorophenyl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

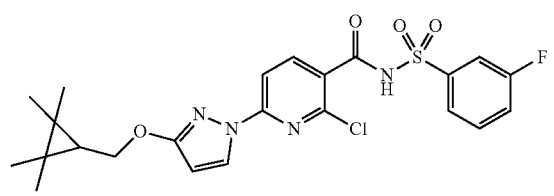

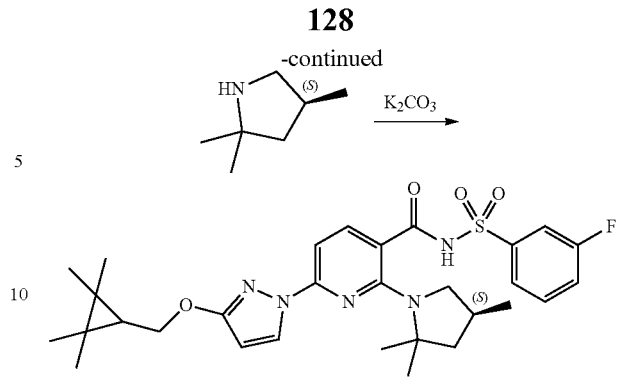

2-Chloro-N-(3-fluorophenyl)sulfonyl-6-[3-[(2,2,3,3-tetramethylcyclopropyl)methoxy]pyrazol-1-yl]pyridine-3-carboxamide (158 mg, 0.312 mmol), and (4S)-2,2,4-trimethylpyrrolidine (Hydrochloride salt) (105.9 mg, 0.935 mmol) were combined and dissolved in DMSO (1 mL). Finely ground potassium carbonate (258 mg, 1.87 mmol) was added. The reaction mixture was sealed and heated overnight at 130° C. After cooling to room temperature, the reaction mixture was diluted with EtOAc (50 mL) and washed with aqueous citric acid (1 M, 2×50 mL) and brine (150 mL). The organic layer was dried over sodium sulfate, filtered and concentrated under reduced pressure. The product was isolated by column chromatography eluting with a 0-5% MeOH/DCM gradient on a 12 gram silica gel column. N-(3-fluorophenyl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (28.4 mg, 16%) was obtained. ESI-MS m/z calc. 583.2629, found 584.6 (M+1)⁺; Retention time: 2.46 minutes. ¹H NMR (400 MHz, DMSO-d6) δ 12.61 (s, 1H), 8.19 (d, J=2.8 Hz, 1H), 7.87-7.81 (m, 2H), 7.79-7.71 (m, 2H), 7.63 (tdd, J=8.6, 2.6, 1.1 Hz, 1H), 6.93 (d, J=8.2 Hz, 1H), 6.13 (d, J=2.8 Hz, 1H), 4.24 (d, J=7.7 Hz, 2H), 2.44 (t, J=10.4 Hz, 1H), 2.36-2.26 (m, 1H), 2.13 (td, J=11.8, 6.0 Hz, 1H), 1.84 (dd, J=11.8, 5.5 Hz, 1H), 1.54 (s, 3H), 1.52 (s, 3H), 1.39 (t, J=12.1 Hz, 1H), 1.10 (s, 6H), 1.04 (s, 6H), 0.74 (d, J=7.7 Hz, 1H), 0.70 (t, J=6.6 Hz, 3H).

SYNTHETIC EXAMPLE 17

Synthesis of Compound 17: N-(Benzenesulfonyl)-2-[(4S)-3,3-dideuterio-2,2-dimethyl-4-(trideuteriomethyl)pyrrolidin-1-yl]-6-[3-[2-[1-(trifluoromethyl)cyclopropyl]ethoxy]pyrazol-1-yl]pyridine-3-carboxamide

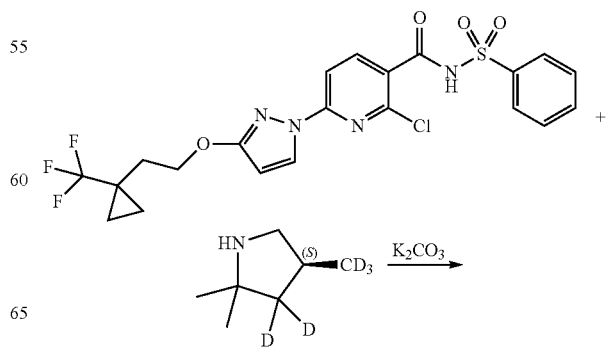

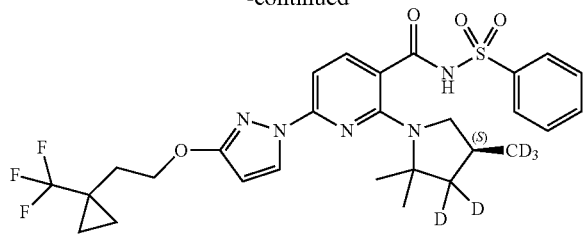

N-(Benzenesulfonyl)-2-chloro-6-[3-[2-[1-(trifluoromethyl)cyclopropyl]ethoxy]pyrazol-1-yl]pyridine-3-carboxamide (2 g, 3.884 mmol) was dissolved in NMP (10.00 mL) and 1,2-diethoxyethane (2.000 mL). Potassium carbonate (approximately 2.684 g. 19.42 mmol) and (4S)-3,3-dideuterio-2,2-dimethyl-4-(trideuteriomethyl)pyrrolidine (Hydrochloride salt) (approximately 1.502 g, 9.710 mmol) were added, and the resulting slurry heated was to 130° C. and stirred overnight. The reaction mixture was cooled and poured into rapidly stirred ice (60.00 mL) and acetic acid (approximately 3.499 g, 3.313 mL, 58.26 mmol). After stirring for 20 minutes to form a fairly uniform flowing solid, the solids were filtered off and washed with water. The cake was dissolved in dichloromethane, and the resulting aqueous forced out was separated. The dichloromethane layer was washed with water twice and brine and dried over sodium sulfate and concentrated. Ethanol (20 mL) was added, and the solution was concentrated to a few milliliters. Water was very slowly added dropwise. The suspension that formed was warmed to a thin suspension and allowed to cool over 30 minutes. Crystalline solids were filtered and washed with small amount of ethanol to give N-(benzenesulfonyl)-2-[(4S)-3,3-dideuterio-2,2-dimethyl-4-(trideuteriomethyl)pyrrolidin-1-yl]-6-[3-[2-[1-(trifluoromethyl)cyclopropyl]ethoxy]pyrazol-1-yl]pyridine-3-carboxamide (600 mg, 26%). ESI-MS m/z calc. 596.24, found 597.0 (M+1)$^+$; Retention time: 2.29 minutes.

SYNTHETIC EXAMPLE 18

Synthesis of Compound 18: N-(Benzenesulfonyl)-6-[3-[(cis)-2-(trifluoromethyl)cyclopropoxy]pyrazol-1-yl]-2-[(4S)-2,2,4-trimethylpyrrolidin-1-yl]pyridine-3-carboxamide

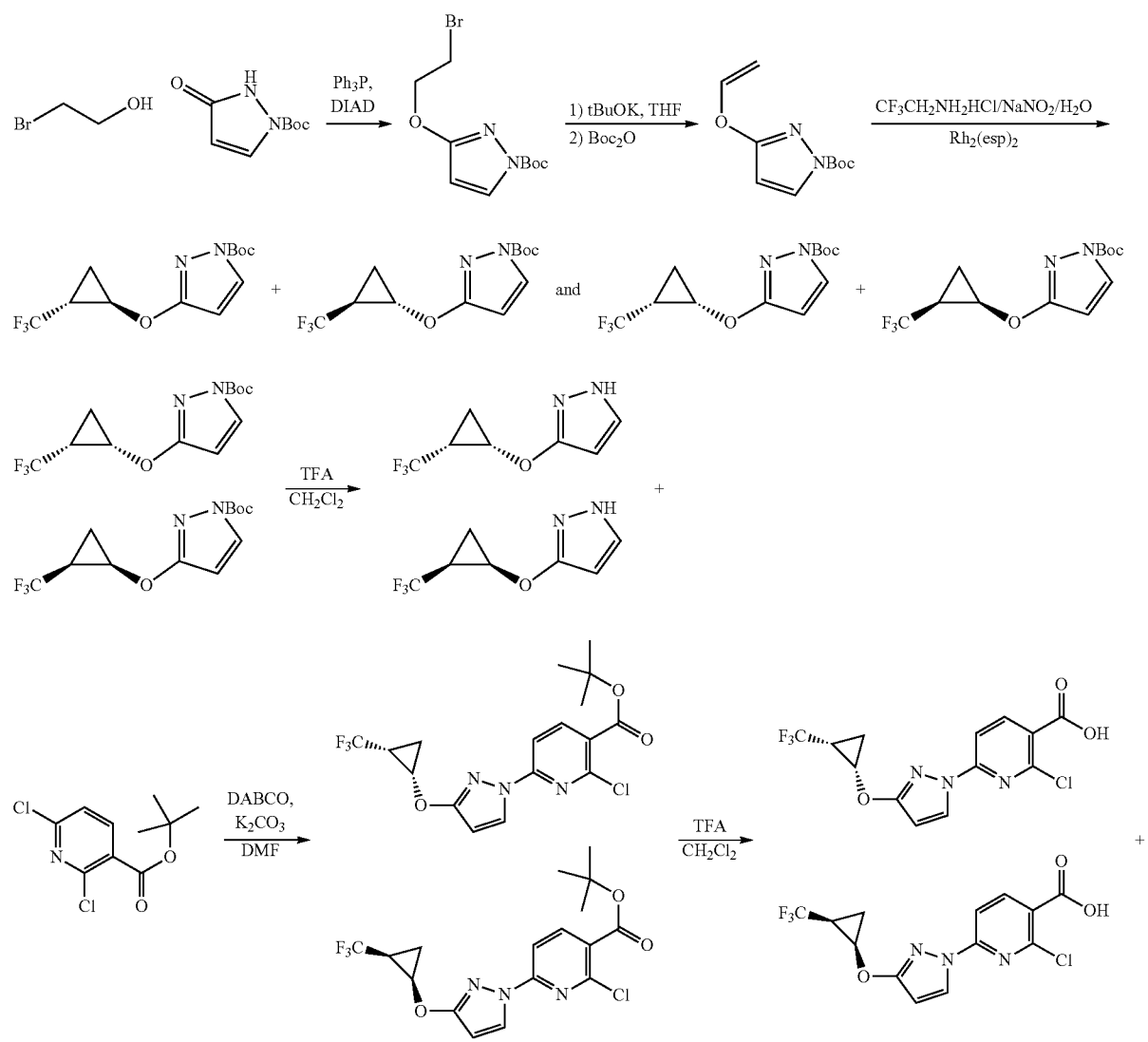

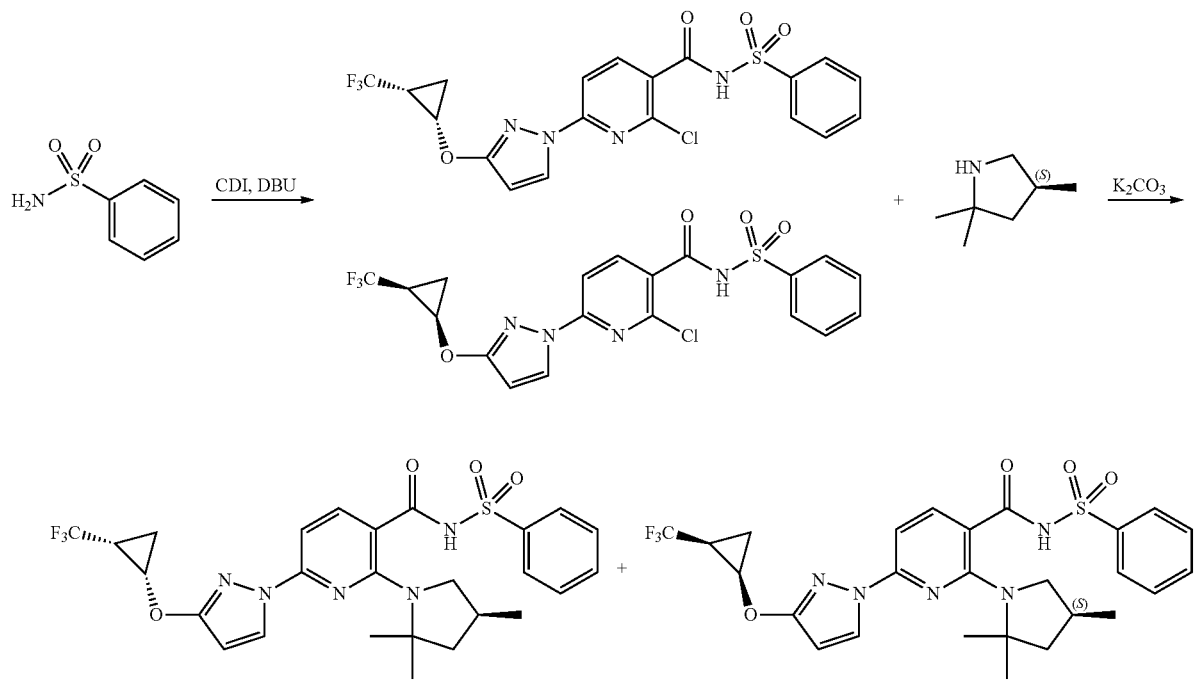

Step A: tert-Butyl 3-(2-bromoethoxy)-1H-pyrazole-1-carboxylate

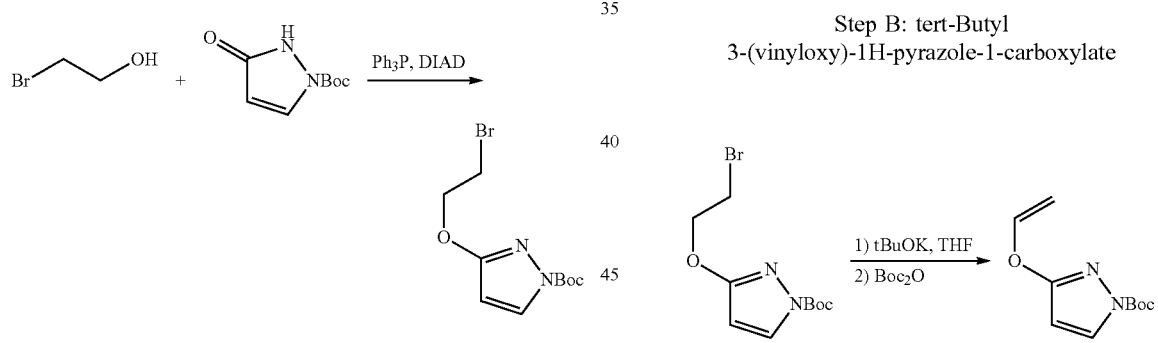

To the solution of 2-bromoethanol (1.69 g, 13.53 mmol), tert-butyl-2,3-dihydro-3-oxopyrazole-1-carboxylate (2.08 g, 11.28 mmol) and triphenylphosphine (3.55 g, 13.53 mmol) in anhydrous tetrahydrofuran (45 mL) at 0° C. diisopropyl azodicarboxylate (2.74 g, 13.53 mmol) was added dropwise. After the addition was complete, the reaction solution was stirred at 0° C. for 1 hour, then warmed up to room temperature and stirred for additional 2 hours. Ether (400 mL) was added. The organic solution was washed with saturated sodium carbonate aqueous solution (80 mL), brine (50 mL), then dried over magnesium sulfate, filtered and concentrated under reduced pressure. The residue obtained was purified by silica gel chromatography using hexanes-ethyl acetate gradient method (0 to 15% ethyl acetate) to afford tert-butyl 3-(2-bromoethoxy)-1H-pyrazole-1-carboxylate (2.56 g, 78%) as white solid. $^1$H NMR (250 MHz, CDCl$_3$) δ (ppm): 7.85 (d, J=3.0 Hz, 1H), 5.92 (d, J=3.0 Hz, 1H), 4.63 (t, J=6.0 Hz, 2H), 3.68 (t, J=6.0 Hz, 2H), 1.64 (s, 9H). ESI-MS min calc. 292.0 found 292.9 (M+1)$^+$. Retention time: 4.91 minutes.

Step B: tert-Butyl 3-(vinyloxy)-1H-pyrazole-1-carboxylate

To the solution of tert-butyl 3-(2-bromoethoxy)-1H-pyrazole-1-carboxylate (2.52 g, 8.66 mmol) in anhydrous tetrahydrofuran (90 mL) was added potassium tert-butoxide (1.46 g, 13.0 mmol). The resulting solution was stirred for 2 hours, then di-tert-butyl dicarbonate (5.67 g, 26.0 mmol) and stirred for another 1 hour. Diethyl ether (400 mL) was added. Organic layers were washed with water (50 mL), brine (2×50 mL), dried over dried over magnesium sulfate, filtered and concentrated under reduced pressure. The residue obtained was purified by silica gel chromatography using hexanes-ethyl acetate gradient method (0 to 10% ethyl acetate) to afford tert-butyl 3-(vinyloxy)-1H-pyrazole-1-carboxylate (1.10 g, 60%) as colorless oil. $^1$H NMR (250 MHz, CDCl$_3$) δ (ppm): 7.89 (d, J=3.0 Hz, 1H), 7.24 (dd, J=6, 13.5 Hz, 1H), 5.95 (d, J=3.0 Hz, 1H), 4.88 (dd, J=1.8, 13.5 Hz, 1H), 4.50 (dd, J=1.8, 6.0 Hz, 1H), 1.62 (s, 9H). ESI-MS m/z calc. 210.1 found 211.0 (M+1)$^+$. Retention time: 4.74 minutes.

Step C: tert-Butyl 3-(2-(trifluoromethyl)cyclopropoxy)-1H-pyrazole-1-carboxylate

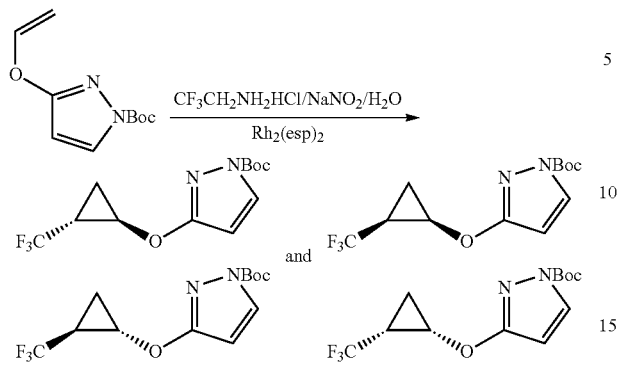

tert-Butyl 3-(vinyloxy)-1H-pyrazole-1-carboxylate (1.10 g, 5.23 mmol) in pear-shape flask (100 mL) was added water (20 mL) and bubbled with argon for 5 minutes, then sodium acetate (85.8 mg, 1.05 mmol) was added followed by 2,2,2-trifluoroethylamine hydrochloride (3.57 g, 26.17 mmol) and concentrated sulfuric acid (51.3 mg, 0.523 mmol). The solution was bubbled with argon for another 5 minutes before bis[rhodium($\alpha,\alpha,\alpha',\alpha'$-tetramethyl-1,3-benzenedipropionic acid)] (397 mg, 0.523 mmol) was added. The reaction solution was kept under argon with balloon while aqueous solution of sodium nitrite (2.17 g, 31.4 mmol) in water (12.8 mL) was added by syringe pump within 10 hours. After the addition was complete, the resulting solution was stirred for an additional 6 hours. Diethyl ether (300 mL) was added and the organic layer was separated. Then organic layer was washed with brine (30 mL), dried over magnesium sulfate, filtered and concentrated under reduced pressure. The residue obtained was purified by silica gel chromatography using hexanes-dichloromethane gradient method (0 to 100% dichloromethane). The residue obtained was subjected to silica gel chromatography again (hexanes and ethyl acetate, 0 to 10% ethyl acetate gradient) to afford tert-butyl 3-(1,2-trans-2-(trifluoromethyl)cyclopropoxy)-1H-pyrazole-1-carboxylate and tert-butyl 3-(1,2-cis-2-(trifluoromethyl)cyclopropoxy)-1H-pyrazole-1-carboxylate.
tert-butyl 3-(1,2-trans-2-(trifluoromethyl)cyclopropoxy)-1H-pyrazole-1-carboxylate: (366 mg, 24%); a white solid. $^1$H NMR (250 MHz, CDCl$_3$) δ (ppm): 7.84 (d, J=2.8 Hz, 1H), 5.91 (d, J=2.8 Hz, 1H), 4.49 (m, 1H), 1.75 (m, 1H), 1.62 (s, 9H), 1.56-1.25 (m, 2H). ESI-MS m/z calc. 292.1 found 293.1 (M+1)$^+$. Retention time: 5.22 minutes. tert-butyl 3-(1,2-cis-2-(trifluoromethyl)cyclopropoxy)-1H-pyrazole-1-carboxylate: (314 mg, 21%); a white solid. $^1$H NMR (250 MHz, CDCl$_3$) δ (ppm): 7.90 (d, J=2.8 Hz, 1H), 5.92 (d, J=2.8 Hz, 1H), 4.49 (m, 1H), 1.94 (m, 1H), 1.62 (s, 9H), 1.30 (m, 2H). ESI-MS m/z calc. 292.1 found 293.1 (M+1)$^+$. Retention time: 5.48 minutes.

Step D: 3-(1,2-cis-2-(Trifluoromethyl)cyclopropoxy)-1H-pyrazole

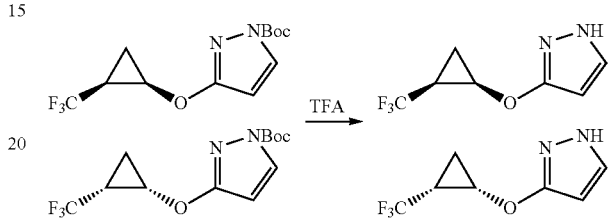

Trifluoroacetic acid (2.76 g, 24.3 mmol) was added to the solution of tert-butyl 3-(1,2-cis-2-(trifluoromethyl)cyclopropoxy)-1H-pyrazole-1-carboxylate (708 mg, 2.43 mmol) in anhydrous dichloromethane (24 mL). The resulting solution was stirred at room temperature for 16 hours. 1,2-Dichloroethane (10 mL) was added to the reaction solution. All the solvents were removed under reduced pressure. The residue obtained was dissolved in ethyl ether (150 mL), washed with saturated sodium bicarbonate aqueous solution (30 mL). The organic solution was dried over magnesium sulfate, filtered and concentrated under the reduced pressure to afford crude 3-(1,2-cis-2-(trifluoromethyl)cyclopropoxy)-1H-pyrazole (461 mg, 99° %) as yellow-brown oil. The crude product was used directly in next step without any further purification. ESI-MS m/z calc. 192.1 found 193.0 (M+1). Retention time: 3.26 minutes.

Step E: tert-Butyl 6-(3-(1,2-cis-2-(trifluoromethyl)cyclopropoxy)-1H-pyrazol-1-yl)-2-chloropyridine-3-carboxylate

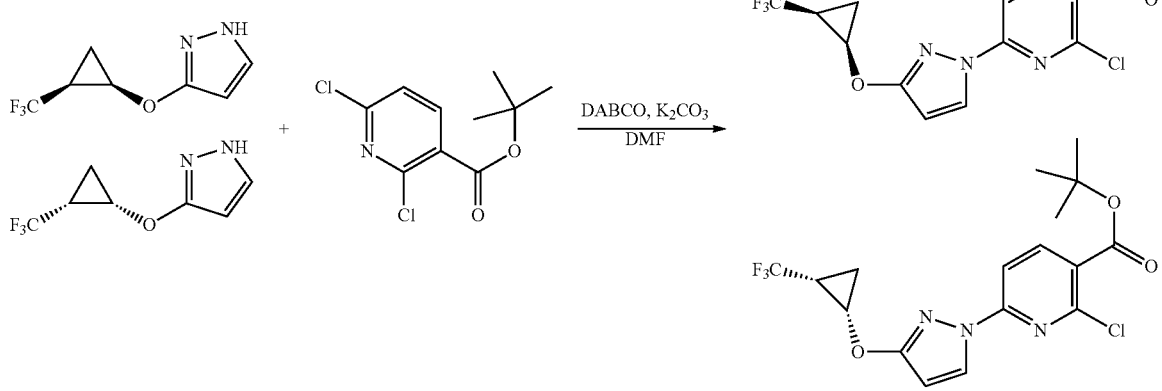

To the solution of crude 3-(1,2-cis-2-(trifluoromethyl)cyclopropoxy)-1H-pyrazole (461 mg, 2.43 mmol) in dimethylformamide (8 mL) was added tert-butyl 2,6-dichloropyridine-3-carboxylate (659 mg, 2.67 mmol), potassium carbonate (669 mg, 4.85 mmol) and 1,4-diazabicyclo [2.2.2] octane (55 mg, 0.49 mmol). The reaction was stirred at room temperature for 48 hours. The reaction solution was diluted with ether (200 mL), washed with water (4×20 mL) and brine (20 mL). The organic layer was dried over magnesium sulfate, filtered and concentrated under reduced pressure. The residue obtained was purified by silica gel chromatography using hexanes-dichloromethane gradient method (0 to 100% dichloromethane) to afford tert-butyl 6-(3-(1,2-cis-2-(trifluoromethyl)cyclopropoxy)-1H-pyrazol-1-yl)-2-chloropyridine-3-carboxylate (731 mg, 68%) as a white solid. $^1$H NMR (250 MHz, CDCl$_3$) δ (ppm): 8.39 (d, J=2.8 Hz, 1H), 8.22 (d, J=8.5 Hz, 1H), 7.74 (d, J=8.5 Hz, 1H), 6.01 (d, J=2.8 Hz, 1H), 4.33 (m, 1H), 1.93 (m, 1H), 1.62 (s, 9H), 1.45-1.26 (m, 2H). ESI-MS m/z calc. 403.1 found 404.1 (M+1)$^+$. Retention time: 7.29 minutes.

Step F: 6-(3-(1,2-cis-2-(Trifluoromethyl)cyclopropoxy)-1H-pyrazol-1-yl)-chloropyridine-3-carboxylic acid

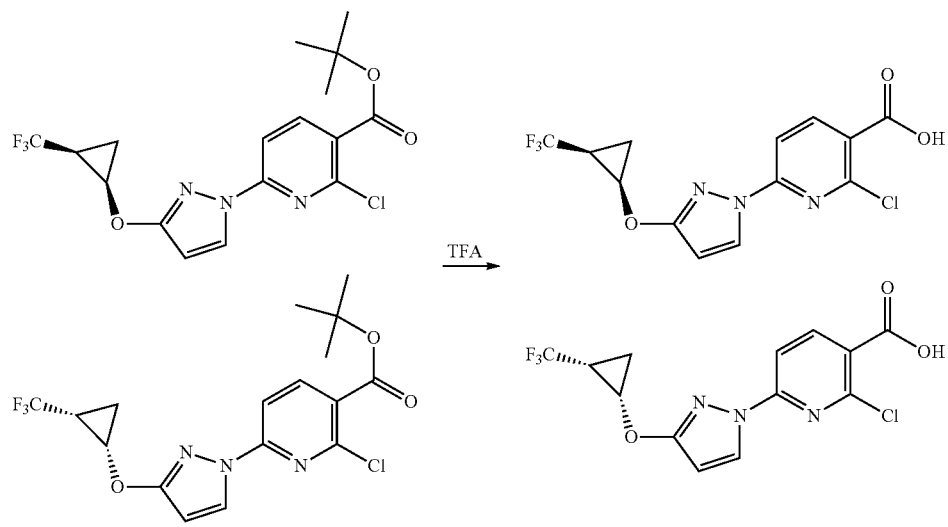 [SMILES: CC(C)(C)OC(=O)c1ccc(-n2ccc(O[C@@H]3C[C@@H]3C(F)(F)F)n2)nc1Cl ; O=C(O)c1ccc(-n2ccc(O[C@@H]3C[C@@H]3C(F)(F)F)n2)nc1Cl ; CC(C)(C)OC(=O)c1ccc(-n2ccc(O[C@H]3C[C@H]3C(F)(F)F)n2)nc1Cl ; O=C(O)c1ccc(-n2ccc(O[C@H]3C[C@H]3C(F)(F)F)n2)nc1Cl]

Trifluoroacetic acid (2.03 g, 17.8 mmol) was added to the solution of tert-butyl 6-(3-(1,2-cis-2-(trifluoromethyl)cyclopropoxy)-1H-pyrazol-1-yl)-2-chloropyridine-3-carboxylate (718 mg, 1.78 mmol) in anhydrous dichloromethane (18 mL). The resulting solution was stirred at room temperature for 16 hours. 1,2-Dichloroethane (10 mL) was added to the reaction solution. All the solvents were removed under the reduced pressure. The crude solid obtained was added 10% ethyl ether in hexanes (25 mL) and sonicated for 30 minutes, filtered, washed with 10/o ethyl ether in hexanes (10 ml), hexanes (10 mL) and dried under high vacuum to afford 6-(3-(1,2-cis-2-(trifluoromethyl)cyclopropoxy)-1H-pyrazol-1-yl)-2-chloropyridine-3-carboxylic acid (517 mg, 84%) as a white solid. $^1$H NMR (500 MHz, DMSO) δ (ppm): 13.6 (bs, 1H), 8.47 (d, J 3.0 Hz, 1H), 8.42 (d, J=8.8 Hz, 1H), 7.72 (d, J=8.8 Hz, 1H), 6.27 (d, J=3.0 Hz, 1H), 4.46 (m, 1H), 2.40 (m, 1H), 1.47 (m, 1H), 1.32 (m, 1H). ESI-MS m/z calc. 347.0 found 347.9 (M+1)$^+$. Retention time: 5.20 minutes.

Step G: N-(Benzenesulfonyl)-2-chloro-6-[3-[(cis)-2-(trifluoromethyl)cyclopropoxy]pyrazol-1-yl]pyridine-3-carboxamide

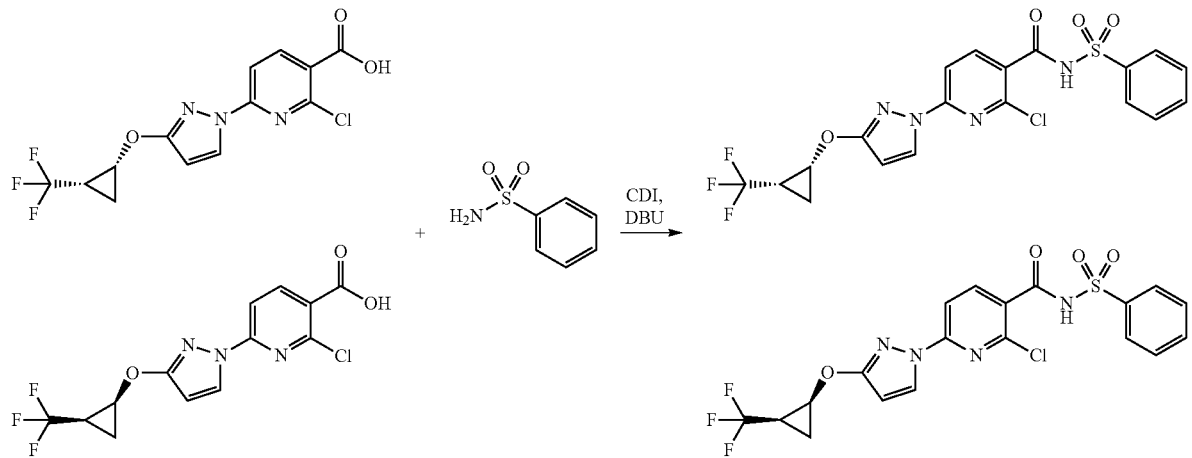 [SMILES: O=C(O)c1ccc(-n2ccc(O[C@@H]3C[C@@H]3C(F)(F)F)n2)nc1Cl ; O=C(O)c1ccc(-n2ccc(O[C@H]3C[C@H]3C(F)(F)F)n2)nc1Cl ; NS(=O)(=O)c1ccccc1 ; O=C(NS(=O)(=O)c1ccccc1)c1ccc(-n2ccc(O[C@@H]3C[C@@H]3C(F)(F)F)n2)nc1Cl ; O=C(NS(=O)(=O)c1ccccc1)c1ccc(-n2ccc(O[C@H]3C[C@H]3C(F)(F)F)n2)nc1Cl]

6-(3-(1,2-Cis-2-(trifluoromethyl)cyclopropoxy)-1H-pyrazol-1-yl)-2-chloropyridine-3-carboxylic acid (125 mg, 0.360 mmol) was dissolved in THF (1 mL). 1,1'-Carbonyldiimidazole (75.6 mg, 0.431 mmol) was added. The reaction mixture was allowed to stir at room temperature for 1 hour. benzenesulfonamide (67.8 mg, 0.431 mmol) was added followed by DBU (64.5 µL, 0.431 mmol). The final reaction mixture was allowed to stir overnight at room temperature. Volatiles were removed by evaporation. It was taken up in EtOAc (50 mL) and washed with aqueous 1 M citric acid solution (2×50 mL) and brine (1×50 mL). The organic layer was dried over sodium sulfate, filtered and concentrated under reduced pressure. N-(benzenesulfonyl)-2-chloro-6-[3-[(cis)-2-(trifluoromethyl)cyclopropoxy]pyrazol-1-yl]pyridine-3-carboxamide (201 mg) was obtained. ESI-MS m/z calc. 486.03763, found 486.9 (M+1)$^+$; Retention time: 0.67 minutes (1 minute run).

Step H; N-(Benzenesulfonyl)-6-[3-[(cis)-2-(trifluoromethyl)cyclopropoxy]pyrazol-1-yl]-2-[(4S)-2,2,4-trimethylpyrrolidin-1-yl]pyridine-3-carboxamide

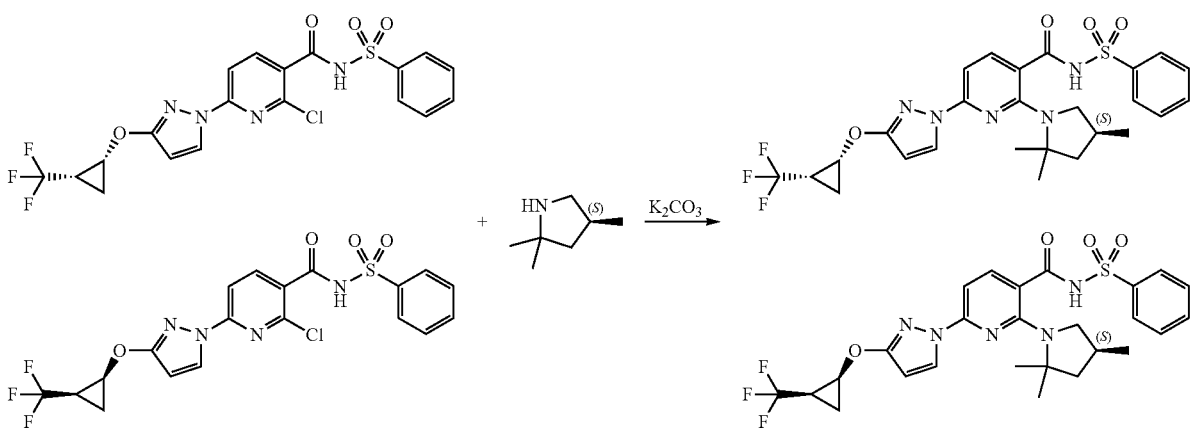

N-(benzenesulfenyl)-2-chloro-6-[3-[(cis)-2-(trifluoromethyl)cyclopropoxy]pyrazol-1-yl]pyridine-3-carboxamide (175 mg, 0.3595 mmol) was dissolved in DMSO (1 mL). (4S)-2,2,4-trimethylpyrrolidine (Hydrochloride salt) (161 mg, 1.08 mmol) was added followed by potassium carbonate (298 mg, 2.16 mmol). The reaction mixture was allowed to stir at 130° C. overnight. After cooling to room temperature, the reaction mixture was diluted with EtOAc (50 mL) and washed with aqueous citric acid (1 M, 2×50 mL) and brine (1×50 mL). The organic layer was dried over sodium sulfate, filtered and concentrated under reduced pressure. The product was isolated by silica gel column chromatography on a 12 gram silica gel column eluting with a 0-10% EtOAc/hexane gradient. N-(benzenesulfonyl)-6-[3-[(cis)-2-(trifluoromethyl)cyclopropoxy]pyrazol-1-yl]-2-[(4S)-2,2,4-trimethylpyrrolidin-1-yl]pyridine-3-carboxamide (114.3 mg, 56%) was obtained. ESI-MS m/z calc. 563.1814, found 564.5 (M+1)$^+$; Retention time: 2.08 minutes

SYNTHETIC EXAMPLE 19

Synthesis of Compound 19: N-(Benzenesulfonyl)-6-[3-[(trans)-2-(trifluoromethyl)cyclopropoxy]pyrazol-1-yl]-2-[(4S)-2,2,4-trimethylpyrrolidin-1-yl]pyridine-3-carboxamide

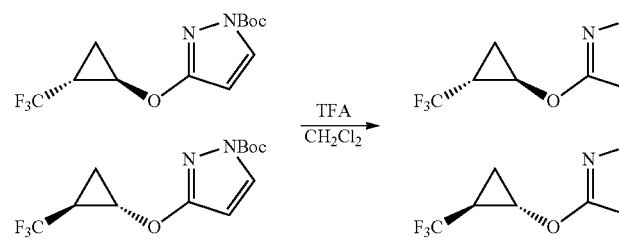

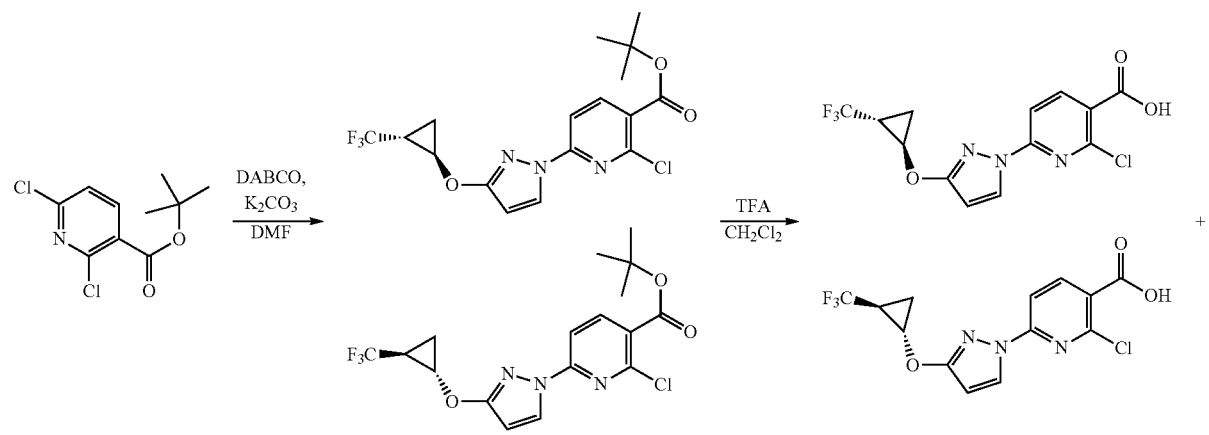

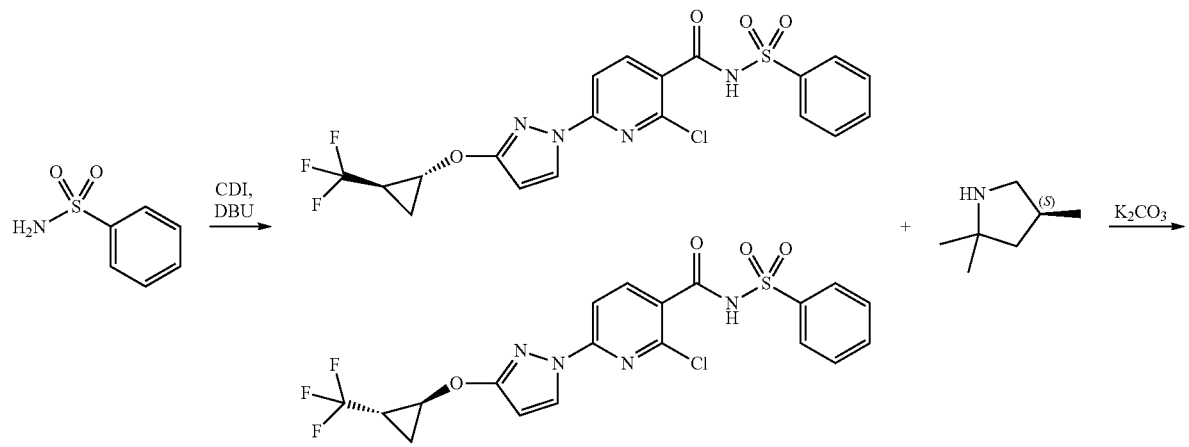

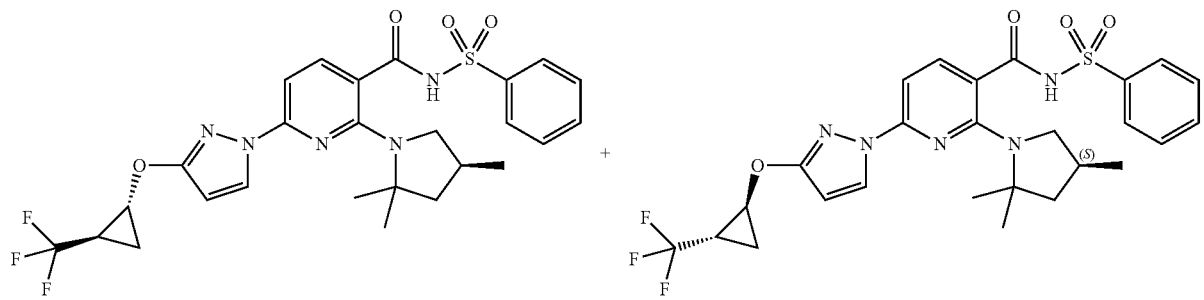

Step A: 3-(1,2-trans-2-(Trifluoromethyl)cyclopropoxy)-1H-pyrazole

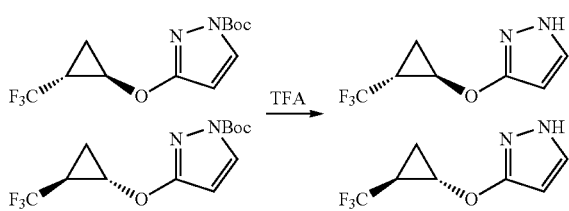

Trifluoroacetic acid (3.15 g, 27.64 mmol) was added to the solution of tert-butyl 3-(1,2-trans-2-(trifluoromethyl)cyclopropoxy)-1H-pyrazole-1-carboxylate (807 mg, 2.76 mmol) in anhydrous dichloromethane (28 mL). The resulting solution was stirred at room temperature for 16 hours. 1,2-Dichloroethane (15 mL) was added to the reaction solution. All the solvents were removed under the reduced pressure. The residue obtained was dissolved in ethyl ether (200 mL), washed with saturated sodium bicarbonate aqueous solution (30 mL). The organic solution was dried over magnesium sulfate, filtered and concentrated under reduced pressure to afford crude 3-(1,2-trans-2-(trifluoromethyl)cyclopropoxy)-1H-pyrazole (525 mg, 99%) as yellow-brown oil. The crude product was used directly in next step without any further purification. ESI-MS m/z calc. 192.1 found 193.0 (M+1)$^+$. Retention time: 2.97 minutes.

Step B: tert-Butyl 6-(3-(1,2-trans-2-(trifluoromethyl)cyclopropoxy)-1H-pyrazol-1-yl)-2-chloropyridine-3-carboxylate

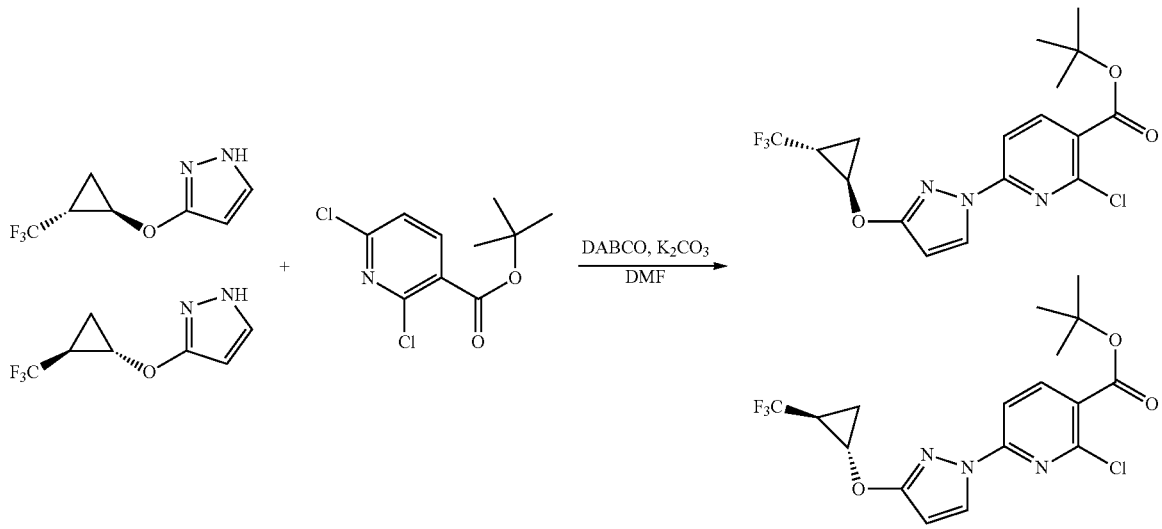

To the solution of crude 3-(1,2-trans-2-(trifluoromethyl) cyclopropoxy)-1H-pyrazole (525 mg, 2.76 mmoL) in dimethylformamide (9.2 mL) was added tert-butyl 2,6-dichloropyridine-3-carboxylate (751 mg, 3.04 mmol), potassium carbonate (763 mg, 5.53 mmol) and 1,4-diazabicyclo [2.2.2] octane (62 mg, 0.55 mmol). The reaction was stirred at room temperature for 48 hours. The reaction solution was diluted with ether (250 mL), washed with water (4×20 mL) and brine (20 mL). The organic layer was dried over magnesium sulfate, filtered and concentrated under reduced pressure. The residue obtained was purified by silica gel chromatography using hexanes-dichloromethane gradient method (0 to 100% dichloromethane) to afford tert-butyl 6-(3-(1,2-trans-2-(trifluoromethyl)cyclopropoxy)-1H-pyrazol-1-yl)-2-chloropyridine-3-carboxylate (314 mg, 21%) as a colorless oil. ESI-MS m/z calc. 403.1 found 404.1 (M+1)$^+$. Retention time: 6.92 minutes. $^1$H NMR (250 MHz, CDCl$_3$) δ (ppm): 8.38 (d, J=3.0 Hz, 1H), 8.20 (d, J=8.5 Hz, 1H), 7.73 (d, J=8.5 Hz, 1H), 6.03 (d, J=3.0 Hz, 1H), 4.39 (m, 1H), 1.77 (m, 1H), 1.62 (s, 9H), 1.44 (m, 1H), 1.31 (m, 1H).

Step C: 6-(3-(1,2-Trans-2-(trifluoromethyl)cyclopropoxy)-1H-pyrazol-1-yl)-2-chloropyridine-3-carboxylic acid

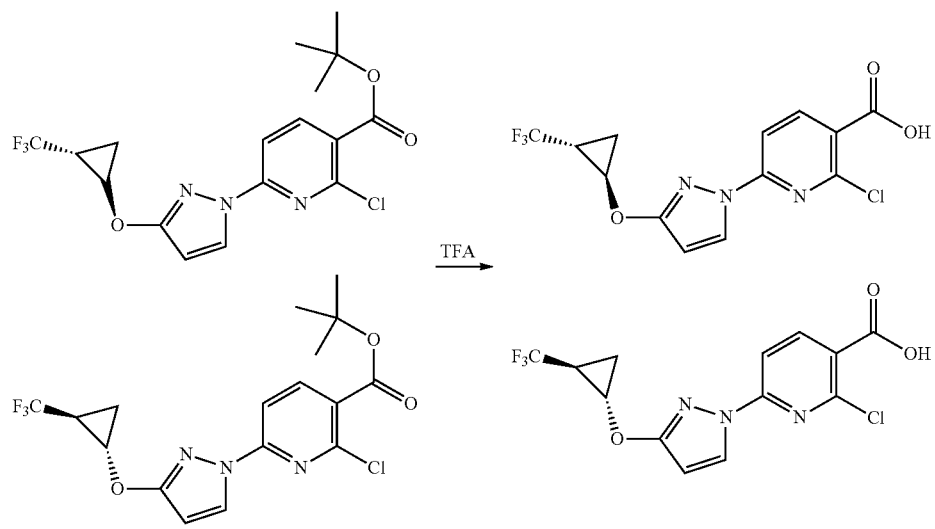

Trifluoroacetic acid (2.39 g, 21.0 mmol) was added to the solution of tert-butyl 6-(3-(1,2-trans-2-(trifluoromethyl)cyclopropoxy)-1H-pyrazol-1-yl)-2-chloropyridine-3-carboxylate (847 mg, 2.10 mmol) in anhydrous dichloromethane (21 mL). The resulting solution was stirred at room temperature for 20 hours. 1,2-Dichloroethane (15 mL) was added to the reaction mixture. All the solvents were removed under reduced pressure. Crude solid obtained was added 10% ethyl ether in hexanes (30 mL) and sonicated for 30 minutes, filtered, washed with 10% ethyl ether in hexanes (10 mL), hexanes (10 mL) and dried under high vacuum to afford 6-(3-(1,2-trans-2-(trifluoromethyl)cyclopropoxy)-1H-pyrazol-1-yl)-2-chloropyridine-3-carboxylic acid (600 mg, 82%) as a white solid. ESI-MS m/z calc. 347.0 found 347.9 (M+1)$^+$. Retention time: 4.91 minutes. $^1$H NMR (500 MHz, DMSO) δ (ppm): 8.46 (d, J=2.8 Hz, 1H), 8.41 (d, J=8.3 Hz, 1H), 7.74 (d, J=8.3 Hz, 1H), 6.30 (d, J=2.8 Hz, 1H), 4.46 (m, 1H), 2.15 (m, 1H), 1.40 (m, 1H), 1.34 (m, 1H).

Step D: N-(Benzenesulfonyl)-2-chloro-6-[3-[(trans)-2-(trifluoromethyl)cyclopropoxy]pyrazol-1-yl]pyridine-3-carboxamide

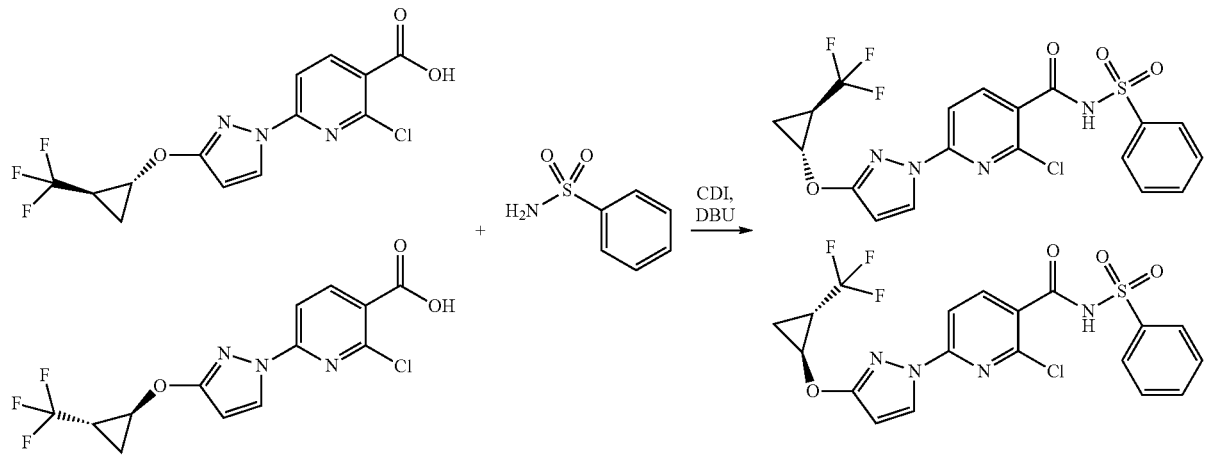

6-(3-(1,2-trans-2-(Trifluoromethyl)cyclopropoxy)-1H-pyrazol-1-yl)-2-chloropyridine-3-carboxylic acid (125 mg, 0.360 mmol) was dissolved in THF (1 mL). 1,1'-Carbonyldiimidazole (75.6 mg, 0.431 mmol) was added. The reaction mixture was allowed to stir at room temperature for 1 hour. Benzenesulfonamide (67.8 mg, 0.431 mmol) was added followed by DBU (64.5 µL, 0.431 mmol). The final reaction mixture was allowed to stir overnight at room temperature. Volatiles were removed by evaporation. It was taken up in EtOAc (50 mL) and washed with aqueous 1 M citric acid solution (2×50 mL) and brine (150 mL). The organic layer was dried over sodium sulfate, filtered and concentrated under reduced pressure. N-(benzenesulfonyl)-2-chloro-6-[3-[(trans)-2-(trifluoromethyl)cyclopropoxy]pyrazol-1-yl]pyridine-3-carboxamide (199 mg) was obtained. ESI-MS m/z calc. 486.0, found 486.9 (M+1)$^+$; Retention time: 0.65 minutes (1 minute run)

Step E: N-(Benzenesulfonyl)-6-[3-[(trans)-2-(trifluoromethyl)cyclopropoxy]pyrazol-1-yl]-2-[(4S)-2,2,4-trimethylpyrrolidin-1-yl]pyridine-3-carboxamide

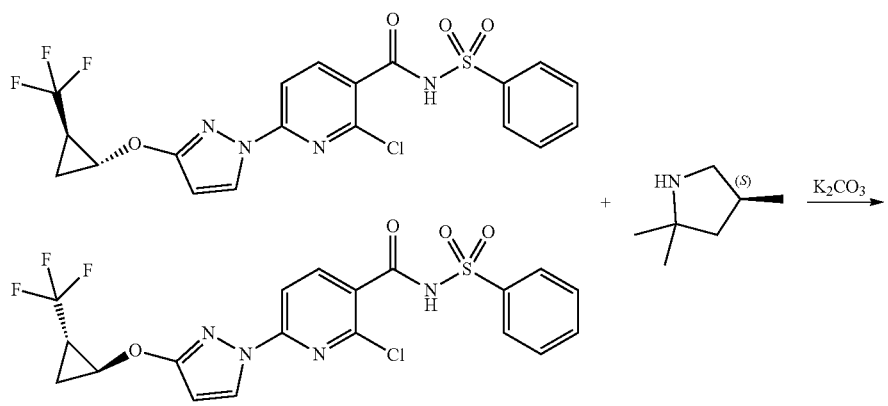

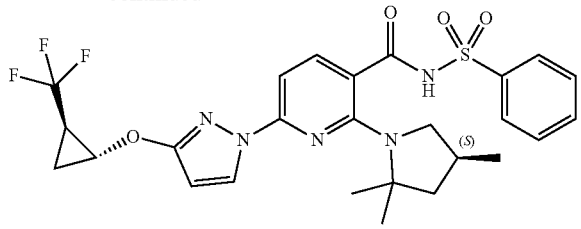

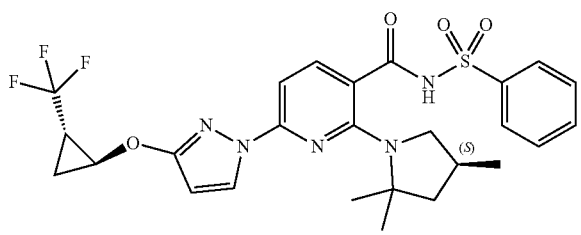

N-(Benzenesulfonyl)-2-chloro-6-[3-[(trans)-2-(trifluoromethyl)cyclopropoxy]pyrazol-1-yl]pyridine-3-carboxamide (175 mg, 0.3595 mmol) was dissolved in DMSO (1 mL). (4S)-2,2,4-Trimethylpyrrolidine (Hydrochloride salt) (161 mg, 1.08 mmol) was added followed by potassium carbonate (298 mg, 2.16 mmol). The reaction mixture was allowed to stir at 130° C. overnight. After cooling to room temperature, the reaction mixture was diluted with EtOAc (50 mL) and washed with aqueous citric acid (1 M, 2×50 mL) and brine (1×50 mL). The organic layer was dried over sodium sulfate, filtered and concentrated under reduced pressure. The product was isolated by silica gel column chromatography on a 12 gram silica gel column eluting with a 0-10% EtOAc/hexane gradient. N-(benzenesulfonyl)-6-[3-[(trans)-2-(trifluoromethyl)cyclopropoxy]pyrazol-1-yl]-2-[(4S)-2,2,4-trimethylpyrrolidin-1-yl]pyridine-3-carboxamide (115.7 mg, 57%) was obtained. ESI-MS m/z calc. 563.1814, found 564.5 (M+1)$^+$; Retention time: 2.01 minutes

SYNTHETIC EXAMPLE 20

Synthesis of Compound 20: N-(2-Hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(2-hydroxyphenyl)sulfonyl-6-[3-[[1-(trifluoromethyl)cyclopropyl]methoxy]pyrazol-1-yl]pyridine-3-carboxamide

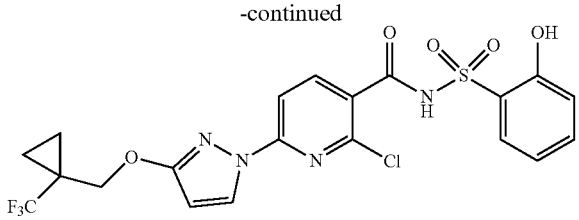

A solution of 2-chloro-6-[3-[[1-(trifluoromethyl)cyclopropyl]methoxy]pyrazol-1-yl]pyridine-3-carboxylic acid (181 mg, 0.5 mmol) and carbonyldiimidazole (approximately 97.3 mg, 0.60 mmol) in DMF (2.5 mL) was stirred for 30 minutes. A solution of 2-hydroxybenzenesulfonamide (approximately 113 mg, 0.65 mmol) and sodium hexamethyldisilazide (approximately 600 µL of 1 M, 0.60 mmol) in DMF (2.5 mL) was stirred for 30 minutes. The two solutions were combined and stirred for 15 h at room temperature. The reaction mixture was acidified with 10 mL 1 M aqueous citric acid, and extracted with 10 mL ethyl acetate. The combined extracts were dried over sodium sulfate and concentrated under reduced pressure. The crude material was purified by silica gel chromatography eluting with a 0-5% gradient of methanol in dichloromethane to give 2-chloro-N-(2-hydroxyphenyl)sulfonyl-6-[3-[[1-(trifluoromethyl)cyclopropyl]methoxy]pyrazol-1-yl]pyridine-3-carboxamide (82 mg, 32%) ESI-MS m/z calc. 516.0, found 517.2 (M+1)$^+$; Retention time: 0.67 minutes.

Step B: N-(2-Hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

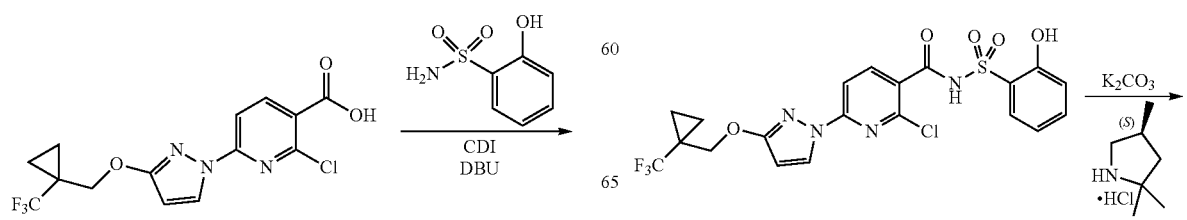

149

-continued

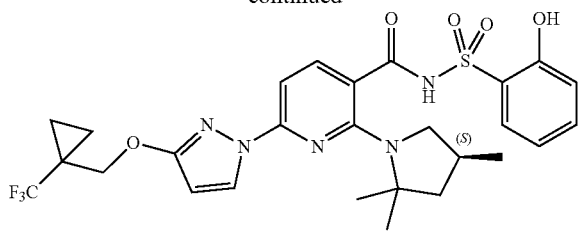

2-Chloro-N-(2-hydroxyphenyl)sulfonyl-6-[3-[[1-(trifluoromethyl)cyclopropyl]methoxy]pyrazol-1-yl]pyridine-3-carboxamide (82 mg, 0.16 mmol), (4S)-2,2,4-trimethylpyrrolidine (Hydrochloride salt) (approximately 71 mg, 0.48 mmol), and potassium carbonate (approximately 132 mg, 0.95 mmol) were combined in DMSO (793 µL) and heated at 130° C. for 15 h. The reaction was filtered and purified using a reverse phase HPLC-MS method using a Luna C18 (2) column (75×30 mm, 5 µm particle size) sold by Phenomenex (pn: 00C-4252-U0-AX), and a dual gradient run from 30-99% mobile phase B over 15.0 minutes [mobile phase A=H$_2$O (5 mM HCl); mobile phase B=acetonitrile; flow rate=50 mL/min, and column temperature=25° C.] to give N-(2-hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (44 mg, 46%) ESI-MS m/z calc. 593.2, found 594.3 (M+1)$^+$; Retention time: 2.07 minutes.

SYNTHETIC EXAMPLE 21

Synthesis of Compound 21: N-(3-Hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(3-hydroxyphenyl)sulfonyl-6-[3-[[1-(trifluoromethyl)cyclopropyl]methoxy]pyrazol-1-yl]pyridine-3-carboxamide

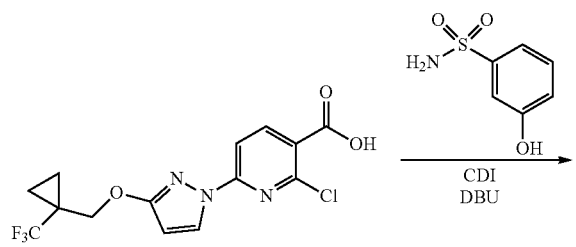

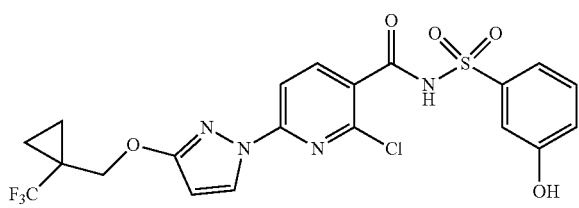

150

2-Chloro-6-[3-[[1-(trifluoromethyl)cyclopropyl]methoxy]pyrazol-1-yl]pyridine-3-carboxylic acid (181 mg, 0.50 mmol) and carbonyl diimidazole (approximately 97 mg, 0.60 mmol) in DMF (2.5 mL) was stirred for 30 minutes. 3-hydroxybenzenesulfonamide (approximately 113 mg, 0.65 mmol) and NaH (approximately 24.0 mg of 60% w/w, 0.60 mmol) in DMF (2.5 mL) was stirred for 30 minutes. The two solutions were combined and stirred for 4 h at room temperature. The reaction mixture was acidified with O1 mL 1 M aqueous citric acid, and extracted with 10 mL ethyl acetate. The combined extracts were dried over sodium sulfate and concentrated under reduced pressure. The crude material was purified by silica gel chromatography eluting with a 0-8% gradient of methanol in dichloromethane to give 2-chloro-N-(3-hydroxyphenyl)sulfonyl-6-[3-[[1-(trifluoromethyl)cyclopropyl]methoxy]pyrazol-1-yl]pyridine-3-carboxamide (250 mg, 97%) E SI-MS m/z calc. 516.0482, found 517.2 (M+1)$^+$; Retention time: 0.67 minutes.

Step B: N-(3-Hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

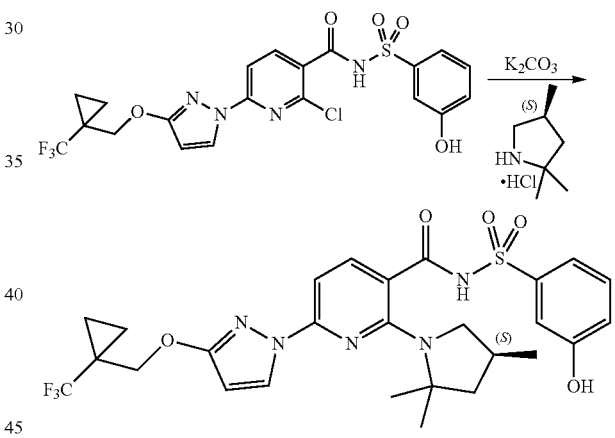

2-Chloro-N-(3-hydroxyphenyl)sulfonyl-6-[3-[[1-(trifluoromethyl)cyclopropyl]methoxy]pyrazol-1-yl]pyridine-3-carboxamide (290 mg, 0.56 mmol), (4S)-2,2,4-trimethylpyrrolidine (Hydrochloride salt) (approximately 252 mg, 1.68 mmol), and potassium carbonate (approximately 465 mg, 3.37 mmol) in DMSO (2.80 mL) was heated at 130° C. for 15 h. The reaction was filtered and purified using a reverse phase HPLC-MS method using a Luna C18 (2) column (75×30 mm, 5 µm particle size) sold by Phenomenex (pn: 00C-4252-U0-AX), and a dual gradient run from 30-99% mobile phase B over 15.0 minutes [mobile phase A=H$_2$O (5 mM HCl); mobile phase B=acetonitrile; flow rate=50 mL/min, and column temperature=25° C.] to give N-(3-hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (37 mg, 11%) ESI-MS m/z calc. 593.2, found 594.3 (M+1)$^+$; Retention time: 1.98 minutes.

SYNTHETIC EXAMPLE 22

Synthesis of Compound 22: N-(4-Hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(4-hydroxyphenyl)sulfonyl-6-[3-[[1-(trifluoromethyl)cyclopropyl]methoxy]pyrazol-1-yl]pyridine-3-carboxamide

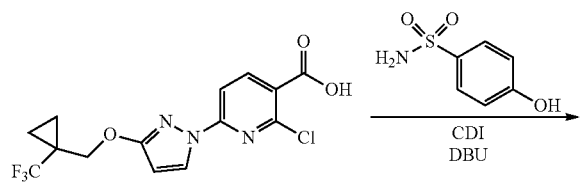

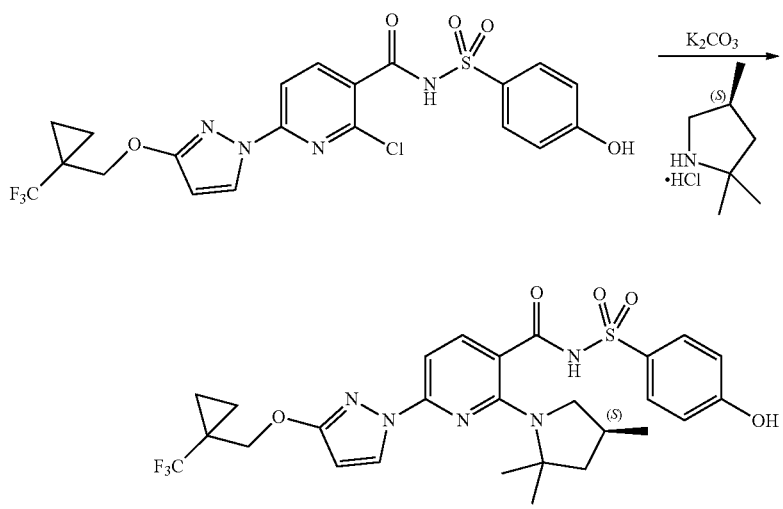

-continued

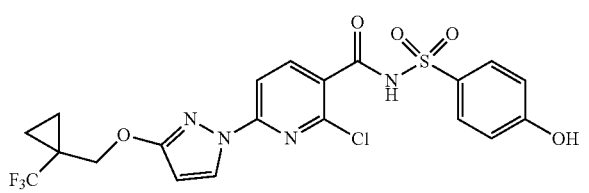

2-Chloro-6-[3-[[1-(trifluoromethyl)cyclopropyl]methoxy]pyrazol-1-yl]pyridine-3-carboxylic acid (181 mg, 0.50 mmol) and carbonyl diimidazole (approximately 97 mg, 0.60 mmol) in DMF (2.5 mL) was stirred for 30 minutes. 4-hydroxybenzenesulfonamide (approximately 113 mg, 0.65 mmol) and NaH (approximately 24.0 mg of 60% w/w, 0.60 mmol) in DMF (2.5 mL) was stirred for 30 minutes. The two solutions were combined and stirred for 4 h at room temperature. The reaction mixture was acidified with 10 mL 1 M aqueous citric acid, and extracted with 10 mL ethyl acetate. The combined extracts were dried over sodium sulfate and concentrated under reduced pressure. The crude material was purified by silica gel chromatography eluting with a 0-8% gradient of methanol in dichloromethane to give 2-chloro-N-(4-hydroxyphenyl)sulfonyl-6-[3-[[1-(trifluoromethyl)cyclopropyl]methoxy]pyrazol-1-yl]pyridine-3-carboxamide (210 mg, 81%) ESI-MS m/z calc. 516.0, found 517.2 (M+1)$^+$; Retention time: 0.64 minutes.

Step B: N-(4-Hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide 2-Chloro-N-(4-hydroxyphenyl)sulfonyl-6-[3-[[1-(trifluoromethyl)cyclopropyl]methoxy]pyrazol-1-yl]pyridine-3-carboxamide (220 mg, 0.42 mmol), (4S)-2,2,4-trimethylpyrrolidine (Hydrochloride salt) (approximately 191 mg, 1.28 mmol), and potassium carbonate (approximately 353 mg, 2.56 mmol) in DMSO (2.13 mL) was heated at 130° C. for 15 h. The reaction was filtered and purified using a reverse phase HPLC-MS method using a Luna C18 (2) column (75×30 mm, 5 μm particle size) sold by Phenomenex (pn: 00C-4252-U0-AX), and a dual gradient run from 30-99% mobile phase B over 15.0 minutes [mobile phase A=H$_2$O (5 mM HCl); mobile phase B=acetonitrile; flow rate=50 mL/min, and column temperature=25° C.] to give N-(4-hydroxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (48 mg, 190%) ESI-MS m/z calc. 593.2, found 594.3 (M+1)$^+$; Retention time: 1.98 minutes.

SYNTHETIC EXAMPLE 23

Synthesis of Compound 23: N-(o-Tolylsulfonyl)-6-[3-[[1-(trifluoromethyl)cyclopropyl]methoxy]pyrazol-1-yl]-2-[(4S)-2,2,4-trimethylpyrrolidin-1-yl]]pyridine-3-carboxamide Step A: 2-Chloro-N-(o-tolylsulfonyl)-6-[3-[[1-(trifluoromethyl)cyclopropyl]methoxy]pyrazol-1-yl]pyridine-3-carboxamide

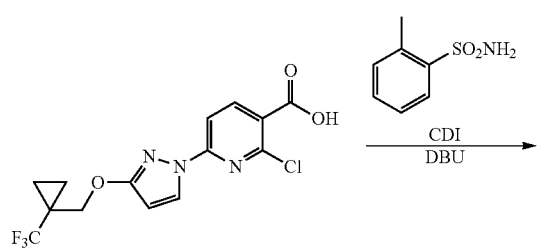

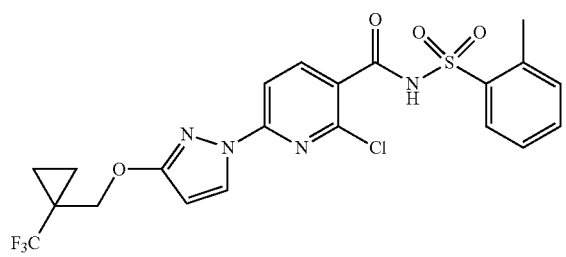

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (960 µL) and stirred at room temperature for 2 hours. 2-methylbenzenesulfonamide (approximately 123.1 mg, 0.7188 mmol) was added followed by DBU (approximately 101.0 mg, 99.21 µL, 0.6635 mmol) and the reaction was stirred for an additional 16 h at room temperature. A 1M citric acid solution (1 mL) was added and the reaction was stirred for 20 min. The resulting solid was collected by vacuum filtration (washing with water) and dried under vacuum to give a white powder, which was used in the next step without further purification. 2-chloro-N-(o-tolylsulfonyl)-6-[3-[[1-(trifluoromethyl)cyclopropyl]methoxy]pyrazol-1-yl]pyridine-3-carboxamide (280 mg, 98%) ESI-MS m/z calc. 514.1, found 515.1 (M+1)$^+$; Retention time: 0.73 minutes. $^1$H NMR (400 MHz, DMSO) δ d 13.56-12.55 (s, 1H), 8.42 (d, J=2.8 Hz, 1H), 8.12 (d, J=8.3 Hz, 1H), 8.04 (d, J=7.9 Hz, 1H), 7.71 (d, J=8.3 Hz, 1H), 7.63 (t, J=7.6 Hz, 1H), 7.47 (t, J=7.6 Hz, 2H), 6.23 (d, J=2.9 Hz, 1H), 4.39 (s, 2H), 2.64 (s, 3H), 1.12-1.06 (m, 4H).

Step B: N-(o-Tolylsulfonyl)-6-[3-[[1-(trifluoromethyl)cyclopropyl]methoxy]pyrazol-I-yl]-2-[(4S)-2,2,4-trimethylpyrrolidin-1-yl]pyridine-3-carboxamide

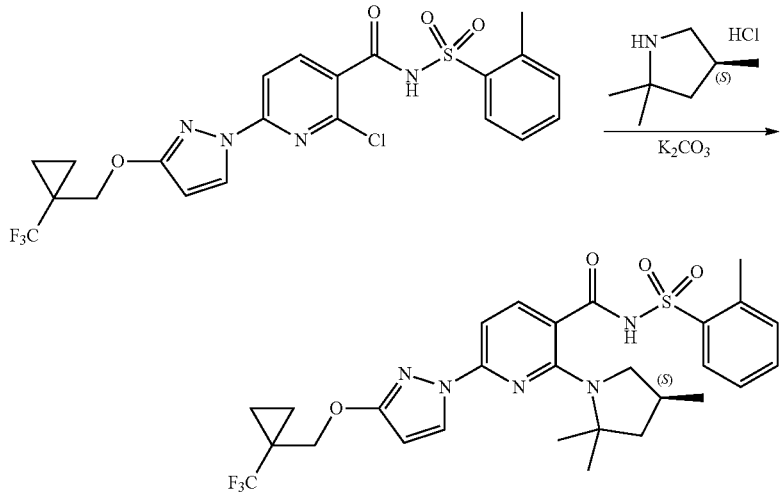

2-Chloro-N-(o-tolylsulfonyl)-6-[3-[[1-(trifluoromethyl)cyclopropyl]methoxy]pyrazol-1-yl]pyridine-3-carboxamide (114.7 mg, 0.2227 mmol), (4S)-2,2,4-trimethylpyrrolidine (hydrochloride salt) (100 mg, 0.6682) and, K$_2$CO$_3$ (184.6 mg, 1.336 mmol) were combined in DMSO (0.5 mL) in a screwcap tube and heated to 130° C. for 16 hours. After cooling to room temperature, the reaction mixture was diluted with 20 mL of ethyl acetate, and 10 mL water and transferred to a separatory funnel. AN aqueous 15 mL 1 M citric acid was added, and the organic layer was separated. The aqueous layer was extracted two additional times with 15 mL ethyl acetate, and the combined organics were washed with brine, dried over sodium sulfate and concentrated. The resulting crude material was purified by flash chromatography on silica gel, eluting with a 0-10% methanol in dichloromethane gradient to give N-(o-tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (101 mg, 77%). ESI-MS m/z calc. 591.21, found 592.3 (M+1)⁺; Retention time: 2.22 minutes. ¹H NMR (400 MHz, DMSO) δ 12.74 (s, 1H), 8.38 (t, J=1.7 Hz, 1H), 8.33-8.22 (m, 2H), 8.21 (d, J=2.8 Hz, 1H), 7.90 (d, J=7.9 Hz, 1H), 7.89-7.85 (m, 1H), 6.93 (d, J=8.3 Hz, 1H), 6.15 (d, J=2.7 Hz, 1H), 4.41-4.31 (m, 2H), 3.36-3.29 (m, 3H), 2.40 (t, J=10.4 Hz, 1H), 2.27 (t, J=8.6 Hz, 1H), 2.11 (tt, J=12.1, 6.3 Hz, 1H), 1.88-1.81 (m, 1H), 1.53 (d, J=9.8 Hz, 6H), 1.39 (t, J=12.1 Hz, 1H), 1.09 (dt, J=6.7, 2.2 Hz, 4H), 0.68 (d, J=6.2 Hz, 3H).

SYNTHETIC EXAMPLE 24

Synthesis of Compound 24: N-(p-Tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(p-tolylsulfonyl)-6-[3-[[1-(trifluoromethyl)cyclopropyl]methoxy]pyrazol-1-yl]pyridine-3-carboxamide

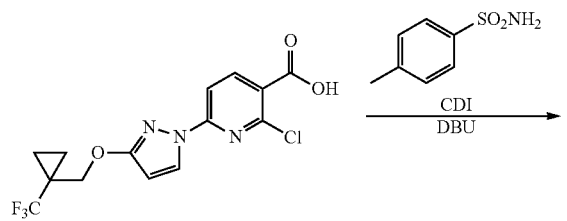

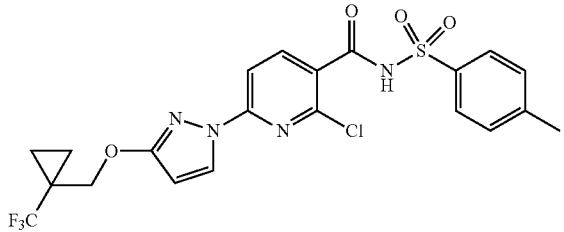

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 4-methylbenzenesulfonamide (approximately 123.1 mg, 0.7188 mmol) was added followed by DBU (approximately 101.0 mg, 99.21 µL, 0.6635 mmol) and the reaction was stirred for an additional 16 h at room temperature. The reaction mixture was diluted with 1M aqueous citric acid and water, then extracted 3×20 mL ethyl acetate. The combined organics were washed with 10 mL 1M citric acid, followed by brine, dried over sodium sulfate and concentrated, then purified by silica gel chromatography, eluting with 0-10% methanol/dichloromethane to give 2-chloro-N-(p-tolyl sulfonyl)-6-[3-[[1-(trifluoromethyl)cyclopropyl]methoxy]pyrazol-1-yl]pyridine-3-carboxamide (262 mg, 92%) ESI-MS m/z calc. 514.0689, found 515.1 (M+1)⁺; Retention time: 0.74 minutes.

Step B: N-(p-tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

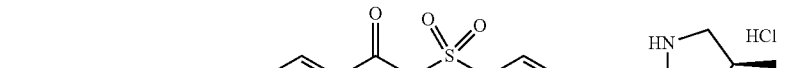
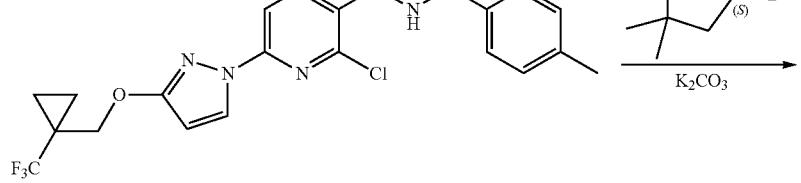

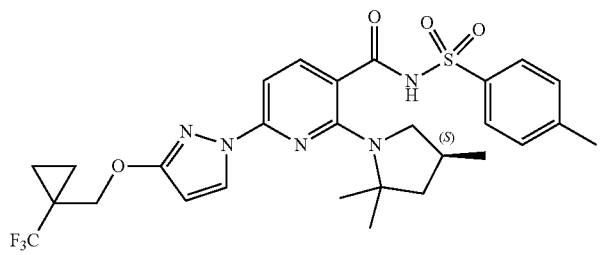

2-chloro-N-(p-Tolylsulfonyl)-6-[3-[[1-(trifluoromethyl)cyclopropyl]methoxy]pyrazol-1-yl]pyridine-3-carboxamide (114.7 mg, 0.2227), (4S)-2,2,4-trimethylpyrrolidine (Hydrochloride salt) (100 mg, 0.6682) and, $K_2CO_3$ (184.6 mg, 1.336 mmol) were combined in DMSO (0.5 mL) in a screwcap tube and heated to 130° C. for 16 hours. After cooling to room temperature, the reaction mixture was diluted with 20 mL of ethyl acetate, and 10 mL water and transferred to a separatory funnel. An aqueous 15 mL 1 M citric acid was added, and the organic layer was separated. The aqueous layer was extracted two additional times with 15 mL ethyl acetate, and the combined organics were washed with brine, dried over sodium sulfate and concentrated. The resulting crude material was purified by flash chromatography on silica gel, eluting with a 0-10% methanol in dichloromethane gradient to give N-(p-tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (65 mg, 49%). ESI-MS m/z calc. 591.21, found 592.3 (M+1)$^+$; Retention time: 2.25 minutes. $^1$H NMR (400 MHz, DMSO) δ 12.74 (s, 1H), 8.38 (t, J=1.7 Hz, 1H), 8.33-8.22 (m, 2H), 8.21 (d, J=2.8 Hz, 1H), 7.90 (d, J=7.9 Hz, 1H), 7.89-7.85 (m, 1H), 6.93 (d, J=8.3 Hz, 1H), 6.15 (d, J=2.7 Hz, 1H), 4.41-4.31 (m, 2H), 3.36-3.29 (m, 3H), 2.40 (t, J=10.4 Hz, 1H), 2.27 (t, J=8.6 Hz, 1H), 2.11 (tt, J=12.1, 6.3 Hz, 1H), 1.88-1.81 (m, 1H), 1.53 (d, J=9.8 Hz, 6H), 1.39 (t, J=12.1 Hz, 1H), 1.09 (dt, J=6.7, 2.2 Hz, 4H), 0.68 (d, J=6.2 Hz, 3H).

SYNTHETIC EXAMPLE 25

Synthesis of Compound 25: N-(3-Cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(3-cyanophenyl)sulfonyl-6-[3-[[1-(trifluoromethyl)cyclopropyl]methoxy]pyrazol-1-yl]pyridine-3-carboxamide

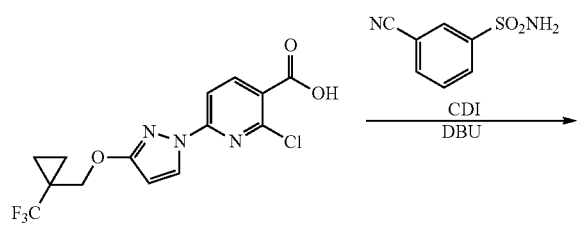

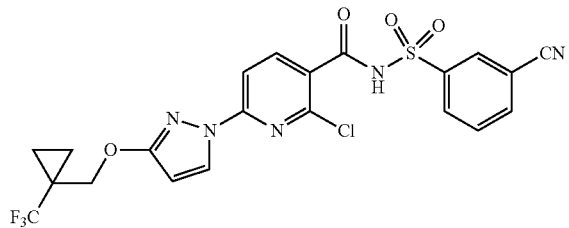

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 3-cyanobenzenesulfonamide (approximately 131.0 mg, 0.7188 mmol) was added followed by DBU (approximately 101.0 mg, 99.21 µL, 0.6635 mmol) and the reaction was stirred for an additional 16 h at room temperature. The reaction mixture was diluted with 1M aqueous citric acid and water, and extracted 3×20 mL ethyl acetate. The combined organics were washed with 10 mL 1M citric acid, followed by brine, then dried over sodium sulfate and concentrated and used in the next step without further purification. 2-chloro-N-(3-cyanophenyl)sulfonyl-6-[3-[[1-(trifluoromethyl)cyclopropyl]methoxy]pyrazol-1-yl]pyridine-3-carboxamide (228 mg, 78%) ESI-MS m/z calc. 525.0485, found 526.0 (M+1)$^+$; Retention time: 0.7 minutes.

Step B: N-(3-cyanophenyl)sulfonyl-6-[3-[[1-(trifluoromethyl)cyclopropyl]methoxy]pyrazol-1-yl]-2-(4S)-2,2,4-trimethylpyrrolidin-1-yl]pyridine-3-carboxamide

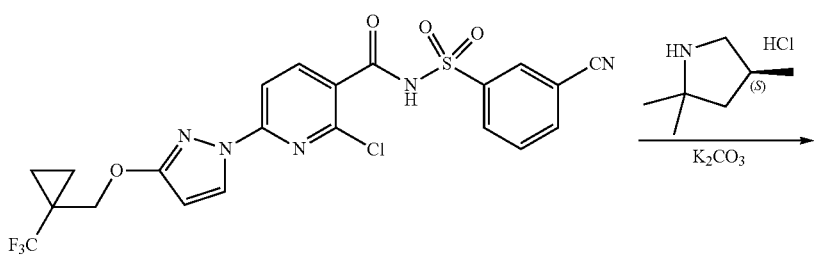

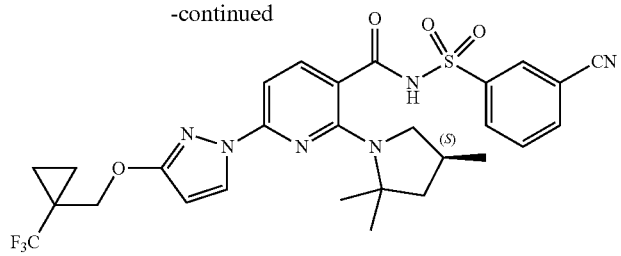

2-Chloro-N-(3-cyanophenyl)sulfonyl-6-[3-[[1-(trifluoromethyl)cyclopropyl]methoxy]pyrazol-1-yl]pyridine-3-carboxamide (117.1 mg, 0.2227), (4S)-2,2,4-trimethylpyrrolidine (hydrochloride salt) (100 mg, 0.6682) and, K$_2$CO$_3$ (184.6 mg, 1.336 mmol) were combined in DMSO (0.5 mL) in a screwcap tube and heated to 130° C. for 16 hours. After cooling to room temperature, the reaction mixture was diluted with 20 mL ethyl acetate, and 10 mL water and transferred to a separatory funnel. An aqueous 15 mL 1 M citric acid was added, and the organic layer was separated. The aqueous layer was extracted two additional times with 15 mL ethyl acetate, and the combined organics were washed with brine, dried over sodium sulfate and concentrated. The resulting crude material was purified by flash chromatography on silica gel, eluting with a 0-10% methanol in dichloromethane gradient to give N-(3-cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide, (73 mg, 54%) ESI-MS m/z calc. 602.19, found 603.3 (M+1)$^+$; Retention time: 2.04 minutes. $^1$H NMR (400 MHz, DMSO) δ 12.74 (s, 1H), 8.38 (t, J=1.7 Hz, 1H), 8.30 (ddd, J=8.1, 1.9, 1.1 Hz, 1H), 8.24 (dt, J=7.8, 1.3 Hz, 1H), 8.21 (d, J=2.8 Hz, 1H), 7.92-7.84 (m, 2H), 6.93 (d, J=8.3 Hz, 1H), 6.15 (d, J=2.7 Hz, 1H), 4.42-4.31 (m, 2H), 2.40 (t, J=10.4 Hz, 1H), 2.27 (t, J=8.6 Hz, 1H), 2.11 (tt, J=12.1, 6.3 Hz, 1H), 1.89-1.78 (m, 1H), 1.53 (d, J=9.8 Hz, 6H), 1.39 (t, J=12.1 Hz, 1H), 1.09 (dt, J=6.7, 2.2 Hz, 4H), 0.68 (d, J=6.2 Hz, 3H).

SYNTHETIC EXAMPLE 26

Synthesis of Compound 26: N-(2-Cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(2-cyanophenyl)sulfonyl-6-[3-[[1-(trifluoromethyl)cyclopropyl]methoxy]pyrazol-1-yl]pyridine-3-carboxamide

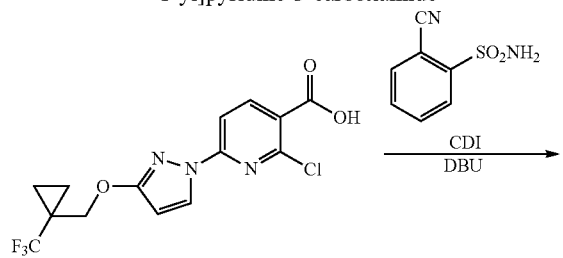

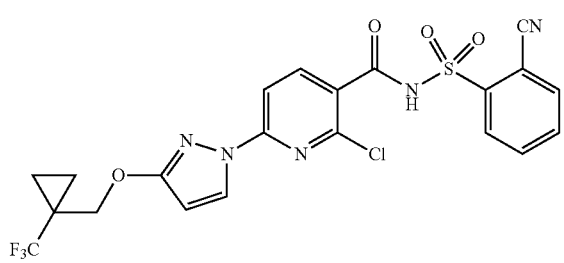

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (1.200 mL) and stirred at room temperature for 2 hours. 2-Cyanobenzenesulfonamide (approximately 131.0 mg, 0.7188 mmol) was added followed by DBU (approximately 101.0 mg, 99.21 μL, 0.6635 mmol) and the reaction was stirred for an additional 16 h at room temperature. A 1M citric acid solution (1 mL) was added and the reaction was stirred for 20 minutes. The resulting solid precipitate was collected by vacuum filtration (washing with water) to give a white solid, which was dried on under vacuum and used in the next step without further purification, 2-chloro-N-(2-cyanophenyl)sulfonyl-6-[3-[[1-(trifluoromethyl)cyclopropyl]methoxy]pyrazol-1-yl]pyridine-3-carboxamide (279 mg, 96%) ESI-MS m/z calc. 525.0485, found 526.1 (M+1)$^+$; Retention time: 0.69 minutes. 1H NMR (400 MHz, DMSO) δ 12.23 (s, 1H), 8.49 (d, J=2.9 Hz, 1H), 8.46-8.39 (m, 1H), 8.35 (d, J=8.3 Hz, 1H), 8.21-8.13 (m, 1H), 7.96-7.90 (m, 2H), 7.82 (d, J=8.3 Hz, 1H), 6.27 (d, J=2.9 Hz, 1H), 4.42 (s, 2H), 1.11 (dt, J=7.6, 2.2 Hz, 4H).

Step B: N-(2-Cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

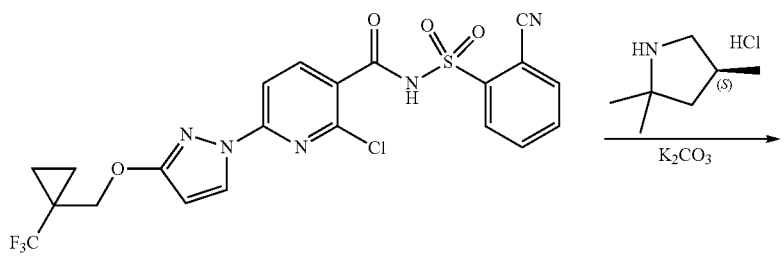

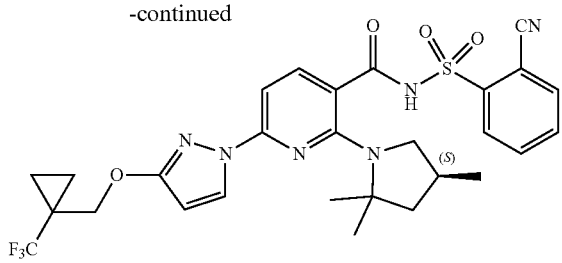

2-Chloro-N-(2-cyanophenyl)sulfonyl-6-[3-[[1-(trifluoromethyl)cyclopropyl]methoxy]pyrazol-1-yl]pyridine-3-carboxamide (117.1 mg, 0.2227), (4S)-2,2,4-trimethylpyrrolidine (hydrochloride salt) (100 mg, 0.6682) and, $K_2CO_3$ (184.6 mg, 1.336 mmol) were combined in DMSO (0.5 mL) in a screwcap tube and heated to 130° C. for 16 hours. After cooling to room temperature, the reaction mixture was diluted with 20 mL ethyl acetate, and 10 mL water and transferred to a separatory funnel. An aqueous 15 mL 1 M citric acid solution was added, and the organic layer was separated. The aqueous layer was extracted two additional times with 15 mL ethyl acetate, and the combined organics were washed with brine, dried over sodium sulfate and concentrated. The resulting crude material was purified by flash chromatography on silica gel, eluting with a 0-10% methanol in dichloromethane gradient to give. N-(2-cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide, (41 mg, 31%) ESI-MS m/z calc. 602.19, found 603.2 (M+1)$^+$; Retention time: 2.12 minutes. 1H NMR (400 MHz, DMSO) δ 11.77 (s, 1H), 8.47 (s, 1H), 8.29 (d, J=2.8 Hz, 1H), 8.17-8.11 (m, 1H), 8.06 (d, J=8.3 Hz, 1H), 7.94-7.87 (m, 2H), 6.97 (d, J=8.3 Hz, 1H), 6.20 (d, J=2.8 Hz, 1H), 4.44-4.32 (m, 2H), 3.07-2.91 (m, 2H), 2.32 (d, J=19.0 Hz, 1H), 1.98 (q, J=5.9, 5.5 Hz, 1H), 1.67 (s, 3H), 1.63 (s, 3H), 1.57 (t, J=10.4 Hz, 1H), 1.13-1.06 (m, 4H), 1.02 (d, J=6.3 Hz, 3H).

SYNTHETIC EXAMPLE 27

Synthesis of Compound 27: N-(4-Cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(4-cyanophenyl)sulfonyl-6-[3-[[1-(trifluoromethyl)cyclopropyl]methoxy]pyrazol-1-yl]pyridine-3-carboxamide

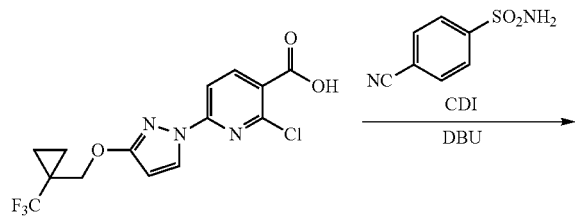

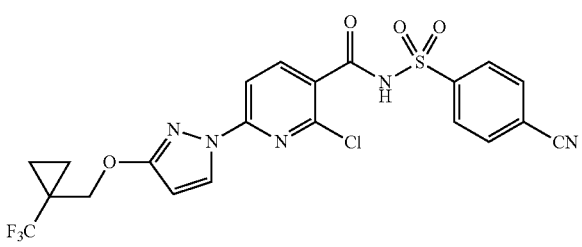

2-Chloro-6-[3-[[1-(trifluoromethyl)cyclopropyl]methoxy]pyrazol-1-yl]pyridine-3-carboxylic acid (150 mg, 0.4147 mmol) and CDI (81 mg, 0.4995 mmol) were combined in THF (900.0 μL) and stirred at room temperature for 2 hours. 4-cyanobenzenesulfonamide (98 mg, 0.5379 mmol) was added followed by DBU (75 μL, 0.5015 mmol) and the reaction was stirred at room temperature for 2 hours. Additional DBU (80 μL, 0.5350 mmol) was added, and the reaction was stirred for one additional hour at room temperature. The reaction mixture was diluted with 20 mL of a 1M citric acid solution and water and extracted 3×20 mL ethyl acetate. The combined organics were washed with 10 mL 1M citric acid, followed by brine, then dried over sodium sulfate and concentrated. The resulting material was further purified by silica gel chromatography eluting with a 0-10% gradient of methanol in dichloromethane, to give a white solid; 2-chloro-N-(4-cyanophenyl)sulfonyl-6-[3-[[1-(trifluoromethyl)cyclopropyl]methoxy]pyrazol-1-yl]pyridine-3-carboxamide (192 mg, 88%) ESI-MS m/z calc. 525.0485, found 526.0 (M+1)$^+$; Retention time: 0.71 minutes.

Step B: N-(4-Cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

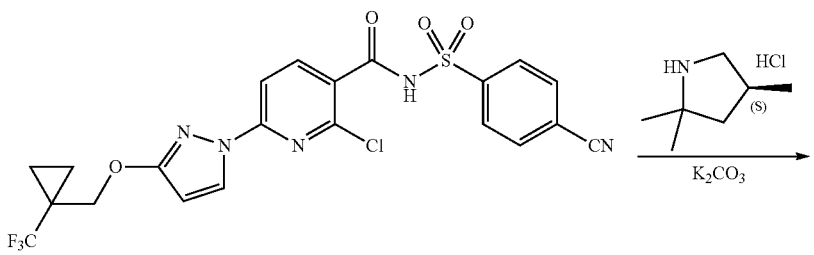

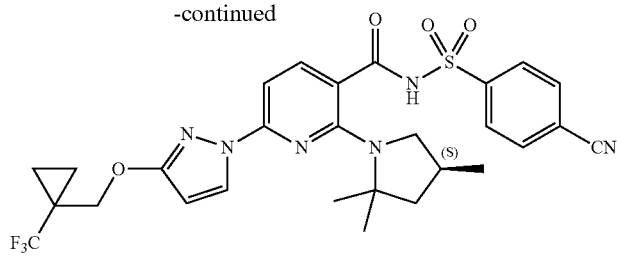

2-Chloro-N-(4-cyanophenyl)sulfonyl-6-[3-[[1-(trifluoromethyl)cyclopropyl]methoxy]pyrazol-1-yl]pyridine-3-carboxamide (117.1 mg, 0.2227), (4S)-2,2,4-trimethylpyrrolidine (hydrochloride salt) (100 mg, 0.6682) and, $K_2CO_3$ (184.6 mg, 1.336 mmol) were combined in DMSO (0.5 mL) in a screwcap tube and heated to 130° C. for 16 hours. After cooling to room temperature, the reaction mixture was diluted with 20 mL ethyl acetate, and 10 mL water and transferred to a separatory funnel. An aqueous 15 mL 1 M citric acid solution was added, and the organic layer was separated. The aqueous layer was extracted two additional times with 15 mL ethyl acetate, and the combined organics were washed with brine, dried over sodium sulfate and concentrated. The resulting crude material was purified by flash chromatography on silica gel, eluting with a 0-10% methanol in dichloromethane gradient to give N-(4-cyanophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide, (62 mg, 46%) ESI-MS m/z calc. 602.19, found 603.3 (M+1)$^+$; Retention time: 2.04 minutes. $^1$H NMR (400 MHz, DMSO) δ 12.77 (s, 1H), 8.20 (d, J=2.8 Hz, 1H), 8.16 (s, 4H), 7.87 (d, J=8.3 Hz, 1H), 6.93 (d, J=8.3 Hz, 1H), 6.15 (d, J=2.7 Hz, 1H), 4.50-4.17 (m, 2H), 2.33 (t, J=10.3 Hz, 1H), 2.20 (dd, J=10.2, 6.9 Hz, 1H), 2.11 (tt, J=11.9, 6.4 Hz, 1H), 1.83 (dd, J=11.8, 5.4 Hz, 1H), 1.52 (d, J=5.6 Hz, 6H), 1.37 (t, J=12.1 Hz, 1H), 1.13-1.05 (m, 4H), 0.66 (d, J=6.2 Hz, 3H).

SYNTHETIC EXAMPLE 28

Synthesis of Compound 28: N-(m-Tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(m-tolylsulfonyl)-6-[3-[[1-(trifluoromethyl)cyclopropyl]methoxy]pyrazol-1-yl]pyridine-3-carboxamide

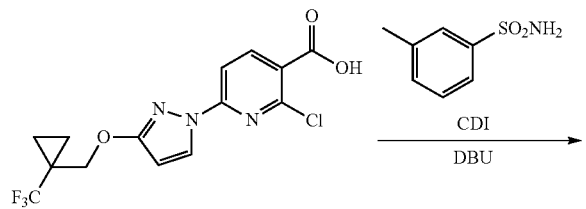

-continued

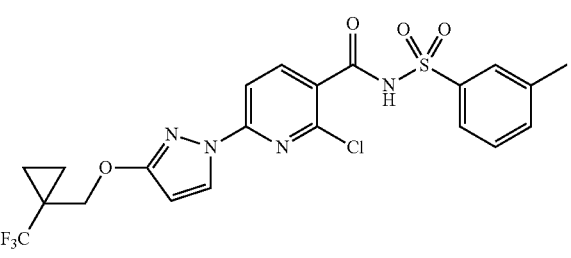

2-Chloro-6-[3-[[1-(trifluoromethyl)cyclopropyl]methoxy]pyrazol-1-yl]pyridine-3-carboxylic acid (200 mg, 0.5529 mmol) and CDI (approximately 107.6 mg, 0.6635 mmol) were combined in THF (964.9 μL) and stirred at room temperature for 2 hours. 3-methylbenzenesulfonamide (approximately 123.1 mg, 0.7188 mmol) was added followed by DBU (approximately 101.0 mg, 99.21 μL, 0.6635 mmol) and the reaction was stirred for an additional 16 h at room temperature. The reaction mixture was diluted with a 1M aqueous citric acid solution and water, and extracted 3×20 mL ethyl acetate. The combined organics were washed with 10 mL 1M citric acid, followed by brine, dried over sodium sulfate, concentrated, and finally purified by silica gel chromatography eluting with 0-10% methanol/dichloromethane to give a white solid, 2-chloro-N-(m-tolylsulfonyl)-6-[3-[[1-(trifluoromethyl)cyclopropyl]methoxy]pyrazol-1-yl]pyridine-3-carboxamide (178 mg, 63%) ESI-MS m/z calc. 514.0689, found 515.1 (M+1)$^+$; Retention time: 0.74 minutes Step B: N-(m-Tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

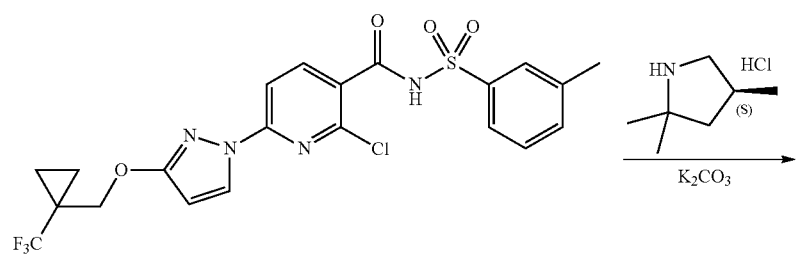

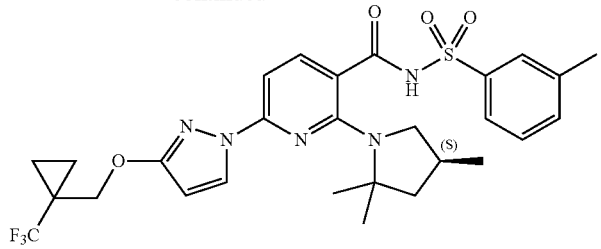

2-Chloro-N-m-tolylsulfonyl)-6-[3-[[1-(trifluoromethyl)cyclopropyl]methoxy]pyrazol-1-yl]pyridine-3-carboxamide (114.7 mg, 0.2227 mmol), (4S)-2,2,4-trimethylpyrrolidine (hydrochloride salt) (100 mg, 0.6682) and, K₂CO₃ (184.6 mg, 1.336 mmol) were combined in DMSO (0.5 mL) in a screwcap tube and heated to 130° C. for 16 hours. After cooling to room temperature, the reaction mixture was diluted with 20 mL ethyl acetate, and 10 mL water and transferred to a separatory funnel. An aqueous 15 mL 1 M citric acid solution was added, and the organic layer was separated. The aqueous layer was extracted two additional times with 15 mL ethyl acetate, and the combined organics were washed with brine, dried over sodium sulfate and concentrated. The resulting crude material was purified by flash chromatography on silica gel, eluting with a 0-10% methanol in dichloromethane gradient to give N-(m-tolylsulfonyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide, (45 mg, 34%) ESI-MS m/z calc. 591.2, found 592.2 (M+1)⁺; Retention time: 2.24 minutes. ¹H NMR (400 MHz, DMSO) δ 12.41 (s, 1H), 8.20 (d, J=2.8 Hz, 1H), 7.79 (tt, J=6.0, 2.5 Hz, 3H), 7.57-7.50 (m, 2H), 6.91 (d, J=8.2 Hz, 1H), 6.15 (d, J=2.7 Hz, 1H), 4.48-4.24 (m, 2H), 2.46 (s, 1H), 2.42 (s, 3H), 2.29 (t, J=8.8 Hz, 1H), 2.11 (dt, J=13.2, 6.5 Hz, 1H), 1.83 (dd, J=11.8, 5.5 Hz, 1H), 1.53 (d, J=12.0 Hz, 6H), 1.38 (t, J=12.1 Hz, 1H), 1.09 (dd, J=4.5, 3.2 Hz, 4H), 0.66 (d, J=6.2 Hz, 3H).

SYNTHETIC EXAMPLE 29

Synthesis of Compound 29: Synthesis of N-(Benzenesulfonyl)-6-[3-[(1-methylcyclopropoxy)methyl]pyrazol-1-yl]-2-[(4S)-2,2,4-trimethylpyrrolidin-1-yl]pyridine-3-carboxamide Step A:
(1-Methyl-1-(prop-2-yn-1-yloxy)cyclopropane

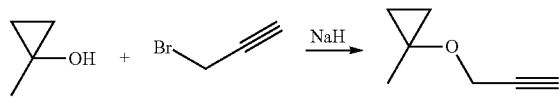

1-Methylcyclopropan-1-ol (1.0 g, 13.9 mmol) was dissolved in Et₂O (50 mL and cooled to 0° C. NaH (50% in oil, 0.67 g, 13.9 mmol) was added portion wise. The mixture was stirred for 10 min at 0° C. before propargyl bromide (80% in toluene, 3.1 g, 20.9 mmol) was added dropwise. The mixture was stirred for 1 hour at 0° C. Since the reaction did not proceed, DMF (20 mL) was added. The mixture was stirred for an additional hour at 0° and quenched with sat. aq. NH₄Cl. The mixture was extracted with Et₂O (2×50 mL).

The combined organic layers were washed with water twice and brine, dried over Na₂SO₄ and concentrated (at 40° C., 500 mbar) to afford crude (1-methyl-1-(prop-2-yn-1-yloxy)cyclopropane which was used as such in the next step. ¹H NMR (CDCl₃, 300 MHz): δ 0.39 (m, 2H); 0.85 (m, 2H); 1.40 (s, 3H); 2.37 (s, 1H); 4.10 (s, 2H).

Step B:
3-((1-methylcyclopropoxy)methyl)-1H-pyrazole

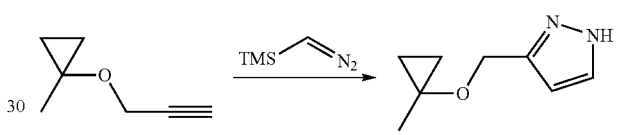

Crude (1-methyl-1-(prop-2-yn-1-yloxy)cyclopropane from several batches (max 27.8 mmol, 3.0 g) was mixed with trimethylsilyl diazomethane (2.0 M in hexane, 10 mL, 20 mmol) and stirred in a sealed tube at 115° C. for 18 hours. The mixture was cooled to 40° C. and quenched with MeOH (20 mL) and concentrated. Column chromatography (silica; heptanes/EtOAc 2:1) gave 3-((1-methylcyclopropoxy)methyl)-1H-pyrazole as colorless oil (1.2 g, 28% over two steps). ¹H NMR (CDCl₃, 300 MHz): δ 0.44 (m, 2H); 0.85 (m, 2H); 1.44 (s, 3H); 4.60 (s, 2H); 6.23 (s, 1H); 7.51 (s, 1H). 13C-NMR (75 MHz, CDCl3): δ 13.4, 20.3, 58.4, 61.9, 103.9, 132.9 (one quaternary carbon not shown).

Step C: N-(Benzenesulfonyl)-6-[3-[[(1-methylcyclopropoxy)methyl]pyrazol-1-yl]-2-[(4S)-2,2,4-trimethylpyrrolidin-1-yl]pyridine-3-carboxamide

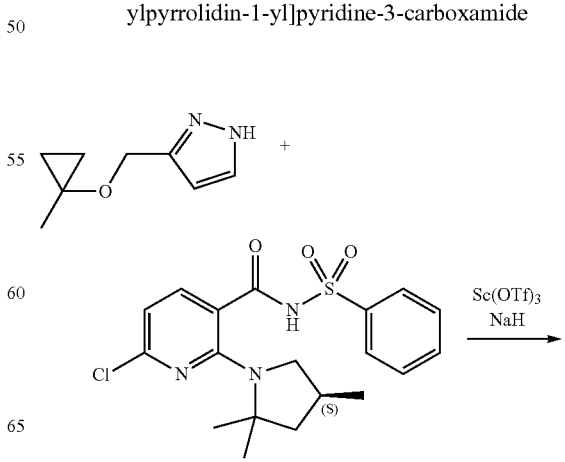

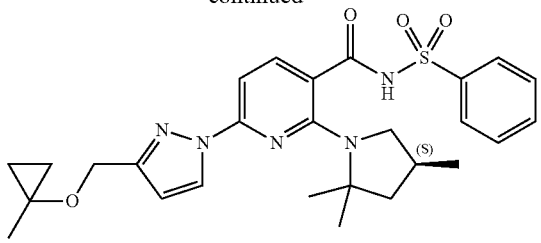

N-(Benzenesulfonyl)-6-chloro-2-[(4S)-2,2,4-trimethyl-pyrrolidin-1-yl]pyridine-3-carboxamide (83 mg, 0.2035 mmol), 3-[(1-methylcyclopropoxy)methyl]-1H-pyrazole (62 mg, 0.4074 mmol), and scandium triflate (10 mg, 0.02032 mmol) were combined in DMSO (1.660 mL). NaH (41 mg of 60% w/w, 1.025 mmol) was added and the reaction was stirred for 15 minutes before it was sealed and heated to 160° C. for 16 h. The reaction was cooled and partitioned between ethyl acetate and a 1 M citric acid solution. The organics were separated, washed with brine, and dried over sodium sulfate. The organics were then evaporated under reduced pressure, and the crude material was purified by preparative HPLC (1-99 CH₃CN in water with 5 mM HCl), over 30 minutes. Fractions containing product were diluted with water and extracted with ethyl acetate to give, upon concentration N-(benzenesulfonyl)-6-[3-[(1-methylcyclopropoxy)methyl]pyrazol-1-yl]-2-[(4S)-2,2,4-trimethylpyrrolidin-1-yl]pyridine-3-carboxamide (10 mg, 9%) ESI-MS m/z calc. 523.22534, found 524.2 (M+1)⁺; Retention time: 2.04 minutes.

SYNTHETIC EXAMPLE 30

Synthesis of Compound 30: N-(Benzenesulfonyl)-6-[3-[(2,2,3,3-tetramethylcyclopropyl)methoxy]pyrazol-1-yl]-2-[(4S)-2,2,4-trimethylpyrrolidin-1-yl]pyridine-3-carboxamide Step A: N-(Benzenesulfonyl)-2-chloro-6-[3-[(2,2,3,3-tetramethylcyclopropyl)methoxy]pyrazol-1-yl]pyridine-3-carboxamide

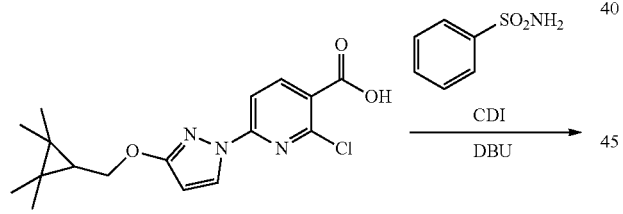

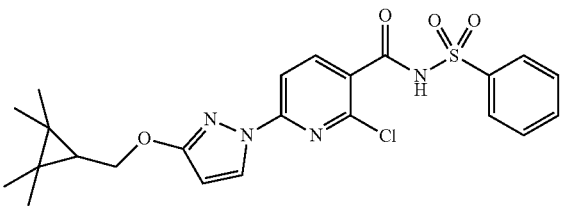

2-Chloro-6-[3-[(2,2,3,3-tetramethylcyclopropyl)methoxy]pyrazol-1-yl]pyridine-3-carboxylic acid (200 mg, 0.5717 mmol) and CDI (111 mg, 0.6846 mmol) were combined in THF (1.2 mL) and stirred at room temperature for 2 hours. Benzenesulfonamide (117 mg, 0.7443 mmol) was added followed by DBU (102 µL, 0.6821 mmol) and the reaction was stirred for an additional 6 h at room temperature. The reaction mixture was diluted with a 1M citric acid solution and water, and extracted 3×20 mL ethyl acetate. The combined organics were washed with brine, dried over sodium sulfate and concentrated, then purified by silica gel chromatography using a gradient of 0-10% methanol in dichloromethane to give a white powder. N-(Benzenesulfonyl)-2-chloro-6-[3-[(2,2,3,3-tetramethylcyclopropyl)methoxy]pyrazol-1-yl]pyridine-3-carboxamide (250 mg, 89%) ESI-MS m/z calc. 488.1285, found 489.2 (M+1)⁺; Retention time: 0.81 minutes.

Step B: N-(Benzenesulfonyl)-6-[3-[(2,2,3,3-tetramethylcyclopropyl)methoxy]pyrazol-1-yl]-2-[(4S)-2,2,4-trimethylpyrrolidin-1-yl]pyridine-3-carboxamide

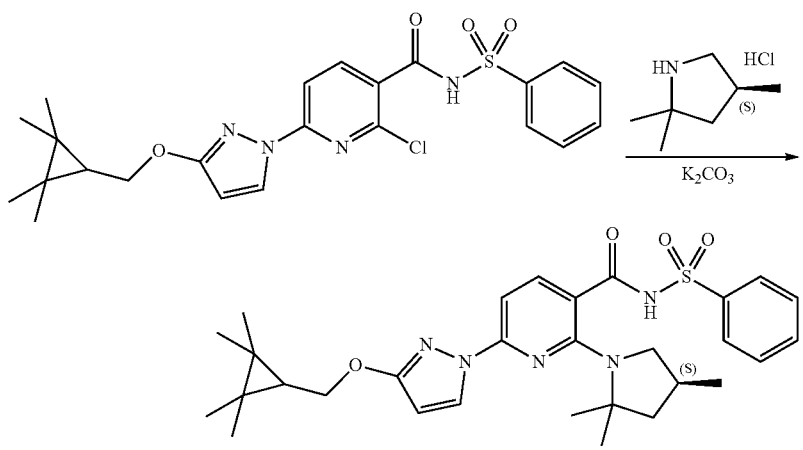

N-(Benzenesulfonyl)-2-chloro-6-[3-[(2,2,3,3-tetramethylcyclopropyl)methoxy]pyrazol-1-yl]pyridine-3-carboxamide (115 mg, 0.2352 mmol), (4S)-2,2,4-trimethylpyrrolidine (hydrochloride salt) (approximately 105.9 mg, 0.7077 mmol), and potassium carbonate (approximately 195.6 mg, 1.415 mmol) were combined in DMSO (575.0 μL) and heated at 130° C. for 16 h. The reaction was cooled to room temperature, diluted with 15 mL water, 15 mL 1M citric acid, and 30 mL ethyl acetate. The aqueous and the organic layers were separated, and the aqueous layer was extracted two additional times with 30 mL ethyl acetate, the organics were combined, washed with brine, dried over sodium sulfate and concentrated. The resulting solid was purified by silica gel chromatography eluting with 0-10% methanol in dichloromethane, and then additionally purified by silica chromatography using 0-100% ethyl acetate in dichloromethane, to give N-(benzenesulfonyl)-6-[3-[(2,2,3,3-tetramethyl cyclopropyl)methoxy]pyrazol-1-yl]-2-[(4S)-2,2,4-trimethylpyrrolidin-1-yl]pyridine-3-carboxamide (43 mg, 32%) ESI-MS m/z calc. 565.2723, found 566.3 (M+1)$^+$; Retention time: 2.43 minutes. $^1$H NMR (400 MHz, DMSO) δ 12.47 (s, 1H), 8.18 (d, J=2.8 Hz, 1H), 8.02-7.95 (m, 2H), 7.79 (d, J=8.3 Hz, 1H), 7.76-7.69 (m, 1H), 7.68-7.62 (m, 2H), 6.92 (d, J=8.3 Hz, 1H), 6.13 (d, J=2.7 Hz, 1H), 4.24 (d, J=7.7 Hz, 2H), 2.42 (t, J=10.5 Hz, 1H), 2.28 (dd, J=10.2, 7.1 Hz, 1H), 2.17-2.03 (m, 1H), 1.82 (dd, J=11.8, 5.5 Hz, 1H), 1.52 (d, J=9.4 Hz, 6H), 1.36 (t, J=12.1 Hz, 1H), 1.10 (s, 6H), 1.04 (s, 6H), 0.73 (t, J=7.7 Hz, 1H), 0.65 (d, J=6.2 Hz, 3H).

SYNTHETIC EXAMPLE 31

Synthesis of Compound 31: N N-(4-Hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide Step A: 2-Chloro-N-(4-hydroxyphenyl)sulfonyl-6-[3-[2-1[1-(trifluoromethyl)cyclopropyl]ethoxy]pyrazol-1-yl]pyridine-3-carboxamide

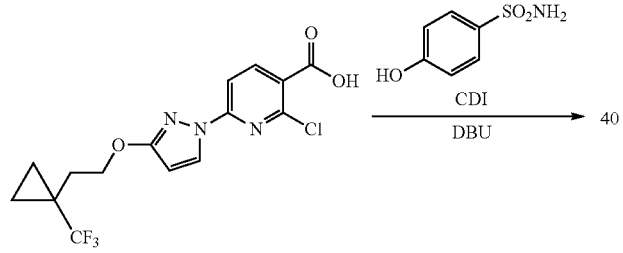

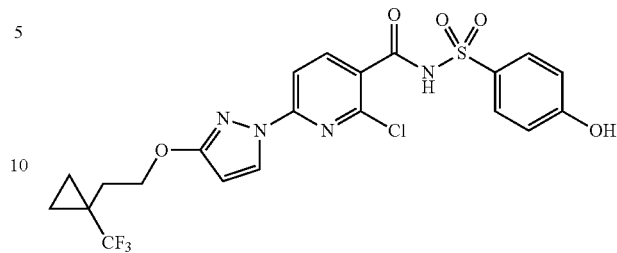

2-Chloro-6-[3-[2-[1-(trifluoromethyl)cyclopropyl] ethoxy]pyrazol-1-yl]pyridine-3-carboxylic acid (100 mg, 0.2661 mmol) and CDI (approximately 51.38 mg, 0.3169 mmol) were combined in THF (600.0 μL) and stirred at room temperature for 2 hours. 4-Hydroxybenzenesulfonamide (approximately 50.69 mg, 0.2927 mmol) was added followed by DBU (approximately 53.45 μL, 0.3574 mmol) and the reaction was stirred for an additional 16 h at room temperature. The reaction mixture was diluted with 10 mL 1M citric acid, and extracted 3 times with 10 mL of ethyl acetate. The combined organics were washed with brine, dried over sodium sulfate, and concentrated to give a white solid, which was used in the next step without further purification. 2-chloro-N-(4-hydroxyphenyl)sulfonyl-6-[3-[2-[1-(trifluoromethyl)cyclopropyl]ethoxy]pyrazol-1-yl] pyridine-3-carboxamide (128 mg, 91%) ESI-MS m/z calc. 530.06384, found 531.0 (M+1)$^+$; Retention time: 0.69 minutes.

Step B: N-(4-Hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

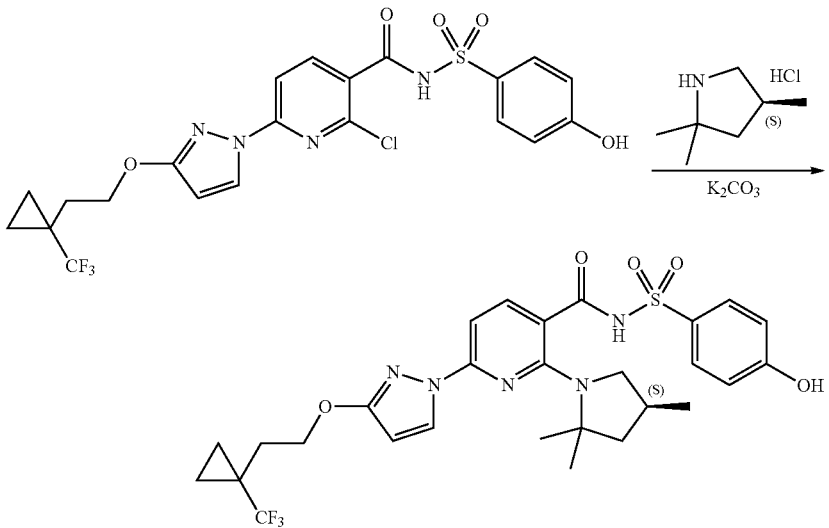

2-Chloro-N-(4-hydroxyphenyl)sulfonyl-6-[3-[2-[1-(trifluoromethyl)cyclopropyl]ethoxy]pyrazol-1-yl]pyridine-3-carboxamide (134 mg, 0.2524 mmol), (4S)-2,2,4-trimethylpyrrolidine (hydrochloride salt) (113 mg, 0.7550 mmol), and potassium carbonate (210 mg, 1.519 mmol) were combined in dimethyl sulfoxide (670.0 μL) and heated at 130° C. for 16 h. The reaction was cooled to room temperature, and 1 mL of water was added. After 15 minutes stirring, the contents of the vial were allowed to settle, the liquid portion was removed by pipette and the remaining solids were dissolved with 20 mL ethyl acetate. The organics were washed with 15 mL 1M citric acid. The aqueous and the organic layers were separated, and the aqueous layer was extracted two additional times with 15 mL ethyl acetate. The organics were combined, washed with brine, dried over sodium sulfate and concentrated. The resulting crude solid was purified by silica gel chromatography eluting with 0-10% methanol in dichloromethane to give N-(4-hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (43 mg, 28%) ESI-MS m/z calc. 607.20764, found 608.2 (M+1)$^+$; Retention time: 2.07 minutes. $^1$H NMR (400 MHz, DMSO) δ 12.25 (s, 1H), 10.58 (s, 1H), 8.19 (d, J=2.8 Hz, 1H), 7.87-7.79 (m, 2H), 7.75 (d, J=8.2 Hz, 1H), 6.97-6.91 (m, 2H), 6.89 (d, J=8.2 Hz, 1H), 6.10 (d, J=2.7 Hz, 1H), 4.31 (t, J=7.1 Hz, 2H), 2.44 (t, J=10.4 Hz, 1H), 2.16-2.09 (m, 1H), 2.26 (t, J=8.8 Hz, 1H), 2.07 (t, J=7.0 Hz, 2H), 1.82 (dd, J=11.9, 5.5 Hz, 1H), 1.54 (s, 3H), 1.51 (s, 3H), 1.38 (t, J=12.1 Hz, 1H), 1.00-0.93 (m, 2H), 0.91-0.86 (m, 2H), 0.69 (d, J=6.2 Hz, 3H).

SYNTHETIC EXAMPLE 32

Synthesis of Compound 32: N-(Benzenesulfonyl)-6-[5-fluoro-3-[2-[1-(trifluoromethyl)cyclopropyl]ethoxy]pyrazol-1-yl]-2-[(4S)-2,2,4-trimethylpyrrolidin-1-yl]pyridine-3-carboxamide

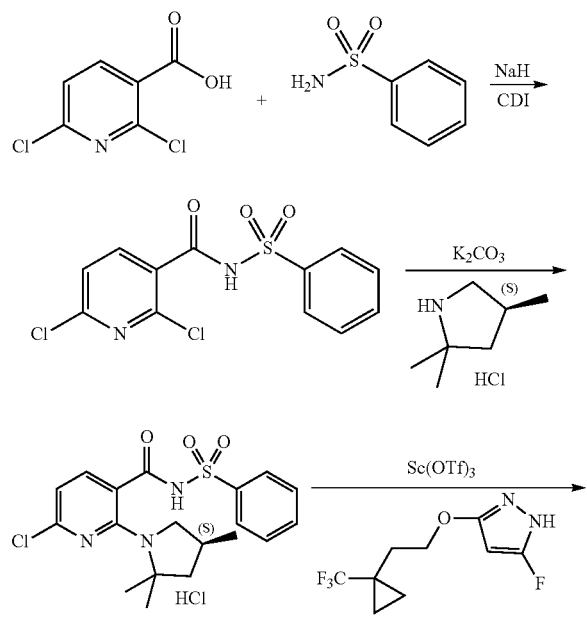

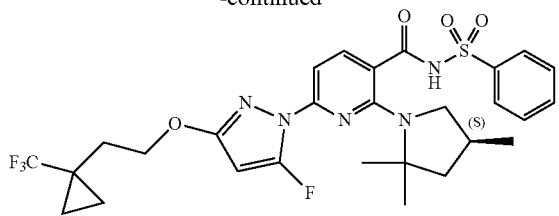

Step A: N-(benzenesulfonyl)-2,6-dichloro-pyridine-3-carboxamide

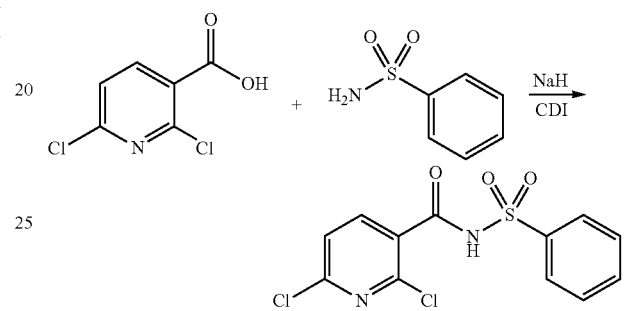

A 5000 mL, 3 neck round bottom flask was fitted with a mechanical stirrer, a cooling bath, a J-Kem temperature probe/controller, a water cooled reflux condenser, an addition funnel and a nitrogen inlet/outlet. The vessel was charged under a nitrogen atmosphere with 60 wt % sodium hydride in mineral oil (26.04 g, 0.6510 mol). The vessel was then slowly charged with N,N-dimethylformamide (200 mL). Stirring was commenced and the pot temperature was recorded at 19° C. The addition funnel was then charged with a solution of benzenesulfonamide (102.3 g, 0.6510 mol) in N,N-dimethylformamide (868 ml, ~8.5 mL/g, 0.75M), requiring some gentle heating to get a homogenous solution. The resulting clear pale yellow solution of benzenesulfonamide was subsequently added dropwise over 1 hour to the round bottom flask which resulted in some slight foaming and gas evolution. After the completed addition, the pot temperature was recorded at 28° C. The vessel was then fitted with a heating mantle and the greyish mixture was warmed to 60° C. Stirring of the mixture was continued at 60° C. for 1 hour at which point gas evolution appeared to have ceased. Stirring of the mixture was continued while the mixture was allowed to cool to room temperature. Meanwhile, a 1000 mL, 3 neck round bottom flask was fitted with a mechanical stirrer, a heating mantle, a J-Kem temperature probe/controller, a water cooled reflux condenser and a nitrogen inlet/outlet. The vessel was charged under a nitrogen atmosphere with 2,6-dichloropyridine-3-carboxylic acid (100 g, 0.5208 mol) and N,N-dimethylformamide (500 mL, 5 ml/g) which provided a clear light yellow solution. Stirring was commenced and the pot temperature was recorded at 17° C. The vessel was then charged with carbonyl diimidazole (84.45 g, 0.5208 mol) added as a solid in portions over 10 minutes which resulted in slight foaming and gas evolution, no exotherm was observed. Stirring of the resulting clear light amber solution was continued at room temperature for 1 hour. The flask which contained the previously formed benzenesulfonamide sodium salt in N,N-dimethylformamide was treated dropwise over 45 minutes with the clear amber solution 2,6-dichloropyridin-3-yl)(H-imidazol-1-yl)methanone intermediate. After the completed addition, the vessel was fitted with a heating mantle and the mixture was warmed to 60° C. and the condition was maintained for 1 hour when analysis by LC/MS indicated complete consumption of the intermediate. The reaction was allowed to cool to room temperature and then poured into ice cold 6M HCl solution (500 mL). The resulting mixture was further diluted with water (500 mL) and then transferred to a separatory funnel and partitioned with ethyl acetate (1000 mL). The organic layer was removed and the residual aqueous was extracted with ethyl acetate (2×500 mL). The combined organic layers were washed with saturated sodium chloride solution (3×500 mL), dried over sodium sulfate (300 g) and then filtered through a glass frit Buchner funnel. The clear pale yellow solution was concentrated under reduced pressure to a volume of about 200 mL. The clear residual oil was diluted with methyl tert-butyl ether (1000 mL) and then concentrated again under reduced pressure during which time a solid began to precipitate. The volume was reduced to about 200 mL. The resulting slurry was allowed to stand at room temperature for 30 minutes and then filtered through a glass frit Buchner funnel. The filter cake was displacement washed methyl tert-butyl ether (2×150 mL) and then pulled in the Buchner funnel for 30 minutes. The material was further dried in a vacuum oven at 45° C. for 2 hours to provide a white solid (101 g, 0.305 mol, 58% yield) as the desired product, N-(benzenesulfonyl)-2,6-dichloro-pyridine-3-carboxamide. ESI-MS m/z calc. 329.96326, found 330.9 (M+1)+; Retention time: 1.22 minutes.

Step B: N-(benzenesulfonyl)-6-chloro-2-[(4S)-2,2,4-trimethylpyrrolidin-1-yl]pyridine-3-carboxamide

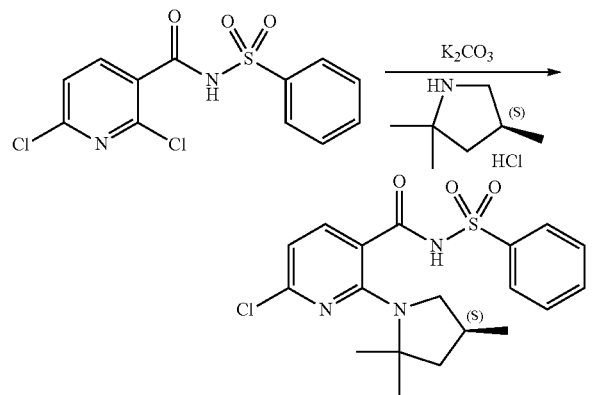

A 5000 mL 3 neck RB flask was fitted with a mechanical stirrer, a heating mantle, a J-Kem temperature probe/controller, a water cooled reflux condenser and a nitrogen inlet/outlet. The vessel was charged under a nitrogen atmosphere with N-(benzenesulfonyl)-2,6-dichloro-pyridine-3-carboxamide (100 g, 0.3020 mol), (4S)-2,2,4-trimethylpyrrolidine hydrochloride (54.24 g, 0.3624 mol) and dimethyl sulfoxide (500 ml, 5 mL/g) which provided a clear pale yellow solution. Stirring was commenced and the pot temperature was recorded at 19° C. The vessel was then charged with potassium carbonate powder (167 g, 1.208 mol, 325 mesh) added as a solid in portions over 10 minutes which resulted in some minor gas evolution and foaming. The resulting off-white suspension was stirred at room temperature for 10 minutes and then heated to a pot temperature of 115° C. and the condition was maintained for 24 hours. Analysis by LC/MS indicated reaction completion and the amber suspension was allowed to cool to room temperature. A 5000 mL 3 neck RB flask was fitted with a mechanical stirrer, a cooling bath and a J-Kem temperature probe. The vessel was charged with 2M HCl (1057 ml, 2.114 mol) and stirring was commenced at a vigorous rate. The cooling bath was charged with crushed ice/water and the pot temperature was lowered to 0° C. The amber suspension reaction mixture was subsequently added slowly in portions over 30 minutes which resulted in the precipitation of a solid and an exotherm to 8° C. Note: Mild foaming upon addition. After the completed addition the resulting suspension was continued to stir at ~5° C. for 1 hour and then collected by vacuum filtration in a glass frit Buchner funnel. The filter cake was displacement washed with water (4×500 mL) and then pulled for 2 hours in the Buchner funnel to provide a white solid (150 g). A 5000 mL 3 neck RB flask was fitted with a mechanical stirrer, a heating mantle, a J-Kem temperature probe/controller, a water cooled reflux condenser and a nitrogen inlet/outlet. The vessel was charged under a nitrogen atmosphere with the isolated product (150 g) and 2-propanol (1050 ml, 7 ml/g) which provided a pale yellow suspension. Stirring was commenced and the pot temperature was recorded at 19° C. The pot temperature was increased to reflux (~82° C.) and the condition was maintained for 10 minutes which resulted in a clear pale amber solution. Stirring of the solution was continued and the solution was allowed to slowly cool to room temperature during which time a solid began to form. Stirring of the suspension was continued and the vessel was fitted with a cooling bath which was charged with crushed ice/water. The pot temperature was lowered to 0° C. and stirring of the thick suspension continued at 0° C. for 1 hour. The material was collected by vacuum filtration in a glass frit Buchner funnel and the filter cake was displacement washed with ice cold 2-propanol (2×50 mL) and then pulled in the Buchner for 30 minutes. The material was further dried in a vacuum oven at 45° C. for 15 hours to provide a white solid (100 g, 0.245 mol, 81% yield) as the product, N-(benzenesulfonyl)-6-chloro-2-[(4S)-2,2,4-trimethylpyrrolidin-1-yl]pyridine-3-carboxamide as 2-propanol solvate with 11 wt % 2-propanol. ESI-MS m/z calc. 407.10703, found 408.1 (M+1)+; Retention time: 1.9 minutes.

Step C: 5-Fluoro-3-[2-[1-(trifluoromethyl)cyclopropyl]ethoxy]-1H-pyrazole

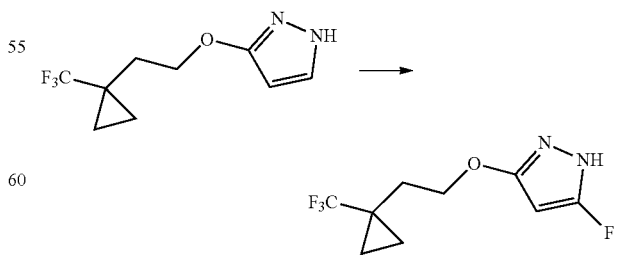

A solution of 3-[2-[1-(trifluoromethyl)cyclopropyl]ethoxy]-1H-pyrazole (0.68 g, 3.088 mmol) and 1-(chloromethyl)-4-fluoro-1,4-diazoniabicyclo[2.2.2]octane;ditetrafluoroborate (1.3 g, 3.7 mmol) in acetonitrile (15 mL) was stirred at 50° C. for 17 hours. The reaction was diluted with water and extracted with ethyl acetate. The combined extracts were washed with water, dried over sodium sulfate, and evaporated. The residue was purified by silica gel column chromatography eluting with a 0-30% ethyl acetate in hexanes gradient to give the still impure product as a brown oil which was further purified using a reverse phase HPLC-MS method using a Luna C18 (2) column (75×30 mm, 5 μm particle size) sold by Phenomenex (pn: 00C-4252-U0-AX), and a dual gradient run from 1-99% mobile phase B over 15.0 minutes (Mobile phase A=H$_2$O (5 mM HCl). Mobile phase B=CH$_3$CN. Flow rate=50 mL/min, and column temperature=25° C.) giving 5-fluoro-3-[2-[1-(trifluoromethyl)cyclopropyl]ethoxy]-1H-pyrazole (90 mg) as a tan oil. ESI-MS m/z calc. 238.07292, found 239.1 (M+1)$^+$; Retention time: 0.56 minutes. $^1$H NMR (400 MHz, DMSO-d6) δ 7.70 (d, J=4.5 Hz, 1H), 4.30-4.16 (m, 2H), 2.04 (t, J=7.1 Hz, 2H), 0.97-0.91 (m, 2H), 0.88-0.81 (m, 2H).

Step D: N-(benzenesulfonyl)-6-[5-fluoro-3-[2-[1-(trifluoromethyl)cyclopropyl]ethoxy]pyrazol-1-yl]-2-[(4S)-2,2,4-trimethylpyrrolidin-1-yl]pyridine-3-carboxamide

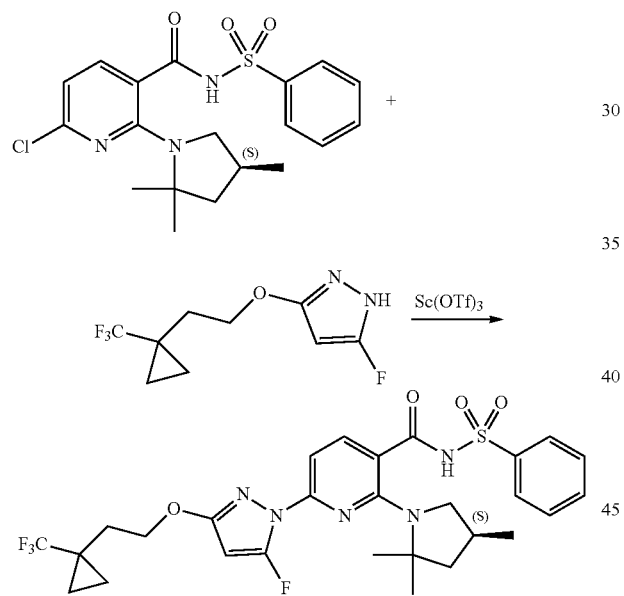

A mixture of 5-fluoro-3-[2-[1-(trifluoromethyl)cyclopropyl]ethoxy]-1H-pyrazole (87 mg, 0.3653 mmol), N-(benzenesulfonyl)-6-chloro-2-[(4S)-2,2,4-trimethylpyrrolidin-1-yl]pyridine-3-carboxamide (79 mg, 0.19 mmol), scandium triflate (10 mg, 0.020 mmol) and sodium hydride (38 mg of 60% w/w, 0.95 mmol) in DMSO (0.92 mL) was stirred at 160° C. for 15 hours. The reaction was filtered and purified using a reverse phase HPLC-MS method using a Luna C18 (2) column (75×30 mm, 5 μm particle size) sold by Phenomenex (pn: 00C-4252-U0-AX), and a dual gradient run from 50-99% mobile phase B over 15.0 minutes (Mobile phase A=H$_2$O (5 mM HCl). Mobile phase B=CH$_3$CN. Flow rate=50 mL/min, and column temperature=25° C.) giving N-(benzenesulfonyl)-6-[5-fluoro-3-[2-[1-(trifluoromethyl)cyclopropyl]ethoxy]pyrazol-1-yl]-2-[(4S)-2,2,4-trimethylpyrrolidin-1-yl]pyridine-3-carboxamide (11 mg, 10%). ESI-MS m/z calc. 609.2033, found 610.3 (M+1)$^+$; Retention time: 2.3 minutes. $^1$H NMR (400 MHz, DMSO-d6) δ 12.53 (s, 1H), 8.26 (d, J=4.5 Hz, 1H), 8.00 (t, J=1.3 Hz, 1H), 7.98 (d, J=1.5 Hz, 1H), 7.82 (d, J=8.3 Hz, 1H), 7.73 (d, J=7.4 Hz, 1H), 7.66 (dd, J=8.2, 6.7 Hz, 2H), 6.90 (d, J=8.3 Hz, 1H), 4.41 (s, 2H), 2.38 (d, J=10.5 Hz, 1H), 2.29-2.21 (m, 1H), 2.10 (q, J=7.0 Hz, 3H), 1.82 (dd, J=12.0, 5.5 Hz, 1H), 1.52 (s, 3H), 1.50 (s, 3H), 1.36 (s, 1H), 0.96 (dd, J=3.7, 2.4 Hz, 2H), 0.89 (dt, J=3.7, 1.9 Hz, 2H), 0.64 (d, J=6.3 Hz, 3H).

SYNTHETIC EXAMPLE 33

Synthesis of Compound 33: N-(4-Hydroxyphenyl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide Step A: 2-Chloro-N-(4-hydroxyphenyl)sulfonyl-6-[3-[(2,2,3,3-tetramethylcyclopropyl)methoxy]pyrazol-1-yl]pyridine-3-carboxamide

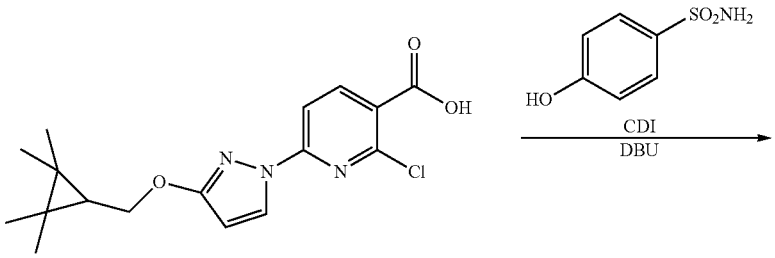

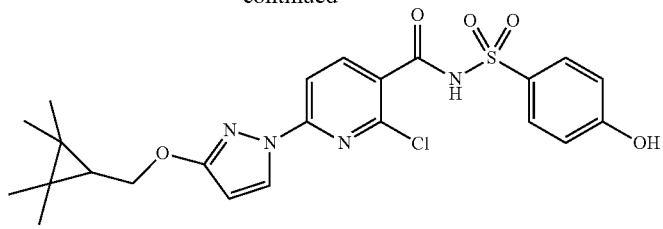

2-Chloro-6-[3-[(2,2,3,3-tetramethylcyclopropyl)methoxy]pyrazol-1-yl]pyridine-3-carboxylic acid (150 mg, 0.4288 mmol) and CDI (83 mg, 0.5119 mmol) were combined in THF (750 µL) and stirred at room temperature for 2 hours. 4-Hydroxybenzenesulfonamide (86 mg, 0.4966 mmol) was added followed by DBU (90 µL, 0.6018 mmol) and the reaction was stirred for an additional 16 h at room temperature. The reaction mixture was diluted with 10 mL 1 M citric acid, and extracted 3×10 mL ethyl acetate. The combined organics were washed with water, washed with brine, dried over sodium sulfate, and concentrated to give a white solid, which was used in the next step without further purification. 2-chloro-N-(4-hydroxyphenyl)sulfonyl-6-[3-[(2,2,3,3-tetramethylcyclopropyl)methoxy]pyrazol-1-yl]pyridine-3-carboxamide (235 mg, 94%) ESI-MS m/z calc. 504.1234, found 505.2 (M+1)⁺; Retention time: 0.75 minutes.

Step 2: N-(4-Hydroxyphenyl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide 387.4 mg, 2.803 mmol) were combined in DMSO (775.7 µL) and heated at 130° C. for 16 h. The reaction was cooled to room temperature, and 1 mL of water was added. After 15 minutes stirring, the contents of the vial were allowed to settle, the liquid portion was removed by pipette and the remaining solids were dissolved with 20 mL ethyl acetate, then washed with 15 mL 1M citric acid. The aqueous and the organic layers were separated, and the aqueous layer was extracted two additional times with 15 mL ethyl acetate. The organics were combined, washed with brine, dried over sodium sulfate and concentrated. The resulting solid was purified by silica gel chromatography eluting with 0-10% methanol in dichloromethane to give N-(4-hydroxyphenyl)sulfonyl-6-[3-[(2,2,3,3-tetramethylcyclopropyl)methoxy]pyrazol-1-yl]-2-[(4S)-2,2,4-trimethylpyrrolidin-1-yl]pyridine-3-carboxamide (30 mg, 11%) ESI-MS m/z calc. 581.2672, found 582.3 (M+1)⁺; Retention time: 2.26 minutes. ¹H NMR (400 MHz, DMSO) δ 12.24 (s, 1H), 10.58 (s, 1H), 8.18 (d, J=2.7 Hz, 1H), 7.86-7.78 (m, 2H), 7.74 (d, J=8.2 Hz, 1H), 6.97-6.92 (m, 2H), 6.90 (d, J=8.3 Hz, 1H),

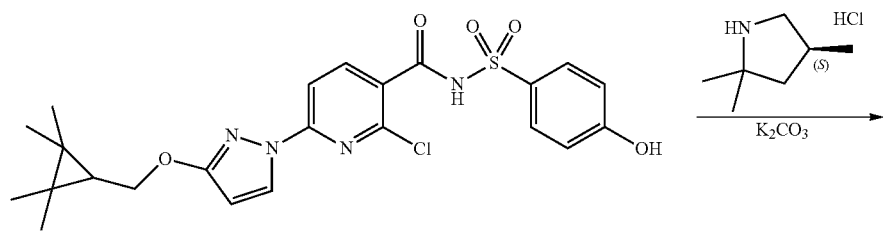

2-Chloro-N-(4-hydroxyphenyl)sulfonyl-6-[3-[(2,2,3,3-tetramethylcyclopropyl)methoxy]pyrazol-1-yl]pyridine-3-carboxamide (235 mg, 0.4654 mmol), (4S)-2,2,4-trimethylpyrrolidine (hydrochloride salt) (approximately 209.2 mg, 1.398 mmol), and potassium carbonate (approximately

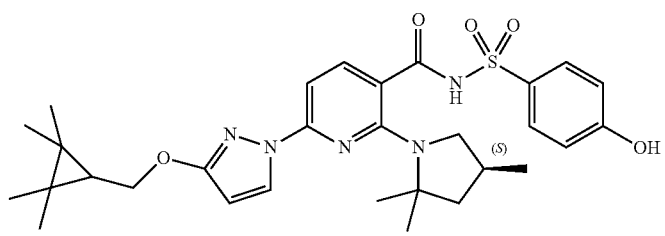

6.13 (d, J=2.6 Hz, 1H), 4.23 (d, J=7.7 Hz, 2H), 2.43 (t, J=10.4 Hz, 1H), 2.26 (t, J=9.0 Hz, 1H), 2.10 (dt, J=13.1, 6.8 Hz, 1H), 1.82 (dd, J=11.9, 5.4 Hz, 1H), 1.54 (s, 3H), 1.51 (s, 3H), 1.37 (t, J=12.1 Hz, 1H), 1.10 (s, 6H), 1.04 (s, 6H), 0.73 (t, J=7.7 Hz, 1H), 0.69 (d, J=6.2 Hz, 3H).

SYNTHETIC EXAMPLE 34

Synthesis of Compound 34: N-(2-hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide Step A: 2-Chloro-N-(2-hydroxyphenyl)sulfonyl-6-[3-[2-[1-(trifluoromethyl)cyclopropyl]ethoxy]pyrazol-1-yl]pyridine-3-carboxamide

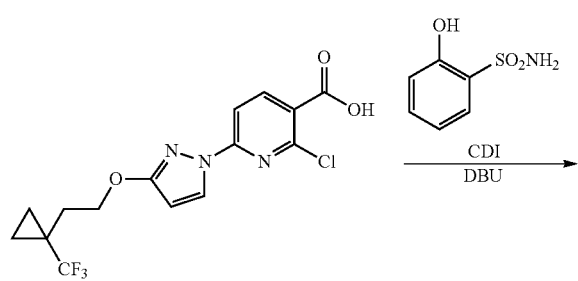

2-Chloro-6-[3-[2-[1-(trifluoromethyl)cyclopropyl]ethoxy]pyrazol-1-yl]pyridine-3-carboxylic acid (100 mg, 0.2661 mmol) and CDI (51 mg, 0.3145 mmol) were combined in THF (600.0 µL) and stirred at room temperature for 2 hours. 2-hydroxybenzenesulfonamide (51 mg, 0.2945 mmol) was added followed by DBU (55 µL, 0.3678 mmol) and the reaction was stirred for an additional 16 h at room temperature. The reaction mixture was diluted with 10 mL 1 M citric acid, and extracted 3×10 mL ethyl acetate. The combined organics were washed with water, brine, dried over sodium sulfate, and concentrated to give a white solid, which was used in the next step without further purification. 2-chloro-N-(2-hydroxyphenyl)sulfonyl-6-[3-[2-[1-(trifluoromethyl)cyclopropyl]ethoxy]pyrazol-1-yl]pyridine-3-carboxamide (132 mg, 93%) ESI-MS m/z calc. 530.06384, found 531.1 (M+1)$^+$; Retention time: 0.7 minutes.

Step B: N-(2-hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

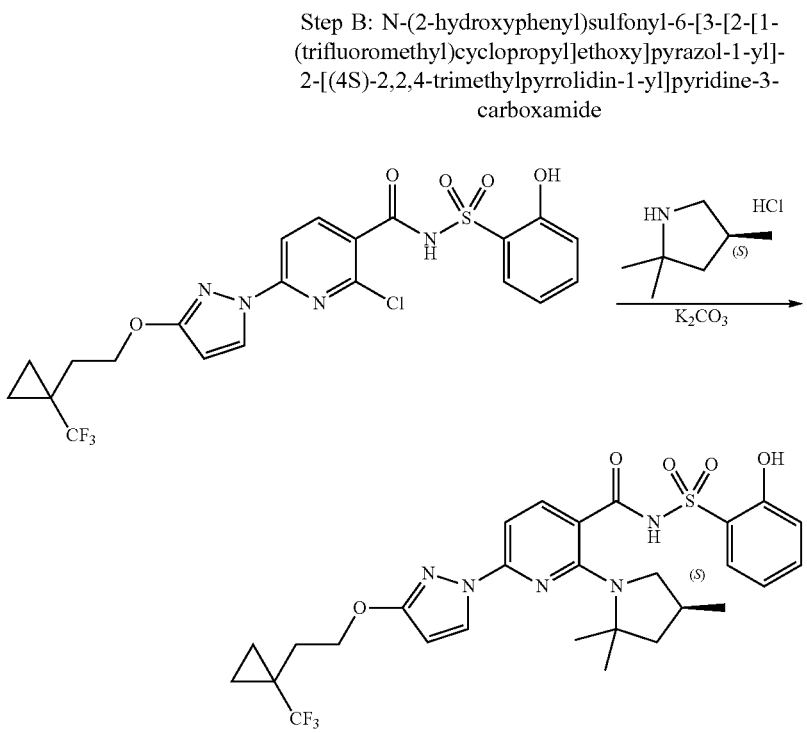

-continued

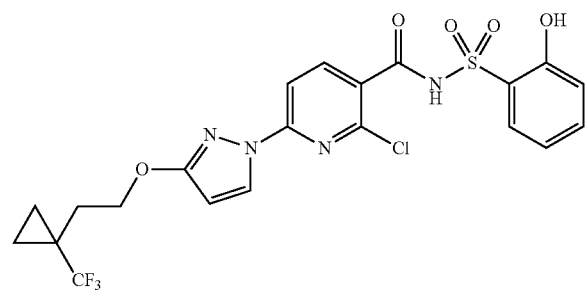

2-Chloro-N-(2-hydroxyphenyl)sulfonyl-6-[3-[2-[1-(trifluoromethyl)cyclopropyl]ethoxy]pyrazol-1-yl]pyridine-3-carboxamide (132 mg, 0.2486 mmol), (4S)-2,2,4-trimethylpyrrolidine (hydrochloride salt) (190 mg, 1.270 mmol), and potassium carbonate (345 mg, 2.496 mmol) were combined in DMSO (660.0 µL) and heated at 130° C. for 16 h. The reaction was cooled to room temperature, and 1 mL of water was added. After 15 minutes stirring, the contents of the vial were allowed to settle, the liquid portion was removed by pipette and the remaining solids were dissolved with 20 mL ethyl acetate, then washed with 15 mL 1M citric acid. The aqueous and the organic layers were separated, and the aqueous layer was extracted two additional times with 15 mL ethyl acetate. The organics were combined, washed with brine, dried over sodium sulfate and concentrated. The resulting solid was further purified by silica gel chromatography eluting with 0-10% methanol in dichloromethane to give N-(2-hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (51 mg, 31%) ESI-MS m/z calc. 607.20764, found 608.3 (M+1)+; Retention time: 2.14 minutes $^1$H NMR (400 MHz, DMSO) δ 12.41 (s, 1H), 10.89 (s, 1H), 8.20 (d, J=2.8 Hz, 1H), 7.79 (dd, J=8.1, 2.1 Hz, 2H), 7.56-7.43 (m, 1H), 7.07-6.95 (m, 2H), 6.88 (d, J=8.2 Hz, 1H), 6.11 (d, J=2.7 Hz, 1H), 4.31 (t, J=7.1 Hz, 2H), 2.64 (d, J=8.1 Hz, 1H), 2.58 (d, J=10.6 Hz, 1H), 2.19 (d, J=11.0 Hz, 1H), 2.08 (t, J=7.0 Hz, 2H), 1.85 (dd, J=11.9, 5.6 Hz, 1H), 1.54 (d, J=8.1 Hz, 6H), 1.39 (t, J=12.1 Hz, 1H), 1.00-0.92 (m, 2H), 0.90 (d, J=10.8 Hz, 2H), 0.82 (d, J=6.3 Hz, 3H).

SYNTHETIC EXAMPLE 35

Synthesis of Compound 35: N-(3-Hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide Step A: 2-Chloro-N-(3-hydroxyphenyl)sulfonyl-6-[3-[2-[1-(trifluoromethyl)cyclopropyl]ethoxy]pyrazol-1-yl]pyridine-3-carboxamide

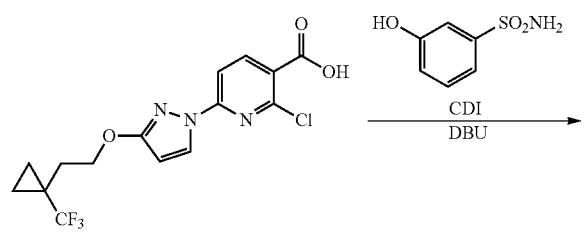

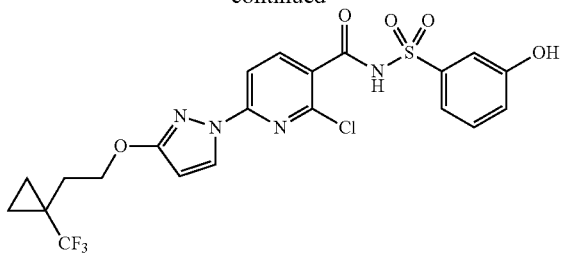

2-Chloro-6-[3-[2-[1-(trifluoromethyl)cyclopropyl]ethoxy]pyrazol-1-yl]pyridine-3-carboxylic acid (100 mg, 0.2661 mmol) and CDI (51 mg, 0.3145 mmol) were combined in THF (600.0 μL) and stirred at room temperature for 2 hours. 3-Hydroxybenzenesulfonamide (51 mg, 0.2945 mmol) was added followed by DBU (55 μL, 0.3678 mmol) and the reaction was stirred for an additional 16 h at room temperature. The reaction mixture was diluted with 10 mL 1 M citric acid, and extracted 3×10 mL ethyl acetate. The combined organics were washed with water, brine, dried over sodium sulfate, and concentrated to give a white solid, which was used in the next step without further purification. 2-chloro-N-(3-hydroxyphenyl)sulfonyl-6-[3-[2-[1-(trifluoromethyl)cyclopropyl]ethoxy]pyrazol-1-yl]pyridine-3-carboxamide (135 mg, 96%) ESI-MS m/z calc. 530.06384, found 531.2 (M+1)+, Retention time: 0.69 minutes.

Step B: N-(3-Hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

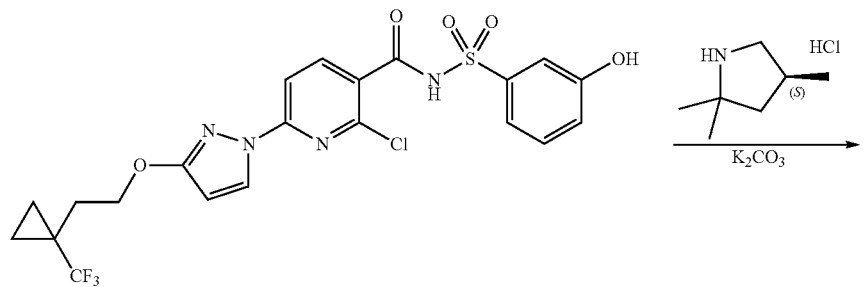

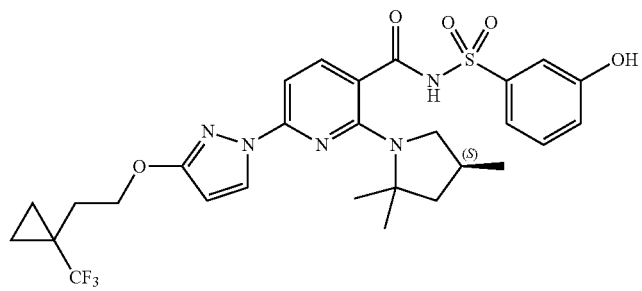

2-Chloro-N-(3-hydroxyphenyl)sulfonyl-6-[3-[2-[1-(trifluoromethyl)cyclopropyl]ethoxy]pyrazol-1-yl]pyridine-3-carboxamide (135 mg, 0.2543 mmol), (4S)-2,2,4-trimethylpyrrolidine (hydrochloride salt) (193 mg, 1.290 mmol), and potassium carbonate (352 mg, 2.547 mmol) were combined in DMSO (508.6 μL) and heated at 130° C. for 16 h. The reaction was cooled to room temperature, and 1 mL of water was added. After 15 minutes stirring, the contents of the vial were allowed to settle and the liquid portion was removed by pipette and discarded. The remaining solids were dissolved in 20 mL ethyl acetate then washed with 15 mL 1M citric acid. The aqueous and the organic layers were separated, and the aqueous layer was extracted two additional times with 15 mL ethyl acetate. The organics were combined, washed with brine, dried over sodium sulfate and concentrated. The resulting solid was purified by silica gel chromatography eluting with 0-10% methanol in dichloromethane to give N-(3-hydroxyphenyl)sulfonyl-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (40 mg, 26%) ESI-MS m/z calc. 607.20764, found 608.3 (M+1)$^+$; Retention time: 2.05 minutes. $^1$H NMR (400 MHz, DMSO) δ 12.44 (s, 1H), 10.19 (s, 1H), 8.20 (d, J=2.8 Hz, 1H), 7.79 (d, J=8.2 Hz, 1H), 7.44 (t, J=8.0 Hz, 1H), 7.40-7.37 (m, 2H), 7.06 (d, J=7.9 Hz, 1H), 6.91 (d, J=8.2 Hz, 1H), 6.11 (d, J=2.7 Hz, 1H), 4.31 (t, J=7.1 Hz, 2H), 2.47 (d, J=10.0 Hz, 1H), 2.33 (s, 2H), 2.08 (m, J=8.1, 7.0 Hz, 2H), 1.84 (dd, J=11.8, 5.5 Hz, 1H), 1.54 (s, 3H), 1.52 (s, 3H), 1.38 (t, J=12.1 Hz, 1H), 0.96 (td, J=5.0, 3.3 Hz, 2H), 0.90 (d, J=11.1 Hz, 2H), 0.70 (d, J=6.2 Hz, 3H).

SYNTHETIC EXAMPLE 36

Synthesis of Compound 36: N-(Benzenesulfonyl)-6-[3-[dideuterio-(2,2,3,3-tetramethylcyclopropyl)methoxy]pyrazol-1-yl]-2-[(4S)-2,2,4-trimethylpyrrolidin-1-yl]pyridine-3-carboxamide Step A: Dideuterio-(2,2,3,3-tetramethylcyclopropyl)methanol

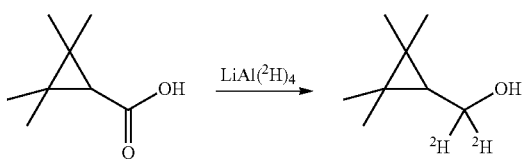

2,2,3,3-Tetramethylcyclopropanecarboxylic acid (1.077 g, 7.574 mmol) was dissolved in anhydrous diethyl ether in a nitrogen purged 100 mL round bottom flask. The reaction mixture was cooled to 0° C. Solid tetradeuterioalumanuide (lithium salt) (420 mg, 10.01 mmol) was added in 3 portions. The reaction mixture was allowed to gradually reach room temperature and stirred for a total of 16 hours. The reaction mixture was then again cooled to 0° C. HCl (aq, 0.2 N, 5 mL) was added dropwise, followed by 20 mL water. The aqueous phase was extracted with diethyl ether (2×30 mL). The combined organic phases were washed with aqueous NaHCO$_3$, followed by brine, then dried over sodium sulfate, filtered and evaporated to give dideuterio-(2,2,3,3-tetramethylcyclopropyl)methanol (920 mg, 93%). $^1$H NMR (400 MHz, DMSO) δ 4.11 (s, 1H), 1.04 (s, 6H), 0.93 (s, 6H), 0.37 (s, 1H).

Step B: tert-Butyl 3-[dideuterio-(2,2,3,3-tetramethylcyclopropyl)methoxy]pyrazole-1-carboxylate

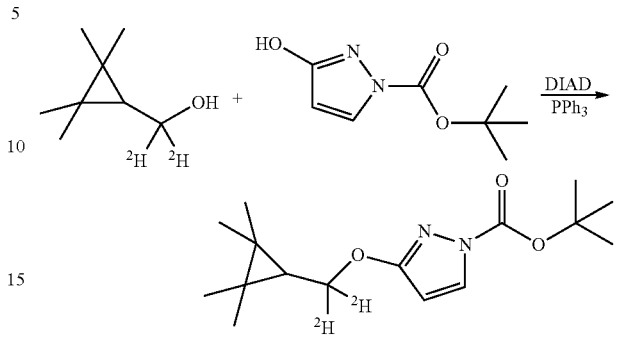

DIAD (1.4 mL, 7.111 mmol) was added dropwise to a solution of triphenyl phosphine (1.815 g, 6.920 mmol) in 40 mL anhydrous toluene, at 0° C. After 30 minutes at 0° C., a solution of tert-butyl 3-hydroxypyrazole-1-carboxylate (1.155 g, 6.271 mmol) and dideuterio-(2,2,3,3-tetramethylcyclopropyl)methanol (980 mg, 7.525 mmol) in 30 mL toluene was slowly added by syringe. The reaction was warmed to room temperature for 45 minutes, and then was heated to 55° C. for 18 h. The mixture was evaporated and the resulting material was partitioned between ethyl acetate (30 mL) and 1N sodium hydroxide (30 mL). The organics were separated, washed with brine (30 mL), dried over sodium sulfate and evaporated. The crude material was purified by silica gel chromatography eluting with 0-30% ethyl acetate in hexanes to give an oil that eventually solidified to a slightly yellow solid: tert-butyl 3-[dideuterio-(2,2,3,3-tetramethylcyclopropyl)methoxy]pyrazole-1-carboxylate (820 mg, 44%) ESI-MS m/z calc. 296.2069, found 297.2 (M+1)$^+$; Retention time: 0.79 minutes.

Step C: 3-[Dideuterio-(2,2,3,3-tetramethylcyclopropyl)methoxy]-1H-pyrazole

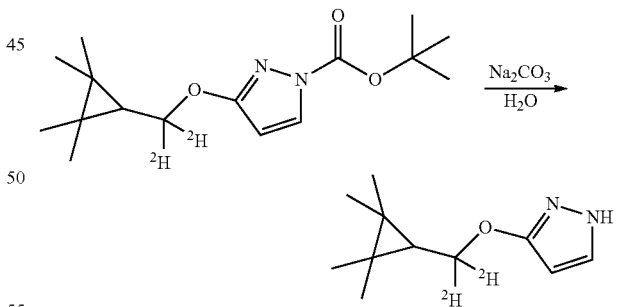

To tert-butyl 3-[dideuterio-(2,2,3,3-tetramethylcyclopropyl)methoxy]pyrazole-1-carboxylate (800 mg, 2.699 mmol) in 1,2-dimethoxyethane (10 mL) was added sodium carbonate (460 mg, 4.340 mmol) in water (3 mL), and the reaction mixture was heated to 90° C. for 16 hours in a screwcap vial. The reaction mixture was cooled to room temperature and diluted with water (50 mL) and ethyl acetate (50 mL). The organics were separated, and the aqueous layer was extracted 2×25 mL ethyl acetate. The combined organics were washed with brine, and dried over sodium sulfate, then concentrated to give a colorless oil. 3-[dideuterio-(2,2,3,3- tetramethylcyclopropyl)methoxy]-1H-pyrazole (492 mg, 93%) ESI-MS m/z calc. 196.15446, found 197.1 (M+1)+; Retention time: 0.57 minutes, ¹H NMR (400 MHz, DMSO) δ 11.78 (s, 1H), 7.48 (t, J=2.1 Hz, 1H), 5.65 (t, J=2.3 Hz, 1H), 1.08 (s, 6H), 1.00 (s, 6H), 0.66 (s, 1H).

Step D: Ethyl 2-chloro-6-[3-[dideuterio-(2,2,3,3-tetramethylcyclopropyl)methoxy]pyrazol-1-yl]pyridine-3-carboxylate

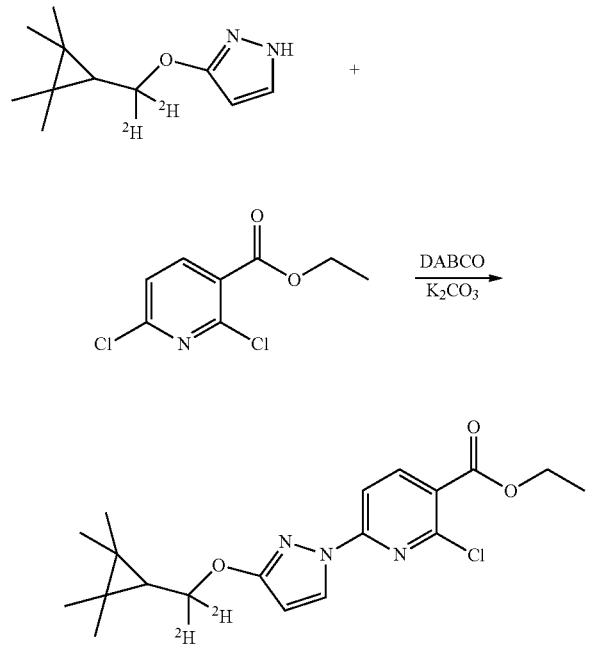

A round bottom flask was charged under nitrogen with 3-[dideuterio-(2,2,3,3-tetramethylcyclopropyl)methoxy]-1H-pyrazole (485 mg, 2.471 mmol), ethyl 2,6-dichloropyridine-3-carboxylate (545 mg, 2.477 mmol), K₂CO₃ (513 mg, 3.712 mmol) (freshly ground in a mortar) and anhydrous DMF (4.128 mL). DABCO (50 mg, 0.4457 mmol) was added and the mixture was stirred at room temperature under nitrogen for 16 hours. The reaction mixture was diluted with ethyl acetate (50 mL) and water (50 mL) and the two phases were separated. The aqueous phase was further extracted with ethyl acetate (2×30 mL), and the combined extracts were washed with brine and dried over sodium sulfate, after which the solvent was removed under reduced pressure. The material was subjected to flash chromatography on silica gel using a gradient of 0-20% ethyl acetate in hexanes. The pure fractions were combined and the solvents removed under reduced pressure to provide a white solid; ethyl 2-chloro-6-[3-[dideuterio-(2,2,3,3-tetramethylcyclopropyl)methoxy]pyrazol-1-yl]pyridine-3-carboxylate (505 mg, 54%) ESI-MS m/z calc. 379.16318, found 380.1 (M+1)+; Retention time: 0.9 minutes ¹H NMR (400 MHz, DMSO) δ 8.42 (d, J=2.9 Hz, 1H), 8.39 (d, J=8.5 Hz, 1H), 7.76 (d, J=8.4 Hz, 1H), 6.24 (d, J=2.9 Hz, 1H), 4.34 (q, J=7.1 Hz, 2H), 1.33 (t, J=7.1 Hz, 3H), 1.11 (s, 6H), 1.04 (s, 6H), 0.74 (s, 1H).

Step E: 2-Chloro-6-[3-[dideuterio-(2,2,3,3-tetramethylcyclopropyl)methoxy]pyrazol-1-yl]pyridine-3-carboxylic acid

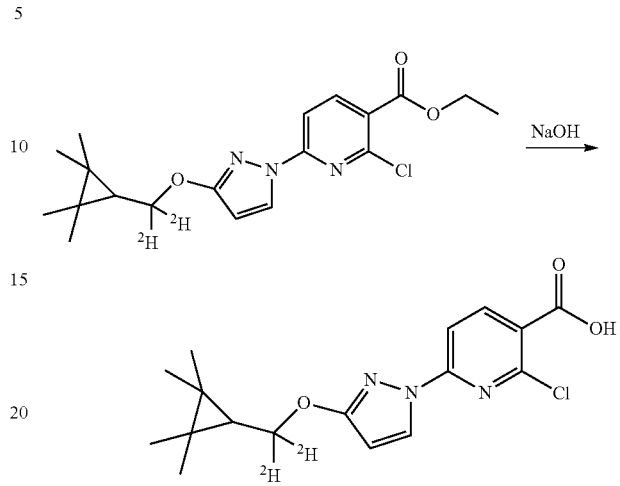

A solution of sodium hydroxide (275 mg, 6.875 mmol) in water (2.500 mL) was added to a solution of ethyl 2-chloro-6-[3-[dideuterio-(2,2,3,3-tetramethylcyclopropyl)methoxy]pyrazol-1-yl]pyridine-3-carboxylate (500 mg, 1.316 mmol) in isopropanol (2.500 mL) and stirred at 90° C. for 45 minutes. The reaction was cooled to room temperature then diluted with 50 mL ethyl acetate, 20 mL 1M citric acid, and 10 mL water. The organics were separated, and the aqueous portion was extracted 2×25 mL ethyl acetate. The combined organics were washed with brine, dried over sodium sulfate and concentrated. The resulting solid was triturated in 40 mL water, briefly sonicated, and collected by filtration then dried to give a white solid, 2-chloro-6-[3-[dideuterio-(2,2,3,3-tetramethylcyclopropyl)methoxy]pyrazol-1-yl]pyridine-3-carboxylic acid (404 mg, 87%) ESI-MS m/z calc. 351.13187, found 352.1 (M+1)+; Retention time: 0.77 minutes. ¹H NMR (400 MHz, DMSO) δ 8.41 (d, J=2.9 Hz, 1H), 8.38 (d, J=8.4 Hz, 1H), 7.74 (d, J=8.4 Hz, 1H), 6.22 (d, J=2.8 Hz, 1H), 1.11 (s, 6H), 1.04 (s, 6H), 0.74 (s, 1H).

Step F: N-(Benzenesulfonyl)-2-chloro-6-[3-[dideuterio-(2,2,33-tetramethylcyclopropyl)methoxy]pyrazol-1-yl]pyridine-3-carboxamide

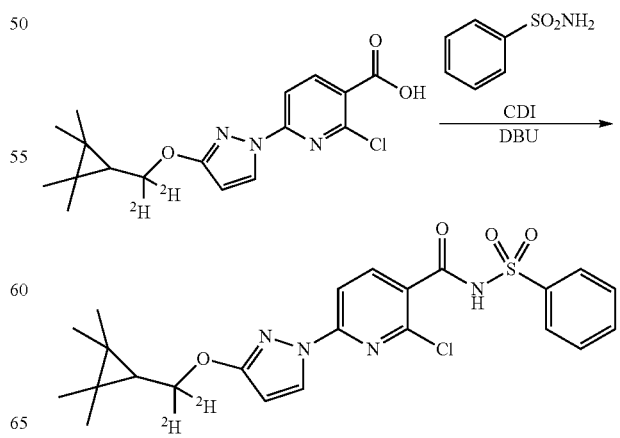

2-Chloro-6-[3-[dideuterio-(2,2,3,3-tetramethylcyclopropyl)methoxy]pyrazol-1-yl]pyridine-3-carboxylic acid (100 mg, 0.2842 mmol) and CDI (55 mg, 0.3392 mmol) were combined in THF (600.0 μL) and stirred at room temperature for 2 hours. benzenesulfonamide (49 mg, 0.3117 mmol) was added followed by DBU (57 μL, 0.3812 mmol) and the reaction was stirred for an additional 16 h at room temperature. The reaction mixture was diluted with 10 mL 1 M citric acid, and extracted 3×10 mL ethyl acetate. The combined organics were washed with water, brine, dried over sodium sulfate, and concentrated to give approximately 135 mg of a white solid, which was used in the next step without further purification. N-(benzenesulfonyl)-2-chloro-6-[3-[dideuterio-(2,2,3,3-tetramethylcyclopropyl)methoxy]pyrazol-1-yl]pyridine-3-carboxamide ESI-MS m/z calc. 490.14105, found 491.2 (M+1)⁺; Retention time: 0.81 minutes.

Step G: N-(Benzenesulfonyl)-6-[3-[dideuterio-(2,2,3,3-tetramethylcyclopropyl)methoxy]pyrazol-1-yl]-2-[(4S)-2,2,4-trimethylpyrrolidin-1-yl]pyridine-3-carboxamide

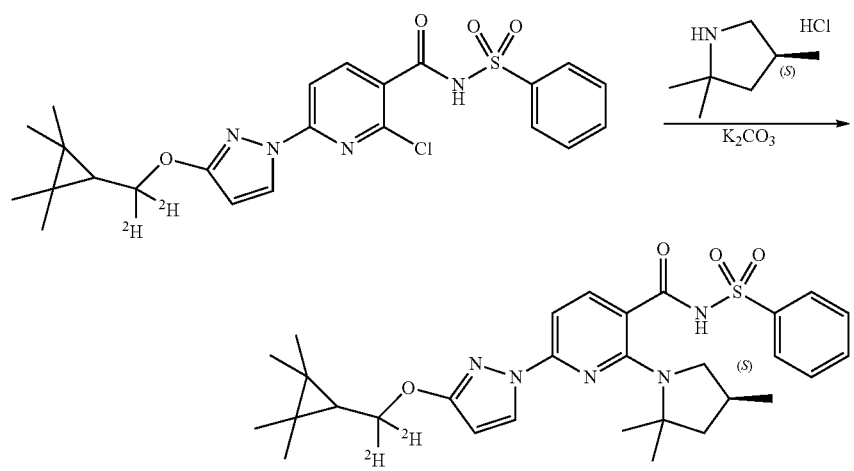

N-(Benzenesulfonyl)-2-chloro-6-[3-[dideuterio-(2,2,3,3-tetramethylcyclopropyl)methoxy]pyrazol-1-yl]pyridine-3-carboxamide (135 mg, 0.2749 mmol), (4S)-2,2,4-trimethylpyrrolidine (Hydrochloride salt) (128 mg, 0.8553 mmol), and potassium carbonate (237 mg, 1.715 mmol) were combined in DMSO (458.2 L) and heated at 130° C. for 16 h. The reaction was cooled to room temperature, and 1 mL of water was added. After 15 minutes stirring, the contents of the vial were allowed to settle, the liquid portion was removed by pipette and the remaining solids were dissolved with 20 mL ethyl acetate then washed with 15 mL 1M citric acid. The aqueous and the organic layers were separated, and the aqueous layer was extracted two additional times with 15 mL ethyl acetate. The organics were combined, washed with brine, dried over sodium sulfate and concentrated. The resulting solid was further purified by silica gel chromatography eluting with 0-10% methanol in dichloromethane to give N-(benzenesulfonyl)-6-[3-[dideuterio-(2,2,3,3-tetramethylcyclopropyl)methoxy]pyrazol-1-yl]-2-[(4S)-2,2,4-trimethylpyrrolidin-1-yl]pyridine-3-carboxamide (112 mg, 72%) ESI-MS m/z calc. 567.28485, found 568.3 (M+1)⁺; Retention time: 2.42 minutes. ¹H NMR (400 MHz, DMSO) δ 12.51 (s, 1H), 8.18 (d, J=2.8 Hz, 1H), 7.99 (dt, J=7.1, 1.4 Hz, 2H), 7.80 (d, J=8.3 Hz, 1H), 7.76-7.70 (m, 1H), 7.70-7.62 (m, 2H), 6.92 (d, J=8.3 Hz, 1H), 6.13 (d, J=2.7 Hz, 1H), 2.40 (t, J=10.4 Hz, 1H), 2.26 (t, J=8.7 Hz, 1H), 2.09 (dq, J=11.7, 6.0 Hz, 1H), 1.82 (dd, J=11.8, 5.4 Hz, 1H), 1.52 (d, J=9.5 Hz, 6H), 1.36 (t, J=12.2 Hz, 1H), 1.10 (s, 6H), 1.04 (s, 6H), 0.72 (s, 1H), 0.64 (d, J=6.2 Hz, 3H).

SYNTHETIC EXAMPLE 37

Synthesis of Compound 37: N-(Benzenesulfonyl)-6-[3-[[1-(trifluoromethyl)cyclopropyl]methoxymethyl]pyrazol-1-yl]-2-[(4S)-2,2,4-trimethylpyrrolidin-1-yl]pyridine-3-carboxamide Step A: 3-(tert-butoxymethyl)-1H-pyrazole

-continued

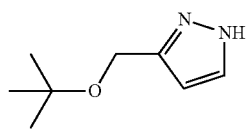

tert-Butylpropargyl alcohol (2.5 g, 22.2 mmol) was mixed with trimethylsilyl diazomethane (2.0 M in hexane, 11.1 mL, 22.2 mmol) and stirred in a sealed tube at 115° C. for 18 hours. The mixture was cooled to 40° C. and quenched with methanol (5 mL) and concentrated. Column chromatography (silica; heptanes/EtOAc 2:1 to 1:1) afforded 3-(tert-butoxymethyl)-1H-pyrazole as colorless oil (1.5 g, 44%). ¹H NMR (CDCl3, 300 MHz): δ 1.26 (s, 9H); 4.53 (s, 2H); 6.22 (s, 1H); 7.48 (s, 1H). 13C-NMR (75 MHz, CDCl3): δ 27.3, 57.2, 73.9, 103.5, 134.0 (one quaternary carbon not shown).

Step B: tert-Butyl 6-[3-(tert-butoxymethyl)pyrazol-1-yl]-2-chloro-pyridine-3-carboxylate

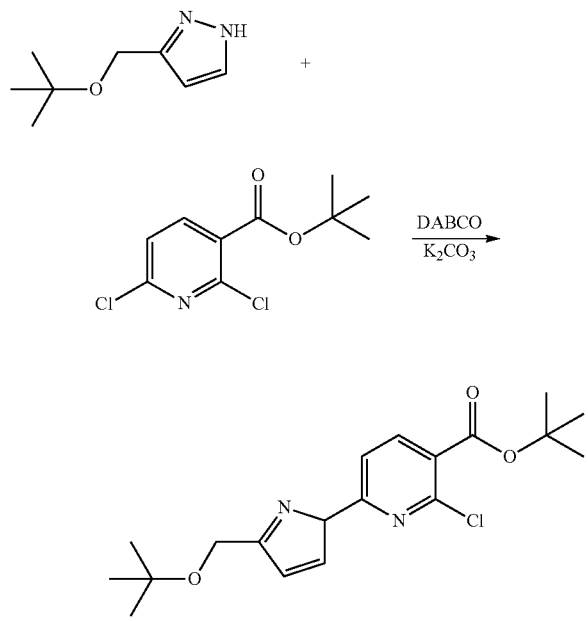

A 100 mL round bottom flask was charged under nitrogen with 3-(tert-butoxymethyl)-1H-pyrazole (1.241 g, 8.047 mmol), tert-butyl 2,6-dichloropyridine-3-carboxylate (2.0 g, 8.061 mmol), K$_2$CO$_3$ (1.448 g, 10.48 mmol) (freshly ground in a mortar) and anhydrous DMF (12.41 mL). DABCO (163 mg, 1.453 mmol) was added and the mixture was stirred at room temperature under nitrogen for 16 hours. The reaction mixture was diluted with ethyl acetate (50 mL) and water and brine (50 mL) and the two phases were separated. The aqueous phase was further extracted with ethyl acetate (2×30 mL). The combined extracts were washed with brine, dried over sodium sulfate and the solvent removed under reduced pressure. The material was subjected to flash chromatography on silica gel using a gradient of ethyl acetate (0 to 10%) in hexanes. The pure fractions were combined and the solvents removed under reduced pressure to provide tert-butyl 6-[3-(tert-butoxymethyl)pyrazol-1-yl]-2-chloro-pyridine-3-carboxylate (1.956 g, 66%) as a colorless oil, which solidified to a white solid overnight on high vac. ESI-MS m/z calc. 365.1506, found 366.2 (M+1)$^+$; Retention time: 0.82 minutes

Step C: 2-Chloro-6-[3-(hydroxymethyl)pyrazol-1-yl]pyridine-3-carboxylic acid

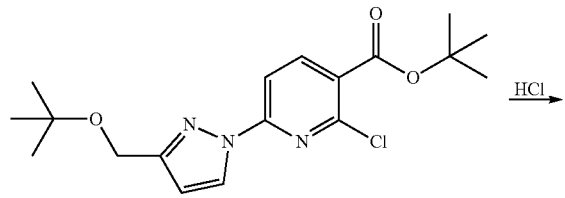

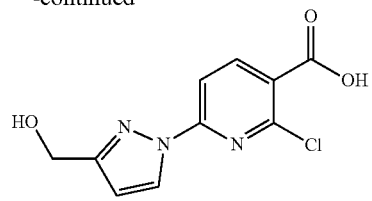

tert-Butyl 6-[3-(tert-butoxymethyl)pyrazol-1-yl]-2-chloro-pyridine-3-carboxylate (538 mg, 1.471 mmol) was dissolved in HCl in dioxane (8.0 mL of 4 M, 32.00 mmol) and heated at 60° C. for 2 hours. The reaction mixture was then cooled to room temperature and concentrated to dryness, giving a white powder. 2-chloro-6-[3-(hydroxymethyl)pyrazol-1-yl]pyridine-3-carboxylic acid (370 mg, 99%) ESI-MS m/z calc. 253.02542, found 254.1 (M+1)$^+$; Retention time: 0.33 minutes

Step D: 2-Chloro-6-[3-[[1-(trifluoromethyl)cyclopropyl]methoxymethyl]pyrazol-1-yl]pyridine-3-carboxylic acid

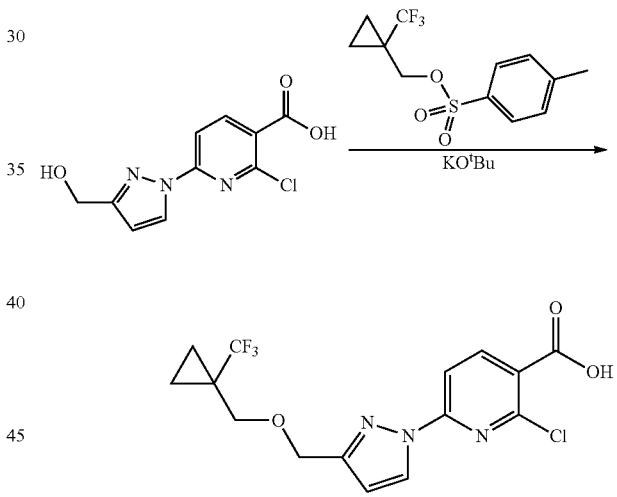

[1-(Trifluoromethyl)cyclopropyl]methyl 4-methylbenzenesulfonate (1.3 g, 4.417 mmol), and 2-chloro-6-[3-(hydroxymethyl)pyrazol-1-yl]pyridine-3-carboxylic acid (370 mg, 1.459 mmol), were combined in anhydrous DMSO (9.250 mL). tert-butoxypotassium (660 mg, 5.882 mmol) was added and the reaction mixture was stirred at room temperature. After 30 minutes the reaction mixture was poured into 1 M citric acid (15 mL) and extracted 3×15 mL ethyl acetate. The combined organics were washed with brine, dried over sodium sulfate and concentrated. The resulting material was purified by chromatography on silica gel using a 0-10% methanol in dichloromethane gradient. The fractions containing product were collected and concentrated to give a white solid. 2-Chloro-6-[3-[[1-(trifluoromethyl)cyclopropyl]methoxymethyl]pyrazol-1-yl]pyridine-3-carboxylic acid (292 mg, 53%) ESI-MS m/z calc. 375.05975, found 376.1 (M+1)$^+$; Retention time: 0.62 minutes.

Step E: N-(Benzenesulfonyl)-2-chloro-6-[3-[[1-(trifluoromethyl)cyclopropyl]methoxymethyl]pyrazol-1-yl]pyridine-3-carboxamide

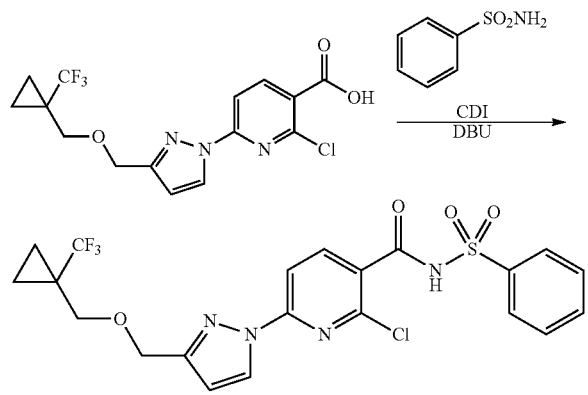

2-Chloro-6-[3-[[1-(trifluoromethyl)cyclopropyl]methoxymethyl]pyrazol-1-yl]pyridine-3-carboxylic acid (60 mg, 0.1597 mmol) and CDI (31 mg, 0.1912 mmol) were combined in THF (360.0 μL) and stirred at room temperature for 2 hours. Benzenesulfonamide (28 mg, 0.1781 mmol) was added followed by DBU (35 μL, 0.2340 mmol) and the reaction was stirred for an additional 16 h at room temperature. The reaction mixture was diluted with 10 mL 1 M citric acid, and extracted 3×10 mL ethyl acetate. The combined organics were washed with water, brine, dried over sodium sulfate, and concentrated to give a white solid, which was used in the next step without further purification. N-(benzenesulfonyl)-2-chloro-6-[3-[[1-(trifluoromethyl)cyclopropyl]methoxymethyl]pyrazol-1-yl]pyridine-3-carboxamide (approximately 78 mg) ESI-MS m/z calc. 514.0689, found 515.1 (M+1)$^+$; Retention time: 0.69 minutes.

Step G: N-(Benzenesulfonyl)-6-[3-[[1-(trifluoromethyl)cyclopropyl]methoxymethyl]pyrazol-1-yl]-2-[(4S)-2,2,4-trimethylpyrrolidin-1-yl]pyridine-3-carboxamide

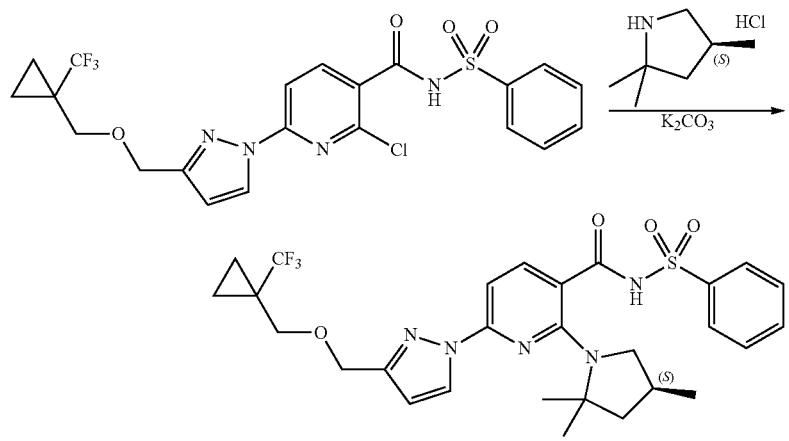

N-(Benzenesulfonyl)-2-chloro-6-[3-[[1-(trifluoromethyl)cyclopropyl]methoxymethyl]pyrazol-1-yl]pyridine-3-carboxamide (78 mg, 0.1515 mmol), (4S)-2,2,4-trimethylpyrrolidine (Hydrochloride salt) (115 mg, 0.7684 mmol), and Potassium carbonate (210 mg, 1.519 mmol) were combined in DMSO (390.0 μL) and heated at 130° C. for 16 h. The reaction was cooled to room temperature, and 1 mL of water was added. After 15 minutes stirring, the contents of the vial were allowed to settle, the liquid portion was removed by pipette and the remaining solids were dissolved with 20 mL ethyl acetate, then washed with 15 mL 1M citric acid. The aqueous and the organic layers were separated, and the aqueous layer was extracted two additional times with 15 mL ethyl acetate. The organics were combined, washed with brine, dried over sodium sulfate and concentrated. The resulting solid was further purified by silica gel chromatography eluting with 0-10% methanol in dichloromethane to give N-(benzenesulfonyl)-6-[3-[[1-(trifluoromethyl)cyclopropyl]methoxymethyl]pyrazol-1-yl]-2-[(4S)-2,2,4-trimethylpyrrolidin-1-yl]pyridine-3-carboxamide (46 mg, 51%) ESI-MS m/z calc. 591.2127, found 592.3 (M+1)$^+$; Retention time: 2.11 minutes. $^1$H NMR (400 MHz, DMSO) δ 12.56 (s, 1H), 8.33 (d, J=2.6 Hz, 1H), 8.04-7.97 (m, 2H), 7.89-7.79 (m, 1H), 7.73 (t, J=7.1 Hz, 1H), 7.70-7.60 (m, 2H), 7.07 (d, J=8.2 Hz, 1H), 6.56 (d, J=2.6 Hz, 1H), 4.55 (s, 2H), 3.59 (s, 2H), 2.42 (t, J=10.4 Hz, 1H), 2.29 (d, J=9.6 Hz, 1H), 2.18-2.04 (m, 1H), 1.83 (dd, J=11.7, 5.5 Hz, 1H), 1.54 (d, J=9.4 Hz, 6H), 1.37 (t, J=12.1 Hz, 1H), 1.03-0.94 (m, 2H), 0.91-0.80 (m, 2H), 0.65 (d, J=6.2 Hz, 3H).

SYNTHETIC EXAMPLE 38

Synthesis of Compound 38: N-(Benzenesulfonyl)-6-[3-[2-hydroxy-2-[1-(trifluoromethyl)cyclopropyl]ethoxy]pyrazol-1-yl]-2-[(4S)-2,2,4-trimethylpyrrolidin-1-yl]pyridine-3-carboxamide Steps A-B: 1-[1-(Trifluoromethyl)cyclopropyl]prop-2-en-1-ol

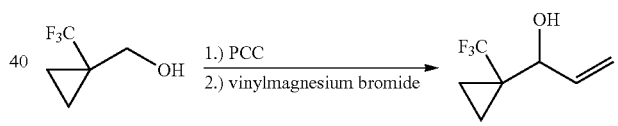

[1-(Trifluoromethyl)cyclopropyl]methanol (1 g, 7.138 mmol) was stirred in dry dichloromethane (30 mL) and cooled to 0° C. in an ice bath. Chloro-hydroxy-dioxochromium;pyridine (2.77 g, 12.85 mmol) was added in one portion, and the ice bath was removed and the reaction was stirred for 24 hours at room temperature. The reaction mixture was poured into 100 mL diethyl ether and filtered through a pad of silica with a layer of celite on top, eluting with diethyl ether. The resulting filtrate was dried over sodium sulfate, then filtered through cotton and used in the next step without concentration due to the volatility of the aldehyde. The crude filtrate was cooled to 0° C., and bromo(vinyl)magnesium (14.5 mL of 1 M, 14.50 mmol) (in THF) was slowly added. The reaction mixture was allowed to slowly warm to near room temperature over 2 hours. The reaction mixture was then cooled to 0° C., quenched with 1M HCl, and diluted with water. The layers were separated, and the aqueous was extracted 4 additional times with diethyl ether. The combined organics were washed with brine, dried over sodium sulfate and partially concentrated. The resulting crude material was used in the next step without further purification. 1-[1-(trifluoromethyl)cyclopropyl]prop-2-en-1-ol (approximately 1.25 g crude, with substantial THF remaining) Crude $^1$H NMR (400 MHz, DMSO) δ 5.95-5.84 (m, 1H), 5.36 (d, J=5.2 Hz, 1H), 5.32 (ddd, J=17.1, 2.1, 1.4 Hz, 1H), 5.18 (ddd, J=10.4, 2.0, 1.3 Hz, 1H), 4.17 (tt, J=6.4, 1.4 Hz, 1H), 0.95-0.87 (m, 4H).

Step C: tert-Butyl-dimethyl-[1-[1-(trifluoromethyl)cyclopropyl]allyloxy]silane

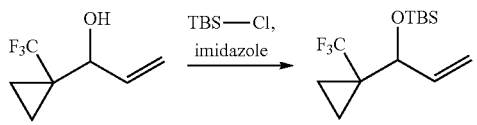

[1-(Trifluoromethyl)cyclopropyl]prop-2-en-1-ol (270 mg, 1.625 mmol) and imidazole (220 mg, 3.232 mmol) were dissolved in DMF (2 mL) and cooled to 0° C. in an ice bath. TBS-Cl (tert-butyldimethylsilyl chloride) (370 mg, 2.455 mmol) was then added in a single portion, and after 15 minutes the ice bath was removed and the reaction mixture was allowed to stir 16 hours at room temperature. Saturated aqueous ammonium chloride (1 mL) was then added, and the reaction mixture was stirred for 20 minutes. The reaction mixture was then diluted with 30 mL diethyl ether and 20 mL of water. The organics were separated, and the aqueous layer was extracted 2×15 mL diethyl ether. The combined organics were washed with water, then brine and dried over sodium sulfate, and concentrated under vacuum. The crude material was then passed through a silica plug, eluting with hexanes, and concentrated to an oil containing substantial overlapping silyl impurities, but used in the next step without further purification, tert-butyl-dimethyl-[1-[1-(trifluoromethyl)cyclopropyl]allyloxy]silane (approximately 317 mg, crude).

Steps D-F: tert-butyl 3-[2-[tert-butyl(dimethyl)silyl]oxy-2-[1-(trifluoromethyl)cyclopropyl]ethoxy]pyrazole-1-carboxylate

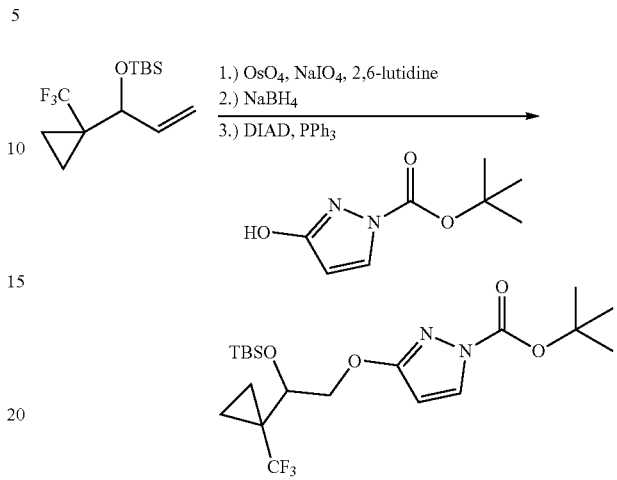

tert-Butyl-dimethyl-[1-[1-(trifluoromethyl)cyclopropyl]allyloxy]silane (220 mg, 0.7846 mmol) (crude) was combined in dioxane (6 mL) and water (2 mL) with 2,6-dimethylpyridine (185 μL, 1.597 mmol) and sodium periodate (675 mg, 3.156 mmol). Tetraoxoosmium (420 μL, 0.3139 mmol) was then added and the reaction mixture was stirred for 20 hours at room temperature. The reaction was then diluted with 30 mL dichloromethane and 30 mL water. The organics were separated, and the aqueous layer was extracted 2×25 mL dichloromethane. The combined organics were dried over sodium sulfate, and concentrated to about 8 mL and used in the next step, without isolation.

The crude mixture from the previous step was diluted with methanol (10 mL), and cooled to 0° C. Sodium borohydride (90 mg, 2.379 mmol) was added and the reaction mixture stirred for 1 hour. The reaction mixture was then quenched with acetic acid and concentrated. The resulting material was partitioned between ethyl acetate and aqueous sodium bicarbonate and the layers were separated. The aqueous portion was extracted 2× ethyl acetate, and the combined organics were washed with brine, dried over sodium sulfate and concentrated. The resulting crude alcohol was used in the next step without purification. The crude product was combined with triphenylphosphine (300 mg, 1.144 mmol) and tert-butyl 3-hydroxypyrazole-1-carboxylate (145 mg, 0.7872 mmol) dissolved in THF (15 mL). The reaction mixture was cooled to 0° C. and DIAD (230 μL, 1.187 mmol) was slowly added. The ice bath was removed, and the reaction was stirred at room temperature for an hour then heated to 55° C. for an additional 16 hours. The reaction mixture was partially concentrated, dissolved in 100 mL ethyl acetate, washed with 25 mL 1N NaOH, brine, dried over sodium sulfate and concentrated. The resulting material was purified by chromatography on silica gel eluting with 0-50% ethyl acetate in hexanes to give, with an overlapping UV active impurity tert-butyl 3-[2-[tert-butyl(dimethyl)silyl]oxy-2-[1-(trifluoromethyl)cyclopropyl]ethoxy]pyrazole-1-carboxylate (63 mg, 18%) ESI-MS m/z calc. 450.21616, found 451.3 (M+1)$^+$; Retention time: 0.95 minutes

Step G: 3-(2-((tert-butyldimethylsilyl)oxy)-2-(1-(trifluoromethyl)cyclopropyl)ethoxy)-1H-pyrazole

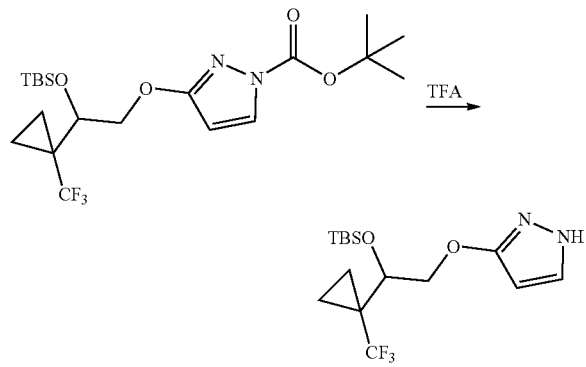

tert-Butyl 3-[2-[tert-butyl(dimethyl)silyl]oxy-2-[1-(trifluoromethyl)cyclopropyl]ethoxy]pyrazole-1-carboxylate (63 mg, 0.1398 mmol) (with a major impurity present) was dissolved in dichloromethane (1.312 mL) with TFA (trifluoroacetic acid) (approximately 194.3 mg, 131.3 µL, 1.704 mmol) and the reaction was stirred at room temperature for 30 minutes. Hexanes (1 mL) were added, and reaction was evaporated and the resulting oil was partitioned between ethyl acetate (10 mL) and a saturated sodium bicarbonate solution. The organics were separated, washed with brine, dried over sodium sulfate and evaporated to give a colorless oil, 3-(2-((tert-butyldimethylsilyl)oxy)-2-(1-(trifluoromethyl)cyclopropyl)ethoxy)-1H-pyrazole (37 mg, 76%) ESI-MS m/z calc. 350.16373, found 351.2 (M+1)$^+$; Retention time: 0.81 minutes.

Step H: tert-Butyl 6-[3-[2-[tert-butyl(dimethyl)silyl]oxy-2-[1-(trifluoromethyl)cyclopropyl]ethoxy]pyrazol-1-yl]-2-chloro-pyridine-3-carboxylate

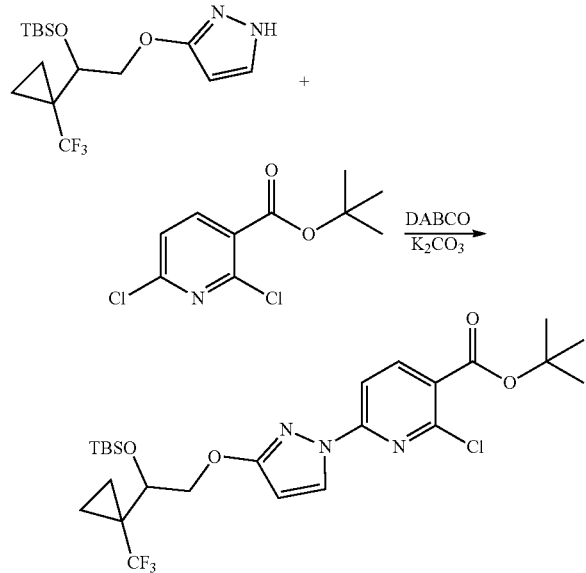

A round bottom flask was charged under nitrogen with tert-butyl-dimethyl-[2-(1H-pyrazol-3-yloxy)-1-[1-(trifluoromethyl)cyclopropyl]ethoxy]silane (37 mg, 0.1056 mmol), tert-butyl 2,6-dichloropyridine-3-carboxylate (26 mg, 0.1048 mmol), K$_2$CO$_3$ (25 mg, 0.1809 mmol) (freshly ground in a mortar) and anhydrous DMF (250 µL). DABCO (2 mg, 0.01783 mmol) was added and the mixture was stirred at room temperature under nitrogen for 16 hours. The reaction mixture was diluted with ethyl acetate (15 mL) and water (15 mL) and the two phases were separated. The aqueous phase was further extracted with ethyl acetate (2×15 mL). The combined extracts were washed with brine and dried over sodium sulfate and the solvent removed under reduced pressure. The material was subjected to flash chromatography on silica gel using a gradient of ethyl acetate (0 to 20%) in hexanes. The pure fractions were combined and the solvents removed under reduced pressure to provide a colorless oil, tert-butyl 6-[3-[2-[tert-butyl(dimethyl)silyl]oxy-2-[1-(trifluoromethyl)cyclopropyl]ethoxy]pyrazol-1-yl]-2-chloro-pyridine-3-carboxylate (20 mg, 34%). ESI-MS m/z calc. 561.20374, found 562.4 (M+1)$^+$; Retention time: 0.84 minutes, $^1$H NMR (400 MHz, DMSO) δ 8.44 (d, J=2.9 Hz, 1H), 8.34 (d, J=8.4 Hz, 1H), 7.71 (d, J=8.4 Hz, 1H), 6.17 (d, J=2.9 Hz, 1H), 4.44 (dd, J=10.7, 2.9 Hz, 1H), 0.13-0.03 (m, 6H), 4.32-4.25 (m, 1H), 3.89 (s, 1H), 1.56 (s, 9H), 0.98 (d, J=35.8 Hz, 4H), 0.86 (s, 9H)

Step I: 6-[3-[2-[tert-Butyl(dimethyl)silyl]oxy-2-[1-(trifluoromethyl)cyclopropyl]ethoxy]pyrazol-1-yl]-2-chloro-pyridine-3-carboxylic acid

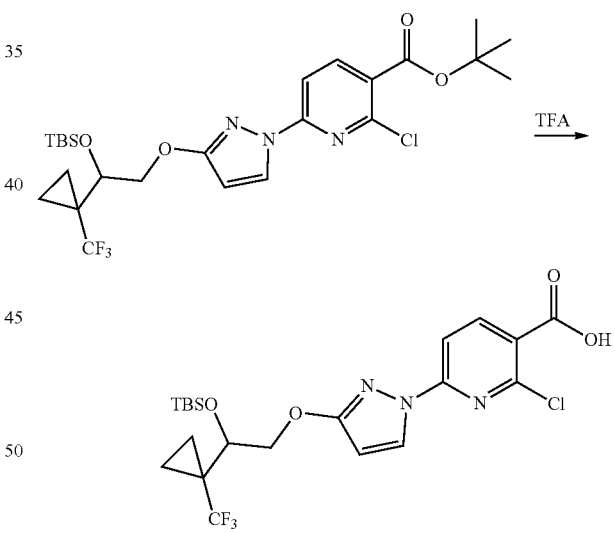

tert-Butyl 6-[3-[2-[tert-butyl(dimethyl)silyl]oxy-2-[1-(trifluoromethyl)cyclopropyl]ethoxy]pyrazol-1-yl]-2-chloro-pyridine-3-carboxylate (20 mg, 0.03558 mmol) and TFA (50 µL, 0.6490 mmol) were combined in dichloromethane (0.75 mL) and heated at 45° C. for 3 h. The reaction was evaporated. Hexanes were added and the mixture evaporated again to give a white solid 6-[3-[2-[tert-butyl(dimethyl)silyl]oxy-2-[1-(trifluoromethyl)cyclopropyl]ethoxy]pyrazol-1-yl]-2-chloro-pyridine-3-carboxylic acid (18 mg, 100%) ESI-MS m/z calc. 505.14114, found 506.3 (M+1)$^+$; Retention time: 0.59 minutes.

Step J: N-(Benzenesulfonyl)-6-[3-[2-[tert-butyl(dimethyl)silyl]oxy-2-[1-(trifluoromethyl)cyclopropyl]ethoxy]pyrazol-1-yl]-2-chloro-pyridine-3-carboxamide

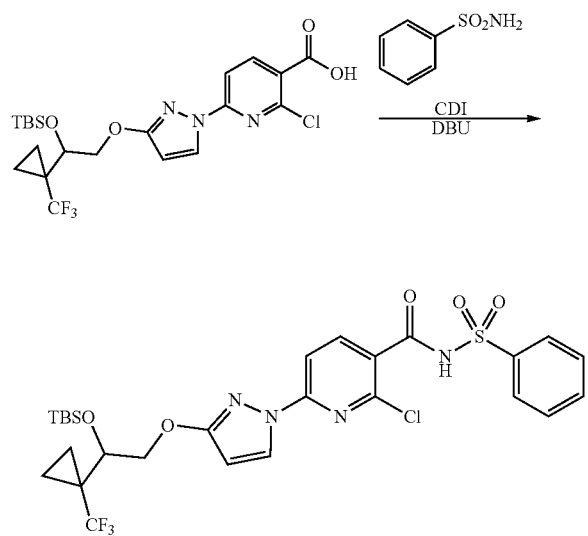

6-[3-[2-[tert-Butyl(dimethyl)silyl]oxy-2-[1-(trifluoromethyl)cyclopropyl]ethoxy]pyrazol-1-yl]-2-chloro-pyridine-3-carboxylic acid (19 mg, 0.03755 mmol) and CDI (8 mg, 0.04934 mmol) were combined in THF (200 μL) and stirred at room temperature for 2 hours. benzenesulfonamide (7 mg, 0.04453 mmol) was added followed by DBU (10 μL, 0.06687 mmol) and the reaction was stirred for an additional 2 h at room temperature. The reaction mixture was then diluted with 10 mL 1 M citric acid, and extracted 3×10 mL ethyl acetate. The combined organics were washed with water, brine, dried over sodium sulfate, and concentrated to give a white solid, which was used in the next step without further purification N-(benzenesulfonyl)-6-[3-[2-[tert-butyl(dimethyl)silyl]oxy-2-[1-(trifluoromethyl)cyclopropyl]ethoxy]pyrazol-1-yl]-2-chloro-pyridine-3-carboxamide (approximately 22 mg) ESI-MS m/z calc. 644.1503, found 645.3 (M+1)$^+$; Retention time: 0.8 minutes.

Step O: N-(Benzenesulfonyl)-6-[3-[2-[tert-butyl(dimethyl)silyl]oxy-2-[1-(trifluoromethyl)cyclopropyl]ethoxy]pyrazol-1-yl]-2-[(4S)-2,2,4-trimethylpyrrolidin-1-yl]pyridine-3-carboxamide

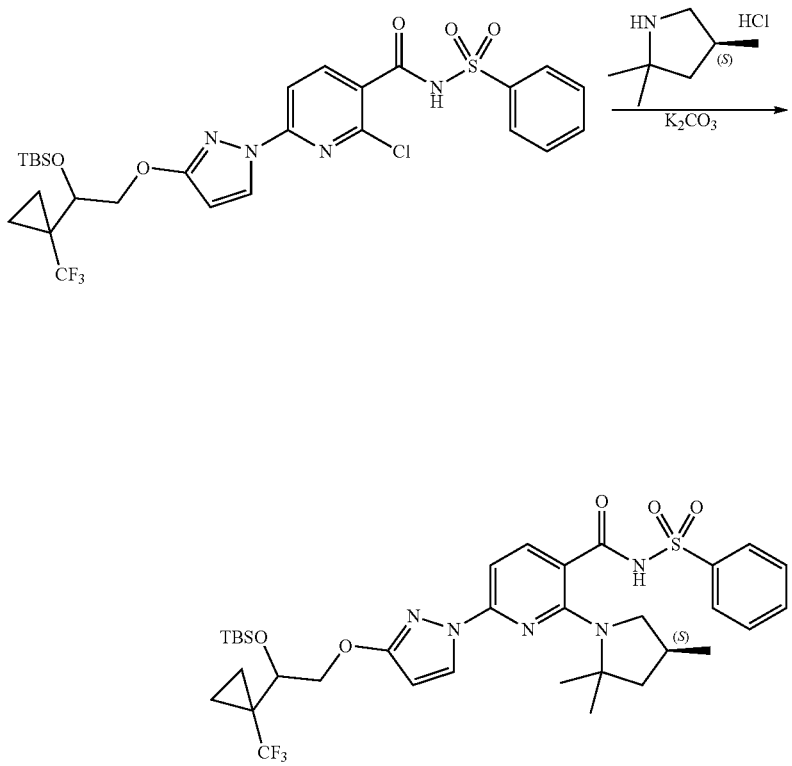

N-(Benzenesulfonyl)-6-[3-[2-[tert-butyl(dimethyl)silyl]oxy-2-[1-(trifluoromethyl)cyclopropyl]ethoxy]pyrazol-1-yl]-2-chloro-pyridine-3-carboxamide (22 mg, 0.03410 mmol), (4S)-2,2,4-trimethylpyrrolidine (Hydrochloride salt) (approximately 40.83 mg, 0.2728 mmol), and potassium carbonate (approximately 75.40 mg, 0.5456 mmol) were combined in DMSO (180 μL) and heated at 130° C. for 24 hours. The reaction was cooled to room temperature and diluted with 15 mL 1M citric acid and 20 mL ethyl acetate. The aqueous and the organic layers were separated, and the aqueous layer was extracted two additional times with 15 mL ethyl acetate. The organics were combined, washed with brine, dried over sodium sulfate and concentrated. The resulting solid was purified by silica gel chromatography eluting with 0-10% methanol in dichloromethane to give the TBS protected material as a white solid, N-(benzenesulfonyl)-6-[3-[2-[tert-butyl(dimethyl)silyl]oxy-2-[1-(trifluoromethyl)cyclopropyl]ethoxy]pyrazol-1-yl]-2-[(4S)-2,2,4-trimethylpyrrolidin-1-yl]pyridine-3-carboxamide (8 mg, 32%) ESI-MS m/z calc. 721.2941, found 722.4 (M+1)+; Retention time: 0.88 minutes Step P: N-(Benzenesulfonyl)-6-[3-[2-hydroxy-2-[1-(trifluoromethyl)cyclopropyl]ethoxy]pyrazol-1-yl]-2-[(4S)-2,2,4-trimethylpyrrolidin-1-yl]pyridine-3-carboxamide

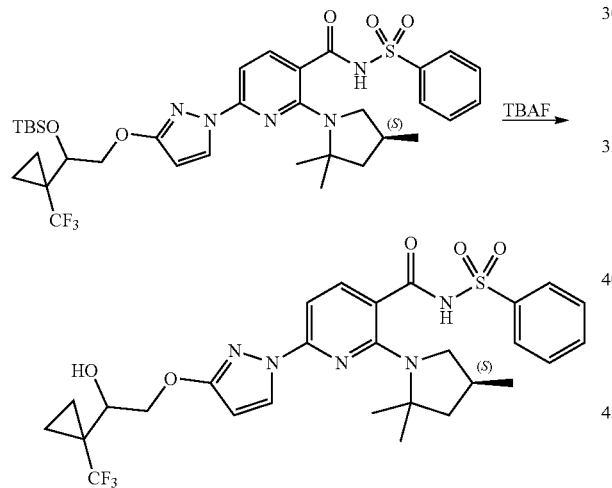

N-(Benzenesulfonyl)-6-[3-[2-[tert-butyl(dimethyl)silyl]oxy-2-[1-(trifluoromethyl)cyclopropyl]ethoxy]pyrazol-1-yl]-2-[(4S)-2,2,4-trimethylpyrrolidin-1-yl]pyridine-3-carboxamide (8 mg, 0.0341 mmol) was then dissolved in THF (0.4 mL), cooled to 0° C., and tetrabutylammonium fluoride (1M in THF, approximately 0.17 mL, 0.1705 mmol) was added by syringe. After 5 minutes the reaction was allowed to warm to room temperature. After 20 minutes at room temperature the reaction mixture was poured into 10 mL 1M citric acid, and extracted 3×10 mL ethyl acetate. The combined organics were washed with brine, dried over sodium sulfate, and concentrated. The resulting crude material was then purified twice by silica gel chromatography eluting with a 0-10% methanol in dichloromethane to give N-(Benzenesulfonyl)-6-[3-[2-hydroxy-2-[1-(trifluoromethyl)cyclopropyl]ethoxy]pyrazol-1-yl]-2-[(4S)-2,2,4-trimethylpyrrolidin-1-yl]pyridine-3-carboxamide (3 mg, 14%) ESI-MS m/z calc. 607.20764, found 608.3 (M+1)+; Retention time: 1.99 minutes. ¹H NMR (400 MHz, DMSO) δ 12.51 (s, 1H), 8.19 (d, J=2.8 Hz, 1H), 7.97 (d, J=7.5 Hz, 2H), 7.79 (d, J=8.2 Hz, 1H), 7.70 (d, J=9.6 Hz, 1H), 7.64 (d, J=7.9 Hz, 2H), 6.89 (d, J=8.2 Hz, 1H), 6.11 (d, J=2.8 Hz, 1H), 5.57 (dd, J=5.5, 2.6 Hz, 1H), 4.40-4.32 (m, 1H), 2.46-2.39 (m, 1H), 4.20-4.12 (m, 1H), 3.89 (s, 1H), 2.28 (s, 1H), 2.09 (s, 1H), 1.82 (dd, J=12.1, 5.5 Hz, 1H), 1.52 (d, J=9.7 Hz, 6H), 1.43-1.36 (m, 1H), 1.03-0.89 (m, 4H), 0.65 (d, J=6.2 Hz, 3H).

SYNTHETIC EXAMPLE 39

Synthesis of Compound 39: N-(benzenesulfonyl)-6-[3-[(1R,2S,4S)-norbornan-2-yl]oxypyrazol-1-yl]-2-[(4S)-2,2,4-trimethylpyrrolidin-1-yl]pyridine-3-carboxamide Step A: tert-Butyl 3-(((1R,2S,4S)-bicyclo[2.2.1]heptan-2-yl)oxy)-1H-pyrazole-1-carboxylate

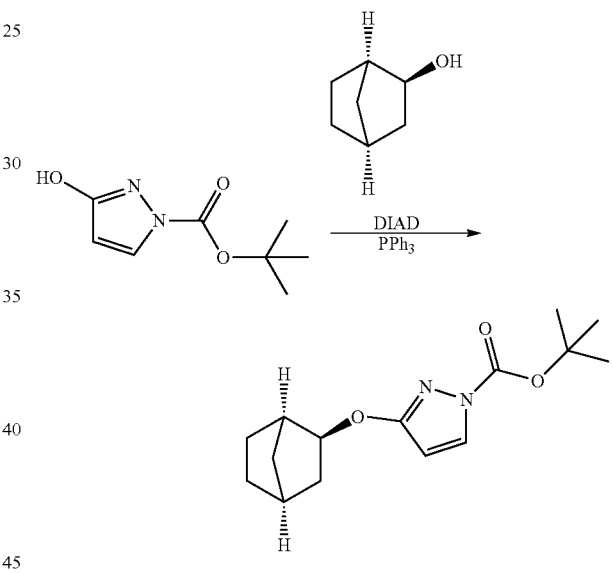

tert-Butyl 3-hydroxypyrazole-1-carboxylate (1.632 g, 8.860 mmol), (+)-endo-2-norborneol (1 g, 8.915 mmol), and triphenyl phosphine (2.57 g, 9.798 mmol) were combined in THF (21.98 mL) and the reaction was cooled in an ice bath. To the mixture was added DIAD (2 mL, 10.16 mmol) dropwise and the reaction was allowed to warm to room temperature and stir for 16 h. The mixture was evaporated and the resulting material was partitioned between ethyl acetate (30 mL) and 1N sodium hydroxide (30 mL). The organics were separated, washed with brine (30 mL), dried over sodium sulfate and evaporated. The crude material was purified by silica gel chromatography eluting with 0-30% ethyl acetate in hexanes to give tert-butyl 3-(((1R,2S,4S)-bicyclo[2.2.1]heptan-2-yl)oxy)-1H-pyrazole-1-carboxylate (2.08 g, 84%) ESI-MS m/z calc. 278.16306, found 279.3 (M+1)+; Retention time: 0.72 minutes. ¹H NMR (400 MHz, DMSO) δ 8.05 (d, J=3.0 Hz, 1H), 6.07 (d, J=3.0 Hz, 1H), 4.47 (d, J=6.8 Hz, 1H), 2.43-2.36 (m, 1H), 2.32-2.22 (m, 1H), 1.75 (td, J=6.7, 2.4 Hz, 1H), 1.54 (s, 9H), 1.53-1.49 (m, 2H), 1.42 (ddt, J=14.8, 7.8, 4.4 Hz, 2H), 1.18-1.07 (m, 3H).

Step B: 3-[(1R,2S,4S)-norbornan-2-yl]oxy-1H-pyrazole

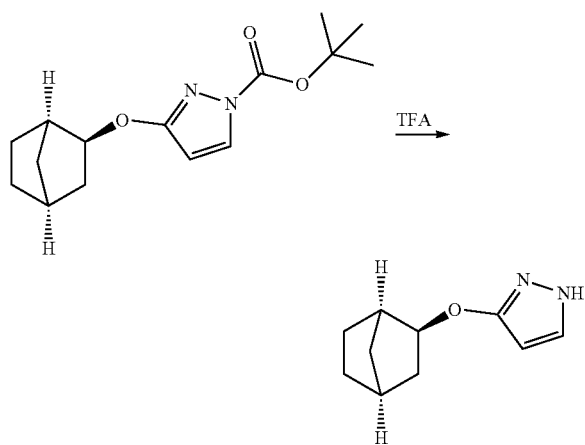

tert-Butyl 3-[(1R,2S,4S)-norbornan-2-yl]oxypyrazole-1-carboxylate (2.08 g, 7.473 mmol) was dissolved in CH₂Cl₂ (20.80 mL) with trifluoroacetic acid (5.8 mL, 75.28 mmol) and the reaction was stirred at room temperature for 1 h. The reaction was evaporated under reduced pressure and the resulting oil was partitioned between ethyl acetate (50 mL) and a saturated sodium bicarbonate solution (30 mL). The organics were separated, washed with brine, dried over sodium sulfate and concentrated under vacuum to give an oil, 3-[(1R,2S,4S)-norbornan-2-yl]oxy-1H-pyrazole (1.29 g, 97%) ESI-MS m/z calc. 178.11061, found 179.2 (M+1)⁺; Retention time: 0.45 minutes.

Step C: tert-Butyl 2-chloro-6-[3-[(1R,2S,4S)-norbornan-2-yl]oxypyrazol-1-yl]pyridine-3-carboxylate

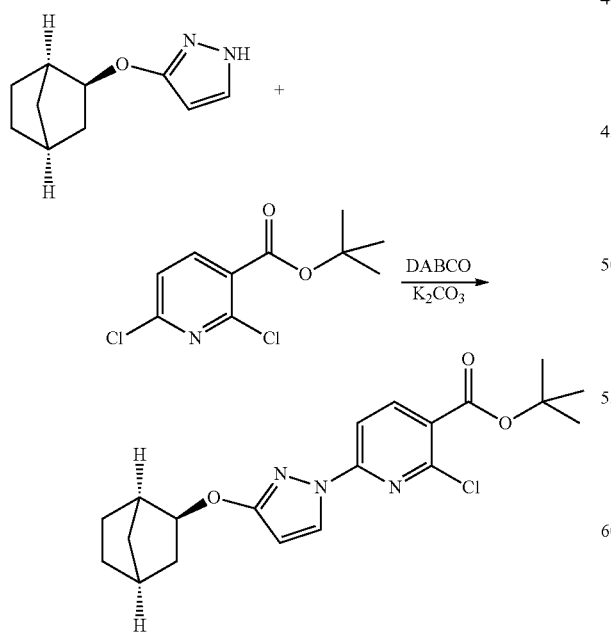

A 100 mL round bottom flask was charged under nitrogen with tert-butyl 2,6-dichloropyridine-3-carboxylate (1.796 g, 7.239 mmol), 3-[(1R,2S,4S)-norbornan-2-yl]oxy-1H-pyrazole (1.29 g, 7.238 mmol), and K₂CO₃ (1.310 g, 9.479 mmol) (freshly ground in a mortar) and anhydrous DMF (12 mL). DABCO (146 mg, 1.302 mmol) was added and the mixture was stirred at room temperature under nitrogen for 8 hours. The reaction mixture was diluted with ethyl acetate (50 mL), water and brine (50 mL) and the two phases were separated. The aqueous phase was further extracted with ethyl acetate (2×50 mL). The combined extracts were dried over sodium sulfate and the solvent removed under reduced pressure. The material was subjected to flash chromatography on silica gel using a gradient of ethyl acetate (0 to 20%) in hexanes. The pure fractions were combined and the solvents removed under reduced pressure to provide tert-butyl 2-chloro-6-[3-[(1R,2S,4S)-norbornan-2-yl]oxypyrazol-1-yl]pyridine-3-carboxylate (1.814 g, 64%) ESI-MS m/z calc. 389.1506, found 390.3 (M+1)⁺; Retention time: 0.92 minutes ¹H NMR (400 MHz, DMSO) δ 8.40 (d, J=2.9 Hz, 1H), 8.32 (d, J=8.4 Hz, 1H), 7.72 (d, J=8.4 Hz, 1H), 6.18 (d, J=2.9 Hz, 1H), 4.53 (d, J=6.6 Hz, 1H), 1.88-1.78 (m, 1H), 2.45 (d, J=4.6 Hz, 1H), 2.29 (t, J=4.3 Hz, 1H), 1.56 (s, 9H), 1.55-1.39 (m, 4H), 1.22-1.08 (m, 3H).

Step D: 2-Chloro-6-[3-[(1R,2S,4S)-norbornan-2-yl]oxypyrazol-1-yl]pyridine-3-carboxylic acid

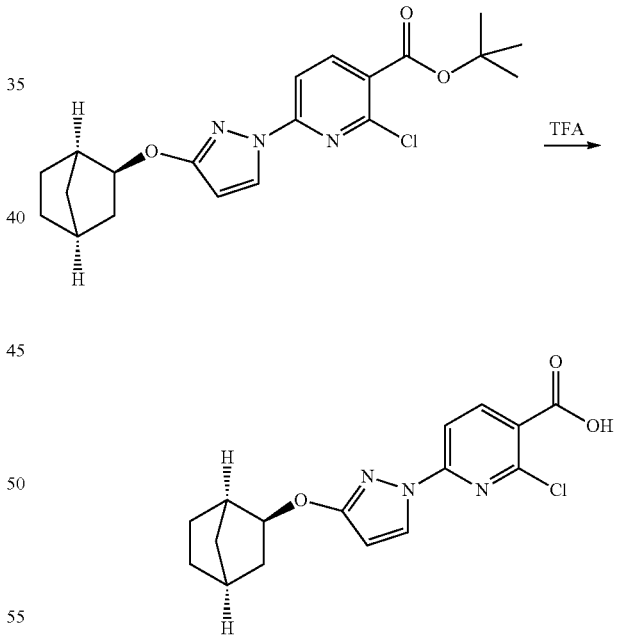

tert-Butyl 2-chloro-6-[3-[(1R,2S,4S)-norbornan-2-yl]oxypyrazol-1-yl]pyridine-3-carboxylate (1.814 g, 4.653 mmol) and TFA (5 mL, 64.90 mmol) were combined in dichloromethane (18.14 mL) and heated at 40° C. for 2 h. The reaction was evaporated. Hexanes were added and the mixture evaporated again to give a white solid, which was used in the next step without further purification. 2-chloro-6-[3-[(1R,2S,4S)-norbornan-2-yl]oxypyrazol-1-yl]pyridine-3-carboxylic acid (1.47 g, 790%) ESI-MS m/z calc. 333.088, found 334.2 (M+1)⁺; Retention time: 0.71 minutes.

Step E: N-(Benzenesulfonyl)-2-chloro-6-[3-[(1R,2S,4S)-norbornan-2-yl]oxypyrazol-1-yl]pyridine-3-carboxamide

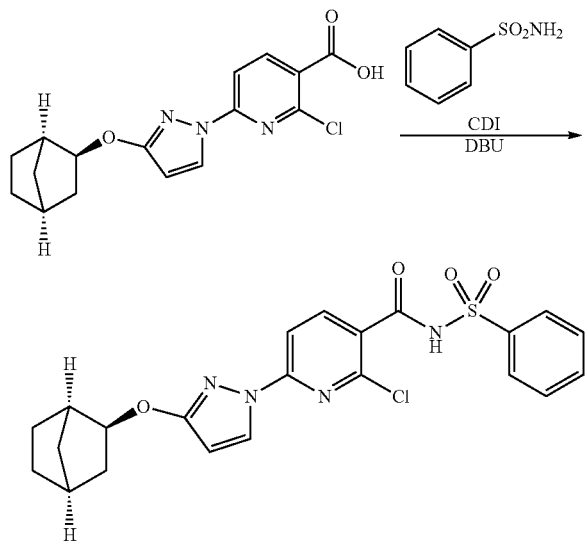

2-Chloro-6-[3-[(R,2S,4S)-norbornan-2-yl]oxypyrazol-1-yl]pyridine-3-carboxylic acid (100 mg)) and CDI (52 mg, 0.323 mmol) were combined in THF and stirred for 2 hours at room temperature. Benzene sulfonamide (52 mg, 0.331 mmol) and DBU (0.048 mL, 0.323 mmol) were then added and the reaction was stirred an additional 2 hours at room temperature. The reaction mixture was then poured into 20 mL 1 M citric acid and extracted 3×20 mL ethyl acetate. The combined organics were washed with water, then brine, dried over sodium sulfate, and concentrated to give approximately 122 mg N-(benzenesulfonyl)-2-chloro-6-[3-[(1R,2S,4S)-norbornan-2-yl]oxypyrazol-1-yl]pyridine-3-carboxamide which was used in the next step without further purification. ESI-MS m/z calc. 490.12, found 491.3 (M+1)$^+$; Retention time: 0.75 minutes.

Step F: N-(Benzenesulfonyl)-6-[3-[(1R,2S,4S)-norbornan-2-yl]oxypyrazol-1-yl]-2-[(4S)-2,2,4-trimethylpyrrolidin-1-yl]pyridine-3-carboxamide

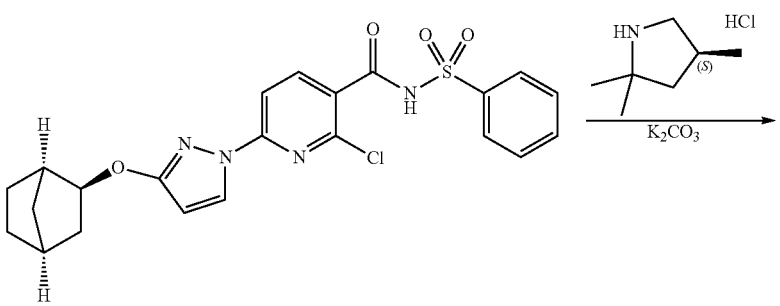

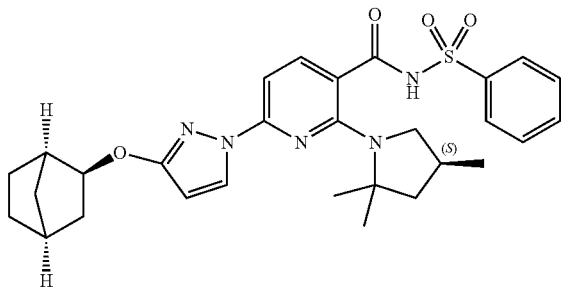

N-(benzenesulfonyl)-2-chloro-6-[3-[(R,2S,4S)-norbornan-2-yl]oxypyrazol-1-yl]pyridine-3-carboxamide (120 mg, 0.2537 mmol), (4S)-2,2,4-trimethylpyrrolidine (hydrochloride salt) (113.9 mg, 0.7611 mmol), and potassium carbonate (210.3 mg, 1.522 mmol) were combined in 0.423 mL DMSO in a screwcap vial and heated to 130° C. for 16 hours. The reaction mixture was then cooled to room temperature, and 3 mL of water was added, resulting in the formation of a precipitate. After 30 minutes, the liquid portion was removed by syringe and discarded, and the remaining solids were dissolved in 15 mL ethyl acetate. The organics were washed with 15 mL 1M citric acid, and the aqueous layer was extracted an additional time with 15 mL ethyl acetate. The combined organics were washed with brine, dried over sodium sulfate and concentrated. The crude material was purified by column chromatography on silica gel using a gradient of 0-10% methanol in dichloromethane. The pure fractions were combined and concentrated to give N-(benzenesulfonyl)-6-[3-[(1R,2S,4S)-norbornan-2-yl]oxypyrazol-1-yl]-2-[(4S)-2,2,4-trimethylpyrrolidin-1-yl]pyridine-3-carboxamide (59 mg, 40%). ESI-MS m/z calc. 549.24, found 550.4 (M+1)$^+$; Retention time: 2.37 minutes $^1$H NMR (400 MHz, DMSO) δ 12.50 (s, 1H), 8.17 (d, J=2.8 Hz, 1H), 8.02-7.97 (m, 2H), 7.80 (d, J=8.2 Hz, 1H), 7.77-7.70 (m, 1H), 7.70-7.63 (m, 2H), 6.90 (d, J=8.2 Hz, 1H), 6.08 (d, J=2.7 Hz, 1H), 4.49 (d, J=6.7 Hz, 1H), 2.46-2.37 (m, 2H), 2.27 (q, J=10.0, 7.6 Hz, 2H), 2.09 (dq, J=11.6, 5.9, 5.4 Hz, 1H), 1.86-1.77 (m, 1H), 1.56 (d, J=6.9 Hz, 1H), 1.53 (s, 3H), 1.51 (s, 3H), 1.46 (dd, J=13.8, 6.6 Hz, 3H), 1.36 (t, J=12.1 Hz, 1H), 1.25-1.06 (m, 4H), 0.64 (d, J=6.3 Hz, 3H).

SYNTHETIC EXAMPLE 40

Synthesis of Compound 40: N-(Benzenesulfonyl)-6-[3-[[(1R,4R)-norbornan-2-yl]methoxy]pyrazol-1-yl]-2-[(4S)-2,2,4-trimethylpyrrolidin-1-yl]pyridine-3-carboxamide Step A: tert-butyl 3-[[(1S,4R)-norbornan-2-yl]methoxy]pyrazole-1-carboxylate

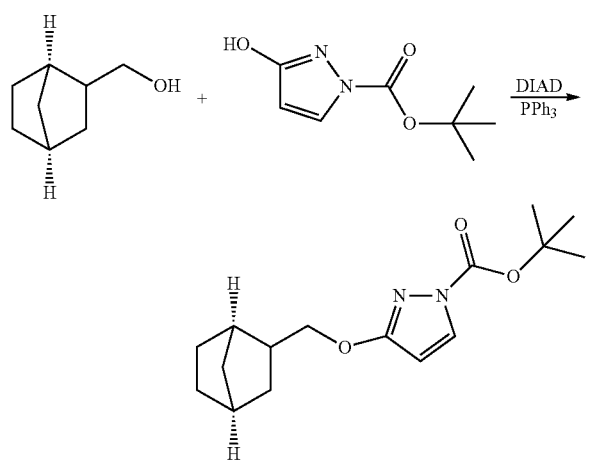

tert-Butyl 3-hydroxypyrazole-1-carboxylate (1.327 g, 7.204 mmol), [(1S,4R)-norbornan-2-yl]methanol (1 g, 7.924 mmol) (mixture of endo and exo), and triphenyl phosphine (2.09 g, 7.968 mmol) were combined in THF (17.87 mL) and the reaction was cooled in an ice bath. To the mixture was added DIAD (1.627 mL, 8.263 mmol) dropwise and the reaction was allowed to warm to room temperature and stirred for 72 h. The mixture was evaporated and the resulting material was partitioned between ethyl acetate (50 mL) and 1N sodium hydroxide (50 mL). The organics were separated, washed with brine, dried over sodium sulfate and evaporated. The crude material was purified by silica gel chromatography eluting with 0-30% ethyl acetate in hexanes to give tert-butyl 3-[[(1S,4R)-norbornan-2-yl]methoxy]pyrazole-1-carboxylate (1.698 g, 81%) ESI-MS m/z calc. 292.17868, found 293.3 (M+1)$^+$; Retention time: 0.77 minutes. (2 diastereomers—mix of endo and exo substituted norbornane) $^1$H NMR (400 MHz, DMSO) δ 8.06 (d, J=2.9 Hz, 1H), 6.10 (dd, J=2.9, 1.0 Hz, 1H), 4.23-3.81 (m, 2H), 2.29-2.15 (m, 2H), 1.69 (dq, J=12.1, 4.2 Hz, 1H), 1.54 (d, J=1.4 Hz, 9H), 1.51-1.03 (m, 7H), 0.75 (dd, J=5.0, 2.4 Hz, 1H).

Step B: 3-[[(1S,4R)-norbornan-2-yl]methoxy]-1H-pyrazole

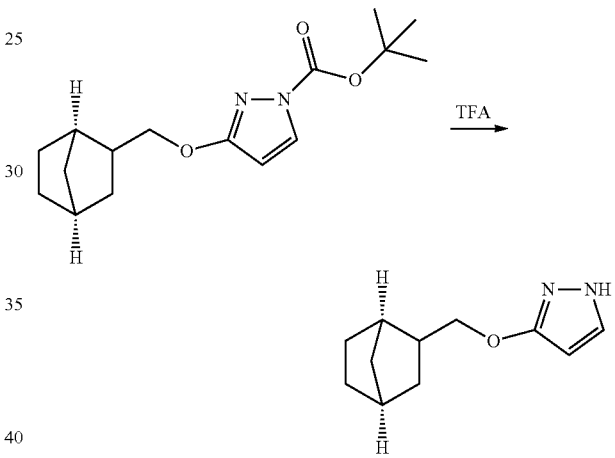

tert-Butyl 3-[[(1S,4R)-norbornan-2-yl]methoxy]pyrazole-1-carboxylate (1.698 g, 5.808 mmol) was dissolved in CH$_2$Cl$_2$ (16.98 mL) with trifluoroacetic acid (approximately 6.622 g, 4.474 mL, 58.08 mmol) and the reaction was stirred at room temperature for 2 h. The reaction was evaporated and the resulting oil was partitioned between ethyl acetate (50 mL) and a saturated sodium bicarbonate solution (30 mL). The organics were separated, washed with brine, dried over sodium sulfate and concentrated under vacuum to give an oil, 3-[[(1S,4R)-norbornan-2-yl]methoxy]-1H-pyrazole (1.11 g, 99%) ESI-MS m/z calc. 192.12627, found 193.2 (M+1)$^+$; Retention time: 0.52 minutes.

Step C: tert-Butyl 2-chloro-6-[3-[[(1S,4R)-norbornan-2-yl]methoxy]pyrazol-1-yl]pyridine-3-carboxylate

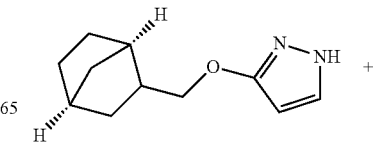

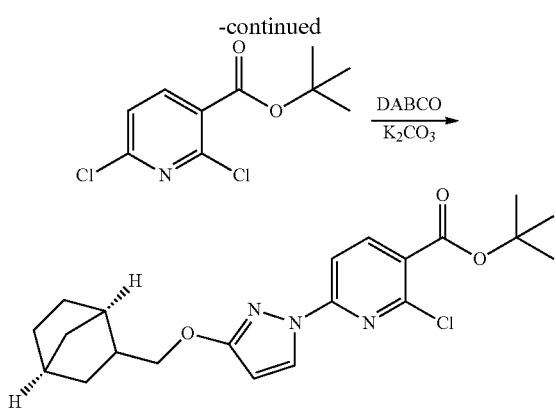

A round bottom flask was charged under nitrogen with 3-[[(1S,4R)-norbornan-2-yl]methoxy]-1H-pyrazole (1.11 g, 5.774 mmol) (mix of two diastereomers), tert-butyl 2,6-dichloropyridine-3-carboxylate (1.433 g, 5.776 mmol), K₂CO₃ (1.05 g, 7.597 mmol) (freshly ground in a mortar) and anhydrous DMF (10 mL). DABCO (117 mg, 1.043 mmol) was added and the mixture was stirred at room temperature under nitrogen for 16 hours. The reaction mixture was diluted with ethyl acetate (50 mL) and water (50 mL) and the two phases were separated. The aqueous phase was further extracted with ethyl acetate (2×30 mL). The combined extracts were washed with brine, dried over sodium sulfate and the solvent removed under reduced pressure. The material was subjected to flash chromatography on silica gel using a gradient of ethyl acetate (0 to 20%) in hexanes. The pure fractions were combined and the solvents removed under reduced pressure to provide tert-butyl 2-chloro-6-[3-[[(1S,4R)-norbornan-2-yl]methoxy]pyrazol-1-yl]pyridine-3-carboxylate (1.88 g, 81%) ESI-MS m/z calc. 403.16626, found 404.3 (M+1)⁺; Retention time: 0.94 minutes Step D: 2-Chloro-6-[3-[[(1S,4R)-norbornan-2-yl]methoxy]pyrazol-1-yl]pyridine-3-carboxylic acid

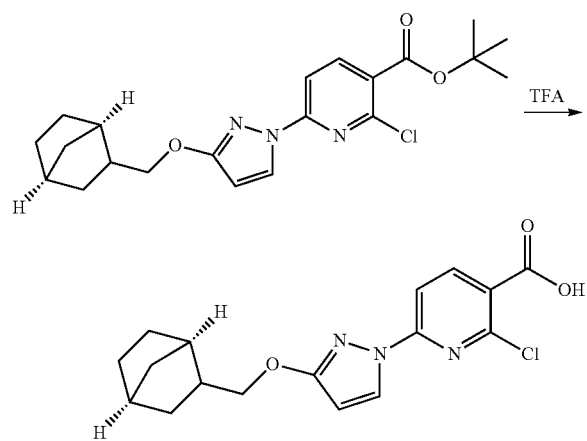

tert-Butyl 2-chloro-6-[3-[[(1S,4R)-norboman-2-yl]methoxy]pyrazol-1-yl]pyridine-3-carboxylate (1.88 g, 4.655 mmol) and TFA (5 mL, 64.90 mmol) were combined in dichloromethane (18.80 mL) and heated at 40° C. for 2 h. The reaction was evaporated. Hexanes were added and the mixture evaporated again to give a white solid 2-chloro-6-[3-[[(1S,4R)-norbornan-2-yl]methoxy]pyrazol-1-yl]pyridine-3-carboxylic acid (1.58 g, 98%) ESI-MS m/z calc. 347.10367, found 348.2 (M+1)⁺; Retention time: 0.75 minutes.

Step E: N-(Benzenesulfonyl)-2-chloro-6-[3-[[(11R,4R)-norbornan-2-yl]methoxy]pyrazol-1-yl]pyridine-3-carboxamide 2-Chloro-6-[3-[[(1S,4R)-norbornan-2-yl]methoxy]pyrazol-1-yl]pyridine-3-carboxylic acid (100 mg, 0.2875 mmol) and CDI (60.59 mg, 0.3737 mmol) were stirred in THF (0.5 mL) at room temperature for 2 hours. Benzenesulfonamide (50 mg, 0.3181 mmol) was then added, followed by DBU (0.05588 mL, 0.3737) and the reaction was stirred an additional 4 hours at room temperature. The reaction mixture was then diluted with 25 mL ethyl acetate and poured 25 mL citric acid. The aqueous layer was extracted with an additional 25 mL ethyl acetate, and the combined organics were washed with water then brine, dried over sodium sulfate, and concentrated to give N-(benzenesulfonyl)-2-chloro-6-[3-[[(1R,4R)-norbornan-2-yl]methoxy]pyrazol-1-yl]pyridine-3-carboxamide (approximately 135 mg), which was used in the next step without further purification. ESI-MS m/z calc. 486.11, found 487.2 (M+1)⁺; Retention time: 0.84 minutes.

Step F: N-(benzenesulfonyl)-6-[3-[[(1R,4R)-norbornan-2-yl]methoxy]pyrazol-1-yl]-2-[(4S)-2,2,4-trimethylpyrrolidin-1-yl]pyridine-3-carboxamide

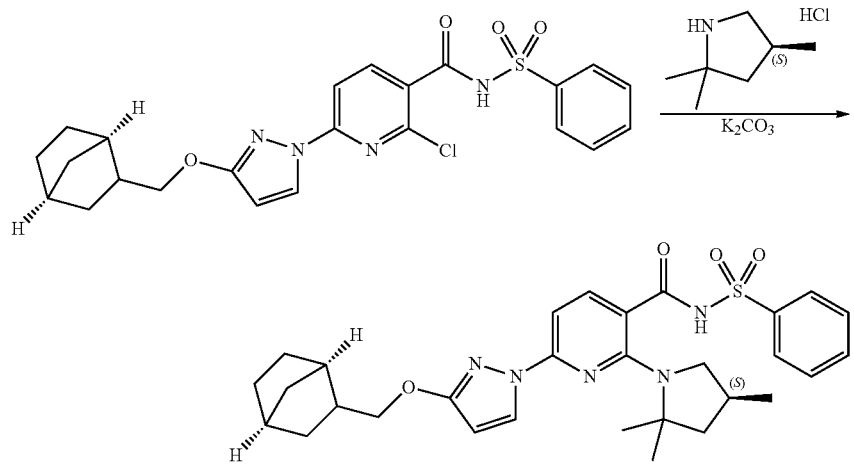

N-(Benzenesulfonyl)-2-chloro-6-[3-[[(1R,4R)-norbornan-2-yl]methoxy]pyrazol-1-yl]pyridine-3-carboxamide, (135 mg, 0.2772 mmol), (4S)-2,2,4-trimethylpyrrolidine (Hydrochloride salt) (124.5 mg, 0.8316 mmol), and potassium carbonate (229.8 mg, 1.663 mmol) were combined in DMSO in a screwcap vial and heated to 130° C. for 16 hours. The reaction mixture was then cooled to room temperature, and 3 mL of water was added, resulting in the formation of a precipitate. After 30 minutes, the liquid portion was removed by syringe and discarded, and the remaining solids were dissolved in 15 mL ethyl acetate. The organics were washed with 15 mL 1M citric acid, and the aqueous layer was extracted an additional time with 15 mL ethyl acetate. The combined organics were washed with brine, dried over sodium sulfate and concentrated. The crude material was purified by column chromatography on silica gel using a gradient of 0-10% methanol in dichloromethane. The pure fractions were combined and concentrated to give N-(benzenesulfonyl)-6-[3-[[(1R,4R)-norboman-2-yl] methoxy]pyrazol-1-yl]-2-[(4S)-2,2,4-trimethylpyrrolidin-1-yl]pyridine-3-carboxamide, (mixture of endo and exo norbornane) ESI-MS m/z calc. 563.26, found 564.4 (M+1)$^+$;

Retention time: 2.45 minutes. $^1$H NMR (400 MHz, DMSO) δ 12.50 (s, 1H), 8.18 (dd, J=2.8, 1.0 Hz, 1H), 7.99 (dd, J=7.2, 1.7 Hz, 2H), 7.80 (dd, J=8.3, 1.1 Hz, 1H), 7.79-7.70 (m, 1H), 7.66 (dd, J=8.3, 6.7 Hz, 2H), 6.92 (dd, J=8.3, 5.8 Hz, 1H), 6.12 (t, J=2.9 Hz, 1H), 4.23-3.90 (m, 2H), 2.40 (t, J=10.5 Hz, 1H), 2.35-2.16 (m, 4H), 2.09 (tt, J=12.3, 6.2 Hz, 1H), 1.82 (dd, J=11.9, 5.5 Hz, 1H), 1.73 (s, 1H), 1.52 (d, J=9.7 Hz, 7H), 1.50-1.45 (m, 1H), 1.42-1.27 (m, 4H), 1.21-1.08 (m, 2H), 0.75 (ddd, J=12.5, 5.0, 2.2 Hz, 1H), 0.64 (d, J=6.2 Hz, 3H).

SYNTHETIC EXAMPLE 41

Synthesis of Compound 41: N-(Benzenesulfonyl)-6-[3-(2, 2-dicyclopropylethoxy) pyrazol-1-yl]-2-[(4S)-2, 2, 4-trimethylpyrrolidin-1-yl]pyridine-3-carboxamide

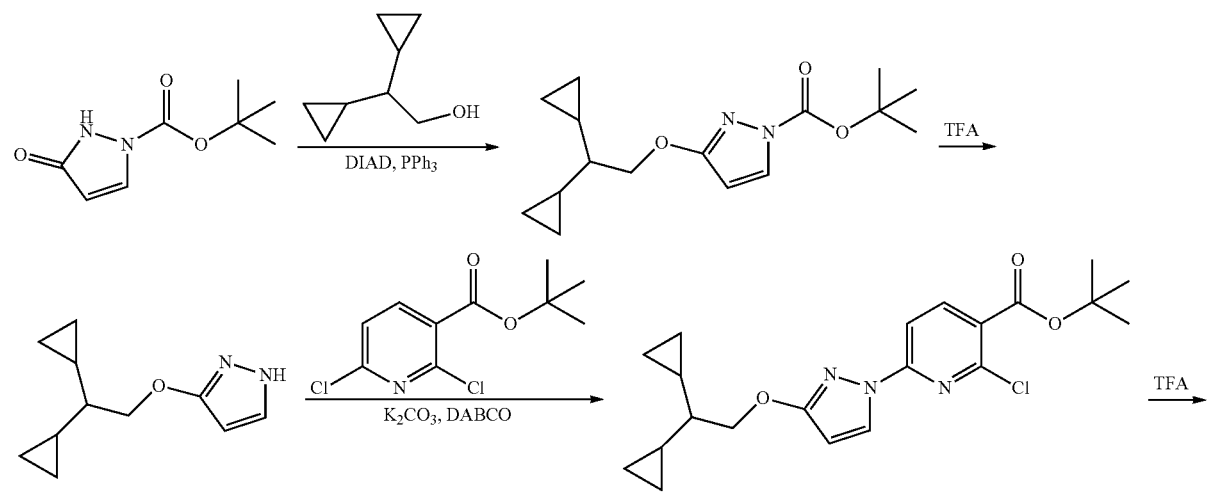

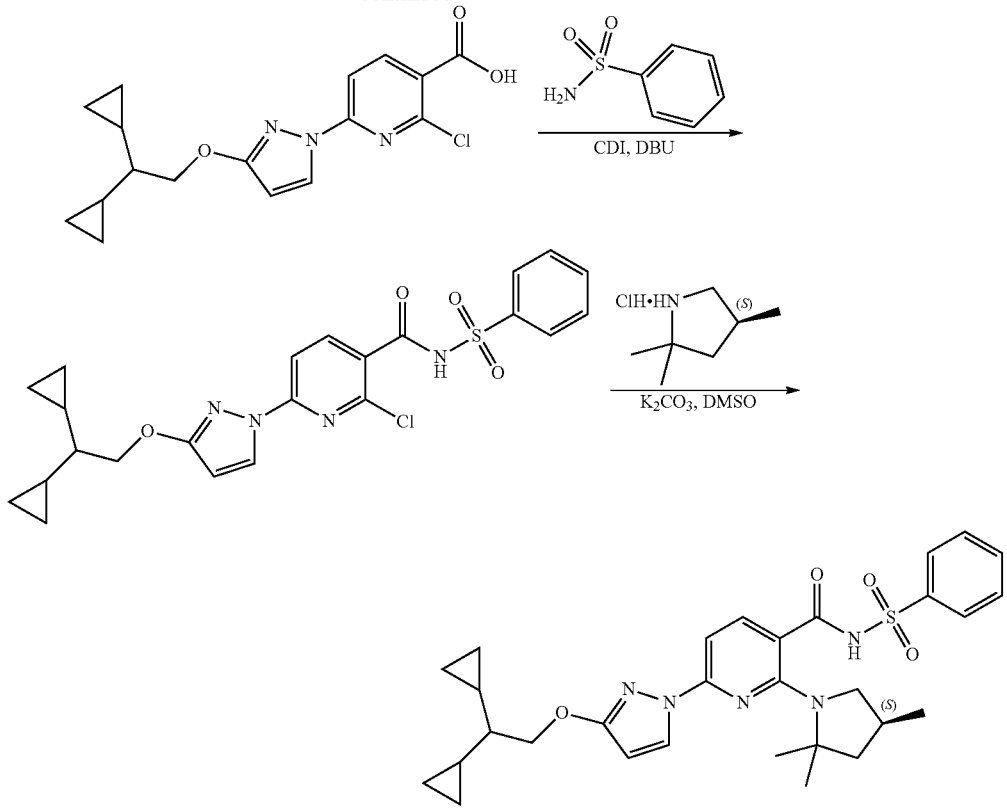

Step A: tert-Butyl 3-(2, 2-dicyclopropylethoxy) pyrazole-1-carboxylate

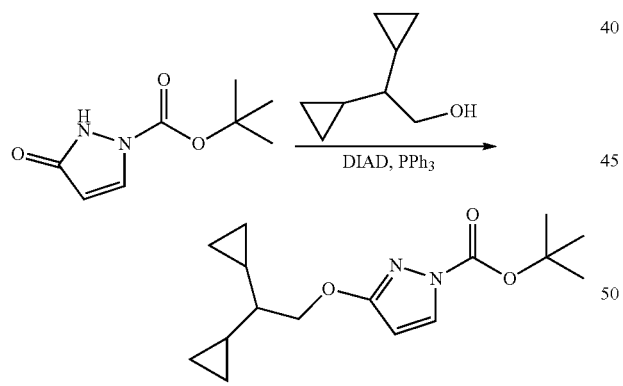

A solution of 2,2-dicyclopropylethanol (500 mg, 3.962 mmol), tert-butyl 3-hydroxypyrazole-1-carboxylate (730 mg, 3.963 mmol), and triphenylphosphane (1.1 g, 4.194 mmol) in dry THF (20.0 mL) was cooled in an ice bath, and DIAD (800.0 μL, 4.063 mmol) was slowly added under $N_2$ atmosphere. The reaction was allowed to slowly warm to room temperature and was stirred for 16 h. The reaction mixture was diluted with ethyl acetate, washed with saturated aqueous sodium bicarbonate, brine, dried over sodium sulfate, and concentrated. The residue was purified by silica gel chromatography with 100% hexanes to 50% ethyl acetate in hexanes to afford tert-butyl 3-(2, 2-dicyclopropylethoxy)pyrazole-1-carboxylate (783 mg, 68%) as colorless oil. ESI-MS m/z calc. 292.17868, found 293.3 (M+1)+; Retention time: 1.98 minutes. $^1$H NMR (400 MHz, Chloroform-d) δ 7.62 (d, J=3.0 Hz, 1H), 5.67 (s, 1H), 4.13 (d, J=5.3 Hz, 2H), 1.44 (s, 9H), 0.58 (qt, J=8.2, 5.0 Hz, 2H), 0.36 (tt, J=8.9, 5.6 Hz, 1H), 0.32-0.12 (m, 4H) 0.10-0.08 (m, 4H).

Step B: 3-(2, 2-Dicyclopropylethoxy)-1H-pyrazole

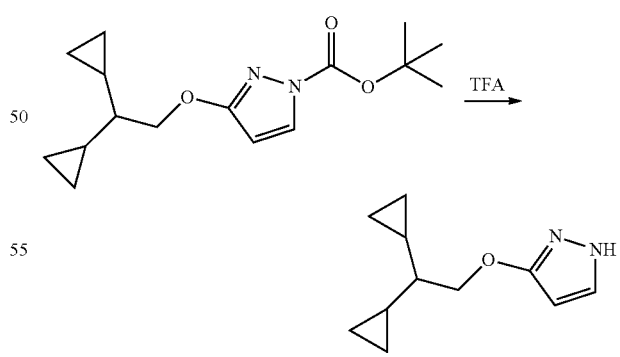

A solution of tert-butyl 3-(2, 2-dicyclopropylethoxy) pyrazole-1-carboxylate (750 mg, 2.565 mmol) and trifluoroacetic acid (1.0 mL, 12.98 mmol) in dichloromethane (4 mL) was stirred for 2.5 hours. The volatiles were removed under reduced pressure and the residue was basified with saturated aqueous sodium bicarbonate and extracted with ethyl acetate. The combined extracts were dried over sodium sulfate and evaporated to give 3-(2,2-dicyclopropylethoxy)-1H-pyrazole as colorless oil which was used as it is without further purification for next reaction. ESI-MS m/z calc. 192.12627, found 193.3 (M+1)⁺; Retention time: 1.32 minutes.

Step C: tert-Butyl 2-chloro-6-[3-(2, 2-dicyclopropylethoxy) pyrazol-1-yl]pyridine-3-carboxylate

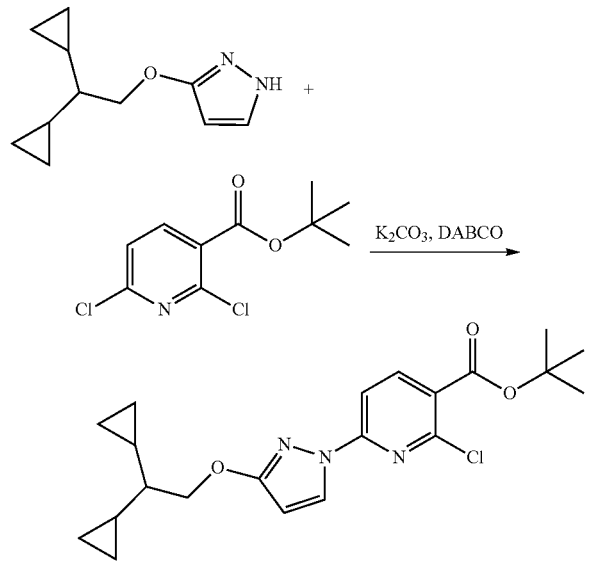

A mixture of 3-(2,2-dicyclopropylethoxy)-1H-pyrazole (493.0 mg, 2.564 mmol), tert-butyl 2,6-dichloropyridine-3-carboxylate (682.0 mg, 2.749 mmol), potassium carbonate (430.0 mg, 3.111 mmol), and 1,4-diazabicyclo[2.2.2]octane (60 mg, 0.5349 mmol) in DMSO (20.0 mL) was stirred at room temperature for 15 hours. The reaction was diluted with water and extracted with ethyl acetate. The combined extracts were washed with brine and dried over sodium sulfate and evaporated. The residue was purified by silica gel column chromatography with 100% hexanes to 20% ethyl acetate in hexanes to afford tert-butyl 2-chloro-6-[3-(2,2-dicyclopropylethoxy)pyrazol-1-yl]pyridine-3-carboxylate (680 mg, 66%) as colorless oil. ESI-MS m/z calc. 403.16626, found 404.4 (M+1)⁺; Retention time: 2.49 minutes. ¹H NMR (400 MHz, Chloroform-d) δ 8.35 (d, J=2.8 Hz, 1H), 8.18 (d, J=8.4 Hz, 1H), 7.70 (d, J=8.5 Hz, 1H), 5.98 (d, J=2.9 Hz, 1H), 4.32 (d, J=5.6 Hz, 2H), 1.61 (s, 9H), 0.92-0.75 (m, 2H), 0.70-0.56 (m, 1H), 0.54-0.36 (m, 4H), 0.32-0.13 (m, 4H).

Step D: 2-Chloro-6-[3-(2, 2-dicyclopropylethoxy) pyrazol-1-yl]pyridine-3-carboxylic acid

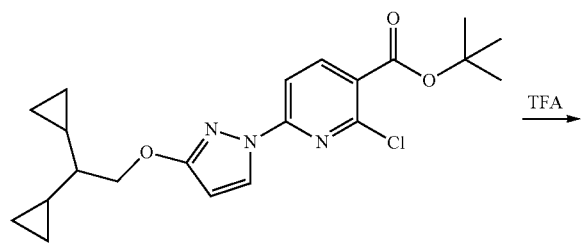

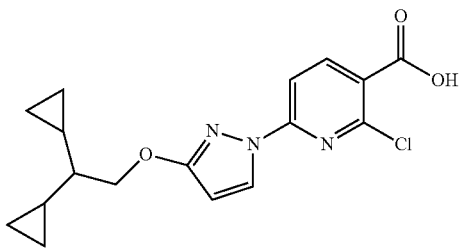

A solution of tert-butyl 2-chloro-6-[3-(2,2-dicyclopropylethoxy)pyrazol-1-yl]pyridine-3-carboxylate (675 mg, 1.671 mmol) in trifluoroacetic acid (1.5 mL, 19.47 mmol) and dichloromethane (4.5 mL) was stirred for 4 hours at room temperature. The solvent was evaporated, and twice the residue was taken up in THF and concentrated under vacuum to afford 2-chloro-6-[3-(2, 2-dicyclopropylethoxy) pyrazol-1-yl]pyridine-3-carboxylic acid (580 mg, 100%). ESI-MS m/z calc. 347.10367, found 348.3 (M+1)⁺; Retention time: 1.95 minutes.

Step E: N-(Benzenesulfonyl)-2-chloro-6-[3-(2, 2-dicyclopropylethoxy) pyrazol-1-yl]pyridine-3-carboxamide

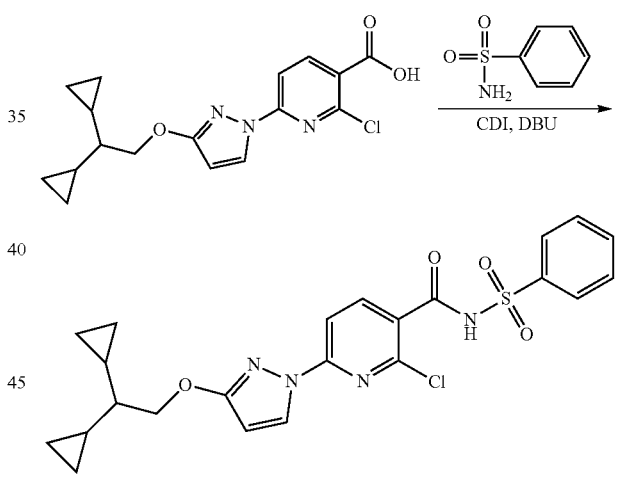

A solution of 2-chloro-6-[3-(2, 2-dicyclopropylethoxy) pyrazol-1-yl]pyridine-3-carboxylic acid (100 mg, 0.2875 mmol) and carbonyl diimidazole (60.0 mg, 0.3700 mmol) in THF (2.0 mL) was stirred for 45 minutes. Then, benzenesulfonamide (50 mg, 0.3181 mmol) and DBU (60 µL, 0.4012 mmol) were added and the reaction mixture was stirred for additional 2 hours at room temperature. The reaction mixture was quenched with saturated ammonium chloride solution and extracted with ethyl acetate. The combined organic extracts were washed with brine, dried over sodium sulfate and evaporated to afford N-(benzenesulfonyl)-2-chloro-6-[3-(2,2-dicyclopropylethoxy)pyrazol-1-yl]pyridine-3-carboxamide which was used as it is for next reaction. ESI-MS m/z calc. 486.11285, found 487.4 (M+1)⁺; Retention time: 0.79 minutes.

Step F: N-(Benzenesulfonyl)-6-[3-(2, 2-dicyclopropylethoxy) pyrazol-1-yl]-2-[(4S)-2, 2, 4-trimethyl-pyrrolidin-1-yl]pyridine-3-carboxamide

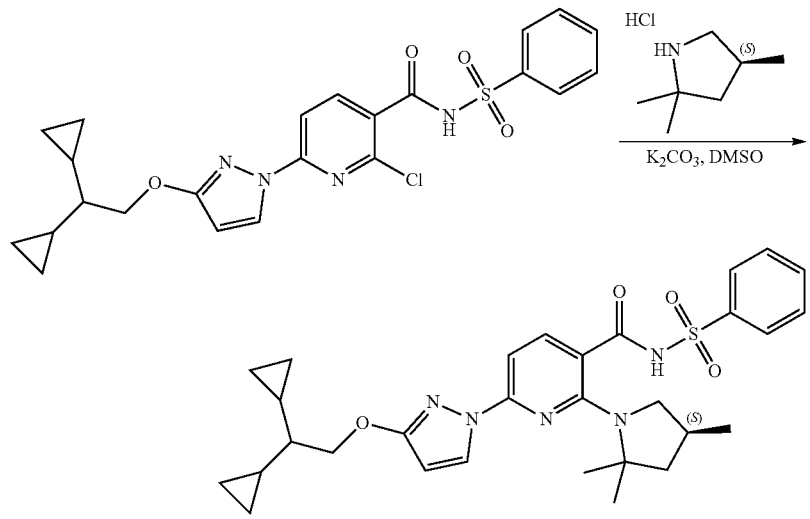

A mixture of N-(benzenesulfonyl)-2-chloro-6-[3-(2, 2-dicyclopropylethoxy) pyrazol-1-yl]pyridine-3-carboxamide (140.0 mg, 0.2875 mmol), (4S)-2, 2, 4-trimethylpyrrolidine (Hydrochloride salt) (145.0 mg, 0.9689 mmol), and potassium carbonate (240.0 mg, 1.737 mmol) in DMSO (2 mL) was stirred at 130° C. for 15 hours. The reaction mixture was filtered through Whatman filter disc (puradisc 25 TF) and filtrate was purified by a reverse phase HPLC-MS method using a dual gradient run from 50-99% mobile phase B over 15.0 minutes (Mobile phase A=$H_2O$ (5 mM HCl) and Mobile phase B=$CH_3CN$) to afford N-(benzenesulfonyl)-6-[3-(2,2-dicyclopropylethoxy)pyrazol-1-yl]-2-[(4S)-2,2,4-trimethylpyrrolidin-1-yl]pyridine-3-carboxamide (75.9 mg, 45%) as off white solid. ESI-MS m/z calc. 563.25665, found 564.5 (M+1)[+]; Retention time: 2.3 minutes. $^1$H NMR (400 MHz, Chloroform-d) δ 8.35 (d, J=8.6 Hz, 1H), 8.21 (d, J=2.8 Hz, 1H), 8.18-8.08 (m, 2H), 7.66-7.47 (m, 5H), 5.96 (d, J=2.8 Hz, 1H), 4.32 (d, J=5.6 Hz, 2H), 3.48 (dd, J=10.4, 8.4 Hz, 1H), 3.08 (dd, J=10.4, 7.6 Hz, 1H), 2.61 (dt, J=15.3, 7.8 Hz, 1H), 2.14 (dd, J=12.4, 7.9 Hz, 1H), 1.73 (dd, J=12.4, 9.5 Hz, 1H), 1.36 (s, 3H), 1.28 (s, 3H), 1.20 (d, J=6.6 Hz, 3H), 0.81 (qt, J=8.3, 5.0 Hz, 2H), 0.61 (tt, J=8.8, 5.6 Hz, 1H), 0.55-0.38 (m, 4H), 0.23 (p, J=4.8 Hz, 4H).

SYNTHETIC EXAMPLE 42

Synthesis of Compound 42: N-(Benzenesulfonyl)-6-[3-(3, 3-dicyclopropylpropoxy) pyrazol-1-yl]-2-[(4S)-2, 2, 4-trimethylpyrrolidin-1-yl]pyridine-3-carboxamide

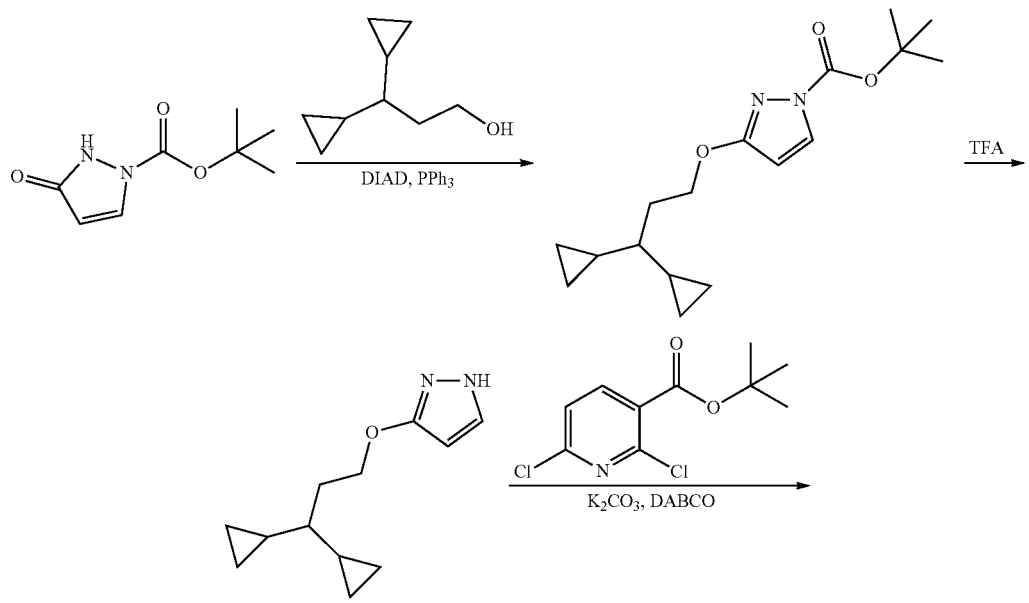

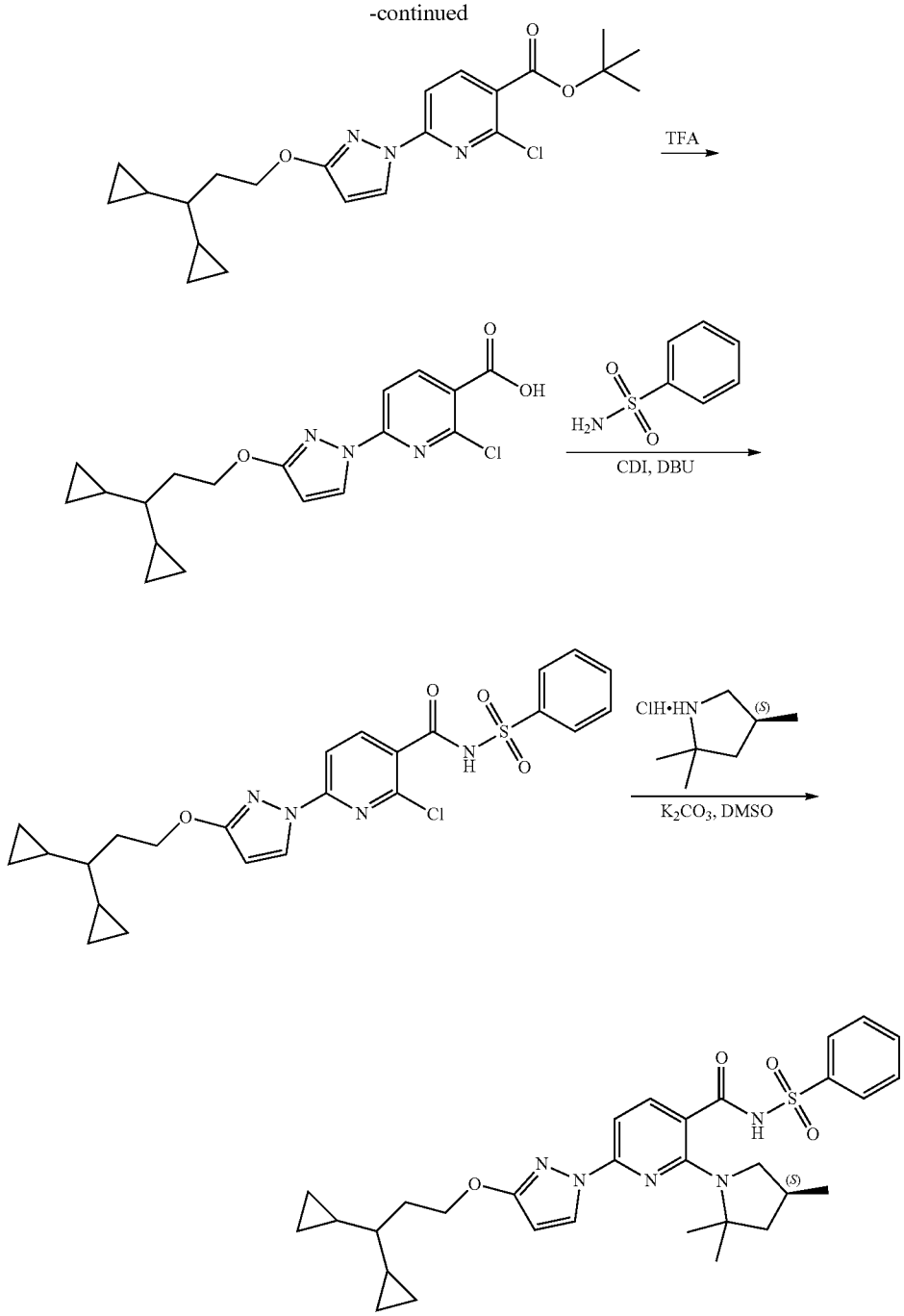

3,3-dicyclopropylpropan-1-ol

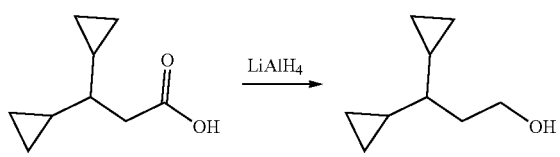 [SMILES: O=C(O)CC(C1CC1)C1CC1 ; "LiAlH4" ; OCCC(C1CC1)C1CC1]

To a solution of 3,3-cyclopropylpropanoic acid (200 mg, 1.297 mmol) in dry THF (2.000 mL) was added lithium aluminum hydride (845.0 μL of 2 M, 1.690 mmol) in an ice/water bath under N₂ atmosphere slowly drop wise. The mixture was allowed to gradually warm to room temperature and stirred for 16 hours. The flask was again cooled in an ice-bath and sequentially quenched with water (70.0 μL, 3.886 mmol) (slowly), followed by NaOH (70.0 L of 6 M, 0.4200 mmol), then water (200 μL, 11.10 mmol) affording a white granular solid in the mixture. To this mixture anhydrous MgSO₄ was added and stirred for 10 minutes. The resultant white heterogeneous mixture was filtered through celite and the precipitate was washed with ether. The filtrate was concentrated to afford 3, 3-dicyclopropylpropan-1-ol (140 mg, 77%). ESI-MS m/z calc. 140.12012, found 141.2 (M+1)⁺; Retention time: 0.5 minutes.

Step A: tert-butyl 3-(3, 3-dicyclopropyipropoxy) pyrazole-1-carboxylate

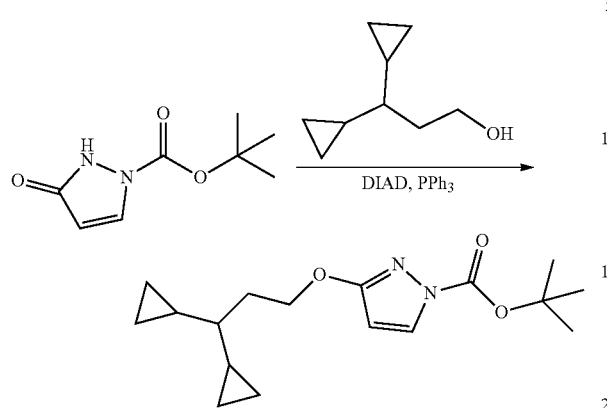

A solution of 3, 3-dicyclopropylpropan-1-ol (140.0 mg, 0.9984 mmol), tert-butyl 3-hydroxypyrazole-1-carboxylate (185.0 mg, 1.004 mmol), and triphenylphosphane (278 mg, 1.060 mmol) in dry THF (7.0 mL) was cooled in an ice bath, and DIAD (200.0 µL, 1.016 mmol) was slowly added under a $N_2$ atmosphere. The reaction was allowed to slowly warm to room temperature and was stirred for 16 hours. The reaction mixture was diluted with ethyl acetate, washed with saturated aqueous sodium bicarbonate solution, brine, dried over sodium sulfate, and evaporated under vacuum. The residue was purified by silica gel chromatography using 100% hexanes to 50% ethyl acetate in hexanes to afford tert-butyl 3-(3,3-dicyclopropylpropoxy)pyrazole-1-carboxylate (255 mg, 83%) as colorless oil. ESI-MS m/z calc. 306.19434, found 307.4 (M+1)$^+$; Retention time: 0.81 minutes.

Step B: 3-(3, 3-dicyclopropylpropoxy)-1H-pyrazole

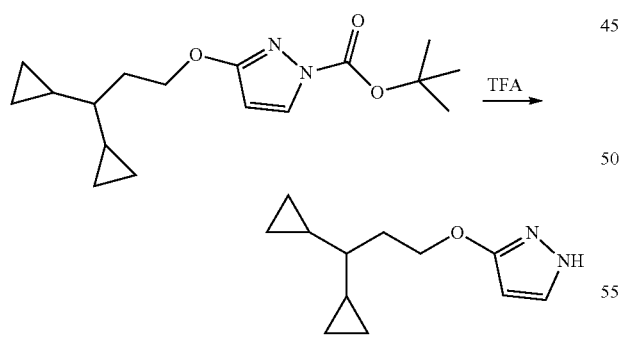

A solution of tert-butyl 3-(3, 3-dicyclopropylpropoxy) pyrazole-1-carboxylate (255 mg, 0.8322 mmol) and trifluoroacetic acid (325.0 µL, 4.218 mmol) in dichloromethane (1 mL) was stirred for 2.5 hours. The volatiles were removed under vacuum to afford 3-(3, 3-dicyclopropylpropoxy)-1H-pyrazole (Trifluoroacetate salt) as colorless oil which was used as it is without further purification for next reaction. ESI-MS m/z calc. 206.1419, found 207.2 (M+1)$^+$; Retention time: 0.59 minutes.

Step C: tert-Butyl 2-chloro-6-[3-(3, 3-dicyclopropylpropoxy) pyrazol-1-yl]pyridine-3-carboxylate

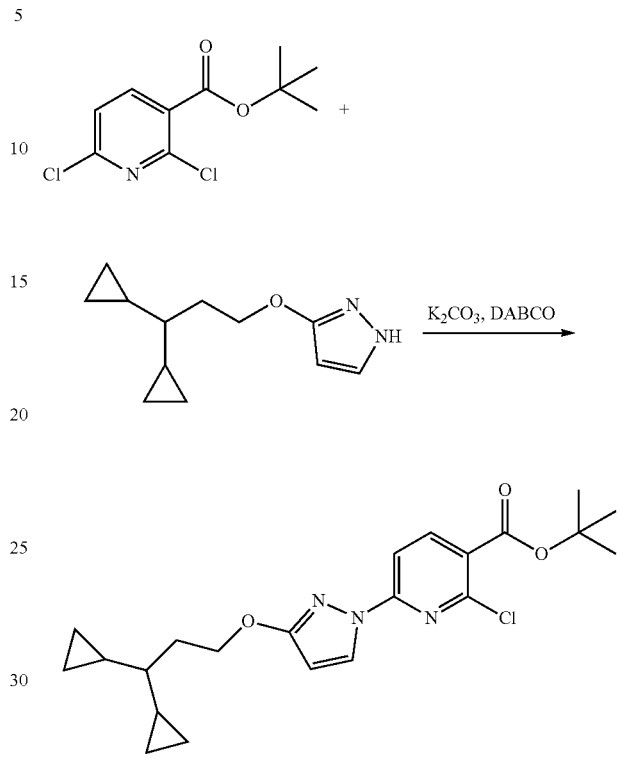

A mixture of tert-butyl 2,6-dichloropyridine-3-carboxylate (220.0 mg, 0.8867 mmol), 3-(3,3-dicyclopropylpropoxy)-1H-pyrazole (266.0 mg, 0.8305 mmol), potassium carbonate (230 mg, 1.664 mmol) and 1,4-diazabicyclo [2.2.2]octane (20 mg, 0.1783 mmol) in DMSO (10 mL) was stirred at room temperature for 15 hours. The reaction was diluted with water and extracted with ethyl acetate. The combined organic extracts were washed with brine, dried over sodium sulfate and evaporated. The residue was purified by silica gel column chromatography using 100% hexanes to 20% ethyl acetate in hexanes to afford tert-butyl 2-chloro-6-[3-(3,3-dicyclopropylpropoxy)pyrazol-1-yl] pyridine-3-carboxylate (245 mg, 71%) as colorless oil. ESI-MS m/z calc. 417.18192, found 418.4 (M+1)$^+$; Retention time: 1.28 minutes.

Step D: 2-Chloro-6-[3-(3, 3-dicyclopropylpropoxy) pyrazol-1-yl]pyridine-3-carboxylic acid

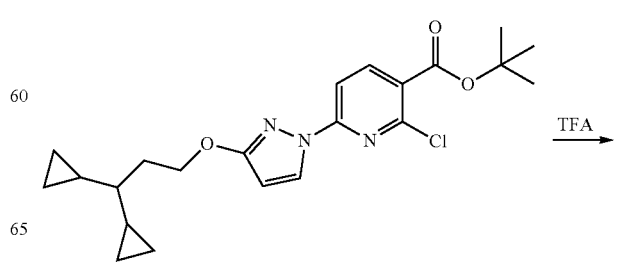

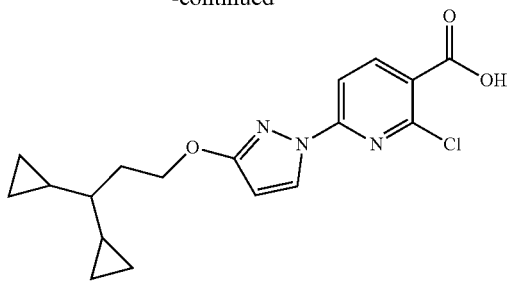

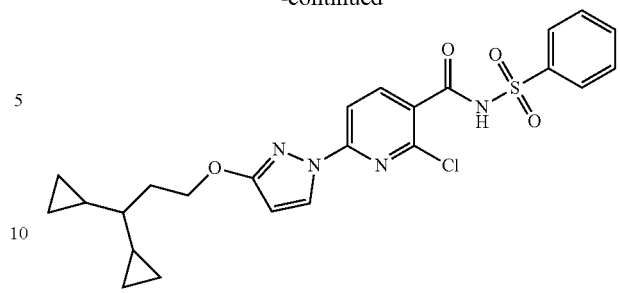

A solution of tert-butyl 2-chloro-6-[3-(3, 3-dicyclopropylpropoxy) pyrazol-1-yl]pyridine-3-carboxylate (245.0 mg, 0.5862 mmol) in trifluoroacetic acid (500.0 µL, 6.490 mmol) and dichloromethane (1.5 mL) was stirred for 4 hours at room temperature. The solvent was evaporated, and twice the residue was taken up in THF and concentrated under vacuum to afford 2-chloro-6-[3-(3,3-dicyclopropylpropoxy) pyrazol-1-yl]pyridine-3-carboxylic acid (204 mg, 96%) as white solid which was used as it is for the next reaction. ESI-MS m/z calc. 361.11932, found 362.3 (M+1)$^+$; Retention time: 0.8 minutes. $^1$H NMR (400 MHz, Methanol-d4) 8.47-8.32 (m, 2H), 7.73 (d, J=8.5 Hz, 1H), 6.03 (d, J=2.9 Hz, 1H), 4.45 (t, J=6.7 Hz, 2H), 1.98 (q, J=7.0 Hz, 2H), 0.75-0.64 (m, 2H), 0.50-0.39 (m, 4H), 0.35-0.26 (m, 1H), 0.26-0.19 (m, 2H), 0.15-0.06 (m, 2H).

Step E: N-(Benzenesulfonyl)-2-chloro-6-[3-(3, 3-dicyclopropylpropoxy) pyrazol-1-yl]pyridine-3-carboxamide

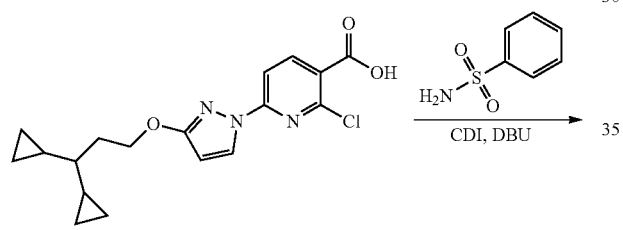

A solution of 2-chloro-6-[3-(3, 3-dicyclopropylpropoxy) pyrazol-1-yl]pyridine-3-carboxylic acid (50.0 mg, 0.1382 mmol) and carbonyl diimidazole (30.0 mg, 0.1850 mmol) in THF (2.0 mL) was stirred for 45 minutes. Then, benzenesulfonamide (25.0 mg, 0.1590 mmol) and DBU (30 µL, 0.2006 mmol) were added. The reaction mixture was stirred for additional 2 hours at room temperature. The reaction mixture was quenched with saturated ammonium chloride solution and extracted with ethyl acetate. The combined organic extracts were washed with brine, dried over sodium sulfate and evaporated to afford N-(benzenesulfonyl)-2-chloro-6-[3-(3,3-dicyclopropylpropoxy)pyrazol-1-yl]pyridine-3-carboxamide (84 mg, 121%) a s light brown viscous oil which was used (considering 100% conversion) as it is for next reaction. ESI-MS m/z calc. 500.1285, found 501.4 (M+1)$^+$; Retention time: 0.83 minutes.

Step F: N-(Benzenesulfonyl)-6-[3-(3, 3-dicyclopropylpropoxy) pyrazol-1-yl]-2-[(4S)-2, 2, 4-trimethylpyrrolidin-1-yl]pyridine-3-carboxamide

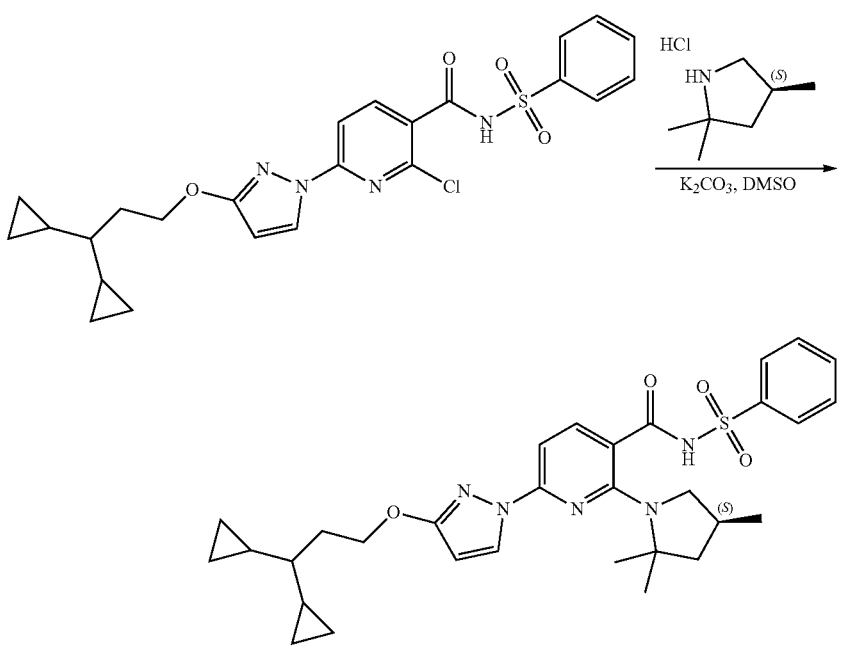

A mixture of N-(benzenesulfonyl)-2-chloro-6-[3-(3,3-dicyclopropylpropoxy)pyrazol-1-yl]pyridine-3-carboxamide (68.0 mg, 0.1357 mmol), (4S)-2,2,4-trimethylpyrrolidine (Hydrochloride salt) (70.0 mg, 0.4677 mmol), and potassium carbonate (115.0 mg, 0.8321 mmol) in DMSO (1 mL) was stirred at 130° C. for 15 hours. The reaction mixture was filtered through Whatman filter disc (puradisc 25 TF) and filtrate was purified by a reverse phase HPLC-MS method using dual gradient run from 50-99% mobile phase B over 15.0 minutes (Mobile phase A=H$_2$O (5 mM HCl) and Mobile phase B=CH$_3$CN to afford N-(benzenesulfonyl)-6-[3-(3,3-dicyclopropylpropoxy)pyrazol-1-yl]-2-[(4S)-2,2,4-trimethylpyrrolidin-1-yl]pyridine-3-carboxamide (23.1 mg, 29%). ESI-MS m/z calc. 577.2723, found 578.5 (M+1)$^+$; Retention time: 1.0 minutes. $^1$H NMR (400 MHz, Chloroform-d) δ 8.36 (d, J=8.6 Hz, 1H), 8.21 (d, J=2.8 Hz, 1H), 8.17 (d, J=1.2 Hz, 1H), 8.15 (d, J=1.6 Hz, 1H), 7.64-7.57 (m, 2H), 7.57-7.51 (m, 2H), 5.94 (d, J=2.8 Hz, 1H), 4.43 (t, J=6.8 Hz, 2H), 3.49 (dd, J=10.3, 8.5 Hz, 1H), 3.09 (dd, J=10.4, 7.6 Hz, 1H), 2.70-2.56 (m, 1H), 2.14 (dd, J=12.4, 7.9 Hz, 1H), 1.97 (q, J=6.8 Hz, 2H), 1.73 (dd, J=12.4, 9.4 Hz, 1H), 1.36 (s, 3H), 1.28 (s, 3H), 1.21 (d, J=6.7 Hz, 3H), 0.73-0.59 (m, 2H), 0.50-0.37 (m, 4H), 0.37-0.29 (m, 1H), 0.24-0.15 (m, 2H), 0.12-0.07 (m, 2H).

SYNTHETIC EXAMPLE 43

Synthesis of Compound 43: N-(2-chlorophenyl) sulfonyl-6-[3-[2-[1-(trifluoromethyl) cyclopropyl]ethoxy]pyrazol-1-yl]-2-[(4S)-2, 2, 4-trimethylpyrrolidin-[1-yl]pyridine-3-carboxamide Step A: 2-Chloro-N-(2-chlorophenyl) sulfonyl-6-[3-[2-[1-(trifluoromethyl) cyclopropyl]ethoxy]pyrazol-1-yl]pyridine-3-carboxamide

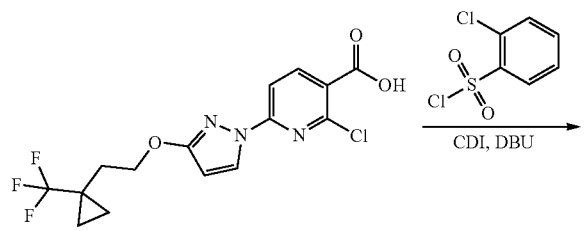

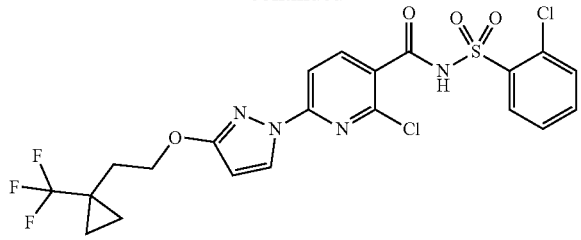

Step 1: 2-Chlorobenzenesulfonyl chloride (50 µL, 0.3667 mmol) was dissolved in ammonia in methanol (150 µL of 7 M, 1.050 mmol) and stirred at room temperature for 30 minutes. The mixture was evaporated to dryness and re-evaporated from dichloromethane. The solids were dissolved in THF (1 mL) and DBU (60 µL, 0.4012 mmol) was added. The mixture was stirred at 70° C. for 30 minutes to liberate any remaining ammonia from the reaction.

Step 2: 2-Chloro-6-[3-[2-[1-(trifluoromethyl) cyclopropyl]ethoxy]pyrazol-1-yl]pyridine-3-carboxylic acid (100 mg, 0.2661 mmol) and carbonyl diimidazole (53 mg, 0.3269 mmol) were combined in THF (1.000 mL) and stirred for 2 hours. At this point, this mixture was added to the sulfonamide mixture (from step-1) and the reaction was stirred for overnight at room temperature. The reaction was diluted with ethyl acetate and washed with a 1 M citric acid solution, followed by brine. The organics were separated, dried over magnesium sulfate, and evaporated to afford 2-chloro-N-(2-chlorophenyl) sulfonyl-6-[3-[2-[1-(trifluoromethyl) cyclopropyl]ethoxy]pyrazol-1-yl]pyridine-3-carboxamide along with starting material and primary amide. The mixture was used as it is for the next reaction. ESI-MS m/z calc. 548.02997, found 549.28 (M+1)$^+$; Retention time: 0.76 minutes.

Step B: N-(2-Chlorophenyl) sulfonyl-6-[3-[2-[1-(trifluoromethyl) cyclopropyl]ethoxy]pyrazol-1-yl]-2-[(4S)-2, 2, 4-trimethylpyrrolidin-1-yl]pyridine-3-carboxamide

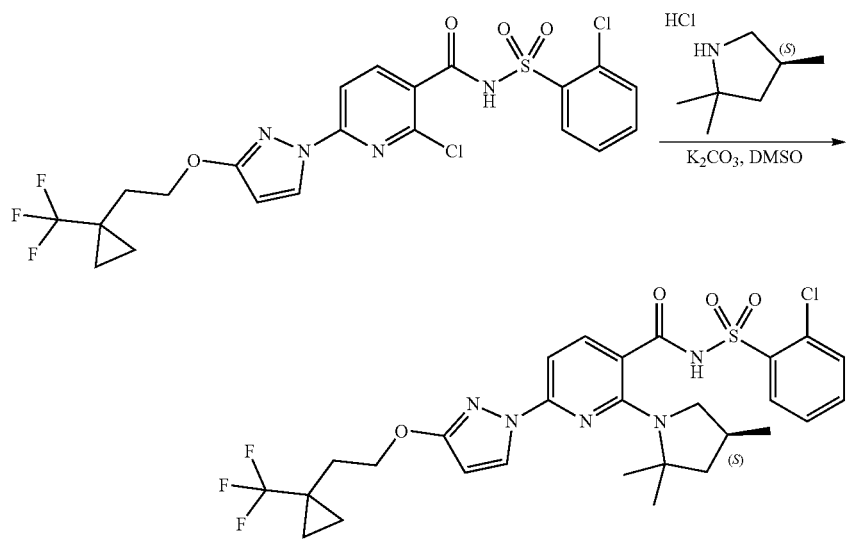

A mixture of 2-chloro-N-(2-chlorophenyl) sulfonyl-6-[3-[2-[1-(trifluoromethyl) cyclopropyl]ethoxy]pyrazol-1-yl] pyridine-3-carboxamide (50.0 mg, 0.09102 mmol) (mixture as it from Step A), (4S)-2,2,4-trimethylpyrrolidine (Hydrochloride salt) (50.0 mg, 0.3341 mmol), and potassium carbonate (80.0 mg, 0.5788 mmol) in DMSO (2.0 mL) was stirred at 130° C. for 15 hours. The reaction mixture was filtered through Whatman filter disc (puradisc 25 TF) and filtrate was purified by a reverse phase HPLC-MS method using a dual gradient run from 50-99% mobile phase B over 15.0 minutes (Mobile phase A=H$_2$O (5 mM HCl) and Mobile phase B=CH$_3$CN) to afford N-(2-chlorophenyl) sulfonyl-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (18.7 mg, 31%). ESI-MS m/z calc. 625.17377, found 626.5 (M+1)$^+$; Retention time: 2.35 minutes. $^1$H NMR (400 MHz, Chloroform-d) δ 8.43-8.36 (m, 1H), 8.32 (d, J=8.5 Hz, 1H), 8.21 (d, J=2.8 Hz, 1H), 7.55 (d, J=8.6 Hz, 1H), 7.53-7.44 (m, 3H), 5.94 (d, J=2.7 Hz, 1H), 4.40 (t, J=7.1 Hz, 2H), 3.51 (t, J=9.5 Hz, 1H), 3.13 (dd, J=10.6, 8.1 Hz, 1H), 2.73-2.55 (m, 1H), 2.16 (dd, J=12.4, 7.7 Hz, 1H), 2.09 (t, J=7.1 Hz, 2H), 1.77 (dd, J=12.5, 9.6 Hz, 1H), 1.47 (s, 3H), 1.41 (s, 3H), 1.20 (d, J=6.6 Hz, 3H), 1.09-0.97 (m, 2H), 0.81-0.64 (m, 2H).

SYNTHETIC EXAMPLE 44

Synthesis of Compound 44: Preparation of (S)—N-(phenylsulfonyl)-6-(3-(2-(1-(trifluoromethyl)cyclopropyl)ethoxy)-1H-pyrazol-1-yl)-4-(2,2,4-trimethylpyrrolidin-1-yl)nicotinamide Step A: Methyl 6-(3-(2-(1-(trifluoromethyl)cyclopropyl)ethoxy)-1H-pyrazol-1-yl)-4-chloropyridine-3-carboxylate

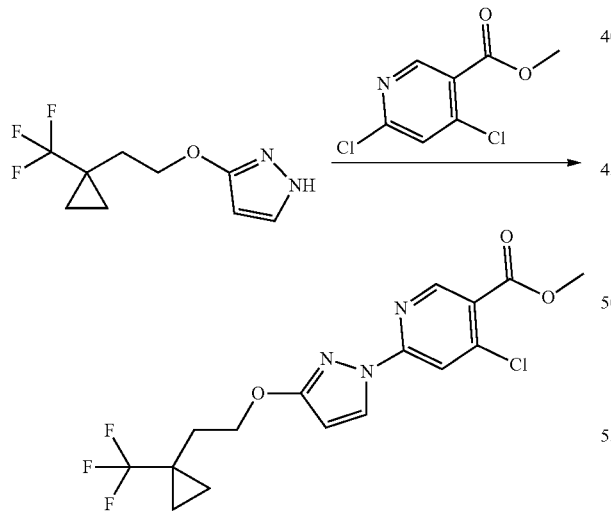

To the solution of 3-(2-(1-(trifluoromethyl)cyclopropyl) ethoxy)-1H-pyrazole (720 mg, 3.27 mmol) and methyl 4,6-dichloropyridine-3-carboxylate (742 mg, 3.60 mmol) in N,N-dimethylformamide (11 mL) were added potassium carbonate (9.36 g, 9.82 mmol) and 1,4-diazabicyclo [2.2.2] octane (110 mg, 0.98 mmol). The resulting solution was heated at 80° C. for 16 hours. The reaction solution was cooled to room temperature and diluted with diethyl ether (400 mL). Then water (50 mL) was added, and the organic layers were separated. The organic layers were washed with 1N aqueous hydrogen chloride solution (15 mL), brine (3×15 mL), dried over magnesium sulfate, filtered and concentrated. The residue was purified by silica gel column chromatography using 0-20% hexanes-ethyl acetate to afford methyl 6-(3-(2-(1-(trifluoromethyl)cyclopropyl) ethoxy)-1H-pyrazol-1-yl)-4-chloropyridine-3-carboxylate (631 mg, 49%) as a white solid. $^1$H NMR (250 MHz, CDCl$_3$) δ (ppm): 8.84 (s, 1H), 8.36 (d, J=2.8 Hz, 1H), 7.85 (s, 1H), 5.96 (d, J=2.8 Hz, 1H), 4.42 (t, J=7.0 Hz, 2H), 3.96 (s, 3H), 2.11 (t, J=7.0 Hz, 2H), 1.05 (m, 2H), 0.76 (m, 2H). ESI-MS m/z calc. 389.1 found 390.0 (M1). Retention time: 7.08 minutes.

Step B: 6-(3-(2-(1-(Trifluoromethyl)cyclopropyl) ethoxy)-1H-pyrazol-1-yl)-4-chloropyridine-3-carboxylic acid

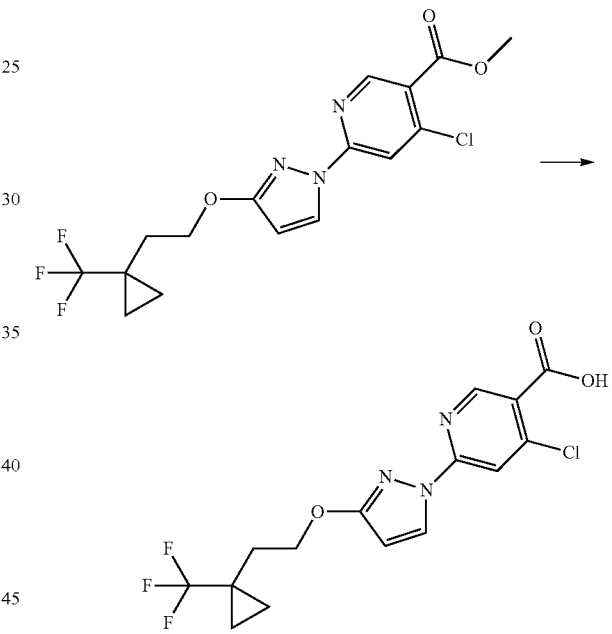

Methyl 6-(3-(2-(1-(trifluoromethyl)cyclopropyl)ethoxy)-1H-pyrazol-1-yl)-4-chloropyridine-3-carboxylate (553 mg, 1.42 mmol) was dissolved in a mixture of tetrahydrofuran (3.5 mL) and methanol (3.5 mL), then 2N aqueous sodium hydroxide solution (1.4 mL, 2.84 mmol) was added. The resulting solution was stirred at room temperature for 3 hours. All solvents were removed under the reduced pressure. The residue was acidified with 1N aqueous hydrogen chloride solution until pH value reached 2 and it was then extracted with ethyl acetate (3×80 mL). The organic layer was washed with brine (2×20 mL), dried over magnesium sulfate, filtered and concentrated to afford 6-(3-(2-(1-(trifluoromethyl)cyclopropyl)ethoxy)-1H-pyrazol-1-yl)-4-chloropyridine-3-carboxylic acid (534 mg, 97%) as a white solid. $^1$H NMR (250 MHz, DMSO) δ (ppm): 8.85 (s, 1H), 8.51 (d, J=3.0 Hz, 1H), 7.76 (s, 1H), 6.21 (d, J=3.0 Hz, 1H), 4.36 (t, J=7.0 Hz, 2H), 2.11 (t, J=7.0 Hz, 2H), 0.95 (m, 2H), 0.90 (m, 2H). ESI-MS m/z calc. 375.1 found 376.0 (M+1)$^+$ Retention time: 5.80 minutes.

Step C: 4-Chloro-N-(phenylsulfonyl)-6-(3-(2-(1-(trifluoromethyl)cyclopropyl)ethoxy)-1H-pyrazol-1-yl)nicotinamide

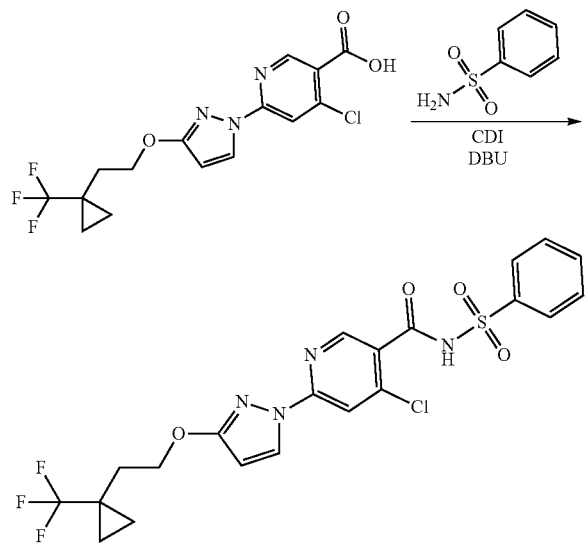

6-(3-(2-(1-(Trifluoromethyl)cyclopropyl)ethoxy)-1H-pyrazol-1-yl)-4-chloropyridine-3-carboxylic acid (528 mg, 1.40 mmol) and 1,1'-carbonyldiimidazole (341 mg, 2.11 mmol) in tetrahydrofuran (9 mL) was stirred for 2 hours at room temperature, then benzenesulfonamide (220 mg, 1.40 mmol) and 1,8-diazabicyclo[5.4.0]undec-7-ene (641 mg, 4.21 mmol) were added. The reaction solution was stirred for additional 16 hours and diluted with ethyl acetate (200 mL). The solution was washed with saturated aqueous tartaric acid solution (25 mL), water (40 mL), brine (40 mL), then dried over magnesium sulfate, filtered and concentrated. The residue was purified by silica gel chromatography using ethyl acetate to afford 4-chloro-N-(phenylsulfonyl)-6-(3-(2-(1-(trifluoromethyl)cyclopropyl)ethoxy)-1H-pyrazol-1-yl)nicotinamide (411 mg, 57%) as a white solid. $^1$H NMR (250 MHz, DMSO) δ (ppm): 8.56 (s, 1H), 8.47 (d, J=2.5 Hz, 1H), 7.94 (d, J=6.8 Hz, 2H), 7.67 (s, 1H), 7.59 (m, 3H), 6.16 (d, J=2.5 Hz, 1H), 4.34 (t, J=7.0 Hz, 2H), 2.09 (t, J=7.0 Hz, 2H), 0.94 (m, 2H), 0.89 (m, 2H). ESI-MS m/z calc. 514.1 found 515.0 (M1). Retention time: 6.31 minutes.

Step D: (S)—N-(Phenylsulfonyl)-6-(3-(2-(1-(trifluoromethyl)cyclopropyl)ethoxy)-1H-pyrazol-1-yl)-4-(2,2,4-trimethylpyrrolidin-1-yl)nicotinamide

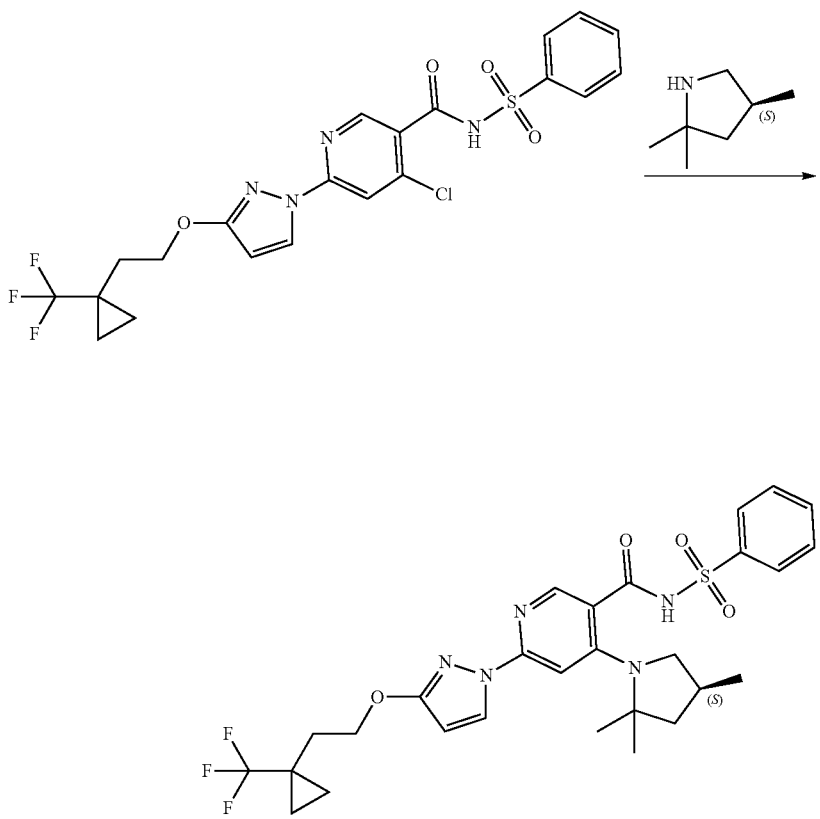

To the solution of 4-chloro-N-(phenylsulfonyl)-6-(3-(2-(1-(trifluoromethyl)cyclopropyl)ethoxy)-1H-pyrazol-1-yl)nicotinamide (54.6 mg, 0.11 mmol) in dimethyl sulfoxide (0.5 mL) were added (S)-2,2,4-trimethylpyrrolidine hydrochloride (96 mg, 0.64 mmol) and cesium fluoride (97 mg, 0.64 mmol). The resulting solution was heated at 120° C. for 48 hours. The mixture was purified by reverse phase HPLC using 5-100% water-acetonitrile (containing 0.1% trifluoroacetic acid). Pure fractions were combined and lyophilized to afford the product as trifluoroacetic acid salt, which was re-dissolved in 50% water-acetonitrile (0.1% hydrogen chloride) and lyophilized again to afford (S)—N-(phenylsulfonyl)-6-(3-(2-(1-(trifluoromethyl)cyclopropyl)ethoxy)-1H-pyrazol-1-yl)-4-(2,2,4-trimethylpyrrolidin-1-yl)nicotinamide hydrogen chloride salt (27.8 mg, 42%). $^1$H NMR (250 MHz, DMSO) δ (ppm): 12.65 (s, 1H), 8.40 (s, 1H), 8.08 (d, J=1.3 Hz, 1H), 8.02 (d, J=8.0 Hz, 2H), 7.70 (m. 3H), 7.24 (s, 1H), 6.05 (dd, J=1.3, 2.5 Hz, 1H), 4.34 (d, J=7.0 Hz, 2H), 2.50 (m, 3H), 2.09 (t, J=7.0 Hz, 2H), 2.10 (m, 1H), 1.91 (m, 1H), 1.53 (s, 6H), 0.87 (m, 2H), 0.84 (m, 2H), 0.64 (d, J=6.0 Hz, 3H). ESI-MS m/z calc. 591.2 found 592.6 (M1). Retention time: 2.88 minutes.

SYNTHETIC EXAMPLE 45

Synthesis of Compound 45, 46, & 47: N-(amino(oxo)(phenyl)-λ$^6$-sulfanylidene)-6-(3-((1-(trifluoromethyl)cyclopropyl)methoxy)-1H-pyrazol-1-yl)-2-((S)-2,2,4-trimethylpyrrolidin-1-yl)nicotinamide isomer 1 and isomer 2

Step A: tert-Butyl 2,6-difluoropyridine-3-carboxylate

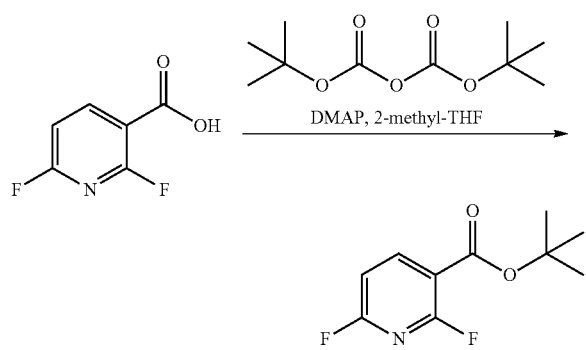

2,6-Difluoropyridine-3-carboxylic acid (1.0 g, 6.3 mmol) was dissolved in anhydrous 2-methyl tetrahydrofuran (12 mL). Di-tert-butyl dicarbonate (1.5 g, 6.9 mmol) was added in one portion followed by 4-(dimethylamino)pyridine (462 mg, 3.78 mmol). The mixture became a slurry, with large amount of gas evolution. The heterogeneous mixture was stirred at room temperature over weekend and then diluted with methyl tert-butyl ether (30 mL). The organic layer was washed successively with 1 M aqueous HCl (10 mL), 5% w/v saturated aqueous sodium bicarbonate solution (10 mL), dried over anhydrous sodium sulfate, filtered and concentrated under reduced pressure. The residue was purified by silica gel chromatography, eluting with 0-30% ethyl acetate in heptanes, to provide tert-butyl 2,6-difluoropyridine-3-carboxylate (360 mg, 26% yield) as a light yellow oil. $^1$H NMR (300 MHz, CDCl$_3$) ppm 1.60 (s, 9H), 6.88 (ddd, J=8.4, 3.0, 0.5 Hz, 1H), 8.40-8.47 (m, 1H). $^{19}$F NMR (282 MHz, CDCl$_3$) ppm −61.5--−61.4 (m, 1F), −60.3 (t, J=8.6 Hz, 1F).

Step B: tert-Butyl 2-fluoro-6-[3-[[1-(trifluoromethyl)cyclopropyl]methoxy]pyrazol-1-yl]pyridine-3-carboxylate

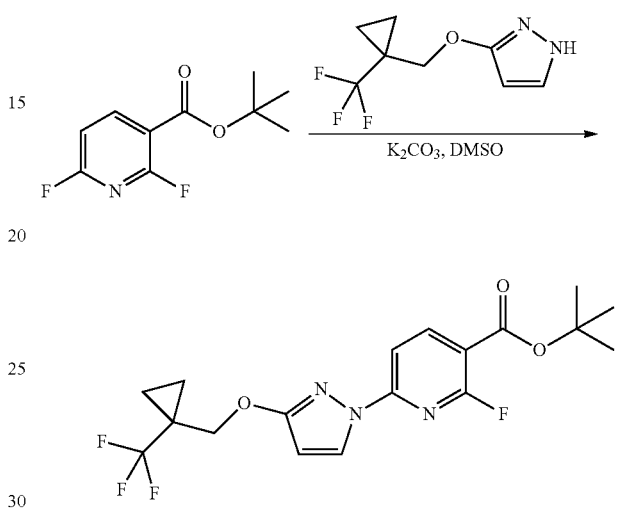

tert-Butyl 2,6-difluoropyridine-3-carboxylate (1.8 g, 8.4 mmol), 3-[[1-(trifluoromethyl)cyclopropyl]methoxy]-1H-pyrazole (1.8 g, 8.7 mmol) and freshly ground potassium carbonate (1.7 g, 12 mmol) were added to anhydrous dimethylsulfoxide (20 mL). The mixture was stirred at 20° C. under nitrogen for 16 hours and then diluted with ethyl acetate (100 mL). The organic layer was washed with water (3×30 mL), dried over anhydrous sodium sulfate, filtered and concentrated under reduced pressure. The residue was purified by silica gel chromatography, eluting with 0-15% ethyl acetate in heptanes, to afford tert-butyl 2-fluoro-6-[3-[[1-(trifluoromethyl)cyclopropyl]methoxy]pyrazol-1-yl]pyridine-3-carboxylate (1.9 g, 57% yield) as a white solid. $^1$H NMR (300 MHz, CDCl$_3$) ppm 0.92-0.99 (m, 2H), 1.13-1.18 (m, 2H), 1.60 (s, 9H), 4.40 (s, 2H), 6.00 (d, J=2.8 Hz, 1H), 7.61 (d, J=8.4 Hz, 1H), 8.30 (d, J=2.8 Hz, 1H), 8.37 (t, J=8.4 Hz, 1H). $^{19}$F NMR (282 MHz, CDCl$_3$) ppm −69.7 (s, 3F), −62.2 (d, J=9.2 Hz, 1F). LCMS: [M+H]$^+$=402.1.

Step C: 2-Fluoro-6-[3-[[1-(trifluoromethyl)cyclopropyl]methoxy]pyrazol-1-yl]pyridine-3-carboxylic acid

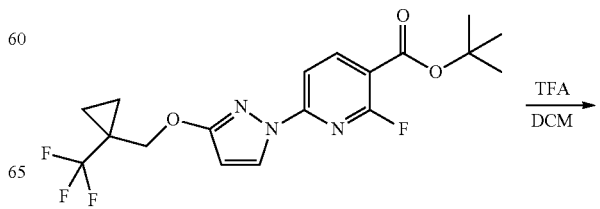

-continued

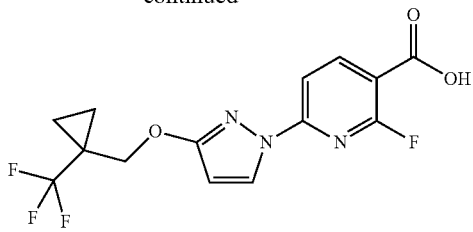

Trifluoroacetic acid (4 mL) was added to a solution of tert-butyl 2-fluoro-6-[3-[[1-(trifluoromethyl)cyclopropyl]methoxy]pyrazol-1-yl]pyridine-3-carboxylate (1.9 g, 4.7 mmol) in dichloromethane (16 mL). The mixture was stirred at 40° C. for 4 hours, after which TLC showed full conversion. The mixture was concentrated under reduced pressure and the residue was triturated with heptanes, filtered and dried under high vacuum to provide 2-fluoro-6-[3-[[1-(trifluoromethyl)cyclopropyl]methoxy]pyrazol-1-yl]pyridine-3-carboxylic acid (1.6 g, 98% yield) as a white solid. $^1$H NMR (300 MHz, DMSO-$d_6$) ppm 1.06-1.11 (m, 4H), 4.39 (s, 2H), 6.24 (d, J=2.8 Hz, 1H), 7.66 (dd, J=8.3, 1.0 Hz, 1H), 8.43 (d, J=8.3 Hz, 1H), 8.47 (dd, J=9.6, 8.4 Hz, 1H). $^{19}$F NMR (282 MHz, DMSO-$d_6$) ppm −67.9 (s, 3F), −63.2 (d, J=7.9 Hz, 1F). LCMS: [M+H]$^+$=346.1.

Step D: 2-Fluoro-6-[3-[[11-(trifluoromethyl)cyclopropyl]methoxy]pyrazol-1-yl]pyridine-3-carboxamide

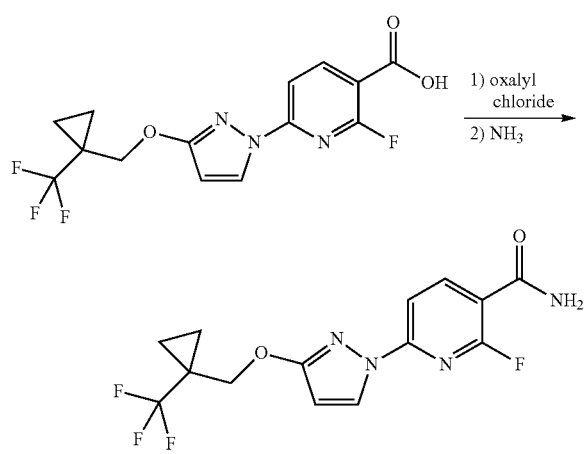

To a suspension of 2-fluoro-6-[3-[[1-(trifluoromethyl)cyclopropyl]methoxy]pyrazol-1-yl]pyridine-3-carboxylic acid (1.6 g, 4.6 mmol) in dichloromethane (20 mL) was added one drop of N,N-dimethylformamide followed by the dropwise addition of oxalyl chloride (0.52 mL, 6.0 mmol). The reaction was stirred at room temperature for two hours until bubbling had stopped. The solvent was removed under reduced pressure. The resulting white solid was dissolved in anhydrous tetrahydrofuran (10 mL) and added to a mixture of 28% ammonium hydroxide (10 mL) and tetrahydrofuran (5 mL) cooled with an ice-water bath. The reaction was stirred at room temperature for 1 hour and then diluted with ethyl acetate (100 mL), washed with water (20 mL), dried over anhydrous sodium sulfate, filtered and concentrated under reduced pressure to afford 2-fluoro-6-[3-[1-(trifluoromethyl)cyclopropyl]methoxy]pyrazol-1-yl]pyridine-3-carboxamide (1.55 g, 98% yield) as a white solid. $^1$H NMR (300 MHz, CDCl$_3$) ppm 1.06-1.11 (m, 4H), 4.38 (s, 2H), 6.21 (d, J=2.7 Hz, 1H), 7.61 (dd, J=8.2, 1.5 Hz, 1H), 7.76 (d, J=8.2 Hz, 2H), 8.33 (dd, J=9.4, 8.4 Hz, 1H), 8.4 (d, J=2.7 Hz, 1H). $^{19}$F NMR (282 MHz, CDCl$_3$) ppm −67.9 (s, 3F), −66.3 (d, J=8.9 Hz, 1F). LCMS: [M+H]$^+$; =345.1.

Step E: 2-Fluoro-N-phenylsulfanyl-6-[3-[[1-(trifluoromethyl)cyclopropyl]methoxy]pyrazol-1-yl]pyridine-3-carboxamide

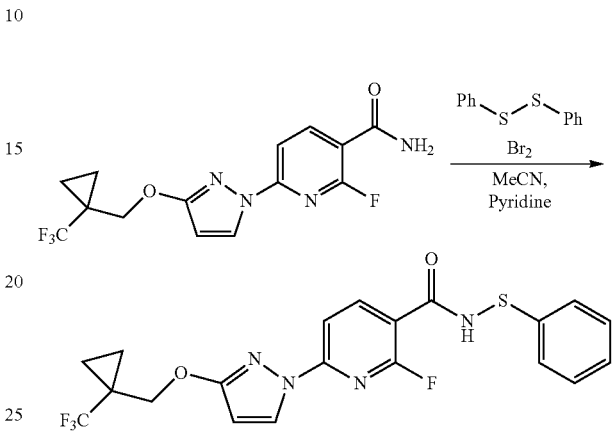

Bromine (0.14 mL, 2.7 mmol) was slowly added to a suspension of diphenyl di sulfide (596 mg, 2.73 mmol) in anhydrous acetonitrile (4 mL) at 0° C. The reaction was stirred at room temperature for 2 minutes to afford a solution. This solution was added to a solution of 2-fluoro-6-[3-[[1-(trifluoromethyl)cyclopropyl]methoxy]pyrazol-1-yl]pyridine-3-carboxamide (940 mg, 2.73 mmol) in anhydrous acetonitrile (4 mL) and pyridine (4 mL) at 0° C. The resulting dark mixture was stirred at room temperature overnight, then concentrated under reduced pressure and co-evaporated with toluene (10 mL). The residual brown solid was purified by silica gel chromatography, eluting with 0-30% ethyl acetate in heptanes, to give 2-fluoro-N-phenyl sulfanyl-6-[3-[[1-(trifluoromethyl)cyclopropyl]methoxy]pyrazol-1-yl]pyridine-3-carboxamide (380 mg, 31% yield) as a white solid. $^1$H NMR (300 MHz, CDCl$_3$) ppm 0.93-1.00 (m, 2H), 1.14-1.19 (m, 2H), 4.41 (s, 2H), 6.03 (d, J=3.0 Hz, 1H), 7.20-7.26 (m, 1H), 7.30-7.42 (m, 4H), 7.73 (dd, J=8.4, 1.8 Hz, 1H), 7.84 (d, J=15 Hz, 1H), 8.28 (d, J=3.0 Hz, 1H), 8.63 (t, J=9.0 Hz, 1H). LCMS: [M+H]$^+$=453.0.

Step F: rac-N-(benzenesulfinyl)-2-fluoro-6-[3-[[1-(trifluoromethyl)cyclopropyl]methoxy]pyrazol-1-yl]pyridine-3-carboxamide

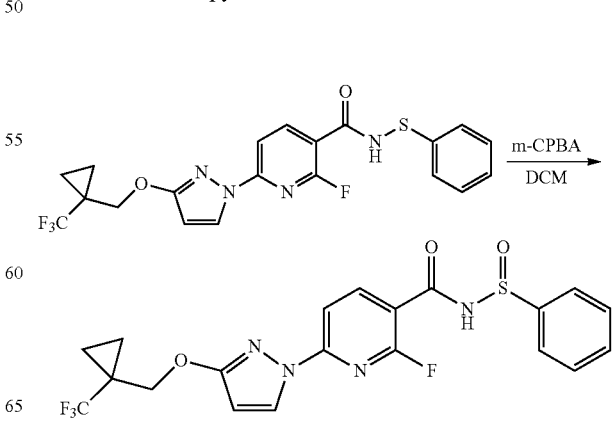

meta-Chloroperoxybenzoic acid (469 mg of 77%, 2.1 mmol) was added to a solution of 2-fluoro-N-phenylsulfanyl-6-[3-[[1-(trifluoromethyl)cyclopropyl]methoxy]pyrazol-1-yl]pyridine-3-carboxamide (860 mg, 1.90 mmol) in dichloromethane (30 mL) at 0° C. and the reaction was stirred at the same temperature for 1 hour. The reaction mixture was diluted with dichloromethane (70 mL), washed successively with 10% w/v sodium thiosulfate, 5% w/v sodium bicarbonate, dried over anhydrous sodium sulfate, filtered and concentrated under reduced pressure. The residue was purified by silica gel chromatography, eluting with 0-40% ethyl acetate in heptanes, to afford racemic N-(benzenesulfinyl)-2-fluoro-6-[3-[[1-(trifluoromethyl)cyclopropyl]methoxy]pyrazol-1-yl]pyridine-3-carboxamide (700 mg, 78% yield) as a white solid. $^1$H NMR (300 MHz, CDCl$_3$) ppm 0.92-1.00 (m, 2H), 1.13-1.20 (m, 2H), 4.38 (d, J=12.1, 1 H), 4.43 (d, J=12.1, 1 H), 6.03 (d, J=3.0 Hz, 1H), 7.56-7.65 (m, 3H), 7.70-7.78 (m, 1H), 7.80-7.88 (m, 2H), 8.24 (d, J=3.0 Hz, 1H), 8.40 (d, J=12 Hz, 1H), 9.61 (t, J=8.5 Hz, 1H). $^{19}$F NMR (282 MHz, CDCl$_3$) ppm −69.7 (s, 3F), −63.2 (t, J=10.5 Hz, 1F). LCMS: [M+H]$^+$=469.0.

Step G: N-(Benzenesulfinyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

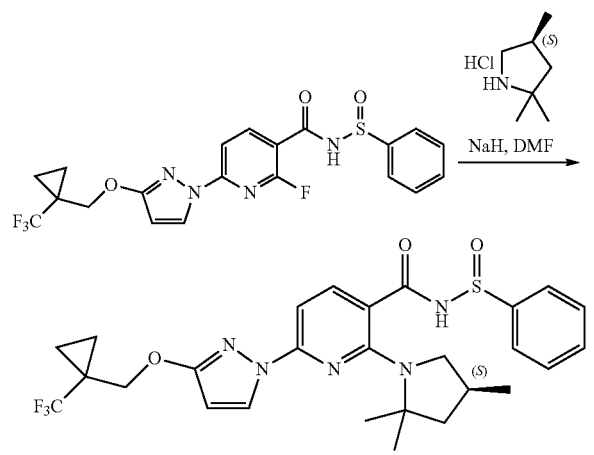

(4S)-2,2,4-Trimethylpyrrolidine hydrochloride (400 mg, 2.67 mmol) was dissolved in anhydrous N,N-dimethylformamide (10 mL), the mixture was cooled with ice-water and sodium hydride (287 mg of 60% dispersion in mineral oil, 7.2 mmol) was added. The reaction was stirred at room temperature for 10 minutes and cooled back to 0° C. A solution of racemic N-(benzenesulfinyl)-2-fluoro-6-[3-[[1-(trifluoromethyl)cyclopropyl]methoxy]pyrazol-1-yl]pyridine-3-carboxamide (960 mg, 2.05 mmol) in N,N-dimethylformamide (10 mL) was added. After stirring at room temperature for 10 minutes the reaction mixture was stirred at 50° C. for 3 hours (LCMS showed 60% conversion; there was a lot of unconsumed sodium hydride). Anhydrous tetrahydrofuran (0.5 mL) was added and the reaction was stirred at room temperature overnight. The mixture was quenched with water (10 mL) at 0° C. then extracted with ethyl acetate (80 mL). The organic layer was washed with water (3×20 mL), brine (10 mL), dried over anhydrous sodium sulfate, filtered and concentrated under reduced pressure. The residue was purified by silica gel chromatography, eluting with 0-50% ethyl acetate in heptanes. The fractions containing product and starting material were combined and concentrated under reduced pressure. The residue was stirred in a mixture of heptanes (10 mL) and dichloromethane (10 mL) for 30 minutes and then filtered. The filtrate was concentrated under reduced pressure to afford N-(benzenesulfinyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (500 mg, 88% purity by LCMS, 38% yield) as a yellow solid that was used in the following step without further purification. LCMS: [M+H]$^+$=562.2.

Step H: Synthesis of N-(phenylsulfonimidoyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide

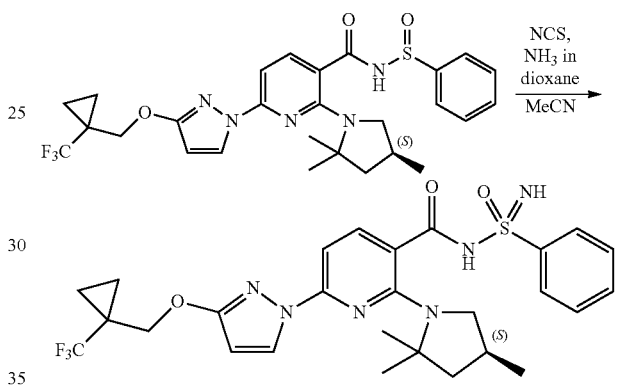

Ammonia (7.8 mL of a 0.5 M solution in dioxane, 3.9 mmol) was added to a solution of N-(benzenesulfinyl)-6-[3-[[1-(trifluoromethyl)cyclopropyl]methoxy]pyrazol-1-yl]-2-[(4S)-2,2,4-trimethylpyrrolidin-1-yl]pyridine-3-carboxamide (500 mg, 88% purity, 0.78 mmol) in anhydrous acetonitrile (20 mL) at 0° C. N-Chlorosuccinimide (120 mg, 0.90 mmol) was added in one portion (the mixture turned orange) and the reaction was stirred at 0° C. for one hour. Additional N-chlorosuccinimide (12 mg, 0.090 mmol) was added and the reaction was stirred at the same temperature for 30 minutes and then quenched with 10% w/v aqueous sodium thiosulfate solution and extracted with ethyl acetate (50 mL). The organic layer was washed successively with 5% w/v aqueous sodium bicarbonate solution, brine, dried over anhydrous sodium sulfate, filtered and concentrated under reduced pressure. The residue was purified by silica gel chromatography, eluting with 5-45% ethyl acetate in heptanes, to afford a white solid (300 mg) which was triturated with acetonitrile (3 mL) to provide a diastereomeric mixture of N-(amino(oxo)(phenyl)-λ$^6$-sulfaneylidene)-6-(3-((1-(trifluoromethyl)cyclopropyl)methoxy)-1H-pyrazol-1-yl)-2-((S)-2,2,4-trimethylpyrrolidin-1-yl) nicotinamide (Compound 45) (180 mg, 97% purity by LCMS, 38% yield) as a white solid. $^1$H NMR (300 MHz, CDCl$_3$) ppm 0.89-1.06 (m, 5H), 1.08-1.18 (m, 2H), 1.59-1.72 (m, 7H), 1.81-1.95 (m, 1H), 2.07-2.40 (m, 1H), 2.59-2.71 (m, 0.4 H), 2.82-2.96 (m, 0.6 H), 3.18 (t, J=10.6 Hz, 0.4 H), 3.29 (t, J=10.7 Hz, 0.6 H), 4.32-4.43 (m, 2H), 5.90 (d, J=2.6 Hz, 1H), 6.25 (br. s., 2H), 6.90-6.97 (m, 1H), 7.48-7.57 (m, 2H), 7.58-7.66 (m, 1H), 7.97-8.09 (m, 2.6 H), 8.16

(d, J=8.2 Hz, 0.4 H), 8.20-8.23 (m, 1H). $^{19}$F NMR (282 MHz, CDCl$_3$) ppm −69.7 (s, 3F). LCMS: [M+H]$^+$=577.2.

The isomers were separated by chiral supercritical fluid chromatography utilizing a Phenomenex Lux-1 (250×21.2 mm), 5 μm column and eluting with 20% MeOH, 80% CO$_2$ with a flow rate of 70 mL/minute.

Diastereoisomer 1 (Compound 46): >98% de ESI-MS m/z calc. 576.2131, found 577.4 (M+1)$^+$; Retention time: 1.82 minutes; $^1$H NMR (400 MHz, DMSO-d6) δ 8.19 (d, J=2.7 Hz, 1H), 7.95 (dd, J=8.1, 1.6 Hz, 3H), 7.75 (s, 2H), 7.68-7.49 (m, 3H), 6.85 (d, J=8.1 Hz, 1H), 6.12 (d, J=2.7 Hz, 1H), 4.35 (s, 2H), 3.08 (t, J=10.6 Hz, 1H), 2.76 (dd, J=10.6, 7.1 Hz, 1H), 2.21 (dq, J=12.1, 6.2 Hz, 1H), 1.97-1.79 (m, 1H), 1.55 (d, J=1.7 Hz, 6H), 1.44 (t, J=12.0 Hz, 1H), 1.09 (dd, J=4.5, 3.1 Hz, 4H), 0.92 (d, J=6.2 Hz, 3H).

Diastereoisomer 2 (Compound 47): >98% de. ESI-MS m/z calc. 576.2131, found 577.3 (M+1)$^+$; Retention time: 1.81 minutes; 1H NMR (400 MHz, DMSO-d6) δ 8.19 (d, J=2.7 Hz, 1H), 7.99-7.88 (m, 3H), 7.79 (s, 2H), 7.69-7.55 (m, 3H), 6.87 (d, J=8.1 Hz, 1H), 6.11 (d, J=2.7 Hz, 1H), 4.44-4.28 (m, 2H), 2.63 (t, J=10.8 Hz, 1H), 2.21-2.03 (m, 1H), 1.80 (dd, J=11.8, 5.4 Hz, 1H), 1.52 (d, J=1.7 Hz, 6H), 1.33 (t, J=12.2 Hz, 2H), 1.09 (dt, J=5.6, 2.1 Hz, 4H), 0.71 (d, J=6.2 Hz, 3H).

SYNTHETIC EXAMPLE 46

Synthesis of Compound 48

N-(Benzenesulfonyl)-6-[3-(cyclopropoxy)pyrazol-1-yl]-2-[(4S)-2,2,4-trimethylpyrrolidin-1-yl]pyridine-3-carboxamide

Step A: tert-Butyl 3-cyclopropoxy-1H-pyrazole-1-carboxylate

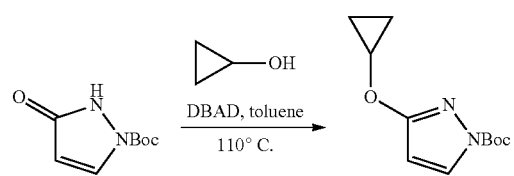

To a solution of cyclopropanol (30.8 mg, 0.531 mmol), tert-butyl 2,3-dihydro-3-oxopyrazole-1-carboxylate (97.7 mg, 0.531 mmol) and triphenylphosphine (139.3 mg, 0.531 mmol) in anhydrous toluene (2 mL) was added di-tert-butyl azodicarboxylate (122.2 mg, 0.531 mmol). The solution was purged with argon for 1 minute, and stirred at ambient temperature for 30 minutes. Then the reaction solution was heated at 110° C. for additional 5 hours before it cooled to ambient temperature. The solution was diluted with ether (50 mL), washed with NaOH aqueous solution, brine, dried over sodium sulfate, filtered and concentrated under the reduced pressure. Residue obtained was purified by silica gel chromatography (hexane and ethyl acetate, 0 to 10% ethyl acetate gradient) to afford tert-butyl 3-cyclopropoxy-1H-pyrazole-1-carboxylate (52 mg, 46%) as a white solid. ESI-MS m/z calc. 224.116, found 225.0 (M+1)$^+$; Retention time: 4.38 minutes. $^1$H NMR (250 MHz, CDCl$_3$) δ (ppm) 7.86 (d, J=2.8 Hz, 1H), 5.93 (d, J=2.8 Hz, 1H), 4.20-4.15 (m, 1H), 1.61 (s, 9H), 0.85-0.72 (m, 4H).

Step B: 3-Cyclopropoxy-1H-pyrazole

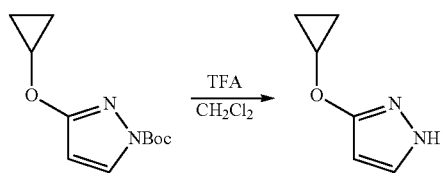

To a solution of tert-butyl 3-cyclopropoxy-1H-pyrazole-1-carboxylate (131 mg, 0.584 mmol) in dichloromethane (6 mL) was added TFA (667 mg, 0.38 mL, 5.84 mmol). The resulting solution was stirred at ambient temperature for 3 hours. All solvents were removed under the reduced pressure. The residue obtained was dissolved in ether (100 mL), washed with saturated sodium bicarbonate aqueous solution, dried over magnesium sulfate, filtered and concentrated under the reduced pressure to afford 3-cyclopropoxy-1H-pyrazole as a pale yellow oil. Crude product obtained was directly used in next step.

Step 3: tert-Butyl 2-chloro-6-(3-cyclopropoxy-1H-pyrazole-1-yl)pyridine-3-carboxylate

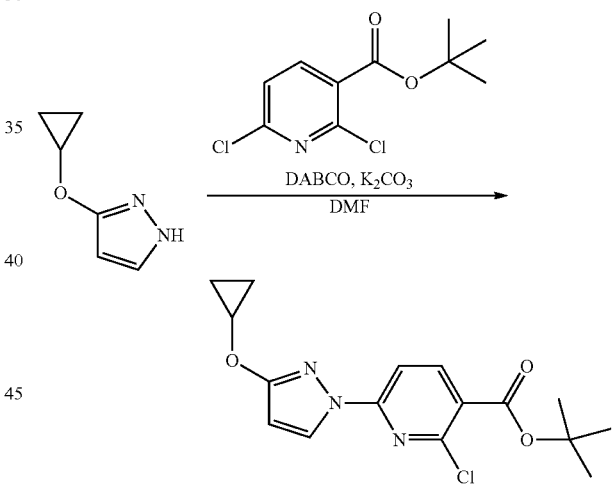

Crude 3-cyclopropoxy-1H-pyrazole (73 mg, 0.584 mmol), tert-butyl 2,6-dichloro pyridine-3-carboxylate (159 mg, 0.643 mmol), K$_2$CO$_3$ (162 mg, 1.17 mmol) and DABCO (13 mg, 0.117 mmol) were dissolved in anhydrous DMF (1.5 mL). The reaction solution was stirred at ambient temperature for 16 hours. The reaction solution was diluted with ether (100 mL), washed with water (3×25 mL) and brine (25 mL). Organic layers were separated, dried over magnesium sulfate, filtered and concentrated under the reduced pressure. Residue obtained was purified by silica gel chromatography (hexane and dichloromethane, 0 to 100% dichloromethane gradient) to afford tert-butyl 2-chloro-6-(3-cyclopropoxy-1H-pyrazole-1-yl)pyridine-3-carboxylate (153 mg, 78%) as a sticky oil. ESI-MS m/z calc. 335.104, found 336.1 (M+1)$^+$; Retention time: 6.84 minutes.

Step D: 2-Chloro-6-(3-cyclopropoxy-1H-pyrazole-1-yl)pyridine-3-carboxylic acid

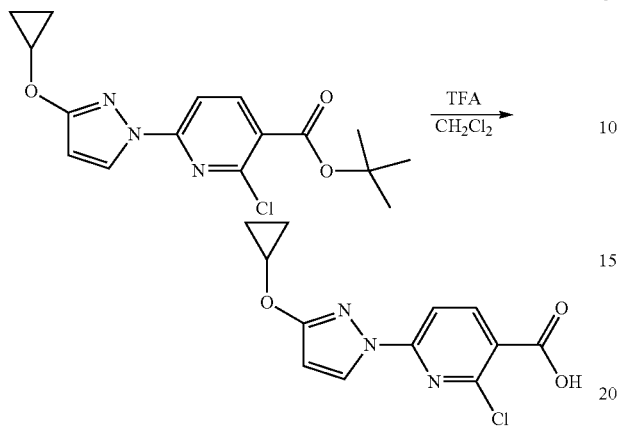

To a solution of tert-butyl 2-chloro-6-(3-cyclopropoxy-1H-pyrazole-1-yl)pyridine-3-carboxylate (153 mg, 0.456 mmol) in dichloromethane (2.2 mL) was added TFA (519 mg, 0.35 mL, 4.56 mmol). The resulting solution was stirred at ambient temperature for 48 hours. Then 1,2-dichloroethane (2 mL) was added, and all solvents were removed under the reduced pressure. White solid obtained was suspended in the mixture of hexane and ether (10 mL, hexane/ether, 19/1), sonicated, filtered, washed with hexane (10 mL) and dried to afford 2-chloro-6-(3-cyclopropoxy-1H-pyrazole-1-yl)pyridine-3-carboxylic acid (122 mg, 97%) as a white solid. ESI-MS m/z calc. 279.041, found 279.9 (M+1)$^+$; Retention time: 4.43 minutes. $^1$H NMR (500 MHz, DMSO-d6) δ (ppm) 13.6 (s, 1H), 8.43 (d, J=3.0 Hz, 1H), 8.39 (d, J=8.5 Hz, 1H), 7.72 (d, J=8.5 Hz, 1H), 6.28 (d, J=3.0 Hz, 1H), 4.16-4.13 (m, 1H), 0.79-0.71 (m, 4H).

Step E: N-(Benzenesulfonyl)-2-chloro-6-[3-(cyclopropoxy)pyrazol-1-yl]pyridine-3-carboxamide

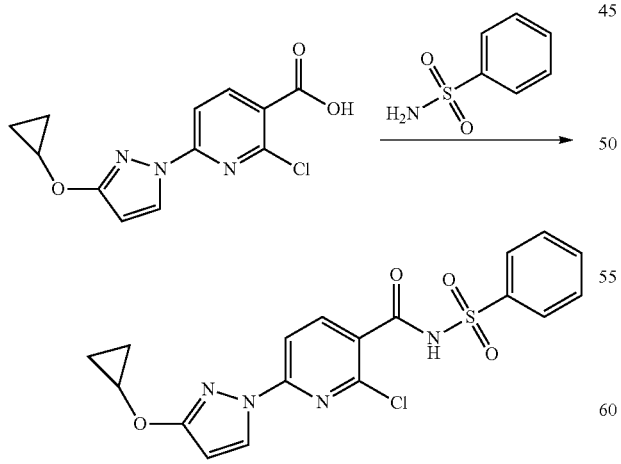

2-Chloro-6-[3-(cyclopropoxy)pyrazol-1-yl]pyridine-3-carboxylic acid (30 mg, 0.1073 mmol) in DMF (600.0 μL), HATU (1-[bis(dimethylamino)methylene]-1H-1,2,3-triazolo[4,5-b]pyridinium 3-oxide hexafluorophosphate) (85 mg, 0.2235 mmol), and DIEA (diisopropylethylamine) (38 μL, 0.2182 mmol) were combined and stirred at room temperature for 16 h. The reaction mixture was filtered and purified on reverse phase HPLC utilizing a gradient of 25-75% acetonitrile in water containing 5 mM HCl to give N-(benzenesulfonyl)-2-chloro-6-[3-(cyclopropoxy)pyrazol-1-yl]pyridine-3-carboxamide $^1$H NMR (400 MHz, DMSO-d6) δ 12.97 (s, 1H), 8.43 (d, J=2.8 Hz, 1H), 8.12 (d, J=8.3 Hz, 1H), 8.01 (d, J=9.4 Hz, 2H), 7.77 (s, 1H), 7.69 (d, J=6.0 Hz, 3H), 6.31-6.26 (m, 1H), 4.16 (s, 1H), 0.76 (s, 4H). ESI-MS m/z calc. 418.05026, found 419.0 (M+1)$^+$; Retention time: 1.63 minutes (3 min run).

Step F: N-(Benzenesulfonyl)-6-[3-(cyclopropoxy)pyrazol-1-yl]-2-[(4S)-2,2,4-trimethylpyrrolidin-1-yl]pyridine-3-carboxamide

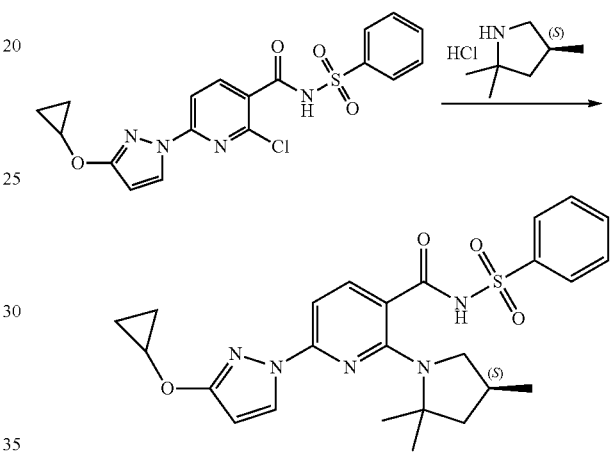

A mixture of N-(benzenesulfonyl)-2-chloro-6-[3-(cyclopropoxy)pyrazol-1-yl]pyridine-3-carboxamide, (4S)-2,2,4-trimethylpyrrolidine (Hydrochloride salt) (approximately 24.01 mg, 0.1604 mmol), CsF (approximately 36.00 mg, 0.2370 mmol), K$_2$CO$_3$ (approximately 72.01 mg, 0.5210 mmol) in DMSO (0.5 mL) was stirred at 140° C. for 16 h. The reaction was filtered and purified on purified on reverse phase HPLC utilizing a gradient of 25-75% acetonitrile in water containing 5 mM HCl to give N-(benzenesulfonyl)-6-[3-(cyclopropoxy)pyrazol-1-yl]-2-[(4S)-2,2,4-trimethylpyrrolidin-1-yl]pyridine-3-carboxamide (5.6 mg, 11% over 2 steps) ESI-MS m/z calc. 495.19403, found 496.0 (M+1)$^+$; Retention time: 1.98 minutes] (3 min run)

SYNTHETIC EXAMPLE 47

Synthesis of Compound 49: N-(3-methoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: (1-(Trifluoromethyl)cyclopropyl)methanol

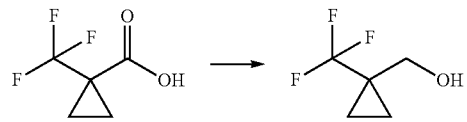 [SMILES: O=C(O)C1(C(F)(F)F)CC1 ; OCC1(C(F)(F)F)CC1]

1-(Trifluoromethyl)cyclopropane-1-carboxylic acid (858 mg, 5.57 mmol, 1.00 eq.) was dissolved in diethyl ether (15 mL). The reaction mixture was cooled to 0° C. Lithium aluminum hydride (274 mg, 7.24 mmol, 1.30 eq.) was added portionwise. The reaction mixture was stirred overnight and allowed to reach room temperature. The reaction mixture was cooled to 0° C. HCl (aq., 1 N, 25 mL) was added dropwise. The aqueous phase was extracted with diethyl ether (2×25 mL). The combined organic phases were washed with brine (25 mL), dried over sodium sulfate, filtered and evaporated in vacuo (Tbath<30° C.) to give (1-(trifluoromethyl)cyclopropyl)methanol (547 mg, 3.90 mmol, 70% yield) as a colorless oil. $^1$H NMR (CDCl3): d 3.73 (s, 2H), 1.58 (br, 1H), 1.07-1.01 (m, 2H), 0.82-0.75 (m, 2H).

Step B: 1-(3-hydroxypyrazol-1-yl)ethanone

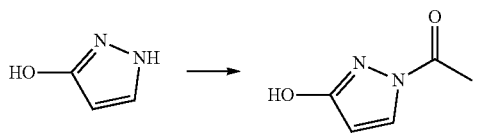

A 100 mL round bottom flask equipped with a stir bar and a condenser was charged with 1H-pyrazol-5-ol (4.97 g, 59.11 mmol) and pyridine (25 mL, 309.1 mmol). The mixture was stirred at 95° C. A solution of acetic anhydride (5.6 mL, 59.35 mmol) in pyridine (10 mL, 123.6 mmol) was added dropwise over a period of 3 minutes. The mixture was then stirred at 95° C. for an additional three hours. The solvents were removed under reduced pressure. The solid residue was triturated in 40 mL of diethyl ether, filtered, washed with diethyl ether and dried to give 1-(3-hydroxy-pyrazol-1-yl)ethanone (6.96 g, 93%). $^1$H NMR (400 MHz, DMSO-d6) δ 10.96 (s, 1H), 8.13 (d, J=3.0 Hz, 1H), 6.01 (d, J=3.0 Hz, 1H), 2.48 (s, 3H).

Step C: 1-(3-((1-(trifluoromethyl)cyclopropyl)methoxy)-1H-pyrazol-1-yl)ethan-1-one

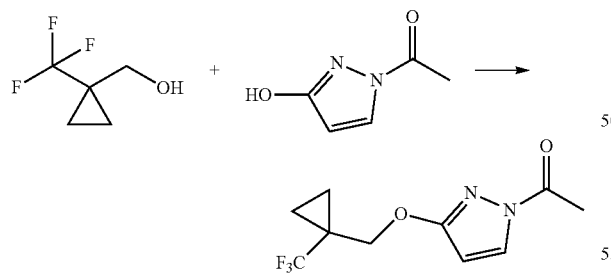

1-(3-Hydroxy-1H-pyrazol-1-yl)ethan-1-one (443 mg, 3.51 mmol, 1.00 eq.) was dissolved in THF (8 mL). (1-(Trifluoromethyl)cyclopropyl)methanol (547 mg, 3.90 mmol, 1.11 eq.) and triphenyl phosphine (1.10 g, 4.21 mmol, 1.20 eq.) were added. The reaction mixture was cooled to 0° C. Diisopropyl azodicarboxylate (829 mL, 851 mg, 4.21 mmol, 1.20 eq.) was added dropwise (maintaining temperature <5° C.). The reaction mixture was stirred at room temperature over the weekend. Evaporation of the volatiles in vacuo gave a slightly yellow oil (2.88 g). The crude material was purified by silica gel chromatography eluting with 0-25% ethyl acetate in heptanes to give 1-(3-((1-(trifluoromethyl)cyclopropyl)methoxy)-1H-pyrazol-1-yl)ethan-1-one (701 mg, 2.82 mmol, 80% yield) as a white solid. $^1$H NMR (CDCl3): δ 8.06 (d, 1H), 5.99 (d, 1H), 4.36 (d, 2H), 2.57 (s, 3H), 1.18-1.12 (m, 2H), 0.98-0.90 (m, 2H). $^{19}$F NMR (CDCl3): δ-69.77.

Step D: 3-((1-(Trifluoromethyl)cyclopropyl)methoxy)-1H-pyrazole

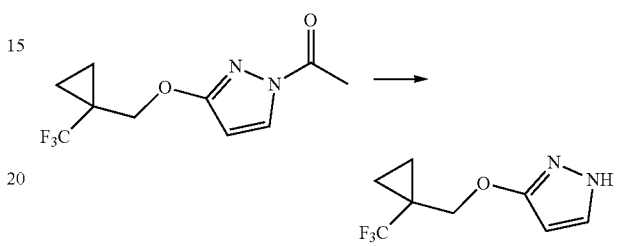

1-(3-((1-(Trifluoromethyl)cyclopropyl)methoxy)-1H-pyrazol-1-yl)ethan-1-one (695 mg, 2.80 mmol, 1.00 eq.) was dissolved in MeOH (30 mL). NaOH (aq., 3000, 421 mL, 560 mg, 4.20 mmol, 1.50 eq.) was added. The reaction mixture was stirred at room temperature overnight. Evaporation of the volatiles in vacuo gave a white solid (940 mg). The residue was partitioned between ethyl acetate (25 mL) and water (25 mL). The aqueous phase was extracted with ethyl acetate (2×25 mL). The combined organic phases were washed with brine (25 mL), dried over sodium sulfate, filtered and evaporated in vacuo to give 3-((1-(trifluoromethyl)cyclopropyl)methoxy)-1H-pyrazole (548 mg, 2.66 mmol, 95% yield) as a slightly yellow oil. $^1$H NMR (CDCl3): δ 9.10 (br, 1H), 7.36 (d, 1H), 5.77 (d, 1H), 4.29 (s, 2H), 1.14-1.08 (m, 2H), 0.96-0.89 (m, 2H). $^{19}$F NMR (CDCl3): δ −69.75.

Step E: tert-Butyl 2-chloro-6-[3-[[1-(trifluoromethyl)cyclopropyl]methoxy]pyrazol-1-yl]pyridine-3-carboxylate

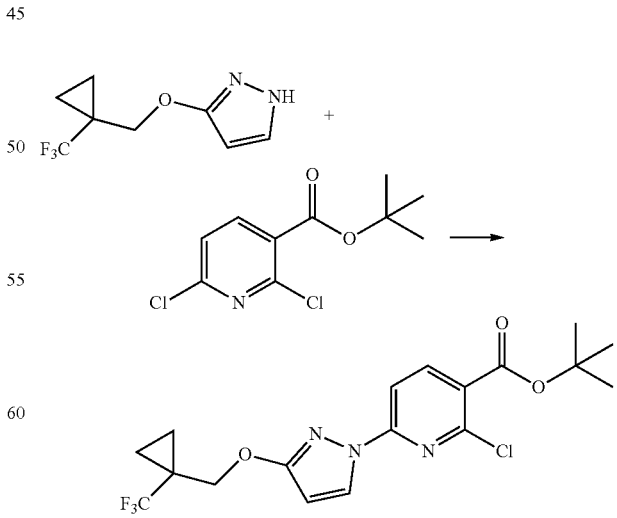

tert-Butyl 2,6-dichloropyridine-3-carboxylate (approximately 451.3 mg, 1.819 mmol), 3-[[1-(trifluoromethyl)cyclopropyl]methoxy]-1H-pyrazole (375 mg, 1.819 mmol), and potassium carbonate (approximately 301.7 mg, 2.183 mmol) (freshly ground) were combined in anhydrous DMSO (9.026 mL). 1,4-diazabicyclo[2.2.2]octane (approximately 40.81 mg, 0.3638 mmol) was added and the mixture was stirred at room temperature under nitrogen for 16 hours. The reaction mixture was diluted with ethyl acetate (10 mL) and water (2×5 mL) and the two phases were separated. The organics were washed with brine, dried over sodium sulfate and evaporated. The crude material was purified by silica gel chromatography eluting with 0-30% ethyl acetate in hexanes to give tert-butyl 2-chloro-6-[3-[[1-(trifluoromethyl)cyclopropyl]methoxy]pyrazol-1-yl]pyridine-3-carboxylate (620 mg, 82%) ESI-MS m % calc. 417.1067, found 418.1 (M+1)$^+$; Retention time: 0.85 minutes.

Step F: 2-Chloro-6-[3-[[1-(trifluoromethyl)cyclopropyl]methoxy]pyrazol-1-yl]pyridine-3-carboxylic acid

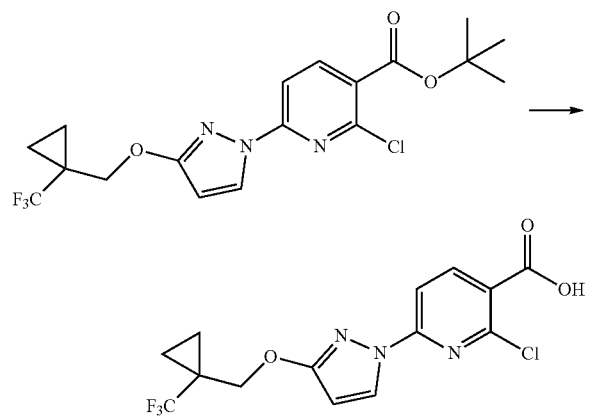

tert-Butyl 2-chloro-6-[3-[[1-(trifluoromethyl)cyclopropyl]methoxy]pyrazol-1-yl]pyridine-3-carboxylate (620 mg, 1.484 mmol) and TFA (approximately 1.692 g, 1.143 mL, 14.84 mmol) were combined in DCM (5 mL) and heated at 40° C. for 16 h. The reaction was evaporated to a white solid. Hexanes was added and the mixture was evaporated again to give 2-chloro-6-[3-[[1-(trifluoromethyl)cyclopropyl]methoxy]pyrazol-1-yl]pyridine-3-carboxylic acid (500 mg, 93%) ESI-MS m z calc. 361.0441, found 362.1 (M+1)$^+$; Retention time: 0.66 minutes.

Step G: 2-Chloro-N-(3-methoxyphenyl)sulfonyl-6-[3-[[1-(trifluoromethyl)cyclopropyl]methoxy]pyrazol-1-yl]pyridine-3-carboxamide

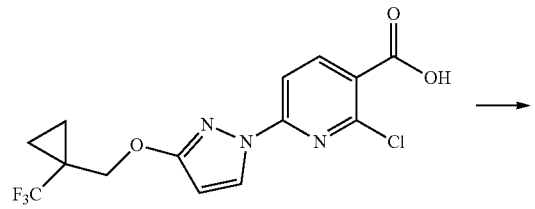

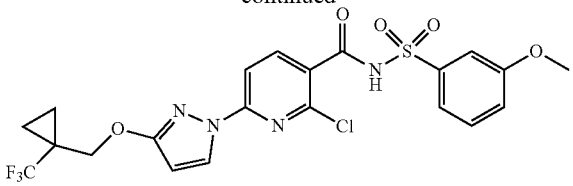

2-Chloro-6-[3-[[1-(trifluoromethyl)cyclopropyl]methoxy]pyrazol-1-yl]pyridine-3-carboxylic acid (200 mg, 0.55 mmol) and carbonyldiimidazole (110 mg, 0.66 mmol) were combined in THF (2 mL) and stirred at room temperature for 2 hours. 3-methoxybenzenesulfonamide (104 mg, 0.55 mmol) was added, followed by DBU (0.25 mL, 1.66 mmol) and the reaction mixture was stirred for 2 h at room temperature. The reaction mixture was diluted with 10 mL ethyl acetate, and washed with 10 mL 1M aqueous citric acid. The aqueous layer was extracted with ethyl acetate (2×10 mL), and the combined organics were washed with brine, dried over sodium sulfate, and concentrated under reduced pressure. The crude material was purified by silica gel chromatography eluting with a 0-10% gradient of methanol in dichloromethane to give 2-chloro-N-(3-methoxyphenyl)sulfonyl-6-[3-[[1-(trifluoromethyl)cyclopropyl]methoxy]pyrazol-1-yl]pyridine-3-carboxamide (217 mg, 74%) ESI-MS m/z calc. 530.06384, found 531.1 (M+1)$^+$; Retention time: 0.72 minutes.

Step H: N-(3-methoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

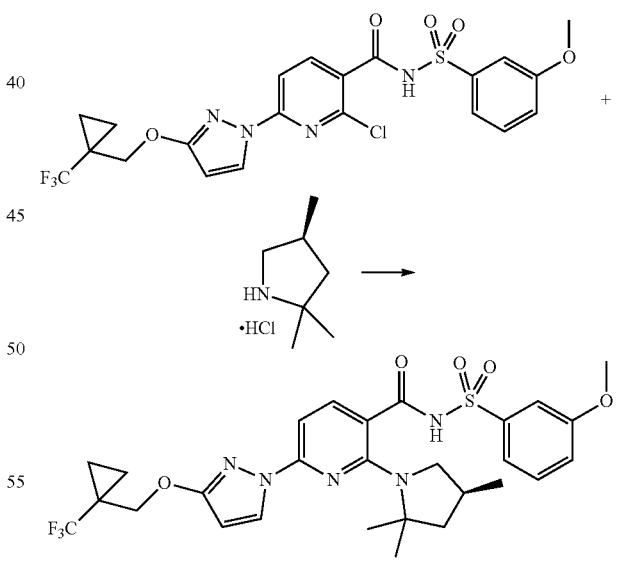

2-Chloro-N-(3-methoxyphenyl)sulfonyl-6-[3-[[1-(trifluoromethyl)cyclopropyl]methoxy]pyrazol-1-yl]pyridine-3-carboxamide (120 mg, 0.23 mmol), (4S)-2,2,4-trimethylpyrrolidine (hydrochloride salt) (107 mg, 0.71 mmol), and potassium carbonate (173 mg, 1.25 mmol) were combined in DMSO (600 µL) and heated at 130° C. for 16 h. The reaction was partitioned between ethyl acetate and water. The organics were separated, washed with a 1M citric acid solution, brine, dried over sodium sulfate and evaporated. The crude material was purified by silica gel chromatography eluting with 0-10% methanol in dichloromethane to give N-(3-methoxyphenyl)sulfonyl-6-[3-[[1-(trifluoromethyl)cyclopropyl]methoxy]pyrazol-1-yl]-2-[(4 S)-2,2,4-trimethylpyrrolidin-1-yl]pyridine-3-carboxamide (92 mg, 67%) ESI-MS m/z calc. 607.20764, found 608.3 (M+1)+; Retention time: 2.17 minutes. $^1$H NMR (400 MHz, DMSO-d6) δ 12.43 (s, 1H), 8.20 (d, J=2.8 Hz, 1H), 7.82 (d, J=8.2 Hz, 1H), 7.61-7.53 (m, 2H), 7.48-7.45 (m, 1H), 7.32-7.27 (m, 1H), 6.92 (d, J=8.2 Hz, 1H), 6.15 (d, J=2.8 Hz, 1H), 4.42-4.31 (m, 2H), 3.84 (s, 3H), 2.45 (d, J=10.5 Hz, 1H), 2.35-2.28 (m, 1H), 2.20-2.03 (m, 1H), 1.84 (dd, J=11.9, 5.6 Hz, 1H), 1.53 (d, J=10.9 Hz, 6H), 1.38 (t, J=12.1 Hz, 1H), 1.12-1.05 (m, 4H), 0.67 (d, J=6.2 Hz, 3H).

SYNTHETIC EXAMPLE 48

Synthesis of Compound 50: N-(2-fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(2-fluorophenyl)sulfonyl-6-[3-[[1-(trifluoromethyl)cyclopropyl]methoxy]pyrazol-1-yl]pyridine-3-carboxamide

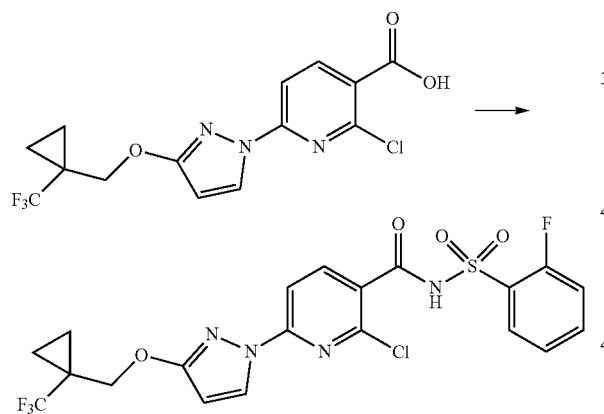

2-Chloro-6-[3-[[1-(trifluoromethyl)cyclopropyl]methoxy]pyrazol-1-yl]pyridine-3-carboxylic acid (181 mg, 0.5 mmol) and carbonyldiimidazole (97 mg, 0.6 mmol) were combined in THF (2.5 mL) and stirred at room temperature for 30 minutes. 2-fluorobenzenesulfonamide (114 mg, 0.65 mmol) was added, followed by DBU (0.09 mL, 0.6 mmol) and the reaction mixture was stirred for 3 h at room temperature. The reaction mixture was diluted with 10 mL ethyl acetate, and washed with 10 mL 1M aqueous citric acid. The organics were dried over sodium sulfate, and concentrated under reduced pressure. The crude material was purified by silica gel chromatography eluting with a 0-8% gradient of methanol in dichloromethane to give 2-chloro-N-(2-fluorophenyl)sulfonyl-6-[3-[[1-(trifluoromethyl)cyclopropyl]methoxy]pyrazol-1-yl]pyridine-3-carboxamide (180 mg, 69%) ESI-MS m/z calc. 518.0439, found 519.1 (M+1)+; Retention time: 0.70 minutes.

Step B: N-(2-fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

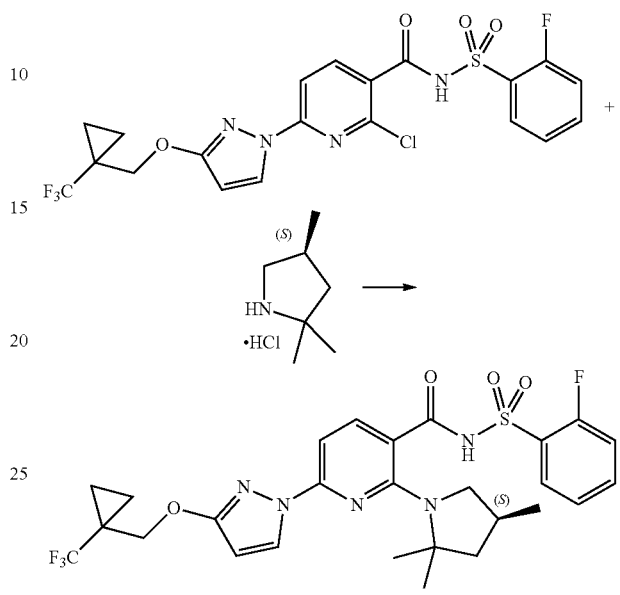

2-Chloro-N-(2-fluorophenyl)sulfonyl-6-[3-[[1-(trifluoromethyl)cyclopropyl]methoxy]pyrazol-1-yl]pyridine-3-carboxamide (78 mg, 0.15 mmol), (4S)-2,2,4-trimethylpyrrolidine (hydrochloride salt) (67 mg, 0.45 mmol), and potassium carbonate (124 mg, 0.9 mmol) were combined in DMSO (600 μL) and heated at 130° C. for 16 h. The reaction mixture was filtered and purified by LC/MS utilizing a gradient of 30-99% acetonitrile in 5 mM aq HCl to give N-(2-fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (28 mg, 31%) ESI-MS m/z calc. 595.1876, found 596.3 (M+1)+; Retention time: 2.08 minutes.

SYNTHETIC EXAMPLE 49

Synthesis of Compound 51: N-(3-Fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(3-fluorophenyl)sulfonyl-6-[3-[[1-(trifluoromethyl)cyclopropyl]methoxy]pyrazol-1-yl]pyridine-3-carboxamide

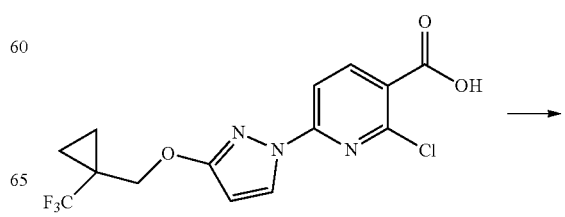

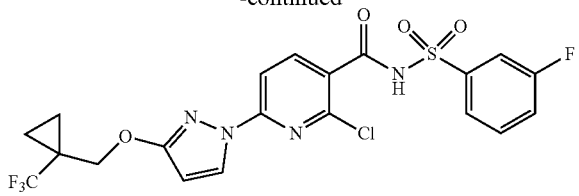

2-chloro-6-[3-[[1-(trifluoromethyl)cyclopropyl]methoxy]pyrazol-1-yl]pyridine-3-carboxylic acid (181 mg, 0.5 mmol) and carbonyldiimidazole (97 mg, 0.6 mmol) were combined in THF (2.5 mL) and stirred at room temperature for 30 minutes. 3-fluorobenzenesulfonamide (114 mg, 0.65 mmol) was added, followed by DBU (0.09 mL, 0.6 mmol) and the reaction mixture was stirred for 3 h at room temperature. The reaction mixture was diluted with 10 mL ethyl acetate, and washed with 10 mL 1M aqueous citric acid. The organics were dried over sodium sulfate, and concentrated under reduced pressure. The crude material was purified by silica gel chromatography eluting with a 0-8% gradient of methanol in dichloromethane to give 2-chloro-N-(3-fluorophenyl)sulfonyl-6-[3-[[1-(trifluoromethyl)cyclopropyl]methoxy]pyrazol-1-yl]pyridine-3-carboxamide (190 mg, 73%) ESI-MS m/z calc. 518.0439, found 519.1 (M+1)$^+$; Retention time: 0.72 minutes.

Step B: N-(3-Fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

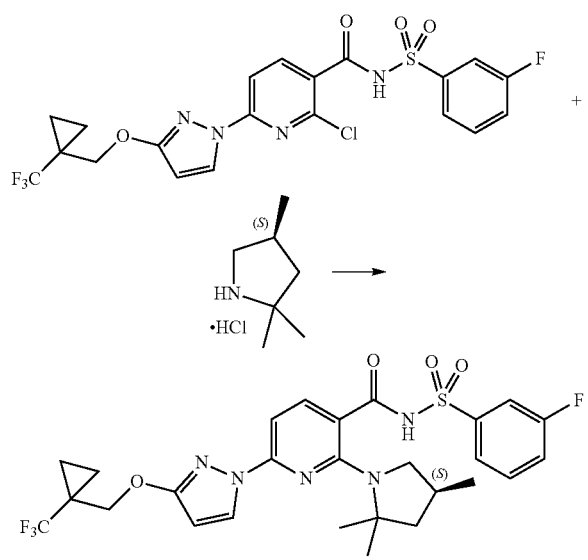

2-Chloro-N-(3-fluorophenyl)sulfonyl-6-[3-[[1-(trifluoromethyl)cyclopropyl]methoxy]pyrazol-1-yl]pyridine-3-carboxamide (78 mg, 0.15 mmol), (4S)-2,2,4-trimethylpyrrolidine (hydrochloride salt) (67 mg, 0.45 mmol), and potassium carbonate (124 mg, 0.9 mmol) were combined in DMSO (600 μL) and heated at 130° C. for 16 h. The reaction mixture was filtered and purified by LC-MS to give N-(3-fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (47 mg, 52%) ESI-MS m/z calc. 595.1876, found 596.3 (M+1)$^+$; Retention time: 2.14 minutes. 1H NMR (400 MHz, DMSO-d6) δ 8.21 (d, J=2.8 Hz, 1H), 7.90-7.82 (m, 2H), 7.80-7.69 (m, 2H), 7.68-7.59 (m, 1H), 6.93 (d, J=8.2 Hz, 1H), 6.15 (d, J=2.8 Hz, 1H), 4.43-4.27 (m, 2H), 2.44 (t, J=10.4 Hz, 1H), 2.30 (dd, J=10.2, 7.0 Hz, 1H), 2.23-2.08 (m, 1H), 1.84 (dd, J=11.9, 5.5 Hz, 1H), 1.53 (d, J=9.7 Hz, 6H), 1.39 (t, J=12.2 Hz, 1H), 1.17-1.02 (m, 4H), 0.69 (d, J=6.3 Hz, 3H).

SYNTHETIC EXAMPLE 50

Synthesis of Compound 52: N-(4-fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(4-fluorophenyl)sulfonyl-6-[3-[[1-(trifluoromethyl)cyclopropyl]methoxy]pyrazol-1-yl]pyridine-3-carboxamide

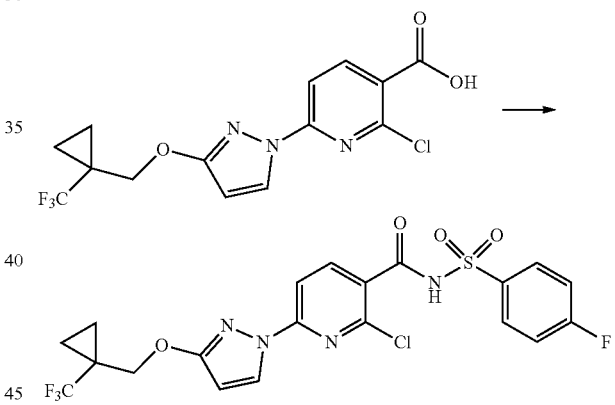

2-Chloro-6-[3-[[1-(trifluoromethyl)cyclopropyl]methoxy]pyrazol-1-yl]pyridine-3-carboxylic acid (181 mg, 0.5 mmol) and carbonyldiimidazole (97 mg, 0.6 mmol) were combined in THF (2.5 mL) and stirred at room temperature for 30 minutes. 4-fluorobenzenesulfonamide (114 mg, 0.65 mmol) was added, followed by DBU (0.09 mL, 0.6 mmol) and the reaction mixture was stirred for 3 h at room temperature. The reaction mixture was diluted with 10 mL ethyl acetate, and washed with 10 mL 1M aqueous citric acid. The organics were dried over sodium sulfate, and concentrated under reduced pressure. The crude material was purified by silica gel chromatography eluting with a 0-8% gradient of methanol in dichloromethane to give 2-chloro-N-(4-fluorophenyl)sulfonyl-6-[3-[[1-(trifluoromethyl)cyclopropyl]methoxy]pyrazol-1-yl]pyridine-3-carboxamide (160 mg, 62%) ESI-MS m/z calc. 518.0439, found 519.1 (M+1)$^+$; Retention time: 0.72 minutes.

Step B: N-(4-Fluorophenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

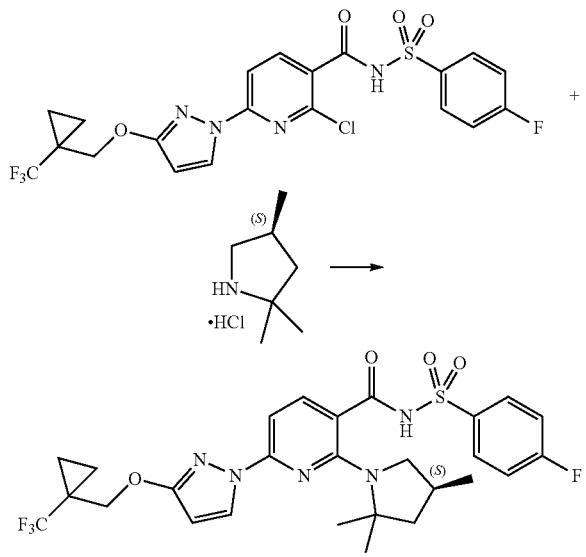

2-Chloro-N-(4-fluorophenyl)sulfonyl-6-[3-[[1-(trifluoromethyl)cyclopropyl]methoxy]pyrazol-1-yl]pyridine-3-carboxamide (78 mg, 0.15 mmol), (4S)-2,2,4-trimethylpyrrolidine (hydrochloride salt) (67 mg, 0.45 mmol), and potassium carbonate (124 mg, 0.9 mmol) were combined in DMSO (600 μL) and heated at 130° C. for 16 h. The reaction mixture was filtered and purified by LC/MS utilizing a gradient of 30-99% acetonitrile in 5 mM aq HCl to give N-(4-fluorophenyl)sulfonyl-6-[3-[[1-(trifluoromethyl)cyclopropyl]methoxy]pyrazol-1-yl]-2-[(4 S)-2,2,4-trimethylpyrrolidin-1-yl]pyridine-3-carboxamide (34 mg, 38%) ESI-MS m/z calc. 595.1876, found 596.3 (M+1)⁺; Retention time: 2.16 minutes. 1H NMR (400 MHz, DMSO-d6) δ 8.20 (d, J=2.8 Hz, 1H), 8.12-8.02 (m, 2H), 7.82 (d, J=8.3 Hz, 1H), 7.59-7.45 (m, 2H), 6.92 (d, J=8.2 Hz, 1H), 6.15 (d, J=2.7 Hz, 1H), 4.43-4.30 (m, 2H), 2.37 (t, J=10.4 Hz, 1H), 2.22 (dd, J=10.1, 7.0 Hz, 1H), 2.18-2.05 (m, 1H), 1.83 (dd, J=11.9, 5.5 Hz, 1H), 1.52 (d, J=8.8 Hz, 6H), 1.37 (t, J=12.1 Hz, 1H), 1.15-1.00 (m, 4H), 0.67 (d, J=6.3 Hz, 3H).

SYNTHETIC EXAMPLE 51

Synthesis of Compound 53: N-(2-methoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-chloro-N-(2-methoxyphenyl)sulfonyl-6-[3-[[1-(trifluoromethyl)cyclopropyl]methoxy]pyrazol-1-yl]pyridine-3-carboxamide

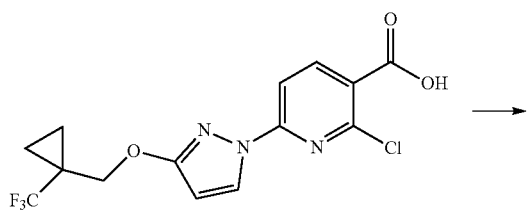

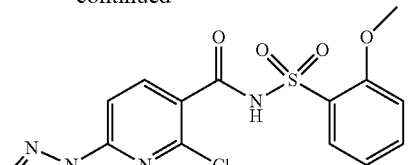

2-Chloro-6-[3-[[1-(trifluoromethyl)cyclopropyl]methoxy]pyrazol-1-yl]pyridine-3-carboxylic acid (200 mg, 0.55 mmol) and carbonyldiimidazole (110 mg, 0.66 mmol) were combined in THF (2 mL) and stirred at room temperature for 2 hours. 2-methoxybenzenesulfonamide (104 mg, 0.55 mmol) was added, followed by DBU (0.25 mL, 1.66 mmol) and the reaction mixture was stirred for 2 h at room temperature. The reaction mixture was diluted with 10 mL ethyl acetate, and washed with 10 mL 1M aqueous citric acid. The aqueous layer was extracted with ethyl acetate (2×10 mL), and the combined organics were washed with brine, dried over sodium sulfate, and concentrated under reduced pressure. The crude material was used without further purification. 2-Chloro-N-(2-methoxyphenyl)sulfonyl-6-[3-[[1-(trifluoromethyl)cyclopropyl]methoxy]pyrazol-1-yl]pyridine-3-carboxamide (286 mg, 97%) ESI-MS m/z calc. 530.06384, found 531.1 (M+1)⁺; Retention time: 0.70 minutes.

Step B: N-(2-methoxyphenyl)sulfonyl-6-[3-[[11-(trifluoromethyl)cyclopropyl]methoxy]pyrazol-1-yl]-2-[(4S)-2,2,4-trimethylpyrrolidin-1-yl]pyridine-3-carboxamide

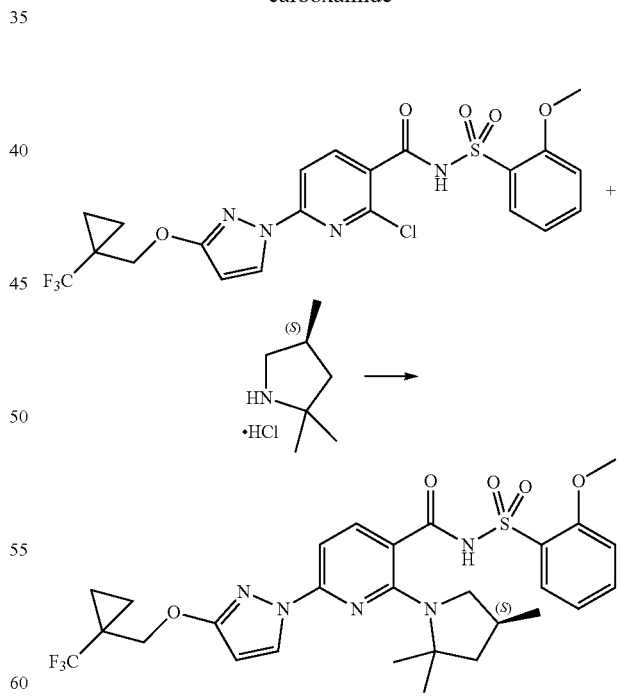

2-Chloro-N-(2-methoxyphenyl)sulfonyl-6-[3-[[1-(trifluoromethyl)cyclopropyl]methoxy]pyrazol-1-yl]pyridine-3-carboxamide (120 mg, 0.23 mmol), (4S)-2,2,4-trimethylpyrrolidine (hydrochloride salt) (107 mg, 0.71 mmol), and potassium carbonate (173 mg, 1.25 mmol) were combined in DMSO (600 µL) and heated at 130° C. for 16 h. The reaction was partitioned between ethyl acetate and water. The organics were separated, washed with a 1M citric acid solution, brine, dried over sodium sulfate and evaporated. The crude material was purified by silica gel chromatography eluting with 0-10% methanol in dichloromethane to give N-(2-methoxyphenyl)sulfonyl-6-[3-[[1-(trifluoromethyl)cyclopropyl]methoxy]pyrazol-1-yl]-2-[(4 S)-2,2,4-trimethylpyrrolidin-1-yl]pyridine-3-carboxamide (82 mg, 60%) ESI-MS m/z calc. 607.20764, found 608.3 (M+1)⁺; Retention time: 2.15 minutes.

SYNTHETIC EXAMPLE 52

Synthesis of Compound 54: N-(4-methoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide Step A: 2-Chloro-N-(4-methoxyphenyl)sulfonyl-6-[3-[[1-(trifluoromethyl)cyclopropyl]methoxy]pyrazol-1-yl]pyridine-3-carboxamide

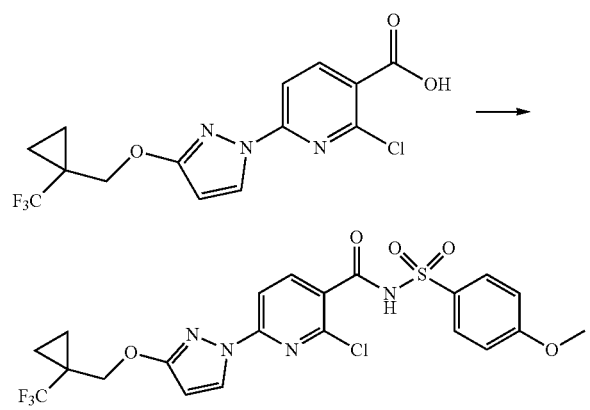

2-Chloro-6-[3-[[1-(trifluoromethyl)cyclopropyl]methoxy]pyrazol-1-yl]pyridine-3-carboxylic acid (300 mg, 0.83 mmol) and carbonyldiimidazole (162 mg, 1.0 mmol) were combined in THF (4 mL) and stirred at room temperature for 30 minutes. 4-Methoxybenzenesulfonamide (203 mg, 1.08 mmol) was added, followed by DBU (0.15 mL, 1.0 mmol) and the reaction mixture was stirred for 2 h at room temperature. The reaction mixture was diluted with 10 mL ethyl acetate, and washed with 10 mL 1M aqueous citric acid. The organics were dried over sodium sulfate and concentrated under reduced pressure. The crude material was purified by silica gel chromatography eluting with 0-8% methanol in dichloromethane to give 2-chloro-N-(4-methoxyphenyl)sulfonyl-6-[3-[[1-(trifluoromethyl)cyclopropyl]methoxy]pyrazol-1-yl]pyridine-3-carboxamide (430 mg, 97%) ESI-MS m/z calc. 530.06384, found 531.1 (M+1)⁺; Retention time: 0.71 minutes.

Step B: N-(4-Methoxyphenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

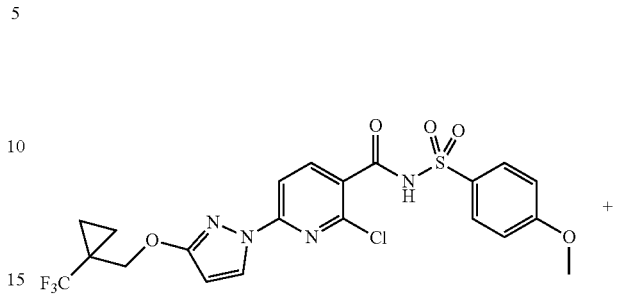

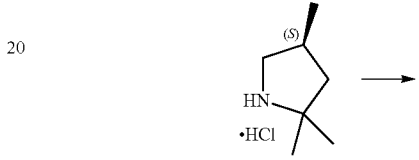

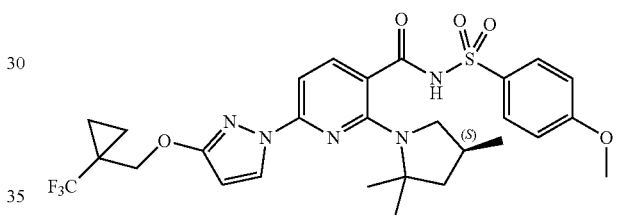

2-Chloro-N-(4-methoxyphenyl)sulfonyl-6-[3-[[1-(trifluoromethyl)cyclopropyl]methoxy]pyrazol-1-yl]pyridine-3-carboxamide (210 mg, 0.39 mmol), (4S)-2,2,4-trimethylpyrrolidine (hydrochloride salt) (180 mg, 1.2 mmol), and potassium carbonate (330 mg, 2.39 mmol) were combined in DMSO (2 mL) and heated at 130° C. for 15 h. The reaction was partitioned between ethyl acetate and water. The organics were separated, washed with a 1M citric acid solution, brine, dried over sodium sulfate and evaporated. The crude material was purified by silica gel chromatography eluting with 0-5% methanol in dichloromethane. The material was further purified by LC/MS utilizing a gradient of 30-99% acetonitrile in 5 mM aq HCl to yield N-(4-methoxyphenyl)sulfonyl-6-[3-[[1-(trifluoromethyl)cyclopropyl]methoxy]pyrazol-1-yl]-2-[(4 S)-2,2,4-trimethylpyrrolidin-1-yl]pyridine-3-carboxamide (25 mg, 10%) ESI-MS m/z calc. 607.20764, found 608.3 (M+1)⁺; Retention time: 2.16 minutes. 1H NMR (400 MHz, DMSO-d6) δ 8.19 (d, J=2.8 Hz, 1H), 7.99-7.87 (m, 2H), 7.77 (d, J=8.2 Hz, 1H), 7.26-7.10 (m, 2H), 6.91 (d, J=8.2 Hz, 1H), 6.14 (d, J=2.8 Hz, 1H), 4.44-4.28 (m, 2H), 3.84 (s, 3H), 2.40 (t, J=10.5 Hz, 1H), 2.29-2.21 (m, 1H), 2.16-2.00 (m, 1H), 1.82 (dd, J=11.9, 5.6 Hz, 1H), 1.52 (d, J=10.7 Hz, 6H), 1.37 (t, J=12.1 Hz, 1H), 1.16-1.02 (m, 4H), 0.64 (d, J=6.3 Hz, 3H).

SYNTHETIC EXAMPLE 53

Synthesis of Compound 55: N-(Benzenesulfonyl)-6-[3-[[1-(difluoromethyl)cyclopropyl]methoxy]pyrazol-1-yl]-2-[(4S)-2,2,4-trimethylpyrrolidin-1-yl]pyridine-3-carboxamide

Step A: tert-Butyl 3-((1-(difluoromethyl)cyclopropyl)methoxy)-1H-pyrazole-1-carboxylate

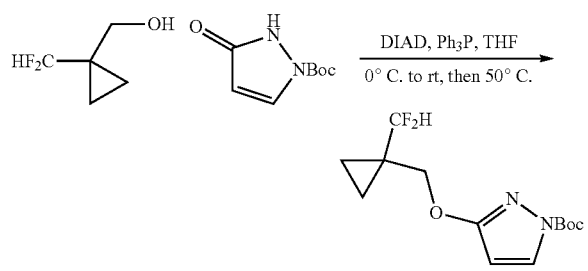

To the solution of (1-(difluoromethyl)cyclopropyl)methanol (867 mg, 7.11 mmol), tert-butyl 2,3-dihydro-3-oxopyrazole-1-carboxylate (1.19 g, 6.46 mmol), and triphenylphosphine (1.86 g, 7.11 mmol) in tetrahydrofuran (22 mL) at 0° C. was added diisopropyl azodicarboxylate (1.44 g, 7.11 mmol) dropwise. After the addition was complete, the reaction was allowed to warm to room temperature, then heated at 50° C. for 1 hour. The reaction solution was cooled to room temperature and ethyl acetate (300 mL) was added. The solution was then washed with aqueous sodium hydroxide (20 mL, 1M), water, brine and dried over magnesium sulfate, filtered and concentrated. The residue obtained was purified by silica gel chromatography (hexane and dichloromethane, 0 to 100% dichloromethane gradient) to afford tert-butyl 3-((1-(difluoromethyl)cyclopropyl) methoxy)-1H-pyrazole-1-carboxylate as a white solid (1.50 g, 80% yield). ESI-MS m/z calc. 288.1, found 289.2 (M+1)$^+$. Retention time: 3.08 minutes. $^1$H NMR (250 MHz, CDCl$_3$) δ (ppm): 7.84 (d, J=3.0 Hz, 1H), 5.97 (t, J=57.8 Hz, 1H), 5.89 (d, J=3.0 Hz, 1H), 4.32 (s, 2H), 1.61 (s, 9H), 0.97 (m, 2H), 0.75 (m, 2H).

Step B: 3-((1-(Difluoromethyl)cyclopropyl)methoxy)-1H-pyrazole

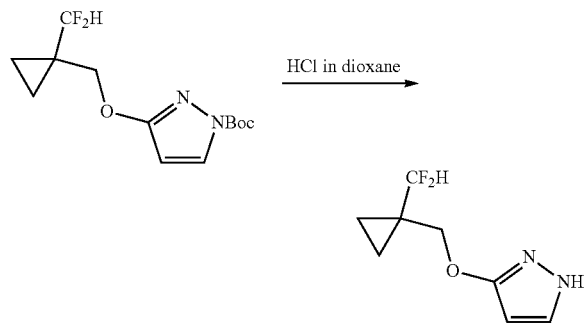

Cold hydrogen chloride solution (30 mL, 4.0M in 1,4-dioxane) was added to tert-butyl 3-((1-(difluoromethyl)cyclopropyl)methoxy)-1H-pyrazole-1-carboxylate (1.69 g, 5.88 mmol) in a round-bottom flask, and the reaction solution was warmed to room temperature and stirred for 3 hours. After removal of all the solvents under reduced pressure, the residue so obtained was partitioned between water (50 mL) and diethyl ether (80 mL). The organic layer was separated and the aqueous layer extracted with diethyl ether (2×80 mL). The combined organic layers were washed with brine (2×30 mL), dried over sodium sulfate, filtered and concentrated under reduced pressure. The residue so obtained was purified by silica gel chromatography (hexanes and ethyl acetate, 0 to 40% ethyl acetate gradient) to afford 3-((1-(difluoromethyl)cyclopropyl)methoxy)-1H-pyrazole as a white solid (997 mg, 90% yield). ESI-MS m/z calc. 188.1, found 189.1 (M+1)$^+$. Retention time: 1.94 minutes.

$^1$H NMR (250 MHz, DMSO) δ (ppm): 11.87 (s, 1H), 7.51 (m, 1H), 5.98 (t, J=57.0 Hz, 1H), 5.66 (m, 1H), 4.10 (s, 2H), 0.80 (m, 4H).

Step C: tert-butyl 2-chloro-6-[3-[[1-(difluoromethyl)cyclopropyl]methoxy]pyrazol-1-yl]pyridine-3-carboxylate

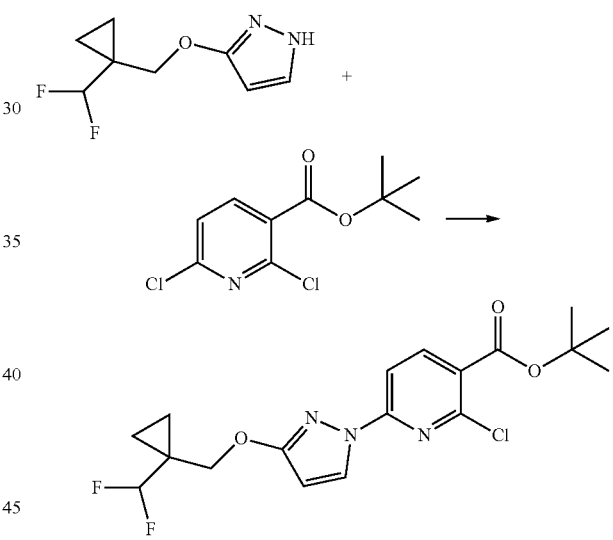

tert-Butyl 2,6-dichloropyridine-3-carboxylate (approximately 659.2 mg, 2.657 mmol), 3-[[1-(difluoromethyl)cyclopropyl]methoxy]-1H-pyrazole (500 mg, 2.657 mmol), and potassium carbonate (approximately 440.6 mg, 3.188 mmol) (freshly ground) were combined in anhydrous DMSO (13.18 mL). 1,4-diazabicyclo[2.2.2]octane (approximately 59.61 mg, 0.5314 mmol) was added and the mixture was stirred at room temperature under nitrogen for 16 hours. The reaction mixture was diluted with water (20 mL) and stirred for 15 min. The resulting solid was collected and washed with water. The solid was dissolved in dichloromethane and the small amount of aqueous layer removed. The organics were dried over sodium sulfate and evaporated to give tert-butyl 2-chloro-6-[3-[[1-(difluoromethyl)cyclopropyl]methoxy]pyrazol-1-yl]pyridine-3-carboxylate (842 mg, 79%). ESI-MS m/z calc. 399.11612, found 400.1 (M+1)$^+$; Retention time: 0.82 minutes.

Step D: 2-chloro-6-[3-[[1-(difluoromethyl)cyclopropyl]methoxy]pyrazol-1-yl]pyridine-3-carboxylic acid

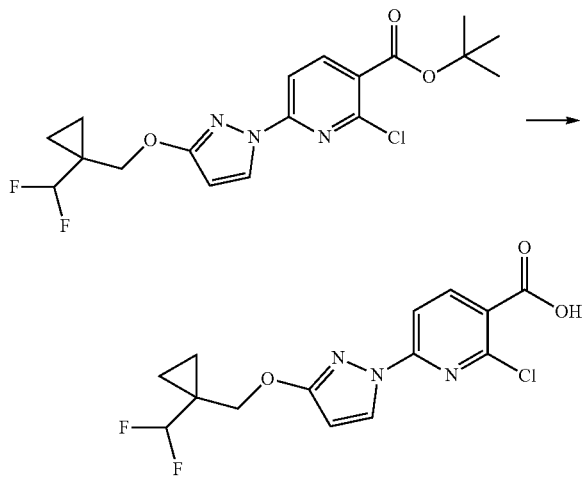

tert-Butyl 2-chloro-6-[3-[[1-(difluoromethyl)cyclopropyl]methoxy]pyrazol-1-yl]pyridine-3-carboxylate (842 mg, 2.106 mmol) and TFA (approximately 2.401 g, 1.622 mL, 21.06 mmol) were dissolved in dichloromethane (8.420 mL) and heated at 40° C. for 3 h. The reaction was evaporated and the resulting solid was triturated with hexanes and re-evaporated to give 2-chloro-6-[3-[[1-(difluoromethyl)cyclopropyl]methoxy]pyrazol-1-yl]pyridine-3-carboxylic acid (710 mg, 98%). ESI-MS m % z calc. 343.05353, found 344.1 (M+1)⁺; Retention time: 0.62 minutes. 1H NMR (400 MHz, DMSO-d6) δ 13.59 (s, 1H), 8.43 (d, J=2.9 Hz, 1H), 8.39 (d, J=8.4 Hz, 1H), 7.73 (d, J=8.4 Hz, 1H), 6.22 (d, J=2.9 Hz, 1H), 5.98 (t, J=56.4 Hz, 1H), 4.32 (s, 2H), 0.93-0.84 (m, 4H).

Step E: N-(Benzenesulfonyl)-2-chloro-6-[3-[[1-(difluoromethyl)cyclopropyl]methoxy]pyrazol-1-yl]pyridine-3-carboxamide

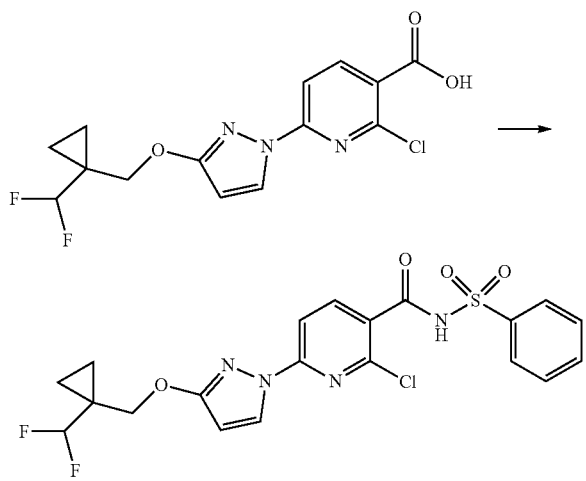

2-Chloro-6-[3-[[1-(difluoromethyl)cyclopropyl]methoxy]pyrazol-1-yl]pyridine-3-carboxylic acid (200 mg, 0.5819 mmol) and carbonyl diimidazole (approximately 113.2 mg, 0.6983 mmol) were combined in THF (2.5 mL) and stirred for 2 h. At this point, benzenesulfonamide (approximately 91.47 mg, 0.5819 mmol) was added followed by DBU (approximately 265.8 mg, 261.1 μL, 1.746 mmol) and the reaction was stirred for an additional 2 h at room temperature. A 1M citric acid solution (5 mL) was added and the reaction was stirred for 20 min. The solution was extracted with ethyl acetate. The organics were washed with brine, dried over sodium sulfate and evaporated. The crude material was purified by silica gel chromatography eluting with 0-10% methanol in dichloromethane to give N-(benzenesulfonyl)-2-chloro-6-[3-[[1-(difluoromethyl)cyclopropyl]methoxy]pyrazol-1-yl]pyridine-3-carboxamide (153.6 mg, 55%) ESI-MS m/z calc. 482.0627, found 483.1 (M+1)⁺; Retention time: 0.68 minutes.

Step F: N-(benzenesulfonyl)-6-[3-[[1-(difluoromethyl)cyclopropyl]methoxy]pyrazol-1-yl]-2-[(4S)-2,2,4-trimethylpyrrolidin-1-yl]pyridine-3-carboxamide

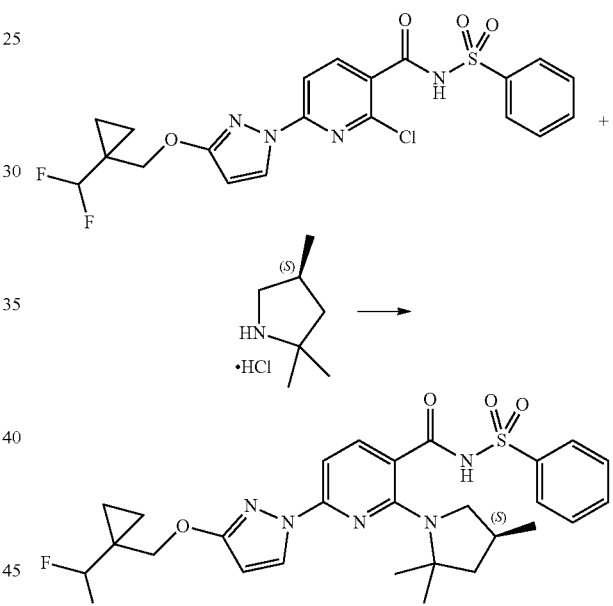

N-(Benzenesulfonyl)-2-chloro-6-[3-[[1-(difluoromethyl)cyclopropyl]methoxy]pyrazol-1-yl]pyridine-3-carboxamide (116 mg, 0.24 mmol), (4S)-2,2,4-trimethylpyrrolidine (hydrochloride salt) (71 mg, 0.63 mmol), and potassium carbonate (145 mg, 1.05 mmol) were combined in DMSO (600 μL) and heated at 130° C. for 16 h. The reaction was partitioned between ethyl acetate and water. The organics were separated, washed with a 1M citric acid solution, brine, dried over sodium sulfate and evaporated. The crude material was purified by silica gel chromatography eluting with 0-10% methanol in dichloromethane to give N-(benzenesulfonyl)-6-[3-[[1-(difluoromethyl)cyclopropyl]methoxy]pyrazol-1-yl]-2-[(4S)-2,2,4-trimethylpyrrolidin-1-yl]pyridine-3-carboxamide (87 mg, 65%) ESI-MS m/z calc. 559.2065, found 560.3 (M+1)⁺; Retention time: 2.06 minutes. 1H NMR (400 MHz, DMSO-d6) δ 12.47 (s, 1H), 8.19 (d, J=2.8 Hz, 1H), 8.00 (t, J=1.3 Hz, 1H), 7.98 (d, J=1.6 Hz, 1H), 7.80 (d, J=8.2 Hz, 1H), 7.76-7.70 (m, 1H), 7.65 (tt, J=6.8, 1.6 Hz, 2H), 6.91 (d, J=8.3 Hz, 1H), 6.13 (d, J=2.8 Hz, 2H), 4.32-4.23 (m, 2H), 2.47-2.37 (m, 1H), 2.28 (dd, J=10.3, 7.0 Hz, 1H), 2.09 (dq, J=11.9, 6.2 Hz, 1H), 1.82 (dd, J=11.9, 5.6 Hz, 1H), 1.52 (d, J=9.5 Hz, 6H), 1.36 (t, J=12.1 Hz, 1H), 0.87 (dt, J=5.1, 2.0 Hz, 4H), 0.65 (d, J=6.2 Hz, 3H).

SYNTHETIC EXAMPLE 54

Synthesis of Compound 56: N-(Benzenesulfonyl)-2-(2,2,4,4-tetramethylpyrrolidin-1-yl)-6-[3-[[1-(trifluoromethyl)cyclopropyl]methoxy]pyrazol-1-yl]pyridine-3-carboxamide Step A: N-(2,4,4-Trimethylpentan-2-yl)picolinamide

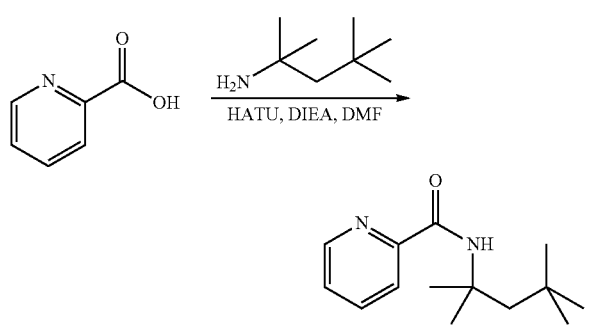

At 5° C., to picolinic acid (20.5 g, 167 mmol) in DMF (200 mL) was added HATU (65 g, 171 mmol, ~1.0 eq), followed by 2,4,4-trimethylpentan-2-amine (27.0 mL, ~1.0 eq), and then DIEA (65 mL, ~2.5 eq). The reaction was stirred at RT for 1.0 h. The reaction mixture was poured to ice-water (350 mL) and extracted with EtOAc (2×600 mL). The combined extract was washed with water (2×300 mL) and brine (150 mL), dried over Na$_2$SO$_4$, and concentrated to give crude product, which was purified by plug filtration through a pad of silica gel, eluted with 25% EtOAc in hexanes, giving a light yellow oil. N-(2,4,4-trimethylpentan-2-yl)picolinamide (36 g, 92%); MS [M+1]: 235.

Step B: Pyridin-2-yl(2,2,4,4-tetramethylpyrrolidin-1-yl)methanone

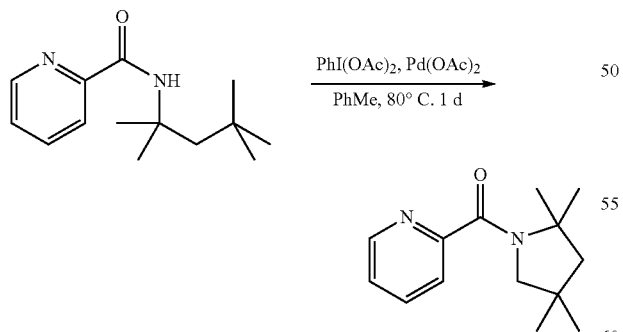

N-(2,4,4-trimethylpentan-2-yl)picolinamide (36.0 g, 153 mmol), Pd(OAc)2 (1.72 g, 5%), PhI(OAc)2 (99.2 g, 308 mmol) were mixed in toluene (600 mL) and heated at 80° C. overnight (~18 h). The reaction was concentrated to remove most of the toluene and the residue loaded to a silica gel column, eluted with 50% EtOAc in hexanes, resulting in a light yellow solid. pyridin-2-yl(2,2,4,4-tetramethylpyrrolidin-1-yl)methanone (32 g, 90%); MS [M+1]: 233. 1HNMR (250 MHz, CDCl3) 8.56 (d, J=4.8 Hz, 1H), 7.76 (td, J=7.7, 1.7 Hz, 1H), 7.61 (d, J=7.8 Hz, 1H), 7.35-7.25 (m, 1H), 3.36 (s, 2H), 1.79 (s, 2H), 1.67 (s, 6H), 1.08 (s, 6H)

Step C: 2,2,4,4-Tetramethylpyrrolidine (HCl salt)

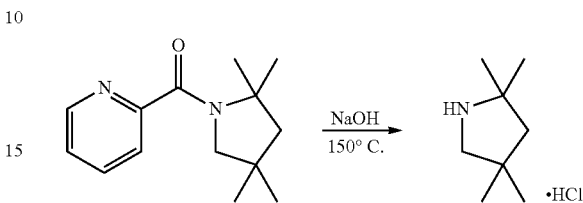

Pyridin-2-yl(2,2,4,4-tetramethylpyrrolidin-1-yl)methanone (6 g, 25.9 mmol) was dissolved in a mixture of NaOH (9.0 g, 225 mmol) in water (6 mL) and EtOH (18 mL) in a small pressure reactor (~45 mL) and heated at 140° C. for 48 h. The reaction was completed. The mixture was dissolved with 80 mL of water and extracted with Et$_2$O (3×200 mL). The extract was washed with water (2×100 mL) and dried over Mg$_2$SO$_4$. After filtering, HCl gas was bubbled through the filtrate for 5 min. An oil formed on the bottom of the flask. The top ether layer was decanted carefully, the remaining oil was washed with ether (2×30 mL) and the washing was decanted. The final oil was evaporated to give a white semi-solid, which was dried in a vacuum oven at 50° C. for 1 day, to give an off-white solid. 2,2,4,4-tetramethylpyrrolidine (HCl salt) (4.0 g, 95%). MS [M+1]: 128. 1HNMR (250 MHz, DMSO-d6) 9.39 (s, 2H), 3.01 (t, J=5.5 Hz, 2H), 1.69 (s, 2H), 1.40 (s, 6H), 1.16 (s, 6H).

Step D: N-(benzenesulfonyl)-2-(2,2,4,4-tetramethylpyrrolidin-1-yl)-6-[3-[[1-(trifluoromethyl)cyclopropyl]methoxy]pyrazol-1-yl]pyridine-3-carboxamide

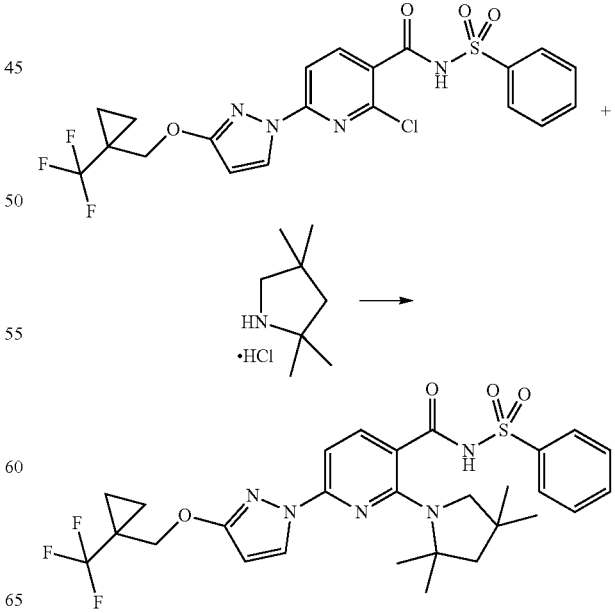

N-(Benzenesulfonyl)-2-chloro-6-[3-[[1-(trifluoromethyl) cyclopropyl]methoxy]pyrazol-1-yl]pyridine-3-carboxamide (100 mg, 0.2 mmol), 2,2,4,4-tetramethylpyrrolidine (hydrochloride salt) (98 mg, 0.6 mmol), and potassium carbonate (138 mg, 1.0 mmol) were combined in DMSO (500 µL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(benzenesulfonyl)-2-(2,2,4,4-tetramethylpyrrolidin-1-yl)-6-[3-[[1-(trifluoromethyl)cyclopropyl] methoxy]pyrazol-1-yl]pyridine-3-carboxamide (57 mg, 48%) ESI-MS m/z calc. 591.2127, found 592.2 (M+1)$^+$; Retention time: 2.20 minutes. 1H NMR (400 MHz, DMSO-d6) δ 12.52 (s, 1H), 8.20 (d, J=2.8 Hz, 1H), 8.04-7.97 (m, 2H), 7.82-7.72 (m, 2H), 7.72-7.63 (m, 2H), 6.94 (d, J=8.0 Hz, 1H), 6.14 (d, J=2.8 Hz, 1H), 4.36 (s, 2H), 2.38 (s, 2H), 1.72 (s, 2H), 1.58 (s, 6H), 1.14-1.04 (m, 4H), 0.81 (s, 6H).

SYNTHETIC EXAMPLE 55

Synthesis of Compound 57: N-(4-Methoxy-2-methyl-phenyl)sulfonyl-6-[3-[[1-(trifluoromethyl) cyclopropyl]methoxy]pyrazol-1-yl]-2-[(4S)-2,2,4-trimethylpyrrolidin-1-yl]pyridine-3-carboxamide Step A: 2-Chloro-N-(4-methoxy-2-methyl-phenyl) sulfonyl-6-[3-[[1-(trifluoromethyl)cyclopropyl] methoxy]pyrazol-1-yl]pyridine-3-carboxamide

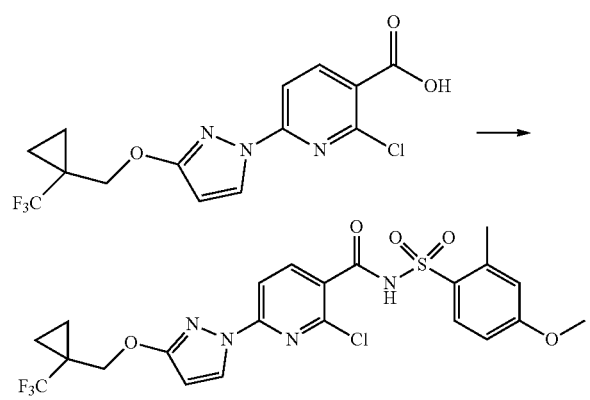

2-Chloro-6-[3-[[1-(trifluoromethyl)cyclopropyl] methoxy]pyrazol-1-yl]pyridine-3-carboxylic acid (150 mg, 0.4023 mmol) and carbonyl diimidazole (82 mg, 0.5057 mmol) were combined in THF (1.299 mL) and stirred for 2 h. At this point, 4-methoxy-2-methyl-benzenesulfonamide (85 mg, 0.4224 mmol) was added followed by DBU (200 µL, 1.337 mmol) and the reaction was stirred for an additional 2 h at room temperature. The reaction was diluted with ethyl acetate and washed with a 1M citric acid solution, followed by brine. The organics were separated, dried over sodium sulfate, and evaporated to give 2-chloro-N-(4-methoxy-2-methyl-phenyl)sulfonyl-6-[3-[[1-(trifluoromethyl)cyclopropyl]methoxy]pyrazol-1-yl]pyridine-3-carboxamide (205 mg, 94%) ESI-MS min calc. 544.0795, found 545.0 (M+1)$^+$; Retention time: 0.73 minutes.

Step B: N-(4-Methoxy-2-methyl-phenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide

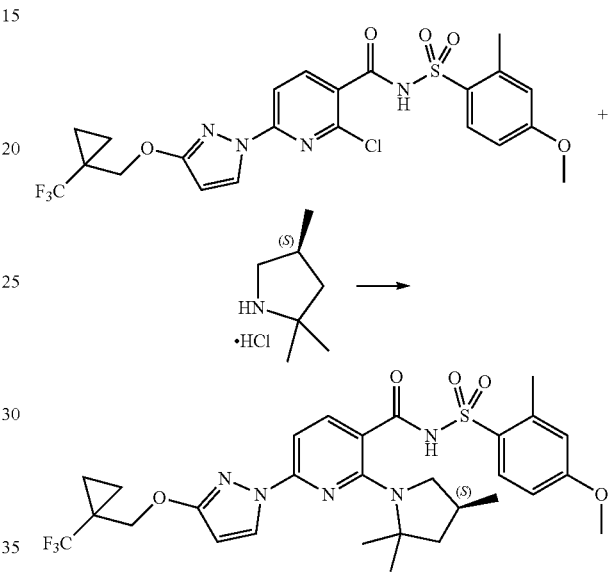

2-Chloro-N-(4-methoxy-2-methyl-phenyl)sulfonyl-6-[3-[[1-(trifluoromethyl)cyclopropyl]methoxy]pyrazol-1-yl] pyridine-3-carboxamide (100 mg, 0.18 mmol), (4S)-2,2,4-trimethylpyrrolidine (hydrochloride salt) (90 mg, 0.6 mmol), and potassium carbonate (138 mg, 1.0 mmol) were combined in DMSO (500 µL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(4-methoxy-2-methyl-phenyl)sulfonyl-6-[3-[[1-(trifluoromethyl)cyclopropyl]methoxy]pyrazol-1-yl]-2-[(4S)-2,2,4-trimethylpyrrolidin-1-yl]pyridine-3-carboxamide (75 mg, 67%) ESI-MS m/z calc. 621.22327, found 622.3 (M+1)$^+$; Retention time: 2.23 minutes. 1H NMR (400 MHz, DMSO-d6) δ 12.46 (s, 1H), 8.20 (d, J=2.8 Hz, 1H), 7.98 (d, J=8.7 Hz, 1H), 7.78 (d, J=8.3 Hz, 1H), 7.01-6.94 (m, 2H), 6.92 (d, J=8.2 Hz, 1H), 6.14 (d, J=2.7 Hz, 1H), 4.41-4.32 (m, 2H), 3.82 (s, 3H), 2.59 (s, 3H), 2.41-2.29 (m, 2H), 2.22-2.10 (m, 1H), 1.82 (dd, J=11.9, 5.6 Hz, 1H), 1.52 (s, 6H), 1.36 (t, J=12.1 Hz, 1H), 1.12-1.06 (m, 4H), 0.70 (d, J=6.2 Hz, 3H).

SYNTHETIC EXAMPLE 56

Synthesis of Compound 58: N-(o-Tolylsulfonyl)-6-[3-[[1-(trifluoromethyl)cyclobutyl]methoxy]pyrazol-1-yl]-2-[(4S)-2,2,4-trimethylpyrrolidin-1-yl]pyridine-3-carboxamide Step A: 2-Chloro-N-(o-tolylsulfonyl)-6-[3-[[1-(trifluoromethyl)cyclobutyl methoxy]pyrazol-1-yl]pyridine-3-carboxamide

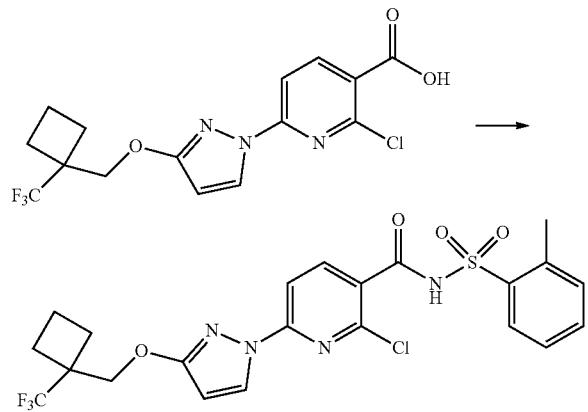

2-Chloro-6-[3-[[1-(trifluoromethyl)cyclobutyl]methoxy]pyrazol-1-yl]pyridine-3-carboxylic acid (150 mg, 0.3992 mmol) and carbonyl diimidazole (approximately 81.69 mg, 0.5038 mmol) were combined in THF (1.339 mL) and stirred for 2 h. At this point, 2-methylbenzenesulfonamide (approximately 71.77 mg, 0.4192 mmol) was added, followed by DBU (approximately 202.6 mg, 199.0 µL, 1.331 mmol) and the reaction was stirred for an additional 2 h at room temperature. The reaction was diluted with ethyl acetate and washed with a 1 M citric acid solution, followed by brine. The organics were separated, dried over sodium sulfate, and evaporated to give 2-chloro-N-(o-tolylsulfonyl)-6-[3-[[1-(trifluoromethyl)cyclobutyl]methoxy]pyrazol-1-yl]pyridine-3-carboxamide (208 mg, 99%) ESI-MS m/z calc. 528.0846, found 529.0 (M+1)$^+$; Retention time: 0.77 minutes Step B: N-(o-tolylsulfonyl)-6-[3-[[1-(trifluoromethyl)cyclobutyl]methoxy]pyrazol-1-yl]-2-[(4S)-2,2,4-trimethylpyrrolidin-1-yl]pyridine-3-carboxamide

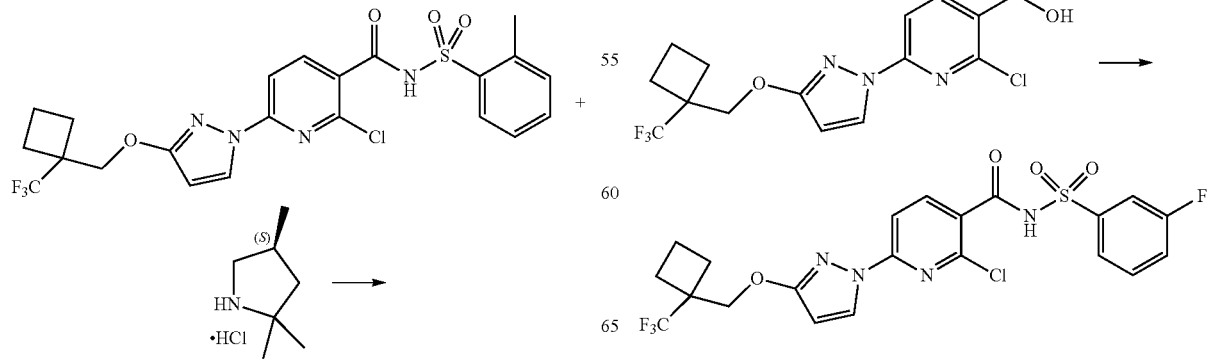

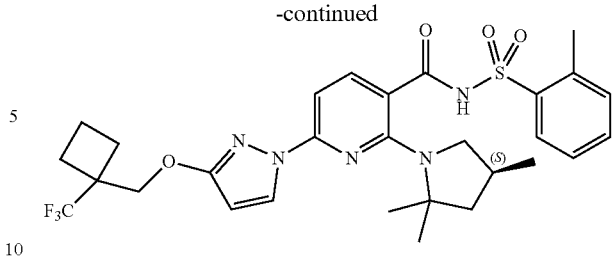

2-Chloro-N-(o-tolylsulfonyl)-6-[3-[[1-(trifluoromethyl)cyclobutyl]methoxy]pyrazol-1-yl]pyridine-3-carboxamide (100 mg, 0.19 mmol), (4S)-2,2,4-trimethylpyrrolidine (hydrochloride salt) (90 mg, 0.6 mmol), and potassium carbonate (138 mg, 1.0 mmol) were combined in DMSO (500 µL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(o-tolylsulfonyl)-6-[3-[[1-(trifluoromethyl)cyclobutyl]methoxy]pyrazol-1-yl]-2-[(4S)-2,2,4-trimethylpyrrolidin-1-yl]pyridine-3-carboxamide (69 mg, 60%) ESI-MS m/z calc. 605.22833, found 606.5 (M+1)$^+$; Retention time: 2.33 minutes. 1H NMR (400 MHz, DMSO-d6) δ 12.63 (s, 1H), 8.22 (d, J=2.8 Hz, 1H), 8.04 (d, J=7.9 Hz, 1H), 7.82 (d, J=8.2 Hz, 1H), 7.59 (td, J=7.5, 1.5 Hz, 1H), 7.49-7.40 (m, 2H), 6.96 (d, J=8.3 Hz, 1H), 6.18 (d, J=2.7 Hz, 1H), 4.48 (s, 2H), 2.63 (s, 3H), 2.39 (d, J=8.8 Hz, 2H), 2.35-2.23 (m, 2H), 2.21-2.04 (m, 4H), 2.02-1.91 (m, 1H), 1.83 (dd, J=11.9, 5.6 Hz, 1H), 1.53 (s, 6H), 1.35 (t, J=12.1 Hz, 1H), 0.69 (d, J=6.2 Hz, 3H).

SYNTHETIC EXAMPLE 57

Synthesis of Compound 59: N-(3-Fluorophenyl)sulfonyl-6-[3-[[1-(trifluoromethyl)cyclobutyl]methoxy]pyrazol-1-yl]-2-[(4S)-2,2,4-trimethylpyrrolidin-1-yl]pyridine-3-carboxamide Step A: 2-Chloro-N-(3-fluorophenyl)sulfonyl-6-[3-[[1-(trifluoromethyl)cyclobutyl]methoxy]pyrazol-1-yl]pyridine-3-carboxamide

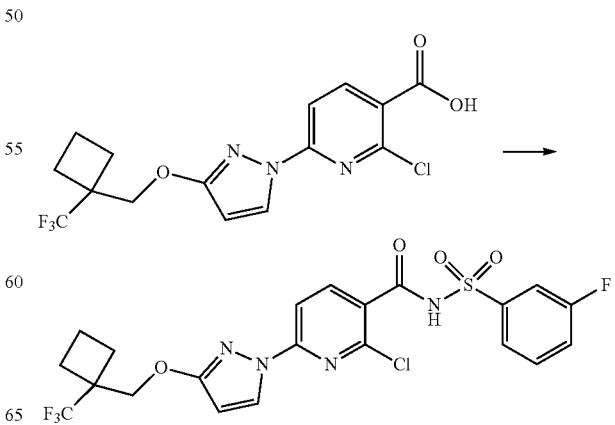

2-Chloro-6-[3-[[1-(trifluoromethyl)cyclobutyl]methoxy] pyrazol-1-yl]pyridine-3-carboxylic acid (150 mg, 0.3992 mmol) and carbonyl diimidazole (approximately 81.69 mg, 0.5038 mmol) were combined in THF (1.339 mL) and stirred for 2 h. At this point, 3-fluorobenzenesulfonamide (approximately 69.93 mg, 0.3992 mmol) was added followed by DBU (approximately 202.6 mg, 199.0 µL, 1.331 mmol) and the reaction was stirred for an additional 2 h at room temperature. The reaction was diluted with ethyl acetate and washed with a 1M citric acid solution, followed by brine. The organics were separated, dried over sodium sulfate, and evaporated to give 2-chloro-N-(3-fluorophenyl) sulfonyl-6-[3-[[1-(trifluoromethyl)cyclobutyl]methoxy] pyrazol-1-yl]pyridine-3-carboxamide (210 mg, 99%) ESI-MS m/z calc. 532.0595, found 533.0 (M+1)+; Retention time: 0.77 minutes.

Step B: N-(3-Fluorophenyl)sulfonyl-6-[3-[[1-(trifluoromethyl)cyclobutyl]methoxy]pyrazol-1-yl]-2-(4S)-2,2,4-trimethylpyrrolidin-1-yl]pyridine-3-carboxamide

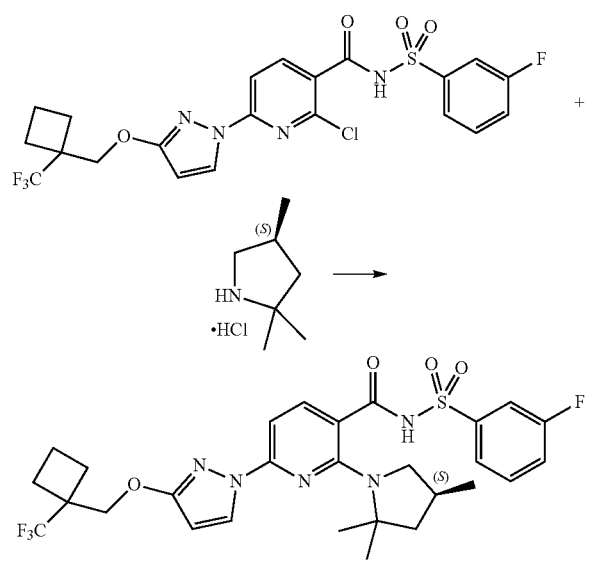

2-Chloro-N-(3-fluorophenyl)sulfonyl-6-[3-[[1-(trifluoromethyl)cyclobutyl]methoxy]pyrazol-1-yl]pyridine-3-carboxamide (100 mg, 0.19 mmol), (4S)-2,2,4-trimethylpyrrolidine (hydrochloride salt) (90 mg, 0.6 mmol), and potassium carbonate (138 mg, 1.0 mmol) were combined in DMSO (500 µL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(3-fluorophenyl)sulfonyl-6-[3-[[1-(trifluoromethyl)cyclobutyl]methoxy]pyrazol-1-yl]-2-[(4S)-2,2,4-trimethylpyrrolidin-1-yl]pyridine-3-carboxamide (73 mg, 63%) ESI-MS m/z calc. 609.2033, found 610.2 (M+1)+; Retention time: 2.27 minutes. 1H NMR (400 MHz, DMSO-d6) δ 12.63 (s, 1H), 8.22 (d, J=2.8 Hz, 1H), 7.86 (d, J=2.3 Hz, 1H), 7.84 (d, J=2.0 Hz, 1H), 7.78-7.70 (m, 2H), 7.66-7.59 (m, 1H), 6.96 (d, J=8.2 Hz, 1H), 6.18 (d, J=2.7 Hz, 1H), 4.48 (s, 2H), 2.43 (d, J=10.4 Hz, 1H), 2.35-2.25 (m, 3H), 2.19-2.05 (m, 4H), 1.96 (td, J=10.0, 5.3 Hz, 1H), 1.84 (dd, J=11.8, 5.6 Hz, 1H), 1.55 (s, 3H), 1.52 (s, 3H), 1.40 (t, J=12.2 Hz, 1H), 0.69 (d, J=6.2 Hz, 3H).

SYNTHETIC EXAMPLE 58

Synthesis of Compound 60: N-(Benzenesulfonyl)-6-[3-(spiro[2.2]pentan-2-ylmethoxy)pyrazol-1-yl]-2-[(4S)-2,2,4-trimethylpyrrolidin-1-yl]pyridine-3-carboxamide Step A: spiro[2.2]Pent-1-yl-methanol

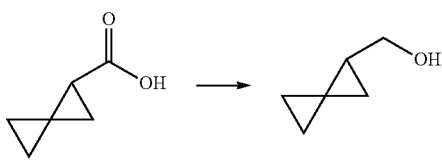 [SMILES: O=C(O)C1CC12CC2 ; OCC1CC12CC2]

To a suspension of lithium aluminum hydride (888 mg, 23.4 mmol) in tetrahydrofuran (30 mL) was added spiro [2.2]pentane-1-carboxylic acid (1.75 g, 15.6 mmol) in tetrahydrofuran (5 mL) dropwise over 5 minutes. The reaction was heated to 50° C. for 16 hours. The reaction was diluted with diethyl ether (20 mL) and quenched with solid sodium sulfate decahydrate. The mixture was diluted with diethyl ether (100 mL), filtered through celite pad and concentrated to give spiro[2.2]pent-1-yl-methanol (793 mg, 52%) as an oil. ESI-MS m/z calc. 98.15 found 98.8 (M+1)+. Retention time: 2.54 minutes. 1H NMR (250 MHz, CDCl3) ppm 0.58-0.89 (m, 4H) 0.91-1.09 (m, 1H) 1.20-1.37 (m, 1H) 1.43 (m, 1H) 3.60 (dd, J=11.98, 6.37 Hz, 2H)

Step B: 3-(spiro[2.2]Pent-1-ylmethoxy)-pyrazole-1-carboxylic acid tert-butyl ester

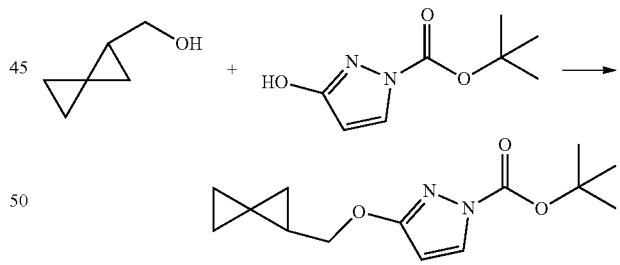

To a solution of crude spiro[2.2]pent-1-yl-methanol (966 mg, 9.8 mmol) in tetrahydrofuran (40 mL) was added triphenyl phosphine (2.58 g, 9.8 mmol), 3-hydroxy-pyrazole-1-carboxylic acid tert-butyl ester (1.64 g, 8.9 mmol). The reaction mixture was cooled in an ice bath followed by the addition of diisopropyl azodicarboxylate (1.9 mL, 9.8 mmol). The ice bath was removed and the reaction was stirred for 2 hours. The solvent was removed in vacuum and the crude mixture was purified by silica gel column chromatography using 10-20% hexanes-diethyl ether to give 3-(spiro[2.2]pent-1-ylmethoxy)-pyrazole-1-carboxylic acid tert-butyl ester (1.20 g, 44%) as a clear oil. ESI-MS m/z calc. 264.33 found 265.1 (M+1)+. Retention time: 3.36 minutes

Step C: 3-(spiro[2.2]Pent-1-ylmethoxy)-1H-pyrazole

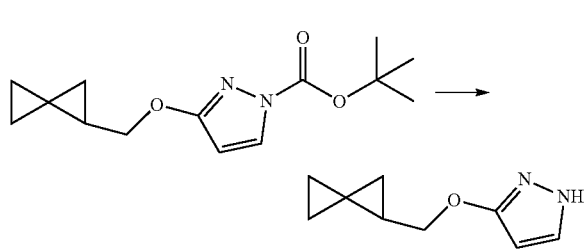

To 3-(spiro[2.2]pent-1-ylmethoxy)-pyrazole-1-carboxylic acid tert-butyl ester (1.2 g, 4.54 mmol) was added dichloromethane (30 mL) and trifluoroacetic acid (3.4 mL, 45 mmol). The reaction mixture was stirred for 2 hours at room temperature and concentrated to dryness in vacuum. The residue was azeotroped twice with 1,2-dichloroethane (15 mL) to give crude 3-(spiro[2.2]pent-1-ylmethoxy)-1H-pyrazole (1.87 g, 51%) as a yellow oil. ESI-MS m/z calc. 164.09 found 164.6 (M+1)+. Retention time: 2.11 minutes

Step D: 2-Chloro-6-[3-(spiro[2.2]pent-1-ylmethoxy) pyrazol-1-yl]-nicotinic acid methyl ester

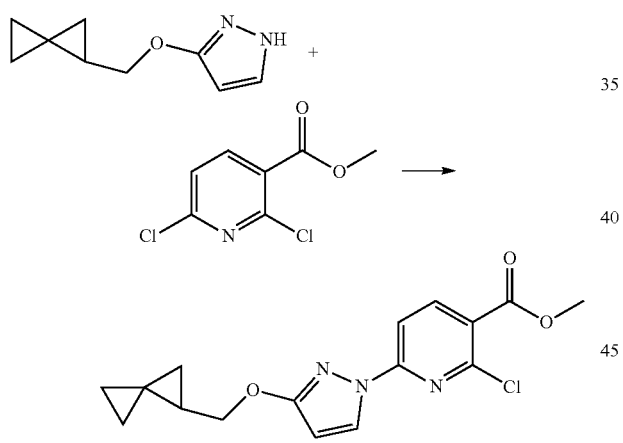

To crude 3-(spiro[2.2]pent-1-ylmethoxy)-1H-pyrazole (1.87 g, assumed 4.54 mmol) was added methyl 2,6-dichloronicotinate (935 mg, 4.54 mmol), 1,4-diazabicyclo[2.2.2]octane (102 mg, 0.91 mmol), dimethylformamide (8 mL) and potassium carbonate (1.9 g, 13.6 mmol). The reaction was stirred for 48 hours at room temperature, diluted with diethyl ether (75 mL) and washed with water containing a small amount of brine (3×50 mL) and brine (50 mL). This organic layer was dried over sodium sulfate and concentrated in vacuum. The crude reaction mixture was purified by silica gel column chromatography using 0-15% hexanes:diethyl ether to afford 2-chloro-6-[3-(spiro[2.2]pent-1-ylmethoxy) pyrazol-1-yl]-nicotinic acid methyl ester (1.02 g, 67%) as an off-white solid. ESI-MS m/z calc. 333.09 found 333.9 (M+1)+. Retention time: 3.85 minutes.

Step E: 2-Chloro-6-[3-(spiro[2.2]pent-1-ylmethoxy)-pyrazol-1-yl]-nicotinic acid

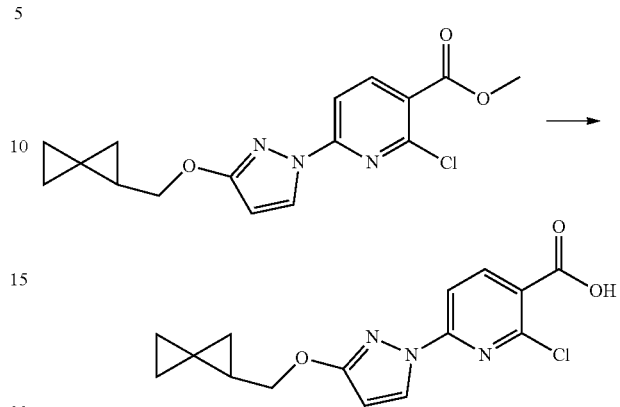

To 2-Chloro-6-[3-(spiro[2.2]pent-1-ylmethoxy) pyrazol-1-yl]-nicotinic acid methyl ester (990 mg, 2.97 mmol) was added water (6 mL), methanol (6 mL) and tetrahydrofuran (6 mL) followed by lithium hydroxide (285 mg, 11.88 mmol). The reaction was stirred for 1 hour and 1M hydrochloric acid (12 mL) was added. Formed white solid was filtered off, washed with water and hexanes to give 2-chloro-6-[3-(spiro[2.2]pent-1-ylmethoxy)-pyrazol-1-yl]-nicotinic acid (927 mg, 98%) as a white solid. ESI-MS m/z calc. 319.07 found 320.0 (M+1)+. Retention time: 3.25 minutes 1H NMR (250 MHz, CDCl3) ppm: 0.76-0.88 (m, 5H), 1.11-1.13 (m, 1H), 1.60-1.75 (m, 1H), 4.22 (dd, J=7.0, 3.3, Hz, 2H) 6.00 (d, J=2.5 Hz, 1H), 7.76 (d, J=8.5 Hz, 1H), 8.38 (d, J=2.5 Hz, 1H), 8.43 (d, J=8.5 Hz, 1H).

Step F: N-(benzenesulfonyl)-2-chloro-6-[3-(spiro[2.2]pentan-2-ylmethoxy)pyrazol-1-yl]pyridine-3-carboxamide

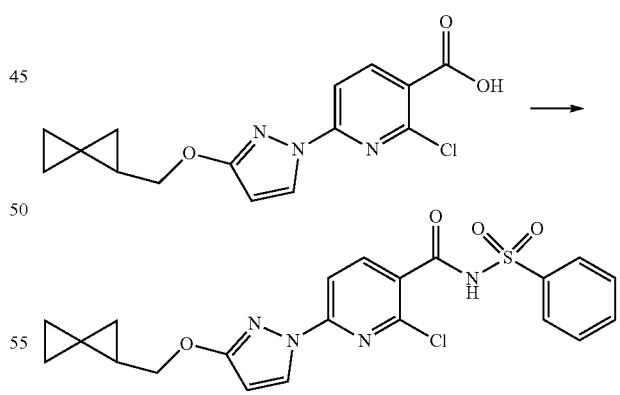

2-Chloro-6-[3-(spiro[2.2]pentan-2-ylmethoxy)pyrazol-1-yl]pyridine-3-carboxylic acid (50 mg, 0.16 mmol) and carbonyl diimidazole (38 mg, 0.23 mmol) were combined in THF (1.5 mL) and stirred for 2 h. At this point, benzenesulfonamide (25 mg, 0.16 mmol) was added followed by DBU (70 µL, 0.47 mmol) and the reaction was stirred for an additional 2 h at room temperature. The reaction was diluted with ethyl acetate and washed with a 1M citric acid solution, followed by brine. The organics were separated, dried over

265 sodium sulfate, and evaporated to give N-(benzenesulfonyl)-2-chloro-6-[3-(spiro[2.2]pentan-2-ylmethoxy)pyrazol-1-yl]pyridine-3-carboxamide (72 mg, 98%) ESI-MS m/z calc. 458.08154, found 459.2 (M+1)⁺; Retention time: 0.75 minutes.

Step G: N-(benzenesulfonyl)-6-[3-(spiro[2.2 pentan-2-ylmethoxy)pyrazol-1-yl]-2-[(4S)-2,2,4-trimethyl-pyrrolidin-1-yl]pyridine-3-carboxamide

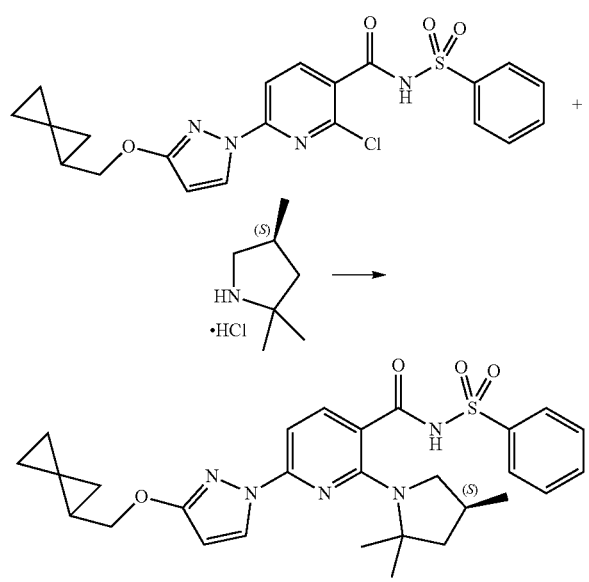

N-(benzenesulfonyl)-2-chloro-6-[3-(spiro[2.2]pentan-2-ylmethoxy)pyrazol-1-yl]pyridine-3-carboxamide (72 mg, 0.16 mmol), (4S)-2,2,4-trimethylpyrrolidine (hydrochloride salt) (63 mg, 0.42 mmol), and potassium carbonate (97 mg, 0.7 mmol) were combined in DMSO (1 mL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(benzenesulfonyl)-6-[3-(spiro[2.2]pentan-2-ylmethoxy)pyrazol-1-yl]-2-[(4S)-2,2,4-trimethylpyrrolidin-1-yl]pyridine-3-carboxamide (38 mg, 45%) ESI-MS m/z calc. 535.22534, found 536.1 (M+1)⁺; Retention time: 2.22 minutes.

SYNTHETIC EXAMPLE 59

Synthesis of Compound 61: (5S)-7-(benzenesulfonyl)-3,3,5-trimethyl-2-(3-{2-[1-(trifluoromethyl)cyclopropyl]ethoxy)-1H-pyrazol-1-yl)-2,7,13-triazatricyclo[7.4.0.02,6]trideca-1(9),10,12-trien-8-one

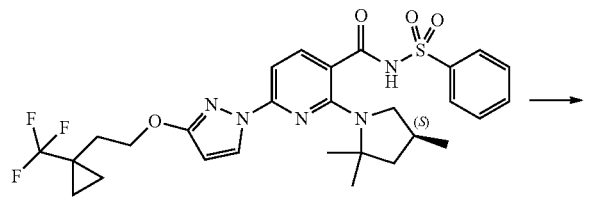

266

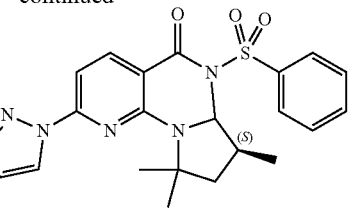

N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (52 mg, 0.08789 mmol), NaOAc (14 mg, 0.1707 mmol), water (16 μL, 0.89 mmol), and [Ir{dF(CF3)ppy}2 (dtbpy)]PF6 (5 mg, 0.004 mmol) were combined in DMA (dimethylacetamide) (0.9 μL) and the reaction mixture was placed next to a 23 W CFL light source for 1.5 h. The reaction was injected directly onto a silica gel column without any workup. The crude mixture was purified by silica gel chromatography eluting with 0-100% ethyl acetate in hexanes to give (5S)-7-(benzenesulfonyl)-3,3,5-trimethyl-12-(3-{2-[1-(trifluoromethyl)cyclopropyl]ethoxy}-1H-pyrazol-1-yl)-2,7,13-triazatricyclo[7.4.0.02,6]trideca-1(9),10,12-trien-8-one (10 mg, 19%) ESI-MS m/z calc. 589.1971, found 590.3 (M+1)⁺; Retention time: 2.51 minutes. ¹H NMR (400 MHz, DMSO-d6) δ 8.26 (d, J=2.8 Hz, 1H), 8.06 (d, J=7.7 Hz, 2H), 7.81 (d, J=8.2 Hz, 1H), 7.73 (t, J=7.4 Hz, 1H), 7.66 (t, J=7.6 Hz, 2H), 6.97 (d, J=8.2 Hz, 1H), 6.07 (d, J=2.7 Hz, 1H), 6.02 (d, J=3.9 Hz, 1H), 4.36 (t, J=7.0 Hz, 2H), 3.04 (dt, J=12.2, 5.7 Hz, 1H), 2.17 (dd, J=13.4, 7.3 Hz, 1H), 2.11 (m, 2H), 1.86 (d, J=13.2 Hz, 1H), 1.71 (s, 3H), 1.61 (s, 3H), 1.21 (d, J=6.3 Hz, 3H), 0.97 (m, 2H), 0.88 (m, 2H).

SYNTHETIC EXAMPLE 60

Synthesis of Compound 62: (5S)-3,3,5-trimethyl-12-(3-(2-[1-(trifluoromethyl)cyclopropyl]ethoxy)-1H-pyrazol-1-yl)-7-oxa-2,13-diazatricyclo[7.4.0.02,6]trideca-1(13),9,11-trien-8-one Step A: 6-[3-[2-[1-(Trifluoromethyl)cyclopropyl]ethoxy]pyrazol-1-yl]-2-[(4S)-2,2,4-trimethylpyrrolidin-1-yl]pyridine-3-carboxylic acid

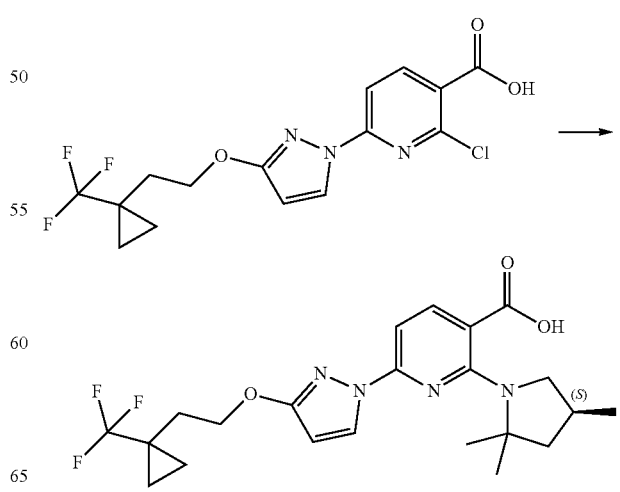

267

To a mixture of 2-chloro-6-[3-[2-[1-(trifluoromethyl)cyclopropyl]ethoxy]pyrazol-1-yl]pyridine-3-carboxylic acid (1 g, 2.661 mmol) and (4S)-2,2,4-trimethylpyrrolidine (Hydrochloride salt) (620 mg, 4.143 mmol) in N-methylpyrrolidinone (5 mL) and 1,2-diethoxyethane (1 mL) was added potassium carbonate (1.8 g, 13.02 mmol). The slurry was heated at 125° C. for 68 h. LC/MS showed 40% conversion. More (4S)-2,2,4-trimethylpyrrolidine (400 mg) was added and the reaction was continued for 18 h at 135° C. Cooled reaction suspension to ambient temperature and added slowly to a rapidly stirred solution of HCl (2 mL of 6 M, 12.00 mmol) in ice (foams!) affording a brown slurry. The slurry was extracted with ethyl acetate. The organic was washed with water, brine, dried over sodium sulfate and concentrated. The crude material was chromatographed on silica using a gradient of hexane/ethyl acetate. Product came out ~30% ethyl acetate. 6-[3-[2-[1-(trifluoromethyl)cyclopropyl]ethoxy]pyrazol-1-yl]-2-[(4S)-2,2,4-trimethylpyrrolidin-1-yl]pyridine-3-carboxylic acid (667.8 mg, 55%). ESI-MS m/z calc. 452.20352, found 453.0 (M+1)$^+$; Retention time: 1.87 minutes. 1H NMR (400 MHz, DMSO-d6) δ 12.68 (s, 1H), 8.24 (s, 1H), 7.92 (d, J=8.2 Hz, 1H), 6.86 (dd, J=32.9, 7.9 Hz, 1H), 6.29-6.01 (m, 1H), 4.31 (s, 2H), 3.54 (s, 1H), 2.89 (s, 1H), 2.33 (s, 1H), 2.08 (s, 2H), 1.95 (s, 1H), 1.74-1.46 (m, 7H), 1.12-1.01 (m, 3H), 0.92 (d, J=29.3 Hz, 4H).

Step B: (5S)-3,3,5-Trimethyl-12-(3-{2-[1-(trifluoromethyl)cyclopropyl]ethoxy)-1H-pyrazol-1-yl)-7-oxa-2,13-diazatricyclo[7.4.0.02,6]trideca-1(13),9,11-trien-8-one

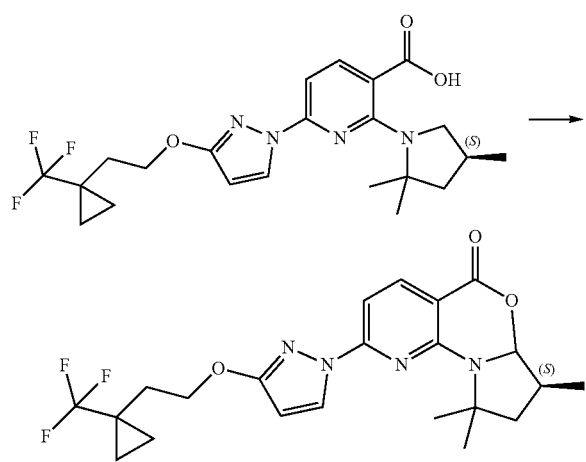

6-[3-[2-[1-(Trifluoromethyl)cyclopropyl]ethoxy]pyrazol-1-yl]-2-[(4S)-2,2,4-trimethylpyrrolidin-1-yl]pyridine-3-carboxylic acid (50 mg, 0.1105 mmol), water (20 µL, 1.110 mmol), NaOAc (18 mg, 0.22 mmol), and [Ir(dF(CF3)ppy}2 (dtbpy)]PF6 (4 mg, 0.003565 mmol) were dissolved in DMA (0.9 mL) and the reaction mixture was placed next to a 23 W CFL light source for 1.5 h. The reaction was injected directly onto a silica gel column without any workup. The crude mixture was purified by silica gel chromatography eluting with 0-100% ethyl acetate in hexanes to give (5S)-3,3,5-trimethyl-12-(3-{2-[1-(trifluoromethyl)cyclopropyl]ethoxy}-1H-pyrazol-1-yl)-7-oxa-2,13-diazatricyclo[7.4.0.02,6]trideca-1(13),9,11-trien-8-one (30.8 mg, 62%) ESI-MS m/z calc. 450.18787, found 451.3 (M+1)$^+$; Retention time: 2.35 minutes.

268

SYNTHETIC EXAMPLE 61

Synthesis of Compound 63: N-(Benzenesulfonyl)-6-[3-[(3-fluoro-1-bicyclo[1.1.1]pentanyl)methoxy]pyrazol-1-yl]-2-[(4S)-2,2,4-trimethylpyrrolidin-1-yl]pyridine-3-carboxamide Step A: tert-Butyl 3-[(3-fluoro-1-bicyclo[1.1.1]pentanyl)methoxy]pyrazole-1-carboxylate

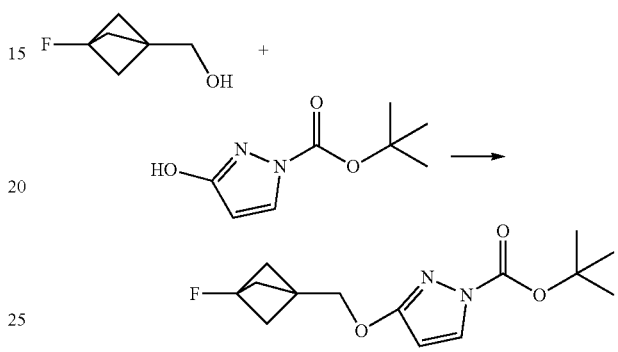

A solution of (3-fluoro-1-bicyclo[1.1.1]pentanyl)methanol (0.27 g, 2.3 mmol), tert-butyl 3-hydroxypyrazole-1-carboxylate (0.46 g, 2.5 mmol), and triphenyl phosphine (0.67 g, 2.6 mmol) in THF (12 mL) was cooled in an ice bath, and isopropyl N-isopropoxycarbonyliminocarbamate (0.50 mL, 2.6 mmol) was slowly added. The reaction was allowed to slowly warm to room temperature and was stirred for three days. It was diluted with ethyl acetate, washed with saturated aqueous sodium bicarbonate, dried over sodium sulfate, and evaporated under vacuum. The residue was purified by silica gel chromatography with 0-40% ethyl acetate in hexanes to give tert-butyl 3-[(3-fluoro-1-bicyclo[1.1.1]pentanyl)methoxy]pyrazole-1-carboxylate (0.43 g, 66%) ESI-MS m/z calc. 282.13797, found 283.3 (M+1)$^+$; Retention time: 0.65 minutes.

Step B: 3-[(3-Fluoro-1-bicyclo[1.1.1]pentanyl)methoxy]-1H-pyrazole

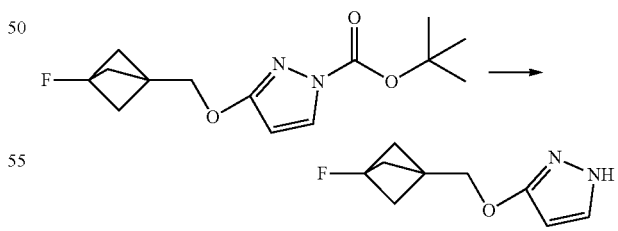

A solution of tert-butyl 3-[(3-fluoro-1-bicyclo[1.1.1]pentanyl)methoxy]pyrazole-1-carboxylate (0.43 g, 1.523 mmol) and trifluoroacetic acid (587 µL, 7.62 mmol) in dichloromethane (4 mL) was stirred for 5 hours. The volatiles were removed under vacuum, and the residue was basified with saturated aqueous sodium bicarbonate and extracted with ethyl acetate. The combined extracts were dried over sodium sulfate and evaporated to give 3-[(3-fluoro-1-bicyclo[1.1.1]

pentanyl)methoxy]-1H-pyrazole (0.28 g, 100%) ESI-MS m/z calc. 182.08554, found 183.1 (M+1)+; Retention time: 0.39 minutes.

Step C: tert-Butyl 2-chloro-6-[3-[(3-fluoro-1-bicyclo[1.1.1]pentanyl)methoxy]pyrazol-1-yl]pyridine-3-carboxylate

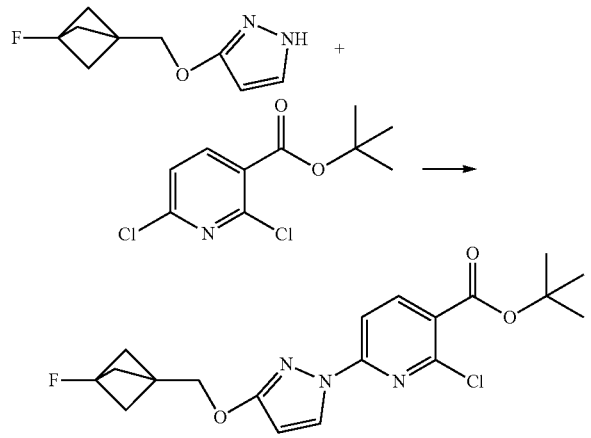

A mixture of 3-[(3-fluoro-1-bicyclo[1.1.1]pentanyl)methoxy]-1H-pyrazole (0.28 g, 1.5 mmol), tert-butyl 2,6-dichloropyridine-3-carboxylate (0.38 g, 1.5 mmol), potassium carbonate (0.26 g, 1.9 mmol), and 1,4-diazabicyclo[2.2.2]octane (34 mg, 0.30 mmol) in DMSO (7.5 mL) was stirred at room temperature for 16 h. The reaction was diluted with water and extracted with ethyl acetate. The combined extracts were washed with brine and water, dried over sodium sulfate, and evaporated. The residue was purified by silica gel chromatography with 0-5% methanol in dichloromethane to give tert-butyl 2-chloro-6-[3-[(3-fluoro-1-bicyclo[1.1.1]pentanyl)methoxy]pyrazol-1-yl]pyridine-3-carboxylate (0.50 g, 85%) ESI-MS m/z calc. 393.12555, found 394.2 (M+1)+; Retention time: 0.86 minutes.

Step D: 2-Chloro-6-[3-[(3-fluoro-1-bicyclo[1.1.1]pentanyl)methoxy]pyrazol-1-yl]pyridine-3-carboxylic acid

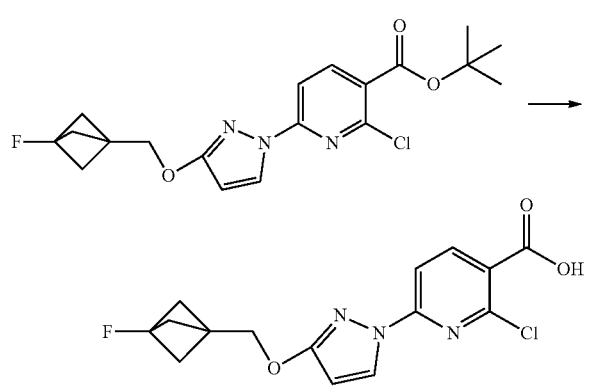

A solution of tert-butyl 2-chloro-6-[3-[(3-fluoro-1-bicyclo[1.1.1]pentanyl)methoxy]pyrazol-1-yl]pyridine-3-carboxylate (0.50 g, 1.270 mmol) and trifluoroacetic acid (978 µL, 12.7 mmol) in dichloromethane (6 mL) was stirred for 15 hours. The solvent was evaporated, and the residue was taken up in acetonitrile. The solvent was evaporated to give 2-chloro-6-[3-[(3-fluoro-1-bicyclo[1.1.1]pentanyl)methoxy]pyrazol-1-yl]pyridine-3-carboxylic acid (0.43 g, 100%) ESI-MS m/z calc. 337.06296, found 338.1 (M+1)+; Retention time: 0.63 minutes 1H NMR (400 MHz, Chloroform-d) δ 8.43 (d, J=8.5 Hz, 1H), 8.39 (d, J=2.9 Hz, 1H), 7.73 (d, J=8.5 Hz, 1H), 6.00 (d, J=2.8 Hz, 1H), 4.51 (s, 2H), 2.13 (d, J=2.6 Hz, 6H).

Step E: N-(benzenesulfonyl)-2-chloro-6-[3-[(3-fluoro-1-bicyclo[1.1.1]pentanyl)methoxy]pyrazol-1-yl]pyridine-3-carboxamide

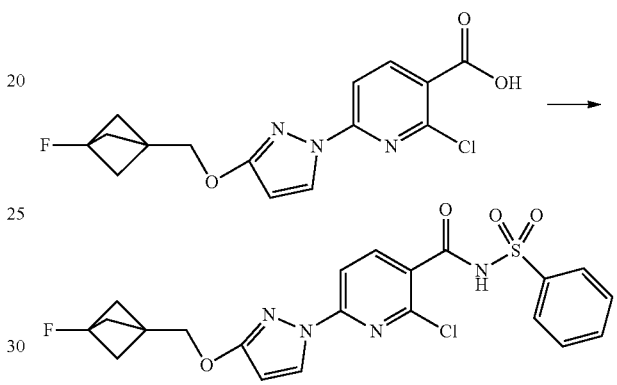

2-Chloro-6-[3-[(3-fluoro-1-bicyclo[1.1.1]pentanyl)methoxy]pyrazol-1-yl]pyridine-3-carboxylic acid (100 mg, 0.3 mmol) and carbonyl diimidazole (58 mg, 0.36 mmol) were combined in THF (1.5 mL) and stirred for 2 h. At this point, benzenesulfonamide (61 mg, 0.39 mmol) was added followed by DBU (54 µL, 0.36 mmol) and the reaction was stirred for an additional 16 h at room temperature. The reaction was diluted with ethyl acetate and washed with a 1M citric acid solution, followed by brine. The organics were separated, dried over sodium sulfate, and evaporated to give N-(benzenesulfonyl)-2-chloro-6-[3-[(3-fluoro-1-bicyclo[1.1.1]pentanyl)methoxy]pyrazol-1-yl]pyridine-3-carboxamide (190 mg, 135%) ESI-MS m/z calc. 476.07214, found 477.2 (M+1)+; Retention time: 0.69 minutes.

Step F: N-(Benzenesulfonyl)-6-[3-[(3-fluoro-1-bicyclo[1.1.1]pentanyl)methoxy]pyrazol-1-yl]-2-[(4S)-2,2,4-trimethylpyrrolidin-1-yl]pyridine-3-carboxamide

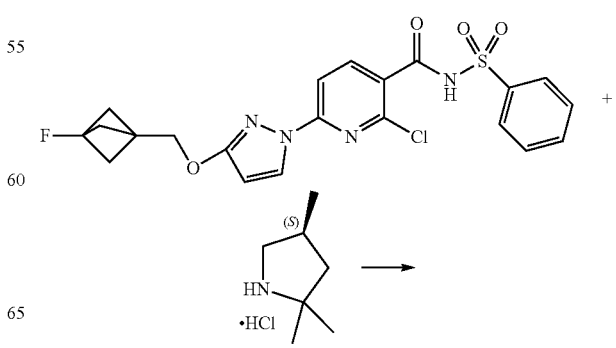

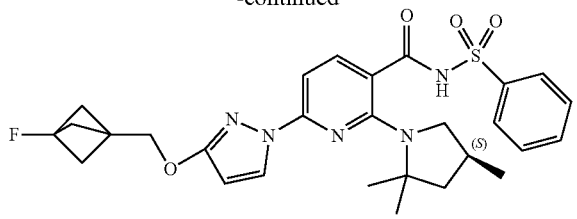

N-(Benzenesulfonyl)-2-chloro-6-[3-[(3-fluoro-1-bicyclo[1.1.1]pentanyl)methoxy]pyrazol-1-yl]pyridine-3-carboxamide (140 mg, 0.29 mmol), (4S)-2,2,4-trimethylpyrrolidine (hydrochloride salt) (131 mg, 0.88 mmol), and potassium carbonate (243 mg, 1.76 mmol) were combined in DMSO (1.5 mL) and heated at 130° C. for 16 h. The reaction mixture was filtered and purified by LC/MS utilizing a gradient of 30-99% acetonitrile in 5 mM aq HCl to give N-(benzenesulfonyl)-6-[3-[(3-fluoro-1-bicyclo[1.1.1]pentanyl)methoxy]pyrazol-1-yl]-2-[(4S)-2,2,4-trimethylpyrrolidin-1-yl]pyridine-3-carboxamide (89 mg, 54%) ESI-MS m/z calc. 553.2159, found 554.4 (M+1)$^+$; Retention time: 2.16 minutes. 1H NMR (400 MHz, DMSO-d6) δ 8.19 (d, J=2.8 Hz, 1H), 8.05-7.95 (m, 2H), 7.81 (d, J=8.3 Hz, 1H), 7.77-7.70 (m, 1H), 7.70-7.61 (m, 2H), 6.91 (d, J=8.2 Hz, 1H), 6.14 (d, J=2.8 Hz, 1H), 4.47 (s, 2H), 2.45-2.36 (m, 1H), 2.31-2.22 (m, 1H), 2.15-2.08 (m, 7H), 1.82 (dd, J=11.9, 5.5 Hz, 1H), 1.52 (d, J=9.2 Hz, 6H), 1.36 (t, J=12.1 Hz, 1H), 0.64 (d, J=6.2 Hz, 3H)

SYNTHETIC EXAMPLE 62

Synthesis of Compound 64: N-(Benzenesulfonyl)-6-[3-(dispiro[2.0.2.1]heptan-7-ylmethoxy)pyrazol-1-yl]-2-[(4S)-2,2,4-trimethylpyrrolidin-1-yl]pyridine-3-carboxamide Step A: tert-Butyl 3-(dispiro[2.0.2.1]heptan-7-yl methoxy)-1H-pyrazole-1-carboxylate

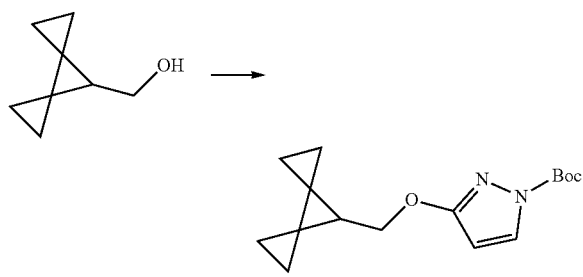

A solution of dispiro[2.0.2.1]heptan-7-yl methanol (1.36 g, 11.0 mmol) (Meijere, et al., Eur. J. Org. Chem. 2002, 485-492), tert-butyl 3-hydroxypyrazole-1-carboxylate (2.3 g, 12 mmol), and triphenyl phosphine (3.2 g, 12 mmol) in THF (28 mL) was cooled in an ice bath, and diisopropyl azodicarboxylate (DIAD) (2.4 mL, 12 mmol) was slowly added. The cooling bath was removed, and the reaction was stirred for 15 hours. The reaction was diluted with ethyl acetate, washed with saturated aqueous sodium bicarbonate, dried over sodium sulfate, and evaporated under vacuum. The residue was purified by silica gel chromatography eluting with 0-20% ethyl acetate in hexanes to give tert-butyl 3-(dispiro[2.0.2.1]heptan-7-yl methoxy)-1H-pyrazole-1-carboxylate (1.57 g, 49% yield) as a colorless oil. ESI-MS m/z calc. 290.16306, found 291.3 (M+1)$^+$; Retention time: 0.76 minutes.

Step B: 3-(Dispiro[2.0.2.1]heptan-7-ylmethoxy)-1H-pyrazole

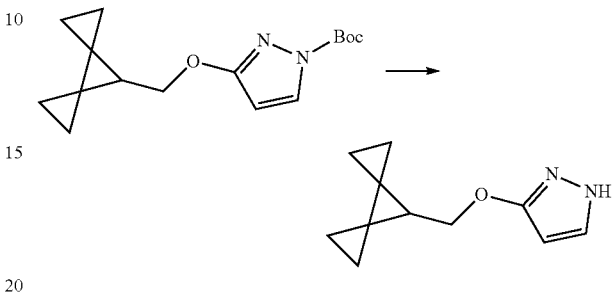

A solution of tert-butyl 3-(dispiro[2.0.2.1]heptan-7-yl methoxy)-1H-pyrazole-1-carboxylate (1.57 g, 5.41 mmol) and trifluoroacetic acid (2.2 mL, 29 mmol) in dichloromethane (20 mL) was stirred for three hours. The volatiles were removed under vacuum, and the residue was basified with saturated aqueous sodium bicarbonate and extracted with ethyl acetate. The combined extracts were dried over sodium sulfate and evaporated to give 3-(dispiro[2.0.2.1]heptan-7-ylmethoxy)-1H-pyrazole (0.94 g, 91% yield) as pale yellow oil. ESI-MS m/z calc. 190.11061, found 191.1 (M+1)$^+$; Retention time: 0.52 minutes Step C: Ethyl 2-chloro-6-(3-(dispiro[2.0.2.1]heptan-7-ylmethoxy)-1H-pyrazol-1-yl)nicotinate

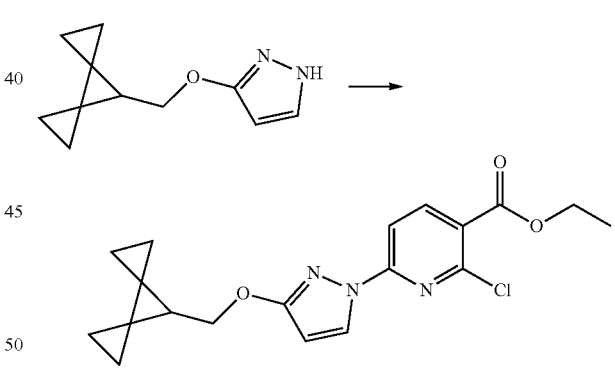

A mixture of 3-(dispiro[2.0.2.1]heptan-7-ylmethoxy)-1H-pyrazole (0.94 g, 4.9 mmol), ethyl 2,6-dichloropyridine-3-carboxylate (1.15 g, 5.23 mmol), potassium carbonate (0.83 g, 6.0 mmol), and 1,4-diazabicyclo[2.2.2]octane (0.12 g, 1.1 mmol) in DMSO (16 mL) was stirred for 24 hours. The reaction was diluted with water and extracted with ethyl acetate. The combined extracts were washed with brine and water, dried over sodium sulfate, and evaporated under vacuum. The residue was purified by silica gel column chromatography eluting with 0-20% ethyl acetate in hexanes to give ethyl 2-chloro-6-(3-(dispiro[2.0.2.1]heptan-7-ylmethoxy)-1H-pyrazol-1-yl)nicotinate (1.39 g, 75% yield) as a colorless solid. ESI-MS m/z calc. 373.11932, found 374.2 (M+1)$^+$; Retention time: 0.87 minutes. $^1$H NMR (400 MHz, Chloroform-d) δ 8.36 (d, J=2.8 Hz, 1H), 8.27 (d, J=8.5 Hz, 1H), 7.72 (d, J=8.5 Hz, 1H), 5.96 (d, J=2.9 Hz, 1H), 4.41 (q, J=7.1 Hz, 2H), 4.30 (d, J=7.0 Hz, 2H), 1.94 (t, J=7.0 Hz, 1H), 1.42 (t, J=7.1 Hz, 3H), 1.02-0.89 (m, 4H), 0.75-0.65 (m, 2H), 0.65-0.53 (m, 2H)

Step D: 2-Chloro-6-[3-(dispiro[2.0.2.1]heptan-7-ylmethoxy)pyrazol-1-yl]pyridine-3-carboxylic acid

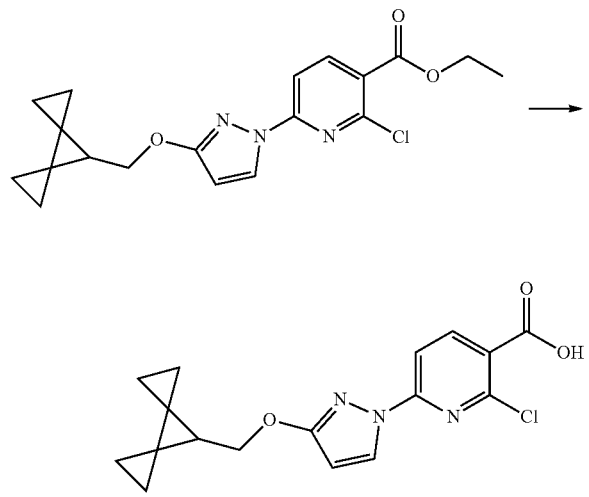

A solution of ethyl 2-chloro-6-(3-(dispiro[2.0.2.1]heptan-7-ylmethoxy)-1H-pyrazol-1-yl)nicotinate (1.39 g, 3.72 mmol) and sodium hydroxide (7.5 mL of 1 M solution, 7.5 mmol) in THF (6 mL) and ethanol (3 mL) was stirred for 90 minutes. The volatiles were removed under vacuum, and water was added. The reaction was cooled in an ice bath, and hydrochloric acid (7.5 mL of 1 M solution, 7.5 mmol) was slowly added. The reaction was diluted with water and extracted with ethyl acetate. The combined extracts were washed with brine, dried over sodium sulfate, and evaporated to give 2-chloro-6-[3-(dispiro[2.0.2.1]heptan-7-ylmethoxy)pyrazol-1-yl]pyridine-3-carboxylic acid (1.16 g, 82% yield) as a colorless solid. ESI-MS m/z calc. 345.088, found 346.1 (M+1)$^+$; Retention time: 0.73 minutes. $^1$H NMR (400 MHz, DMSO-d6) δ 8.41 (d, J=2.9 Hz, 1H), 8.38 (d, J=8.4 Hz, 1H), 7.73 (d, J=8.4 Hz, 1H), 6.19 (d, J=2.8 Hz, 1H), 4.27 (d, J=7.0 Hz, 2H), 1.93 (t, J=7.0 Hz, 1H), 0.97-0.79 (m, 4H), 0.76-0.66 (m, 2H), 0.65-0.56 (m, 2H)

Step E: N-(Benzenesulfonyl)-2-chloro-6-[3-(dispiro[2.0.2.1]heptan-7-ylmethoxy)pyrazol-1-yl]pyridine-3-carboxamide

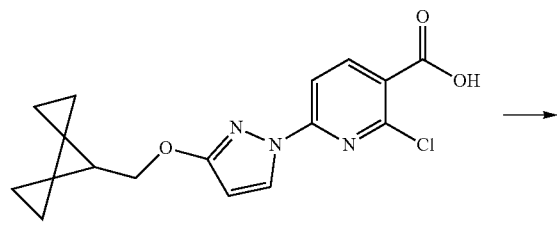

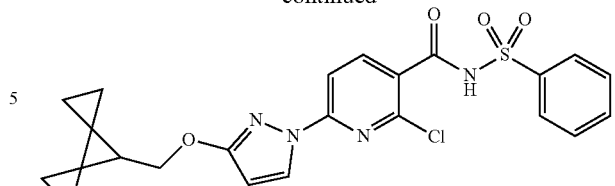

A solution of 2-chloro-6-[3-(dispiro[2.0.2.1]heptan-7-ylmethoxy)pyrazol-1-yl]pyridine-3-carboxylic acid (0.10 g, 0.29 mmol) and carbonyl diimidazole (0.06 g, 0.4 mmol) in THF (1.4 mL) was stirred for 45 minutes, and benzenesulfonamide (55 mg, 0.35 mmol) and 1,8-diazabicyclo(5.4.0)undec-7-ene (DBU) (130 µL, 0.87 mmol) were added. After 15 hours the reaction was diluted with 1 M aqueous citric acid and extracted with ethyl acetate. The combined extracts were washed with brine, dried over sodium sulfate, and evaporated to give crude N-(benzenesulfonyl)-2-chloro-6-[3-(dispiro[2.0.2.1]heptan-7-ylmethoxy)pyrazol-1-yl]pyridine-3-carboxamide (0.16 g) which was used in the next step as-is. ESI-MS m/z calc. 484.0972, found 485.2 (M+1)$^+$; Retention time: 0.81 minutes.

Step F: N-(Benzenesulfonyl)-6-[3-(dispiro[2.0.2.1]heptan-7-ylmethoxy)pyrazol-1-yl]-2-[(4S)-2,2,4-trimethylpyrrolidin-1-yl]pyridine-3-carboxamide

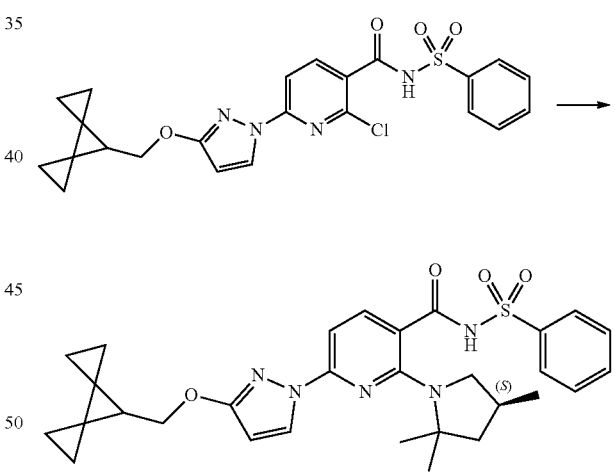

A mixture of N-(benzenesulfonyl)-2-chloro-6-[3-(dispiro[2.0.2.1]heptan-7-ylmethoxy)pyrazol-1-yl]pyridine-3-carboxamide (0.14 g, 0.29 mmol), (4S)-2,2,4-trimethylpyrrolidine hydrochloride (0.14 g, 0.94 mmol), and potassium carbonate (0.24 g, 1.7 mmol) in NMP (1.3 mL) was stirred at 130° C. for 15 hours. The reaction was filtered and purified using a reverse phase HPLC-MS method using a dual gradient run from 30-99% acetonitrile in 5 mM aqueous HCl. N-(Benzenesulfonyl)-6-[3-(dispiro[2.0.2.1]heptan-7-ylmethoxy)pyrazol-1-yl]-2-[(4S)-2,2,4-trimethylpyrrolidin-1-yl]pyridine-3-carboxamide (65 mg, 40% yield) was obtained. ESI-MS m/z calc. 561.24097, found 562.3 (M+1)$^+$; Retention time: 2.35 minutes.

SYNTHETIC EXAMPLE 63

Synthesis of Compound 65: N-(benzenesulfonyl)-6-(3-hydroxypyrazol-1-yl)-2-[(4S)-2,2,4-trimethylpyrrolidin-1-yl]pyridine-3-carboxamide

Step A: tert-Butyl 3-((1-ethylcyclopropyl)methoxy)-1H-pyrazole-1-carboxylate

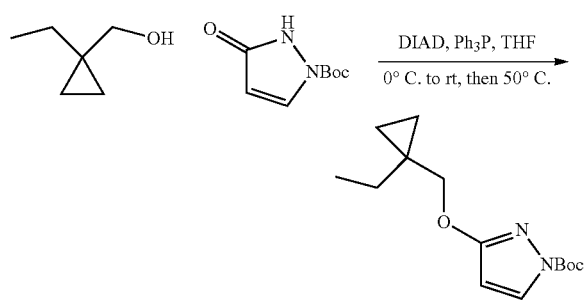

To the solution of (1-ethylcyclopropyl)methanol (1.68 g, 16.73 mmol), tert-butyl 2,3-dihydro-3-oxopyrazole-1-carboxylate (2.80 g, 15.21 mmol) and triphenylphosphine (4.39 g, 16.73 mmol) in tetrahydrofuran (40 mL) at 0° C. was added diisopropyl azodicarboxylate (3.38 g, 16.73 mmol) dropwise. The reaction was warmed up to room temperature, then heated at 50° C. for 21 hours. The reaction solution was cooled to room temperature and ethyl acetate (500 mL) was added. The organic layer was washed with 0.3M aqueous sodium hydroxide solution (100 mL), brine (2×50 mL) and dried over magnesium sulfate, filtered and concentrated. The residue was purified by silica gel chromatography using 0 to 80% hexanes/dichloromethane gradient method to afford tert-butyl 3-((1-ethylcyclopropyl)methoxy)-1H-pyrazole-1-carboxylate (1.73 g, 43%) as a yellow oil. ESI-MS m/z calc. 266.2, found 267.3 (M+1)$^+$. Retention time: 3.47 minutes. $^1$HNMR (250 MHz, CDCl$_3$) δ (ppm): 7.82 (d, J=2.5 Hz, 1H), 5.88 (d, J=2.5 Hz, 1H), 4.09 (s, 2H), 1.60 (s, 9H), 1.48 (q, J=7.5 Hz, 2H), 0.94 (t, J=7.5 Hz, 3H), 0.49 (m, 2H), 0.42 (m, 2H).

Step B: 3-((1-Ethylcyclopropyl)methoxy)-1H-pyrazole

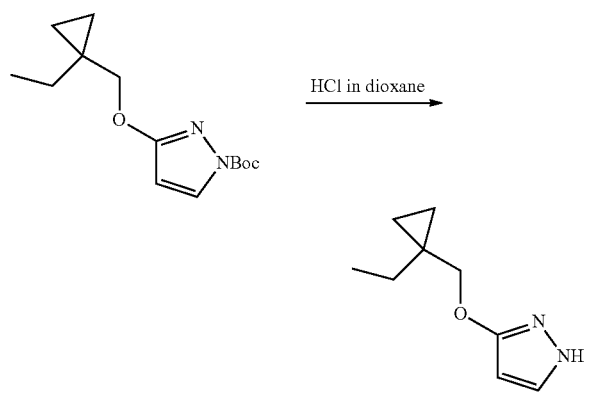

A solution of 4M hydrogen chloride in 1,4-dioxane (65 mL) was added to tert-butyl 3-((1-ethylcyclopropyl)methoxy)-1H-pyrazole-1-carboxylate (1.73 g, 6.49 mmol) and the reaction solution was stirred at room temperature for 16 hours and concentrated to dryness to obtain crude 3-((1-ethylcyclopropyl)methoxy)-1H-pyrazole as an oil which was used directly in next step. ESI-MS m. calc. 166.1, found 167.3 (M+1)$^+$. Retention time: 0.60 minutes.

Step C: Methyl 2-chloro-6-(3-((1-ethylcyclopropyl)methoxy)-1H-pyrazol-1-yl)nicotinate

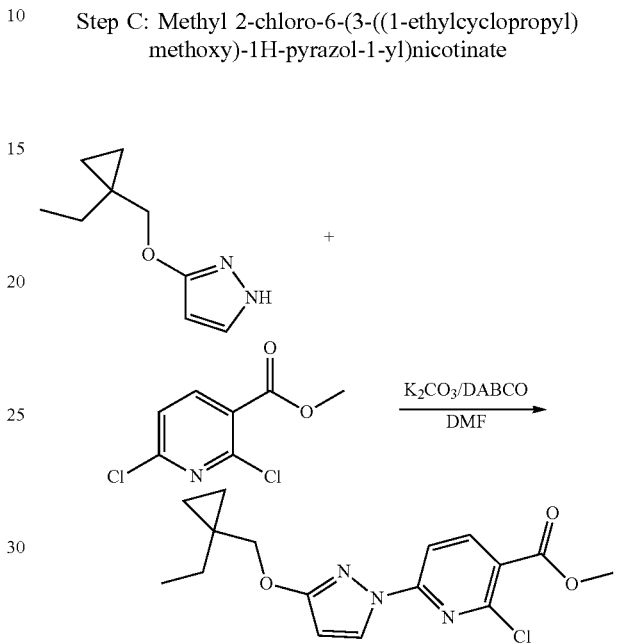

3-((1-Ethylcyclopropyl)methoxy)-1H-pyrazole (6.49 mmol) and methyl 2,6-dichloronicotinate (1.81 g, 8 mmol) were added into dimethylformamide (20 mL). Potassium carbonate (2.8 g, 20 mmol) and 1,4-diazabicyclo[2.2.2]octane (0.167 g, 1.5 mmol) were added into reaction mixture which was allowed to stir at room temperature for 16 hours. The reaction mixture was diluted with water (60 mL) and extracted with diethyl ether (3×60 mL). Combined organic layer was dried over sodium sulfate and evaporated under reduced pressure. The residue was subjected to flash chromatography on silica gel using 0 to 100% hexanes/dichloromethane gradient method to give methyl 2-chloro-6-(3-((1-ethylcyclopropyl)methoxy)-1H-pyrazol-1-yl)nicotinate (1.7 g, 77%) as a white solid. ESI-MS m/z calc. 335.10, found 336.5 (M+1)$^+$. Retention time: 4.29 minutes. $^1$H NMR (250 MHz, DMSO) δ (ppm): 8.43 (d, J=2.8 Hz, 1H), 8.41 (d, J=8.4 Hz, 1H), 7.74 (d, J=8.4 Hz, 1H), 6.23 (d, J=2.8 Hz, 1H), 4.08 (s, 2H), 3.88 (s, 3H), 1.44 (q, J=7.4 Hz, 2H), 0.93 (t, J=7.4 Hz, 3H), 0.53 (m, 2H), 0.42 (m, 2H).

Step D: 2-Chloro-6-(3-((1-ethylcyclopropyl)methoxy)-1H-pyrazol-1-yl)nicotinic acid

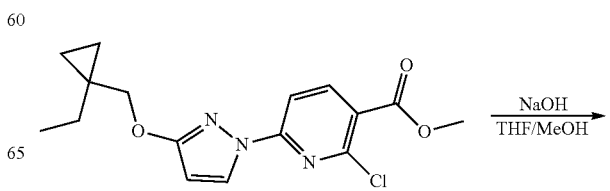

-continued

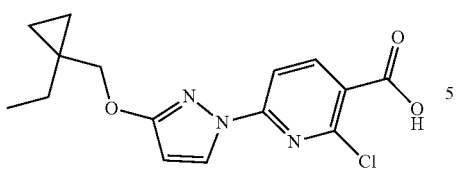

Methyl 2-chloro-6-(3-((1-ethylcyclopropyl)methoxy)-1H-pyrazol-1-yl)nicotinate (1.7 g, 50 mmol) was added in a ice-cooled round bottom flask with tetrahydrofuran (5 mL) and methanol (5 mL). Sodium hydroxide (0.4 g, 10 mmol) in water (5 mL) was added slowly and reaction solution was stirred at room temperature for 5 hours. The resulting reaction mixture was concentrated under reduced pressure to remove tetrahydrofuran and acidified by 1N aqueous hydrogen chloride solution to pH=1 in ice bath. Formed white solid was filtered off to give 2-chloro-6-(3-((1-ethylcyclopropyl)methoxy)-1H-pyrazol-1-yl)-nicotinic acid (1.54 g, 95.0%). ESI-MS m/z calc. 321.09, found 322.2 (M+1)$^+$. Retention time: 3.59 minutes. $^1$H NMR (250 MHz, DMSO) δ (ppm): 8.43 (d, J=2.8 Hz, 1H), 8.42 (d, J=8.4 Hz, 1H), 7.72 (d, J=8.4 Hz, 1H), 6.24 (d, J=2.8 Hz, 1H), 4.09 (s, 2H), 1.45 (q, J=7.4 Hz, 2H), 0.92 (t, J=7.4 Hz, 3H), 0.54 (m, 2H), 0.44 (m, 2H).

Step E: N-(Benzenesulfonyl)-2-chloro-6-[3-[(1-ethylcyclopropyl)methoxy]pyrazol-1-yl]pyridine-3-carboxamide 2-Chloro-6-[3-[(1-ethylcyclopropyl)methoxy]pyrazol-1-yl]pyridine-3-carboxylic acid (157 mg, 0.4879 mmol) and carbonyl diimidazole (100 mg, 0.6167 mmol) were combined in THF (2 mL) and stirred for 2 h. At this point, benzenesulfonamide (77 mg, 0.4899 mmol) was added followed by DBU (243 µL, 1.625 mmol) and the reaction was stirred an additional 30 min at room temperature. The reaction was diluted with ethyl acetate and washed with a 1M citric acid solution, followed by brine. The organics were separated, dried over sodium sulfate, and evaporated to give crude N-(benzenesulfonyl)-2-chloro-6-[3-[(1-ethylcyclopropyl)methoxy]pyrazol-1-yl]pyridine-3-carboxamide (224 mg, 100%) ESI-MS m/z calc. 460.0972, found 461.1 (M+1)$^+$; Retention time: 0.75 minutes.

Step F: N-(Benzenesulfonyl)-2-chloro-6-(3-hydroxypyrazol-1-yl)pyridine-3-carboxamide

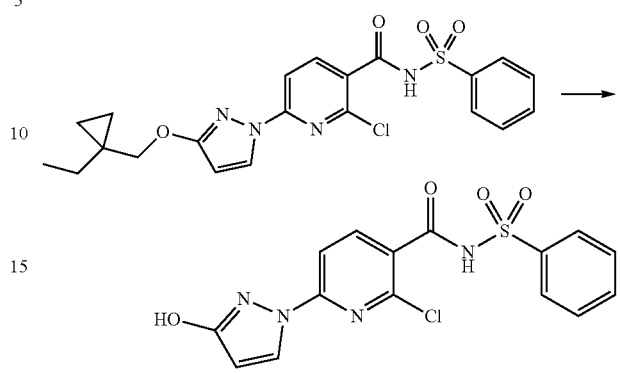

N-(Benzenesulfonyl)-2-chloro-6-[3-[(1-ethylcyclopropyl)methoxy]pyrazol-1-yl]pyridine-3-carboxamide (224 mg, 100%) was dissolved in dichloromethane (2 mL) with TFA (1 mL, 12.98 mmol) and the reaction was stirred for 4 h. The reaction was evaporated to dryness to give N-(benzenesulfonyl)-2-chloro-6-(3-hydroxypyrazol-1-yl)pyridine-3-carboxamide (136 mg, 74%) ESI-MS m/z calc. 378.01895, found 379.1 (M+1)$^+$; Retention time: 0.54 minutes.

Step G: N-(benzenesulfonyl)-6-(3-hydroxypyrazol-1-yl)-2-[(4S)-2,2,4-trimethylpyrrolidin-1-yl]pyridine-3-carboxamide

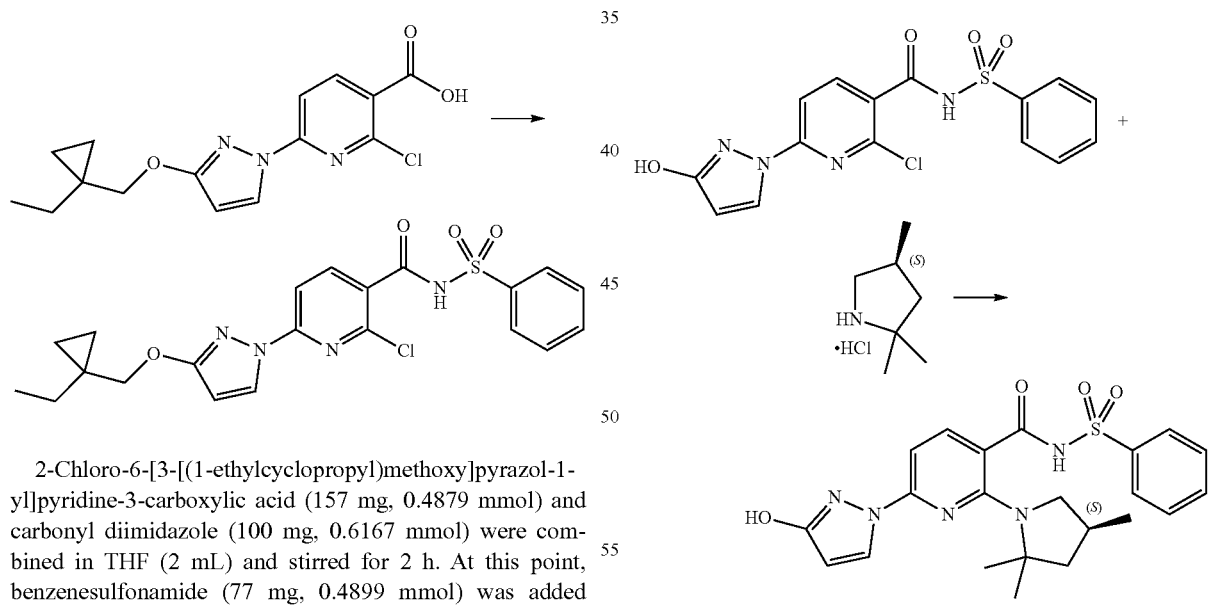

N-(benzenesulfonyl)-2-chloro-6-(3-hydroxypyrazol-1-yl)pyridine-3-carboxamide (100 mg, 0.26 mmol), (4S)-2,2,4-trimethylpyrrolidine (hydrochloride salt) (110 mg, 0.76 mmol), and potassium carbonate (180 mg, 1.3 mmol) were combined in DMSO (0.5 mL) and heated at 130° C. for 16 h. The reaction was diluted with water (3 mL) and stirred for 20 min. A solid formed and the aqueous liquid was decanted. The solid was dissolved in ethyl acetate and washed with a 1M citric acid solution, then brine. The organics were dried over sodium sulfate and evaporated. The crude material was purified by silica gel chromatography eluting with 0-10% methanol in dichloromethane to give N-(benzenesulfonyl)-6-(3-hydroxypyrazol-1-yl)-2-[(4S)-2,2,4-trimethylpyrrolidin-1-yl]pyridine-3-carboxamide (4.6 mg, 4%) ESI-MS m/z calc. 455.16272, found 456.3 (M+1)$^+$; Retention time: 1.50 minutes.

EXAMPLE 5

ASSAYS & DATA

5A. Assays for Detecting and Measuring F508del-CFTR modulator Properties of Compounds
Membrane Potential Optical Methods for Assaying Properties of F508del-CFTR Modulators The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation and concurrent with compound treatment by a single liquid addition step after the cells have previously been loaded with a voltage sensing dye.

5A-A1. Identification of F508del-CFTR Modulators

To identify modulators of F508del, a fluorescence based HTS assay format was developed. This HTS assay utilizes fluorescent voltage sensing dyes to measure changes in membrane potential on the FLIPR III as a measurement for increase in gating (conductance) of F508del NIH 3T3 cells. The driving force for the response is the creation of a chloride ion gradient in conjunction with channel activation and concurrent with compound treatment by a single liquid addition step after the cells have previously been loaded with a voltage sensing dye. Data for Compounds 1-65 that were obtained using the assay described here are summarized in Table 6 below. For example, using this method, Compound 1 had an EC$_{50}$ of less than 3 µM and a % Efficacy of ≥100% relative to Compound II.

Solutions

Bath Solution #1: (in mM) NaCl 160, KCl 4.5, CaCl$_2$ 2, MgCl$_2$ 1, HEPES 10, pH 7.4 with NaOH, Glucose 10.

Chloride-free bath solution: Chloride salts in Bath Solution #1 (above) are substituted with gluconate salts.

Cell Culture

NIH3T3 mouse fibroblasts stably expressing F508del are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, 13-ME, 1× pen/strep, and 25 mM HEPES in 175 cm$^2$ culture flasks. For all optical assays, the cells were seeded at 12,000 cells/well in 384-well matrigel-coated plates and cultured for 18-24 hrs at 37° C. for the potentiator assay. For the correction assays, the cells are cultured at 37° C. with and without compounds for 18-24 hours.

Electrophysiological Assays for Assaying F508del Modulation Properties of Compounds.

Ussing Chamber Assay

Ussing chamber experiments were performed on polarized airway epithelial cells expressing F508del to further characterize the F508del modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for F508del or compound heterozygous for F508del with an different disease causing mutation on the other allele.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl$^-$ gradient (I$_{SC}$) were measured using a voltage-clamp system (Department of Bioengineering, University of Iowa, IA). Briefly, HBE were examined under voltage-clamp recording conditions (V$_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

5A-A2. Identification of F5008del-CFTR Modulators

Typical protocol utilized a basolateral to apical membrane Cl$^-$ concentration gradient. To set up this gradient, normal ringers was used on the basolateral membrane, whereas apical NaCl was replaced by equimolar sodium gluconate (titrated to pH 7.4 with NaOH) to give a large Cl$^-$ concentration gradient across the epithelium. Modulators were added either to the basolateral side 18-24 prior to assay or to the apical side during the assay. Forskolin (10 µM) was added to the apical side during the assay to stimulate CFTR-mediated Cl$^-$ transport.

Patch-Clamp Recordings

Total Cl$^-$ current in F508del-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 µg/mL amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate F508del, 10 µM forskolin and 20 µM genistein were added to the bath and the current-voltage relation was monitored every 30 sec.

5A-A3. Identification of F508del-CFTR Modulators

The ability of F508del-CFTR modulators to increase the macroscopic F508del Cl$^-$ current (I$_{F508del}$) in NIH3T3 cells stably expressing F508del was also investigated using perforated-patch-recording techniques. Modulators identified from the optical assays evoked a dose-dependent increase in IA$_{F508}$ with similar potency and efficacy observed in the optical assays.

Cell Culture

NIH3T3 mouse fibroblasts stably expressing F508del are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, (3-ME, 1× pen/strep, and 25 mM HEPES in 175 cm² culture flasks. For whole-cell recordings, 2,500-5,000 cells were seeded on poly-L-lysine-coated glass coverslips and cultured for 18-24 hrs in the presence or absence of modulators 37° C.

Single-Channel Recordings

Gating activity of F508del-CFTR expressed in NIH3T3 cells following modulator treatment was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 CaCl₂, 2 MgCl₂, and 10 HEPES (pH adjusted to 7.35 with Tris base). The bath contained (in mM): 150 NMDG-Cl, 2 MgCl₂, 5 EGTA, 10 TES, and 14 Tris base (pH adjusted to 7.35 with HCl). After excision, both wt- and F508del were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing F508del are used for excised-membrane patch-clamp recordings. The cells are maintained at 37° C. in 5% CO₂ and 90% humidity in Dulbecco's modified Eagle's medium supplemented with 2 mM glutamine, 10% fetal bovine serum, 1×NEAA, (3-ME, 1× pen/strep, and 25 mM HEPES in 175 cm² culture flasks. For single channel recordings, 2,500-5,000 cells were seeded on poly-L-lysine-coated glass coverslips and cultured for 18-24 hrs in the presence or absence of modulators at 37° C.

5B. Chromatographic Determination of Human Serum Albumin (HSA) Assay

Chromatographic determination of Human Serum Albumin (HSA) values was performed on a UPLC-MS system using a ChiralPak® HSA column (p/n: 58469AST) from Sigma Aldrich. Mobile phase A consisted of 50 mM ammonium acetate buffer in water adjusted to pH=7.4, and mobile phase B was 2-propanol. The column compartment was kept at constant temperature of 30° C. Determination of retention time on the HSA column was performed by injecting 3 mL of 0.5 mM of compound (in DMSO) using a linear gradient from 0%-30% B in 2.5 minutes, followed by a hold at 30% B for 2 minutes, and the final equilibration step from 30% 0% B in 1.5 minutes, for a total run time of 6 minutes. Flow rate was kept constant throughout the gradient and set to 1.8 mL/min. Compound retention time on the HSA column was converted to % HSA values according to a previously published protocol (Valko, et. al, 2003) correlating column retention times to standard plasma protein binding (PPB) values obtained from dialysis experiments. HSA data for certain compounds are summarized below in Table 8 below.

Valko, K., Nunhuck, S., Bevan, C., Abraham, M. H., Reynolds, D. P. Fast Gradient HPLC Method to Determine Compounds Binding to Human Serum Albumin. Relationships with Octanol/Water and Immobilized Artificial Membrane Lipophilicity. J. of Pharm. Sci. 2003, 92, 2236-2248.

5C. Experimental Protocol for Rat IV and PO PK Studies

The tested compound was administered to male Sprague-Dawley rats as a single nominal intravenous dose of 3.0 mg/kg as a solution in 10% NMP, 10% solutol, 15% EtOH, 35% PEG400 and 30% D5W. The tested compound was also administered to male Sprague-Dawley rats at single nominal oral dose of 3 mg/kg as a solution in 5% NMP, 30% PEG400, 10% TPGS, 5% PVP-K30 at 5 mL/kg dose volume. Analyses of plasma and dose preparations were performed using LC/MS/MS.

Plasma concentration-time profiles of the tested compound in Sprague-Dawley rats at scheduled (nominal) sampling times were analyzed by noncompartmental pharmacokinetic methods using PK function within Watson LIMS software, Version 7.4.2 (Thermo Scientific Inc, Waltham, Mass.). AUC values were calculated using the linear trapezoidal rule.

5D. Experimental Protocol for PXR assay

The propensity for PXR mediated CYP3A4 induction is assessed using the DPX-2 cell line in vitro. This cell line, which has been licensed from Puracyp Inc. was derived from HepG2 cells and has been stably transfected with genes encoding human PXR as well as a modified luciferase reporter linked to the CYP3A4 promoter region and related distal and proximal enhancers.

The assay is run in 384 well format and each test article is administered in 11 doses ranging from 0.1 to 60 µM. On day 1, DPX-2 cells which have previously been expanded in-house and cryopreserved are thawed and seeded in tissue culture plates. The following day, media is changed and cells are cultured in media containing test article, vehicle control or the positive control compound, the clinically validated CYP3A4 inducer rifampicin. Cells are cultured in the presence of test article for 48 hours and then cell viability is assessed using fluorescence based assay (Cell Titer-Fluor, Promega) with an EnVision Plate Reader (PerkinElmer). Subsequently, CYP3A4 transactivation, which is proportional to luciferase activity, is measured by reading luminescense using the Promega One-Glo reagent system using the same plate reader.

Data processing within the Genedata software package allows reporting of max fold induction compared to vehicle control, an $EC_{50}$ value for CYP3A4 inducers and an 11 point-dose response curve. Wells with cell viability less than 70% are not used for the analysis and plates where the rifampicin positive control response falls outside of the expected range, either in potency or max fold induction, are not reported.

5E. CFTR Data of Compounds 1-65

The compounds of formula (I) are useful as modulators of CFTR activity. The Table 6 below illustrates the EC50 of the compounds of Table 6 using procedures described above (assay described above in Example 5A-A1). In Table 6 below, the following meanings apply. EC50: "+++" means <0.1 uM; "++" means between 0.1 uM and 1 uM; "+" means greater than 1 uM.

TABLE 6

CFTR Activity

| Comp. No. | CFTRdF508 EC50 (uM) |
|---|---|
| 1 | +++ |
| 2 | ++ |
| 3 | +++ |
| 4 | +++ |
| 5 | +++ |
| 6 | NA[a] |
| 7 | NA[a] |
| 8 | +++ |
| 9 | ++ |
| 10 | +++ |
| 11 | ++ |
| 12 | +++ |
| 13 | ++ |
| 14 | +++ |
| 15 | +++ |
| 16 | +++ |
| 17 | +++ |
| 18 | ++ |
| 19 | ++ |
| 20 | ++ |
| 21 | +++ |
| 22 | ++ |
| 23 | +++ |
| 24 | +++ |
| 25 | +++ |
| 26 | + |
| 27 | ++ |
| 28 | +++ |
| 29 | ++ |
| 30 | +++ |
| 31 | +++ |
| 32 | +++ |
| 33 | +++ |
| 34 | +++ |
| 35 | +++ |
| 36 | +++ |
| 37 | +++ |
| 38 | ++ |
| 39 | +++ |
| 40 | +++ |
| 41 | +++ |
| 42 | +++ |
| 43 | +++ |
| 44 | ++ |
| 45 | ++ |
| 46 | ++ |
| 47 | +++ |
| 48 | + |
| 49 | +++ |
| 50 | +++ |
| 51 | +++ |
| 52 | ++ |
| 53 | +++ |
| 54 | +++ |
| 55 | +++ |
| 56 | ++ |
| 57 | +++ |
| 58 | +++ |
| 59 | +++ |
| 60 | ++ |
| 61 | NA[a] |
| 62 | + |
| 63 | ++ |
| 64 | +++ |
| 65 | + |

[a] not measured.

5F. Metabolites

It has been determined that Compound 1 is metabolized both in vitro and in vivo, mostly by oxidative metabolism. Compound 1 and the metabolites shown in the following table were prepared and tested.

TABLE 7

Data for Metabolites

| Metabolite | CFTRdF508 EC50 (uM) | Deuterated analog of metabolite |
|---|---|---|
| Compound 1 (Parent Compound) | 0.03 | Compound 17 |
| Compound 38 | 0.24 | Compound 7 |

TABLE 7-continued

Data for Metabolites

| Metabolite | CFTRdF508 EC50 (uM) | Deuterated analog of metabolite |
|---|---|---|
| Compound 62 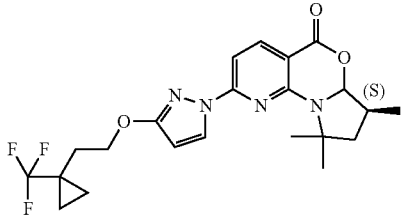 | >30 | |
| Compound 31 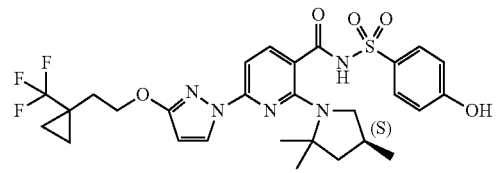 | 0.03 | |
| Compound 34 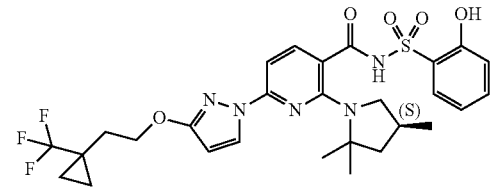 | 0.09 | |

5G. Acylsulfoxamides.

Compounds comprising an acylsulfoxamide moiety (i.e., sulfonimidoylamide moiety—wherein X in Formulae I or II is chosen from substituted or unsubstituted amines) were determined to result in decreased human serum albumin binding and enhanced free fraction as compared to compounds comprising an acylsulfonamide group (i.e., wherein X in Formulae I or II is chosen from O). The HAS data were measured as described above in Example 5B. Decreased human serum albumin binding may result in a higher amount of free (unbound) drug which can affect biological activity.

TABLE 8

HSA Data

| Acylsulfonamide | HSA binding | Sulfoxamine | HSA binding |
|---|---|---|---|
| Compound 15 | 99.1% | | 98.1% |

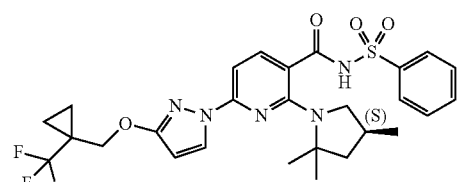

(diastereomeric mixture: Compound 45))

TABLE 8-continued

HSA Data

| Acylsulfonamide | HSA binding | Sulfoxamine | HSA binding |
|---|---|---|---|
| | | (diastereoisomer 1: Compound 46) | 97.9% |
| | | (diastereoisomer 2: Compound 47) | 98.4% |

Table 8 below summarizes CFTR activity (CFTR dF508 EC50), PXR Max induction, Rat IV clearance, Rat PO AUC, and Rat PO data for certain compounds described above.

TABLE 9

Comparative Data

| Compound No. | Compounds | CFTR dF508 EC50 (µM) | PXR Max Induction (% of rifampicin) | Rat iv CL (mL/min/kg) | Rat po AUC (µg·hr/mL at 3 mg/kg dose[a]) | Rat po % F |
|---|---|---|---|---|---|---|
| Comp. A | | 0.06 | 2 | 17.8 | 1.2[a] | 28% |
| Comp. B | | 0.12 | 9 | 29.2 | | |

TABLE 9-continued
| | | Comparative Data | | | |
|---|---|---|---|---|---|
| Compound No. | Compounds | CFTR dF508 EC50 (μM) | PXR Max Induction (% of rifampicin) | Rat iv CL (mL/min/kg) | Rat po AUC (μg.hr/mL at 3 mg/kg dose[a]) | Rat po % F |
| Comp. C | 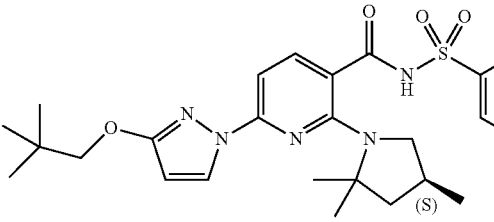 | 0.26 | 3 | | | |
| Comp. D | 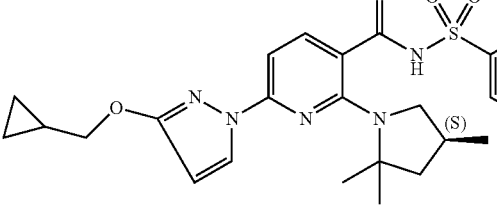 | 0.4 | 20 | | | |
| Comp. E | 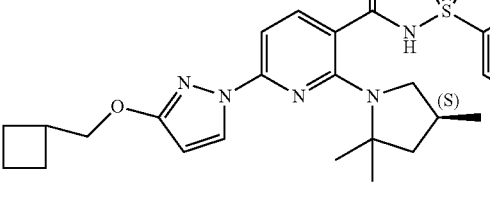 | 0.21 | 10 | | | |
| Comp. 49 | 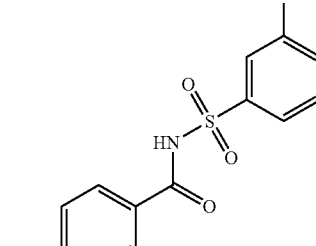 | 0.02 | 19 | | | |

TABLE 9-continued
Comparative Data
| Compound No. | Compounds | CFTR dF508 EC50 (μM) | PXR Max Induction (% of rifampicin) | Rat iv CL (mL/min/kg) | Rat po AUC (μg·hr/mL at 3 mg/kg dose[a]) | Rat po % F |
|---|---|---|---|---|---|---|
| Comp. 4 | 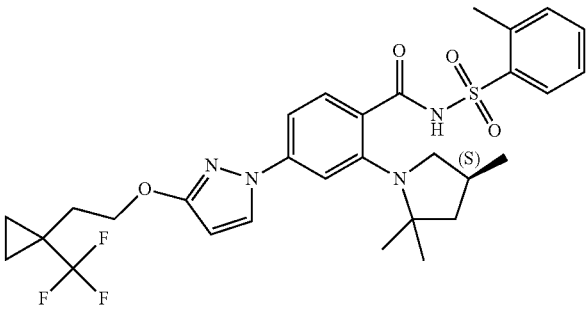 | 0.02 | 4 | | | |
| Comp. 15 | 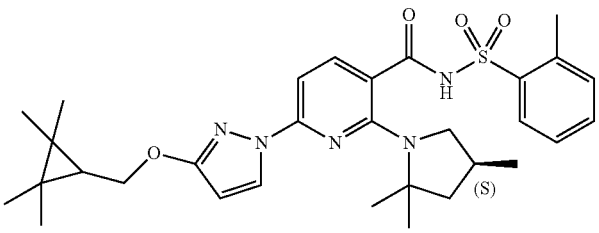 | 0.02 | 0 | | | |
| Comp. 16 | 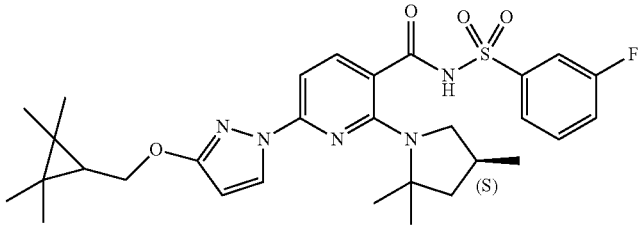 | 0.02 | 2 | 24.8 | 0.25 | 12% |
| Comp. 1 | 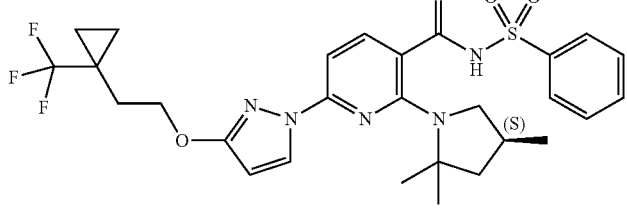 | 0.03 | 3 | 1.6 | 21 | 63% |
| Comp. 50 | 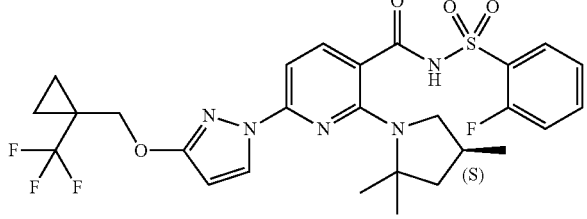 | 0.03 | 32 | | | |

TABLE 9-continued
Comparative Data
| Compound No. | Compounds | CFTR dF508 EC50 (μM) | PXR Max Induction (% of rifampicin) | Rat iv CL (mL/min/kg) | Rat po AUC (μg·hr/mL at 3 mg/kg dose<sup>a</sup>) | Rat po % F |
|---|---|---|---|---|---|---|
| Comp. 23 | 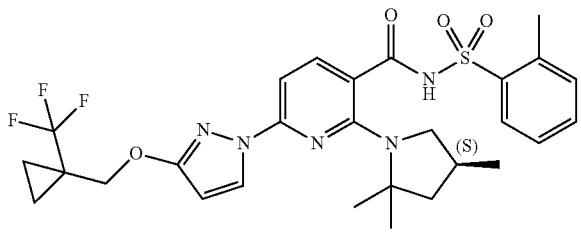 | 0.03 | 22 | 2.7 | 12.5 | 69% |
| Comp. 28 | 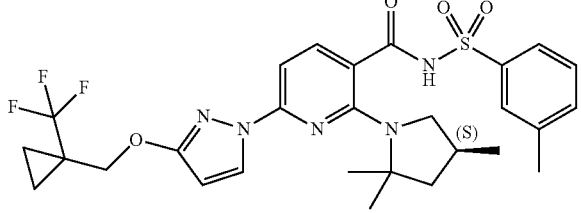 | 0.03 | 17 | | | |
| Comp. 31 | 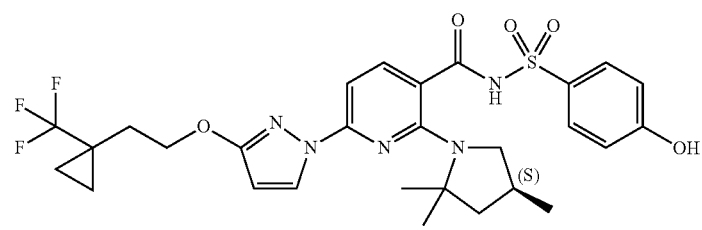 | 0.03 | 7 | | | |
| Comp. 14 | 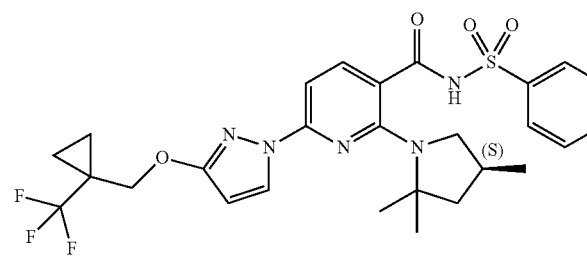 | 0.04 | 19 | 2.0 | 14.7 | 58% |
| Comp. 53 | 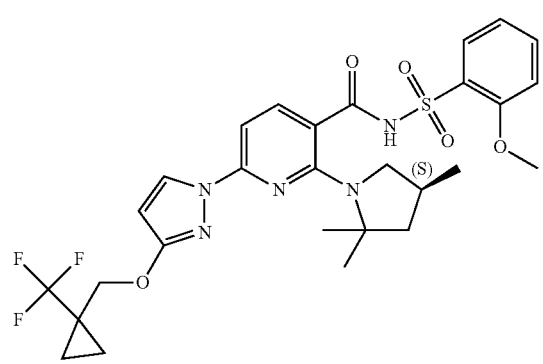 | 0.04 | 39 | 2.3 | 13.7 | 98% |

TABLE 9-continued

Comparative Data

| Compound No. | Compounds | CFTR dF508 EC50 (µM) | PXR Max Induction (% of rifampicin) | Rat iv CL (mL/min/kg) | Rat po AUC (µg·hr/mL at 3 mg/kg dose[a]) | Rat po % F |
|---|---|---|---|---|---|---|
| Comp. 10 | | 0.04 | 6 | 11.2 | 2.2 | 41% |
| Comp. 32 | | 0.04 | 4 | | | |
| Comp. 51 | | 0.05 | 17 | 5.2 | 10.5 | 100% |
| Comp. 55 | | 0.05 | 22 | | | |

TABLE 9-continued

Comparative Data

| Compound No. | Compounds | CFTR dF508 EC50 (µM) | PXR Max Induction (% of rifampicin) | Rat iv CL (mL/min/kg) | Rat po AUC (µg.hr/mL at 3 mg/kg dose[a]) | Rat po % F |
|---|---|---|---|---|---|---|
| Comp. 5 | | 0.05 | 0 | 9.6 | 2.7 | 50% |
| Comp. 58 | | 0.05 | 4 | | | |
| Comp. 64 | | 0.05 | 4 | 3.4 | 9b | 79% |
| Comp. 43 | | 0.05 | 12 | | | |
| Comp. 42 | | 0.05 | 3 | 5.4 | 4.4b | 51% |

TABLE 9-continued

Comparative Data

| Compound No. | Compounds | CFTR dF508 EC50 (μM) | PXR Max Induction (% of rifampicin) | Rat iv CL (mL/min/kg) | Rat po AUC (μg.hr/mL at 3 mg/kg dose[a]) | Rat po % F |
|---|---|---|---|---|---|---|
| Comp. 41 | | 0.07 | 6 | 1.9 | 6.4 | 41% |
| Comp. 24 | | 0.07 | 9 | 2.6 | 20 | 98% |
| Comp. 37 | | 0.07 | 8 | | | |
| Comp. 39 | | 0.07 | 13 | | | |
| Comp. 30 | | 0.09 | 0 | 6.1 | 2.3 | 26% |

TABLE 9-continued

Comparative Data

| Compound No. | Compounds | CFTR dF508 EC50 (µM) | PXR Max Induction (% of rifampicin) | Rat iv CL (mL/min/kg) | Rat po AUC (µg·hr/mL at 3 mg/kg dose[a]) | Rat po % F |
|---|---|---|---|---|---|---|
| Comp. 57 | | 0.08 | 2 | | | |
| Comp. 13 | | 0.11 | 2 | | | |
| Comp. 33 | | 0.08 | 0 | | | |
| Comp. 40 | | 0.08 | 2 | | | |
| Comp. 27 | | 0.27 | 8 | 3.6 | 20.3 | 100% |

TABLE 9-continued

Comparative Data

| Compound No. | Compounds | CFTR dF508 EC50 (µM) | PXR Max Induction (% of rifampicin) | Rat iv CL (mL/min/kg) | Rat po AUC (µg·hr/mL) at 3 mg/kg dose[a] | Rat po % F |
|---|---|---|---|---|---|---|
| Comp. 44 | 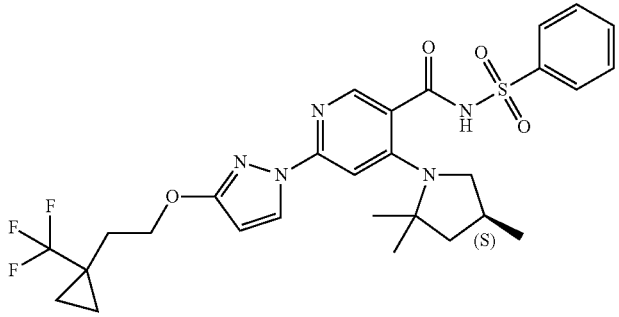 | 0.62 | 18 | 5.0 | 8.5 | 81% |
| Comp. 22 | 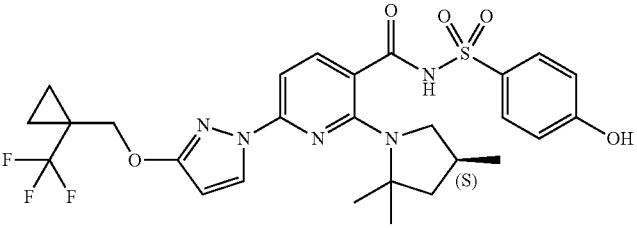 | 0.12 | 4 | 6.7 | 3.6 | 31% |

[a]: 10 mg/kg for Compound A, and for the other compounds at 3 mg/kg.

EXAMPLE 6

Chloride Transport Experiments

In one Ussing Chamber experiment with F508del/F508del-HBE cells, Compound 1 enhanced chloride transport. The effect of Compound 1 on chloride transport was additive to the effect of Compound II. In addition, F508del-CFTR delivered to the cell surface by either Compound I alone or in combination with Compound II was potentiated by Compound III. The triple combination of Compound I/Compound II/Compound III provided a superior (approximately 3-fold) increase in chloride transport compared to the 3 dual regimens under most conditions tested.

EXAMPLE 7

F508del-CFTR Processing and Trafficking In Vitro Experiments

In vitro, Compound 1 improved the processing and trafficking of F508del-CFTR, thereby increasing the quantity of functional F508del-CFTR protein at the cell surface. The CFTR protein delivered to the cell surface by Compound 1 alone or in combination with Compound II (Compound I/Compound II) was potentiated by Compound III. In human bronchial epithelial (HBE) cells studied in vitro, the triple combination of Compound I, Compound II, and Compound III (Compound I/Compound II/Compound III) increased CFTR chloride transport more than any of the dual combinations (Compound I/Compound II, Compound I/Compound III, and Compound II/Compound III) or individual components (Compound I, Compound II, and Compound III) under most conditions studied.

Processing and trafficking of F508del-CFTR was directly monitored by the appearance of a 170 to 180 kDa band Such monitoring established that Compound 1 is a CFTR corrector, as it facilitates the processing and trafficking of F508del-CFTR to increase the amount of functional F508del-CFTR at the cell surface.

Incubation of F508del/F508del-HBE cells for 16 to 24 hours with 1M Compound 1 alone or in combination with 3 µM Compound II resulted in an increase in steady-state levels, reaching 6.5-fold and 18.7-fold of untreated levels, respectively.

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A compound having the following formula:

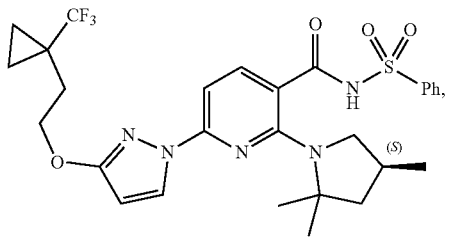

a pharmaceutical acceptable salt thereof, or a deuterated derivative of any of the foregoing.

2. A pharmaceutical composition comprising the compound, pharmaceutically acceptable salt, or deuterated derivative of claim 1, a pharmaceutically acceptable carrier and optionally one or more of:
(a) Compound II:

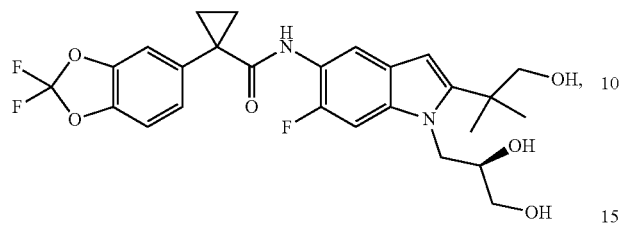

a pharmaceutically acceptable salt thereof, or a deuterated derivative of any of the foregoing; and
(b) Compound III:

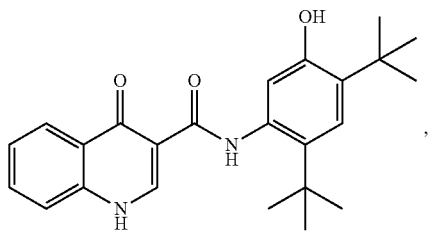 [SMILES: CC(C)(C)c1cc(C(C)(C)C)c(NC(=O)c2c[nH]c3ccccc3c2=O)cc1O]

a pharmaceutically acceptable salt thereof, or a deuterated derivative of any of the foregoing.

3. A method of treating cystic fibrosis comprising administering to a patient in need thereof a pharmaceutical composition according to claim 2.

4. A compound of the formula:

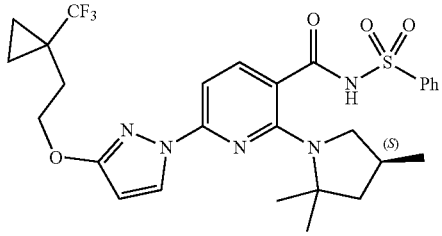

in the form of a pharmaceutically acceptable salt.

5. A compound having the following formula:

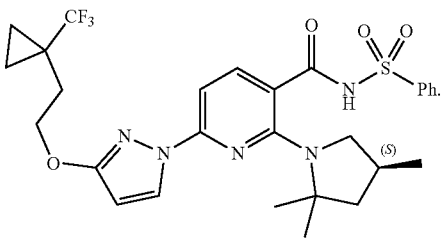

6. A pharmaceutical composition comprising the compound of claim 1.

7. A pharmaceutical composition comprising the compound of claim 4.

8. A pharmaceutical composition comprising the compound of claim 5.

9. A pharmaceutical composition comprising a compound having the following formula:

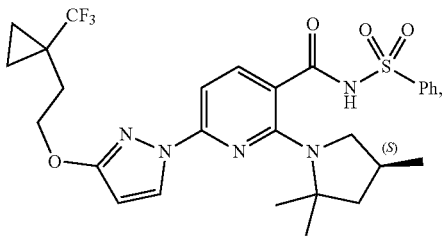

or a pharmaceutically acceptable salt thereof; a pharmaceutically acceptable carrier; and optionally one or more of:
(a) Compound II:

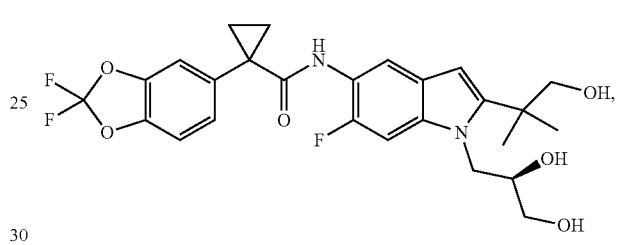

a pharmaceutically acceptable salt thereof, or a deuterated derivative of any of the foregoing; and
(b) Compound III:

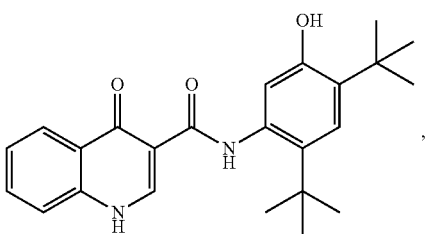

a pharmaceutically acceptable salt thereof, or a deuterated derivative of any of the foregoing.

10. The pharmaceutical composition of claim 9, wherein the compound having the following formula:

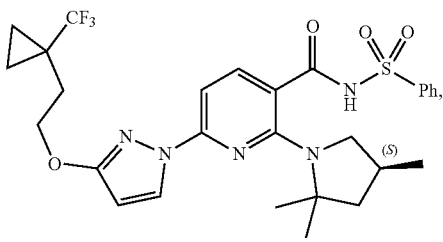

is in the form of a pharmaceutically acceptable salt.

11. A method of treating cystic fibrosis comprising administering to a patient in need thereof the compound according to claim 1.

12. A method of treating cystic fibrosis comprising administering to a patient in need thereof the compound according to claim 4.

13. A method of treating cystic fibrosis comprising administering to a patient in need thereof the compound according to claim 5.

14. A method of treating cystic fibrosis comprising administering to a patient in need thereof the pharmaceutical composition according to claim 6.

15. A method of treating cystic fibrosis comprising administering to a patient in need thereof the pharmaceutical composition according to claim 7.

16. A method of treating cystic fibrosis comprising administering to a patient in need thereof the pharmaceutical composition according to claim 8.

17. A method of treating cystic fibrosis comprising administering to a patient in need thereof the pharmaceutical composition according to claim 9.

18. A method of treating cystic fibrosis comprising administering to a patient in need thereof the pharmaceutical composition according to claim 10.

* * * * *

UNITED STATES PATENT AND TRADEMARK OFFICE
CERTIFICATE OF CORRECTION

PATENT NO.         : 10,570,115 B2
APPLICATION NO.    : 15/721390
DATED              : February 25, 2020
INVENTOR(S)        : Timothy Alcacio et al.

Page 1 of 1

It is certified that error appears in the above-identified patent and that said Letters Patent is hereby corrected as shown below:

On the Title Page

Item (72), under "Inventors" (last two lines), delete "David Andrew Siesel, San Diego, CA (US)".

In the Claims

Claim 1, Column 304, Line 66, "a pharmaceutical acceptable salt thereof" should read
--a pharmaceutically acceptable salt thereof--.

Claim 2, Column 305, Line 3, "a pharmaceutically acceptable carrier" should read
--a pharmaceutically acceptable carrier,--.

Signed and Sealed this
Twenty-first Day of July, 2020

Andrei Iancu
*Director of the United States Patent and Trademark Office*